US012540185B2

(12) United States Patent
Wu

(10) Patent No.: US 12,540,185 B2
(45) **Date of Patent: *Feb. 3, 2026**

(54) FABS-IN-TANDEM IMMUNOGLOBULIN AND USES THEREOF

(71) Applicant: EpimAb Biotherapeutics, Inc., Shanghai (CN)

(72) Inventor: Chengbin Wu, Shanghai (CN)

(73) Assignee: EPIMAB BIOTHERAPEUTICS, INC., Shanghai (CN)

( * ) Notice: Subject to any disclaimer, the term of this patent is extended or adjusted under 35 U.S.C. 154(b) by 857 days.

This patent is subject to a terminal disclaimer.

(21) Appl. No.: 17/811,926

(22) Filed: Jul. 12, 2022

(65) Prior Publication Data

US 2023/0220080 A1 Jul. 13, 2023

Related U.S. Application Data

(63) Continuation of application No. 16/075,922, filed as application No. PCT/US2017/016691 on Feb. 6, 2017, now Pat. No. 11,421,028.

(51) Int. Cl.

| | |
|---|---|
| ***C07H 21/04*** | (2006.01) |
| ***A61K 39/395*** | (2006.01) |
| ***A61P 25/28*** | (2006.01) |
| ***A61P 29/00*** | (2006.01) |
| ***A61P 35/00*** | (2006.01) |
| ***A61P 37/06*** | (2006.01) |
| ***C07K 16/18*** | (2006.01) |
| ***C07K 16/22*** | (2006.01) |
| ***C07K 16/24*** | (2006.01) |
| ***C07K 16/28*** | (2006.01) |
| ***C07K 16/32*** | (2006.01) |
| ***C07K 16/36*** | (2006.01) |
| *A61K 39/00* | (2006.01) |

(52) U.S. Cl.

CPC ........ *C07K 16/2818* (2013.01); *A61K 39/395* (2013.01); *A61P 25/28* (2018.01); *A61P 29/00* (2018.01); *A61P 35/00* (2018.01); *A61P 37/06* (2018.01); *C07K 16/18* (2013.01); *C07K 16/22* (2013.01); *C07K 16/241* (2013.01); *C07K 16/244* (2013.01); *C07K 16/2803* (2013.01); *C07K 16/2809* (2013.01); *C07K 16/2827* (2013.01); *C07K 16/2863* (2013.01); *C07K 16/2887* (2013.01); *C07K 16/32* (2013.01); *C07K 16/36* (2013.01); *A61K 2039/505* (2013.01); *C07K 2317/14* (2013.01); *C07K 2317/31* (2013.01); *C07K 2317/35* (2013.01); *C07K 2317/55* (2013.01); *C07K 2317/64* (2013.01); *C07K 2317/76* (2013.01); *C07K 2317/92* (2013.01); *C07K 2317/94* (2013.01)

(58) Field of Classification Search

None

See application file for complete search history.

(56) References Cited

U.S. PATENT DOCUMENTS

2009/0155275 A1* 6/2009 Wu ........................ A61P 35/02
530/387.3

* cited by examiner

*Primary Examiner* — Meera Natarajan

(74) *Attorney, Agent, or Firm* — Finnegan, Henderson, Farabow, Garrett & Dunner, LLP

(57) ABSTRACT

The present invention provides multivalent and multispecific binding proteins that are capable of binding two or more antigens, or two or more epitopes. The present invention also provides methods of making and using such multivalent and multispecific binding proteins, including methods of using such binding proteins for prevention or treatment of various diseases, or for detecting specific antigens in vitro or in vivo.

14 Claims, 51 Drawing Sheets

Specification includes a Sequence Listing.

| | FIT10-Ig | Ipilimumab | hIgG Control |
|---|---|---|---|
| EC50 | 0.2254 | 0.2699 | ~~51256~~ |

| | FIT10-Ig | Nivolumab | hIgG Control |
|---|---|---|---|
| EC50 | 0.4465 | 0.2412 | ~~10.58~~ |

| | RT | Area | % Area | Height |
|---|---|---|---|---|
| 1 | 24.464 | 2257050 | 100.00 | 18483 |

| | NBS3R | Nivolumab | hIgG |
|---|---|---|---|
| EC50 | 4.237 | 0.3743 | ~~14.46~~ |

| | NBS3R | Ipilimumab | hIgG |
|---|---|---|---|
| EC50 | 1.113 | 0.5680 | ~~106.7~~ |

| PK parameters | CTLA-4 plate | PD-1 plate |
|---|---|---|
| | IV, 5 mg/kg | IV, 5 mg/kg |
| CL, mL/day/kg | 11.8 | 11.0 |
| Alpha $t_{1/2}$, Day | 0.106 | 0.113 |
| Beta $t_{1/2}$, Day | 8.58 | 9.13 |
| V1, mL/kg | 48.6 | 59.7 |
| $C_{max}$, µg/mL | NA | NA |
| $T_{max}$, day | NA | NA |
| F% | NA | NA |

| | IC50 |
|---|---|
| Nivolumab | 1.360 |
| human IgG4 | ~~0.9962~~ |
| NBS3 | 2.816 |
| NBS3-C | 2.925 |
| NBS3R-C | 2.415 |

| | h1332 | panitumumab | h1332/panitumumab | FIT013a |
|---|---|---|---|---|
| Bottom | 44.57 | 91.43 | 41.08 | 20.80 |
| Top | 96.23 | 110.8 | 108.5 | 108.2 |
| LogEC50 | -0.9674 | ~ -0.5155 | -0.9547 | -0.8738 |
| HillSlope | -1.953 | ~ -19.32 | -1.802 | -1.424 |
| EC50 | 0.11078 | ~ 0.3051 | 0.1110 | 0.1337 |
| Span | 51.67 | 19.38 | 67.40 | 87.41 |

| | EC50 |
|---|---|
| mAb FIX | ~~50.26~~ |
| mAb FX | ~~~ 0.0001819~~ |
| mAb FIX+mAb FX | ~~162.4~~ |
| Emicizumab | 20.72 |
| FIT014a | 5.814 |
| Purified FVIIIa | 6.254 |

| | EC50 |
|---|---|
| CD3 mAb | ~ 8164 |
| FIT018a | 16.77 |
| Ofatumumab/CD3 mAb (1:1) | 3.317 |
| Ofatumumab | 3.335 |
| human IgG1 | ~ 8.414e-008 |

| | EC50 |
|---|---|
| CD3 mAb | 0.8479 |
| human IgG1 | |
| FIT018a | 2.667 |
| Ofatumumab/CD3 mAb (1:1) | 1.061 |

| | EC50 |
|---|---|
| Ofatumumab (CD20) | 3.068 |
| Anti-RAC-human IgG1 | |
| FIT018a (CD20/CD3) | 14.31 |

| | Ofatumumab | CD3 mAb | FIT018a |
|---|---|---|---|
| EC50 | 489.9 | 1.146 | 3.850 |

| | EC50 |
|---|---|
| FIT020b | 0.08446 |
| Nivolumab | 0.7368 |
| 1B12 | 0.4043 |
| Nivolumab+1B12 | 0.1835 |

| | EC50 |
|---|---|
| Epratuzumab | 13.20 |
| Ofatumumab | 3.335 |
| Anti-RAC-human IgG1 | ~8.414e-008 |
| FIT021b | 7.661 |
| Epratuzuman/ Ofatumumab (1:1) | 3.245 |

| | EC50 |
|---|---|
| Epratuzumab | 18.55 |
| Ofatumumab | 5.089 |
| human IgG1 | ~960710 |
| FIT021b | 19.29 |
| Epratuzumab/ Ofatumumab (1:1) | 6.983 |

FIT022a have multiple antigen binding ability

| | TOP (pg/ml) | EC50 (nM) |
|---|---|---|
| Nivolumab | 1178.0 | 0.874 |
| FIT024a | 1282.9 | 0.243 |
| FIT024b | 1376 | 0.287 |

FABS-IN-TANDEM IMMUNOGLOBULIN AND USES THEREOF

CROSS-REFERENCE TO RELATED APPLICATIONS

This application is a continuation of U.S. application Ser. No. 16/075,922, filed Aug. 6, 2018, which is a U.S. national stage entry under 35 U.S.C. § 371 of International Application No. PCT/US2017/016691, filed Feb. 6, 2017, which designates the U.S. and claims priority to, and the benefit of International Patent Application Serial No. PCT/CN2016/073722, filed Feb. 6, 2016, each of which is herein incorporated by reference in its entirety.

FIELD OF INVENTION

The present invention relates to multivalent and multispecific binding proteins, and to methods of making and using multivalent and multispecific binding proteins.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: EPBI_002_01WO_SeqList_ST25.txt, date recorded: Feb. 3, 2017, file size 510 KB).

BACKGROUND OF THE INVENTION

Bispecific or multispecific antibodies have been generated in attempts to prepare molecules useful for the treatment of various inflammatory diseases, cancers, and other disorders.

Bispecific antibodies have been produced using the quadroma technology (see Milstein, C. and A. C. Cuello, Nature, 1983. 305(5934): p. 537-40) based on the somatic fusion of two different hybridoma cell lines expressing murine monoclonal antibodies with the desired specificities of the bispecific antibody. Bispecific antibodies can also be produced by chemical conjugation of two different mAbs (see Staerz, U. D., et al., Nature, 1985. 314(6012): p. 628-31). Other approaches have used chemical conjugation of two different monoclonal antibodies or smaller antibody fragments (see Brennan, M., et al., Science, 1985. 229 (4708): p. 81-3).

Another method is the coupling of two parental antibodies with a hetero-bifunctional crosslinker. In particular, two different Fab fragments have been chemically crosslinked at their hinge cysteine residues in a site-directed manner (see Glennie, M. J., et al., J Immunol, 1987. 139(7): p. 2367-75).

Other recombinant bispecific antibody formats have been developed in the recent past (see Kriangkum, J., et al., Biomol Eng, 2001. 18(2): p. 31-40). Amongst them tandem single-chain Fv molecules and diabodies, and various derivatives thereof, have been used for the construction of recombinant bispecific antibodies. Normally, construction of these molecules starts from two single-chain Fv (scFv) fragments that recognize different antigens (see Economides, A. N., et al., Nat Med, 2003. 9(1): p. 47-52). Tandem scFv molecules (taFv) represent a straightforward format simply connecting the two scFv molecules with an additional peptide linker. The two scFv fragments present in these tandem scFv molecules form separate folding entities. Various linkers can be used to connect the two scFv fragments and linkers with a length of up to 63 residues (see Nakanishi, K., et al. Annu Rev Immunol, 2001. 19: p. 423-74).

In a recent study, in vivo expression by transgenic rabbits and cattle of a tandem scFv directed against CD28 and a melanoma-associated proteoglycan was reported (see Gracie, J. A., et al., J Clin Invest, 1999. 104(10): p. 1393-401). In this construct the two scFv molecules were connected by a CH1 linker and serum concentrations of up to 100 mg/L of the bispecific antibody were found. A few studies have now reported expression of soluble tandem scFv molecules in bacteria (see Leung, B. P., et al., J Immunol, 2000. 164(12): p. 6495-502; Ito, A., et al., J Immunol, 2003. 170(9): p. 4802-9; Karni, A., et al., J Neuroimmunol, 2002. 125(1-2): p. 134-40) using either a very short Ala3 linker or long glycine/serine-rich linkers.

In a recent study, phage display of a tandem scFv repertoire containing randomized middle linkers with a length of 3 or 6 residues enriched those molecules which are produced in soluble and active form in bacteria. This approach resulted in the isolation of a preferred tandem scFv molecule with a 6 amino acid residue linker (see Arndt, M. and J. Krauss, Methods Mol Biol, 2003. 207: p. 305-21).

Bispecific diabodies (db) utilize the diabody format for expression. Diabodies are produced from scFv fragments by reducing the length of the linker connecting the VH and VL domain to approximately 5 residues (see Peipp, M. and T. Valerius, Biochem Soc Trans, 2002. 30(4): p. 507-11). This reduction of linker size facilitates dimerization of two polypeptide chains by crossover pairing of the VH and VL domains. Bispecific diabodies are produced by expressing two polypeptide chains with either the structure VHA-VLB and VHB-VLA (VH-VL configuration) or VLA-VHB and VLB-VHA (VL-VH configuration) within the same cell. A recent comparative study demonstrates that the orientation of the variable domains can influence expression and formation of active binding sites (see Mack, M., G. Riethmuller, and P. Kufer, Proc Natl Acad Sci USA, 1995. 92(15): p. 7021-5).

One approach to force the generation of bispecific diabodies is the production of knob-into-hole diabodies (see Holliger, P., T. Prospero, and G. Winter, Proc Natl Acad Sci USA, 1993. 90(14): p. 6444-8.18). This was demonstrated for a bispecific diabody directed against HER2 and CD3. A large knob was introduced in the VH domain by exchanging Val37 with Phe and Leu45 with Trp and a complementary hole was produced in the VL domain by mutating Phe98 to Met and Tyr87 to Ala, either in the anti-HER2 or the anti-CD3 variable domains. By using this approach the production of bispecific diabodies could be increased from 72% by the parental diabody to over 90% by the knob-into-hole diabody.

Single-chain diabodies (scDb) represent an alternative strategy to improve the formation of bispecific diabody-like molecules (see Holliger, P. and G. Winter, Cancer Immunol Immunother, 1997. 45(3-4): p. 128-30; Wu, A. M., et al., Immunotechnology, 1996. 2(1): p. 21-36). Bispecific single-chain diabodies are produced by connecting the two diabody-forming polypeptide chains with an additional middle linker with a length of approximately 15 amino acid residues. Consequently, all molecules with a molecular weight corresponding to monomeric single-chain diabodies (50-60 kDa) are bispecific. Several studies have demonstrated that bispecific single chain diabodies are expressed in bacteria in soluble and active form with the majority of purified molecules present as monomers (see Holliger, P. and G. Winter, Cancer Immunol Immunother, 1997. 45(3-4): p. 128-30;

Wu, A. M., et al., Immunotechnology, 1996. 2(1): p. 21-36; Pluckthun, A. and P. Pack, Immunotechnology, 1997. 3(2): p. 83-105; Ridgway, J. B., et al., Protein Eng, 1996. 9(7): p. 617-21).

Diabody have been fused to Fc to generate more Ig-like molecules, named di-diabody (see Lu, D., et al., J Biol Chem, 2004. 279(4): p. 2856-65). In addition, multivalent antibody construct comprising two Fab repeats in the heavy chain of an IgG and capable of binding four antigen molecules has been described (see U.S. Pat. No. 8,722,859 B2, and Miller, K., et al., J Immunol, 2003. 170(9): p. 4854-61).

The most recent examples are tetravalent IgG-single-chain variable fragment (scFv) fusions (Dong J, et al. 2011 MAbs 3:273-288; Coloma M J, Morrison S L 1997 Nat Biotechnol 15:159-163; Lu D, et al. 2002 J Immunol Methods 267:213-226), catumaxomab, a trifunctional rat/mouse hybrid bispecific epithelial cell adhesion molecule-CD3 antibody (Lindhofer H, et al 1995 J Immunol 155:219-225), the bispecific CD19-CD3 scFv antibody blinatumomab (Bargou R, et al. 2008 Science 321:974-977), "dual-acting Fab" (DAF) antibodies (BostromJ, et al. 2009 Science 323:1610-1614), covalently linked pharmacophore peptides to catalytic anti-bodies (Doppalapudi V R, et al. 2010 Proc Natl Acad Sci USA 107:22611-22616), use of the dynamic exchange between half IgG4 molecules to generate bispecific antibodies (van der Neut Kolfschoten M, et al. 2007 Science 317:1554-1557; Stubenrauch K, et al. 2010 Drug Metab Dispos 38:84-91), or by exchange of heavy-chain and light-chain domains within the antigen binding fragment (Fab) of one half of the bispecific antibody (CrossMab format) (Schaefer W et al 2011 Proc Natl Acad Sci 108: 11187-92).

There is a need in the art for single molecular entities with dual antigen binding function, and for methods of generating such multivalent and multispecific binding proteins. The present invention addresses these and other needs.

SUMMARY OF THE INVENTION

The present invention provides multivalent and multispecific binding proteins, and methods of making and using such binding proteins. In one embodiment, the multivalent and multispecific binding proteins provided herein are Fabs-in-tandem immunoglobulins (FIT-Ig), and are capable of binding two or more antigens, or two or more epitopes of the same antigen, or two or more copies of the same epitope. The multivalent and multispecific binding proteins provided herein are useful for treatment and/or prevention of acute and chronic inflammatory diseases and disorders, autoimmune diseases, cancers, spinal cord injuries, sepsis, and other diseases, disorders, and conditions. Pharmaceutical compositions comprising the multivalent and multispecific binding proteins are provided herein. In addition, nucleic acids, recombinant expression vectors, and host cells for making such FIT-Igs are provided herein. Methods of using the FIT-Igs of the invention to detect specific antigens, in vivo or in vitro, are also encompassed by the invention.

The present invention provides a family of binding proteins that are capable of binding two or more antigens, e.g., with high affinity. In one aspect, the present invention provides an approach to construct a bispecific binding protein using two parental monoclonal antibodies: mAb A, which binds to antigen A, and mAb B, which binds to antigen B. The binding proteins disclosed herein, in one embodiment, are capable of binding antigens, cytokines, chemokines, cytokine receptors, chemokine receptors, cytokine- or chemokine-related molecules, or cell surface proteins.

Thus, in one aspect, binding proteins capable of binding two or more antigens are provided. In one embodiment, the present invention provides a binding protein comprising at least two polypeptide chains, wherein the polypeptide chains pair to form IgG-like molecules capable of binding two or more antigens. In one embodiment, the binding protein comprises two, three, four, five, or more polypeptide chains. In one embodiment, the binding protein comprises at least one $VL_A$, at least one $VL_B$, at least one $VH_A$, at least one $VH_B$, at least one CL, and at least one CH1, wherein VL is a light chain variable domain, VH is a heavy chain variable domain, CL is a light chain constant domain, CH1 is the first constant domain of the heavy chain, A is a first antigen, and B is a second antigen. In a further embodiment, the first polypeptide chain comprises a $VL_A$, a CL, a $VH_B$, and a CH1. In a further embodiment, the binding protein further comprises an Fc. In another embodiment, the Fc region is a variant Fc region. In a further embodiment, the variant Fc region exhibits modified effector function, such as ADCC or CDC. In another embodiment, the variant Fc region exhibits modified affinity or avidity for one or more FcγR.

In one embodiment, the binding protein comprises three polypeptide chains, wherein the first polypeptide chain comprises a $VL_A$, a CL, a $VH_B$, and a CH1, the second polypeptide chain comprises $VH_A$ and CH1, and the third polypeptide chain comprises $VL_B$ and CL. In a further embodiment, the first polypeptide chain of the binding protein further comprises an Fc. In another embodiment, the binding protein comprises two polypeptide chains, wherein the first polypeptide chain comprises a $VL_A$, a CL, a $VH_B$, and a CH1, the second polypeptide chain comprises $VH_A$, CH1, $VL_B$, and CL. In a further embodiment, the first polypeptide chain further comprises an Fc.

In one embodiment, the binding protein comprises three polypeptide chains, and their corresponding cDNA during co-transfection are present at a molar ratio of first:second: third of 1:1:1, 1:1.5:1, 1:3:1, 1:1:1.5, 1:1:3, 1:1.5:1.5, 1:3: 1.5, 1:1.5:3, or 1:3:3. In another embodiment, the binding protein comprises two polypeptide chains, and their corresponding cDNA during co-transfection are present at a molar ratio of first:second of 1:1, 1:1.5, or 1:3, or any other ratios, through optimization, in an effort to maximize the monomeric FIT-Ig fraction in any given transfection.

In one embodiment, the binding protein of the present invention does not comprise a peptide linker. In one embodiment, the binding protein of the present invention comprises at least one amino acid or polypeptide linker. In a further embodiment, the linker is selected from the group consisting of G, GS, SG, GGS, GSG, SGG, GGG, GGGS (SEQ ID NO: 489), SGGG (SEQ ID NO: 490), GGGGS (SEQ ID NO: 491), GGGGSGS (SEQ ID NO: 492), GGGGSGGS (SEQ ID NO: 493), GGGGSGGGGS (SEQ ID NO: 494), GGGGSGGGGSGGGGS (SEQ ID NO: 495), AKTTPKLEEGEFSEAR (SEQ ID NO: 496), AKTTPKLEEGEFSEARV (SEQ ID NO: 497), AKTTPKLGG (SEQ ID NO: 498), SAKTTPKLGG (SEQ ID NO: 499), SAKTTP (SEQ ID NO: 500), RADAAP (SEQ ID NO: 501), RADAAPTVS (SEQ ID NO: 502), RADAAAAGGPGS (SEQ ID NO: 503), RADAAAA $(G_4S)_4$ (SEQ ID NO: 504), SAKTTPKLEEGEFSEARV (SEQ ID NO: 505), ADAAP (SEQ ID NO: 506), ADAAPTVSIFPP (SEQ ID NO: 507), TVAAP (SEQ ID NO: 508), TVAAPSVFIFPP (SEQ ID NO: 509), QPKAAP (SEQ ID NO: 510), QPKAAPSVTLFPP (SEQ ID NO: 511), AKTTPP (SEQ ID NO: 512), AKTTPPSVTPLAP (SEQ ID NO: 513), AKTTAPSVYPLAP (SEQ ID NO: 514), ASTKGP (SEQ ID NO: 515), ASTKGPSVFPLAP (SEQ ID NO: 516), GENKVEYAPALMALS (SEQ ID NO: 517), GPAKELTPLKEAKVS (SEQ ID NO: 518), GHEAAAVMQVQYPAS (SEQ ID NO: 519), and AKTTAP (SEQ ID NO: 80). The linkers can also be in vivo cleavable peptide linkers, protease (such as MMPs) sensitive linkers, disulfide bond-based linkers that can be cleaved by reduction, etc., as previously described (Fusion Protein Technologies for Biopharmaceuticals: Applications and Challenges, edited by Stefan R. Schmidt), or any cleavable linkers known in the art. Such cleavable linkers can be used to release the top Fab in vivo for various purposes, in order to improve tissue/cell penetration and distribution, to enhance binding to targets, to reduce potential side effect, as well as to modulate in vivo functional and physical half-life of the 2 different Fab regions.

In one embodiment, the binding protein comprises a first polypeptide comprising, from amino to carboxyl terminus, $VL_A$-CL-$VH_B$-CH1-Fc, a second polypeptide chain comprising, from amino to carboxyl terminus, $VH_A$-CH1, and a third polypeptide chain comprising, from amino to carboxyl terminus, $VL_B$-CL; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In a further embodiment, the CL of the first polypeptide chain is fused directly to $VH_B$. In another embodiment, the CL of the first polypeptide chain is linked to $VH_B$ via an amino acid or an oligopeptide linker. In a further embodiment, the linker is GSG (SEQ ID NO: 26) or GGGGSGS (SEQ ID NO: 28).

In another embodiment, the binding protein comprises a first polypeptide comprising, from amino to carboxyl terminus, $VH_B$-CH1-$VL_A$-CL-Fc, a second polypeptide chain comprising, from amino to carboxyl terminus, $VH_A$-CH1, and a third polypeptide chain comprising, from amino to carboxyl terminus, $VL_B$-CL; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In one embodiment, the CH1 of the first polypeptide chain is fused directly to $VL_A$. In another embodiment, the CH1 of the first polypeptide chain is linked to $VL_A$ via an amino acid or an oligopeptide linker. In a further embodiment, the linker is GSG (SEQ ID NO: 26) or GGGGSGS (SEQ ID NO: 28).

In another embodiment, the binding protein comprises a first polypeptide comprising, from amino to carboxyl terminus, $VL_A$-CL-$VH_B$-CH1-Fc, and a second polypeptide chain comprising, from amino to carboxyl terminus, $VH_A$-CH1-$VL_B$-CL; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In a further embodiment, the CL of the first polypeptide chain is fused directly to $VH_B$. In another embodiment, the CL of the first polypeptide chain is linked to $VH_B$ via an amino acid or an oligopeptide linker. In a further embodiment, the linker is GSG (SEQ ID NO: 26) or GGGGSGS (SEQ ID NO: 28).

In another embodiment, binding protein comprises a first polypeptide comprising, from amino to carboxyl terminus, $VH_B$-CH1-$VL_A$-CL-Fc, and a second polypeptide chain comprising, from amino to carboxyl terminus, $VL_B$-CL-$VH_A$-CH1; wherein VL is a light chain variable domain, CL is a light chain constant domain, VH is a heavy chain variable domain, CH1 is the first constant domain of the heavy chain, A is a first epitope or antigen, and B is a second epitope or antigen. In one embodiment, the Fc region is human IgG1. In another embodiment, the Fc region is a variant Fc region. In a further embodiment, the amino acid sequence of the Fc region is at least 65%, at least 70%, at least 75%, at least 80%, at least 85%, at least 90%, at least 95%, at least 99%, or 100% identical to SEQ ID NO: 20. In one embodiment, the CH1 of the first polypeptide chain is fused directly to $VL_A$. In another embodiment, the CH1 of the first polypeptide chain is linked to $VL_A$ via an amino acid or an oligopeptide linker. In a further embodiment, the linker is GSG (SEQ ID NO: 26) or GGGGSGS (SEQ ID NO: 28).

The binding proteins of the present invention are capable of binding pairs of cytokines. For example, the binding proteins of the present invention are capable of binding pairs of cytokines selected from the group consisting of IL-1α and IL-1β; IL-12 and IL-18, TNFα and IL-23, TNFα and IL-13; TNF and IL-18; TNF and IL-12; TNF and IL-1beta; TNF and MIF; TNF and IL-6, TNF and IL-6 Receptor, TNF and IL-17; IL-17 and IL-20; IL-17 and IL-23; TNF and IL-15; TNF and VEGF; VEGFR and EGFR; PDGFR and VEGF, IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; IL-13 and ADAM8; and TNFα and PGE4, IL-13 and PED2, TNF and PEG2. In one embodiment, the binding proteins of the present invention are capable of binding IL-17 and IL-20. The binding proteins of the present invention, in one embodiment, are capable of binding IL-17 and IL-20 and comprise variable heavy and light chains derived from the anti-IL-17 antibody LY and the anti-IL-20 antibody 15D2. In one embodiment, the binding proteins of the present invention are capable of binding IL-17 and TNF. The binding proteins of the present invention, in one embodiment, are capable of binding IL-17 and TNF and comprise variable heavy and light chains derived from the anti-IL-17 antibody LY and the TNF antibody golimumab.

In one embodiment, the binding proteins of the present invention bind IL-17 and IL-20 and comprise a first polypeptide comprising, consisting essentially of, or consisting of an amino acid sequence selected from the group consisting of SEQ ID NOs: 15, 25, and 27; a second polypeptide chain comprising, consisting essentially of, or consisting of an amino acid sequence according to SEQ ID NO: 21; and a third polypeptide chain comprising, consisting essentially of, or consisting of a sequence according to SEQ ID NO: 23. In another embodiment, the binding proteins of the present invention bind IL-27 and IL-20 and comprise a first polypeptide chain comprising, consisting essentially of, or consisting of an amino acid sequence selected from the group consisting of SEQ ID NOs: 15, 25, and 27, and a second polypeptide chain comprising, consisting essentially of, or consisting of an amino acid sequence selected from the group consisting of SEQ ID NOs: 29, 30, and 31.

In one embodiment, the binding proteins of the present invention bind TNF and IL-17 and comprise a first polypeptide comprising, consisting essentially of, or consisting of an amino acid sequence according to SEQ ID NOs: 87; a second polypeptide chain comprising, consisting essentially of, or consisting of an amino acid sequence according to SEQ ID NO: 89; and a third polypeptide chain comprising, consisting essentially of, or consisting of a sequence according to SEQ ID NO: 91. In another embodiment, the binding protein is capable of binding pairs of targets selected from the group consisting of CD137 and CD20, CD137 and EGFR, CD137 and Her-2, CD137 and PD-1, CD137 and PDL-1, VEGF and PD-L1, Lag-3 and TIM-3, OX40 and PD-1, TIM-3 and PD-1, TIM-3 and PDL-1, EGFR and DLL-4, CD138 and CD20; CD138 and CD40; CD19 and CD20; CD20 and CD3; CD3 and CD33; CD3 and CD133; CD47 and CD20, CD38 and CD138; CD38 and CD20; CD20 and CD22; CD38 and CD40; CD40 and CD20; CD-8 and IL-6; CSPGs and RGM A; CTLA-4 and BTNO2; IGF1 and IGF2; IGF1/2 and Erb2B; IGF-1R and EGFR; EGFR and CD13; IGF-1R and ErbB3; EGFR-2 and IGFR; VEGFR-2 and Met; VEGF-A and Angiopoietin-2 (Ang-2); IL-12 and TWEAK; IL-13 and IL-1beta; PDGFR and VEGF, EpCAM and CD3, Her2 and CD3, CD19 and CD3, EGFR and Her3, CD16a and CD30, CD30 and PSMA, EGFR and CD3, CEA and CD3, TROP-2 and HSG, TROP-2 and CD3, MAG and RGM A; NgR and RGM A; NogoA and RGM A; OMGp and RGM A; PDL-1 and CTLA-4; CTLA-4 and PD-1; PD-1 and TIM-3; RGM A and RGM B; Te38 and TNFα; TNFα and Blys; TNFα and CD-22; TNFα and CTLA-4 domain; TNFα and GP130; TNFα and IL-12p40; and TNFα and RANK ligand, Factor IXa and Factor X; EGFR and PD-L1; EGFR and cMet; Her3 and IGF-IR; DLL-4 and VEGF; PD-1 and PD-L1; and Her3 and PD-1.

In one embodiment, the binding proteins of the present invention are capable of binding CD3 and CD20. The binding proteins of the present invention, in one embodiment, are capable of binding CD3 and CD20 and comprise variable heavy and light chains derived from the anti-CD3 antibody OKT3 or the anti-CD3 antibody disclosed in U.S. 2009/0252683, which is incorporated herein by reference in it entirety; and the anti-CD20 antibody ofatumumab. In some embodiments, the polypeptide derived from CD3 antibody is in the upper domain and the polypeptide derived from CD20 antibody is in the lower domain. As used herein, the upper domain is the N-terminal or "amino proximal" domain, and the lower domain is the C-terminal domain or the domain closer to the Fc, if present. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is CD3, and antigen B is CD20. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is CD3, and antigen A is CD20. In some embodiments, polypeptide derived from CD3 antibody is in the lower domain and polypeptide derived from CD20 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is CD20, and antigen B is CD-3. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is CD20, and antigen A is CD3.

In one embodiment, the binding proteins of the present invention bind CD3 and CD20 and comprise a first polypeptide chain comprising, consisting essentially of, or consisting of an amino acid sequence selected from the group consisting of SEQ ID NOs: 41 and 48; a second polypeptide chain comprising, consisting essentially of, or consisting of an amino acid sequence according to SEQ ID NO: 44; and a third polypeptide chain comprising, consisting essentially of, or consisting of an amino acid sequence according to SEQ ID NO: 46. In another embodiment, the binding proteins of the present invention bind CD20 and CD3 and comprise a first polypeptide chain comprising, consisting essentially of, or consisting of an amino acid sequence according to SEQ ID NO: 114; a second polypeptide chain comprising, consisting essentially of, or consisting of an amino acid sequence according to SEQ ID NO: 115; and a third polypeptide chain comprising, consisting essentially of, or consisting of an amino acid sequence according to SEQ ID NO: 116.

In one embodiment, the binding protein of the present invention is capable of binding the same epitope of CD20 and the same epitope of CD3 as that of bispecific binding protein FIT018a, wherein the bispecific binding protein FIT018a comprises a first polypeptide chain comprising an amino acid sequence of SEQ ID NO: 316; a second polypeptide chain comprising an amino acid sequence of SEQ ID NO: 325; and a third polypeptide chain comprising an amino acid sequence of SEQ ID NO: 330.

In one embodiment, the binding proteins of the present invention bind CD3 and CD20 and comprise a $VL_A$ on the first polypeptide, wherein the $VL_A$ of the first polypeptide comprises a $VL_A$ CDR1 of SEQ ID NO: 318, a $VL_A$ CDR2 of SEQ ID NO: 319, and a $VL_A$ CDR3 of SEQ ID NO: 320.

In one embodiment, the binding proteins of the present invention bind CD3 and CD20 and comprise a $VH_B$ on the first polypeptide, wherein the $VH_B$ of the first polypeptide comprises a $VH_B$ CDR1 of SEQ ID NO: 322, a $VH_B$ CDR2 of SEQ ID NO: 323, and a $VH_B$ CDR3 of SEQ ID NO: 324.

In one embodiment, the binding proteins of the present invention bind CD3 and CD20 and comprise a $VH_A$ on the second polypeptide, wherein the $VH_A$ of the second polypeptide comprises a $VH_A$ CDR1 of SEQ ID NO: 327, a $VH_A$ CDR2 of SEQ ID NO: 328, and a $VH_A$ CDR3 of SEQ ID NO: 329.

In one embodiment, the binding proteins of the present invention bind CD3 and CD20 and comprise a $VL_B$ on the third polypeptide, wherein the $VL_B$ of the third polypeptide comprises a $VL_B$ CDR1 of SEQ ID NO: 332, a $VL_B$ CDR2 of SEQ ID NO: 333, and a $VL_B$ CDR3 of SEQ ID NO: 334.

In one embodiment, the binding proteins of the present invention bind CD3 and CD20 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 318, a $VL_A$ CDR2 of SEQ ID NO: 319, and a $VL_A$ CDR3 of SEQ ID NO: 320; wherein the $VH_B$ of the first polypeptide comprises a $VH_B$ CDR1 of SEQ ID NO: 322, a $VH_B$ CDR2 of SEQ ID NO: 323, and a $VH_B$ CDR3 of SEQ ID NO: 324, wherein the $VH_A$ of the second polypeptide comprises a $VH_A$ CDR1 of SEQ ID NO: 327, a $VH_A$ CDR2 of SEQ ID NO: 328, and a $VH_A$ CDR3 of SEQ ID NO: 329; and wherein the $VL_B$ of the third polypeptide comprises a $VL_B$ CDR1 of SEQ ID NO: 332, a $VL_B$ CDR2 of SEQ ID NO: 333, and a $VL_B$ CDR3 of SEQ ID NO: 334.

In one embodiment, the binding proteins of the present invention bind CD3 and CD20 and comprise a first polypeptide chain comprising a $VL_A$ having the sequence of SEQ ID NO: 317, and a $VH_B$ having the sequence of SEQ ID NO: 321, wherein the binding protein comprises a second polypeptide chain comprising a $VH_A$ having the sequence of SEQ ID NO: 326, and wherein the binding protein comprises a third polypeptide chain comprising a $VL_B$ having the sequence of SEQ ID NO: 331.

In one embodiment, the binding proteins of the present invention bind CD3 and CD20 and comprising, consisting essentially of, or consisting of a first polypeptide chain comprising an amino acid sequence of SEQ ID NO: 316; a second polypeptide chain comprising an amino acid sequence of SEQ ID NO: 325; and a third polypeptide chain comprising an amino acid sequence of SEQ ID NO: 330.

In one embodiment, the binding proteins of the present invention bind CD3 and CD20, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding CTLA-4 and PD-1. The binding proteins of the present invention, in one embodiment, are capable of binding CTLA-4 and PD-1 and comprise variable heavy and light chains derived from the CTLA-4 antibody ipilimumab and the PD-1 antibody nivolumab.

In one embodiment, the binding proteins of the present invention bind CTLA-4 and PD-1 and comprise a first polypeptide chain comprising, consisting essentially of, or consisting of an amino acid sequence according to SEQ ID NO: 92; a second polypeptide chain comprising, consisting essentially of, or consisting of an amino acid sequence according to SEQ ID NO: 95; and a third polypeptide chain comprising, consisting essentially of, or consisting of an amino acid sequence according to SEQ ID NO: 97. In one embodiment, the binding protein provided herein is capable of binding one or more epitopes on CTLA-4. In one embodiment, the binding protein provided herein is capable of binding one or more epitopes on PD-1. In some embodiments, polypeptide derived from CTLA-4 antibody is in the upper domain and polypeptide derived from PD-1 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is CTLA-4, and antigen B is PD-1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is CTLA-4, and antigen A is PD-1. In some embodiments, polypeptide derived from CTLA-4 antibody is in the lower domain and polypeptide derived from PD-1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-1, and antigen B is CTLA-4. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-1, and antigen A is CTLA-4.

In one embodiment, the binding protein of the present invention is capable of binding the same epitope of CTLA-4 and the same epitope of PD-1 as that of bispecific binding proteins NBS3, NBS3R, NBS3-C, or NBS3R-C, as described herein.

The bispecific binding protein NBS3 comprises a first polypeptide chain comprising an amino acid sequence of SEQ ID NO: 126; a second polypeptide chain comprising an amino acid sequence of SEQ ID NO: 135; and a third polypeptide chain comprising an amino acid sequence of SEQ ID NO: 140.

The bispecific binding protein NBS3R comprises a first polypeptide chain comprising an amino acid sequence of SEQ ID NO: 145; a second polypeptide chain comprising an amino acid sequence of SEQ ID NO: 154; and a third polypeptide chain comprising an amino acid sequence of SEQ ID NO: 159.

The bispecific binding protein NBS3-C comprises a first polypeptide chain comprising an amino acid sequence of SEQ ID NO: 164; a second polypeptide chain comprising an amino acid sequence of SEQ ID NO: 173; and a third polypeptide chain comprising an amino acid sequence of SEQ ID NO: 178.

The bispecific binding protein NBS3R-C comprises a first polypeptide chain comprising an amino acid sequence of SEQ ID NO: 183; a second polypeptide chain comprising an amino acid sequence of SEQ ID NO: 192; and a third polypeptide chain comprising an amino acid sequence of SEQ ID NO: 197.

In one embodiment, the binding proteins of the present invention bind CTLA4 and PD-1 and comprise a $VL_A$ on the first polypeptide, wherein the $VL_A$ of the first polypeptide comprises a $VL_A$ CDR1 of SEQ ID NO: 128, a $VL_A$ CDR2 of SEQ ID NO: 129, and a $VL_A$ CDR3 of SEQ ID NO: 130 (e.g., those on NBS3). In one embodiment, the binding proteins of the present invention bind CTLA4 and PD-1 and comprises a $VL_A$ on the first polypeptide, wherein the $VL_A$ of the first polypeptide comprises a $VL_A$ CDR1 of SEQ ID NO: 147, a $VL_A$ CDR2 of SEQ ID NO: 148, and a $VL_A$ CDR3 of SEQ ID NO: 149 (e.g., those on NBS3R). In one embodiment, the binding proteins of the present invention bind CTLA4 and PD-1 and comprises a $VL_A$ on the first polypeptide, wherein the $VL_A$ of the first polypeptide comprises a $VL_A$ CDR1 of SEQ ID NO: 166, a $VL_A$ CDR2 of SEQ ID NO: 167, and a $VL_A$ CDR3 of SEQ ID NO: 168 (e.g., those on NBS3-C). In one embodiment, the binding proteins of the present invention bind CTLA4 and PD-1 and comprises a $VL_A$ on the first polypeptide, wherein the $VL_A$ of the first polypeptide comprises a $VL_A$ CDR1 of SEQ ID NO: 185, a $VL_A$ CDR2 of SEQ ID NO: 186, and a $VL_A$ CDR3 of SEQ ID NO: 187 (e.g., those on NBS3R-C).

In one embodiment, the binding proteins of the present invention bind CTLA4 and PD-1 and comprise a $VH_B$ on the first polypeptide, wherein the $VH_B$ of the first polypeptide comprises a $VH_B$ CDR1 of SEQ ID NO: 132, a $VH_B$ CDR2 of SEQ ID NO: 133, and a $VH_B$ CDR3 of SEQ ID NO: 134 (e.g., those on NBS3). In one embodiment, the binding proteins of the present invention bind CTLA4 and PD-1 and comprise a $VH_B$ on the first polypeptide, wherein the $VH_B$ of the first polypeptide comprises a $VH_B$ CDR1 of SEQ ID NO: 151, a $VH_B$ CDR2 of SEQ ID NO: 152, and a $VH_B$ CDR3 of SEQ ID NO: 153 (e.g., those on NBS3R). In one embodiment, the binding proteins of the present invention bind CTLA4 and PD-1 and comprise a $VH_B$ on the first polypeptide, wherein the $VH_B$ of the first polypeptide comprises a $VH_B$ CDR1 of SEQ ID NO: 166, a $VH_B$ CDR2 of SEQ ID NO: 167, and a $VH_B$ CDR3 of SEQ ID NO: 168 (e.g., those on NBS3-C). In one embodiment, the binding proteins of the present invention bind CTLA4 and PD-1 and comprise a $VH_B$ on the first polypeptide, wherein the $VH_B$ of the first polypeptide comprise a $VH_B$ CDR1 of SEQ ID NO: 185, a $VH_B$ CDR2 of SEQ ID NO: 186, and a $VH_B$ CDR3 of SEQ ID NO: 187 (e.g., those on NBS3R-C).

In one embodiment, the binding proteins of the present invention bind CTLA4 and PD-1 and comprise a $VH_A$ on the second polypeptide, wherein the $VH_A$ of the second polypeptide comprises a $VH_A$ CDR1 of SEQ ID NO: 137, a $VH_A$ CDR2 of SEQ ID NO: 138, and a $VH_A$ CDR3 of SEQ ID NO: 139 (e.g., those on NBS3). In one embodiment, the binding proteins of the present invention bind CTLA4 and PD-1 and comprises a $VH_A$ on the second polypeptide, wherein the $VH_A$ of the second polypeptide comprises a $VH_A$ CDR1 of SEQ ID NO: 156, a $VH_A$ CDR2 of SEQ ID NO: 157, and a $VH_A$ CDR3 of SEQ ID NO: 158 (e.g., those on NBS3R). In one embodiment, the binding proteins of the present invention bind CTLA4 and PD-1 and comprises a $VH_A$ on the second polypeptide, wherein the $VH_A$ of the second polypeptide comprises a $VH_A$ CDR1 of SEQ ID NO: 175, a $VH_A$ CDR2 of SEQ ID NO: 176, and a $VH_A$ CDR3 of SEQ ID NO: 177 (e.g., those on NBS-C). In one embodiment, the binding proteins of the present invention bind CTLA4 and PD-1 and comprises a $VH_A$ on the second polypeptide, wherein the $VH_A$ of the second polypeptide comprises a $VH_A$ CDR1 of SEQ ID NO: 194, a $VH_A$ CDR2 of SEQ ID NO: 195, and a $VH_A$ CDR3 of SEQ ID NO: 196 (e.g., those on NBS3R-C).

In one embodiment, the binding proteins of the present invention bind CTLA4 and PD-1 and comprise a $VL_B$ on the third polypeptide, wherein the $VL_B$ of the third polypeptide comprises a $VL_B$ CDR1 of SEQ ID NO: 142, a $VL_B$ CDR2 of SEQ ID NO: 143, and a $VL_B$ CDR3 of SEQ ID NO: 144 (e.g., those on NBS3). In one embodiment, the binding proteins of the present invention bind CTLA4 and PD-1 and comprises a $VL_B$ on the third polypeptide, wherein the $VL_B$ of the third polypeptide comprises a $VL_B$ CDR1 of SEQ ID NO: 161, a $VL_B$ CDR2 of SEQ ID NO: 162, and a $VL_B$ CDR3 of SEQ ID NO: 163 (e.g., those on NBS3R). In one embodiment, the binding proteins of the present invention bind CTLA4 and PD-1 and comprises a $VL_B$ on the third polypeptide, wherein the $VL_B$ of the third polypeptide comprises a $VL_B$ CDR1 of SEQ ID NO: 180, a $VL_B$ CDR2 of SEQ ID NO: 181, and a $VL_B$ CDR3 of SEQ ID NO: 182 (e.g., those on NBS3-C). In one embodiment, the binding proteins of the present invention bind CTLA4 and PD-1 and comprises a $VL_B$ on the third polypeptide, wherein the $VL_B$ of the third polypeptide comprises a $VL_B$ CDR1 of SEQ ID NO: 199, a $VL_B$ CDR2 of SEQ ID NO: 200, and a $VL_B$ CDR3 of SEQ ID NO: 201 (e.g., those on NBS3R-C).

In one embodiment, the binding proteins of the present invention bind CTLA4 and PD-1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 128, a $VL_A$ CDR2 of SEQ ID NO: 129, and a $VL_A$ CDR3 of SEQ ID NO: 130; wherein the $VH_B$ of the first polypeptide comprises a $VH_B$ CDR1 of SEQ ID NO: 132, a $VH_B$ CDR2 of SEQ ID NO: 133, and a $VH_B$ CDR3 of SEQ ID NO: 134; wherein the $VH_A$ of the second polypeptide comprises a $VH_A$ CDR1 of SEQ ID NO: 137, a $VH_A$ CDR2 of SEQ ID NO: 138, and a $VH_A$ CDR3 of SEQ ID NO: 139; and wherein the $VL_B$ of the third polypeptide comprises a $VL_B$ CDR1 of SEQ ID NO: 142, a $VL_B$ CDR2 of SEQ ID NO: 143, and a $VL_B$ CDR3 of SEQ ID NO: 144 (e.g., those on NBS3).

In one embodiment, the binding proteins of the present invention bind CTLA4 and PD-1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 147, a $VL_A$ CDR2 of SEQ ID NO: 148, and a $VL_A$ CDR3 of SEQ ID NO: 149; wherein the $VH_B$ of the first polypeptide comprises a $VH_B$ CDR1 of SEQ ID NO: 151, a $VH_B$ CDR2 of SEQ ID NO: 152, and a $VH_B$ CDR3 of SEQ ID NO: 153; wherein the $VH_A$ of the second polypeptide comprises a $VH_A$ CDR1 of SEQ ID NO: 156, a $VH_A$ CDR2 of SEQ ID NO: 157, and a $VH_A$ CDR3 of SEQ ID NO: 158; and wherein the $VL_B$ of the third polypeptide comprises a $VL_B$ CDR1 of SEQ ID NO: 161, a $VL_B$ CDR2 of SEQ ID NO: 162, and a $VL_B$ CDR3 of SEQ ID NO: 163 (e.g., those on NBS3R).

In one embodiment, the binding proteins of the present invention bind CTLA4 and PD-1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 166, a $VL_A$ CDR2 of SEQ ID NO: 167, and a $VL_A$ CDR3 of SEQ ID NO: 168; wherein the $VH_B$ of the first polypeptide comprises a $VH_B$ CDR1 of SEQ ID NO: 170, a $VH_B$ CDR2 of SEQ ID NO: 171, and a $VH_B$ CDR3 of SEQ ID NO: 172; wherein the $VH_A$ of the second polypeptide comprises a $VH_A$ CDR1 of SEQ ID NO: 175, a $VH_A$ CDR2 of SEQ ID NO: 176, and a $VH_A$ CDR3 of SEQ ID NO: 177; and wherein the $VL_B$ of the third polypeptide comprises a $VL_B$ CDR1 of SEQ ID NO: 180, a $VL_B$ CDR2 of SEQ ID NO: 181, and a $VL_B$ CDR3 of SEQ ID NO: 182 (e.g., those on NBS3-C).

In one embodiment, the binding proteins of the present invention bind CTLA4 and PD-1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 166, a $VL_A$ CDR2 of SEQ ID NO: 167, and a $VL_A$ CDR3 of SEQ ID NO: 168; wherein the $VH_B$ of the first polypeptide comprises a $VH_B$ CDR1 of SEQ ID NO: 170, a $VH_B$ CDR2 of SEQ ID NO: 171, and a $VH_B$ CDR3 of SEQ ID NO: 172; wherein the $VH_A$ of the second polypeptide comprises a $VH_A$ CDR1 of SEQ ID NO: 175, a $VH_A$ CDR2 of SEQ ID NO: 176, and a $VH_A$ CDR3 of SEQ ID NO: 177; and wherein the $VL_B$ of the third polypeptide comprises a $VL_B$ CDR1 of SEQ ID NO: 180, a $VL_B$ CDR2 of SEQ ID NO: 181, and a $VL_B$ CDR3 of SEQ ID NO: 182 (e.g., those on NBS3R-C).

In one embodiment, the binding proteins of the present invention bind CTLA4 and PD-1 and comprise a first polypeptide chain comprising a $VL_A$ having the sequence of SEQ ID NO: 127, and a $VH_B$ having the sequence of SEQ ID NO: 131, wherein the binding protein comprises a second polypeptide chain comprising a $VH_A$ having the sequence of SEQ ID NO: 136, and wherein the binding protein comprises a third polypeptide chain comprising a $VL_B$ having the sequence of SEQ ID NO: 141 (e.g., those on NBS3).

In one embodiment, the binding proteins of the present invention bind CTLA4 and PD-1 and comprise a first polypeptide chain comprising a $VL_A$ having the sequence of SEQ ID NO: 146, and a $VH_B$ having the sequence of SEQ ID NO: 150, wherein the binding protein comprises a second polypeptide chain comprising a $VH_A$ having the sequence of SEQ ID NO: 155, and wherein the binding protein comprises a third polypeptide chain comprising a $VL_B$ having the sequence of SEQ ID NO: 160 (e.g., those on NBS3R).

In one embodiment, the binding proteins of the present invention bind CTLA4 and PD-1 and comprise a first polypeptide chain comprising a $VL_A$ having the sequence of SEQ ID NO: 165, and a $VH_B$ having the sequence of SEQ ID NO: 169, wherein the binding protein comprises a second polypeptide chain comprising a $VH_A$ having the sequence of SEQ ID NO: 174, and wherein the binding protein comprises a third polypeptide chain comprising a $VL_B$ having the sequence of SEQ ID NO: 179 (e.g., those on NBS3-C).

In one embodiment, the binding proteins of the present invention bind CTLA4 and PD-1 and comprise a first polypeptide chain comprising a $VL_A$ having the sequence of SEQ ID NO: 184, and a $VH_B$ having the sequence of SEQ ID NO: 188, wherein the binding protein comprises a second polypeptide chain comprising a $VH_A$ having the sequence of SEQ ID NO: 193, and wherein the binding protein comprises a third polypeptide chain comprising a $VL_B$ having the sequence of SEQ ID NO: 198 (e.g., those on NBS3R-C).

In one embodiment, the binding proteins of the present invention bind CTLA4 and PD-1 and comprising, consisting essentially of, or consisting of a first polypeptide chain comprising an amino acid sequence of SEQ ID NO: 126; a second polypeptide chain comprising an amino acid sequence of SEQ ID NO: 135; and a third polypeptide chain comprising an amino acid sequence of SEQ ID NO: 140 (e.g., those on NBS3).

In one embodiment, the binding proteins of the present invention bind CTLA4 and PD-1 and comprising, consisting essentially of, or consisting of a first polypeptide chain comprising an amino acid sequence of SEQ ID NO: 145; a second polypeptide chain comprising an amino acid sequence of SEQ ID NO: 154; and a third polypeptide chain comprising an amino acid sequence of SEQ ID NO: 159 (e.g., those on NBS3R).

In one embodiment, the binding proteins of the present invention bind CTLA4 and PD-1 and comprising, consisting essentially of, or consisting of a first polypeptide chain comprising an amino acid sequence of SEQ ID NO: 164; a second polypeptide chain comprising an amino acid sequence of SEQ ID NO: 173; and a third polypeptide chain comprising an amino acid sequence of SEQ ID NO: 178 (e.g., those on NBS3-C).

In one embodiment, the binding proteins of the present invention bind CTLA4 and PD-1 and comprising, consisting essentially of, or consisting of a first polypeptide chain comprising an amino acid sequence of SEQ ID NO: 183; a second polypeptide chain comprising an amino acid sequence of SEQ ID NO: 192; and a third polypeptide chain comprising an amino acid sequence of SEQ ID NO: 197 (e.g., those on NBS3R-C).

In one embodiment, the binding proteins of the present invention bind CTLA4 and PD-1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution.

In one embodiment, the binding proteins of the present invention are capable of binding EGFR and PD-L1. The binding proteins of the present invention, in one embodiment, are capable of binding EGFR and PD-L1 and comprise variable heavy and light chains derived from the EGFR antibody panitumumab and the PD-L1 antibody 1B12. In some embodiments, polypeptide derived from EGFR antibody is in the upper domain and polypeptide derived from PD-L1 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is EGFR, and antigen B is PD-L1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is EGFR, and antigen A is PD-L1. In some embodiments, polypeptide derived from EGFR antibody is in the lower domain and polypeptide derived from PD-L1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-L1, and antigen B is EGFR. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-L1, and antigen A is EGFR.

In one embodiment, the binding proteins of the present invention bind EGFR and PD-L1 and comprise a first polypeptide chain comprising, consisting essentially of, or consisting of an amino acid sequence according to SEQ ID NO: 99; a second polypeptide chain comprising, consisting essentially of, or consisting of an amino acid sequence according to SEQ ID NO: 100; and a third polypeptide chain comprising, consisting essentially of, or consisting of an amino acid sequence according to SEQ ID NO: 101. In one embodiment, the binding proteins of the present invention are capable of binding the same epitope of EGFR and the same epitope of PD-L1 as that of bispecific binding protein FIT012a, wherein the bispecific binding protein FIT012a comprises a first polypeptide chain comprising an amino acid sequence of SEQ ID NO: 99; a second polypeptide chain comprising an amino acid sequence of SEQ ID NO: 100; and a third polypeptide chain comprising an amino acid sequence of SEQ ID NO: 101 (e.g., those on FIT012a).

In one embodiment, the binding proteins of the present invention are capable of binding the same epitope of EGFR and the same epitope of PD-L1 as that of bispecific binding protein FIT012b, wherein the bispecific binding protein FIT012b comprises a first polypeptide chain comprising an amino acid sequence of SEQ ID NO: 202; a second polypeptide chain comprising an amino acid sequence of SEQ ID NO: 211; and a third polypeptide chain comprising an amino acid sequence of SEQ ID NO: 216 (e.g., those on FIT012b).

In one embodiment, the binding proteins of the present invention are capable of binding the same epitope of EGFR and the same epitope of PD-L1 as that of bispecific binding protein FIT012d, wherein the bispecific binding protein FIT012d comprises a first polypeptide chain comprising an amino acid sequence of SEQ ID NO: 221; a second polypeptide chain comprising an amino acid sequence of SEQ ID NO: 230; and a third polypeptide chain comprising an amino acid sequence of SEQ ID NO: 235 (e.g., those on FIT012d).

In one embodiment, the binding proteins of the present invention bind EGFR and PD-L1 and comprise a $VL_A$ on the first polypeptide, wherein the $VL_A$ of the first polypeptide comprises a $VL_A$ CDR1 of SEQ ID NO: 204, a $VL_A$ CDR2 of SEQ ID NO: 205, and a $VL_A$ CDR3 of SEQ ID NO: 206 (e.g., those on FIT012b). In one embodiment, the binding proteins of the present invention bind EGFR and PD-L1 and comprise a $VL_A$ on the first polypeptide, wherein the $VL_A$ of the first polypeptide comprises a $VL_A$ CDR1 of SEQ ID NO:

223, a $VL_A$ CDR2 of SEQ ID NO: 224, and a $VL_A$ CDR3 of SEQ ID NO: 225 (e.g., those on FIT012d).

In one embodiment, the binding proteins of the present invention bind EGFR and PD-L1 and comprise a $VH_B$ on the first polypeptide, wherein the $VH_B$ of the first polypeptide comprises a $VH_B$ CDR1 of SEQ ID NO: 208, a $VH_B$ CDR2 of SEQ ID NO: 209, and a $VH_B$ CDR3 of SEQ ID NO: 210 (e.g., those on FIT012b). In one embodiment, the binding proteins of the present invention bind EGFR and PD-L1 and comprise a $VH_B$ on the first polypeptide, wherein the $VH_B$ of the first polypeptide comprises a $VH_B$ CDR1 of SEQ ID NO: 227, a $VH_B$ CDR2 of SEQ ID NO: 228, and a $VH_B$ CDR3 of SEQ ID NO: 229 (e.g., those on FIT012d).

In one embodiment, the binding proteins of the present invention bind EGFR and PD-L1 and comprise a $VH_A$ on the second polypeptide, wherein the $VH_A$ of the second polypeptide comprises a $VH_A$ CDR1 of SEQ ID NO: 213, a $VH_A$ CDR2 of SEQ ID NO: 214, and a $VH_A$ CDR3 of SEQ ID NO: 215 (e.g., those on FIT012b). In one embodiment, the binding proteins of the present invention bind EGFR and PD-L1 and comprise a $VH_A$ on the second polypeptide, wherein the $VH_A$ of the second polypeptide comprises a $VH_A$ CDR1 of SEQ ID NO: 232, a $VH_A$ CDR2 of SEQ ID NO: 233, and a $VH_A$ CDR3 of SEQ ID NO: 234 (e.g., those on FIT012d).

In one embodiment, the binding proteins of the present invention bind EGFR and PD-L1 and comprise a $VL_B$ on the third polypeptide, wherein the $VL_B$ of the third polypeptide comprises a $VL_B$ CDR1 of SEQ ID NO: 218, a $VL_B$ CDR2 of SEQ ID NO: 219, and a $VL_B$ CDR3 of SEQ ID NO: 220 (e.g., those on FIT012b). In one embodiment, the binding proteins of the present invention bind EGFR and PD-L1 and comprise a $VL_B$ on the third polypeptide, wherein the $VL_B$ of the third polypeptide comprises a $VL_B$ CDR1 of SEQ ID NO: 237, a $VL_B$ CDR2 of SEQ ID NO: 238, and a $VL_B$ CDR3 of SEQ ID NO: 239 (e.g., those on FIT012d).

In one embodiment, the binding proteins of the present invention bind EGFR and PD-L1 and comprise a $VL_A$ and $VH_B$ on the first polypeptide, a $VH_A$ on the second polypeptide, and a $VL_B$ on the third polypeptide, wherein the $VL_A$ comprises a $VL_A$ CDR1 of SEQ ID NO: 204, a $VL_A$ CDR2 of SEQ ID NO: 205, and a $VL_A$ CDR3 of SEQ ID NO: 206, the $VH_B$ comprises a $VH_B$ CDR1 of SEQ ID NO: 208, a $VH_B$ CDR2 of SEQ ID NO: 209, and a $VH_B$ CDR3 of SEQ ID NO: 210, the $VH_A$ comprises a $VH_A$ CDR1 of SEQ ID NO: 213, a $VH_A$ CDR2 of SEQ ID NO: 214, and a $VH_A$ CDR3 of SEQ ID NO: 215, and the $VL_B$ comprises a $VL_B$ CDR1 of SEQ ID NO: 218, a $VL_B$ CDR2 of SEQ ID NO: 219, and a $VL_B$ CDR3 of SEQ ID NO: 220 (e.g., those on FIT012b).

In one embodiment, the binding proteins of the present invention bind EGFR and PD-L1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 223, a $VL_A$ CDR2 of SEQ ID NO: 224, and a $VL_A$ CDR3 of SEQ ID NO: 225; wherein the $VH_B$ of the first polypeptide comprises a $VH_B$ CDR1 of SEQ ID NO: 227, a $VH_B$ CDR2 of SEQ ID NO: 228, and a $VH_B$ CDR3 of SEQ ID NO: 229; wherein the $VH_A$ of the second polypeptide comprises a $VH_A$ CDR1 of SEQ ID NO: 232, a $VH_A$ CDR2 of SEQ ID NO: 233, and a $VH_A$ CDR3 of SEQ ID NO: 234; and wherein the $VL_B$ of the third polypeptide comprises a $VL_B$ CDR1 of SEQ ID NO: 237, a $VL_B$ CDR2 of SEQ ID NO: 239, and a $VL_B$ CDR3 of SEQ ID NO: 239 (e.g., those on FIT012d).

In one embodiment, the binding proteins of the present invention bind EGFR and PD-L1 and comprise a first polypeptide chain comprising a $VL_A$ having the sequence of SEQ ID NO: 203, and a $VH_B$ having the sequence of SEQ ID NO: 207, wherein the binding protein comprises a second polypeptide chain comprising a $VH_A$ having the sequence of SEQ ID NO: 212, and wherein the binding protein comprises a third polypeptide chain comprising a $VL_B$ having the sequence of SEQ ID NO: 217 (e.g., those on FIT012b).

In one embodiment, the binding proteins of the present invention bind EGFR and PD-L1 and comprise a first polypeptide chain comprising a $VL_A$ having the sequence of SEQ ID NO: 222, and a $VH_B$ having the sequence of SEQ ID NO: 226, wherein the binding protein comprises a second polypeptide chain comprising a $VH_A$ having the sequence of SEQ ID NO: 231, and wherein the binding protein comprises a third polypeptide chain comprising a $VL_B$ having the sequence of SEQ ID NO: 236 (e.g., those on FIT012d).

In one embodiment, the binding proteins of the present invention bind EGFR and PD-L1 and comprising, consisting essentially of, or consisting of a first polypeptide chain comprising an amino acid sequence of SEQ ID NO: 202; a second polypeptide chain comprising an amino acid sequence of SEQ ID NO: 211; and a third polypeptide chain comprising an amino acid sequence of SEQ ID NO: 216 (e.g., those on FIT012b).

In one embodiment, the binding proteins of the present invention bind EGFR and PD-L1 and comprising, consisting essentially of, or consisting of a first polypeptide chain comprising an amino acid sequence of SEQ ID NO: 221; a second polypeptide chain comprising an amino acid sequence of SEQ ID NO: 230; and a third polypeptide chain comprising an amino acid sequence of SEQ ID NO: 235 (e.g., those on FIT012d).

In one embodiment, the binding proteins of the present invention bind EGFR and PD-L1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding cMet and EGFR. The binding proteins of the present invention, in one embodiment, are capable of binding cMet and EGFR and comprise variable heavy and light chains derived from the cMet antibody (h1332 (13.3.2L-A91T,H-42K,S97T)) and the EGFR antibody panitumumab. In some embodiments, polypeptide derived from cMet antibody is in the upper domain and polypeptide derived from EGFR antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is cMet, and antigen B is EGFR. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is cMet, and antigen A is EGFR. In some embodiments, polypeptide derived from cMet antibody is in the lower domain and polypeptide derived from EGFR antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is EGFR, and antigen B is cMet. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is EGFR, and antigen A is cMet.

In one embodiment, the binding proteins of the present invention bind cMet and EGFR and comprise a first polypeptide chain comprising, consisting essentially of, or consisting of an amino acid sequence according to SEQ ID NO: 102; a second polypeptide chain comprising, consisting essentially of, or consisting of an amino acid sequence according to SEQ ID NO: 103; and a third polypeptide chain comprising, consisting essentially of, or consisting of an amino acid sequence according to SEQ ID NO: 104.

In one embodiment, the binding protein of the present invention is capable of binding the same epitope of cMet and the same epitope of EGFR as that of bispecific binding protein FIT013a, wherein the bispecific binding protein FIT013a comprises a first polypeptide chain comprising an amino acid sequence of SEQ ID NO: 240; a second polypeptide chain comprising an amino acid sequence of SEQ ID NO: 249; and a third polypeptide chain comprising an amino acid sequence of SEQ ID NO: 254.

In one embodiment, the binding proteins of the present invention bind cMet and EGFR and comprise a $VL_A$ on the first polypeptide, wherein the $VL_A$ of the first polypeptide comprises a $VL_A$ CDR1 of SEQ ID NO: 242, a $VL_A$ CDR2 of SEQ ID NO: 243, and a $VL_A$ CDR3 of SEQ ID NO: 244.

In one embodiment, the binding proteins of the present invention bind cMet and EGFR and comprise a $VH_B$ on the first polypeptide, wherein the $VH_B$ of the first polypeptide comprises a $VH_B$ CDR1 of SEQ ID NO: 246, a $VH_B$ CDR2 of SEQ ID NO: 247, and a $VH_B$ CDR3 of SEQ ID NO: 248.

In one embodiment, the binding proteins of the present invention bind cMet and EGFR and comprise a $VH_A$ on the second polypeptide, wherein the $VH_A$ of the second polypeptide comprises a $VH_A$ CDR1 of SEQ ID NO: 251, a $VH_A$ CDR2 of SEQ ID NO: 252, and a $VH_A$ CDR3 of SEQ ID NO: 253.

In one embodiment, the binding proteins of the present invention bind cMet and EGFR and comprise a $VL_B$ on the third polypeptide, wherein the $VL_B$ of the third polypeptide comprises a $VL_B$ CDR1 of SEQ ID NO: 256, a $VL_B$ CDR2 of SEQ ID NO: 257, and a $VL_B$ CDR3 of SEQ ID NO: 258.

In one embodiment, the binding proteins of the present invention bind cMet and EGFR and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 242, a $VL_A$ CDR2 of SEQ ID NO: 243, and a $VL_A$ CDR3 of SEQ ID NO: 244; wherein the $VH_B$ of the first polypeptide comprises a $VH_B$ CDR1 of SEQ ID NO: 246, a $VH_B$ CDR2 of SEQ ID NO: 247, and a $VH_B$ CDR3 of SEQ ID NO: 248; wherein the $VH_A$ of the second polypeptide comprises a $VH_A$ CDR1 of SEQ ID NO: 251, a $VH_A$ CDR2 of SEQ ID NO: 252, and a $VH_A$ CDR3 of SEQ ID NO: 253; wherein the $VL_B$ of the third polypeptide comprises a $VL_B$ CDR1 of SEQ ID NO: 256, a $VL_B$ CDR2 of SEQ ID NO: 257, and a $VL_B$ CDR3 of SEQ ID NO: 258.

In one embodiment, the binding proteins of the present invention bind cMet and EGFR and comprise a first polypeptide chain comprising a $VL_A$ having the sequence of SEQ ID NO: 241, and a $VH_B$ having the sequence of SEQ ID NO: 245, wherein the binding protein comprises a second polypeptide chain comprising a $VH_A$ having the sequence of SEQ ID NO: 250, and wherein the binding protein comprises a third polypeptide chain comprising a $VL_B$ having the sequence of SEQ ID NO: 255.

In one embodiment, the binding proteins of the present invention bind cMet and EGFR and comprising, consisting essentially of, or consisting of a first polypeptide chain comprising an amino acid sequence of SEQ ID NO: 240; a second polypeptide chain comprising an amino acid sequence of SEQ ID NO: 249; and a third polypeptide chain comprising an amino acid sequence of SEQ ID NO: 254.

In one embodiment, the binding proteins of the present invention bind cMet and EGFR, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding Factor IXa and Factor X. The binding proteins of the present invention, in one embodiment, are capable of binding Factor IXa and Factor X and comprise variable heavy and light chains derived from an anti-Factor IXa antibody and variable light and heavy chains derived from an anti-Factor X antibody. In some embodiments, polypeptide derived from Factor IXa antibody is in the upper domain and polypeptide derived from Factor X antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is Factor IXa, and antigen B is Factor X. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is Factor IXa, and antigen A is Factor X. In some embodiments, polypeptide derived from Factor IXa antibody is in the lower domain and polypeptide derived from Factor X antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is Factor X, and antigen B is Factor IXa. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is Factor X, and antigen A is Factor IXa.

In one embodiment, the binding proteins of the present invention bind Factor IXa and Factor X and comprise a first polypeptide chain comprising, consisting essentially of, or consisting of an amino acid sequence according to SEQ ID NO: 105; a second polypeptide chain comprising, consisting essentially of, or consisting of an amino acid sequence according to SEQ ID NO: 106; and a third polypeptide chain comprising, consisting essentially of, or consisting of an amino acid sequence according to SEQ ID NO: 107.

In one embodiment, the binding protein of the present invention is capable of binding the same epitope of Factor IXa and the same epitope of Factor X as that of bispecific binding protein FIT014a, wherein the bispecific binding protein FIT014a comprises a first polypeptide chain comprising an amino acid sequence of SEQ ID NO: 259; a second polypeptide chain comprising an amino acid sequence of SEQ ID NO: 268; and a third polypeptide chain comprising an amino acid sequence of SEQ ID NO: 273.

In one embodiment, the binding proteins of the present invention bind Factor IXa and Factor X and comprise a $VL_A$ on the first polypeptide, wherein the $VL_A$ of the first polypeptide comprises a $VL_A$ CDR1 of SEQ ID NO: 261, a $VL_A$ CDR2 of SEQ ID NO: 262, and a $VL_A$ CDR3 of SEQ ID NO: 263.

In one embodiment, the binding proteins of the present invention bind Factor IXa and Factor X and comprise a $VH_B$ on the first polypeptide, wherein the $VH_B$ of the first polypeptide comprises a $VH_B$ CDR1 of SEQ ID NO: 265, a $VH_B$ CDR2 of SEQ ID NO: 266, and a $VH_B$ CDR3 of SEQ ID NO: 267.

In one embodiment, the binding proteins of the present invention bind Factor IXa and Factor X and comprise a $VH_A$ on the second polypeptide, wherein the $VH_A$ of the second polypeptide comprises a $VH_A$ CDR1 of SEQ ID NO: 270, a $VH_A$ CDR2 of SEQ ID NO: 271, and a $VH_A$ CDR3 of SEQ ID NO: 272.

In one embodiment, the binding proteins of the present invention bind Factor IXa and Factor X and comprise a $VL_B$ on the third polypeptide, wherein the $VL_B$ of the third polypeptide comprises a $VL_B$ CDR1 of SEQ ID NO: 275, a $VL_B$ CDR2 of SEQ ID NO: 276, and a $VL_B$ CDR3 of SEQ ID NO: 277.

In one embodiment, the binding proteins of the present invention bind Factor IXa and Factor X and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 261, a $VL_A$ CDR2 of SEQ ID NO: 262, and a $VL_A$ CDR3 of SEQ ID NO: 263; wherein the $VH_B$ of the first polypeptide comprises a $VH_B$ CDR1 of SEQ ID NO: 265, a $VH_B$ CDR2 of SEQ ID NO: 266, and a $VH_B$ CDR3 of SEQ ID NO: 267; wherein the $VH_A$ of the second polypeptide comprises a $VH_A$ CDR1 of SEQ ID NO: 270, a $VH_A$ CDR2 of SEQ ID NO: 271, and a $VH_A$ CDR3 of SEQ ID NO: 272; and wherein the $VL_B$ of the third polypeptide comprises a $VL_B$ CDR1 of SEQ ID NO: 275, a $VL_B$ CDR2 of SEQ ID NO: 276, and a $VL_B$ CDR3 of SEQ ID NO: 277.

In one embodiment, the binding proteins of the present invention bind Factor IXa and Factor X and comprise a first polypeptide chain comprising a $VL_A$ having the sequence of SEQ ID NO: 260, and a $VH_B$ having the sequence of SEQ ID NO: 264, wherein the binding protein comprises a second polypeptide chain comprising a $VH_A$ having the sequence of SEQ ID NO: 269, and wherein the binding protein comprises a third polypeptide chain comprising a $VL_B$ having the sequence of SEQ ID NO: 274.

In one embodiment, the binding proteins of the present invention bind Factor IXa and Factor X and comprising, consisting essentially of, or consisting of a first polypeptide chain comprising an amino acid sequence of SEQ ID NO: 259; a second polypeptide chain comprising an amino acid sequence of SEQ ID NO: 268; and a third polypeptide chain comprising an amino acid sequence of SEQ ID NO: 273.

In one embodiment, the binding proteins of the present invention bind Factor IXa and Factor X, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding Her3 and IGF-1R. The binding proteins of the present invention, in one embodiment, are capable of binding Her3 and IGF-1R and comprise variable heavy and light chains derived from the Her3 antibody patritumab and the IGF-1R antibody figitumumab. In some embodiments, polypeptide derived from Her3 antibody is in the upper domain and polypeptide derived from IGF-1R antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is Her3, and antigen B is IGF-1R. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is Her3, and antigen A is IGF-IR. In some embodiments, polypeptide derived from Her3 antibody is in the lower domain and polypeptide derived from IGF-1R antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is IGF-1R, and antigen B is Her3. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is IGF-1R, and antigen A is Her3.

In one embodiment, the binding proteins of the present invention bind Her3 and IGF-1R and comprise a first polypeptide chain comprising, consisting essentially of, or consisting of an amino acid sequence according to SEQ ID NO: 108; a second polypeptide chain comprising, consisting essentially of, or consisting of an amino acid sequence according to SEQ ID NO: 109; and a third polypeptide chain comprising, consisting essentially of, or consisting of an amino acid sequence according to SEQ ID NO: 110.

In one embodiment, the binding protein of the present invention is capable of binding the same epitope of Her3 and the same epitope of IGF-1R as that of bispecific binding protein FIT016a, wherein the bispecific binding protein FIT016a comprises a first polypeptide chain comprising an amino acid sequence of SEQ ID NO: 278; a second polypeptide chain comprising an amino acid sequence of SEQ ID NO: 287; and a third polypeptide chain comprising an amino acid sequence of SEQ ID NO: 292.

In one embodiment, the binding proteins of the present invention bind Her3 and IGF-1R and comprise a $VL_A$ on the first polypeptide, wherein the $VL_A$ of the first polypeptide comprises a $VL_A$ CDR1 of SEQ ID NO: 280, a $VL_A$ CDR2 of SEQ ID NO: 281, and a $VL_A$ CDR3 of SEQ ID NO: 282.

In one embodiment, the binding proteins of the present invention bind Her3 and IGF-1R and comprise a $VH_B$ on the first polypeptide, wherein the $VH_B$ of the first polypeptide comprises a $VH_B$ CDR1 of SEQ ID NO: 284, a $VH_B$ CDR2 of SEQ ID NO: 285, and a $VH_B$ CDR3 of SEQ ID NO: 286.

In one embodiment, the binding proteins of the present invention bind Her3 and IGF-1R and comprise a $VH_A$ on the second polypeptide, wherein the $VH_A$ of the second polypeptide comprises a $VH_A$ CDR1 of SEQ ID NO: 289, a $VH_A$ CDR2 of SEQ ID NO: 290, and a $VH_A$ CDR3 of SEQ ID NO: 291.

In one embodiment, the binding proteins of the present invention bind Her3 and IGF-1R and comprise a $VL_B$ on the third polypeptide, wherein the $VL_B$ of the third polypeptide comprises a $VL_B$ CDR1 of SEQ ID NO: 294, a $VL_B$ CDR2 of SEQ ID NO: 295, and a $VL_B$ CDR3 of SEQ ID NO: 296.

In one embodiment, the binding proteins of the present invention bind Her3 and IGF-1R and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 280, a $VL_A$ CDR2 of SEQ ID NO: 281, and a $VL_A$ CDR3 of SEQ ID NO: 282; wherein the $VH_B$ of the first polypeptide comprises a $VH_B$ CDR1 of SEQ ID NO: 284, a $VH_B$ CDR2 of SEQ ID NO: 285, and a $VH_B$ CDR3 of SEQ ID NO: 286; wherein the $VH_A$ of the second polypeptide comprises a $VH_A$ CDR1 of SEQ ID NO: 289, a $VH_A$ CDR2 of SEQ ID NO: 290, and a $VH_A$ CDR3 of SEQ ID NO: 291; wherein the $VL_B$ of the third polypeptide comprises a $VL_B$ CDR1 of SEQ ID NO: 294, a $VL_B$ CDR2 of SEQ ID NO: 295, and a $VL_B$ CDR3 of SEQ ID NO: 296.

In one embodiment, the binding proteins of the present invention bind Her3 and IGF-1R and comprise a first polypeptide chain comprising a $VL_A$ having the sequence of SEQ ID NO: 279, and a $VH_B$ having the sequence of SEQ ID NO: 283, wherein the binding protein comprises a second polypeptide chain comprising a $VH_A$ having the sequence of SEQ ID NO: 288, and wherein the binding protein comprises a third polypeptide chain comprising a $VL_B$ having the sequence of SEQ ID NO: 293.

In one embodiment, the binding proteins of the present invention bind Her3 and IGF-1R and comprising, consisting essentially of, or consisting of a first polypeptide chain comprising an amino acid sequence of SEQ ID NO: 278; a second polypeptide chain comprising an amino acid sequence of SEQ ID NO: 287; and a third polypeptide chain comprising an amino acid sequence of SEQ ID NO: 292.

In one embodiment, the binding proteins of the present invention bind Her3 and IGF-1R, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding DLL-4 and VEGF. The binding proteins of the present invention, in one embodiment, are capable of binding DLL-4 and VEGF and comprise variable heavy and light chains derived from the DLL-4 antibody demcizumab and the VEGF antibody bevicizumab. In some embodiments, polypeptide derived from DLL-4 antibody is in the upper domain and polypeptide derived from VEGF antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is DLL-4, and antigen B is VEGF. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is DLL-4, and antigen A is VEGF. In some embodiments, polypeptide derived from DLL-4 antibody is in the lower domain and polypeptide derived from VEGF antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is VEGF, and antigen B is DLL-4. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is VEGF, and antigen A is DLL-4.

In one embodiment, the binding proteins of the present invention bind DLL-4 and VEGF and comprise a first polypeptide chain comprising, consisting essentially of, or consisting of an amino acid sequence according to SEQ ID NO: 111; a second polypeptide chain comprising, consisting essentially of, or consisting of an amino acid sequence according to SEQ ID NO: 112; and a third polypeptide chain comprising, consisting essentially of, or consisting of an amino acid sequence according to SEQ ID NO: 113.

In one embodiment, the binding protein of the present invention is capable of binding the same epitope of DLL-4 and the same epitope of VEGF as that of bispecific binding protein FIT017a, wherein the bispecific binding protein FIT017a comprises a first polypeptide chain comprising an amino acid sequence of SEQ ID NO: 297; a second polypeptide chain comprising an amino acid sequence of SEQ ID NO: 306; and a third polypeptide chain comprising an amino acid sequence of SEQ ID NO: 311.

In one embodiment, the binding proteins of the present invention bind DLL-4 and VEGF and comprise a $VL_A$ on the first polypeptide, wherein the $VL_A$ of the first polypeptide comprises a $VL_A$ CDR1 of SEQ ID NO: 299, a $VL_A$ CDR2 of SEQ ID NO: 300, and a $VL_A$ CDR3 of SEQ ID NO: 301.

In one embodiment, the binding proteins of the present invention bind DLL-4 and VEGF and comprise a $VH_B$ on the first polypeptide, wherein the $VH_B$ of the first polypeptide comprises a $VH_B$ CDR1 of SEQ ID NO: 303, a $VH_B$ CDR2 of SEQ ID NO: 304, and a $VH_B$ CDR3 of SEQ ID NO: 305.

In one embodiment, the binding proteins of the present invention bind DLL-4 and VEGF and comprise a $VH_A$ on the second polypeptide, wherein the $VH_A$ of the second polypeptide comprises a $VH_A$ CDR1 of SEQ ID NO: 308, a $VH_A$ CDR2 of SEQ ID NO: 309, and a $VH_A$ CDR3 of SEQ ID NO: 310.

In one embodiment, the binding proteins of the present invention bind DLL-4 and VEGF and comprise a $VL_B$ on the third polypeptide, wherein the $VL_B$ of the third polypeptide comprises a $VL_B$ CDR1 of SEQ ID NO: 313, a $VL_B$ CDR2 of SEQ ID NO: 314, and a $VL_B$ CDR3 of SEQ ID NO: 315.

In one embodiment, the binding proteins of the present invention bind DLL-4 and VEGF and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 299, a $VL_A$ CDR2 of SEQ ID NO: 300, and a $VL_A$ CDR3 of SEQ ID NO: 301; wherein the $VH_B$ of the first polypeptide comprises a $VH_B$ CDR1 of SEQ ID NO: 303, a $VH_B$ CDR2 of SEQ ID NO: 304, and a $VH_B$ CDR3 of SEQ ID NO: 305; wherein the $VH_A$ of the second polypeptide comprises a $VH_A$ CDR1 of SEQ ID NO: 308, a $VH_A$ CDR2 of SEQ ID NO: 309, and a $VH_A$ CDR3 of SEQ ID NO: 310; and wherein the $VL_B$ of the third polypeptide comprises a $VL_B$ CDR1 of SEQ ID NO: 313, a $VL_B$ CDR2 of SEQ ID NO: 314, and a $VL_B$ CDR3 of SEQ ID NO: 315.

In one embodiment, the binding proteins of the present invention bind DLL-4 and VEGF and comprise a first polypeptide chain comprising a $VL_A$ having the sequence of SEQ ID NO: 298, and a $VH_B$ having the sequence of SEQ ID NO: 302, wherein the binding protein comprises a second polypeptide chain comprising a $VH_A$ having the sequence of SEQ ID NO: 307, and wherein the binding protein comprises a third polypeptide chain comprising a $VL_B$ having the sequence of SEQ ID NO: 312.

In one embodiment, the binding proteins of the present invention bind DLL-4 and VEGF and comprising, consisting essentially of, or consisting of a first polypeptide chain comprising an amino acid sequence of SEQ ID NO: 297; a second polypeptide chain comprising an amino acid sequence of SEQ ID NO: 306; and a third polypeptide chain comprising an amino acid sequence of SEQ ID NO: 311.

In one embodiment, the binding proteins of the present invention bind DLL-4 and VEGF, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding Her3 and EGFR. The binding proteins of the present invention, in one embodiment, are capable of binding Her3 and EGFR and comprise variable heavy and light chains derived from the Her3 antibody patritumab and the EGFR antibody panitumumab. In some embodiments, polypeptide derived from Her3 antibody is in the upper domain and polypeptide derived from EGFR antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is Her3, and antigen B is EGFR. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is Her3, and antigen A is EGFR. In some embodiments, polypeptide derived from Her3 antibody is in the lower domain and polypeptide derived from EGFR antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is EGFR, and antigen B is Her3. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is EGFR, and antigen A is Her3.

In one embodiment, the binding proteins of the present invention bind Her3 and EGFR and comprise a first polypeptide chain comprising, consisting essentially of, or consisting of an amino acid sequence according to SEQ ID NO: 117; a second polypeptide chain comprising, consisting essentially of, or consisting of an amino acid sequence according to SEQ ID NO: 118; and a third polypeptide chain comprising, consisting essentially of, or consisting of an amino acid sequence according to SEQ ID NO: 119.

In one embodiment, the binding protein of the present invention is capable of binding the same epitope of Her3 and the same epitope of EGFR as that of bispecific binding protein FIT019a, wherein the bispecific binding protein FIT019a comprises a first polypeptide chain comprising an amino acid sequence of SEQ ID NO: 335; a second polypeptide chain comprising an amino acid sequence of SEQ ID NO: 344; and a third polypeptide chain comprising an amino acid sequence of SEQ ID NO: 349. In one embodiment, the binding protein of the present invention is capable of binding the same epitope of Her3 and the same epitope of EGFR as that of bispecific binding protein FIT019b, wherein the bispecific binding protein FIT019b comprises a first polypeptide chain comprising an amino acid sequence of SEQ ID NO: 354; a second polypeptide chain comprising an amino acid sequence of SEQ ID NO: 363; and a third polypeptide chain comprising an amino acid sequence of SEQ ID NO: 368.

In one embodiment, the binding proteins of the present invention bind Her3 and EGFR and comprise a $VL_A$ on the first polypeptide, wherein the $VL_A$ of the first polypeptide comprises a $VL_A$ CDR1 of SEQ ID NO: 337, a $VL_A$ CDR2 of SEQ ID NO: 338, and a $VL_A$ CDR3 of SEQ ID NO: 339 (e.g., those on FIT019a). In one embodiment, the binding proteins of the present invention bind Her3 and EGFR and comprise a $VL_A$ on the first polypeptide, wherein the $VL_A$ of the first polypeptide comprises a $VL_A$ CDR1 of SEQ ID NO: 356, a $VL_A$ CDR2 of SEQ ID NO: 357, and a $VL_A$ CDR3 of SEQ ID NO: 358 (e.g., those on FIT019b).

In one embodiment, the binding proteins of the present invention bind Her3 and EGFR and comprise a $VH_B$ on the first polypeptide, wherein the $VH_B$ of the first polypeptide comprises a $VH_B$ CDR1 of SEQ ID NO: 341, a $VH_B$ CDR2 of SEQ ID NO: 342, and a $VH_B$ CDR3 of SEQ ID NO: 343 (e.g., those on FIT019a). In one embodiment, the binding proteins of the present invention bind Her3 and EGFR and comprise a $VH_B$ on the first polypeptide, wherein the $VH_B$ of the first polypeptide comprises a $VH_B$ CDR1 of SEQ ID NO: 360, a $VH_B$ CDR2 of SEQ ID NO: 361, and a $VH_B$ CDR3 of SEQ ID NO: 362 (e.g., those on FIT019b).

In one embodiment, the binding proteins of the present invention bind Her3 and EGFR and comprise a $VH_A$ on the second polypeptide, wherein the $VH_A$ of the second polypeptide comprises a $VH_A$ CDR1 of SEQ ID NO: 346, a $VH_A$ CDR2 of SEQ ID NO: 347, and a $VH_A$ CDR3 of SEQ ID NO: 348 (e.g., those on FIT019a). In one embodiment, the binding proteins of the present invention bind Her3 and EGFR and comprise a $VH_A$ on the second polypeptide, wherein the $VH_A$ of the second polypeptide comprises a $VH_A$ CDR1 of SEQ ID NO: 365, a $VH_A$ CDR2 of SEQ ID NO: 366, and a $VH_A$ CDR3 of SEQ ID NO: 367 (e.g., those on FIT019b).

In one embodiment, the binding proteins of the present invention bind Her3 and EGFR and comprise a $VL_B$ on the third polypeptide, wherein the $VL_B$ of the third polypeptide comprises a $VL_B$ CDR1 of SEQ ID NO: 351, a $VL_B$ CDR2 of SEQ ID NO: 352, and a $VL_B$ CDR3 of SEQ ID NO: 353 (e.g., those on FIT019a). In one embodiment, the binding proteins of the present invention bind Her3 and EGFR and comprise a $VL_B$ on the third polypeptide, wherein the $VL_B$ of the third polypeptide comprises a $VL_B$ CDR1 of SEQ ID NO: 370, a $VL_B$ CDR2 of SEQ ID NO: 371, and a $VL_B$ CDR3 of SEQ ID NO: 372 (e.g., those on FIT019b).

In one embodiment, the binding proteins of the present invention bind Her3 and EGFR and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 337, a $VL_A$ CDR2 of SEQ ID NO: 338, and a $VL_A$ CDR3 of SEQ ID NO: 339; wherein the $VH_B$ of the first polypeptide comprises a $VH_B$ CDR1 of SEQ ID NO: 341, a $VH_B$ CDR2 of SEQ ID NO: 342, and a $VH_B$ CDR3 of SEQ ID NO: 343; wherein the $VH_A$ of the second polypeptide comprises a $VH_A$ CDR1 of SEQ ID NO: 346, a $VH_A$ CDR2 of SEQ ID NO: 347, and a $VH_A$ CDR3 of SEQ ID NO: 348; and wherein the $VL_B$ of the third polypeptide comprises a $VL_B$ CDR1 of SEQ ID NO: 351, a $VL_B$ CDR2 of SEQ ID NO: 352, and a $VL_B$ CDR3 of SEQ ID NO: 353 (e.g., those on FIT019a).

In one embodiment, the binding proteins of the present invention bind Her3 and EGFR and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 356, a $VL_A$ CDR2 of SEQ ID NO: 357, and a $VL_A$ CDR3 of SEQ ID NO: 358; wherein the $VH_B$ of the first polypeptide comprises a $VH_B$ CDR1 of SEQ ID NO: 360, a $VH_B$ CDR2 of SEQ ID NO: 361, and a $VH_B$ CDR3 of SEQ ID NO: 362; wherein the $VH_A$ of the second polypeptide comprises a $VH_A$ CDR1 of SEQ ID NO: 365, a $VH_A$ CDR2 of SEQ ID NO: 366, and a $VH_A$ CDR3 of SEQ ID NO: 367; and wherein the $VL_B$ of the third polypeptide comprises a $VL_B$ CDR1 of SEQ ID NO: 370, a $VL_B$ CDR2 of SEQ ID NO: 371, and a $VL_B$ CDR3 of SEQ ID NO: 372 (e.g., those on FIT019b).

In one embodiment, the binding proteins of the present invention bind Her3 and EGFR and comprises a first polypeptide chain comprising a $VL_A$ having the sequence of SEQ ID NO: 336, and a $VH_B$ having the sequence of SEQ ID NO: 340, wherein the binding protein comprises a second polypeptide chain comprising a $VH_A$ having the sequence of SEQ ID NO: 345, and wherein the binding protein comprises a third polypeptide chain comprising a $VL_B$ having the sequence of SEQ ID NO: 350 (e.g., those on FIT019a). In one embodiment, the binding proteins of the present invention bind Her3 and EGFR and comprises a first polypeptide chain comprising a $VL_A$ having the sequence of SEQ ID NO: 355, and a $VH_B$ having the sequence of SEQ ID NO: 359, wherein the binding protein comprises a second polypeptide chain comprising a $VH_A$ having the sequence of SEQ ID NO: 364, and wherein the binding protein comprises a third polypeptide chain comprising a $VL_B$ having the sequence of SEQ ID NO: 369 (e.g., those on FIT019b).

In one embodiment, the binding proteins of the present invention bind Her3 and EGFR and comprising, consisting essentially of, or consisting of a first polypeptide chain comprising an amino acid sequence of SEQ ID NO: 335; a second polypeptide chain comprising an amino acid sequence of SEQ ID NO: 344; and a third polypeptide chain comprising an amino acid sequence of SEQ ID NO: 349 (e.g., those on FIT019a). In one embodiment, the binding proteins of the present invention bind Her3 and EGFR and comprising, consisting essentially of, or consisting of a first polypeptide chain comprising an amino acid sequence of SEQ ID NO: 354; a second polypeptide chain comprising an amino acid sequence of SEQ ID NO: 363; and a third polypeptide chain comprising an amino acid sequence of SEQ ID NO: 368 (e.g., those on FIT019b).

In one embodiment, the binding proteins of the present invention bind Her3 and EGFR, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding PD-1 and PD-L1. The binding proteins of the present invention, in one embodiment, are capable of binding PD-1 and PD-L1 and comprise variable heavy and light chains derived from the PD-1 antibody nivolumab and the PD-L1 antibody 1B12. In some embodiments, polypeptide derived from PD-1 antibody is in the upper domain and polypeptide derived from PD-L1 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-1, and antigen B is PD-L1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-1, and antigen A is PD-L1. In some embodiments, polypeptide derived from PD-1 antibody is in the lower domain and polypeptide derived from PD-L1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-L1, and antigen B is PD-1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-L1, and antigen A is PD-1.

In one embodiment, the binding proteins of the present invention bind PD-1 and PD-L1 and comprise a first polypeptide chain comprising, consisting essentially of, or consisting of an amino acid sequence according to SEQ ID NO: 120; a second polypeptide chain comprising, consisting essentially of, or consisting of an amino acid sequence according to SEQ ID NO: 121; and a third polypeptide chain comprising, consisting essentially of, or consisting of an amino acid sequence according to SEQ ID NO: 122.

In one embodiment, the binding protein of the present invention is capable of binding the same epitope of PD-1 and the same epitope of PD-L1 as that of bispecific binding protein FIT020a, wherein the bispecific binding protein FIT020a comprises a first polypeptide chain comprising an amino acid sequence of SEQ ID NO: 120; a second polypeptide chain comprising an amino acid sequence of SEQ ID NO: 121; and a third polypeptide chain comprising an amino acid sequence of SEQ ID NO: 122.

In one embodiment, the binding protein of the present invention is capable of binding the same epitope of PD-1 and the same epitope of PD-L1 as that of bispecific binding protein FIT020b, wherein the bispecific binding protein FIT020b comprises a first polypeptide chain comprising an amino acid sequence of SEQ ID NO: 297; a second polypeptide chain comprising an amino acid sequence of SEQ ID NO: 306; and a third polypeptide chain comprising an amino acid sequence of SEQ ID NO: 311.

In one embodiment, the binding proteins of the present invention bind PD-1 and PD-L1 and comprise a $VL_A$ on the first polypeptide, wherein the $VL_A$ of the first polypeptide comprises a $VL_A$ CDR1 of SEQ ID NO: 389, a $VL_A$ CDR2 of SEQ ID NO: 390, and a $VL_A$ CDR3 of SEQ ID NO: 391 (e.g., those on FIT020a).

In one embodiment, the binding proteins of the present invention bind PD-1 and PD-L1 and comprise a $VL_A$ CDR1 of SEQ ID NO: 375, a $VL_A$ CDR2 of SEQ ID NO: 376, and a $VL_A$ CDR3 of SEQ ID NO: 377 (e.g., those on FIT020b).

In one embodiment, the binding proteins of the present invention bind PD-1 and PD-L1 and comprise a $VH_B$ on the first polypeptide, wherein the $VH_B$ of the first polypeptide comprises a $VH_B$ CDR1 of SEQ ID NO: 384, a $VH_B$ CDR2 of SEQ ID NO: 385, and a $VH_B$ CDR3 of SEQ ID NO: 386 (e.g., those on FIT020a).

In one embodiment, the binding proteins of the present invention bind PD-1 and PD-L1 and comprise a $VH_B$ CDR1 of SEQ ID NO: 379, a $VH_B$ CDR2 of SEQ ID NO: 380, and a $VH_B$ CDR3 of SEQ ID NO: 381 (e.g., those on FIT020b).

In one embodiment, the binding proteins of the present invention bind PD-1 and PD-L1 and comprise a $VH_A$ on the second polypeptide, wherein the $VH_A$ of the second polypeptide comprises a $VH_A$ CDR1 of SEQ ID NO: 379, a $VH_A$ CDR2 of SEQ ID NO: 380, and a $VH_A$ CDR3 of SEQ ID NO: 381 (e.g., those on FIT020a).

In one embodiment, the binding proteins of the present invention bind PD-1 and PD-L1 and comprise a $VH_A$ on the second polypeptide, wherein the $VH_A$ of the second polypeptide comprises a $VH_A$ CDR1 of SEQ ID NO: 384, a $VH_A$ CDR2 of SEQ ID NO: 385, and a $VH_A$ CDR3 of SEQ ID NO: 386 (e.g., those on FIT020b).

In one embodiment, the binding proteins of the present invention bind PD-1 and PD-L1 and comprise a $VL_B$ on the third polypeptide, wherein the $VL_B$ of the third polypeptide comprises a $VL_B$ CDR1 of SEQ ID NO: 375, a $VL_B$ CDR2 of SEQ ID NO: 376, and a $VL_B$ CDR3 of SEQ ID NO: 377 (e.g., those on FIT020a).

In one embodiment, the binding proteins of the present invention bind PD-1 and PD-L1 and comprise a $VL_B$ on the third polypeptide, wherein the $VL_B$ of the third polypeptide comprises a $VL_B$ CDR1 of SEQ ID NO: 389, a $VL_B$ CDR2 of SEQ ID NO: 390, and a $VL_B$ CDR3 of SEQ ID NO: 391 (e.g., those on FIT020b).

In one embodiment, the binding proteins of the present invention bind PD-1 and PD-L1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 389, a $VL_A$ CDR2 of SEQ ID NO: 390, and a $VL_A$ CDR3 of SEQ ID NO: 391; wherein the $VH_B$ of the first polypeptide comprises a $VH_B$ CDR1 of SEQ ID NO: 384, a $VH_B$ CDR2 of SEQ ID NO: 385, and a $VH_B$ CDR3 of SEQ ID NO: 386; wherein the $VH_A$ of the second polypeptide comprises a $VH_A$ CDR1 of SEQ ID NO: 379, a $VH_A$ CDR2 of SEQ ID NO: 380, and a $VH_A$ CDR3 of SEQ ID NO: 381; and wherein the $VL_B$ of the third polypeptide comprises a $VL_B$ CDR1 of SEQ ID NO: 375, a $VL_B$ CDR2 of SEQ ID NO: 376, and a $VL_B$ CDR3 of SEQ ID NO: 377 (e.g., those on FIT020a).

In one embodiment, the binding proteins of the present invention bind PD-1 and PD-L1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 375, a $VL_A$ CDR2 of SEQ ID NO: 376, and a $VL_A$ CDR3 of SEQ ID NO: 377; wherein the $VH_B$ of the first polypeptide comprises a $VH_B$ CDR1 of SEQ ID NO: 379, a $VH_B$ CDR2 of SEQ ID NO: 380, and a $VH_B$ CDR3 of SEQ ID NO: 381; wherein the $VH_A$ of the second polypeptide comprises a $VH_A$ CDR1 of SEQ ID NO: 384, a $VH_A$ CDR2 of SEQ ID NO: 385, and a $VH_A$ CDR3 of SEQ ID NO: 386; and wherein the $VL_B$ of the third polypeptide comprises a $VL_B$ CDR1 of SEQ ID NO: 389, a $VL_B$ CDR2 of SEQ ID NO: 390, and a $VL_B$ CDR3 of SEQ ID NO: 391 (e.g., those on FIT020b).

In one embodiment, the binding proteins of the present invention bind PD-1 and PD-L1 and comprise a first polypeptide chain comprising a $VL_A$ having the sequence of SEQ ID NO: 388, and a $VH_B$ having the sequence of SEQ ID NO: 383, wherein the binding protein comprises a second polypeptide chain comprising a $VH_A$ having the sequence of SEQ ID NO: 378, and wherein the binding protein comprises a third polypeptide chain comprising a $VL_B$ having the sequence of SEQ ID NO: 374 (e.g., those on FIT020a).

In one embodiment, the binding proteins of the present invention bind PD-1 and PD-L1 and comprise a first polypeptide chain comprising a $VL_A$ having the sequence of SEQ ID NO: 374, and a $VH_B$ having the sequence of SEQ ID NO: 378, wherein the binding protein comprises a second polypeptide chain comprising a $VH_A$ having the sequence of SEQ ID NO: 383, and wherein the binding protein comprises a third polypeptide chain comprising a $VL_B$ having the sequence of SEQ ID NO: 388 (e.g., those on FIT020b).

In one embodiment, the binding proteins of the present invention bind PD-1 and PD-L1 and comprising, consisting essentially of, or consisting of a first polypeptide chain comprising an amino acid sequence of SEQ ID NO: 120; a second polypeptide chain comprising an amino acid sequence of SEQ ID NO: 121; and a third polypeptide chain comprising an amino acid sequence of SEQ ID NO: 122 (e.g., those on FIT020a).

In one embodiment, the binding proteins of the present invention bind PD-1 and PD-L1 and comprising, consisting essentially of, or consisting of a first polypeptide chain comprising an amino acid sequence of SEQ ID NO: 373; a second polypeptide chain comprising an amino acid sequence of SEQ ID NO: 382; and a third polypeptide chain comprising an amino acid sequence of SEQ ID NO: 387 (e.g., those on FIT020b).

In one embodiment, the binding proteins of the present invention bind PD-1 and PD-L1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding Her3 and PD-1. The binding proteins of the present invention, in one embodiment, are capable of binding Her3 and PD-1 and comprise variable heavy and light chains derived from the Her3 antibody patritumab and the EGFR antibody nivolumab. In some embodiments, polypeptide derived from Her3 antibody is in the upper domain and polypeptide derived from PD-1 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is Her3, and antigen B is PD-1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is Her3, and antigen A is PD-1. In some embodiments, polypeptide derived from Her3 antibody is in the lower domain and polypeptide derived from PD-1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-1, and antigen B is Her3. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-1, and antigen A is Her3.

In one embodiment, the binding proteins of the present invention bind Her3 and PD-1 and comprise a first polypeptide chain comprising, consisting essentially of, or consisting of an amino acid sequence according to SEQ ID NO: 123; a second polypeptide chain comprising, consisting essentially of, or consisting of an amino acid sequence according to SEQ ID NO: 124; and a third polypeptide chain comprising, consisting essentially of, or consisting of an amino acid sequence according to SEQ ID NO: 125.

In one embodiment, the binding protein of the present invention is capable of binding the same epitope of Her3 and the same epitope of PD-1 as that of bispecific binding protein FIT022a, wherein the bispecific binding protein FIT022a comprises a first polypeptide chain comprising an amino acid sequence of SEQ ID NO: 411; a second polypeptide chain comprising an amino acid sequence of SEQ ID NO: 420; and a third polypeptide chain comprising an amino acid sequence of SEQ ID NO: 425.

In one embodiment, the binding proteins of the present invention bind Her3 and PD-1 and comprise a $VL_A$ on the first polypeptide, wherein the $VL_A$ of the first polypeptide comprises a $VL_A$ CDR1 of SEQ ID NO: 413, a $VL_A$ CDR2 of SEQ ID NO: 414, and a $VL_A$ CDR3 of SEQ ID NO: 415.

In one embodiment, the binding proteins of the present invention bind Her3 and PD-1 and comprise a $VH_B$ on the first polypeptide, wherein the $VH_B$ of the first polypeptide comprises a $VH_B$ CDR1 of SEQ ID NO: 417, a $VH_B$ CDR2 of SEQ ID NO: 418, and a $VH_B$ CDR3 of SEQ ID NO: 419.

In one embodiment, the binding proteins of the present invention bind Her3 and PD-1 and comprise a $VH_A$ on the second polypeptide, wherein the $VH_A$ of the second polypeptide comprises a $VH_A$ CDR1 of SEQ ID NO: 422, a $VH_A$ CDR2 of SEQ ID NO: 423, and a $VH_A$ CDR3 of SEQ ID NO: 424.

In one embodiment, the binding proteins of the present invention bind Her3 and PD-1 and comprise a $VL_B$ on the third polypeptide, wherein the $VL_B$ of the third polypeptide comprises a $VL_B$ CDR1 of SEQ ID NO: 427, a $VL_B$ CDR2 of SEQ ID NO: 428, and a $VL_B$ CDR3 of SEQ ID NO: 429.

In one embodiment, the binding proteins of the present invention bind Her3 and PD-1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 413, a $VL_A$ CDR2 of SEQ ID NO: 414, and a $VL_A$ CDR3 of SEQ ID NO: 415; wherein the $VH_B$ of the first polypeptide comprises a $VH_B$ CDR1 of SEQ ID NO: 417, a $VH_B$ CDR2 of SEQ ID NO: 418, and a $VH_B$ CDR3 of SEQ ID NO: 419; wherein the $VH_A$ of the second polypeptide comprises a $VH_A$ CDR1 of SEQ ID NO: 422, a $VH_A$ CDR2 of SEQ ID NO: 423, and a $VH_A$ CDR3 of SEQ ID NO: 424; and wherein the $VL_B$ of the third polypeptide comprises a $VL_B$ CDR1 of SEQ ID NO: 427, a $VL_B$ CDR2 of SEQ ID NO: 428, and a $VL_B$ CDR3 of SEQ ID NO: 429.

In one embodiment, the binding proteins of the present invention bind Her3 and PD-1 and comprise a first polypeptide chain comprising a $VL_A$ having the sequence of SEQ ID NO: 412, and a $VH_B$ having the sequence of SEQ ID NO: 416, wherein the binding protein comprises a second polypeptide chain comprising a $VH_A$ having the sequence of SEQ ID NO: 421, and wherein the binding protein comprises a third polypeptide chain comprising a $VL_B$ having the sequence of SEQ ID NO: 426.

In one embodiment, the binding proteins of the present invention bind Her3 and PD-1 and comprising, consisting essentially of, or consisting of a first polypeptide chain comprising an amino acid sequence of SEQ ID NO: 411; a second polypeptide chain comprising an amino acid sequence of SEQ ID NO: 420; and a third polypeptide chain comprising an amino acid sequence of SEQ ID NO: 425.

In one embodiment, the binding proteins of the present invention bind Her3 and PD-1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding cMet and PD-L1. The binding proteins of the present invention, in one embodiment, are capable of binding cMet and PD-L1 and comprise variable heavy and light chains derived from the cMet antibody h1332 and the PD-L1 antibody 1B12. In some embodiments, polypeptide derived from cMet antibody is in the upper domain and polypeptide derived from PD-L1 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is cMet, and antigen B is PD-L1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is cMet, and antigen A is PD-L1. In some embodiments, polypeptide derived from cMet antibody is in the lower domain and polypeptide derived from PD-L1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-L1, and antigen B is cMet. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-L1, and antigen A is cMet.

In one embodiment, the binding protein of the present invention is capable of binding the same epitope of cMet and the same epitope of PD-L1 as that of bispecific binding protein FIT023a, wherein the bispecific binding protein FIT023a comprises a first polypeptide chain comprising an amino acid sequence of SEQ ID NO: 430; a second polypeptide chain comprising an amino acid sequence of SEQ ID NO: 439; and a third polypeptide chain comprising an amino acid sequence of SEQ ID NO: 444.

In one embodiment, the binding proteins of the present invention bind cMet and PD-L1 and comprise a $VL_A$ on the first polypeptide, wherein the $VL_A$ of the first polypeptide comprises a $VL_A$ CDR1 of SEQ ID NO: 432, a $VL_A$ CDR2 of SEQ ID NO: 433, and a $VL_A$ CDR3 of SEQ ID NO: 434.

In one embodiment, the binding proteins of the present invention bind cMet and PD-L1 and comprise a $VH_B$ on the first polypeptide, wherein the $VH_B$ of the first polypeptide comprises a $VH_B$ CDR1 of SEQ ID NO: 436, a $VH_B$ CDR2 of SEQ ID NO: 437, and a $VH_B$ CDR3 of SEQ ID NO: 438.

In one embodiment, the binding proteins of the present invention bind cMet and PD-L1 and comprise a $VH_A$ on the second polypeptide, wherein the $VH_A$ of the second polypeptide comprises a $VH_A$ CDR1 of SEQ ID NO: 441, a $VH_A$ CDR2 of SEQ ID NO: 442, and a $VH_A$ CDR3 of SEQ ID NO: 443.

In one embodiment, the binding proteins of the present invention bind cMet and PD-L1 and comprise a $VL_B$ on the third polypeptide, wherein the $VL_B$ of the third polypeptide comprises a $VL_B$ CDR1 of SEQ ID NO: 446, a $VL_B$ CDR2 of SEQ ID NO: 447, and a $VL_B$ CDR3 of SEQ ID NO: 448.

In one embodiment, the binding proteins of the present invention bind cMet and PD-L1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 432, a $VL_A$ CDR2 of SEQ ID NO: 433, and a $VL_A$ CDR3 of SEQ ID NO: 434; wherein the $VH_B$ of the first polypeptide comprises a $VH_B$ CDR1 of SEQ ID NO: 436, a $VH_B$ CDR2 of SEQ ID NO: 437, and a $VH_B$ CDR3 of SEQ ID NO: 438; wherein the $VH_A$ of the second polypeptide comprises a $VH_A$ CDR1 of SEQ ID NO: 441, a $VH_A$ CDR2 of SEQ ID NO: 442, and a $VH_A$ CDR3 of SEQ ID NO: 443; and wherein the $VL_B$ of the third polypeptide comprises a $VL_B$ CDR1 of SEQ ID NO: 446, a $VL_B$ CDR2 of SEQ ID NO: 447, and a $VL_B$ CDR3 of SEQ ID NO: 448.

In one embodiment, the binding proteins of the present invention bind cMet and PD-L1 and comprise a first polypeptide chain comprising a $VL_A$ having the sequence of SEQ ID NO: 431, and a $VH_B$ having the sequence of SEQ ID NO: 435, wherein the binding protein comprises a second polypeptide chain comprising a $VH_A$ having the sequence of SEQ ID NO: 440, and wherein the binding protein comprises a third polypeptide chain comprising a $VL_B$ having the sequence of SEQ ID NO: 445.

In one embodiment, the binding proteins of the present invention bind cMet and PD-L1 and comprising, consisting essentially of, or consisting of a first polypeptide chain comprising an amino acid sequence of SEQ ID NO: 430; a second polypeptide chain comprising an amino acid sequence of SEQ ID NO: 439; and a third polypeptide chain comprising an amino acid sequence of SEQ ID NO: 444.

In one embodiment, the binding proteins of the present invention bind cMet and PD-L1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding BTLA and PD-1. The binding proteins of the present invention, in one embodiment, are capable of binding BTLA and PD-1 and comprise variable heavy and light chains derived from the BTLA antibody 6A5 and the PD-1 antibody Nivolumab. In some embodiments, polypeptide derived from BTLA antibody is in the upper domain and polypeptide derived from PD-1 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is BTLA, and antigen B is PD-1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is BTLA, and antigen A is PD-1. In some embodiments, polypeptide derived from BTLA antibody is in the lower domain and polypeptide derived from PD-1 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-1, and antigen B is BTLA. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-1, and antigen A is BTLA.

In one embodiment, the binding protein of the present invention is capable of binding the same epitope of BTLA and the same epitope of PD-1 as that of bispecific binding protein FIT024a, wherein the bispecific binding protein FIT024a comprises a first polypeptide chain comprising an amino acid sequence of SEQ ID NO: 449; a second polypeptide chain comprising an amino acid sequence of SEQ ID NO: 458; and a third polypeptide chain comprising an amino acid sequence of SEQ ID NO: 463.

In one embodiment, the binding protein of the present invention is capable of binding the same epitope of BTLA and the same epitope of PD-1 as that of bispecific binding protein FIT024b, wherein the bispecific binding protein FIT024b comprises a first polypeptide chain comprising an amino acid sequence of SEQ ID NO: 468; a second polypeptide chain comprising an amino acid sequence of SEQ ID NO: 477; and a third polypeptide chain comprising an amino acid sequence of SEQ ID NO: 482.

In one embodiment, the binding proteins of the present invention bind BTLA and PD-1 and comprise a $VL_A$ on the first polypeptide, wherein the $VL_A$ of the first polypeptide comprises a $VL_A$ CDR1 of SEQ ID NO: 451, a $VL_A$ CDR2 of SEQ ID NO: 452, and a $VL_A$ CDR3 of SEQ ID NO: 453 (e.g., those of FIT024a).

In one embodiment, the binding proteins of the present invention bind BTLA and PD-1 and comprise a $VL_A$ on the first polypeptide, wherein the $VL_A$ of the first polypeptide comprises a $VL_A$ CDR1 of SEQ ID NO: 470, a $VL_A$ CDR2 of SEQ ID NO: 471, and a $VL_A$ CDR3 of SEQ ID NO: 472 (e.g., those of FIT024b).

In one embodiment, the binding proteins of the present invention bind BTLA and PD-1 and comprise a $VH_B$ on the first polypeptide, wherein the $VH_B$ of the first polypeptide comprises a $VH_B$ CDR1 of SEQ ID NO: 455, a $VH_B$ CDR2 of SEQ ID NO: 456, and a $VH_B$ CDR3 of SEQ ID NO: 457 (e.g., those of FIT024a).

In one embodiment, the binding proteins of the present invention bind BTLA and PD-1 and comprise a $VH_B$ on the first polypeptide, wherein the $VH_B$ of the first polypeptide comprises a $VH_B$ CDR1 of SEQ ID NO: 474, a $VH_B$ CDR2 of SEQ ID NO: 475, and a $VH_B$ CDR3 of SEQ ID NO: 476 (e.g., those of FIT024b).

In one embodiment, the binding proteins of the present invention bind BTLA and PD-1 and comprise a $VH_A$ on the second polypeptide, wherein the $VH_A$ of the second polypeptide comprises a $VH_A$ CDR1 of SEQ ID NO: 460, a $VH_A$ CDR2 of SEQ ID NO: 461, and a $VH_A$ CDR3 of SEQ ID NO: 462 (e.g., those of FIT024a).

In one embodiment, the binding proteins of the present invention bind BTLA and PD-1 and comprise a $VH_A$ on the second polypeptide, wherein the $VH_A$ of the second polypeptide comprises a $VH_A$ CDR1 of SEQ ID NO: 479, a $VH_A$ CDR2 of SEQ ID NO: 480, and a $VH_A$ CDR3 of SEQ ID NO: 481 (e.g., those of FIT024b).

In one embodiment, the binding proteins of the present invention bind BTLA and PD-1 and comprise a $VL_B$ on the third polypeptide, wherein the $VL_B$ of the third polypeptide comprises a $VL_B$ CDR1 of SEQ ID NO: 465, a $VL_B$ CDR2 of SEQ ID NO: 466, and a $VL_B$ CDR3 of SEQ ID NO: 467 (e.g., those of FIT024a).

In one embodiment, the binding proteins of the present invention bind BTLA and PD-1 and comprise a $VL_B$ on the third polypeptide, wherein the $VL_B$ of the third polypeptide comprises a $VL_B$ CDR1 of SEQ ID NO: 484, a $VL_B$ CDR2 of SEQ ID NO: 485, and a $VL_B$ CDR3 of SEQ ID NO: 486 (e.g., those of FIT024b).

In one embodiment, the binding proteins of the present invention bind BTLA and PD-1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 451, a $VL_A$ CDR2 of SEQ ID NO: 452, and a $VL_A$ CDR3 of SEQ ID NO: 453; wherein the $VH_B$ of the first polypeptide comprises a $VH_B$ CDR1 of SEQ ID NO: 455, a $VH_B$ CDR2 of SEQ ID NO: 456, and a $VH_B$ CDR3 of SEQ ID NO: 457; wherein the $VH_A$ of the second polypeptide comprises a $VH_A$ CDR1 of SEQ ID NO: 460, a $VH_A$ CDR2 of SEQ ID NO: 461, and a $VH_A$ CDR3 of SEQ ID NO: 462; and wherein the $VL_B$ of the third polypeptide comprises a $VL_B$ CDR1 of SEQ ID NO: 465, a $VL_B$ CDR2 of SEQ ID NO: 466, and a $VL_B$ CDR3 of SEQ ID NO: 467 (e.g., those of FIT024a).

In one embodiment, the binding proteins of the present invention bind BTLA and PD-1 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 470, a $VL_A$ CDR2 of SEQ ID NO: 471, and a $VL_A$ CDR3 of SEQ ID NO: 472; wherein the $VH_B$ of the first polypeptide comprises a $VH_B$ CDR1 of SEQ ID NO: 474, a $VH_B$ CDR2 of SEQ ID NO: 475, and a $VH_B$ CDR3 of SEQ ID NO: 476; wherein the $VH_A$ of the second polypeptide comprises a $VH_A$ CDR1 of SEQ ID NO: 479, a $VH_A$ CDR2 of SEQ ID NO: 480, and a $VH_A$ CDR3 of SEQ ID NO: 481; and wherein the $VL_B$ of the third polypeptide comprises a $VL_B$ CDR1 of SEQ ID NO: 484, a $VL_B$ CDR2 of SEQ ID NO: 485, and a $VL_B$ CDR3 of SEQ ID NO: 486 (e.g., those of FIT024b).

In one embodiment, the binding proteins of the present invention bind BTLA and PD-1 and comprise a first polypeptide chain comprising a $VL_A$ having the sequence of SEQ ID NO: 450, and a $VH_B$ having the sequence of SEQ ID NO: 454, wherein the binding protein comprises a second polypeptide chain comprising a $VH_A$ having the sequence of SEQ ID NO: 459, and wherein the binding protein comprises a third polypeptide chain comprising a $VL_B$ having the sequence of SEQ ID NO: 464 (e.g., those of FIT024a).

In one embodiment, the binding proteins of the present invention bind BTLA and PD-1 and comprise a first polypeptide chain comprising a $VL_A$ having the sequence of SEQ ID NO: 469, and a $VH_B$ having the sequence of SEQ ID NO: 473, wherein the binding protein comprises a second polypeptide chain comprising a $VH_A$ having the sequence of SEQ ID NO: 478, and wherein the binding protein comprises a third polypeptide chain comprising a $VL_B$ having the sequence of SEQ ID NO: 483 (e.g., those of FIT024b).

In one embodiment, the binding proteins of the present invention bind BTLA and PD-1 and comprising, consisting essentially of, or consisting of a first polypeptide chain comprising an amino acid sequence of SEQ ID NO: 449; a second polypeptide chain comprising an amino acid sequence of SEQ ID NO: 458; and a third polypeptide chain comprising an amino acid sequence of SEQ ID NO: 463 (those of FIT024a).

In one embodiment, the binding proteins of the present invention bind BTLA and PD-1 and comprising, consisting essentially of, or consisting of a first polypeptide chain comprising an amino acid sequence of SEQ ID NO: 468; a second polypeptide chain comprising an amino acid sequence of SEQ ID NO: 477; and a third polypeptide chain comprising an amino acid sequence of SEQ ID NO: 482 (those of FIT024b).

In one embodiment, the binding proteins of the present invention bind BTLA and PD-1, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding CD20 and CD22. The binding proteins of the present invention, in one embodiment, are capable of binding CD20 and CD22 and comprise variable heavy and light chains derived from the CD20 antibody Ofatumumab and the CD22 antibody Epratuzumab. In some embodiments, polypeptide derived from CD20 antibody is in the upper domain and polypeptide derived from CD22 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is CD20, and antigen B is CD22. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is CD20, and antigen A is CD22. In some embodiments, polypeptide derived from CD20 antibody is in the lower domain and polypeptide derived from CD22 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is CD22, and antigen B is CD20. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is CD22, and antigen A is CD20.

In one embodiment, the binding protein of the present invention is capable of binding the same epitope of CD20 and the same epitope of CD22 as that of bispecific binding protein FIT021b, wherein the bispecific binding protein FIT021b comprises a first polypeptide chain comprising an amino acid sequence of SEQ ID NO: 392; a second polypeptide chain comprising an amino acid sequence of SEQ ID NO: 401; and a third polypeptide chain comprising an amino acid sequence of SEQ ID NO: 406.

In one embodiment, the binding proteins of the present invention bind CD20 and CD22 and comprise a $VL_A$ on the first polypeptide, wherein the $VL_A$ of the first polypeptide comprises a $VL_A$ CDR1 of SEQ ID NO: 394, a $VL_A$ CDR2 of SEQ ID NO: 395, and a $VL_A$ CDR3 of SEQ ID NO: 396.

In one embodiment, the binding proteins of the present invention bind CD20 and CD22 and comprise a $VH_B$ on the first polypeptide, wherein the $VH_B$ of the first polypeptide comprises a $VH_B$ CDR1 of SEQ ID NO: 398, a $VH_B$ CDR2 of SEQ ID NO: 399, and a $VH_B$ CDR3 of SEQ ID NO: 400.

In one embodiment, the binding proteins of the present invention bind CD20 and CD22 and comprise a $VH_A$ on the second polypeptide, wherein the $VH_A$ of the second polypeptide comprises a $VH_A$ CDR1 of SEQ ID NO: 403, a $VH_A$ CDR2 of SEQ ID NO: 404, and a $VH_A$ CDR3 of SEQ ID NO: 405.

In one embodiment, the binding proteins of the present invention bind CD20 and CD22 and comprise a $VL_B$ on the third polypeptide, wherein the $VL_B$ of the third polypeptide comprises a $VL_B$ CDR1 of SEQ ID NO: 408, a $VL_B$ CDR2 of SEQ ID NO: 409, and a $VL_B$ CDR3 of SEQ ID NO: 410.

In one embodiment, the binding proteins of the present invention bind CD20 and CD22 and comprise a $VL_A$ and $VH_B$ on the first polypeptide, a $VH_A$ on the second polypeptide, and a $VL_B$ on the third polypeptide, wherein the $VL_A$ of the first polypeptide comprises a $VL_A$ CDR1 of SEQ ID NO: 394, a $VL_A$ CDR2 of SEQ ID NO: 395, and a $VL_A$ CDR3 of SEQ ID NO: 396; wherein the $VH_B$ of the first polypeptide comprises a $VH_B$ CDR1 of SEQ ID NO: 398, a $VH_B$ CDR2 of SEQ ID NO: 399, and a $VH_B$ CDR3 of SEQ ID NO: 400; wherein the $VH_A$ of the second polypeptide comprises a $VH_A$ CDR1 of SEQ ID NO: 403, a $VH_A$ CDR2 of SEQ ID NO: 404, and a $VH_A$ CDR3 of SEQ ID NO: 405; and wherein the $VL_B$ of the third polypeptide comprises a $VL_B$ CDR1 of SEQ ID NO: 408, a $VL_B$ CDR2 of SEQ ID NO: 409, and a $VL_B$ CDR3 of SEQ ID NO: 410.

In one embodiment, the binding proteins of the present invention bind CD20 and CD22 and comprise a first polypeptide chain comprising a $VL_A$ having the sequence of SEQ ID NO: 393, and a $VH_B$ having the sequence of SEQ ID NO: 397, wherein the binding protein comprises a second polypeptide chain comprising a $VH_A$ having the sequence of SEQ ID NO: 402, and wherein the binding protein comprises a third polypeptide chain comprising a $VL_B$ having the sequence of SEQ ID NO: 407.

In one embodiment, the binding proteins of the present invention bind CD20 and CD22 and comprising, consisting essentially of, or consisting of a first polypeptide chain comprising an amino acid sequence of SEQ ID NO: 392; a second polypeptide chain comprising an amino acid sequence of SEQ ID NO: 401; and a third polypeptide chain comprising an amino acid sequence of SEQ ID NO: 406.

In one embodiment, the binding proteins of the present invention bind CD20 and CD22, and are derived from binding proteins described herein by replacing 1, 2, 3, 4, 5, 6, 7, 8, 9, 10, 20, 30, 40, 50, 60, 70, 80, 90, 100, 110, 120, 130, 140, 150, 160, 170, 180, 190, 200, or more (inclusive of all values therebetween) amino acids with conservative amino acid substitution, while still maintaining equivalent activity as the corresponding binding proteins without the substitution(s).

In one embodiment, the binding proteins of the present invention are capable of binding PD-L1 and TIM3. In some embodiments, polypeptide derived from PD-L1 antibody is in the upper domain and polypeptide derived from TIM3 antibody is in the lower domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is PD-L1, and antigen B is TIM3. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is PD-L1, and antigen A is TIM3. In some embodiments, polypeptide derived from PD-L1 antibody is in the lower domain and polypeptide derived from TIM3 antibody is in the upper domain. For example, in some embodiments, the binding proteins comprise a first polypeptide of $VL_A$-CL-$VH_B$-CH1-Fc, a second polypeptide of $VH_A$-CH1, and a third polypeptide of $VL_B$-CL, wherein antigen A is TIM3, and antigen B is PD-L1. For another example, in some embodiments, the binding proteins comprise a first polypeptide of $VH_B$-CH1-$VL_A$-CL-Fc, a second polypeptide of $VL_B$-CL, and a third polypeptide of $VH_A$-CH1, wherein antigen B is TIM3, and antigen A is PD-L1.

In one embodiment, the binding protein is capable of binding one or more epitopes on one or more immune checkpoint protein on T cells such as, for example, TIM-3, Lag3, ICOS, BTLA, CD160, 2B4, KIR, CD137, CD27, OX40, CD40L, and A2aR. In another embodiment, the binding protein is capable of binding one or more epitopes on one or more tumor cell surface protein that is involved with immune checkpoint pathways, such as, for example, PD-L1, PD-L2, Galectin9, HVEM, CD48, B7-1, B7-2, ICOSL, B7-H3, B7-H4, CD137L, OX40L, CD70, and CD40.

In one aspect, the present invention provides pharmaceutical compositions comprising the binding proteins described herein. In one embodiment, provided herein are pharmaceutical compositions comprising the binding protein of any one of the preceding claims and one or more pharmaceutically acceptable carrier.

In another aspect, the present invention provides methods of treating or preventing an inflammatory disease, autoimmune disease, neurodegenerative disease, cancer, sepsis, or spinal cord injury in a subject in need thereof. In one embodiment, the method comprises administering to a subject an effective amount of one or more of the binding proteins provided herein, or one or more pharmaceutical compositions comprising the binding proteins provided herein and a pharmaceutically acceptable carrier. Uses of the binding proteins described herein in the manufacture of a medicament for treatment or prevention of an inflammatory disease, autoimmune disease, neurodegenerative disease, cancer, spinal cord injury, or other conditions are also provided herein. In one embodiment, the inflammatory disease, autoimmune disease, cancer, neurodegenerative disease, and other conditions include, but are not limited to, asthma, rheumatoid arthritis, systemic lupus erythematosus, multiple sclerosis, Alzheimer's disease, Parkinson's disease, infectious diseases and disorders, such as psoriasis, psoriatic arthritis, dermatitis, systemic sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, Raynaud's syndrome, Sjögren's syndrome, juvenile onset diabetes, Reiter's disease, Behçet's disease, immune complex nephritis, IgA nephropathy, IgM polyneuropathies, immune-mediated thrombocytopenias, such as acute idiopathic thrombocytopenic purpura and chronic idiopathic thrombocytopenic purpura, hemolytic anemia, myasthenia gravis, lupus nephritis, atopic dermatitis, pemphigus, Graves' disease, severe acute respiratory distress syndrome, choreoretinitis, Hashimoto's thyroiditis, Wegener's granulomatosis, Omenn's syndrome, chronic renal failure, acute infectious mononucleosis, HIV, herpes virus associated diseases, type 1 diabetes, graft versus host disease (GVHD); immune disorders associated with graft transplantation rejection; T cell lymphoma, T cell acute lymphoblastic leukemia, testicular angiocentric T cell lymphoma, benign lymphocytic angiitis, primary myxedema, pernicious anemia, autoimmune atrophic gastritis, Addison's disease, insulin dependent diabetes mellitis, good pasture's syndrome, sympathetic ophthalmia, idiopathic thrombocytopenia, primary biliary cirrhosis, chronic action hepatitis, ulceratis colitis, Sjogren's syndrome, rheumatoid arthritis, polymyositis, scleroderma, mixed connective tissue disease, pemphigus vulgaris, pemphigoid, ankylosing spondylitis, aplastic anemia, autoimmune hepatitis, coeliac disease, dermatomyositis, Goodpasture's syndrome, Guillain-Barre syndrome, idiopathic leucopenia, idiopathic thrombocytopenic purpura, male infertility, phacogenic uveitis, primary myxoedema, Reiter's syndrome, stiff man syndrome, thyrotoxicosis, ulcerative colitis, breast cancer, ovarian cancer, lung cancer, colorectal cancer, anal cancer, prostate cancer, kidney cancer, bladder cancer, head and neck cancer, pancreatic cancer, skin cancer, oral cancer, esophageal cancer, vaginal cancer, cervical cancer, cancer of the spleen, testicular cancer, cancer of the thymus, squamous cell carcinoma, small cell lung cancer, non-small cell lung cancer, blastoma, sarcom, adenocarcinoma of the lung, squamous cell carcinoma of the lung, peritoneal carcinoma, dermal cancer, dermal or intraocular melanoma, rectal cancer, perianal cancer, esophageal cancer, small intestine cancer, endocrine gland cancer, parathyroid cancer, adrenal gland cancer, soft tissue sarcoma, urethral cancer, male/female genital tract cancer, nerve cancer, chronic or acute leukemia, lymphocyte lymphoma, hepatoma, stomach cancer, glioblastoma, ovarian cancer, liver cancer, hepatic tumor, colon cancer, large intestine cancer, endometrial cancer, uterine cancer, salivary gland cancer, renal cancer, vulvar cancer, thyroid cancer, gestational diabetes, chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, septic shock, septicemia, hypotension, adult respiratory distress syndrome (ARDS), disseminated intravascular coagulopathy (DIC), sarcoidosis, arterial arteriosclerosis, peptic ulcers, burns, pancreatitis, polycystic ovarian disease (POD), endometriosis, uterine fibroid, benign prostate hypertrophy, T-cell acute lymphoblastic leukemia (T-ALL), cerebral autosomal dominant arteriopathy with subcortical infarcts and leukoencephalopathy (CADASIL), tetralogy of Fallot (TOF), Alagille syndrome (AS), macular degeneration and age-related macular degeneration diseases, inflammatory fibrosis (e.g., scleroderma, lung fibrosis, and cirrhosis), osteoarthritis, osteoporosis, asthma (including allergic asthma), allergies, chronic obstructive pulmonary disease (COPD), juvenile early-onset Type I diabetes, transplant rejection, and SLE.

In one embodiment, the present disclosure provides methods for treating or preventing rheumatoid arthritis, psoriasis, osteoporosis, stroke, liver disease, or oral cancer to a subject in need thereof, the method comprising administering to the subject a FIT-Ig binding protein described herein, wherein the binding protein is capable of binding IL-17 and IL-20. In a further embodiment, the FIT-Ig binding protein comprises an amino acid sequence selected from SEQ ID NOs: 15, 25, and 27; and amino acid sequence according to SEQ ID NO: 21; and an amino acid sequence according to SEQ ID NO: 23. In another embodiment, the FIT-Ig binding protein comprises an amino acid sequence selected from SEQ ID NOs: 15, 25, and 27; and an amino acid sequence selected from SEQ ID NOs: 29, 30 and 31.

In one embodiment, the present disclosure provides methods for treating or preventing a B cell cancer in a subject in need thereof, the method comprising administering to the subject a FIT-Ig binding protein, wherein the FIT-Ig binding protein is capable of binding one or more B cell antigen. In a further embodiment, the FIT-Ig binding protein is capable of binding CD20. In a further embodiment, the FIT-Ig binding protein is capable of binding CD20 and another antigen. In a further embodiment, the binding protein is capable of binding CD3 and CD20. In a further embodiment, the cancer is a B cell cancer. In a still further embodiment, the B cell cancer is selected from the group consisting of Hodgkin's lymphoma, non-Hodgkin's lymphoma [NHL], precursor B cell lymphoblastic leukemia/lymphoma, mature B cell neoplasms, B cell chronic lymphocytic leukemia/small lymphocytic lymphoma, B cell prolymphocytic leukemia, lymphoplasmacytic lymphoma, mantle cell lymphoma, follicular lymphoma, cutaneous follicle center lymphoma, marginal zone B cell lymphoma, hairy cell leukemia, diffuse large B cell lymphoma, Burkitt's lymphoma, plasmacytoma, plasma cell myeloma, post-transplant lymphoproliferative disorder, Waldenstrom's macroglobulinemia, and anaplastic large-cell lymphoma. In one embodiment, the present disclosure provides methods for treating or preventing a B cell cancer in a subject in need thereof, the method comprising administering to the subject a FIT-Ig binding protein, wherein the FIT-Ig binding protein comprises an amino acid sequence according to SEQ ID NOs: 41 or 48; and amino acid sequence according to SEQ ID NO: 44, and an amino acid sequence according to SEQ ID NO: 46.

In one embodiment, the present disclosure provides methods for treating or preventing an autoimmune disease, inflammatory disease, or infection in a subject in need thereof, the method comprising administering to the subject a FIT-Ig binding protein described herein, wherein the binding protein is capable of binding TNF and IL-17. In a further embodiment, the FIT-Ig binding protein comprises sequences according to SEQ ID NOs: 87, 89, and 91. In another embodiment, the present disclosure provides methods for treating or preventing an autoimmune or inflammatory disease, the method comprising administering to the subject a FIT-Ig binding protein, wherein the binding protein is capable of binding TNF and IL-17, and wherein the autoimmune or inflammatory disease is selected from the group consisting of Crohn's disease, psoriasis (including plaque psoriasis), arthritis (including rheumatoid arthritis, psoratic arthritis, osteoarthritis, or juvenile idiopathic arthritis), multiple sclerosis, ankylosing spondylitis, spondylosing arthropathy, systemic lupus erythematosus, uveitis, sepsis, neurodegenerative diseases, neuronal regeneration, spinal cord injury, primary and metastatic cancers, a respiratory disorder; asthma; allergic and nonallergic asthma; asthma due to infection; asthma due to infection with respiratory syncytial virus (RSV); chronic obstructive pulmonary disease (COPD); a condition involving airway inflammation; eosinophilia; fibrosis and excess mucus production; cystic fibrosis; pulmonary fibrosis; an atopic disorder; atopic dermatitis; urticaria; eczema; allergic rhinitis; allergic enterogastritis; an inflammatory and/or autoimmune condition of the skin; an inflammatory and/or autoimmune condition of gastrointestinal organs; inflammatory bowel diseases (IBD); ulcerative colitis; an inflammatory and/or autoimmune condition of the liver; liver cirrhosis; liver fibrosis; and liver fibrosis caused by hepatitis B and/or C virus; scleroderma. In another embodiment, In another embodiment, the present disclosure provides methods for treating or preventing cancer in a subject in need thereof, the method comprising administering to the subject a FIT-Ig binding protein described herein, wherein the binding protein is capable of binding TNF and IL-17. In a further embodiment, the cancer is hepatocellular carcinoma; glioblastoma; lymphoma; or Hodgkin's lymphoma. In another embodiment, the present disclosure provides methods for treating or preventing and infection in a subject in need thereof, the method comprising administering to the subject a FIT-Ig binding protein described herein, wherein the infection is a viral infection, a bacterial infection, a parasitic infection, HTLV-1 infection. In one embodiment, the present disclosure provides methods for suppression of expression of protective type 1 immune responses, and suppression of expression of a protective type 1 immune response during vaccination.

In one embodiment, the present disclosure provides methods for treating rheumatoid arthritis in a subject in need thereof, the method comprising administering to the subject a FIT-Ig binding protein, wherein the binding protein comprises sequences according to SEQ ID NOs: 87, 89, and 91.

In one embodiment, the present disclosure provides methods for treating or preventing cancer in a subject in need thereof, the method comprising administering to the subject a FIT-Ig binding protein described herein, wherein the binding protein is capable of binding CTLA-4 and PD-1. In a further embodiment, the FIT-Ig binding protein comprises an amino acid sequence comprising SEQ ID NOs: 92, 95, and 97. In another embodiment, the present disclosure provides methods for treating or preventing cancer in a subject in need thereof, wherein the binding protein is capable of binding CTLA-4 and PD-1, and wherein the cancer is a cancer typically responsive to immunotherapy. In another embodiment, the cancer is a cancer that has not been associated with immunotherapy. In another embodiment, the cancer is a cancer that is a refractory or recurring malignancy. In another embodiment, the binding protein inhibits the growth or survival of tumor cells. In another embodiment, the cancer is selected from the group consisting of melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies.

In one embodiment, the present disclosure provides methods for treating or preventing melanoma in a subject in need thereof, the method comprising administering to the subject a FIT-Ig binding protein described herein, wherein the binding protein is capable of binding CTLA-4 and PD-1. In a further embodiment, the present disclosure provides methods for treating or preventing melanoma in a subject in need thereof, wherein the method comprises administering to the subject a FIT-Ig binding protein comprising amino acid sequences according to SEQ ID NOs: 92, 95, and 97.

In another embodiment, the present disclosure provides methods for treating or preventing infections or infectious disease in a subject in need thereof, the method comprising administering to the subject a FIT-Ig binding protein described herein, wherein the binding protein is capable of binding CTLA-4 and PD-1. In one embodiment, the FIT-Ig binding protein is administered alone, or in combination with vaccines, to stimulate the immune response to pathogens, toxins, and self-antigens. Therefore, in one embodiment, the binding proteins provided herein can be used to stimulate immune response to viruses infectious to humans, such as, but not limited to, human immunodeficiency viruses, hepatitis viruses class A, B and C, Epstein Barr virus, human cytomegalovirus, human papilloma viruses, herpes viruses, bacteria, fungal parasites, or other pathogens.

BRIEF DESCRIPTION OF THE DRAWINGS

FIG. 3A shows the results of the Biacore binding assay in which FIT1-Ig was first saturated by IL-17, followed by IL-20. FIG. 3B shows the results of the Biacore assay in which FIT1-Ig was first saturated by IL-20, followed by IL-17.

FIG. 7*a*), FIT13a-Ig (cMet/EGFR; FIG. 7*b*), FIT14-Ig (Factor IXa/Factor X; FIG. 7*c*), FIT16a-Ig (Her3/IGF-1R; FIG. 7*d*), FIT17a-Ig (DLL-4/VEGF; FIG. 7*e*), FIT18a-Ig (CD20/CD3; FIG. 7*f*), FIT19a-Ig (Her3/EGFR; FIG. 7*g*), FIT20a-Ig (PD-1/PD-L1; FIG. 7*h*), and FIT22a-Ig (Her3/PD-1; FIG. 7*i*).

FIG. 18A (right panel) shows dual binding to MKN-45 cell as measured by a BD FACSVerse flow cytometer. FIG. 18A (left panel) indicates that in MKN-45 cell, membrane expression level c-Met is much higher than EGFR, so c-Met binding cite of FIT013a and FIT013a-Fab can be occupied by membrane c-Met, the free EGFR binding cite of FIT013a and FIT013a-Fab can be detected by biotinylated EGFR. FIG. 18B (right panel) shows dual binding to SGC-7901 cell as measured by a BD FACSVerse flow cytometer. FIG. 18B (left panel) indicates that in SGC-7901 cell, membrane expression level EGFR is much higher than c-Met, so EGFR binding cite of FIT013a and FIT013a-Fab can be occupied by membrane EGFR, the free c-Met binding cite of FIT013a and FIT013a-Fab can be detected by biotinylated c-Met. FIG. 18C (right panel) shows dual binding to NCI-H1975 cell as measured by a BD FACSVerse flow cytometer. FIG. 18C (left panel) indicates that in NCI-H1975 cell, membrane expression level c-Met is equal to EGFR, so c-Met and EGFR binding cites of FIT013a and FIT013a-Fab are occupied simultaneously, and no free EGFR or c-Met binding cite of FIT013a and FIT013a-Fab can be detected.

DETAILED DESCRIPTION

Figure 1A:
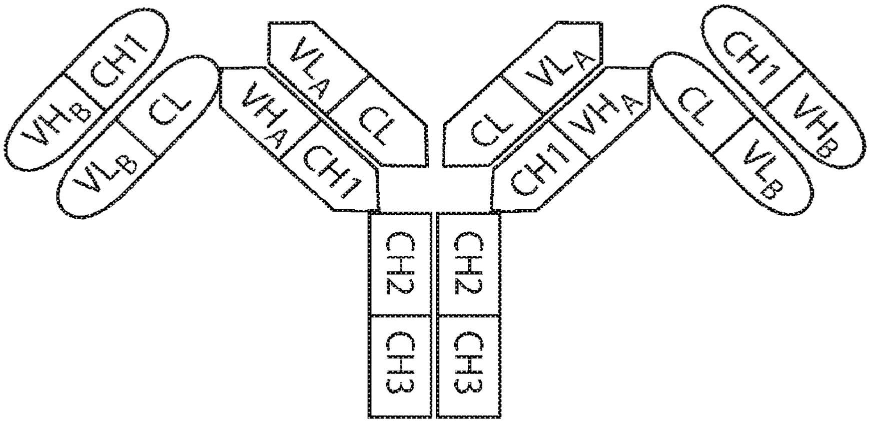
FIG. 1A shows the structure of FIT-Igs that are made up of three constructs, such as FIT1-Ig, FIT2-Ig, and FIT3-Ig.

The present invention relates to multivalent and multispecific binding proteins, methods of making the binding proteins, and to their uses in the prevention and/or treatment of acute and chronic inflammatory diseases and disorders, cancers, and other diseases. This invention pertains to multivalent and/or multispecific binding proteins capable of binding two or more antigens. Specifically, the invention relates to Fabs-in-tandem immunoglobulins (FIT-Ig), and pharmaceutical compositions thereof, as well as nucleic acids, recombinant expression vectors and host cells for making such FIT-Igs. Methods of using the FIT-Igs of the invention to detect specific antigens, either in vitro or in vivo are also encompassed by the invention.

The novel family of binding proteins provided herein are capable of binding two or more antigens, e.g., with high affinity. Specifically, the present invention provides an approach to construct a bispecific binding protein using 2 parental monoclonal antibodies: mAb A, which binds to antigen a; and mAb B, which binds to antigen b.

In one aspect, the present invention provides a binding protein comprising a variable light chain specific for a first antigen or epitope, a first light chain constant domain, a variable heavy chain specific for a second antigen or epitope, a first heavy chain CH1, a variable heavy chain specific for the first antigen or epitope, a second heavy chain CH1, a variable heavy chain specific for the second antigen or epitope, and a second light chain constant domain. In one embodiment, the binding protein further comprises an Fc region. The binding protein may further comprise one or more amino acid or polypeptide linker linking two or more of the components of the binding protein. For example, the binding protein may comprise a polypeptide linker linking the light chain variable region to the light chain constant region.

In one embodiment, the present disclosure provides a binding protein comprising a polypeptide chain comprising $VL_A$-CL-(X1)n-$VH_B$-CH1-(X2)n, wherein $VL_A$ is the light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1.

In one embodiment, the invention provides a binding protein comprising three different polypeptide chains (FIG. 1), wherein the first polypeptide chain (construct #1) comprises $VL_A$-CL-(X1)n-$VH_B$-CH1-(X2)n, wherein $VL_A$ is the light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain (construct #2) comprises $VH_A$-CH1, wherein $VH_A$ is the heavy chain variable domain of mAb A, and CH1 is the first constant domain of the heavy chain. The third polypeptide chain (construct #3) comprises $VL_B$-CL, wherein $VL_B$ is the light chain variable domain of mAb B, and CL is the constant domain of the light chain.

In another embodiment, the invention provides a binding protein comprising three different polypeptide chains with the overall molecular design similar to the previous embodiment except the order of the variable domains are reversed. In the embodiment the first polypeptide chain comprises $VH_B$-CH1-(X1)n-$VL_A$-CL-(X2)n, wherein $VL_A$ is a light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain comprises $VH_A$-CH1, wherein $VH_A$ is the heavy chain variable domain of mAb A and CH1 is the first constant domain of the heavy chain. The third polypeptide chain comprises $VL_B$-CL, wherein $VL_B$ is the light chain variable domain of mAb B and CL is the constant domain of the light chain.

In another embodiment the invention provides a binding protein comprising two different polypeptide chains (FIG. 2), wherein the first polypeptide chain (construct #1) comprises $VL_A$-CL-(X1)n-$VH_B$-CH1-(X2)n, wherein $VL_A$ is a light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain (construct #4) comprises $VH_A$-CH1-(X3)n-$VL_B$-CL, wherein $VH_A$ is the heavy chain variable domain of mAb A, CH1 is the first constant domain of the heavy chain, X3 represents an amino acid or polypeptide that is not a constant domain, n is 0 or 1, $VL_B$ is the light chain variable domain of mAb B, and CL is the constant domain of the light chain.

In another embodiment the invention provides a binding protein comprising two polypeptide chains with the overall molecular design similar to the previous embodiment except the order of the variable domains are reversed. In this embodiment the first polypeptide chain comprises $VH_B$-CH1-(X1)n-$VL_A$-CL-(X2)n, wherein $VL_A$ is a light chain variable domain of mAb A, CL is a light chain constant domain, X1 represents an amino acid or an oligopeptide linker, $VH_B$ is the heavy chain variable domain of mAb B, CH1 is the first constant domain of the heavy chain, X2 represents an Fc region or a different dimerization domain, and n is 0 or 1. The second polypeptide chain comprises $VL_B$-CL-(X3)n-$VH_A$-CH1, wherein $VH_A$ is the heavy chain variable domain of mAb A, CH1 is the first constant domain of the heavy chain, X3 represents an amino acid or an oligopeptide linker, n is 0 or 1, $VL_B$ is the light chain variable domain of mAb B, and CL is the constant domain of the light chain.

In one embodiment, the VH and VL domains in the binding protein are selected from the group consisting of murine heavy/light chain variable domains, fully human heavy/light chain variable domains, CDR grafted heavy/light chain variable domains, humanized heavy/light chain variable domains, and mixtures thereof. In a preferred embodiment $VH_A/VL_A$ and $VH_B/VL_B$ are capable of binding the same antigen. In another embodiment $VH_A/VL_A$ and $VH_B/VL_B$ are capable of binding different antigens.

In one embodiment, the first polypeptide chain comprises $VL_A$-CL-$VH_B$-CH1-Fc, and the CL and $VH_B$ of the first polypeptide chain are directly fused together. In another embodiment, the CL and $VH_B$ are linked by an amino acid or an oligopeptide linker. In another embodiment, the first polypeptide chain comprises $VH_B$-CH1-$VL_A$-CL-Fc, and the CH1 and $VL_A$ are directly fused together. In another embodiment, the CH1 and $VL_A$ are linked by an amino acid or an oligopeptide linker. In a further embodiment, the oligo- or poly-peptide linker comprises 1 or more amino acids of any reasonable sequence that provides flexibility. Preferably the linker is selected from the group consisting of G, GS, SG, GGS, GSG, SGG, GGG, GGGS (SEQ ID NO: 489), SGGG (SEQ ID NO: 490), GGGGS (SEQ ID NO: 491), GGGGSGS (SEQ ID NO: 492), GGGGSGGS (SEQ ID NO: 493), GGGGSGGGGS (SEQ ID NO: 494), GGGGSGGGGSGGGGS (SEQ ID NO: 495), AKTTPKLEEGEFSEAR (SEQ ID NO: 496), AKTTPKLEEGEFSEARV (SEQ ID NO: 497), AKTTPKLGG (SEQ ID NO: 498), SAKTTPKLGG (SEQ ID NO: 499), SAKTTP (SEQ ID NO: 500), RADAAP (SEQ ID NO: 501), RADAAPTVS (SEQ ID NO: 502), RADAAAAGGPGS (SEQ ID NO: 503), RADAAAA $(G_4S)_4$ (SEQ ID NO: 504), SAKTTPKLEEGEFSEARV (SEQ ID NO: 505), ADAAP (SEQ ID NO: 506), ADAAPTVSIFPP (SEQ ID NO: 507), TVAAP (SEQ ID NO: 508), TVAAPSVFIFPP (SEQ ID NO: 509), QPKAAP (SEQ ID NO: 510), QPKAAPSVTLFPP (SEQ ID NO: 511), AKTTPP (SEQ ID NO: 512), AKTTPPSVTPLAP (SEQ ID NO: 513), AKTTAPSVYPLAP (SEQ ID NO: 514), ASTKGP (SEQ ID NO: 515), ASTKGPSVFPLAP (SEQ ID NO: 516), GENKVEYAPALMALS (SEQ ID NO: 517), GPAKELTPLKEAKVS (SEQ ID NO: 518), GHEAAAVMQVQYPAS (SEQ ID NO: 519), and AKTTAP (SEQ ID NO: 80). In one embodiment, the amino acid sequence of the linker may be selected from the group consisting of SEQ ID NOs. 26, 28, and 49-86. In one embodiment, the linker is GSG (SEQ ID NO: 26) or GGGGSGS (SEQ ID NO: 28). The linkers can also be in vivo cleavable peptide linkers, protease (such as MMPs) sensitive linkers, disulfide bond-based linkers that can be cleaved by reduction, etc., as previously described (Fusion Protein Technologies for Biopharmaceuticals: Applications and Challenges, edited by Stefan R. Schmidt), or any cleavable linkers known in the art. Such cleavable linkers can be used to release the top Fab in vivo for various purposes, in order to improve tissue/cell penetration and distribution, to enhance binding to targets, to reduce potential side effect, as well as to modulate in vivo functional and physical half-life of the 2 different Fab regions. In one embodiment, the binding protein comprises an Fc region. As used herein, the term "Fc region" refers to the C-terminal region of an IgG heavy chain. An example of the amino acid sequence containing the human IgG1 Fc region is SEQ ID NO: 20. The Fc region of an IgG comprises two constant domains, CH2 and CH3.

In one embodiment, the Fc region is a variant Fc region. In one embodiment, the variant Fc region has one or more amino acid modifications, such as substitutions, deletions, or insertions, relative to the parent Fc region. In a further embodiment, amino acid modifications of the Fc region alter the effector function activity relative to the parent Fc region activity. For example, in one embodiment, the variant Fc region may have altered (i.e., increased or decreased) antibody-dependent cytotoxicity (ADCC), complement-mediated cytotoxicity (CDC), phagocytosis, opsonization, or cell binding. In another embodiment, amino acid modifications of the Fc region may alter (i.e., increase or decrease) the affinity of the variant Fc region for an FcγR relative to the parent Fc region. For example, the variant Fc region may alter the affinity for FcγRI, FcγRII, FcγRIII.

In one preferred embodiment, the binding proteins provided herein are capable of binding one or more targets. In one embodiment, the target is selected from the group consisting of cytokines, cell surface proteins, enzymes and receptors. Preferably the binding protein is capable of modulating a biological function of one or more targets. More preferably the binding protein is capable of neutralizing one or more targets.

In one embodiment, the binding protein of the invention is capable of binding cytokines selected from the group consisting of lymphokines, monokines, and polypeptide hormones. In a further embodiment, the binding protein is capable of binding pairs of cytokines selected from the group consisting of IL-1α and IL-1β; IL-12 and IL-18, TNFα and IL-23, TNFα and IL-13; TNF and IL-18; TNF and IL-12; TNF and IL-1beta; TNF and MIF; TNF and IL-6, TNF and IL-6 Receptor, TNF and IL-17; IL-17 and IL-20; IL-17 and IL-23; TNF and IL-15; TNF and VEGF; VEGFR and EGFR; IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; IL-13 and ADAM8; and TNFα and PGE4, IL-13 and PED2, TNF and PEG2.

In another embodiment, the binding protein of the invention is capable of binding pairs of targets selected from the group consisting of CD137 and CD20, CD137 and EGFR, CD137 and Her-2, CD137 and PD-1, CD137 and PDL-1, VEGF and PD-L1, Lag-3 and TIM-3, OX40 and PD-1, TIM-3 and PD-1, TIM-3 and PDL-1, EGFR and DLL-4, VEGF and EGFR, HGF and VEGF, VEGF and VEGF (same or a different epitope), VEGF and Ang2, EGFR and cMet, PDGF and VEGF, VEGF and DLL-4, OX40 and PD-L1, ICOS and PD-1, ICOS and PD-L1, Lag-3 and PD-1, Lag-3 and PD-L1, Lag-3 and CTLA-4, ICOS and CTLA-4, CD138 and CD20; CD138 and CD40; CD19 and CD20; CD20 and CD3; CD3 and CD33; CD3 and CD133; CD38 & CD138; CD38 and CD20; CD20 and CD22; CD38 and CD40; CD40 and CD20; CD47 and CD20, CD-8 and IL-6; CSPGs and RGM A; CTLA-4 and BTNO2; CTLA-4 and PD-1; IGF1 and IGF2; IGF1/2 and Erb2B; IGF-1R and EGFR; EGFR and CD13; IGF-1R and ErbB3; EGFR-2 and IGFR; Her2 and Her2 (same or a different epitope); Factor IXa and Factor X, VEGFR-2 and Met; VEGF-A and Angiopoietin-2 (Ang-2); IL-12 and TWEAK; IL-13 and IL-1beta; MAG and RGM A; NgR and RGM A; NogoA and RGM A; OMGp and RGM A; PDL-1 and CTLA-4; PD-1 and CTLA-4, PD-1 and TIM-3; RGM A and RGM B; Te38 and TNFα; TNFα and Blys; TNFα and CD-22; TNFα and CTLA-4 domain; TNFα and GP130; TNFα and IL-12p40; TNFα and RANK ligand; EGFR and PD-L1; EGFR and cMet; Her3 and IGF-IR; DLL-4 and VEGF; PD-1 and PD-L1; Her3 and PD-1, Her3 and EGFR, cMet and PD-L1, and BTLA and PD-1.

In some embodiments, the binding proteins contain variable regions or CDRs derived from CD20 antibodies including, but not limited to, ofatumumab, rituximab, iodine i 131 tositumomab, obinutuzumab, ibritumomab, and those described in U.S. Pat. Nos. 9,228,008, 8,206,711, 7,682,612, 8,562,992, 7,799,900, 7,422,739, 7,850,962, 8,097,713, 8,057,793, 8,592,156, 6,652,852, 6,893,625, 6,120,767, 8,084,582, 8,778,339, 9,184,781, 7,381,560, 8,101,179, 9,382,327, 7,151,164, 7,435,803, 8,529,902, 9,416,187, 7,812,116, 8,329,181, 8,034,902, 9,289,479, 9,234,045, 4,987,084, 9,173,961, 9,175,086, 6,410,319, each of which is incorporated by reference in its entirety.

In some embodiments, the binding proteins contain variable regions or CDRs derived from CD3 antibodies including, but not limited to, muromonab-CD3, otelixizumab, teplizumab and visilizumab, and those described in U.S. Pat. Nos. 8,569,450, 7,635,472,5585097, 6706265, 5834597, 9056906, 9486475, 7728114, 8551478, 9226962, 9192665, 9505849, 8394926, 6306575, 5795727, 8840888, 5627040, 9249217, 8663634, 6491917, 5877299, each of which is incorporated by reference in its entirety.

In some embodiments, the binding proteins contain variable regions or CDRs derived from CTLA-4 antibodies including, but not limited to, ipilimumab and those described in U.S. Pat. Nos. 5,434,131, 5,968,510, 5,844,095, 7,572,772, 6,090,914, 7,311,910, 5,885,796, 5,885,579, 5,770,197, 5,851,795, 5,977,318, 7,161,058, 6,875,904, 7,504,554, 7,034,121, 6,719,972, 7,592,007, each of which is incorporated by reference in its entirety.

In some embodiments, the binding proteins contain variable regions or CDRs derived from PD-1 antibodies including, but are not limited to, pembrolizumab, nivolumab, atezolizumab, and those described in U.S. Pat. Nos. 8,741,295, 7,029,674, 7,722,868, 9,243,052, 8,927,697, 9,181,342, 8,552,154, 9,102,727, 9,220,776, 9,084,776, 8,008,449, 9,387,247, 9,492,540, 8,779,105, 9,358,289, 9,492,539, 9,205,148, 8,900,587, 8,952,136, 8,460,886, 7,414,171, 8,287,856, 8,580,247, 7,488,802, 7,521,051, 8,088,905, 7,709,214, 8,617,546, 9,381,244, 8,993,731, 8,574,872, 7,432,059, 8,216,996, 9,499,603, 9,102,728, 9,212,224, each of which is incorporated by reference in its entirety.

In some embodiments, the binding proteins contain variable regions or CDRs derived from PD-L1 antibodies including, but not limited to, durvalumab, avelumab, and those described in U.S. Pat. Nos. 8,741,295, 9,102,725, 8,168,179, 8,952,136, 8,552,154, 8,617,546, 9,212,224, 8,217,149, 8,383,796, each of which is incorporated by reference in its entirety.

In some embodiments, the binding proteins contain variable regions or CDRs derived from EGFR antibodies including, but not limited to, gefitinib, erlotinib, lapatinib, cetuximab, panitumumab, vandetanib, necitumumab, osimertinib, and those described in U.S. Pat. Nos. 7,723,484, 9,044,460, 9,226,964, 8,658,175, 7,618,631, 8,748,175, 9,499,622, 9,527,913, 9,493,568, 8,580,263, 7,514,240, 9,314,536, 9,051,370, 9,233,171, 9,029,513, 8,592,152, 8,597,652, 9,327,035, 8,628,773, 9,023,356, 9,132,192, 8,637,026, 9,283,276, 9,540,440, 9,545,442, 8,758,756, 9,120,853, 7,981,605, 8,546,107, 7,598,350, 5,212,290, 8,017,321, 7,589,180, 9,260,524, 8,790,649, 9,125,896, 9,238,690, 8,071,093, each of which is incorporated by reference in its entirety.

In some embodiments, the binding proteins contain variable regions or CDRs derived from TIM3 (CD366) antibodies including, but not limited to, 4C4G3, 7D3, B8.2C12, F38-2E2, and those described in U.S. Pat. Nos. 8,841,418, 8,552,156, 9,556,270, each of which is incorporated by reference in its entirety.

In some embodiments, the binding proteins contain variable regions or CDRs derived from cMet antibodies including, but not limited to, h1332, 71-8000, ab74217, and those described in U.S. Pat. Nos. 8,673,302, 9,120,852, 7,476,724, 7,892,550, 9,249,221, 9,535,055, 9,487,589, 8,329,173, 9,101,610, 8,101,727, 9,068,011, 9,260,531, 9,296,817, 8,481,689, 8,546,544, 8,563,696, 8,871,909, 8,889,832, 8,871,910, 9,107,907, 8,747,850, 9,469,691, 8,765,128, 8,729,249, 8,741,290, 8,637,027, 8,900,582, 9,192,666, 9,201,074, 9,505,843, 8,821,869, 8,163,280, 7,498,420, 8,562,985, 8,545,839, 9,213,031, 9,213,032, 8,217,148, 8,398,974, 9,394,367, 9,364,556, 8,623,359, 9,011,865, 9,375,425, 9,233,155, 9,169,329, 9,150,655, each of which is incorporated by reference in its entirety.

In some embodiments, the binding proteins contain variable regions or CDRs derived from Factor IXa antibodies including, but not limited to, ab97619, ab128048, ab128038, and those described in U.S. Pat. Nos. 7,279,161, 7,033,590, 4,786,726, 6,624,295, 7,049,411, 7,297,336, each of which is incorporated by reference in its entirety.

In some embodiments, the binding proteins contain variable regions or CDRs derived from Factor X antibodies including, but not limited to, PA5-22059, ab97632, B122M.

In some embodiments, the binding proteins contain variable regions or CDRs derived from Her3 (ErbB3) antibodies including, but not limited to, duligotumab, elgemtumab, lumretuzumab, patritumab, seribantumab, and those described in U.S. Pat. Nos. 9,346,883, 9,321,839, 8,859,737, 8,362,215, 8,828,388, 9,220,775, 9,217,039, 9,527,913, 9,085,622, 9,192,663, 8,735,551, 9,011,851, 7,846,440, 9,284,380, 8,791,244, 8,691,225, 9,487,588, 8,961,966, 9,034,328, 5,968,511, 9,346,889, 9,217,039, 9,346,890, each of which is incorporated by reference in its entirety.

In some embodiments, the binding proteins contain variable regions or CDRs derived from IGF-1R (CD221) antibodies including, but not limited to cixutumumab, dalotuzumab, figitumumab, ganitumab, robatumumab, teprotumumab, and those described in U.S. Pat. Nos. 7,572,897, 7,579,157, 7,968,093, 7,638,605, 7,329,745, 7,037,498, 7,982,024, 8,642,037, 7,700,742, 9,234,041, 7,815,907, 8,945,871, 8,361,461, 9,056,907, 8,168,410, 7,241,444, 7,914,784, 9,150,644, 7,985,842, 7,538,195, 8,268,617, 8,034,904, 8,344,112, 7,553,485, 8,101,180, 8,105,598, 7,824,681, 8,124,079, 8,420,085, 7,854,930, each of which is incorporated by reference in its entirety.

In some embodiments, the binding proteins contain variable regions or CDRs derived from DLL4 antibodies including, but not limited to demcizumab, enoticumab, navicixizumab, and those described in U.S. Pat. Nos. 9,469,689, 9,115,195, 8,623,358, 9,132,190, 9,469,688, 9,403,904, 8,663,636, 8,192,738, 750,124, each of which is incorporated by reference in its entirety.

In some embodiments, the binding proteins contain variable regions or CDRs derived from VEGF antibodies including, but not limited to Bevacizumab, Brolucizumab, Ranibizumab, and those described in U.S. Pat. Nos. 8,921,537, 7,910,098, 7,365,166, 7,060,269, 7,169,901, 6,884,879, 7,297,334, 7,375,193, 9,388,239, 8,834,883, 8,287,873, 7,998,931, 8,007,799, 7,785,803, 9,102,720, 8,486,397, 6,730,489, 6,383,484, 9,441,034, 7,097,986, 9,079,953, 8,945,552, 8,236,312, 7,740,844, 6,403,088, 9,018,357, 8,975,381, 7,691,977, 7,758,859, 8,512,699, 8,492,527, 9,353,177, 8,092,797, 7,811,785, 8,101,177, 8,592,563, 9,090,684, 8,349,322, each of which is incorporated by reference in its entirety.

In some embodiments, the binding proteins contain variable regions or CDRs derived from CD22 antibodies including, but not limited to bectumomab, epratuzumab, inotuzumab, moxetumomab, pinatuzumab, and those described in U.S. Pat. Nos. 9,181,343, 5,484,892, 9,279,019, 8,591,889, 9,499,632, 8,481,683, 7,355,012, 7,777,019, 8,809,502, 8,389,688, 7,829,086, each of which is incorporated by reference in its entirety.

In some embodiments, the binding proteins contain variable regions or CDRs derived from BTLA (CD272) antibodies including, but not limited to MIH26, AAP44003, MA5-16843, 6A5, and those described in U.S. Pat. Nos. 8,563,694, 9,346,882, 8,580,259, 8,247,537, each of which is incorporated by reference in its entirety.

In some embodiments, the binding proteins contain antibodies as described in WO2015103072, which is herein incorporated by reference in its entirety.

In one embodiment, the binding protein is capable of binding human IL-17 and human IL-20. In a further embodiment, the binding protein is capable of binding human IL-17 and human IL-20 and comprises a FIT-Ig polypeptide chain #1 sequence that is about 65%, about 70%, about 75%, about 80%, about 85%, about 90%, about 95%, about 99%, or 100% identical to a sequence selected from the group consisting of SEQ ID NO. 15, 25, and 27; a polypeptide chain #2 sequence that is about 65%, about 70%, about 75%, about 80%, about 85%, about 90%, about 95%, about 99%, or 100% identical to SEQ ID NO. 21; and a polypeptide chain #3 sequence that is about 65%, about 70%, about 75%, about 80%, about 85%, about 90%, about 95%, about 99%, or 100% identical to SEQ ID NO. 23. In another embodiment, the binding protein is capable of binding human IL-17 and human IL-20 and comprises FIT-Ig polypeptide chain #1 sequence that is about 65%, about 70%, about 75%, about 80%, about 85%, about 90%, about 95%, about 99%, or 100% identical to a sequence selected from the group consisting of SEQ ID NO. 15, 25, and 27; and a polypeptide chain #4 that is about 65%, about 70%, about 75%, about 80%, about 85%, about 90%, about 95%, about 99%, or 100% identical to a sequence selected from the group consisting of SEQ ID NO. 29, 30, and 31.

In one embodiment, the binding protein is capable of binding human CD3 and human CD20. In a further embodiment, the binding protein comprises a FIT-Ig polypeptide chain #1 sequence that is about 65%, about 70%, about 75%, about 80%, about 85%, about 90%, about 95%, about 99%, or 100% identical to a sequence selected from the group consisting of SEQ ID NO. 41, 48 and 316; a polypeptide chain #2 sequence that is about 65%, about 70%, about 75%, about 80%, about 85%, about 90%, about 95%, about 99%, or 100% identical to SEQ ID NO. 44 or SEQ ID NO. 325; and a polypeptide chain #3 sequence that is about 65%, about 70%, about 75%, about 80%, about 85%, about 90%, about 95%, about 99%, or 100% identical to SEQ ID NO. 46 or SEQ ID NO. 330.

In one embodiment, the binding protein is capable of binding human IL-17 and human TNF. In a further embodiment, the binding protein is capable of binding human IL-17 and human TNF and comprises a FIT-Ig polypeptide chain #1 sequence that is about 65%, about 70%, about 75%, about 80%, about 85%, about 90%, about 95%, about 99%, or 100% identical to SEQ ID NO. 87; a polypeptide chain #2 sequence that is about 65%, about 70%, about 75%, about 80%, about 85%, about 90%, about 95%, about 99%, or 100% identical to SEQ ID NO. 89; and a polypeptide chain #3 sequence that is about 65%, about 70%, about 75%, about 80%, about 85%, about 90%, about 95%, about 99%, or 100% identical to SEQ ID NO. 91.

In one embodiment, the binding protein is capable of binding human CTLA-4 and human PD-1. In a further embodiment, the binding protein is capable of binding human CTLA-4 and human PD-1 and comprises a FIT-Ig polypeptide chain #1 sequence that is about 65%, about 70%, about 75%, about 80%, about 85%, about 90%, about 95%, about 99%, or 100% identical to SEQ ID NO. 92, SEQ ID NO. 126, SEQ ID NO. 145, SEQ ID NO. 164, or SEQ ID NO. 183, a polypeptide chain #2 sequence that is about 65%, about 70%, about 75%, about 80%, about 85%, about 90%, about 95%, about 99%, or 100% identical to SEQ ID NO. 95, SEQ ID NO. 135, SEQ ID NO. 154, SEQ ID NO. 173, or SEQ ID NO. 192; and a polypeptide chain #3 sequence that is about 65%, about 70%, about 75%, about 80%, about 85%, about 90%, about 95%, about 99%, or 100% identical to SEQ ID NO. 97, SEQ ID NO. 140, SEQ ID NO. 159, SEQ ID NO. 178, or SEQ ID NO. 197.

In one embodiment, the binding protein is capable of binding EGFR and PD-L1. In a further embodiment, the binding protein is capable of binding EGFR and PD-L1 and comprises a FIT-Ig polypeptide chain #1 sequence that that is about 65%, about 70%, about 75%, about 80%, about 85%, about 90%, about 95%, about 99%, or 100% identical to SEQ ID NO. 99, SEQ ID NO. 202 or SEQ ID NO. 221; a polypeptide chain #2 sequence that is about 65%, about 70%, about 75%, about 80%, about 85%, about 90%, about 95%, about 99%, or 100% identical to SEQ ID NO. 100, SEQ ID NO. 211, or SEQ ID NO. 230; and a polypeptide chain #3 sequence that is about 65%, about 70%, about 75%, about 80%, about 85%, about 90%, about 95%, about 99%, or 100% identical to SEQ ID NO. 101, SEQ ID NO. 216, or SEQ ID NO. 235.

In one embodiment, the binding protein is capable of binding cMet and EGFR. In a further embodiment, the binding protein is capable of binding cMET and EGFR and comprises a FIT-Ig polypeptide chain #1 sequence that that is about 65%, about 70%, about 75%, about 80%, about 85%, about 90%, about 95%, about 99%, or 100% identical to SEQ ID NO. 102 or SEQ ID NO. 240; a polypeptide chain #2 sequence that is about 65%, about 70%, about 75%, about 80%, about 85%, about 90%, about 95%, about 99%, or 100% identical to SEQ ID NO. 103 or SEQ ID NO. 249; and a polypeptide chain #3 sequence that is about 65%, about 70%, about 75%, about 80%, about 85%, about 90%, about 95%, about 99%, or 100% identical to SEQ ID NO. 104 or SEQ ID NO. 254.

In one embodiment, the binding protein is capable of binding Factor IXa and Factor X. In a further embodiment, the binding protein is capable of binding Factor IXa and Factor X and comprises a FIT-Ig polypeptide chain #1 sequence that that is about 65%, about 70%, about 75%, about 80%, about 85%, about 90%, about 95%, about 99%, or 100% identical to SEQ ID NO. 105, or SEQ ID NO. 259; a polypeptide chain #2 sequence that is about 65%, about 70%, about 75%, about 80%, about 85%, about 90%, about 95%, about 99%, or 100% identical to SEQ ID NO. 106 or SEQ ID NO. 268; and a polypeptide chain #3 sequence that is about 65%, about 70%, about 75%, about 80%, about 85%, about 90%, about 95%, about 99%, or 100% identical to SEQ ID NO. 107 or SEQ ID NO. 273.

In one embodiment, the binding protein is capable of binding Her3 and IGF-1R. In a further embodiment, the binding protein is capable of binding Her3 and IGF-1R and comprises a FIT-Ig polypeptide chain #1 sequence that that is about 65%, about 70%, about 75%, about 80%, about 85%, about 90%, about 95%, about 99%, or 100% identical to SEQ ID NO. 108, SEQ ID NO. 278; a polypeptide chain #2 sequence that is about 65%, about 70%, about 75%, about 80%, about 85%, about 90%, about 95%, about 99%, or 100% identical to SEQ ID NO. 109 or SEQ ID NO. 287; and a polypeptide chain #3 sequence that is about 65%, about 70%, about 75%, about 80%, about 85%, about 90%, about 95%, about 99%, or 100% identical to SEQ ID NO. 110 or SEQ ID NO. 292.

In one embodiment, the binding protein is capable of binding DLL-4 and VEGF. In a further embodiment, the binding protein is capable of binding DLL-4 and VEGF and comprises a FIT-Ig polypeptide chain #1 sequence that that is about 65%, about 70%, about 75%, about 80%, about 85%, about 90%, about 95%, about 99%, or 100% identical to SEQ ID NO. 111, or SEQ ID NO. 297; a polypeptide chain #2 sequence that is about 65%, about 70%, about 75%, about 80%, about 85%, about 90%, about 95%, about 99%, or 100% identical to SEQ ID NO. 112, or SEQ ID NO. 306; and a polypeptide chain #3 sequence that is about 65%, about 70%, about 75%, about 80%, about 85%, about 90%, about 95%, about 99%, or 100% identical to SEQ ID NO. 113 or SEQ ID NO. 311.

In one embodiment, the binding protein is capable of binding CD20 and CD3. In a further embodiment, the binding protein is capable of binding CD20 and CD3 and comprises a FIT-Ig polypeptide chain #1 sequence that that is about 65%, about 70%, about 75%, about 80%, about 85%, about 90%, about 95%, about 99%, or 100% identical to SEQ ID NO. 114 or SEQ ID NO. 316; a polypeptide chain #2 sequence that is about 65%, about 70%, about 75%, about 80%, about 85%, about 90%, about 95%, about 99%, or 100% identical to SEQ ID NO. 115 or SEQ ID NO. 325; and a polypeptide chain #3 sequence that is about 65%, about 70%, about 75%, about 80%, about 85%, about 90%, about 95%, about 99%, or 100% identical to SEQ ID NO. 116 or SEQ ID NO. 330.

In one embodiment, the binding protein is capable of binding Her3 and EGFR. In a further embodiment, the binding protein is capable of binding Her3 and EGFR and comprises a FIT-Ig polypeptide chain #1 sequence that that is about 65%, about 70%, about 75%, about 80%, about 85%, about 90%, about 95%, about 99%, or 100% identical to SEQ ID NO. 117, SEQ ID NO. 335, or SEQ ID NO. 354; a polypeptide chain #2 sequence that is about 65%, about 70%, about 75%, about 80%, about 85%, about 90%, about 95%, about 99%, or 100% identical to SEQ ID NO. 118, SEQ ID NO. 344, or SEQ ID NO. 363; and a polypeptide chain #3 sequence that is about 65%, about 70%, about 75%, about 80%, about 85%, about 90%, about 95%, about 99%, or 100% identical to SEQ ID NO. 119, SEQ ID NO. 349, or SEQ ID NO. 368.

In one embodiment, the binding protein is capable of binding PD-1 and PD-L1. In a further embodiment, the binding protein is capable of binding PD-1 and PD-L1 and comprises a FIT-Ig polypeptide chain #1 sequence that that is about 65%, about 70%, about 75%, about 80%, about 85%, about 90%, about 95%, about 99%, or 100% identical to SEQ ID NO. 120 or SEQ ID NO. 373; a polypeptide chain #2 sequence that is about 65%, about 70%, about 75%, about 80%, about 85%, about 90%, about 95%, about 99%, or 100% identical to SEQ ID NO. 121 or SEQ ID NO. 382; and a polypeptide chain #3 sequence that is about 65%, about 70%, about 75%, about 80%, about 85%, about 90%, about 95%, about 99%, or 100% identical to SEQ ID NO. 122 or SEQ ID NO. 387.

In one embodiment, the binding protein is capable of binding Her3 and PD-1. In a further embodiment, the binding protein is capable of binding Her3 and PD-1 and comprises a FIT-Ig polypeptide chain #1 sequence that that is about 65%, about 70%, about 75%, about 80%, about 85%, about 90%, about 95%, about 99%, or 100% identical to SEQ ID NO. 123 or SEQ ID NO. 411; a polypeptide chain #2 sequence that is about 65%, about 70%, about 75%, about 80%, about 85%, about 90%, about 95%, about 99%, or 100% identical to SEQ ID NO. 124 or SEQ ID NO. 420; and a polypeptide chain #3 sequence that is about 65%, about 70%, about 75%, about 80%, about 85%, about 90%, about 95%, about 99%, or 100% identical to SEQ ID NO. 125 or SEQ ID NO. 425.

In one embodiment, the binding protein is capable of binding cMet and PD-L1. In a further embodiment, the binding protein is capable of binding cMet and PD-L1 and comprises a FIT-Ig polypeptide chain #1 sequence that that is about 65%, about 70%, about 75%, about 80%, about 85%, about 90%, about 95%, about 99%, or 100% identical to SEQ ID NO. 430; a polypeptide chain #2 sequence that is about 65%, about 70%, about 75%, about 80%, about 85%, about 90%, about 95%, about 99%, or 100% identical to SEQ ID NO. 439; and a polypeptide chain #3 sequence that is about 65%, about 70%, about 75%, about 80%, about 85%, about 90%, about 95%, about 99%, or 100% identical to SEQ ID NO. 444.

In one embodiment, the binding protein is capable of binding BTLA and PD-1. In a further embodiment, the binding protein is capable of binding BTLA and PD-1 and comprises a FIT-Ig polypeptide chain #1 sequence that that is about 65%, about 70%, about 75%, about 80%, about 85%, about 90%, about 95%, about 99%, or 100% identical to SEQ ID NO. 449 or SEQ ID NO. 468; a polypeptide chain #2 sequence that is about 65%, about 70%, about 75%, about 80%, about 85%, about 90%, about 95%, about 99%, or 100% identical to SEQ ID NO. 458 or SEQ ID NO. 477; and a polypeptide chain #3 sequence that is about 65%, about 70%, about 75%, about 80%, about 85%, about 90%, about 95%, about 99%, or 100% identical to SEQ ID NO. 463 or SEQ ID NO. 482.

In one embodiment, the binding protein is capable of binding CD20 and CD22. In a further embodiment, the binding protein is capable of binding CD20 and CD22 and comprises a FIT-Ig polypeptide chain #1 sequence that that is about 65%, about 70%, about 75%, about 80%, about 85%, about 90%, about 95%, about 99%, or 100% identical to SEQ ID NO. 392; a polypeptide chain #2 sequence that is about 65%, about 70%, about 75%, about 80%, about 85%, about 90%, about 95%, about 99%, or 100% identical to SEQ ID NO. 401; and a polypeptide chain #3 sequence that is about 65%, about 70%, about 75%, about 80%, about 85%, about 90%, about 95%, about 99%, or 100% identical to SEQ ID NO. 406.

Biologically active variants or functional variants of the exemplary binding proteins described herein are also a part of the present invention. As used herein, the phrase “a biologically active variant” or “functional variant” with respect to a protein refers to an amino acid sequence that is altered by one or more amino acids with respect to a reference sequence, while still maintains substantial biological activity of the reference sequence. The variant can have “conservative” changes, wherein a substituted amino acid has similar structural or chemical properties, e.g., replacement of leucine with isoleucine. The following table shows exemplary conservative amino acid substitutions. In some embodiments, the variant has one or more amino acid substitutions, wherein one or more or all substitutions are acidic amino acid, such as Aspartic acid, Asparagine, Glutamc acid, or Glutamine.

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

Alternatively, a variant can have “nonconservative” changes, e.g., replacement of a glycine with a tryptophan. Analogous minor variations can also include amino acid deletion or insertion, or both. Guidance in determining which amino acid residues can be substituted, inserted, or deleted without eliminating biological or immunological activity can be found using computer programs well known in the art, for example, DNASTAR software.

Binding proteins that are capable of binding the same epitopes on a given group of targets as that of an exemplary bispecific binding protein described herein are also a part of the present invention. The epitopes can be linear epitopes, conformational epitopes, or a mixture thereof. In some embodiments, such same epitopes can be identified by a suitable epitope mapping technique, including but not limited to, X-ray co-crystallography, array-based oligo-peptide scanning, site-directed mutagenesis, high throughput mutagenesis mapping, bacteriophage surface display, and hydrogen-deuterium exchange. Additional methods are described in U.S. Pat. Nos. 5,955,264, 65,796,676, 6,984,488, and 8,802,375, each of which is incorporated by reference in its entirety for all purposes.

In another embodiment, the binding protein of the invention is capable of binding one or two cytokines, cytokine-related proteins, and cytokine receptors selected from the group consisting of BMP1, BMP2, BMP313 (GDF10), BMP4, BMP6, BMP8, CSF1 (M-CSF), CSF2 (GM-CSF), CSF3 (G-CSF), EPO, FGF1 (aFGF), FGF2 (bFGF), FGF3 (int-2), FGF4 (HST), FGF5, FGF6 (HST-2), FGF7 (KGF), FGF9, FGF10, FGF11, FGF12, FGF12B, FGF14, FGF16, FGF17, FGF19, FGF20, FGF21, FGF23, IGF1, IGF2, IFNA1, IFNA2, IFNA4, IFNA5, IFNA6, IFNA7, IFNB1, IFNG, IFNW1, FIL1, FIL1 (EPSILON), FIL1 (ZETA), IL1A, IL1B, IL2, IL3, IL4, IL5, IL6, IL7, IL8, IL9, IL10, IL11, IL12A, IL12B, IL13, IL14, IL15, IL16, IL17, IL17B, IL18, IL19, IL20, IL22, IL23, IL24, IL25, IL26, IL27, IL28A, IL28B, IL29, IL30, PDGFA, FGER1, FGFR2, FGFR3, EGFR, ROR1, 2B4, KIR, CD137, CD27, OX40, CD40L, A2aR, CD48, B7-1, B7-2, ICOSL, B7-H3, B7-H4, CD137L, OX40L, CD70, CD40, PDGFB, TGFA, TGFB1, TGFB2, TGFB3, LTA (TNF-b), LTB, TNF (TNF-a), TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TNFSF10 (TRAIL), TNFSF11 (TRANCE), TNFSF12 (APO3L), TNFSF13 (April), TNFSF13B, TNFSF14 (HVEM-L), TNFSF15 (VEGI), TNFSF18, FIGF (VEGFD), VEGF, VEGFB, VEGFC, IL1R1, IL1R2, IL1RL1, IL1RL2, IL2RA, IL2RB, IL2RG, IL3RA, IL4R, IL5RA, IL6R, IL7R, IL8RA, IL8RB, IL9R, IL10RA, IL10RB, IL11RA, IL12RB1, IL12RB2, IL13RA1, IL13RA2, IL15RA, IL17R, IL18R1, IL20RA, IL21R, IL22R, IL1HY1, IL1RAP, IL1RAPL1, IL1RAPL2, IL1RN, IL6ST, IL18BP, IL18RAP, IL22RA2, AIF1, HGF, LEP (leptin), PTN, and THPO.

The binding protein of the invention is capable of binding one or more chemokines, chemokine receptors, and chemokine-related proteins selected from the group consisting of CCL1 (I-309), CCL2 (MCP-1/MCAF), CCL3 (MIP-1a), CCL4 (MIP-1b), CCL5 (RANTES), CCL7 (MCP-3), CCL8 (mcp-2), CCL11 (eotaxin), CCL13 (MCP-4), CCL15 (MIP-1d), CCL16 (HCC-4), CCL17 (TARC), CCL18 (PARC), CCL19 (MIP-3b), CCL20 (MIP-3a), CCL21 (SLC/exodus-2), CCL22 (MDC/STC-1), CCL23 (MPIF-1), CCL24 (MPIF-2/eotaxin-2), CCL25 (TECK), CCL26 (eotaxin-3), CCL27 (CTACK/ILC), CCL28, CXCL1 (GRO1), CXCL2 (GRO2), CXCL3 (GRO3), CXCL5 (ENA-78), CXCL6 (GCP-2), CXCL9 (MIG), CXCL10 (IP 10), CXCL11 (I-TAC), CXCL12 (SDF1), CXCL13, CXCL14, CXCL16, PF4 (CXCL4), PPBP (CXCL7), CX3CL1 (SCYD1), SCYE1, XCL1 (lymphotactin), XCL2 (SCM-1b), BLR1 (MDR15), CCBP2 (D6/JAB61), CCR1 (CKR1/HM145), CCR2 (mcp-1RB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TER1/CKR-L1), CCR9 (GPR-9-6), CCRL1 (VSHK1), CCRL2 (L-CCR), XCR1 (GPR5/CCXCR1), CMKLR1, CMKOR1 (RDC1), CX3CR1 (V28), CXCR4, GPR2 (CCR10), GPR31, GPR81 (FKSG80), CXCR3 (GPR9/CKR-L2), CXCR6 (TYMSTR/STRL33/Bonzo), HM74, IL8RA (IL8Ra), IL8RB (IL8Rb), LTB4R (GPR16), TCP10, CKLFSF2, CKLFSF3, CKLFSF4, CKLFSF5, CKLFSF6, CKLFSF7, CKLFSF8, BDNF, C5R1, CSF3, GRCC10

(C10), EPO, FY (DARC), GDF5, HIF1A, IL8, PRL, RGS3, RGS13, SDF2, SLIT2, TLR2, TLR4, TREM1, TREM2, and VHL.

In another embodiment, a binding protein of the invention is capable of binding cell surface protein such as, for example, integrins. In another embodiment, the binding protein of the invention is capable of binding enzymes selected from the group consisting of kinases and proteases. In yet another embodiment, the binding protein of the invention is capable of binding receptors selected from the group consisting of lymphokine receptors, monokine receptors, and polypeptide hormone receptors.

In one embodiment, the binding protein is multivalent. In another embodiment, the binding protein is multispecific. The multivalent and or multispecific binding proteins described above have desirable properties particularly from a therapeutic standpoint. For instance, the multivalent and or multispecific binding protein may (1) be internalized (and/or catabolized) faster than a bivalent antibody by a cell expressing an antigen to which the antibodies bind; (2) be an agonist antibody; and/or (3) induce cell death and/or apoptosis of a cell expressing an antigen which the multivalent antibody is capable of binding to. The "parent antibody" which provides at least one antigen binding specificity of the multivalent and or multispecific binding proteins may be one which is internalized (and/or catabolized) by a cell expressing an antigen to which the antibody binds; and/or may be an agonist, cell death-inducing, and/or apoptosis-inducing antibody, and the multivalent and or multispecific binding protein as described herein may display improvement(s) in one or more of these properties. Moreover, the parent antibody may lack any one or more of these properties, but may be endowed with them when constructed as a multivalent binding protein as herein described.

In another embodiment a binding protein of the invention has an on rate constant (Kon) to one or more targets selected from the group consisting of: at least about $10^2M^{-1}s^{-1}$; at least about $10^3M^{-1}s^{-1}$; at least about $10^4M^{-1}s^{-1}$; at least about $10^5M^{-1}s^{-1}$; and at least about $10^6M^{-1}s^{-1}$ (inclusive of all values therebetween), as measured by surface plasmon resonance. Preferably, the binding protein of the invention has an on rate constant (Kon) to one or more targets between $10^2M^{-1}s^{-1}$ to $10^3M^{-1}s^{-1}$; between $10^3M^{-1}s^{-1}$ to $10^4M^{-1}s^{-1}$; between $10^4M^{-1}s^{-1}$ to $10^5M^{-1}s^{-1}$; or between $10^5M^{-1}s^{-1}$ to $10^6M^{-1}s^{-1}$ (inclusive of all values therebetween), as measured by surface plasmon resonance.

In another embodiment a binding protein has an off rate constant (Koff) for one or more targets selected from the group consisting of: at most about $10^{-3}$ $s^{-1}$; at most about $10^{-4}$ $s^{-1}$; at most about $10^{-5}$ $s^{-1}$; and at most about $10^{-6}$ $s^{-1}$, as measured by surface plasmon resonance (inclusive of all values therebetween). Preferably, the binding protein of the invention has an off rate constant (Koff) to one or more targets of $10^{-3}$ $s^{-1}$ to $10^{-4}$ $s^{-1}$; of $10^{-4}$ $s^{-1}$ to $10^{-5}$ $s^{-1}$; or of $10^{-5}$ $s^{1}$ to $10^{-6}$ $s^{-1}$, as measured by surface plasmon resonance (inclusive of all values therebetween).

In another embodiment a binding protein has a dissociation constant ($K_D$) to one or more targets selected from the group consisting of: at most about $10^{-7}$ M; at most about $10^{-8}$ M; at most about $10^{-9}$ M; at most about $10^{-10}$ M; at most about $10^{-11}$ M; at most about $10^{-12}$ M; and at most $10^{-13}$ M (inclusive of all values therebetween). Preferably, the binding protein of the invention has a dissociation constant ($K_D$) to IL-12 or IL-23 of $10^{-7}$ M to $10^{-8}$ M; of $10^{-8}$ M to $10^{-9}$ M; of $10^{-9}$ M to $10^{-10}$ M; of $10^{-10}$ to $10^{-11}$ M; of $10^{-11}$ M to $10^{-12}$ M; or of $10^{-12}$ M to $10^{-13}$ M (inclusive of all values therebetween).

In another embodiment a binding protein of the invention has a monomer % of at least about 75%, about 76%, about 77%, about 78%, about 79%, about 80%, about 80%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, about 99.9%, or more, or 100% (inclusive of all values therebetween) in a one-step Protein A purification using Size-exclusion chromatography (SEC)-HPLC.

In another embodiment a binding protein of the invention has an expression level at least about 0.01 mg/L, 0.05 mg/L, 0.1 mg/L, about 0.2 mg/L, about 0.3 mg/L, about 0.4 mg/L, about 0.5 mg/L, about 0.6 mg/L, about 0.7 mg/L, about 0.8 mg/L, about 0.9 mg/L, about 1.0 mg/L, about 2 mg/L, about 3 mg/L, about 4 mg/L, about 5 mg/L, about 6 mg/L, about 7 mg/L, about 8 mg/L, about 9 mg/L, about 10 mg/L, about 11 mg/L, about 12 mg/L, about 13 mg/L, about 14 mg/L, about 15 mg/L, about 16 mg/L, about 17 mg/L, about 18 mg/L, about 19 mg/L, about 20 mg/L, about 21 mg/L, about 22 mg/L, about 23 mg/L, about 24 mg/L, about 25 mg/L, about 26 mg/L, about 27 mg/L, about 28 mg/L, about 29 mg/L, about 30 mg/L, about 40 mg/L, about 50 mg/L, about 60 mg/L, about 70 mg/L, about 80 mg/L, about 90 mg/L, about 100 mg/L, about 200 mg/L, about 300 mg/L, about 400 mg/L, about 500 mg/L, about 600 mg/L, about 700 mg/L, about 800 mg/L, about 900 mg/L, about 1000 mg/L (inclusive of all values therebetween) or more, under optimized conditions. In some embodiments, the binding protein of the invention is expressed in 293E cells or in any other cells suitable for the purpose.

In another embodiment a binding protein of the invention has an Tm1 transition temperature as measured by Differential scanning calorimetry (DSC) which is at least about 50° C., about 51° C., about 52° C., about 53° C., about 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 95° C., about 99° C. (inclusive of all values therebetween) or more.

A binding protein of the invention has great stability in freeze-thaw test. In some embodiments, when a binding protein sample of the invention is thawed and incubated at 4° C., 25° C. and 40° C. for 1 day, 3 days or 7 days, reduction of intact binding protein due to aggregates is less than about 5%, about 4%, about 3%, about 2%, about 1%, about 0.5%, about 0.1%, about 0.05%, about 0.01% (inclusive of all values therebetween), or less, as measured by SEC-HPLC.

In another embodiment, when a binding protein of the invention is administered intravenously, it has one or more of the following PK parameters (1) an Apparent total body clearance of the drug from plasma (CL, mL/day/kg) of about 0.1, 0.5, 1, 2, 3, 4, 5, 6, 7, 8, 9, 10, 15, 20, 25, 30, 35, 40, 45, 50 (inclusive of all values therebetween) or more; (2) an Apparent volume of distribution at steady state (Vss, mL/kg) of about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 (inclusive of all values therebetween), or more; (3) an Apparent volume of the central or plasma compartment in a two-compartment model (V1, mL/kg) of about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 (inclusive of all values therebetween), or more; (4) an initial or disposition half-life (Alpha t½, day) of about 0.01, 0.05, 0.1, 0.2 0.3, 0.4, 0.5, 0.6, 0.7, 0.8, 0.9, 1, 2, 3, 4, 5, 6, 7, 8, 9, 10, 15, 20, 25, 30 (inclusive of all values therebetween) or more; (5) a Terminal elimination half-life (Beta t½, day) of about 0.01, 0.05, 0.1, 0.2 0.3, 0.4, 0.5, 0.6, 0.7, 0.8, 0.9, 1, 2, 3, 4, 5, 6, 7, 8, 9, 10, 15, 20, 25, 30 (inclusive of all values therebetween) or more; (6) an area under the plasma concentration-time curve (AUC, day×μg/mL) of about 10, 20, 30, 40, 50, 60, 70, 80, 90, 100, 200, 300, 400, 500, 600, 700, 800, 900, 1000, 1500, 2000, 2500, 3000 (inclusive of all values therebetween) or more; and (6) a Mean residence time (MRT, day) of about 0.01, 0.05, 0.1, 0.2 0.3, 0.4, 0.5, 0.6, 0.7, 0.8, 0.9, 1, 2, 3, 4, 5, 6, 7, 8, 9, 10, 15, 20, 25, 30 (inclusive of all values therebetween) or more. In some embodiments, the above parameters are associated with a dosage of about 1 mg/kg, 5 mg/kg, 10 mg/kg, 20 mg/kg, 50 mg/kg, 100 mg/kg, 200 mg/kg (inclusive of all values therebetween) or more.

In another embodiment, when a binding protein of the invention is administered subcutaneously, it has one or more of the following PK parameters (1) a Time to reach maximum (peak) plasma concentration following drug administration (Tmax, day) of about 0.05, 0.1, 0.2 0.3, 0.4, 0.5, 0.6, 0.7, 0.8, 0.9, 1, 2, 3, 4, 5, 6, 7, 8, 9, 10, 15, 20, 25, 30 (inclusive of all values therebetween) or more; (2) a Maximum (peak) plasma drug concentration (Cmax, μg/ml) of about 0.1, 0.5, 1, 2, 3, 4, 5, 6, 7, 8, 9, 10, 15, 20, 25, 30, 35, 40, 45, 50, 55, 60, 65, 70, 75, 80, 85, 90, 95, 100, 150, 200, 250, 300, 350, 400, 450, 500 (inclusive of all values therebetween) or more; (3) an Elimination half-life (Terminal $t_{1/2}$, day) of about 0.01, 0.05, 0.1, 0.2 0.3, 0.4, 0.5, 0.6, 0.7, 0.8, 0.9, 1, 2, 3, 4, 5, 6, 7, 8, 9, 10, 15, 20, 25, 30 (inclusive of all values therebetween) or more; (4) an Area under the plasma concentration-time curve from time zero to time of last measurable concentration (AUClast, day×μg/ml) of about 10, 20, 30, 40, 50, 60, 70, 80, 90, 100, 200, 300, 400, 500, 600, 700, 800, 900, 1000, 1500, 2000, 2500, 3000 (inclusive of all values therebetween) or more; (5) an Area under the plasma concentration-time curve from time zero to infinity ($AUC_{inf}$, day×μg/ml) of about 10, 20, 30, 40, 50, 60, 70, 80, 90, 100, 200, 300, 400, 500, 600, 700, 800, 900, 1000, 1500, 2000, 2500, 3000 (inclusive of all values therebetween) or more; (6) a Formation clearance of drug to metabolite (CL/F, mL/day/kg) of about 0.1, 0.5, 1, 2, 3, 4, 5, 6, 7, 8, 9, 10, 15, 20, 25, 30, 35, 40, 45, 50 (inclusive of all values therebetween) or more; (7) a Bioavailability (F, %) of about 1, 5, 10, 15, 20, 25, 30, 35, 40, 45, 50, 55, 60, 65, 70, 75, 80, 85, 90, 95, 100, 110, 120, 130, 140, 150, 160, 170, 180, 190, 200 (inclusive of all values therebetween), or more. In some embodiments, the above parameters are associated with a dosage of about 1 mg/kg, 5 mg/kg, 10 mg/kg, 20 mg/kg, 50 mg/kg, 100 mg/kg, 200 mg/kg (inclusive of all values therebetween) or more.

In another embodiment, the binding protein described above is a conjugate further comprising an agent selected from the group consisting of an immunoadhesion molecule, an imaging agent, a therapeutic agent, and a cytotoxic agent. In one embodiment, the imaging agent is selected from the group consisting of a radiolabel, an enzyme, a fluorescent label, a luminescent label, a bioluminescent label, a magnetic label, and biotin. In a further embodiment, the imaging agent is a radiolabel selected from the group consisting of: $^{3}H$, $^{14}C$, $^{35}S$, $^{90}Y$, $^{99}Tc$, $^{111}In$, $^{125}I$, $^{131}I$, $^{177}Lu$, $^{166}Ho$, and $^{153}Sm$. In one embodiment, the therapeutic or cytotoxic agent is selected from the group consisting of an immunosuppressive agent, an immuno-stimulatory agent, an anti-metabolite, an alkylating agent, an antibiotic, a growth factor, a cytokine, an anti-angiogenic agent, an anti-mitotic agent, an anthracycline, a toxin, and an apoptotic agent. In one embodiment, the binding protein is conjugated directly to the agent. In another embodiment, the binding protein is conjugated to the agent via a linker. Suitable linkers include, but are not limited to, amino acid and polypeptide linkers disclosed herein. Linkers may be cleavable or non-cleavable.

In another embodiment the binding protein described above is a crystallized binding protein and exists as a crystal. Preferably the crystal is a carrier-free pharmaceutical controlled release crystal. More preferably the crystallized binding protein has a greater half life in vivo than the soluble counterpart of said binding protein. Most preferably the crystallized binding protein retains biological activity.

In another embodiment the binding protein described above is glycosylated. Preferably, the glycosylation is a human glycosylation pattern.

One aspect of the invention pertains to an isolated nucleic acid encoding any one of the binding protein disclosed above. A further embodiment provides a vector comprising the isolated nucleic acid disclosed above wherein said vector is selected from the group consisting of pcDNA; pTT (Durocher et al., Nucleic Acids Research 2002, Vol 30, No. 2); pTT3 (pTT with additional multiple cloning site; pEF-BOS (Mizushima, S. and Nagata, S., (1990) Nucleic acids Research Vol 18, No. 17); pBV; pJV; pcDNA3.1 TOPO, pEF6 TOPO and pBJ. The multi-specific binding proteins and methods of making the same are provided. The binding protein can be generated using various techniques. Expression vectors, host cells and methods of generating the binding proteins are provided in this disclosure.

The antigen-binding variable domains of the binding proteins of this disclosure can be obtained from parent binding proteins, including polyclonal Abs, monoclonal Abs, and or receptors capable of binding antigens of interest. These parent binding proteins may be naturally occurring or may be generated by recombinant technology. The person of ordinary skill in the art is well familiar with many methods for producing antibodies and/or isolated receptors, including, but not limited to using hybridoma techniques, selected lymphocyte antibody method (SLAM), use of a phage, yeast, or RNA-protein fusion display or other library, immunizing a non-human animal comprising at least some of the human immunoglobulin locus, and preparation of chimeric, CDR-grafted, and humanized antibodies. See, e.g., US Patent Publication No. 20090311253 A1. Variable domains may also be prepared using affinity maturation techniques. The binding variable domains of the binding proteins can also be obtained from isolated receptor molecules obtained by extraction procedures known in the art (e.g., using solvents, detergents, and/or affinity purifications), or determined by biophysical methods known in the art (e.g., X-ray crystallography, NMR, interferometry, and/or computer modeling).

An embodiment is provided comprising selecting parent binding proteins with at least one or more properties desired in the binding protein molecule. In an embodiment, the desired property is one or more of those used to characterize antibody parameters, such as, for example, antigen specificity, affinity to antigen, potency, biological function, epitope recognition, stability, solubility, production efficiency, immunogenicity, pharmacokinetics, bioavailability, tissue cross reactivity, or orthologous antigen binding. See, e.g., US Patent Publication No. 20090311253.

The multi-specific antibodies may also be designed such that one or more of the antigen binding domain are rendered non-functional. The variable domains may be obtained using recombinant DNA techniques from parent binding proteins generated by any one of the methods described herein. In an embodiment, a variable domain is a murine heavy or light chain variable domain. In another embodiment, a variable domain is a CDR grafted or a humanized variable heavy or light chain domain. In an embodiment, a variable domain is a human heavy or light chain variable domain.

In an embodiment, one or more constant domains are linked to the variable domains using recombinant DNA techniques. In an embodiment, a sequence comprising one or more heavy chain variable domains is linked to a heavy chain constant domain and a sequence comprising one or more light chain variable domains is linked to a light chain constant domain. In an embodiment, the constant domains are human heavy chain constant domains and human light chain constant domains, respectively. In an embodiment, the heavy chain is further linked to an Fc region. The Fc region may be a native sequence Fc region or a variant Fc region. In another embodiment, the Fc region is a human Fc region. In another embodiment, the Fc region includes Fc region from IgG1, IgG2, IgG3, IgG4, IgA, IgM, IgE, or IgD.

Additionally, the binding proteins provided herein can be employed for tissue-specific delivery (target a tissue marker and a disease mediator for enhanced local PK thus higher efficacy and/or lower toxicity), including intracellular delivery (targeting an internalizing receptor and an intracellular molecule), delivering to inside brain (targeting transferrin receptor and a CNS disease mediator for crossing the blood-brain barrier). The binding proteins can also serve as a carrier protein to deliver an antigen to a specific location via binding to a non-neutralizing epitope of that antigen and also to increase the half-life of the antigen. Furthermore, the binding proteins can be designed to either be physically linked to medical devices implanted into patients or target these medical devices (see Burke et al. (2006) Advanced Drug Deliv. Rev. 58(3): 437-446; Hildebrand et al. (2006) Surface and Coatings Technol. 200(22-23): 6318-6324; Drug/device combinations for local drug therapies and infection prophylaxis, Wu (2006) Biomaterials 27(11):2450-2467; Mediation of the cytokine network in the implantation of orthopedic devices, Marques (2005) Biodegradable Systems in Tissue Engineer. Regen. Med. 377-397). Directing appropriate types of cell to the site of medical implant may promote healing and restoring normal tissue function. Alternatively, inhibition of mediators (including but not limited to cytokines), released upon device implantation by a receptor antibody fusion protein coupled to or target to a device is also provided.

In one aspect, a host cell is transformed with the vector disclosed above. In one embodiment, the host cell is a prokaryotic cell. In a further embodiment, the host cell is *Escherichia coli*. In another embodiment, the host cell is an eukaryotic cell. In a further embodiment, the eukaryotic cell is selected from the group consisting of protist cell, animal cell, plant cell and fungal cell. In one embodiment, the host cell is a mammalian cell including, but not limited to, 293, COS, NS0, and CHO and; or a fungal cell such as *Saccharomyces cerevisiae*; or an insect cell such as Sf9.

Another aspect of the invention provides a method of producing a binding protein disclosed above comprising culturing any one of the host cells also disclosed above in a culture medium under conditions sufficient to produce the binding protein. Preferably 50%-75% of the binding protein produced by this method is a dual specific tetravalent binding protein. More preferably 75%-90% of the binding protein produced by this method is a dual specific tetravalent binding protein. Most preferably 90%-95% of the binding protein produced is a dual specific tetravalent binding protein.

Another embodiment provides a binding protein produced according to the method disclosed above.

One embodiment provides a composition for the release of a binding protein wherein the composition comprises a formulation which in turn comprises a crystallized binding protein, as disclosed above and an ingredient; and at least one polymeric carrier. Preferably the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl) methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polyeaccharides, blends and copolymers thereof. Preferably the ingredient is selected from the group consisting of albumin, sucrose, trehalose, lactitol, gelatin, hydroxypropyl-β-cyclodextrin, methoxypolyethylene glycol and polyethylene glycol. Another embodiment provides a method for treating a mammal comprising the step of administering to the mammal an effective amount of the composition disclosed above.

The invention also provides a pharmaceutical composition comprising a binding protein, as disclosed above and a pharmaceutically acceptable carrier. Pharmaceutically acceptable carriers include, but are not limited to, phosphate buffer or saline. Other common parenteral vehicles include sodium phosphate solutions, Ringer's dextrose, dextrose and sodium chloride, lactated Ringer's, or fixed oils. Intravenous vehicles include fluid and nutrient replenishers, electrolyte replenishers, such as those based on Ringer's dextrose, and the like. Preservatives and other additives may also be present such as for example, antimicrobials, antioxidants, chelating agents, and inert gases and the like. More particularly, pharmaceutical compositions suitable for injectable use include sterile aqueous solutions (where water soluble) or dispersions and sterile powders for the extemporaneous preparation of sterile injectable solutions or dispersions. The carrier can be a solvent or dispersion medium containing, for example, water, ethanol, polyol (e.g., glycerol, propylene glycol, and liquid polyethylene glycol, and the like), and suitable mixtures thereof. In some cases, it will be preferable to include isotonic agents, for example, sugars, polyalcohols, such as mannitol, sorbitol, or sodium chloride in the composition. Prolonged absorption of the injectable compositions can be brought about by including in the composition an agent which delays absorption, for example, aluminum monostearate and gelatin.

In a further embodiment the pharmaceutical composition comprises at least one additional therapeutic agent for treating a disorder. In one embodiment, the additional agent is selected from the group consisting of: therapeutic agents, imaging agents, cytotoxic agent, angiogenesis inhibitors (including but not limited to anti-VEGF antibodies or VEGF-trap); kinase inhibitors (including but not limited to KDR and TIE-2 inhibitors); co-stimulation molecule blockers (including but not limited to anti-B7.1, anti-B7.2, CTLA4-Ig, anti-PD-1, anti-CD20); adhesion molecule blockers (including but not limited to anti-LFA-1 Abs, anti-E/L selectin Abs, small molecule inhibitors); anti-cytokine antibody or functional fragment thereof (including but not limited to anti-IL-18, anti-TNF, anti-TL-6/cytokine receptor antibodies); methotrexate; cyclosporin; rapamycin; FK506; detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

In another aspect, the invention provides a method for treating a human subject suffering from a disorder in which the target, or targets, capable of being bound by the binding protein disclosed above is detrimental, comprising administering to the human subject a binding protein disclosed above such that the activity of the target or targets in the human subject is inhibited and treatment or preventions of the disorder is achieved. In one embodiment, the disease or disorder is an inflammatory condition, autoimmune disease, or cancer. In one embodiment, the disease or disorder is selected from the group comprising arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia areata, seronegative arthopathy, arthropathy, Reiter's disease, psoriatic arthropathy, ulcerative colitic arthropathy, enteropathic synovitis, chlamydia, yersinia and salmonella associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjörgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), Th2 Type and Th1 Type mediated diseases, acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *Legionella*, leishmaniasis, leprosy, lesions of the corticospinal system, lipedema, liver transplant rejection, lymphederma, malaria, malignamt Lymphoma, malignant histiocytosis, malignant melanoma, meningitis, meningococcemia, metabolic/idiopathic, migraine headache, mitochondrial multi-system disorder, mixed connective tissue disease, monoclonal gammopathy, multiple myeloma, multiple systems degenerations (Mencel Dejerine-Thomas Shi-Drager and Machado-Joseph), myasthenia gravis, *Mycobacterium avium intracellulare, Mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkin's lymphoma, occlusion of the abdominal aorta and its branches, occlusive arterial disorders, okt3 therapy, orchitis/epidydimitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherlosclerotic disease, peripheral vascular disorders, peritonitis, pernicious anemia, *Pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynoud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, T-cell or FAB ALL, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, xenograft rejection of any organ or tissue.

In another aspect the invention provides a method of treating a patient suffering from a disorder comprising the step of administering any one of the binding proteins disclosed above before, concurrent, or after the administration of a second agent, as discussed above. In a preferred embodiment the second agent is selected from the group consisting of budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-12, IL-13, IL-15, IL-16, IL-18, IL-23, EMAP-II, GM-CSF, FGF, and PDGF, antibodies of CD2, CD3, CD4, CD8, CD-19, CD25, CD28, CD30, CD40, CD45, CD69, CD90 or their ligands, methotrexate, cyclosporin, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signalling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-IRI, sIL-IRII, sTL-6R, antiinflammatory cytokines, IL-4, IL-1β, IL-11, IL-13 and TGFβ.

In one embodiment, the pharmaceutical compositions disclosed above are administered to the subject by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

One aspect of the invention provides at least one anti-idiotype antibody to at least one binding protein of the present invention. The anti-idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or; any portion thereof, that can be incorporated into a binding protein of the present invention.

In another embodiment the binding proteins of the invention are capable of binding one or more targets selected from the group consisting of ABCF1; ACVR1; ACVR1B; ACVR2; ACVR2B; ACVRL1; ADORA2A; Aggrecan; AGR2; AICDA; AIF1; AIG1; AKAP1; AKAP2; AMH; AMHR2; ANGPT1; ANGPT2; ANGPTL3; ANGPTL4; ANPEP; APC; APOC1; AR; AZGP1 (zinc-a-glycoprotein); B7.1; B7.2; BAD; BAFF; BAG1; BAIl; BCL2; BCL6; BDNF; BLNK; BLR1 (MDR15); BlyS; BMP1; BMP2; BMP3B (GDF10); BMP4; BMP6; BMP8; BMPR1A; BMPR1B; BMPR2; BPAG1 (plectin); BRCA1; C19orf10 (IL27w); C3; C4A; C5; C5R1; CANT1; CASP1; CASP4; CAV1; CCBP2 (D6/JAB61); CCL1 (1-309); CCL11 (eotaxin); CCL13 (MCP-4); CCL15 (MIP-1d); CCL16 (HCC-4); CCL17 (TARC); CCL18 (PARC); CCL19 (MIP-3b); CCL2 (MCP-1); MCAF; CCL20 (MIP-3a); CCL21 (MIP-2); SLC; exodus-2; CCL22 (MDC/STC-1); CCL23 (MPIF-1); CCL24 (MPIF-2/eotaxin-2); CCL25 (TECK); CCL26 (eotaxin-3); CCL27 (CTACK/ILC); CCL28; CCL3 (MIP-1a); CCL4 (MIP-1b); CCL5 (RANTES); CCL7 (MCP-3); CCL8 (mcp-2); CCNA1; CCNA2; CCND1; CCNE1; CCNE2; CCR1 (CKR1/HM145); CCR2 (mcp-1RB/RA); CCR3 (CKR3/CMKBR3); CCR4; CCR5 (CMKBR5/ChemR13); CCR6 (CMKBR6/CKR-L3/STRL22/DRY6); CCR7 (CKR7/EBIl); CCR8 (CMKBR8/TER1/CKR-L1); CCR9 (GPR-9-6); CCRL1 (VSHK1); CCRL2 (L-CCR); CD164; CD19; CD1C; CD20; CD200; CD-22; CD24; CD28; CD3; CD37; CD38; CD3E; CD3G; CD3Z; CD4; CD40; CD40L; CD44; CD45RB; CD47, CD48, CD52; CD69; CD70, CD72; CD74; CD79A; CD79B; CD8; CD80; CD81; CD83; CD86; CD137, CD138, B7-1, B7-2, ICOSL, B7-H3, B7-H4, CD137L, OX40L, CDH1 (E-cadherin); CDH10; CDH12; CDH13; CDH18; CDH19; CDH20; CDH5; CDH7; CDH8; CDH9; CDK2; CDK3; CDK4; CDK5; CDK6; CDK7; CDK9; CDKN1A (p21Wap1/Cip1); CDKN1B (p27Kip1); CDKN1C; CDKN2A (p161NK4a); CDKN2B; CDKN2C; CDKN3; CEBPB; CER1; CHGA; CHGB; Chitinase; CHST10; CKLFSF2; CKLFSF3; CKLFSF4; CKLFSF5; CKLFSF6; CKLFSF7; CKLFSF8; CLDN3; CLDN7 (claudin-7); CLN3; CLU (clusterin); cMet; CMKLR1; CMKOR1 (RDC1); CNR1; COL18A1; COL1A1; COL4A3; COL6A1; CR2; CRP; CSF1 (M-CSF); CSF2 (GM-CSF); CSF3 (GCSF); CTLA-4; CTNNB1 (b-catenin); CTSB (cathepsin B); CX3CL1 (SCYD1); CX3CR1 (V28); CXCL1 (GRO1); CXCL10 (IP-10); CXCL11 (I-TAC/IP-9); CXCL12 (SDF1); CXCL13; CXCL14; CXCL16; CXCL2 (GRO2); CXCL3 (GRO3); CXCL5 (ENA-78/LIX); CXCL6 (GCP-2); CXCL9 (MIG); CXCR3 (GPR9/CKR-L2); CXCR4; CXCR6 (TYMSTR/STRL33/Bonzo); CYB5; CYC1; CYSLTR1; DAB2IP; DES; DKFZp451J0118; DLL-4; DNCL1; DPP4; E2F1; ECGF1; EDG1; EFNA1; EFNA3; EFNB2; EGF; EGFR; ELAC2; ENG; ENO1; ENO2; ENO3; EPHB4; EPO; ERBB2 (Her-2); EREG; ERK8; ESR1; ESR2; F3 (TF); FADD; FasL; FASN; FCER1A; FCER2; FCGR3A; FGF; FGF1 (aFGF); FGF10; FGF11; FGF12; FGF12B; FGF13; FGF14; FGF16; FGF17; FGF18; FGF19; FGF2 (bFGF); FGF20; FGF21; FGF22; FGF23; FGF3 (int-2); FGF4 (HST); FGF5; FGF6 (HST-2); FGF7 (KGF); FGF8; FGF9; FGFR3; FIGF (VEGFD); FIL1 (EPSILON); FIL1 (ZETA); FLJ12584; FLJ25530; FLRT1 (fibronectin); FLT1; FOS; FOSL1 (FRA-1); FY (DARC); GABRP (GABAa); GAGEB1; GAGEC1; GALNAC4S-6ST; GATA3; GDF5; GFI1; GGT1; GM-CSF; GNAS1; GNRH1; GPR2 (CCR10); GPR31; GPR44; GPR81 (FKSG80); GRCC10 (C10); GRP; GSN (Gelsolin); GSTP1; HAVCR2; HDAC4; HDAC5; HDAC7A; HDAC9; HGF; HIF1A; HIP1; histamine and histamine receptors; Her3; HLA-A; HLA-DRA; HM74; HMOX1; HUMCYT2A; ICEBERG; ICOSL; ID2; IFN-α; IFNA1; IFNA2; IFNA4; IFNA5; IFNA6; IFNA7; IFNB1; IFNgamma; IFNW1; IGBP1; IGF1; IGF1R; IGF2; IGFBP2; IGFBP3; IGFBP6; IL-1; IL10; IL10RA; IL10RB; IL11; IL11RA; IL-12; IL12A; IL12B; IL12RB1; IL12RB2; IL13; IL13RA1; IL13RA2; IL14; IL15; IL15RA; IL16; IL17; IL17B; IL17C; IL17R; IL18; IL18BP; IL18R1; IL18RAP; IL19; IL1A; IL1B; IL1F10; IL1F5; IL1F6; IL1F7; IL1F8; IL1F9; IL1HY1; IL1R1; IL1R2; IL1RAP; IL1RAPL1; IL1RAPL2; IL1RL1; IL1RL2 IL1RN; IL2; IL20; IL20RA; IL21R; IL22; IL22R; IL22RA2; IL23; IL24; IL25; IL26; IL27; IL28A; IL28B; IL29; IL2RA; IL2RB; IL2RG; IL3; IL30; IL3RA; IL4; IL4R; IL5; IL5RA; IL6; IL6R; IL6ST (glycoprotein 130); IL7; IL7R; IL8; IL8RA; IL8RB; IL8RB; IL9; IL9R; ILK; INHA; INHBA; INSL3; INSL4; IRAK1; IRAK2; ITGA1; ITGA2; ITGA3; ITGA6 (a6 integrin); ITGAV; ITGB3; ITGB4 (b 4 integrin); JAG1; JAK1; JAK3; JUN; K6HF; KAI1; KDR; KITLG; KLF5 (GC Box BP); KLF6; KLK10; KLK12; KLK13; KLK14; KLK15; KLK3; KLK4; KLK5; KLK6; KLK9; KRT1; KRT19 (Keratin 19); KRT2A; KRTHB6 (hair-specific type II keratin); LAMA5; LEP (leptin); Lingo-p75; Lingo-Troy; LPS; LTA (TNF-b); LTB; LTB4R (GPR16); LTB4R2; LTBR; MACMARCKS; MAG or Omgp; MAP2K7 (c-Jun); MDK; MIB1; midkine; MIF; MIP-2; MKI67 (Ki-67); MMP2; MMP9; MS4A1; MSMB; MT3 (metallothionectin-III); MTSS1; MUC1 (mucin); MYC; MYD88; NCK2; neurocan; NFKB1; NFKB2; NGFB (NGF); NGFR; NgR-Lingo; NgR-Nogo66 (Nogo); NgR-p75; NgR-Troy; NME1 (NM23A); NOX5; NPPB; NROB1; NROB2; NR1D1; NR1D2; NR1H2; NR1H3; NR1H4; NR1I2; NR1I3; NR2C1; NR2C2; NR2E1; NR2E3; NR2F1; NR2F2; NR2F6; NR3C1; NR3C2; NR4A1; NR4A2; NR4A3; NR5A1; NR5A2; NR6A1; NRP1; NRP2; NT5E; NTN4; ODZ1; OPRD1; PCSK9; P2RX7; PAP; PART1; PATE; PAWR; PCA3; PCNA; PD-1; PD-L1; alpha4beta7, OX40, GITR, TIM-3, Lag-3, B7-H3, B7-H4, GDF8, CGRP, Lingo-1, Factor IXa, Factor X, ICOS, GARP, BTLA, CD160, ROR1, 2B4, KIR, CD27, OX40, CD40L, A2aR, PDGFA; PDGFB; PECAM1; PF4 (CXCL4); PGF; PGR; phosphacan; PIAS2; PIK3CG; PLAU (uPA); PLG; PLXDC1; PPBP (CXCL7); PPID; PR1; PRKCQ; PRKD1; PRL; PROC; PROK2; PSAP; PSCA; PTAFR; PTEN; PTGS2 (COX-2); PTN; RAC2 (p21Rac2); RARB; RGS1; RGS13; RGS3; RNF110 (ZNF144); ROBO2; S100A2; SCGB1D2 (lipophilin B); SCGB2A1 (mammaglobin 2); SCGB2A2 (mammaglobin 1); SCYE1 (endothelial Monocyte-activating cytokine); SDF2; SERPINA1; SERPINA3; SERPINB5 (maspin); SERPINE1 (PAI-1); SERPINF1; SHBG; SLA2; SLC2A2; SLC33A1; SLC43A1; SLIT2; SPP1; SPRR1B (Spr1); ST6GAL1; STAB1; STAT6; STEAP; STEAP2; TB4R2; TBX21; TCP10; TDGF1; TEK; TGFA; TGFB1; TGFB1I1; TGFB2; TGFB3; TGFB1; TGFBR1; TGFBR2; TGFBR3; TH1L; THBS1 (thrombospondin-1); THBS2; THBS4; THPO; TIE (Tie-1); TIMP3; tissue factor; TLR10; TLR2; TLR3; TLR4; TLR5; TLR6; TLR7; TLR8; TLR9; TNF; TNF-a; TNFAIP2 (B94); TNFAIP3; TNFRSF11A; TNFRSF1A; TNFRSF1B; TNFRSF21; TNFRSF5; TNFRSF6 (Fas); TNFRSF7;

TNFRSF8; TNFRSF9; TNFSF10 (TRAIL); TNFSF11 (TRANCE); TNFSF12 (APO3L); TNFSF13 (April); TNFSF13B; TNFSF14 (HVEM-L); TNFSF15 (VEGI); TNFSF18; TNFSF4 (OX40 ligand); TNFSF5 (CD40 ligand); TNFSF6 (FasL); TNFSF7 (CD27 ligand); TNFSF8 (CD30 ligand); TNFSF9 (4-11B ligand); TOLLIP; Toll-like receptors; TOP2A (topoisomerase Iia); TP53; TPM1; TPM2; TRADD; TRAF1; TRAF2; TRAF3; TRAF4; TRAF5; TRAF6; TREM1; TREM2; TRPC6; TSLP; TWEAK; VEGF; VEGFB; VEGFC; versican; VHL C5; $VL_4$-4; XCL1 (lymphotactin); XCL2 (SCM-1b); XCR1 (GPR5/CCXCR1); YY1; and ZFPM2.

Given their ability to bind to two or more antigens, the binding proteins of the present invention can be used to detect the antigens (e.g., in a biological sample, such as serum or plasma), using a conventional immunoassay, such as an enzyme linked immunosorbent assays (ELISA), an radioimmunoassay (RIA) or tissue immunohistochemistry. The FIT-Ig is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include 3H, 14C, 35S, 90Y, 99Tc, 111In, 125I, 131I, 177Lu, 166Ho, or 153Sm.

The binding proteins of the invention, in one embodiment, are capable of neutralizing the activity of the antigens both in vitro and in vivo. Accordingly, such FIT-Igs can be used to inhibit antigen activity, e.g., in a cell culture containing the antigens, in human subjects or in other mammalian subjects having the antigens with which a binding protein of the invention cross-reacts. In another embodiment, the invention provides a method for reducing antigen activity in a subject suffering from a disease or disorder in which the antigen activity is detrimental. A binding protein of the invention can be administered to a human subject for therapeutic purposes.

As used herein, the term "a disorder in which antigen activity is detrimental" is intended to include diseases and other disorders in which the presence of the antigen in a subject suffering from the disorder has been shown to be or is suspected of being either responsible for the pathophysiology of the disorder or a factor that contributes to a worsening of the disorder. Accordingly, a disorder in which antigen activity is detrimental is a disorder in which reduction of antigen activity is expected to alleviate the symptoms and/or progression of the disorder. Such disorders may be evidenced, for example, by an increase in the concentration of the antigen in a biological fluid of a subject suffering from the disorder (e.g., an increase in the concentration of antigen in serum, plasma, synovial fluid, etc. of the subject). Non-limiting examples of disorders that can be treated with the binding proteins of the invention include those disorders discussed below and in the section pertaining to pharmaceutical compositions of the antibodies of the invention.

The FIT-Igs of the invention may bind one antigen or multiple antigens. Such antigens include, but are not limited to, the targets listed in the following databases, which databases are incorporated herein by reference. These target databases include, but are not limited to, the following listings:

Therapeutic targets (http://xin.cz3.nus.edu.sg/group/cjttd/ttd.asp);

Cytokines and cytokine receptors (http://www.cytokinewebfacts.com/, http://www.copewithcytokines.de/cope.cgi, and http://cmbi.bjmu.edu.cn/cmbidata/cgf/CGF_Database/cytokine.medic.kumamoto-u.ac.jp/CFC/indexR.html);

Chemokines (http://cytokine.medic.kumamoto-u.ac.jp/CFC/CK/Chemokine.html);

Chemokine receptors and GPCRs (http://csp.medic.kumamoto-u.ac.jp/CSP/Receptor.html, http://www.gpcr.org/7tm/);

Olfactory Receptors (http://senselab.med.yale.edu/senselab/ORDB/default.asp);

Receptors (http://www.iuphar-db.org/iuphar-rd/list/index.htm);

Cancer targets (http://cged.hgc.jp/cgi-bin/input.cgi);

Secreted proteins as potential antibody targets (http://spd.cbi.pku.edu.cn/);

Protein kinases (http://spd.cbi.pku.edu.cn/), and

Human CD markers (http://content.labvelocity.com/tools/6/1226/CD_table_final_locked.pdf) and (Zola H, 2005 CD molecules 2005: human cell differentiation molecules Blood, 106:3123-6).

FIT-Igs are useful as therapeutic agents to simultaneously block two different targets to enhance efficacy/safety and/or increase patient coverage. Such targets may include soluble targets (e.g., IL-13 and TNF) and cell surface receptor targets (e.g., VEGFR and EGFR). It can also be used to induce redirected cytotoxicity between tumor cells and T cells (Her2 and CD3) for cancer therapy, or between autoreactive cell and effector cells for autoimmune/transplantation, or between any target cell and effector cell to eliminate disease-causing cells in any given disease.

In addition, FIT-Ig can be used to trigger receptor clustering and activation when it is designed to target two different epitopes on the same receptor. This may have benefit in making agonistic and antagonistic anti-GPCR therapeutics. In this case, FIT-Ig can be used to target two different epitopes on one cell for clustering/signaling (two cell surface molecules) or signaling (on one molecule). Similarly, a FIT-Ig molecule can be designed to trigger CTLA-4 ligation, and a negative signal by targeting two different epitopes (or 2 copies of the same epitope) of CTLA-4 extracellular domain, leading to down regulation of the immune response. CTLA-4 is a clinically validated target for therapeutic treatment of a number of immunological disorders. CTLA-4/B7 interactions negatively regulate T cell activation by attenuating cell cycle progression, IL-2 production, and proliferation of T cells following activation, and CTLA-4 (CD152) engagement can down-regulate T cell activation and promote the induction of immune tolerance. However, the strategy of attenuating T cell activation by agonistic antibody engagement of CTLA-4 has been unsuccessful since CTLA-4 activation requires ligation. The molecular interaction of CTLA-4/B7 is in "skewed zipper" arrays, as demonstrated by crystal structural analysis (Stamper 2001 Nature 410:608). However none of the currently available CTLA-4 binding reagents have ligation properties, including anti-CTLA-4 monoclonal antibodies. There have been several attempts to address this issue. In one case, a cell member-bound single chain antibody was generated, and significantly inhibited allogeneic rejection in mice (Hwang 2002 JI 169:633). In a separate case, artificial APC surface-linked single-chain antibody to CTLA-4 was generated and demonstrated to attenuate T cell responses (Griffin 2000 JI 164:4433). In both cases, CTLA-4 ligation was achieved by closely localized member-bound antibodies in artificial systems. While these experiments provide proof-of-concept for immune down-regulation by triggering CTLA-4 negative signaling, the reagents used in these reports are not suitable for therapeutic use. To this end, CTLA-4 ligation may be achieved by using a FIT-Ig molecule, which target two different epitopes (or 2 copies of the same epitope) of CTLA-4 extracellular domain. The rationale is that the distance spanning two binding sites of an IgG, approximately 150-170A, is too large for active ligation of CTLA-4 (30-50 Å between 2 CTLA-4 homodimer). However the distance between the two binding sites on FIT-Ig (one arm) is much shorter, also in the range of 30-50 Å, allowing proper ligation of CTLA-4.

Similarly, FIT-Ig can target two different members of a cell surface receptor complex (e.g. IL-12R alpha and beta). Furthermore, FIT-Ig can target CR1 and a soluble protein/pathogen to drive rapid clearance of the target soluble protein/pathogen.

Additionally, FIT-Igs of the invention can be employed for tissue-specific delivery (target a tissue marker and a disease mediator for enhanced local PK thus higher efficacy and/or lower toxicity), including intracellular delivery (targeting an internalizing receptor and a intracellular molecule), delivering to inside brain (targeting transferrin receptor and a CNS disease mediator for crossing the blood-brain barrier). FIT-Ig can also serve as a carrier protein to deliver an antigen to a specific location via biding to a non-neutralizing epitope of that antigen and also to increase the half-life of the antigen. Furthermore, FIT-Ig can be designed to either be physically linked to medical devices implanted into patients or target these medical devices (Burke, Sandra E.; Kuntz, Richard E.; Schwartz, Lewis B. Zotarolimus (ABT-578) eluting stents. Advanced Drug Delivery Reviews (2006), 58(3), 437-446. Surface coatings for biological activation and functionalization of medical devices. Hildebrand, H. F.; Blanchemain, N.; Mayer, G.; Chai, F.; Lefebvre, M.; Boschin, F. Surface and Coatings Technology (2006), 200(22-23), 6318-6324; Drug/device combinations for local drug therapies and infection prophylaxis. Wu, Peng; Grainger, David W. Biomaterials (2006), 27(11), 2450-2467; Mediation of the cytokine network in the implantation of orthopedic devices. Marques, A. P.; Hunt, J. A.; Reis, Rui L. Biodegradable Systems in Tissue Engineering and Regenerative Medicine (2005), 377-397; Page: 52

Mediation of the cytokine network in the implantation of orthopedic devices. Marques, A. P.; Hunt, J. A.; Reis, Rui L. Biodegradable Systems in Tissue Engineering and Regenerative Medicine (2005), 377-397.) Briefly, directing appropriate types of cell to the site of medical implant may promote healing and restoring normal tissue function. Alternatively, inhibition of mediators (including but not limited to cytokines), released upon device implantation by a FIT-Ig coupled to or target to a device is also provided. For example, Stents have been used for years in interventional cardiology to clear blocked arteries and to improve the flow of blood to the heart muscle. However, traditional bare metal stents have been known to cause restenosis (re-narrowing of the artery in a treated area) in some patients and can lead to blood clots. Recently, an anti-CD34 antibody coated stent has been described which reduced restenosis and prevents blood clots from occurring by capturing endothelial progenitor cells (EPC) circulating throughout the blood. Endothelial cells are cells that line blood vessels, allowing blood to flow smoothly. The EPCs adhere to the hard surface of the stent forming a smooth layer that not only promotes healing but prevents restenosis and blood clots, complications previously associated with the use of stents (Aoji et al. 2005 J Am Coll Cardiol. 45(10):1574-9). In addition to improving outcomes for patients requiring stents, there are also implications for patients requiring cardiovascular bypass surgery. For example, a prosthetic vascular conduit (artificial artery) coated with anti-EPC antibodies would eliminate the need to use arteries from patients legs or arms for bypass surgery grafts. This would reduce surgery and anesthesia times, which in turn will reduce coronary surgery deaths. FIT-Ig are designed in such a way that it binds to a cell surface marker (such as CD34) as well as a protein (or an epitope of any kind, including but not limited to lipids and polysaccharides) that has been coated on the implanted device to facilitate the cell recruitment. Such approaches can also be applied to other medical implants in general. Alternatively, FIT-Igs can be coated on medical devices and upon implantation and releasing all FITs from the device (or any other need which may require additional fresh FIT-Ig, including aging and denaturation of the already loaded FIT-Ig) the device could be reloaded by systemic administration of fresh FIT-Ig to the patient, where the FIT-Ig is designed to binds to a target of interest (a cytokine, a cell surface marker (such as CD34) etc.) with one set of binding sites and to a target coated on the device (including a protein, an epitope of any kind, including but not limited to lipids, polysaccharides and polymers) with the other. This technology has the advantage of extending the usefulness of coated implants.

FIT-Ig molecules of the invention are also useful as therapeutic molecules to treat various diseases. Such FIT-Ig molecules may bind one or more targets involved in a specific disease. Examples of such targets in various diseases are described below.

Many proteins have been implicated in general autoimmune and inflammatory responses, including C5, CCL1 (I-309), CCL11 (eotaxin), CCL13 (mcp-4), CCL15 (MIP-1d), CCL16 (HCC-4), CCL17 (TARC), CCL18 (PARC), CCL19, CCL2 (mcp-1), CCL20 (MIP-3a), CCL21 (MIP-2), CCL23 (MPIF-1), CCL24 (MPIF-2/eotaxin-2), CCL25 (TECK), CCL26, CCL3 (MIP-1a), CCL4 (MIP-1b), CCL5 (RANTES), CCL7 (mcp-3), CCL8 (mcp-2), CXCL1, CXCL10 (IP-10), CXCL11 (I-TAC/IP-9), CXCL12 (SDF1), CXCL13, CXCL14, CXCL2, CXCL3, CXCL5 (ENA-78/LIX), CXCL6 (GCP-2), CXCL9, IL13, IL8, CCL13 (mcp-4), CCR1, CCR2, CCR3, CCR4, CCR5, CCR6, CCR7, CCR8, CCR9, CX3CR1, IL8RA, XCR1 (CCXCR1), IFNA2, IL10, IL13, IL17C, IL1A, IL1B, IL1F10, IL1F5, IL1F6, IL1F7, IL1F8, IL1F9, IL22, IL5, IL8, IL9, LTA, LTB, MIF, SCYE1 (endothelial Monocyte-activating cytokine), SPP1, TNF, TNFSF5, IFNA2, IL10RA, IL10RB, IL13, IL13RA1, IL5RA, IL9, IL9R, ABCF1, BCL6, C3, C4A, CEBPB, CRP, ICEBERG, IL1R1, IL1RN, IL8RB, LTB4R, TOLLIP, FADD, IRAK1, IRAK2, MYD88, NCK2, TNFAIP3, TRADD, TRAF1, TRAF2, TRAF3, TRAF4, TRAF5, TRAF6, ACVR1, ACVR1B, ACVR2, ACVR2B, ACVRL1, CD28, CD3E, CD3G, CD3Z, CD69, CD80, CD86, CNR1, CTLA-4, CYSLTR1, FCER1A, FCER2, FCGR3A, GPR44, HAVCR2, OPRD1, P2RX7, TLR2, TLR3, TLR4, TLR5, TLR6, TLR7, TLR8, TLR9, TLR10, BLR1, CCL1, CCL2, CCL3, CCL4, CCL5, CCL7, CCL8, CCL11, CCL13, CCL15, CCL16, CCL17, CCL18, CCL19, CCL20, CCL21, CCL22, CCL23, CCL24, CCL25, CCR1, CCR2, CCR3, CCR4, CCR5, CCR6, CCR7, CCR8, CCR9, CX3CL1, CX3CR1, CXCL1, CXCL2, CXCL3, CXCL5, CXCL6, CXCL10, CXCL11, CXCL12, CXCL13, CXCR4, GPR2, SCYE1, SDF2, XCL1, XCL2, XCR1, AMH, AMHR2, BMPR1A, BMPR1B, BMPR2, C19orf10 (IL27w), CER1, CSF1, CSF2, CSF3, DKFZp451J0118, FGF2, GFI1, IFNA1, IFNB1, IFNG, IGF1, IL1A, IL1B, IL1R1, IL1R2, IL2, IL2RA, IL2RB, IL2RG, IL3, IL4, IL4R, IL5, IL5RA, IL6, IL6R, IL6ST, IL7, IL8, IL8RA, IL8RB, IL9, IL9R, IL10, IL10RA, IL10RB, IL11, IL11RA, IL12A, IL12B, IL12RB1, IL12RB2, IL13, IL13RA1, IL13RA2, IL15, IL15RA, IL16, IL17, IL17R, IL18, IL18R1, IL19, IL20, KITLG, LEP, LTA, LTB, LTB4R, LTB4R2, LTBR, MIF, NPPB, PDGFB, TBX21, TDGF1, TGFA, TGFB1, TGFB1I1, TGFB2, TGFB3, TGFB1, TGFBR1, TGFBR2, TGFBR3, TH1L, TNF, TNFRSF1A, TNFRSF1B, TNFRSF7, TNFRSF8, TNFRSF9, TNFRSF11A, TNFRSF21, TNFSF4, TNFSF5, TNFSF6, TNFSF11, VEGF, ZFPM2, and RNF110 (ZNF144). FIT-Igs capable of binding one or more of the targets listed above are also contemplated.

Allergic asthma is characterized by the presence of eosinophilia, goblet cell metaplasia, epithelial cell alterations, airway hyperreactivity (AHR), and Th2 and Th1 cytokine expression, as well as elevated serum IgE levels. It is now widely accepted that airway inflammation is the key factor underlying the pathogenesis of asthma, involving a complex interplay of inflammatory cells such as T cells, B cells, eosinophils, mast cells and macrophages, and of their secreted mediators including cytokines and chemokines. Corticosteroids are the most important anti-inflammatory treatment for asthma today, however their mechanism of action is non-specific and safety concerns exist, especially in the juvenile patient population. The development of more specific and targeted therapies is therefore warranted. There is increasing evidence that IL-13 in mice mimics many of the features of asthma, including AHR, mucus hypersecretion and airway fibrosis, independently of eosinophilic inflammation (Finotto et al., International Immunology (2005), 17(8), 993-1007; Padilla et al., Journal of Immunology (2005), 174(12), 8097-8105).

IL-13 has been implicated as having a pivotal role in causing pathological responses associated with asthma. The development of anti-IL-13 monoclonal antibody therapy to reduce the effects of IL-13 in the lung is an exciting new approach that offers considerable promise as a novel treatment for asthma. However other mediators of differential immunological pathways are also involved in asthma pathogenesis, and blocking these mediators, in addition to IL-13, may offer additional therapeutic benefit. Such target pairs include, but are not limited to, IL-13 and a pro-inflammatory cytokine, such as tumor necrosis factor-α (TNF-α). TNF-α may amplify the inflammatory response in asthma and may be linked to disease severity (McDonnell, et al., Progress in Respiratory Research (2001), 31 (New Drugs for Asthma, Allergy and COPD), 247-250). This suggests that blocking both IL-13 and TNF-α may have beneficial effects, particularly in severe airway disease. In a preferred embodiment the FIT-Ig of the invention binds the targets IL-13 and TNFα and is used for treating asthma.

Animal models such as OVA-induced asthma mouse model, where both inflammation and AHR can be assessed, are known in the art and may be used to determine the ability of various FIT-Ig molecules to treat asthma. Animal models for studying asthma are disclosed in Coffman, et al., Journal of Experimental Medicine (2005), 201(12), 1875-1879; Lloyd, et al., Advances in Immunology (2001), 77, 263-295; Boyce et al., Journal of Experimental Medicine (2005), 201(12), 1869-1873; and Snibson, et al., Journal of the British Society for Allergy and Clinical Immunology (2005), 35(2), 146-52. In addition to routine safety assessments of these target pairs specific tests for the degree of immunosuppression may be warranted and helpful in selecting the best target pairs (see Luster et al., Toxicology (1994), 92(1-3), 229-43; Descotes, et al., Developments in biological standardization (1992), 77 99-102; Hart et al., Journal of Allergy and Clinical Immunology (2001), 108(2), 250-257).

Based on the rationale disclosed above and using the same evaluation model for efficacy and safety other pairs of targets that FIT-Ig molecules can bind and be useful to treat asthma may be determined. Preferably such targets include, but are not limited to, IL-13 and IL-1beta, since IL-1beta is also implicated in inflammatory response in asthma; IL-13 and cytokines and chemokines that are involved in inflammation, such as IL-13 and IL-9; IL-13 and IL-4; IL-13 and IL-5; IL-13 and IL-25; IL-13 and TARC; IL-13 and MDC; IL-13 and MIF; IL-13 and TGF-0; IL-13 and LHR agonist; IL-13 and CL25; IL-13 and SPRR2a; IL-13 and SPRR2b; and IL-13 and ADAM8. The present invention also contemplates FIT-Igs capable of binding one or more targets involved in asthma selected from the group consisting of CSF1 (MCSF), CSF2 (GM-CSF), CSF3 (GCSF), FGF2, IFNA1, IFNB1, IFNG, histamine and histamine receptors, IL1A, IL1B, IL2, IL3, IL4, IL5, IL6, IL7, IL8, IL9, IL10, IL11, IL12A, IL12B, IL13, IL14, IL15, IL16, IL17, IL18, IL19, KITLG, PDGFB, IL2RA, IL4R, IL5RA, IL8RA, IL8RB, IL12RB1, IL12RB2, IL13RA1, IL13RA2, IL18R1, TSLP, CCL1, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCL1, CCR2, CCR3, CCR4, CCR5, CCR6, CCR7, CCR8, CX3CR1, GPR2, XCR1, FOS, GATA3, JAK1, JAK3, STAT6, TBX21, TGFB1, TNFSF6, YY1, CYSLTR1, FCER1A, FCER2, LTB4R, TB4R2, LTBR, and Chitinase.

Rheumatoid arthritis (RA), a systemic disease, is characterized by a chronic inflammatory reaction in the synovium of joints and is associated with degeneration of cartilage and erosion of juxta-articular bone. Many pro-inflammatory cytokines including TNF, chemokines, and growth factors are expressed in diseased joints. Systemic administration of anti-TNF antibody or sTNFR fusion protein to mouse models of RA was shown to be anti-inflammatory and joint protective. Clinical investigations in which the activity of TNF in RA patients was blocked with intravenously administered infliximab (Harriman G, Harper L K, Schaible T F. 1999 Summary of clinical trials in rheumatoid arthritis using infliximab, an anti-TNFalpha treatment. Ann Rheum Dis 58 Suppl 1:I61-4), a chimeric anti-TNF monoclonal antibody (mAB), has provided evidence that TNF regulates IL-6, IL-8, MCP-1, and VEGF production, recruitment of immune and inflammatory cells into joints, angiogenesis, and reduction of blood levels of matrix metalloproteinases-1 and -3. A better understanding of the inflammatory pathway in rheumatoid arthritis has led to identification of other therapeutic targets involved in rheumatoid arthritis. Promising treatments such as interleukin-6 antagonists (MRA), CTLA4Ig (abatacept, Genovese Mc et al 2005 Abatacept for rheumatoid arthritis refractory to tumor necrosis factor alpha inhibition. N Engl J Med. 353:1114-23), and anti-B cell therapy (rituximab, Okamoto H, Kamatani N. 2004 Rituximab for rheumatoid arthritis. N Engl J Med. 351:1909) have already been tested in randomized controlled trials over the past year. Other cytokines have been identified and have been shown to be of benefit in animal models, including interleukin-15, interleukin-17, and interleukin-18, and clinical trials of these agents are currently under way. Dual-specific antibody therapy, combining anti-TNF and another mediator, has great potential in enhancing clinical efficacy and/or patient coverage. For example, blocking both TNF and VEGF can potentially eradicate inflammation and angiogenesis, both of which are involved in pathophysiology of RA. Blocking other pairs of targets involved in RA including, but not limited to, TNF and IL-18; TNF and IL-12; TNF and IL-23; TNF and IL-1beta; TNF and MIF; TNF and IL-17; and TNF and IL-15 with specific FIT-Ig Igs is also contemplated. In addition to routine safety assessments of these target pairs, specific tests for the degree of immunosuppression may be warranted and helpful in selecting the best target pairs (see Luster et al., Toxicology (1994), 92(1-3), 229-43; Descotes, et al., Developments in biological standardization (1992), 77 99-102; Hart et al., Journal of Allergy and Clinical Immunology (2001), 108(2), 250-257). Whether a FIT-Ig Ig molecule will be useful for the treatment of rheumatoid arthritis can be assessed using pre-clinical animal RA models such as the collagen-induced arthritis mouse model. Other useful models are also well known in the art (see Brand D D., Comp Med. (2005) 55(2):114-22).

The immunopathogenic hallmark of systemic lupus erythematosus (SLE) is the polyclonal B cell activation, which leads to hyperglobulinemia, autoantibody production and immune complex formation. The fundamental abnormality appears to be the failure of T cells to suppress the forbidden B cell clones due to generalized T cell dysregulation. In addition, B and T-cell interaction is facilitated by several cytokines such as IL-1β as well as co-stimulatory molecules such as CD40 and CD40L, B7 and CD28 and CTLA-4, which initiate the second signal. These interactions together with impaired phagocytic clearance of immune complexes and apoptotic material, perpetuate the immune response with resultant tissue injury. The following targets may be involved in SLE and can potentially be used for FIT-Ig approach for therapeutic intervention: B cell targeted therapies: CD-20, CD-22, CD-19, CD28, CD4, CD80, HLA-DRA, IL10, IL2, IL4, TNFRSF5, TNFRSF6, TNFSF5, TNFSF6, BLR1, HDAC4, HDAC5, HDAC7A, HDAC9, ICOSL, IGBP1, MS4A1, RGS1, SLA2, CD81, IFNB1, IL10, TNFRSF5, TNFRSF7, TNFSF5, AICDA, BLNK, GALNAC4S-6ST, HDAC4, HDAC5, HDAC7A, HDAC9, IL10, IL11, IL4, INHA, INHBA, KLF6, TNFRSF7, CD28, CD38, CD69, CD80, CD83, CD86, DPP4, FCER2, TL2RA, TNFRSF8, TNFSF7, CD24, CD37, CD40, CD72, CD74, CD79A, CD79B, CR2, IL1R2, ITGA2, ITGA3, MS4A1, ST6GAL1, CD1C, CHST10, HLA-A, HLA-DRA, and NT5E.; co-stimulatory signals: CTLA-4 or B7.1/B7.2; inhibition of B cell survival: BlyS, BAFF; Complement inactivation: C5; Cytokine modulation: the key principle is that the net biologic response in any tissue is the result of a balance between local levels of proinflammatory or anti-inflammatory cytokines (see Sfikakis P P et al 2005 Curr Opin Rheumatol 17:550-7). SLE is considered to be a Th-2 driven disease with documented elevations in serum IL-4, IL-6, IL-10. FIT-Ig Igs capable of binding one or more targets selected from the group consisting of IL-4, IL-6, IL-1β, IFN-a, and TNF-a are also contemplated. Combination of targets discussed above will enhance therapeutic efficacy for SLE which can be tested in a number of lupus preclinical models (see Peng S L (2004) Methods Mol Med.; 102:227-72).

Multiple sclerosis (MS) is a complex human autoimmune-type disease with a predominantly unknown etiology. Immunologic destruction of myelin basic protein (MBP) throughout the nervous system is the major pathology of multiple sclerosis. MS is a disease of complex pathologies, which involves infiltration by CD4+ and CD8+ T cells and of response within the central nervous system. Expression in the CNS of cytokines, reactive nitrogen species and costimulator molecules have all been described in MS. Of major consideration are immunological mechanisms that contribute to the development of autoimmunity. In particular, antigen expression, cytokine and leukocyte interactions, and regulatory T-cells, which help balance/modulate other T-cells such as Th1 and Th2 cells, are important areas for therapeutic target identification.

IL-12 is a proinflammatory cytokine that is produced by APC and promotes differentiation of Th1 effector cells. IL-12 is produced in the developing lesions of patients with MS as well as in EAE-affected animals. Previously it was shown that interference in IL-12 pathways effectively prevents EAE in rodents, and that in vivo neutralization of IL-12p40 using a anti-IL-12 mAb has beneficial effects in the myelin-induced EAE model in common marmosets.

TWEAK is a member of the TNF family, constitutively expressed in the central nervous system (CNS), with pro-inflammatory, proliferative or apoptotic effects depending upon cell types. Its receptor, Fn14, is expressed in CNS by endothelial cells, reactive astrocytes and neurons. TWEAK and Fn14 mRNA expression increased in spinal cord during experimental autoimmune encephalomyelitis (EAE). Anti-TWEAK antibody treatment in myelin oligodendrocyte glycoprotein (MOG) induced EAE in C57BL/6 mice resulted in a reduction of disease severity and leukocyte infiltration when mice were treated after the priming phase.

One aspect of the invention pertains to FIT-Ig Ig molecules capable of binding one or more, preferably two, targets selected from the group consisting of IL-12, TWEAK, IL-23, CXCL13, CD40, CD40L, IL-18, VEGF, $VL_A$-4, TNF, CD45RB, CD200, IFNgamma, GM-CSF, FGF, C5, CD52, and CCR2. A preferred embodiment includes a dual-specific anti-IL-12/TWEAK FIT-Ig Ig as a therapeutic agent beneficial for the treatment of MS. Several animal models for assessing the usefulness of the FIT-Ig molecules to treat MS are known in the art (see Steinman L, et al., (2005) Trends Immunol. 26(11):565-71; Lublin F D., et al., (1985) Springer Semin Immunopathol. 8(3):197-208; Genain C P, et al., (1997) J Mol Med. 75(3):187-97; Tuohy V K, et al., (1999) J Exp Med. 189(7):1033-42; Owens T, et al., (1995) Neurol Clin. 13(1):51-73; and 't Hart B A, et al., (2005) J Immunol 175(7):4761-8. In addition to routine safety assessments of these target pairs specific tests for the degree of immunosuppression may be warranted and helpful in selecting the best target pairs (see Luster et al., Toxicology (1994), 92(1-3), 229-43; Descotes, et al., Developments in biological standardization (1992), 77 99-102; Jones R. 2000 Rovelizumab (ICOS Corp). IDrugs. 3(4):442-6).

The pathophysiology of sepsis is initiated by the outer membrane components of both gram-negative organisms (lipopolysaccharide [LPS], lipid A, endotoxin) and gram-positive organisms (lipoteichoic acid, peptidoglycan). These outer membrane components are able to bind to the CD14 receptor on the surface of monocytes. By virtue of the recently described toll-like receptors, a signal is then transmitted to the cell, leading to the eventual production of the proinflammatory cytokines tumor necrosis factor-alpha (TNF-alpha) and interleukin-1 (IL-I). Overwhelming inflammatory and immune responses are essential features of septic shock and play a central part in the pathogenesis of tissue damage, multiple organ failure, and death induced by sepsis. Cytokines, especially tumor necrosis factor (TNF) and interleukin (IL)-1, have been shown to be critical mediators of septic shock. These cytokines have a direct toxic effect on tissues; they also activate phospholipase A2. These and other effects lead to increased concentrations of platelet-activating factor, promotion of nitric oxide synthase activity, promotion of tissue infiltration by neutrophils, and promotion of neutrophil activity.

The treatment of sepsis and septic shock remains a clinical conundrum, and recent prospective trials with biological response modifiers (i.e. anti-TNF, anti-MIF) aimed at the inflammatory response have shown only modest clinical benefit. Recently, interest has shifted toward therapies aimed at reversing the accompanying periods of immune suppression. Studies in experimental animals and critically ill patients have demonstrated that increased apoptosis of lymphoid organs and some parenchymal tissues contribute to this immune suppression, anergy, and organ system dysfunction. During sepsis syndromes, lymphocyte apoptosis can be triggered by the absence of IL-2 or by the release of glucocorticoids, granzymes, or the so-called 'death' cytokines: tumor necrosis factor alpha or Fas ligand. Apoptosis proceeds via auto-activation of cytosolic and/or mitochondrial caspases, which can be influenced by the pro- and anti-apoptotic members of the Bcl-2 family. In experimental animals, not only can treatment with inhibitors of apoptosis prevent lymphoid cell apoptosis; it may also improve outcome. Although clinical trials with anti-apoptotic agents remain distant due in large part to technical difficulties associated with their administration and tissue targeting, inhibition of lymphocyte apoptosis represents an attractive therapeutic target for the septic patient. Likewise, a dual-specific agent targeting both inflammatory mediator and a apoptotic mediator, may have added benefit. One aspect of the invention pertains to FIT-Ig Igs capable of binding one or more targets involved in sepsis, preferably two targets, selected from the group consisting TNF, IL-1, MIF, IL-6, IL-8, IL-18, IL-12, IL-23, FasL, LPS, Toll-like receptors, TLR-4, tissue factor, MIP-2, ADORA2A, CASP1, CASP4, IL10, IL1B, NFKB1, PROC, TNFRSF1A, CSF3, IL10, IL1B, IL6, ADORA2A, CCR3, IL10, IL1B, IL1RN, MIF, NFKB1, PTAFR, TLR2, TLR4, GPR44, HMOX1, midkine, IRAK1, NFKB2, SERPINA1, SERPINE1, and TREM1. The efficacy of such FIT-Ig Igs for sepsis can be assessed in preclinical animal models known in the art (see Buras J A, et al., (2005) Nat Rev Drug Discov. 4(10):854-65 and Calandra T, et al., (2000) Nat Med. 6(2):164-70).

Chronic neurodegenerative diseases are usually age-dependent diseases characterized by progressive loss of neuronal functions (neuronal cell death, demyelination), loss of mobility and loss of memory. Emerging knowledge of the mechanisms underlying chronic neurodegenerative diseases (e.g. Alzheimer's disease) show a complex etiology and a variety of factors have been recognized to contribute to their development and progression e.g. age, glycemic status, amyloid production and multimerization, accumulation of advanced glycation-end products (AGE) which bind to their receptor RAGE (receptor for AGE), increased brain oxidative stress, decreased cerebral blood flow, neuroinflammation including release of inflammatory cytokines and chemokines, neuronal dysfunction and microglial activation. Thus these chronic neurodegenerative diseases represent a complex interaction between multiple cell types and mediators. Treatment strategies for such diseases are limited and mostly constitute either blocking inflammatory processes with non-specific anti-inflammatory agents (e.g., corticosteroids, COX inhibitors) or agents to prevent neuron loss and/or synaptic functions. These treatments fail to stop disease progression. Recent studies suggest that more targeted therapies such as antibodies to soluble A-β peptide (including the A-b oligomeric forms) can not only help stop disease progression but may help maintain memory as well. These preliminary observations suggest that specific therapies targeting more than one disease mediator (e.g. A-β and a pro-inflammatory cytokine such as TNF) may provide even better therapeutic efficacy for chronic neurodegenerative diseases than observed with targeting a single disease mechanism (e.g. soluble A-Palone) (see C. E. Shepherd, et al, Neurobiol Aging. 2005 Oct. 24; Nelson R B., Curr Pharm Des. 2005; 11:3335; William L. Klein; Neurochem Int. 2002; 41:345; Michelle C Janelsins, et al., J Neuroinflammation. 2005; 2:23; Soloman B., Curr Alzheimer Res. 2004; 1:149; Igor Klyubin, et al., Nat Med. 2005; 11:556-61; Arancio O, et al., EMBO Journal (2004) 1-10; Bornemann K D, et al., Am J Pathol. 2001; 158:63; Deane R, et al., Nat Med. 2003; 9:907-13; and Eliezer Masliah, et al., Neuron. 2005; 46:857).

The FIT-Ig molecules of the invention can bind one or more targets involved in Chronic neurodegenerative diseases such as Alzheimer's. Such targets include, but are not limited to, any mediator, soluble or cell surface, implicated in AD pathogenesis e.g. AGE (S100 A, amphoterin), pro-inflammatory cytokines (e.g. IL-1), chemokines (e.g. MCP 1), molecules that inhibit nerve regeneration (e.g. Nogo, RGM A), molecules that enhance neurite growth (neurotrophins). The efficacy of FIT-Ig molecules can be validated in pre-clinical animal models such as the transgenic mice that over-express amyloid precursor protein or RAGE and develop Alzheimer's disease-like symptoms. In addition, FIT-Ig molecules can be constructed and tested for efficacy in the animal models and the best therapeutic FIT-Ig can be selected for testing in human patients. FIT-Ig molecules can also be employed for treatment of other neurodegenerative diseases such as Parkinson's disease. Alpha-Synuclein is involved in Parkinson's pathology. A FIT-Ig capable of targeting alpha-synuclein and inflammatory mediators such as TNF, IL-1, MCP-1 can prove effective therapy for Parkinson's disease and are contemplated in the invention.

Despite an increase in knowledge of the pathologic mechanisms, spinal cord injury (SCI) is still a devastating condition and represents a medical indication characterized by a high medical need. Most spinal cord injuries are contusion or compression injuries and the primary injury is usually followed by secondary injury mechanisms (inflammatory mediators e.g. cytokines and chemokines) that worsen the initial injury and result in significant enlargement of the lesion area, sometimes more than 10-fold. These primary and secondary mechanisms in SCI are very similar to those in brain injury caused by other means e.g. stroke. No satisfying treatment exists and high dose bolus injection of methylprednisolone (MP) is the only used therapy within a narrow time window of 8 h post injury. This treatment, however, is only intended to prevent secondary injury without causing any significant functional recovery. It is heavily criticized for the lack of unequivocal efficacy and severe adverse effects, like immunosuppression with subsequent infections and severe histopathological muscle alterations. No other drugs, biologics or small molecules, stimulating the endogenous regenerative potential are approved, but promising treatment principles and drug candidates have shown efficacy in animal models of SCI in recent years. To a large extent the lack of functional recovery in human SCI is caused by factors inhibiting neurite growth, at lesion sites, in scar tissue, in myelin as well as on injury-associated cells. Such factors are the myelin-associated proteins NogoA, OMgp and MAG, RGM A, the scar-associated CSPG (Chondroitin Sulfate Proteoglycans) and inhibitory factors on reactive astrocytes (some semaphorins and ephrins). However, at the lesion site not only growth inhibitory molecules are found but also neurite growth stimulating factors like neurotrophins, laminin, L1 and others. This ensemble of neurite growth inhibitory and growth promoting molecules may explain that blocking single factors, like NogoA or RGM A, resulted in significant functional recovery in rodent SCI models, because a reduction of the inhibitory influences could shift the balance from growth inhibition to growth promotion. However, recoveries observed with blocking a single neurite outgrowth inhibitory molecule were not complete. To achieve faster and more pronounced recoveries either blocking two neurite outgrowth inhibitory molecules e.g. Nogo and RGM A, or blocking an neurite outgrowth inhibitory molecule and enhancing functions of a neurite outgrowth enhancing molecule e.g. Nogo and neurotrophins, or blocking a neurite outgrowth inhibitory molecule e.g. Nogo and a pro-inflammatory molecule e.g. TNF, may be desirable (see McGee A W, et al., Trends Neurosci. 2003; 26:193; Marco Domeniconi, et al., J Neurol Sci. 2005; 233:43; Milan Makwanal, et al., FEBS J. 2005; 272:2628; Barry J. Dickson, Science. 2002; 298:1959; Felicia Yu Hsuan Teng, et al., J Neurosci Res. 2005; 79:273; Tara Karnezis, et al., Nature Neuroscience 2004; 7, 736; Gang Xu, et al., J. Neurochem. 2004; 91; 1018).

Other FIT-Igs contemplated are those capable of binding target pairs such as NgR and RGM A; NogoA and RGM A; MAG and RGM A; OMGp and RGM A; RGM A and RGM B; CSPGs and RGM A; aggrecan, midkine, neurocan, versican, phosphacan, Te38 and TNF-$\alpha$; AB globulomer-specific antibodies combined with antibodies promoting dendrite & axon sprouting. Dendrite pathology is a very early sign of AD and it is known that NOGO A restricts dendrite growth. One can combine such type of ab with any of the SCI-candidate (myelin-proteins) Ab. Other FIT-Ig targets may include any combination of NgR-p75, NgR-Troy, NgR-Nogo66 (Nogo), NgR-Lingo, Lingo-Troy, Lingo-p75, MAG or Omgp. Additionally, targets may also include any mediator, soluble or cell surface, implicated in inhibition of neurite e.g Nogo, Ompg, MAG, RGM A, semaphorins, ephrins, soluble A-b, pro-inflammatory cytokines (e.g. IL-1), chemokines (e.g. MIP 1a), molecules that inhibit nerve regeneration. The efficacy of anti-nogo/anti-RGM A or similar FIT-Ig molecules can be validated in pre-clinical animal models of spinal cord injury. In addition, these FIT-Ig molecules can be constructed and tested for efficacy in the animal models and the best therapeutic FIT-Ig can be selected for testing in human patients. In addition, FIT-Ig molecules can be constructed that target two distinct ligand binding sites on a single receptor e.g. Nogo receptor which binds three ligand Nogo, Ompg, and MAG and RAGE that binds A-b and S100 A. Furthermore, neurite outgrowth inhibitors e.g. nogo and nogo receptor, also play a role in preventing nerve regeneration in immunological diseases like multiple sclerosis. Inhibition of nogo-nogo receptor interaction has been shown to enhance recovery in animal models of multiple sclerosis. Therefore, FIT-Ig molecules that can block the function of one immune mediator eg a cytokine like IL-12 and a neurite outgrowth inhibitor molecule eg nogo or RGM may offer faster and greater efficacy than blocking either an immune or an neurite outgrowth inhibitor molecule alone.

Monoclonal antibody therapy has emerged as an important therapeutic modality for cancer (von Mehren M, et al 2003 Monoclonal antibody therapy for cancer. Annu Rev Med.; 54:343-69). Antibodies may exert antitumor effects by inducing apoptosis, redirected cytotoxicity, interfering with ligand-receptor interactions, or preventing the expression of proteins that are critical to the neoplastic phenotype. In addition, antibodies can target components of the tumor microenvironment, perturbing vital structures such as the formation of tumor-associated vasculature. Antibodies can also target receptors whose ligands are growth factors, such as the epidermal growth factor receptor. The antibody thus inhibits natural ligands that stimulate cell growth from binding to targeted tumor cells. Alternatively, antibodies may induce an anti-idiotype network, complement-mediated cytotoxicity, or antibody-dependent cellular cytotoxicity (ADCC). The use of dual-specific antibody that targets two separate tumor mediators will likely give additional benefit compared to a mono-specific therapy. FIT-Ig Igs capable of binding the following pairs of targets to treat oncological disease are also contemplated: IGF1 and IGF2; IGF1/2 and Erb2B; VEGFR and EGFR; CD20 and CD3, CD138 and CD20, CD38 and CD20, CD38 & CD138, CD40 and CD20, CD138 and CD40, CD38 and CD40. Other target combinations include one or more members of the EGF/erb-2/erb-3 family. Other targets (one or more) involved in oncological diseases that FIT-Ig Igs may bind include, but are not limited to those selected from the group consisting of: CD52, CD20, CD19, CD3, CD4, CD8, BMP6, IL12A, IL1A, IL1B, IL2, IL24, INHA, TNF, TNFSF10, BMP6, EGF, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, GRP, IGF1, IGF2, IL12A, IL1A, IL1B, IL2, INHA, TGFA, TGFB1, TGFB2, TGFB3, VEGF, CDK2, EGF, FGF10, FGF18, FGF2, FGF4, FGF7, IGF1, IGF1R, IL2, VEGF, BCL2, CD164, CDKN1A, CDKN1B, CDKN1C, CDKN2A, CDKN2B, CDKN2C, CDKN3, GNRH1, IGFBP6, IL1A, IL1B, ODZ1, PAWR, PLG, TGFB1I1, AR, BRCA1, CDK3, CDK4, CDK5, CDK6, CDK7, CDK9, E2F1, EGFR, ENO1, ERBB2, ESR1, ESR2, IGFBP3, IGFBP6, IL2, INSL4, MYC, NOX5, NR6A1, PAP, PCNA, PRKCQ, PRKD1, PRL, TP53, FGF22, FGF23, FGF9, IGFBP3, IL2, INHA, KLK6, TP53, CHGB, GNRH1, IGF1, IGF2, INHA, INSL3, INSL4, PRL, KLK6, SHBG, NR1D1, NR1H3, NR1I3, NR2F6, NR4A3, ESR1, ESR2, NROB1, NROB2, NR1D2, NR1H2, NR1H4, NR1I2, NR2C1, NR2C2, NR2E1, NR2E3, NR2F1, NR2F2, NR3C1, NR3C2, NR4A1, NR4A2, NR5A1, NR5A2, NR6A1, PGR, RARB, FGF1, FGF2, FGF6, KLK3, KRT1, APOC1, BRCA1, CHGA, CHGB, CLU, COL1A1, COL6A1, EGF, ERBB2, ERK8, FGF1, FGF10, FGF11, FGF13, FGF14, FGF16, FGF17, FGF18, FGF2, FGF20, FGF21, FGF22, FGF23, FGF3, FGF4, FGF5, FGF6, FGF7, FGF8, FGF9, GNRH1, IGF1, IGF2, IGFBP3, IGFBP6, IL12A, IL1A, IL1B, IL2, IL24, INHA, INSL3, INSL4, KLK10, KLK12, KLK13, KLK14, KLK15, KLK3, KLK4, KLK5, KLK6, KLK9, MMP2, MMP9, MSMB, NTN4, ODZ1, PAP, PLAU, PRL, PSAP, SERPINA3, SHBG, TGFA, TIMP3, CD44, CDH1, CDH10, CDH19, CDH20, CDH7, CDH9, CDH1, CDH10, CDH13, CDH18, CDH19, CDH20, CDH7, CDH8, CDH9, ROBO2, CD44, ILK, ITGA1, APC, CD164, COL6A1, MTSS1, PAP, TGFB1I1, AGR2, AIG1, AKAP1, AKAP2, CANT1, CAV1, CDH12, CLDN3, CLN3, CYB5, CYC1, DAB2IP, DES, DNCL1, ELAC2, ENO2, ENO3, FASN, FLJ12584, FLJ25530, GAGEB1, GAGEC1, GGT1, GSTP1, HIP1, HUMCYT2A, IL29, K6HF, KAI1, KRT2A, MIB1, PART1, PATE, PCA3, PIAS2, PIK3CG, PPID, PR1, PSCA, SLC2A2, SLC33A1, SLC43A1, STEAP, STEAP2, TPM1, TPM2, TRPC6, ANGPT1, ANGPT2, ANPEP, ECGF1, EREG, FGF1, FGF2, FIGF, FLT1, JAG1, KDR, LAMA5, NRP1, NRP2, PGF, PLXDC1, STAB1, VEGF, VEGFC, ANGPTL3, BAIl, COL4A3, IL8, LAMA5, NRP1, NRP2, STAB1, ANGPTL4, PECAM1, PF4, PROK2, SERPINF1, TNFAIP2, CCL11, CCL2, CXCL1, CXCL10, CXCL3, CXCL5, CXCL6, CXCL9, IFNA1, IFNB1, IFNG, IL1B, IL6, MDK, EDG1, EFNA1, EFNA3, EFNB2, EGF, EPHB4, FGFR3, HGF, IGF1, ITGB3, PDGFA, TEK, TGFA, TGFB1, TGFB2, TGFBR1, CCL2, CDH5, COL18A1, EDG1, ENG, ITGAV, ITGB3, THBS1, THBS2, BAD, BAG1, BCL2, CCNA1, CCNA2, CCND1, CCNE1, CCNE2, CDH1 (E-cadherin), CDKN1B (p27Kip1), CDKN2A (p161NK4a), COL6A1, CTNNB1 (b-catenin), CTSB (cathepsin B), ERBB2 (Her-2), ESR1, ESR2, F3 (TF), FOSL1 (FRA-1), GATA3, GSN (Gelsolin), IGFBP2, IL2RA, IL6, IL6R, IL6ST (glycoprotein 130), ITGA6 (a6 integrin), JUN, KLK5, KRT19, MAP2K7 (c-Jun), MKI67 (Ki-67), NGFB (NGF), NGFR, NME1 (NM23A), PGR, PLAU (uPA), PTEN, CTLA-4, OX40, GITR, TIM-3, Lag-3, B7-H3, B7-H4, GDF8, CGRP, Lingo-1, ICOS, GARP, BTLA, CD160, ROR1, SERPINB5 (maspin), SERPINE1 (PAI-1), TGFA, THBS1 (thrombospondin-1), TIE (Tie-1), TNFRSF6 (Fas), TNFSF6 (FasL), TOP2A (topoisomerase Iia), TP53, AZGP1 (zinc-a-glycoprotein), BPAG1 (plectin), CDKN1A (p21Wap1/Cip1), CLDN7 (claudin-7), CLU (clusterin), ERBB2 (Her-2), FGF1, FLRT1 (fibronectin), GABRP (GABAa), GNAS1, ID2, ITGA6 (a6 integrin), ITGB4 (b 4 integrin), KLF5 (GC Box BP), KRT19 (Keratin 19), KRTHB6 (hair-specific type II keratin), MACMARCKS, MT3 (metallothionectin-III), MUC1 (mucin), PTGS2 (COX-2), RAC2 (p21Rac2), S100A2, SCGB1D2 (lipophilin B), SCGB2A1 (mammaglobin 2), SCGB2A2 (mammaglobin 1), SPRR1B (Spr1), THBS1, THBS2, THBS4, and TNFAIP2 (B94).

In an embodiment, diseases that can be treated or diagnosed with the compositions and methods provided herein include, but are not limited to, primary and metastatic cancers, including carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), solid tumors arising from hematopoietic malignancies such as leukemias, and lymphomas (both Hodgkin's and non-Hodgkin's lymphomas).

In an embodiment, the antibodies provided herein or antigen-binding portions thereof, are used to treat cancer or in the prevention of metastases from the tumors described herein either when used alone or in combination with radiotherapy and/or other chemotherapeutic agents.

According to another embodiment of the invention, the human immune effector cell is a member of the human lymphoid cell lineage. In this embodiment, the effector cell may advantageously be a human T cell, a human B cell or a human natural killer (NK) cell. Advantageously, such cells will have either a cytotoxic or an apoptotic effect on the target cell. Especially advantageously, the human lymphoid cell is a cytotoxic T cell which, when activated, exerts a cytotoxic effect on the target cell. According to this embodiment, then, the recruited activity of the human effector cell is this cell's cytotoxic activity.

According to a preferred embodiment, activation of the cytotoxic T cell may occur via binding of the CD3 antigen as effector antigen on the surface of the cytotoxic T cell by a bispecific antibody of this embodiment of the invention. The human CD3 antigen is present on both helper T cells and cytotoxic T cells. Human CD3 denotes an antigen which is expressed on T cells as part of the multimolecular T cell complex and which comprises three different chains: CD3-epsilon, CD3-delta and CD3-gamma.

The activation of the cytotoxic potential of T cells is a complex phenomenon which requires the interplay of multiple proteins. The T cell receptor ("TCR") protein is a membrane bound disulfide-linked heterodimer consisting of two different glycoprotein subunits. The TCR recognizes and binds foreign peptidic antigen which itself has been bound by a member of the highly diverse class of major histocompatibility complex ("MHC") proteins and has been presented, bound to the MHC, on the surface of antigen presenting cells ("APCs").

Although the variable TCR binds foreign antigen as outlined above, signaling to the T cell that this binding has taken place depends on the presence of other, invariant, signaling proteins associated with the TCR. These signaling proteins in associated form are collectively referred to as the CD3 complex, here collectively referred to as the CD3 antigen.

The activation of T cell cytotoxicity, then, normally depends first on the binding of the TCR with an MHC protein, itself bound to foreign antigen, located on a separate cell. Only when this initial TCR-MHC binding has taken place can the CD3-dependent signaling cascade responsible for T cell clonal expansion and, ultimately, T cell cytotoxicity ensue.

However, binding of the human CD3 antigen by the first or second portion of a bispecific antibody of the invention activates T cells to exert a cytotoxic effect on other cells in the absence of independent TCR-MHC binding. This means that T cells may be cytotoxically activated in a clonally independent fashion, i.e., in a manner which is independent of the specific TCR clone carried by the T cell. This allows an activation of the entire T cell compartment rather than only specific T cells of a certain clonal identity.

In light of the foregoing discussion, then, an especially preferred embodiment of the invention provides a bispecific antibody in which the effector antigen is the human CD3 antigen. The bispecific antibody according to this embodiment of the invention may have a total of either two or three antibody variable domains.

According to further embodiments of the invention, other lymphoid cell-associated effector antigens bound by a bispecific antibody of the invention may be the human CD16 antigen, the human NKG2D antigen, the human NKp46 antigen, the human CD2 antigen, the human CD28 antigen or the human CD25 antigen.

According to another embodiment of the invention, the human effector cell is a member of the human myeloid lineage. Advantageously, the effector cell may be a human monocyte, a human neutrophilic granulocyte or a human dendritic cell. Advantageously, such cells will have either a cytotoxic or an apoptotic effect on the target cell. Advantageous antigens within this embodiment which may be bound by a bispecific antibody of the invention may be the human CD64 antigen or the human CD89 antigen.

According to another embodiment of the invention, the target antigen is an antigen which is uniquely expressed on a target cell or effector cell in a disease condition, but which remains either non-expressed, expressed at a low level or non-accessible in a healthy condition. Examples of such target antigens which might be specifically bound by a bispecific antibody of the invention may advantageously be selected from EpCAM, CCR5, CD19, HER-2 neu, HER-3, HER-4, EGFR, PSMA, CEA, MUC-1 (mucin), MUC2, MUC3, MUC4, MUC5AC, MUC5B, MUC7, PhCG, Lewis-Y, CD20, CD33, CD30, ganglioside GD3, 9-O-Acetyl-GD3, GM2, Globo H, fucosyl GM1, Poly SA, GD2, Carboanhydrase IX (MN/CA IX), CD44v6, Sonic Hedgehog (Shh), Wue-1, Plasma Cell Antigen, (membrane-bound) IgE, Melanoma Chondroitin Sulfate Proteoglycan (MCSP), CCR8, TNF-alpha precursor, STEAP, mesothelin, A33 Antigen, Prostate Stem Cell Antigen (PSCA), Ly-6; desmoglein 4, E-cadherin neoepitope, Fetal Acetylcholine Receptor, CD25, CA19-9 marker, CA-125 marker and Muellerian Inhibitory Substance (MIS) Receptor type II, sTn (sialylated Tn antigen; TAG-72), FAP (fibroblast activation antigen), endosialin, EGFRvIII, LG, SAS and CD63.

According to a specific embodiment, the target antigen specifically bound by a bispecific antibody may be a cancer-related antigen, e.g., an antigen related to a malignant condition. Such an antigen is either expressed or accessible on a malignant cell, whereas the antigen is either not present, not significantly present, or is not accessible on a non-malignant cell. As such, a bispecific antibody according to this embodiment of the invention is a bispecific antibody which recruits the activity of a human immune effector cell against the malignant target cell bearing the target antigen, or rendering the target antigen accessible.

Gene Therapy: In a specific embodiment, nucleic acid sequences encoding a binding protein provided herein or another prophylactic or therapeutic agent provided herein are administered to treat, prevent, manage, or ameliorate a disorder or one or more symptoms thereof by way of gene therapy. Gene therapy refers to therapy performed by the administration to a subject of an expressed or expressible nucleic acid. In this embodiment, the nucleic acids produce their encoded antibody or prophylactic or therapeutic agent provided herein that mediates a prophylactic or therapeutic effect.

Any of the methods for gene therapy available in the art can be used in the methods provided herein. For general reviews of the methods of gene therapy, see Goldspiel et al. (1993) Clin. Pharmacy 12:488-505; Wu and Wu (1991) Biotherapy 3:87-95; Tolstoshev (1993) Ann Rev. Pharmacol. Toxicol. 32:573-596; Mulligan (1993) Science 260:926-932; Morgan and Anderson (1993) Ann Rev. Biochem. 62:191-217; and May (1993) TIBTECH 11(5):155-215. Methods commonly known in the art of recombinant DNA technology which can be used are described in Ausubel et al. (eds.), Current Protocols in Molecular Biology, John Wiley &Sons, N Y (1993); and Kriegler, Gene Transfer and Expression, A Laboratory Manual, Stockton Press, NY (1990). Detailed description of various methods of gene therapy is disclosed in US Patent Publication No. US20050042664.

Diagnostics: The disclosure herein also provides diagnostic applications including, but not limited to, diagnostic assay methods, diagnostic kits containing one or more binding proteins, and adaptation of the methods and kits for use in automated and/or semi-automated systems. The methods, kits, and adaptations provided may be employed in the detection, monitoring, and/or treatment of a disease or disorder in an individual. This is further elucidated below.

A. Method of Assay: The present disclosure also provides a method for determining the presence, amount or concentration of an analyte, or fragment thereof, in a test sample using at least one binding protein as described herein. Any suitable assay as is known in the art can be used in the method. Examples include, but are not limited to, immunoassays and/or methods employing mass spectrometry. Immunoassays provided by the present disclosure may include sandwich immunoassays, radioimmunoassay (RIA), enzyme immunoassay (EIA), enzyme-linked immunosorbent assay (ELISA), competitive-inhibition immunoassays, fluorescence polarization immunoassay (FPIA), enzyme multiplied immunoassay technique (EMIT), bioluminescence resonance energy transfer (BRET), and homogenous chemiluminescent assays, among others. A chemiluminescent microparticle immunoassay, in particular one employing the ARCHITECT® automated analyzer (Abbott Laboratories, Abbott Park, Ill.), is an example of an immunoassay. Methods employing mass spectrometry are provided by the present disclosure and include, but are not limited to MALDI (matrix-assisted laser desorption/ionization) or by SELDI (surface-enhanced laser desorption/ionization).

Methods for collecting, handling, processing, and analyzing biological test samples using immunoassays and mass spectrometry would be well-known to one skilled in the art, are provided for in the practice of the present disclosure (US 2009-0311253 A1).

B. Kit: A kit for assaying a test sample for the presence, amount or concentration of an analyte, or fragment thereof, in a test sample is also provided. The kit comprises at least one component for assaying the test sample for the analyte, or fragment thereof, and instructions for assaying the test sample for the analyte, or fragment thereof. The at least one component for assaying the test sample for the analyte, or fragment thereof, can include a composition comprising a binding protein, as disclosed herein, and/or an anti-analyte binding protein (or a fragment, a variant, or a fragment of a variant thereof), which is optionally immobilized on a solid phase. Optionally, the kit may comprise a calibrator or control, which may comprise isolated or purified analyte. The kit can comprise at least one component for assaying the test sample for an analyte by immunoassay and/or mass spectrometry. The kit components, including the analyte, binding protein, and/or anti-analyte binding protein, or fragments thereof, may be optionally labeled using any art-known detectable label. The materials and methods for the creation provided for in the practice of the present disclosure would be known to one skilled in the art (US 2009-0311253 A1).

C. Adaptation of Kit and Method: The kit (or components thereof), as well as the method of determining the presence, amount or concentration of an analyte in a test sample by an assay, such as an immunoassay as described herein, can be adapted for use in a variety of automated and semi-automated systems (including those wherein the solid phase comprises a microparticle), as described, for example, in U.S. Pat. Nos. 5,089,424 and 5,006,309, and as commercially marketed, for example, by Abbott Laboratories (Abbott Park, Ill.) as ARCHITECT®. Other platforms available from Abbott Laboratories include, but are not limited to, AxSYM®, IMx® (see, for example, U.S. Pat. No. 5,294,404, PRISM®, EIA (bead), and Quantum™ II, as well as other platforms. Additionally, the assays, kits and kit components can be employed in other formats, for example, on electrochemical or other hand-held or point-of-care assay systems. The present disclosure is, for example, applicable to the commercial Abbott Point of Care (i-STAT®, Abbott Laboratories) electrochemical immunoassay system that performs sandwich immunoassays. Immunosensors and their methods of manufacture and operation in single-use test devices are described, for example in, U.S. Pat. Nos. 5,063,081, 7,419,821, and 7,682,833; and US Publication Nos. 20040018577, 20060160164 and US 20090311253. It will be readily apparent to those skilled in the art that other suitable modifications and adaptations of the methods described herein are obvious and may be made using suitable equivalents without departing from the scope of the embodiments disclosed herein. Having now described certain embodiments in detail, the same will be more clearly understood by reference to the following examples, which are included for purposes of illustration only and are not intended to be limiting.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims. The following examples are provided by way of illustration only and not by way of limitation. Those of skill in the art will readily recognize a variety of non-critical parameters that could be changed or modified to yield essentially similar results.

EXAMPLES

Example 1. Construction, Expression, Purification, and Analysis of Anti-IL17/IL-20 Fabs-In-Tandem Immunoglobulin (FIT-Ig)

Figure 1B:
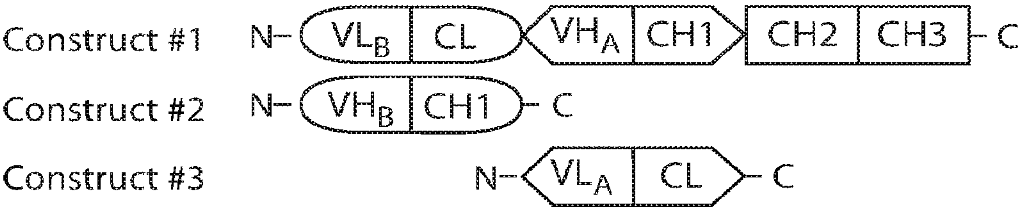
FIG. 1B shows the three constructs used to prepare such FIT1-Igs.

To demonstrate the FIT-Ig technology, we have generated a group of anti-IL-17/IL-20 FIT-Ig molecules: FIT1-Ig, FIT2-Ig, and FIT3-Ig, all of which contains 3 different polypeptides, as shown in FIG. 1, where antigen A is IL-17 and antigen B is IL-20. The DNA construct used to generate FIT-Ig capable of binding IL-17 and IL-20 is illustrated in FIG. 1B. Briefly, parental mAbs included two high affinity antibodies, anti-IL-17 (clone LY) (U.S. Pat. No. 7,838,638) and anti-hIL-20 (clone 15D2) (U.S. Patent Application Publication No. US2014/0194599). To generate FIT-Ig construct #1, the VL-CL of LY was directly (FIT1-Ig), or through a linker of 3 amino acids (FIT2-Ig) or 7 amino acids (FIT3-Ig) fused to the N-terminus of the 15D2 heavy chain (as shown in Table 1). The construct #2 is VH-CH1 of LY, and the 3d construct is VL-CL of 15D2. The 3 constructs for each FIT-Ig were co-transfected in 293 cells, resulting in the expression and secretion of FIT-Ig protein.

Figure 2A:
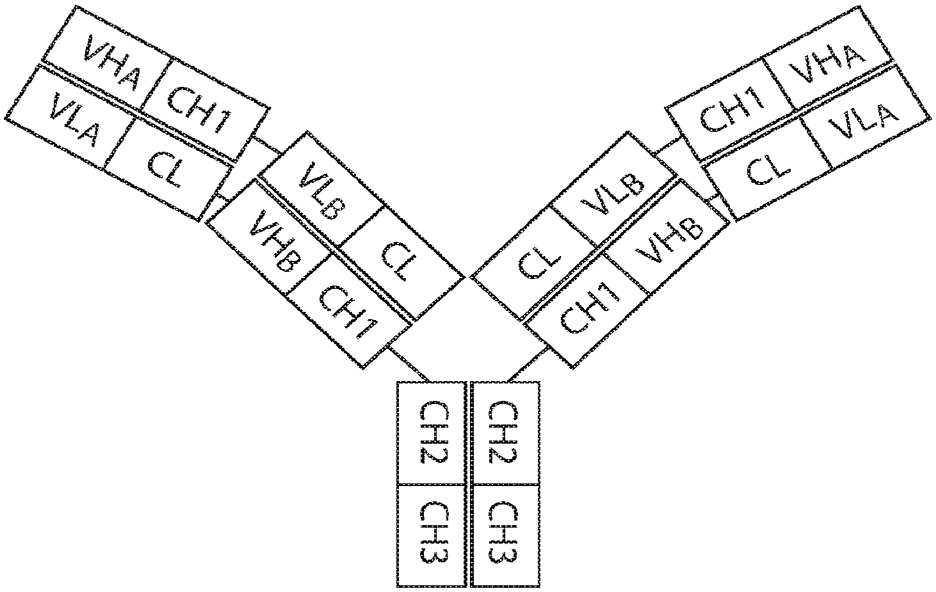
FIG. 2A shows the basic structure of FIT-Igs that are made up of two constructs.
Figure 2B:
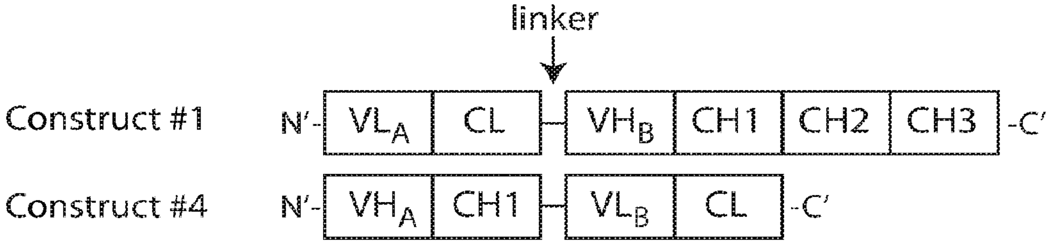
FIG. 2B shows the two constructs used to prepare such FIT-Igs.

We also generated a group of anti-IL-17/IL-20 FIT-Ig molecules: FIT4-Ig, FIT5-Ig, and FIT6-Ig, each of which contains 2 different polypeptides, as shown in FIG. 2. The DNA constructs used to generate FIT-Ig capable of binding IL-17 and IL-20 are illustrated in FIG. 2B, where antigen A is IL-17 and antigen B is IL-20. Briefly, parental mAbs included two high affinity antibodies, anti-IL-17 (clone LY) and anti-hIL-20 (clone 15D2). To generate FIT-Ig construct #1, the VL-CL of LY was directly (FIT4-Ig), or through a linker of 3 amino acids (FIT5-Ig) or 7 amino acids (FIT6-Ig) fused to the N-terminus of the 15D2 heavy chain (as shown in Table 1). To generate FIT-Ig construct #4, the VH-CH1 of LY was directly (FIT4-Ig), or through a linker of 3 amino acids (FIT5-Ig) or 7 amino acids (FIT6-Ig) fused to the N-terminus of the 15D2 light chain. The 2 DNA constructs (construct #1 and #4) for each FIT-Ig were co-transfected in 293 cells, resulting in the expression and secretion of FIT-Ig protein. The detailed procedures of the PCR cloning are described below.

Example 1.1: Molecular Cloning of Anti-IL-17/IL-20 FIT-Ig Molecules

For construct #1 cloning, LY light chain was amplified by PCR using forward primers annealing on light chain signal sequence and reverse primers annealing on C-terminus of the light chain. 15D2 heavy chain was amplified by PCR using forward primers annealing on N-terminus of 15D2 VH and reverse primers annealing on C-terminus of CH. These 2 PCR fragments were gel purified and combined by overlapping PCR using signal peptide and CH primer pair. The combined PCR product was cloned into a 293 expression vector, which already contained the human Fc sequence.

TABLE 1

Anti-IL-17/IL-20 FIT-Ig molecules and DNA constructs.

| FIT-Ig molecule | Construct #1 | Linker | Construct #2 | Construct #3 | Construct #4 |
|---|---|---|---|---|---|
| FIT1-Ig | $VL_{17}$-CL-$VH_{20}$-CH1-Fc | No linker | $VH_{17}$-CH1 | $VL_{20}$-CL | |
| FIT2-Ig | $VL_{17}$-CL-linker-$VH_{20}$-CH1-Fc | GSG | $VH_{17}$-CH1 | $VL_{20}$-CL | |
| FIT3-Ig | $VL_{17}$-CL-linker-$VH_{20}$-CH1-Fc | GGGGSGS | $VH_{17}$-CH1 | $VL_{20}$-CL | |
| FIT4-Ig | $VL_{17}$-CL-$VH_{20}$-CH1-Fc | No linker | | | $VH_{17}$-CH1-$VL_{20}$-CL |
| FIT5-Ig | $VL_{17}$-CL-linker-$VH_{20}$-CH1-Fc | GSG | | | $VH_{17}$-CH1-linker-$VL_{20}$-CL |
| FIT6-Ig | $VL_{17}$-CL-linker-$VH_{20}$-CH1-Fc | GGGGSGS | | | $VH_{17}$-CH1-linker-$VL_{20}$-CL |

For construct #2 cloning, LY VH-CH1 was amplified by PCR using forward primers annealing on heavy chain signal peptide and reverse primer annealing on C-terminal of CH1. The PCR product was gel purified before cloning into 293 expression vector.

For construct #3, 15D32 light chain was amplified by PCR using forward primer annealing on N-terminal of light chain signal peptide and reverse primer annealing on the end of CL. The PCR product was gel purified before cloning into 293 expression vector.

For construct #4 cloning, LY VH-CH1 was amplified by PCR using forward primer annealing on N-terminus of heavy chain signal peptide and reverse primer annealing on the end of CH1. 151D2 VL was amplified using primers annealing on the end of 151D2 VL. Both PCR products were gel purified and combined by overlap PCR. The combined PCR product was gel purified and cloned in 293 expression vector. Table 2 shows sequences of PCR primers used for above molecular cloning.

TABLE 2

| PCR primers used for molecular construction of anti-IL-17/anti-CD20 FIT-Igs | |
|---|---|
| P1: 5' CAGGTGCAGCTGGTGCAGAGCGGCGCCGAAG 3' | SEQ ID NO. 1 |
| P2: 5'GCTGGACCTGAGAGCCTGAACCGCCACCACCACACTCTCCCCTGTTGAAGC 3' | SEQ ID NO. 2 |
| P3: 5' GGTGGTGGCGGTTCAGGCTCTCAGGTCCAGCTTGTGCAATCTGGCGCCGAGG3' | SEQ ID NO. 3 |
| P4: 5' GTCTGCGGCCGCTCATTTACCCGGAGACAGGGAGAG 3' | SEQ ID NO. 4 |
| P5: 5' TAAGCGTACGGTGGCTGCACCATCTGTCTTC 3' | SEQ ID NO. 5 |
| P6: 5' CGGCGCCAGATTGCACAAGCTGGACCTGGCCTGAACCACACTCTCCCCTGTTGAAGCTC 3' | SEQ ID NO. 6 |
| P7: 5' GCTGGACCTGAGAGCCTGAACCGCCACCACCACACTCTCCCCTGTTGAAGC3' | SEQ ID NO. 7 |
| P8: 5' GGTGGTGGCGGTTCAGGCTCTCAGGTCCAGCTTGTGCAATCTGGCGCCGAGG3' | SEQ ID NO. 8 |
| P9: 5' TACCTCGGCGCCAGATTGCACAAGCTGGACCTGACACTCTCCCCTGTTGAAGCTCTTTG 3' | SEQ ID NO. 9 |
| P10: 5' CATGACACCTTAACAGAGGCCCCAGGTCGTTTTACCTCGGCGCCAGATTGCACAAG3' | SEQ ID NO. 10 |
| P11: 5' CAATAAGCTTTACATGACACCTTAACAGAGGCCCCAG3' | SEQ ID NO. 11 |
| P12: 5' TCGAGCGGCCGCTCAACAAGATTTGGGCTCAACTTTCTTG3' | SEQ ID NO. 12 |
| P13: 5'GCTGCTGCTGTGGTTCCCCGGCTCGCGATGCGCTATACAGTTGACACAGTC3' | SEQ ID NO. 13 |
| P14: 5' GAAGATGAAGACAGATGGTGCAGCCACCGTACGCTTGATCTCTACCTTTGTTC 3' | SEQ ID NO. 14 |

The final sequences of hIL-17/hIL-20 FIT1-Ig, FIT2-Ig, FIT3-Ig, FIT4-Ig, FIT5-Ig, and FIT6-Ig are listed in Table 3.

TABLE 3

Amino acid sequences of anti-IL-17/IL-20 FIT-Ig molecules

| Protein | Protein region | Sequence Identifier | Sequence 12345678901234567890 |
|---|---|---|---|
| Anti-IL-17/IL-20 FIT1-Ig POLYPEPTIDE #1 | | SEQ ID NO.: 15 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIKRTVAAPSVFIF PPSDEQLKSGTASVVCLLNNFYPREAKVQWKVDNALQSGNS QESVTEQDSKDSTYSLSSTLTLSKADYEKHKVYACEVTHQG LSSPVTKSFNRGECQVQLVQSGAEVKRPGASVKVSCKASGY TFTNDIIHWVRQAPGQRLEWMGWINAGYGNTQYSQNFQDRV SITRDTSASTAYMELISLRSEDTAVYYCAREPLWFGESSPH DYYGMDVWGQGTTVTVSSASTKGPSVFPLAPSSKSTSGGTA ALGCLVKDYFPEPVTVSWNSGALTSGVHTFPAVLQSSGLYS LSSVVTVPSSSLGTQTYICNVNHKPSNTKVDKKVEPKSCDK THTCPPCPAPELLGGPSVFLFPPKPKDTLMISRTPEVTCVV VDVSHEDPEVKFNWYVDGVEVHNAKTKPREEQYNSTYRVVS VLTVLHQDWLNGKEYKCKVSNKALPAPIEKTISKAKGQPRE PQVYTLPPSREEMTKNQVSLTCLVKGFYPSDIAVEWESNGQ PENNYKTTPPVLDSDGSFFLYSKLTVDKSRWQQGNVFSCSV MHEALHNHYTQKSLSLSPGK |
| | LY VL | SEQ ID NO.: 16 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |

TABLE 3-continued

Amino acid sequences of anti-IL-17/IL-20 FIT-Ig molecules

| Protein | Protein region | Sequence Identifier | Sequence 12345678901234567890 |
|---|---|---|---|
| | Linker | | None |
| | 15D2 VH | SEQ ID NO.: 18 | QVQLVQSGAEVKRPGASVKVSCKASGYTFTNDIIHWVRQAP<br>GQRLEWMGWINAGYGNTQYSQNFQDRVSITRDTSASTAYME<br>LISLRSEDTAVYYCAREPLWFGESSPHDYYGMDVWGQGTTV<br>TVSS |
| | CH1 | SEQ ID NO.: 19 | ASTKGPSVFPLAPSSKSTSGGTAALGCLVKDYFPEPVTVSW<br>NSGALTSGVHTFPAVLQSSGLYSLSSVVTVPSSSLGTQTYI<br>CNVNHKPSNTKVDKKVEPKSC |
| | Fc | SEQ ID NO.: 20 | DKTHTCPPCPAPELLGGPSVFLFPPKPKDTLMISRTPEVTC<br>VVVDVSHEDPEVKFNWYVDGVEVHNAKTKPREEQYNSTYRV<br>VSVLTVLHQDWLNGKEYKCKVSNKALPAPIEKTISKAKGQP<br>REPQVYTLPPSREEMTKNQVSLTCLVKGFYPSDIAVEWESN<br>GQPENNYKTTPPVLDSDGSFFLYSKLTVDKSRWQQGNVFSC<br>SVMHEALHNHYTQKSLSLSPGK |
| Anti-IL-17/IL-20 FIT1-Ig POLYPEPTIDE #2 | | SEQ ID NO.: 21 | QVQLVQSGAEVKKPGSSVKVSCKASGYSFTDYHIHWVRQAP<br>GQGLEWMGVINPMYGTTDYNQRFKGRVTITADESTSTAYME<br>LSSLRSEDTAVYYCARYDYFTGTGVYWGQGTLVTVSSASTK<br>GPSVFPLAPSSKSTSGGTAALGCLVKDYFPEPVTVSWNSGA<br>LTSGVHTFPAVLQSSGLYSLSSVVTVPSSSLGTQTYICNVN<br>HKPSNTKVDKKVEPKSC |
| | LY VH | SEQ ID NO.: 22 | QVQLVQSGAEVKKPGSSVKVSCKASGYSFTDYHIHWVRQAP<br>GQGLEWMGVINPMYGTTDYNQRFKGRVTITADESTSTAYME<br>LSSLRSEDTAVYYCARYDYFTGTGVYWGQGTLVTVSS |
| | CH1 | SEQ ID NO.: 19 | ASTKGPSVFPLAPSSKSTSGGTAALGCLVKDYFPEPVTVSW<br>NSGALTSGVHTFPAVLQSSGLYSLSSVVTVPSSSLGTQTYI<br>CNVNHKPSNTKVDKKVEPKSC |
| Anti-IL-17/IL-20 FIT1-Ig POLYPEPTIDE #3 | | SEQ ID NO.: 23 | AIQLTQSPSSLSASVGDRVTITCRASQGISSALAWYQQKPG<br>KAPKLLIYDASSLESGVPSRFSGSGSGTDFTLTISSLQPED<br>FATYYCQQFNSYPLTFGGGTKVEIKRTVAAPSVFIFPPSDE<br>QLKSGTASVVCLLNNFYPREAKVQWKVDNALQSGNSQESVT<br>EQDSKDSTYSLSSTLTLSKADYEKHKVYACEVTHQGLSSPV<br>TKSFNRGEC |
| | 15D2 VL | SEQ ID NO.: 24 | AIQLTQSPSSLSASVGDRVTITCRASQGISSALAWYQQKPG<br>KAPKLLIYDASSLESGVPSRFSGSGSGTDFTLTISSLQPED<br>FATYYCQQFNSYPLTFGGGTKVEIK |
| | CL | SEQ ID NO.: 17 | RTVAAPSVFIFPPSDEQLKSGTASVVCLLNNFYPREAKVQW<br>KVDNALQSGNSQESVTEQDSKDSTYSLSSTLTLSKADYEKH<br>KVYACEVTHQGLSSPVTKSFNRGEC |
| Anti-IL-17/IL-20 FIT2-Ig POLYPEPTIDE #1 | | SEQ ID NO.: 25 | DIVMTQTPLSLSVTPGQPASISCRSSRSLVHSRGNTYLHWY<br>LQKPGQSPQLLIYKVSNRFIGVPDRFSGSGSGTDFTLKISR<br>VEAEDVGVYYCSQSTHLPFTFGQGTKLEIKRTVAAPSVFIF<br>PPSDEQLKSGTASVVCLLNNFYPREAKVQWKVDNALQSGNS<br>QESVTEQDSKDSTYSLSSTLTLSKADYEKHKVYACEVTHQG<br>LSSPVTKSFNRGECGSGQVQLVQSGAEVKRPGASVKVSCKA<br>SGYTFTNDIIHWVRQAPGQRLEWMGWINAGYGNTQYSQNFQ<br>DRVSITRDTSASTAYMELISLRSEDTAVYYCAREPLWFGES<br>SPHDYYGMDVWGQGTTVTVSSASTKGPSVFPLAPSSKSTSG<br>GTAALGCLVKDYFPEPVTVSWNSGALTSGVHTFPAVLQSSG<br>LYSLSSVVTVPSSSLGTQTYICNVNHKPSNTKVDKKVEPKS<br>CDKTHTCPPCPAPELLGGPSVFLFPPKPKDTLMISRTPEVT<br>CVVVDVSHEDPEVKFNWYVDGVEVHNAKTKPREEQYNSTYR<br>VVSVLTVLHQDWLNGKEYKCKVSNKALPAPIEKTISKAKGQ<br>PREPQVYTLPPSREEMTKNQVSLTCLVKGFYPSDIAVEWES<br>NGQPENNYKTTPPVLDSDGSFFLYSKLTVDKSRWQQGNVFS<br>CSVMHEALHNHYTQKSLSLSPGK |
| | LY VL | SEQ ID NO.: 16 | DIVMTQTPLSLSVTPGQPASISCRSSRSLVHSRGNTYLHWY<br>LQKPGQSPQLLIYKVSNRFIGVPDRFSGSGSGTDFTLKISR<br>VEAEDVGVYYCSQSTHLPFTFGQGTKLEIK |
| | CL | SEQ ID NO.: 17 | RTVAAPSVFIFPPSDEQLKSGTASVVCLLNNFYPREAKVQW<br>KVDNALQSGNSQESVTEQDSKDSTYSLSSTLTLSKADYEKH<br>KVYACEVTHQGLSSPVTKSFNRGEC |
| | Linker | SEQ ID NO.: 26 | GSG |
| | 15D2 VH | SEQ ID NO.: 18 | QVQLVQSGAEVKRPGASVKVSCKASGYTFTNDIIHWVRQAP<br>GQRLEWMGWINAGYGNTQYSQNFQDRVSITRDTSASTAYME<br>LISLRSEDTAVYYCAREPLWFGESSPHDYYGMDVWGQGTTV<br>TVSS |
| | CH1 | SEQ ID NO.: 19 | ASTKGPSVFPLAPSSKSTSGGTAALGCLVKDYFPEPVTVSW<br>NSGALTSGVHTFPAVLQSSGLYSLSSVVTVPSSSLGTQTYI<br>CNVNHKPSNTKVDKKVEPKSC |

TABLE 3-continued

Amino acid sequences of anti-IL-17/IL-20 FIT-Ig molecules

| Protein | Protein region | Sequence Identifier | Sequence 12345678901234567890 |
|---|---|---|---|
| | Fc | SEQ ID NO.: 20 | DKTHTCPPCPAPELLGGPSVFLFPPKPKDTLMISRTPEVTC VVVDVSHEDPEVKFNWYVDGVEVHNAKTKPREEQYNSTYRV VSVLTVLHQDWLNGKEYKCKVSNKALPAPIEKTISKAKGQP REPQVYTLPPSREEMTKNQVSLTCLVKGFYPSDIAVEWESN GQPENNYKTTPPVLDSDGSFFLYSKLTVDKSRWQQGNVFSC SVMHEALHNHYTQKSLSLSPGK |
| Anti-IL-17/IL-20 FIT2-Ig POLYPEPTIDE #2 | | SEQ ID NO.: 21 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSC |
| | LY VH | SEQ ID NO.: 22 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| Anti-IL-17/IL-20 FIT2-Ig POLYPEPTIDE #3 | | SEQ ID NO.: 23 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC |
| | 15D2 VL | SEQ ID NO.: 24 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| Anti-IL-17/IL-20 FIT3-Ig POLYPEPTIDE #1 | | SEQ ID NO.: 27 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIKRTVAAPSVFIF PPSDEQLKSGTASVVCLLNNFYPREAKVQWKVDNALQSGNS QESVTEQDSKDSTYSLSSTLTLSKADYEKHKVYACEVTHQG LSSPVTKSFNRGECGGGGSGSQVQLVQSGAEVKRPGASVKV SCKASGYTFTNDIIHWVRQAPGQRLEWMGWINAGYGNTQYS QNFQDRVSITRDTSASTAYMELISLRSEDTAVYYCAREPLW FGESSPHDYYGMDVWGQGTTVTVSSASTKGPSVFPLAPSSK STSGGTAALGCLVKDYFPEPVTVSWNSGALTSGVHTFPAVL QSSGLYSLSSVVTVPSSSLGTQTYICNVNHKPSNTKVDKKV EPKSCDKTHTCPPCPAPELLGGPSVFLFPPKPKDTLMISRT PEVTCVVVDVSHEDPEVKFNWYVDGVEVHNAKTKPREEQYN STYRVVSVLTVLHQDWLNGKEYKCKVSNKALPAPIEKTISK AKGQPREPQVYTLPPSREEMTKNQVSLTCLVKGFYPSDIAV EWESNGQPENNYKTTPPVLDSDGSFFLYSKLTVDKSRWQQG NVFSCSVMHEALHNHYTQKSLSLSPGK |
| | LY VL | SEQ ID NO.: 16 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| | Linker | SEQ ID NO.: 28 | GGGGSGS |
| | 15D2 VH | SEQ ID NO.: 18 | QVQLVQSGAEVKRPGASVKVSCKASGYTFTNDIIHWVRQAP GQRLEWMGWINAGYGNTQYSQNFQDRVSITRDTSASTAYME LISLRSEDTAVYYCAREPLWFGESSPHDYYGMDVWGQGTTV TVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Fc | SEQ ID NO.: 20 | DKTHTCPPCPAPELLGGPSVFLFPPKPKDTLMISRTPEVTC VVVDVSHEDPEVKFNWYVDGVEVHNAKTKPREEQYNSTYRV VSVLTVLHQDWLNGKEYKCKVSNKALPAPIEKTISKAKGQP REPQVYTLPPSREEMTKNQVSLTCLVKGFYPSDIAVEWESN GQPENNYKTTPPVLDSDGSFFLYSKLTVDKSRWQQGNVFSC SVMHEALHNHYTQKSLSLSPGK |

TABLE 3-continued

Amino acid sequences of anti-IL-17/IL-20 FIT-Ig molecules

| Protein | Protein region | Sequence Identifier | Sequence 12345678901234567890 |
|---|---|---|---|
| Anti-IL-17/IL-20 FIT3-Ig POLYPEPTIDE #2 | | SEQ ID NO.: 21 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSC |
| | LY VH | SEQ ID NO.: 22 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| Anti-IL-17/IL-20 FIT3-Ig POLYPEPTIDE #3 | | SEQ ID NO.: 23 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIKRTVAAPSVFIFPPSDE QLKSGTASVVCLLNNFYPREAKVQWKVDNALQSGNSQESVT EQDSKDSTYSLSSTLTLSKADYEKHKVYACEVTHQGLSSPV TKSFNRGEC |
| | 15D2 VL | SEQ ID NO.: 24 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| Anti-IL-17/IL-20 FIT 4-Ig POLYPEPTIDE #1 | | SEQ ID NO.: 15 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIKRTVAAPSVFIF PPSDEQLKSGTASVVCLLNNFYPREAKVQWKVDNALQSGNS QESVTEQDSKDSTYSLSSTLTLSKADYEKHKVYACEVTHQG LSSPVTKSFNRGECQVQLVQSGAEVKRPGASVKVSCKASGY TFTNDIIHWVRQAPGQRLEWMGWINAGYGNTQYSQNFQDRV SITRDTSASTAYMELISLRSEDTAVYYCAREPLWFGESSPH DYYGMDVWGQGTTVTVSSASTKGPSVFPLAPSSKSTSGGTA ALGCLVKDYFPEPVTVSWNSGALTSGVHTFPAVLQSSGLYS LSSVVTVPSSSLGTQTYICNVNHKPSNTKVDKKVEPKSCDK THTCPPCPAPELLGGPSVFLFPPKPKDTLMISRTPEVTCVV VDVSHEDPEVKFNWYVDGVEVHNAKTKPREEQYNSTYRVVS VLTVLHQDWLNGKEYKCKVSNKALPAPIEKTISKAKGQPRE PQVYTLPPSREEMTKNQVSLTCLVKGFYPSDIAVEWESNGQ PENNYKTTPPVLDSDGSFFLYSKLTVDKSRWQQGNVFSCSV MHEALHNHYTQKSLSLSPGK |
| | LY VL | SEQ ID NO.: 16 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| | Linker | | None |
| | 15D2 VH | SEQ ID NO.: 18 | QVQLVQSGAEVKRPGASVKVSCKASGYTFTNDIIHWVRQAP GQRLEWMGWINAGYGNTQYSQNFQDRVSITRDTSASTAYME LISLRSEDTAVYYCAREPLWFGESSPHDYYGMDVWGQGTTV TVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Fc | SEQ ID NO.: 20 | DKTHTCPPCPAPELLGGPSVFLFPPKPKDTLMISRTPEVTC VVVDVSHEDPEVKFNWYVDGVEVHNAKTKPREEQYNSTYRV VSVLTVLHQDWLNGKEYKCKVSNKALPAPIEKTISKAKGQP REPQVYTLPPSREEMTKNQVSLTCLVKGFYPSDIAVEWESN GQPENNYKTTPPVLDSDGSFFLYSKLTVDKSRWQQGNVFSC SVMHEALHNHYTQKSLSLSPGK |
| Anti-IL-17/IL-20 FIT4-Ig POLYPEPTIDE #4 | | SEQ ID NO.: 29 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSCAIQLTQSPSSLSASVGDRVTITCR ASQGISSALAWYQQKPGKAPKLLIYDASSLESGVPSRFSGS |

TABLE 3-continued

Amino acid sequences of anti-IL-17/IL-20 FIT-Ig molecules

| Protein | Protein region | Sequence Identifier | Sequence 12345678901234567890 |
|---|---|---|---|
| | | | GSGTDFTLTISSLQPEDFATYYCQQFNSYPLTFGGGTKVEI<br>KRTVAAPSVFIFPPSDEQLKSGTASVVCLLNNFYPREAKVQ<br>WKVDNALQSGNSQESVTEQDSKDSTYSLSSTLTLSKADYEK<br>HKVYACEVTHQGLSSPVTKSFNRGEC |
| | LY VH | SEQ ID NO.: 22 | QVQLVQSGAEVKKPGSSVKVSCKASGYSFTDYHIHWVRQAP<br>GQGLEWMGVINPMYGTTDYNQRFKGRVTITADESTSTAYME<br>LSSLRSEDTAVYYCARYDYFTGTGVYWGQGTLVTVSS |
| | CH1 | SEQ ID NO.: 19 | ASTKGPSVFPLAPSSKSTSGGTAALGCLVKDYFPEPVTVSW<br>NSGALTSGVHTFPAVLQSSGLYSLSSVVTVPSSSLGTQTYI<br>CNVNHKPSNTKVDKKVEPKSC |
| | Linker | | none |
| | 15D2VL | SEQ ID NO.: 24 | AIQLTQSPSSLSASVGDRVTITCRASQGISSALAWYQQKPG<br>KAPKLLIYDASSLESGVPSRFSGSGSGTDFTLTISSLQPED<br>FATYYCQQFNSYPLTFGGGTKVEIK |
| | CL | SEQ ID NO.: 17 | RTVAAPSVFIFPPSDEQLKSGTASVVCLLNNFYPREAKVQW<br>KVDNALQSGNSQESVTEQDSKDSTYSLSSTLTLSKADYEKH<br>KVYACEVTHQGLSSPVTKSFNRGEC |
| Anti-IL-17/IL-20 FIT 5-Ig POLYPEPTIDE #1 | | SEQ ID NO.: 25 | DIVMTQTPLSLSVTPGQPASISCRSSRSLVHSRGNTYLHWY<br>LQKPGQSPQLLIYKVSNRFIGVPDRFSGSGSGTDFTLKISR<br>VEAEDVGVYYCSQSTHLPFTFGQGTKLEIKRTVAAPSVFIF<br>PPSDEQLKSGTASVVCLLNNFYPREAKVQWKVDNALQSGNS<br>QESVTEQDSKDSTYSLSSTLTLSKADYEKHKVYACEVTHQG<br>LSSPVTKSFNRGECGSGQVQLVQSGAEVKRPGASVKVSCKA<br>SGYTFTNDIIHWVRQAPGQRLEWMGWINAGYGNTQYSQNFQ<br>DRVSITRDTSASTAYMELISLRSEDTAVYYCAREPLWFGES<br>SPHDYYGMDVWGQGTTVTVSSASTKGPSVFPLAPSSKSTSG<br>GTAALGCLVKDYFPEPVTVSWNSGALTSGVHTFPAVLQSSG<br>LYSLSSVVTVPSSSLGTQTYICNVNHKPSNTKVDKKVEPKS<br>CDKTHTCPPCPAPELLGGPSVFLFPPKPKDTLMISRTPEVT<br>CVVVDVSHEDPEVKFNWYVDGVEVHNAKTKPREEQYNSTYR<br>VVSVLTVLHQDWLNGKEYKCKVSNKALPAPIEKTISKAKGQ<br>PREPQVYTLPPSREEMTKNQVSLTCLVKGFYPSDIAVEWES<br>NGQPENNYKTTPPVLDSDGSFFLYSKLTVDKSRWQQGNVFS<br>CSVMHEALHNHYTQKSLSLSPGK |
| | LY VL | SEQ ID NO.: 16 | DIVMTQTPLSLSVTPGQPASISCRSSRSLVHSRGNTYLHWY<br>LQKPGQSPQLLIYKVSNRFIGVPDRFSGSGSGTDFTLKISR<br>VEAEDVGVYYCSQSTHLPFTFGQGTKLEIK |
| | CL | SEQ ID NO.: 17 | RTVAAPSVFIFPPSDEQLKSGTASVVCLLNNFYPREAKVQW<br>KVDNALQSGNSQESVTEQDSKDSTYSLSSTLTLSKADYEKH<br>KVYACEVTHQGLSSPVTKSFNRGEC |
| | Linker | SEQ ID NO.: 26 | GSG |
| | 15D2 VH | SEQ ID NO.: 18 | QVQLVQSGAEVKRPGASVKVSCKASGYTFTNDIIHWVRQAP<br>GQRLEWMGWINAGYGNTQYSQNFQDRVSITRDTSASTAYME<br>LISLRSEDTAVYYCAREPLWFGESSPHDYYGMDVWGQGTTV<br>TVSS |
| | CH1 | SEQ ID NO.: 19 | ASTKGPSVFPLAPSSKSTSGGTAALGCLVKDYFPEPVTVSW<br>NSGALTSGVHTFPAVLQSSGLYSLSSVVTVPSSSLGTQTYI<br>CNVNHKPSNTKVDKKVEPKSC |
| | Fc | SEQ ID NO.: 20 | DKTHTCPPCPAPELLGGPSVFLFPPKPKDTLMISRTPEVTC<br>VVVDVSHEDPEVKFNWYVDGVEVHNAKTKPREEQYNSTYRV<br>VSVLTVLHQDWLNGKEYKCKVSNKALPAPIEKTISKAKGQP<br>REPQVYTLPPSREEMTKNQVSLTCLVKGFYPSDIAVEWESN<br>GQPENNYKTTPPVLDSDGSFFLYSKLTVDKSRWQQGNVFSC<br>SVMHEALHNHYTQKSLSLSPGK |
| Anti-IL-17/IL-20 FIT5-Ig POLYPEPTIDE #4 | | SEQ ID NO.: 30 | QVQLVQSGAEVKKPGSSVKVSCKASGYSFTDYHIHWVRQAP<br>GQGLEWMGVINPMYGTTDYNQRFKGRVTITADESTSTAYME<br>LSSLRSEDTAVYYCARYDYFTGTGVYWGQGTLVTVSSASTK<br>GPSVFPLAPSSKSTSGGTAALGCLVKDYFPEPVTVSWNSGA<br>LTSGVHTFPAVLQSSGLYSLSSVVTVPSSSLGTQTYICNVN<br>HKPSNTKVDKKVEPKSCGSGAIQLTQSPSSLSASVGDRVTI<br>TCRASQGISSALAWYQQKPGKAPKLLIYDASSLESGVPSRF<br>SGSGSGTDFTLTISSLQPEDFATYYCQQFNSYPLTFGGGTK<br>VEIKRTVAAPSVFIFPPSDEQLKSGTASVVCLLNNFYPREA<br>KVQWKVDNALQSGNSQESVTEQDSKDSTYSLSSTLTLSKAD<br>YEKHKVYACEVTHQGLSSPVTKSFNRGEC |
| | LY VH | SEQ ID NO.: 22 | QVQLVQSGAEVKKPGSSVKVSCKASGYSFTDYHIHWVRQAP<br>GQGLEWMGVINPMYGTTDYNQRFKGRVTITADESTSTAYME<br>LSSLRSEDTAVYYCARYDYFTGTGVYWGQGTLVTVSS |
| | CH1 | SEQ ID NO.: 19 | ASTKGPSVFPLAPSSKSTSGGTAALGCLVKDYFPEPVTVSW<br>NSGALTSGVHTFPAVLQSSGLYSLSSVVTVPSSSLGTQTYI<br>CNVNHKPSNTKVDKKVEPKSC |

TABLE 3-continued

Amino acid sequences of anti-IL-17/IL-20 FIT-Ig molecules

| Protein | Protein region | Sequence Identifier | Sequence 12345678901234567890 |
|---|---|---|---|
| | Linker | SEQ ID NO.: 26 | GSG |
| | 15D2 VL | SEQ ID NO.: 24 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| Anti-IL-17/IL-20 FIT 6-Ig POLYPEPTIDE #1 | | SEQ ID NO.: 27 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIKRTVAAPSVFIF PPSDEQLKSGTASVVCLLNNFYPREAKVQWKVDNALQSGNS QESVTEQDSKDSTYSLSSTLTLSKADYEKHKVYACEVTHQG LSSPVTKSFNRGECGGGGSGSQVQLVQSGAEVKRPGASVKV SCKASGYTFTNDIIHWVRQAPGQRLEWMGWINAGYGNTQYS QNFQDRVSITRDTSASTAYMELISLRSEDTAVYYCAREPLW FGESSPHDYYGMDVWGQGTTVTVSSASTKGPSVFPLAPSSK STSGGTAALGCLVKDYFPEPVTVSWNSGALTSGVHTFPAVL QSSGLYSLSSVVTVPSSSLGTQTYICNVNHKPSNTKVDKKV EPKSCDKTHTCPPCPAPELLGGPSVFLFPPKPKDTLMISRT PEVTCVVVDVSHEDPEVKFNWYVDGVEVHNAKTKPREEQYN STYRVVSVLTVLHQDWLNGKEYKCKVSNKALPAPIEKTISK AKGQPREPQVYTLPPSREEMTKNQVSLTCLVKGFYPSDIAV EWESNGQPENNYKTTPPVLDSDGSFFLYSKLTVDKSRWQQG NVFSCSVMHEALHNHYTQKSLSLSPGK |
| | LY VL | SEQ ID NO.: 16 | DIVMTQTPLSLSVTPGQPASISCRSSRSLVHSRGNTYLHWY LQKPGQSPQLLIYKVSNRFIGVPDRFSGSGSGTDFTLKISR VEAEDVGVYYCSQSTHLPFTFGQGTKLEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |
| | Linker | | GGGGSGS |
| | 15D2 VH | SEQ ID NO.: 18 | QVQLVQSGAEVKRPGASVKVSCKASGYTFTNDIIHWVRQAP GQRLEWMGWINAGYGNTQYSQNFQDRVSITRDTSASTAYME LISLRSEDTAVYYCAREPLWFGESSPHDYYGMDVWGQGTTV TVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Fc | SEQ ID NO.: 20 | DKTHTCPPCPAPELLGGPSVFLFPPKPKDTLMISRTPEVTC VVVDVSHEDPEVKFNWYVDGVEVHNAKTKPREEQYNSTYRV VSVLTVLHQDWLNGKEYKCKVSNKALPAPIEKTISKAKGQP REPQVYTLPPSREEMTKNQVSLTCLVKGFYPSDIAVEWESN GQPENNYKTTPPVLDSDGSFFLYSKLTVDKSRWQQGNVFSC SVMHEALHNHYTQKSLSLSPGK |
| Anti-IL-17/IL-20 FIT6-Ig POLYPEPTIDE #4 | | SEQ ID NO.: 31 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSSASTK GPSVFPLAPSSKSTSGGTAALGCLVKDYFPEPVTVSWNSGA LTSGVHTFPAVLQSSGLYSLSSVVTVPSSSLGTQTYICNVN HKPSNTKVDKKVEPKSCGGGGSGSAIQLTQSPSSLSASVGD RVTITCRASQGISSALAWYQQKPGKAPKLLIYDASSLESGV PSRFSGSGSGTDFTLTISSLQPEDFATYYCQQFNSYPLTFG GGTKVEIKRTVAAPSVFIFPPSDEQLKSGTASVVCLLNNFY PREAKVQWKVDNALQSGNSQESVTEQDSKDSTYSLSSTLTL SKADYEKHKVYACEVTHQGLSSPVTKSFNRGEC |
| | LY VH | SEQ ID NO.: 22 | QVQLVQSGAEVKKPGSSVKVSCKASGYSFTDYHIHWVRQAP GQGLEWMGVINPMYGTTDYNQRFKGRVTITADESTSTAYME LSSLRSEDTAVYYCARYDYFTGTGVYWGQGTLVTVSS |
| | CH1 | SEQ ID NO.: 19 | ASTKGPSVFPLAPSSKSTSGGTAALGCLVKDYFPEPVTVSW NSGALTSGVHTFPAVLQSSGLYSLSSVVTVPSSSLGTQTYI CNVNHKPSNTKVDKKVEPKSC |
| | Linker | SEQ ID NO.: 28 | GGGGSGS |
| | 15D2 VL | SEQ ID NO.: 24 | AIQLTQSPSSLSASVGDRVTITCRASQGISSALAWYQQKPG KAPKLLIYDASSLESGVPSRFSGSGSGTDFTLTISSLQPED FATYYCQQFNSYPLTFGGGTKVEIK |
| | CL | SEQ ID NO.: 17 | RTVAAPSVFIFPPSDEQLKSGTASVVCLLNNFYPREAKVQW KVDNALQSGNSQESVTEQDSKDSTYSLSSTLTLSKADYEKH KVYACEVTHQGLSSPVTKSFNRGEC |

Example 1.2: Expression, Purification, and Analysis of Anti-IL-17/IL-20 FIT-Ig Proteins All DNA constructs of each FIT-Ig were subcloned into pBOS based vectors, and sequenced to ensure accuracy. Construct #1, #2, and #3 of each FIT-Ig (1, 2, and 3), or construct #1 and #4 of each FIT-Ig (4, 5, and 6) were transiently co-expressed using Polyethyleneimine (PEI) in 293E cells. Briefly, DNA in FreeStyle™ 293 Expression Medium was mixed with the PEI with the final concentration of DNA to PEI ratio of 1:2, incubated for 15 min (no more than 20 min) at room temperature, and then added to the 293E cells ($1.0\text{-}1.2\times10^6$/ml, cell viability >95%) at 60 µg DNA/120 ml culture. After 6-24 hours culture in shaker, peptone was added to the transfected cells at a final concentration of 500, with shaking at 125 rpm/min., at 37° C., 8% $CO_2$. On the 6th-7th day, supernatant was harvested by centrifugation and filtration, and FIT-Ig protein was purified using protein A chromatography (Pierce, Rockford, IL) according to the manufacturer's instructions. The proteins were analyzed by SDS-PAGE and their concentrations determined by A280 and BCA (Pierce, Rockford, IL).

For the expression of FIT1-Ig, FIT2-Ig, and FIT3-Ig, different DNA molar ratios of the 3 constructs were used, including construct #1:#2:#3=1:1:1, construct #1:#2:#3=1:1.5:1.5, and construct #1:#2:#3=1:3:3 (Table 4). FIT-Ig proteins were purified by protein A chromatography. The purification yield (7-16 mg/L) was consistent with hIgG quantification of the expression medium for each protein. The composition and purity of the purified FIT-Igs were analyzed by SDS-PAGE in both reduced and non-reduced conditions. In non-reduced conditions, FIT-Ig migrated as a single band of approximately 250 KDa. In reducing conditions, each of the FIT-Ig proteins yielded two bands, one higher MW band is construct #1 of approximately 75 KDa, and one lower MW band corresponds to both construct #2 and #3 overlapped at approximately 25 KDa. The SDS-PAGE showed that each FIT-Ig is expressed as a single species, and the 3 polypeptide chains are efficiently paired to form an IgG-like molecule. The sizes of the chains as well as the full-length protein of FIT-Ig molecules are consistent with their calculated molecular mass based on amino acid sequences.

TABLE 4

Expression and SEC analysis of hIL-17/IL-20 FIT-Ig proteins

| FIT-Ig protein | DNA ratio: Construct 1:2:3 | Expression level (mg/L) | % Peak monomeric fraction by SEC |
|---|---|---|---|
| FIT1-Ig | 1:1:1 | 15.16 | 92.07 |
| | 1:1.5:1.5 | 14.73 | 95.49 |
| | 1:3:3 | 9.87 | 97.92 |
| FIT2-Ig | 1:1:1 | 15.59 | 90.92 |
| | 1:1.5:1.5 | 12.61 | 94.73 |
| | 1:3:3 | 7.03 | 97.29 |
| FIT3-Ig | 1:1:1 | 15.59 | 91.47 |
| | 1:1.5:1.5 | 15.16 | 94.08 |
| | 1:3:3 | 7.75 | 97.57 |

To further study the physical properties of FIT-Ig in solution, size exclusion chromatography (SEC) was used to analyze each protein. For SEC analysis of the FIT-Ig, purified FIT-Ig, in PBS, was applied on a TSKgel SuperSW3000, 300×4.6 mm column (TOSOH). An HPLC instrument, Model U3000 (DIONEX) was used for SEC. All proteins were determined using UV detection at 280 nm and 214 nm. The elution was isocratic at a flow rate of 0.25 mL/min. All 3 FIT-Ig proteins exhibited a single major peak, demonstrating physical homogeneity as monomeric proteins (Table 4). The ratio of construct #1:#2:#3=1:3:3 showed a better monomeric profile by SEC for all 3 FIT-Ig proteins (Table 4).

Table 4 also shows that the expression levels of all the FIT-Ig proteins are comparable to that of the regular mAbs, indicating that the FIT-Ig can be expressed efficiently in mammalian cells. For the expression of FIT4-Ig, FIT5-Ig, and FIT6-Ig, the DNA ration of construct #1:#4=1:1, and the expression level were in the range of 1-10 mg/L, and the % Peak monomeric fraction as determined by SEC was in the range of 58-76%. Based on this particular mAb combination (LY and 15D2), the 3-polypeptide FIT-Ig constructs (FIT1-Ig, FIT2-Ig, and FIT3-Ig) showed better expression profile than that of the 2-polypeptide FIT-Ig constructs (FIT4-Ig, FIT5-Ig, and FIT6-Ig), therefore FIT1-Ig, FIT2-Ig, and FIT3-Ig were further analyzed for functional properties Example 1.3 Determination of Antigen Binding Affinity of Anti-IL-17/IL-20 FIT-Igs The kinetics of FIT-Ig binding to rhIL-17 and rhIL-20 was determined by surface plasmon resonance (Table 5) with a Biacore X100 instrument (Biacore AB, Uppsala, Sweden) using HBS-EP (10 mM HEPES, pH 7.4, 150 mM NaCl, 3 mM EDTA, and 0.005% surfactant P20) at 25° C. Briefly, goat anti-human IgG Fcγ fragment specific polyclonal antibody (Pierce Biotechnology Inc, Rockford, Ill.) was directly immobilized across a CM5 research grade biosensor chip using a standard amine coupling kit according to manufacturer's instructions. Purified FIT-Ig samples were diluted in HEPES-buffered saline for capture across goat anti-human IgG Fc specific reaction surfaces and injected over reaction matrices at a flow rate of 5 µl/min. The association and dissociation rate constants, kon (M-1s-1) and koff (s-1) were determined under a continuous flow rate of 30 µL/min. Rate constants were derived by making kinetic binding measurements at ten different antigen concentrations ranging from 1.25 to 1000 nM. The equilibrium dissociation constant (M) of the reaction between FIT-Ig and the target proteins was then calculated from the kinetic rate constants by the following formula: KD=koff/kon. Aliquots of antigen samples were also simultaneously injected over a blank reference and reaction CM surface to record and subtract any nonspecific binding background to eliminate the majority of the refractive index change and injection noise. Surfaces were regenerated with two subsequent 25 ml injections of 10 mM Glycine (pH 1.5) at a flow rate of 10 µL/min. The anti-Fc antibody immobilized surfaces were completely regenerated and retained their full capture capacity over twelve cycles.

TABLE 5

Functional characterizations of anti-IL-17/IL-20 FIT-Ig molecules

| | | Binding Kinetics by Biacore | | | Neutralization |
|---|---|---|---|---|---|
| mAb or FIT-Ig | Antigen | $k_{on}$ ($M^{-1}s^{-1}$) | $k_{off}$ ($s^{-1}$) | $K_d$ (M) | Potency $IC_{50}$ (pM) |
| LY | hIL-17 | 8.24E+5 | 1.80E−5 | 2.18E−11 | 101 |
| FIT1-Ig | hIL-17 | 1.07E+7 | 3.88E−5 | 3.64E−12 | 102 |
| FIT2-Ig | hIL-17 | 9.24E+6 | 1.53E−5 | 1.65E−12 | 137 |
| FIT3-Ig | hIL-17 | 8.71E+6 | 9.58E−6 | 1.10E−12 | 146 |
| 15D2 | hIL-20 | 1.70E+6 | 8.30E−5 | 5.00E−11 | 50 |

TABLE 5-continued

Functional characterizations of anti-IL-17/IL-20 FIT-Ig molecules

| mAb or FIT-Ig | Antigen | Binding Kinetics by Biacore $k_{on}$ ($M^{-1}s^{-1}$) | $k_{off}$ ($s^{-1}$) | $K_d$ (M) | Neutralization Potency $IC_{50}$ (pM) |
|---|---|---|---|---|---|
| FIT1-Ig | hIL-20 | 1.40E+6 | 3.82E−5 | 2.73E−11 | 54 |
| FIT2-Ig | hIL-20 | 1.80E+6 | 3.50E−5 | 1.95E−11 | 50 |
| FIT3-Ig | hIL-20 | 1.40E+6 | 3.82E−5 | 2.73E−11 | 72 |

The Biacore analysis indicated the overall binding parameters of the three FIT-Igs to hIL-17 and hIL-20 were similar, with the affinities of the FIT-Igs being very close to that of the parental mAb LY and 15D2, and there was no lose of binding affinities for either antigen binding domains (Table 5).

Figure 3A:
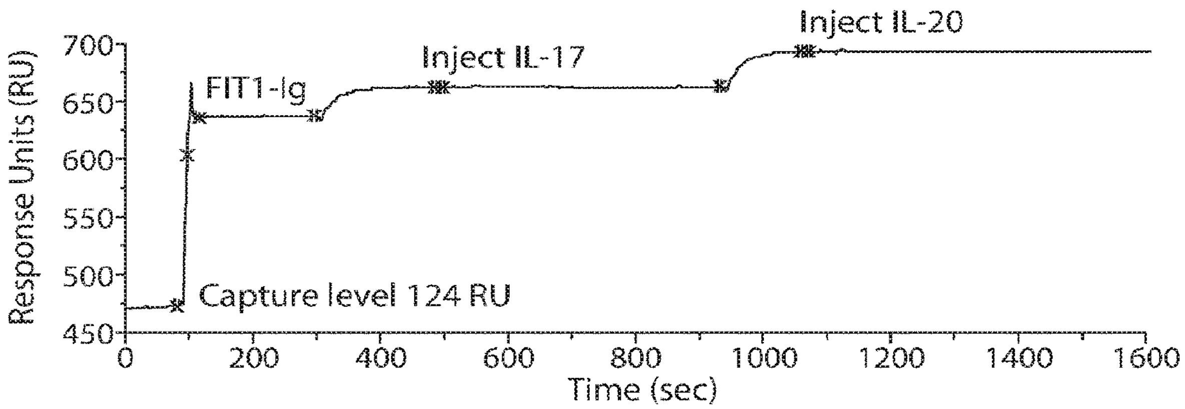
FIGS. 3A and 3B provide the dual-specific antigen binding of FIT1-Ig as measured by Biacore.
Figure 3B:
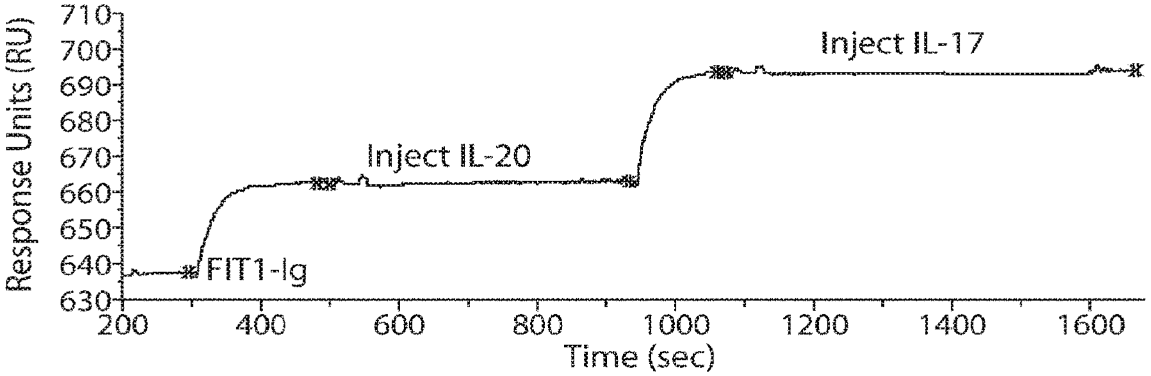

In addition, tetravalent dual-specific antigen binding of FIT-Ig was also analyzed by Biacore. FIT1-Ig was first captured via a goat anti-human Fc antibody on the Biacore sensor chip, and the first antigen was injected and a binding signal observed. As the FIT1-Ig was saturated by the first antigen, the second antigen was then injected and the second signal observed. This was done either by first injecting IL-17 then IL-20 (FIG. 3A) or by first injecting IL-20 followed by IL-17 for FIT2-Ig (FIG. 3B). In either sequence, a dual-binding activity was detected, and both antigen binding was saturated at 25-30 RU. Similar results were obtained for FIT2-Ig and FIT3-Ig. Thus each FIT-Ig was able to bind both antigens simultaneously as a dual-specific tetravalent molecule.

The expression profile and dual-binding properties of FIT-Ig clearly demonstrated that, within the FIT-Ig molecule, both VL-CL paired correctly with their corresponding VH-CH1 to form 2 functional binding domains, and expressed as a single monomeric, tetravalent, and bispecific full length FIT-Ig protein. This is in contrast to the multivalent antibody type of molecules (Miller and Presta, U.S. Pat. No. 8,722,859), which displayed tetravalent but monospecific binding activities to one target antigen.

Example 1.4 Determination of Biological Activity of Anti-IL-17/IL-20 FIT-Ig

The biological activity of FIT-Ig to neutralize IL-17 function was measured using GROα, bioassay. Briefly, Hs27 cells were seeded at 10000 cells/50 μL/well into 96 well plates. FIT-Ig or anti-IL-17 control antibody (25 μL) were added in duplicate wells, with starting concentration at 2.5 nM followed by 1:2 serial dilutions until 5 pM. IL-17A (25 μL) was then added to each well. The final concentration of IL-17A was 0.3 nM. Cells were incubated at 37° C. for 17 h before cell culture supernatant were collected. Concentrations of GRO-α, in cell culture supernatants were measured by human CACL1/GRO alpha Quantikine kit according to the manufacturer's protocol (R&D systems).

The biological activity of FIT-Ig to neutralize IL-20 function was measured using IL-20R$^+$ BAF3 cell proliferation assay. Briefly, 25 μL of recombinant human IL-20 at 0.8 nM was added to each well of 96-well plates (the final concentration of IL-20 is 0.2 nM). Anti-IL20 antibody or FIT-Ig or other control antibody were diluted to 400 nM (working concentration was 100 nM) followed by 5-fold serial dilutions and were added to 96-well assay plates (25 μL per well). BaF3 cells stably transfected with IL-20 receptor were then added to each well at concentration of 10000 cell/well in volume of 50 μL RPMI 1640 plus 10% FBS, Hygromycin B at the concentration of 800 μg/ml, G418 at the concentration of 800 μg/ml. After 48-hr incubation, 100 μL CellTiter-Glo Luminescent buffer were added to each well. Contents were mixed for 2 minutes on an orbital shaker to induce cell lysis and plates were incubated at room temperature for 10 minutes to stabilize luminescent signal. Luminescence was recorded by SpectraMax M5.

As shown in Table 5, all FIT-Igs were able to neutralize both hIL-20 and hIL-17, with affinities similar to that of the paternal antibodies. Based on functional analysis using both Biacore and cell-based neutralization assays, it appears that all 3 FIT-Igs fully retain the activities of the parental mAbs. There was no significant functional difference among the three FIT-Igs, indicating that the linker was optional, and that FIT-Ig construct provided sufficient flexibility and special dimension to allow dual binding in the absence of a peptide spacer between the 2 Fab binding regions. This is in contrast to DVD-Ig type of molecules, where a linker between the 2 variable domains on each of the 2 polypeptide chain is required for retaining activities of the lower ($2^{nd}$) variable domain.

Example 1.5 Stability Study of Anti-IL-17/IL-20 FIT-Ig

FIT1-Ig protein samples in citrate buffer (pH=6.0) were individually incubated at constant 4° C., 25° C. and 40° C. for 1 day, 3 days or 7 days; Similarly, FIT1-Ig protein samples were freeze-thawed once, twice or three times. The fractions of intact full monomeric protein of all samples was detected by SEC-HPLC, with 10 μg of each protein sample injected into Ultimate 3000 HPLC equipping Superdex200 5/150 GL at flow rate 0.3 mL/min for 15 min, and data was recorded and analyzed using Chromeleon software supplied by the manufacturer. Table 6 shows that FIT1-Ig and FIT3-Ig remained full intact monomeric molecule under these thermo-challenged conditions.

TABLE 6

Stability analysis of FIT-Ig by measuring % full monomeric fractions by SEC

| Temp. (° C.) | Time (day) | FIT1-Ig | FIT3-Ig |
|---|---|---|---|
| 4 | 0 (Starting) | 98.74 | 98.60 |
| | 1 | 98.09 | 97.78 |
| | 3 | 97.81 | 97.45 |
| | 7 | 97.63 | 97.65 |
| 25 | 1 | 99.00 | 98.26 |
| | 3 | 99.00 | 98.01 |
| | 7 | 98.86 | 98.53 |
| 40 | 1 | 98.95 | 98.50 |
| | 3 | 98.94 | 98.35 |
| | 7 | 98.82 | 98.37 |
| 1X freeze-thaw | | 98.89 | 98.21 |
| 2X freeze-thaw | | 95.37 | 98.21 |
| 3X freeze-thaw | | 95.24 | 98.35 |

Example 1.6 Solubility Study of Anti-IL-17/IL-20 FIT-Ig

Figure 4A:
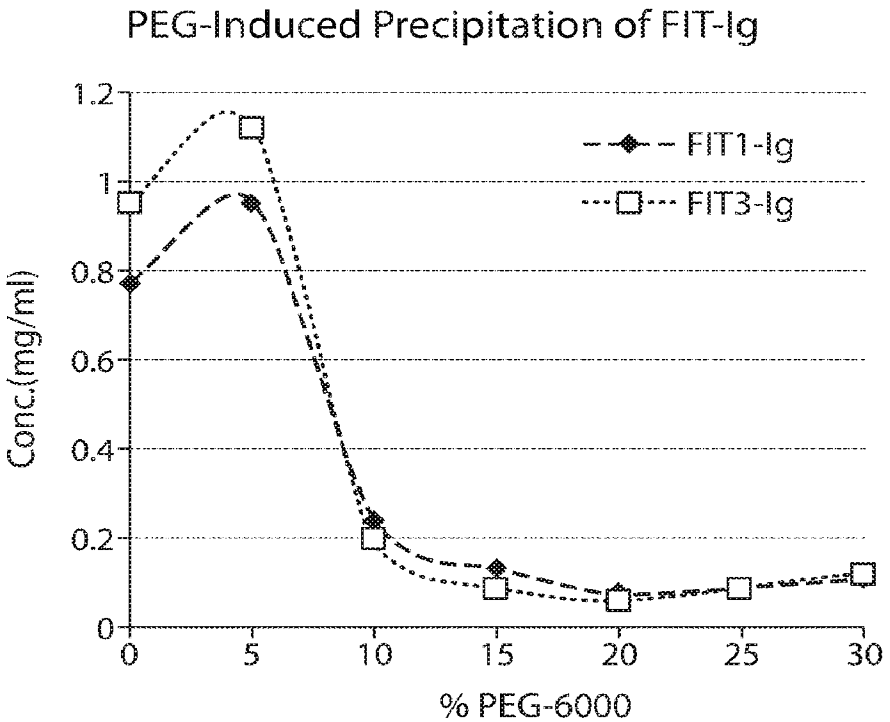
FIG. 4A. shows the solubility at a range of pH of anti-IL-17/IL-20 FIT Ig as measured by PEG-induced precipitation.
Figure 4B:
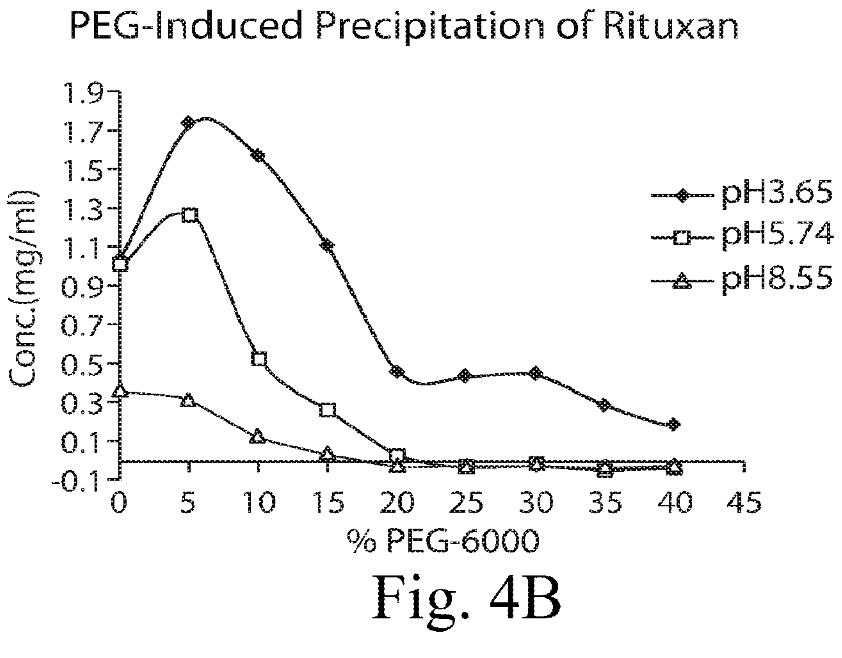
FIG. 4B shows the solubility at a range of pH of monoclonal antibody rituximab as measured by PEG-induced precipitation.

The solubility of FIT1-Ig was analyzed by measuring sign of precipitation in the presence of increasing concentration of PEG6000 (PEG6000 was purchased from Shanghai lingfeng chemical reagent co. Ltd). Briefly, solubility of protein in the presence of PEG6000 was obtained as a function of PEG6000 concentration (0, 5%, 10%, 15%, 20%, 25% and 30%). The solubility studies were conducted at a temperature of 25° C. at a solution pH of 6.0. Briefly, protein was precipitated by mixing appropriate quantities of buffered stock solutions of the protein, PEG and the buffer to get the desired concentration of the components. The final volume was made up to 200 µl and the concentration of protein was set at 1.0 mg/mL. The final solutions were mixed well and equilibrated for 16 h. After equilibration, the solutions were centrifuged at 13000 rpm for 10 min to separate the protein precipitate. Protein solubility was measured at 280 nm using Spectra Max Plus384 (Molecular Device) and obtained from the absorbance of the supernatant, and calculating the concentration based on standard curve of protein concentration (FIG. 4A). We also analyzed a commercial antibody Rituxan using the same experimental method under 3 different pH conditions (FIG. 4B). It appears that the protein solubility is dependent on the pH conditions, and that the predicted solubility of FIT-Ig would be in the range of monoclonal antibodies.

Example 1.7 Pharmacokinetic Study of Anti-IL-17/IL-20 FIT-Ig

Pharmacokinetic properties of FIT1-Ig were assessed in male Sprague-Dawley (SD) rats. FIT-Ig proteins were administered to male SD rats at a single intravenous dose of 5 mg/kg via a jugular cannula or subcutaneously under the dorsal skin. Serum samples were collected at different time points over a period of 28 days with sampling at 0, 5, 15, and 30 min; 1, 2, 4, 8, and 24 hr; and 2, 4, 7, 10, 14, 21, and 28 day serial bleeding via tail vein, and analyzed by human IL-17 capture and/or human IL-20 capture ELISAs. Briefly, ELISA plates were coated with goat anti-biotin antibody (5 µg/ml, 4° C., overnight), blocked with Superblock (Pierce), and incubated with biotinylated human IL-17 (IL-17 capture ELISA) or IL-20 (IL-20 capture ELISA) at 50 ng/ml in 10% Superblock TTBS at room temperature for 2 h. Serum samples were serially diluted (0.5% serum, 10% Superblock in TTBS) and incubated on the plate for 30 min at room temperature. Detection was carried out with HRP-labeled goat anti human antibody and concentrations were determined with the help of standard curves using the four parameter logistic fit. Several animals, especially in the subcutaneous group, showed a sudden drop in FIT-Ig concentrations following day 10, probably due to developing an anti-human response. These animals were eliminated from the final calculations. Values for the pharmacokinetic parameters were determined by non-compartmental model using WinNonlin software (Pharsight Corporation, Mountain View, Calif.).

The rat PK study, FIT1-Ig serum concentrations were very similar when determined by the two different ELISA methods, indicating that the molecule was intact, and capable of binding both antigens in vivo. Upon IV dosing, FIT1-Ig exhibited a bi-phasic pharmacokinetic profile, consisting of a distribution phase followed by an elimination phase, similar to the PK profile of conventional IgG molecules. The pharmacokinetic parameters calculated based on the two different analytical methods were very similar and are shown in Table 7. Clearance of FIT-Ig was low (~12 mL/day/kg), with low volumes of distribution (Vss~130 mL/kg) resulting in a long half-life (T½>10 days). Following subcutaneous administration, FIT-Ig absorbed slowly, with maximum serum concentrations of approximately 26.9 µg/ml reached at 4 days post-dose. The terminal half-life was about 11 days and the subcutaneous bioavailability was close to 100%. As demonstrated by these results, the properties of FIT1-Ig are very similar to a conventional IgG molecule in vivo, indicating a potential for therapeutic applications using comparable dosing regimens.

The pharmacokinetics study of FIT-Ig has demonstrated a surprising breakthrough in the field of multi-specific Ig-like biologics development. The rat pharmacokinetic system is commonly used in the pharmaceutical industry for preclinical evaluation of therapeutic mAbs, and it well predicts the pharmacokinetic profile of mAbs in humans. The long half-life and low clearance of FIT-Ig will enable its therapeutic utility for chronic indications with less frequent dosing, similar to a therapeutic mAb. In addition, FIT-Ig, being 100-kDa larger than an IgG, seemed to penetrate efficiently into the tissues based on its IgG-like volume of distribution parameter from the PK study.

TABLE 7

Pharmacokinetics analysis of FIT1-Ig in SD Rats

| | IV PK parameters | | | | |
|---|---|---|---|---|---|
| | CL | Vss | Beta $t_{1/2}$ | AUC | MRT |
| Unit | mL/day/kg | mL/kg | Day | Day × µg/mL | Day |
| IL-17 ELISA | 12.2 | 131 | 10.8 | 411 | 10.7 |
| IL-20 ELISA | 11.9 | 128 | 10.8 | 421 | 10.7 |

| | SC PK parameters | | | | | |
|---|---|---|---|---|---|---|
| | $T_{max}$ | $C_{max}$ | $t_{1/2}$ | $AUC_{INF}$ | CL/F | F |
| Unit | Day | ug/mL | Day | Day × ug/mL | mL/day/kg | % |
| IL-17 ELISA | 4.00 | 26.9 | 11.0 | 406 | 12.4 | 103.5 |
| IL-20 ELISA | 4.00 | 23.1 | 10.4 | 350 | 14.3 | 86.4 |

Example 1.8 Stable CHO Cell Line Development Studies of FIT-Ig

It has been observed that FIT-Ig was efficiently expressed in transiently-transfected 293E cells. In order to further determine the manufacturing feasibility of FIT-Ig, stable transfections were carried out in both CHO-DG44 and CHO-S cell lines, and subsequent clone selections as well as productivity analysis were performed. Briefly, CHO cells were transfected by electroporation with $8\times10^6$ cells in 400 µl transfection solution plus 20 ug DNA (for CHO DG44 cells) or 25 µg DNA (for CHO-S cells) subcloned in Freedom pCHO vector (Life Technologies). The stable cell line selection was done using routine procedures. Briefly, for CHO-DG44 selection, upon transfection, stable pool was selected (−HT/2P/400G, where P is µg/mL Puromycin, G is g/mL G418), and protein production was analyzed by IgG ELISA. Top pools were selected and proceed to amplification for several rounds with increasing concentration of MTX (50, 100, 200 and 500 nM), followed by analysis of protein production by IgG ELISA. The top pools were then selected for subcloning. For CHO-S cell selection, the first phase selection was performed in medium containing 10P/400G/100M (M is nM MTX), followed by analysis of protein production. Then the top pools were selected and proceed to $2^{nd}$ phase selection in either 30P/400G/500M or 50P/400G/1000M, followed by protein production measurement by ELISA. The top pools were then selected for subcloning. For protein productivity analysis, fully recovered cell pools (viability >90%) were seeded at $5 \times 10^5$ viable cells/mL (CHO DG44) or $3 \times 10^5$ viable cells/mL (CHO-S) using 30 mL fresh medium (CD FortiCHO™ medium supplemented with 6 mM L-glutamine) in 125-mL shake flasks. The cells were incubated on a shaking platform at 37° C., 80% relative humidity, 8% CO2, and 130 rpm. Sample cultures daily or at regular intervals (e.g., on day 0, 3, 5, 7, 10, 12, and 14) to determine the cell density, viability, and productivity until culture viability drops below 50% or day 14 of culture is reached. After sampling, feed the cultures with glucose as needed.

The overall process of FIT1-Ig CHO stable cell line development showed features similar to that of a monoclonal antibody development in CHO cells. For example, during DG44 pool analysis under 2P/400G, the VCD continued to increase until day 10-12 up to about 1.3E7, whereas cell viability remained above 80% up to day 13-14, and the productivity reached almost 40 mg/mL on day 14. Upon amplification at 5P/400G/50M, productivity reached above 50 mg/mL on day 14. For CHO-S cell selection, the titer reached above 200 mg/mL during the phase 1 selection, and above 370 mg/mL at the phase 2 selection. These levels of productivity are similar to what have been previously observed for regular human mAb development is our laboratory, suggesting that FIT-Ig display mAb-like manufacturing feasibility for commercial applications.

Example 2: Construction, Expression, and Purification of Anti-CD3/CD20 Fabs-In-Tandem Immunoglobulin (FIT-Ig)

To demonstrate if a FIT-Ig can bind to cell surface antigens, we have generated an anti-CD3/CD20 FIT-Ig molecule FIT7-Ig and FIT8-Ig, which is the 3-polypeptide construct, as shown in FIG. 1. The construct used to generate FIT-Ig capable of binding cell surface CD3 and CD20 is illustrated in FIG. 1B. Briefly, parental mAbs include two high affinity antibodies, anti-CD3 (OKT3) and anti-CD20 (Ofatumumab). To generate FIT7-Ig construct #1, the VL-CL of #OKT3 was fused directly (FIT7-g) or through a linker of 7 amino acids linker (FIT8-Ig) to the N-terminus of the Ofatumumab heavy chain (as shown in Table 8). The construct #2 is VH-CH1 of OKT3 and the 3rd construct is VL-CL of Ofatumumab. The 3 constructs for FIT-Ig were co-transfected in 293 cells, resulting in the expression and secretion of FIT-Ig proteins. The detailed procedures of the PCR cloning are described below:

Example 2.1 Molecular Cloning of Anti-CD3/CD20 FIT-Ig

The molecular cloning method is similar as that for anti-hIL-17/hIL-20 FIT-Ig.

TABLE 8

Anti-CD3/CD20 FIT-Ig molecules and constructs.

| FIT-Ig molecule | Construct #1 | Linker | Construct #2 | Construct #3 |
|---|---|---|---|---|
| FIT7-Ig | $VL_{CD3}$-CL-$VH_{CD20}$-CH1-Fc | No linker | $VH_{CD3}$-CH1 | $VL_{CD20}$-CL |
| FIT8-Ig | $VL_{CD3}$-CL-linker-$VH_{CD20}$-CH1-Fc | GGGGSGS | $VH_{CD3}$-CH1 | $VL_{CD20}$-CL |

Table 9 shows sequences of PCR primers used for molecular construction above.

TABLE 9

PCR primers used for molecular construction of anti-IL-17/IL-20 FIT-Igs

| | SEQ ID NO. |
|---|---|
| P4: GTCTGCGGCCGCTCATTTACCCGGAGACAGGGAGAG | 32 |
| P12: TCGAGCGGCCGCTCAACAAGATTTGGGCTCAACTT TCTTG | 33 |
| P20: CAGGTCCAGCTGCAGCAGTCTG | 34 |
| P22: GCCTGCGAAGTCACCCATCAGGGCCTGAGCTCGCC CGTCACAAAGAGCTTCAACAGGGG | 35 |
| P23: TACGAGAAACACAAAGTCTACGCCTGCGAAGTCAC CCATCAGGGCCTGAG | 36 |
| P24: TGACGCTGAGCAAAGCAGACTACGAGAAACACAAA GTCTACGCCTGCGAA | 37 |
| P25: CTCGCCCGTCACAAAGAGCTTCAACAGGGGAGAGT GTGAAGTGCAGCTGGTGGAGTCTG | 38 |
| P28: GCTGCTGCTGTGGTTCCCCGGCTCGCGATGCGAAA TTGTGTTGACACAGTC | 39 |
| P29: AAGATGAAGACAGATGGTGCAGCCACCGTACGTTT AATCTCCAGTCGTGTCC | 40 |

The final sequences of anti-CD3/CD20 FIT-Ig are described in Table 10.

TABLE 10

Amino acid sequences of anti-CD3/CD20 FIT-Ig

| Protein | Protein region | Sequence Identifier | Sequence 12345678901234567890 |
|---|---|---|---|
| OKT3/Ofatumumab FIT7-Ig POLYPEPTIDE #1 | | SEQ ID NO.: 41 | QIVLTQSPAIMSASPGEKVTMTCSASSSVSYMNWYQQKS GTSPKRWIYDTSKLASGVPAHFRGSGSGTSYSLTISGME AEDAATYYCQQWSSNPFTFGSGTKLEINRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGECEVQLVESGGGLVQPGRSLRLS CAASGFTFNDYAMHWVRQAPGKGLEWVSTISWNSGSIGY ADSVKGRFTISRDNAKKSLYLQMNSLRAEDTALYYCAKD IQYGNYYYGMDVWGQGTTVTVSSASTKGPSVFPLAPSSK STSGGTAALGCLVKDYFPEPVTVSWNSGALTSGVHTFPA VLQSSGLYSLSSVVTVPSSSLGTQTYICNVNHKPSNTKV DKKVEPKSCDKTHTCPPCPAPELLGGPSVFLFPPKPKDT LMISRTPEVTCVVVDVSHEDPEVKFNWYVDGVEVHNAKT |

TABLE 10-continued

Amino acid sequences of anti-CD3/CD20 FIT-Ig

| Protein | Protein region | Sequence Identifier | Sequence 12345678901234567890 |
|---|---|---|---|
| | | | KPREEQYNSTYRVVSVLTVLHQDWLNGKEYKCKVSNKAL PAPIEKTISKAKGQPREPQVYTLPPSREEMTKNQVSLTC LVKGFYPSDIAVEWESNGQPENNYKTTPPVLDSDGSFFL YSKLTVDKSRWQQGNVFSCSVMHEALHNHYTQKSLSLSP GK |
| | OKT3 VL | SEQ ID NO.: 42 | QIVLTQSPAIMSASPGEKVTMTCSASSSVSYMNWYQQKS GTSPKRWIYDTSKLASGVPAHFRGSGSGTSYSLTISGME AEDAATYYCQQWSSNPFTFGSGTKLEIN |
| | CL | SEQ ID NO.: 17 | RTVAAPSVFIFPPSDEQLKSGTASVVCLLNNFYPREAKV QWKVDNALQSGNSQESVTEQDSKDSTYSLSSTLTLSKAD YEKHKVYACEVTHQGLSSPVTKSFNRGEC |
| | Linker | | none |
| | Ofatumumab VH | SEQ ID NO.: 43 | EVQLVESGGGLVQPGRSLRLSCAASGFTFNDYAMHWVRQ APGKGLEWVSTISWNSGSIGYADSVKGRFTISRDNAKKS LYLQMNSLRAEDTALYYCAKDIQYGNYYYGMDVWGQGTT VTVSS |
| | CH1 | SEQ ID NO.: 19 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |
| | Fc | SEQ ID NO.: 20 | DKTHTCPPCPAPELLGGPSVFLFPPKPKDTLMISRTPEV TCVVVDVSHEDPEVKFNWYVDGVEVHNAKTKPREEQYNS TYRVVSVLTVLHQDWLNGKEYKCKVSNKALPAPIEKTIS KAKGQPREPQVYTLPPSREEMTKNQVSLTCLVKGFYPSD IAVEWESNGQPENNYKTTPPVLDSDGSFFLYSKLTVDKS RWQQGNVFSCSVMHEALHNHYTQKSLSLSPGK |
| OKT3/Ofatumumab FIT7-Ig POLYPEPTIDE #2 | | SEQ ID NO.: 44 | QVQLQQSGAELARPGASVKMSCKASGYTFTRYTMHWVKQ RPGQGLEWIGYINPSRGYTNYNQKFKDKATLTTDKSSST AYMQLSSLTSEDSAVYYCARYYDDHYCLDYWGQGTTLTV SSASTKGPSVFPLAPSSKSTSGGTAALGCLVKDYFPEPV TVSWNSGALTSGVHTFPAVLQSSGLYSLSSVVTVPSSSL GTQTYICNVNHKPSNTKVDKKVEPKSC |
| | OKT3 VH | SEQ ID NO.: 45 | QVQLQQSGAELARPGASVKMSCKASGYTFTRYTMHWVKQ RPGQGLEWIGYINPSRGYTNYNQKFKDKATLTTDKSSST AYMQLSSLTSEDSAVYYCARYYDDHYCLDYWGQGTTLTV SS |
| | CH1 | SEQ ID NO.: 19 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |
| OKT3/Ofatumumab FIT7-Ig POLYPEPTIDE #3 | | SEQ ID NO.: 46 | EIVLTQSPATLSLSPGERATLSCRASQSVSSYLAWYQQK PGQAPRLLIYDASNRATGIPARFSGSGSGTDFTLTISSL EPEDFAVYYCQQRSNWPITFGQGTRLEIKRTVAAPSVFI FPPSDEQLKSGTASVVCLLNNFYPREAKVQWKVDNALQS GNSQESVTEQDSKDSTYSLSSTLTLSKADYEKHKVYACE VTHQGLSSPVTKSFNRGEC |
| | Ofatumumab VL | SEQ ID NO.: 47 | EIVLTQSPATLSLSPGERATLSCRASQSVSSYLAWYQQK PGQAPRLLIYDASNRATGIPARFSGSGSGTDFTLTISSL EPEDFAVYYCQQRSNWPITFGQGTRLEIK |
| | CL | SEQ ID NO.: 17 | RTVAAPSVFIFPPSDEQLKSGTASVVCLLNNFYPREAKV QWKVDNALQSGNSQESVTEQDSKDSTYSLSSTLTLSKAD YEKHKVYACEVTHQGLSSPVTKSFNRGEC |
| OKT3/Ofatumumab FIT8-Ig POLYPEPTIDE #1 | | SEQ ID NO.: 48 | QIVLTQSPAIMSASPGEKVTMTCSASSSVSYMNWYQQKS GTSPKRWIYDTSKLASGVPAHFRGSGSGTSYSLTISGME AEDAATYYCQQWSSNPFTFGSGTKLEINRTVAAPSVFIF PPSDEQLKSGTASVVCLLNNFYPREAKVQWKVDNALQSG NSQESVTEQDSKDSTYSLSSTLTLSKADYEKHKVYACEV THQGLSSPVTKSFNRGECGGGGSGSEVQLVESGGGLVQP GRSLRLSCAASGFTFNDYAMHWVRQAPGKGLEWVSTISW NSGSIGYADSVKGRFTISRDNAKKSLYLQMNSLRAEDTA LYYCAKDIQYGNYYYGMDVWGQGTTVTVSSASTKGPSVF PLAPSSKSTSGGTAALGCLVKDYFPEPVTVSWNSGALTS GVHTFPAVLQSSGLYSLSSVVTVPSSSLGTQTYICNVNH KPSNTKVDKKVEPKSCDKTHTCPPCPAPELLGGPSVFLF PPKPKDTLMISRTPEVTCVVVDVSHEDPEVKFNWYVDGV EVHNAKTKPREEQYNSTYRVVSVLTVLHQDWLNGKEYKC KVSNKALPAPIEKTISKAKGQPREPQVYTLPPSREEMTK NQVSLTCLVKGFYPSDIAVEWESNGQPENNYKTTPPVLD SDGSFFLYSKLTVDKSRWQQGNVFSCSVMHEALHNHYTQ KSLSLSPGK |
| | OKT3 VL | SEQ ID NO.: 42 | QIVLTQSPAIMSASPGEKVTMTCSASSSVSYMNWYQQKS GTSPKRWIYDTSKLASGVPAHFRGSGSGTSYSLTISGME AEDAATYYCQQWSSNPFTFGSGTKLEIN |

TABLE 10-continued

Amino acid sequences of anti-CD3/CD20 FIT-Ig

| Protein | Protein region | Sequence Identifier | Sequence 12345678901234567890 |
|---|---|---|---|
| | CL | SEQ ID NO.: 17 | RTVAAPSVFIFPPSDEQLKSGTASVVCLLNNFYPREAKV<br>QWKVDNALQSGNSQESVTEQDSKDSTYSLSSTLTLSKAD<br>YEKHKVYACEVTHQGLSSPVTKSFNRGEC |
| | Linker | SEQ ID NO.: 28 | GGGGSGS |
| | Ofatumumab VH | | EVQLVESGGGLVQPGRSLRLSCAASGFTFNDYAMHWVRQ<br>APGKGLEWVSTISWNSGSIGYADSVKGRFTISRDNAKKS<br>LYLQMNSLRAEDTALYYCAKDIQYGNYYYGMDVWGQGTT<br>VTVSS |
| | CH1 | SEQ ID NO.: 19 | ASTKGPSVFPLAPSSKSTSGGTAALGCLVKDYFPEPVTV<br>SWNSGALTSGVHTFPAVLQSSGLYSLSSVVTVPSSSLGT<br>QTYICNVNHKPSNTKVDKKVEPKSC |
| | Fc | SEQ ID NO.: 20 | DKTHTCPPCPAPELLGGPSVFLFPPKPKDTLMISRTPEV<br>TCVVVDVSHEDPEVKFNWYVDGVEVHNAKTKPREEQYNS<br>TYRVVSVLTVLHQDWLNGKEYKCKVSNKALPAPIEKTIS<br>KAKGQPREPQVYTLPPSREEMTKNQVSLTCLVKGFYPSD<br>IAVEWESNGQPENNYKTTPPVLDSDGSFFLYSKLTVDKS<br>RWQQGNVFSCSVMHEALHNHYTQKSLSLSPGK |
| OKT3/Ofatumumab FIT8-Ig POLYPEPTIDE #2 | | SEQ ID NO.: 44 | QVQLQQSGAELARPGASVKMSCKASGYTFTRYTMHWVKQ<br>RPGQGLEWIGYINPSRGYTNYNQKFKDKATLTTDKSSST<br>AYMQLSSLTSEDSAVYYCARYYDDHYCLDYWGQGTTLTV<br>SSASTKGPSVFPLAPSSKSTSGGTAALGCLVKDYFPEPV<br>TVSWNSGALTSGVHTFPAVLQSSGLYSLSSVVTVPSSSL<br>GTQTYICNVNHKPSNTKVDKKVEPKSC |
| | OKT3 VH | SEQ ID NO.: 45 | QVQLQQSGAELARPGASVKMSCKASGYTFTRYTMHWVKQ<br>RPGQGLEWIGYINPSRGYTNYNQKFKDKATLTTDKSSST<br>AYMQLSSLTSEDSAVYYCARYYDDHYCLDYWGQGTTLTV<br>SS |
| | CH1 | SEQ ID NO.: 19 | ASTKGPSVFPLAPSSKSTSGGTAALGCLVKDYFPEPVTV<br>SWNSGALTSGVHTFPAVLQSSGLYSLSSVVTVPSSSLGT<br>QTYICNVNHKPSNTKVDKKVEPKSC |
| OKT3/Ofatumumab FIT8-Ig POLYPEPTIDE #3 | | SEQ ID NO.: 46 | EIVLTQSPATLSLSPGERATLSCRASQSVSSYLAWYQQK<br>PGQAPRLLIYDASNRATGIPARFSGSGSGTDFTLTISSL<br>EPEDFAVYYCQQRSNWPITFGQGTRLEIKRTVAAPSVFI<br>FPPSDEQLKSGTASVVCLLNNFYPREAKVQWKVDNALQS<br>GNSQESVTEQDSKDSTYSLSSTLTLSKADYEKHKVYACE<br>VTHQGLSSPVTKSFNRGEC |
| | Ofatumumab VL | SEQ ID NO.: 47 | EIVLTQSPATLSLSPGERATLSCRASQSVSSYLAWYQQK<br>PGQAPRLLIYDASNRATGIPARFSGSGSGTDFTLTISSL<br>EPEDFAVYYCQQRSNWPITFGQGTRLEIK |
| | CL | SEQ ID NO.: 17 | RTVAAPSVFIFPPSDEQLKSGTASVVCLLNNFYPREAKV<br>QWKVDNALQSGNSQESVTEQDSKDSTYSLSSTLTLSKAD<br>YEKHKVYACEVTHQGLSSPVTKSFNRGEC |

Example 2.2 Expression and Purification of Anti-CD3/CD20 FIT-Ig

All DNA constructs of each FIT-Ig were subcloned into pBOS based vectors, and sequenced to ensure accuracy. Construct #1, #2, and #3 of each FIT-Ig were transiently co-expressed using Polyethyleneimine (PEI) in 293E cells. Briefly, DNA in FreeStyle™ 293 Expression Medium was mixed with the PEI with the final concentration of DNA to PEI ratio of 1:2, incubated for 15 min (no more than 20 min) at room temperature, and then added to the 293E cells ($1.0\text{-}1.2\times10^6$/ml, cell viability >95%) at 60 μg DNA/120 ml culture. After 6-24 hours culture in shaker, add peptone to the transfected cells at a final concentration of 5%, with shaking at 125 rpm/min., at 37° C., 8% $CO_2$. On the 6th-7th day, supernatant was harvested by centrifugation and filtration, and FIT-Ig protein purified using protein A chromatography (Pierce, Rockford, Ill.) according to manufacturer's instructions. The proteins were analyzed by SDS-PAGE and their concentration determined by A280 and BCA (Pierce, Rockford, Ill.) (Table 11).

TABLE 11

Expression and SEC analysis of anti-CD3/CD20 FIT-Ig proteins

| FIT-Ig protein | DNA ratio: Construct 1:2:3 | Expression level (mg/L) | % Peak monomeric fraction by SEC |
|---|---|---|---|
| FIT7-Ig | 1:3:3 | 21.3 | 99.53 |
| FIT8-Ig | 1:3:3 | 25.6 | 99.16 |

Example 2.3 Binding Activities of Anti-CD3/CD20 FIT-Ig Molecules

Binding of anti-CD3/CD20 FIT-Igs to both targets were analyzed by FACS, using Jurkat cells that express CD3 on the cell surface, as well as Raji cells that express CD20 on the cell surface. Briefly, $5\times10^5$ cells were washed in ice-cold PBS and blocked with 2% FBS on ice for 1 hr. Cells were incubated with antibody, FIT-Ig (100 nM), or isotype control on ice for 1 hr and washed 3 times with PBS. Secondary antibody (goat anti-human IgG labeled with Alexa Fluor 488, Invitrogen) were added and incubated with cells on ice for 1 hr in dark followed by three times wash with PBS.

Samples were analyzed in FACs calibur. The cell surface binding shows that both FIT7-Ig and FIT8-Ig were able to binding to both cell surface antigens CD3 and CD20 in a concentration dependent manner. Compared to the binding activities of the parental mAbs, FIT-Ig showed a reduced binding intensity to CD3 on Jurkat cells, but an enhanced binding intensity to CD20 on Raji cells. In all binding studies, FIT7-Ig and FIT8-Ig showed similar binding activities to both antigens, indicating the linker did not make a significant impact on its binding ability for FIT8-Ig (Table 12).

TABLE 12

Cell surface antigen binding studies of anti-CD3/CD20 FIT-Ig proteins

| FIT-Ig protein | Antigen (cell line) | Binding Intensity by FACS (MFI) |
|---|---|---|
| OKT3 | CD3 (Jurkat) | 399 |
| FIT7-Ig | | 159 |
| FIT8-Ig | | 211 |
| Ofatumumab | CD20 (Raji) | 181 |
| FIT7-Ig | | 291 |
| FIT8-Ig | | 274 |

Example 3: Construction, Expression, and Purification of Anti-TNF/IL-17 Fabs-In-Tandem Immunoglobulin (FIT-Ig)

Another FIT-Ig that can bind to human IL-17 and human TNFα (FIT9-Ig) was also generated using anti-IL-17 mAb clone LY, and anti-TNF mAb Golimumab, in the 3-polypeptide construct, as shown in FIG. 1. To generate FIT9-Ig construct #1, the VL-CL of Golimumab was fused directly to the N-terminus of LY heavy chain (as shown in Table 13). The construct #2 is VH-CH1 of Golimumab and the 3d construct is VL-CL of LY. The 3 constructs for FIT9-Ig were co-transfected in 293 cells, resulting in the expression and secretion of FIT9-Ig proteins. The final sequences of anti-TNF/IL-17 FIT-Ig are described in Table 14.

Example 3.1 Molecular Cloning of Anti-TNF/IL-17 FIT-Ig

The molecular cloning method is similar as that for anti-hIL-17/hIL-20 FIT-Ig.

TABLE 13

Anti-TNF/IL-17 FIT-Ig molecule and constructs.

| FIT-Ig molecule | Construct #1 | Linker | Construct #2 | Construct #3 |
|---|---|---|---|---|
| FIT9-Ig | $VL_{TNF}$-CL-$VH_{IL-17}$-CH1-Fc | No linker | $VH_{TNF}$-CH1 | $VL_{IL-17}$-CL |

TABLE 14

Amino acid sequences of anti-TNF/IL-17 FIT-Ig molecules

| Protein | Protein region | SEQ ID NO: | Sequence 12345678901234567890 |
|---|---|---|---|
| Anti-IL-TNF/IL-17 FIT9-Ig POLYPEPTIDE #1 | | SEQ ID NO.: 87 | EIVLTQSPATLSLSPGERATLSCRASQSVYSYLAWYQQK PGQAPRLLIYDASNRATGIPARFSGSGSGTDFTLTISSL EPEDFAVYYCQQRSNWPPFTFGPGTKVDIKRTVAAPSVF IFPPSDEQLKSGTASVVCLLNNFYPREAKVQWKVDNALQ SGNSQESVTEQDSKDSTYSLSSTLTLSKADYEKHKVYAC EVTHQGLSSPVTKSFNRGECQVQLVQSGAEVKKPGSSVK VSCKASGYSFTDYHIHWVRQAPGQGLEWMGVINPMYGTT DYNQRFKGRVTITADESTSTAYMELSSLRSEDTAVYYCA RYDYFTGTGVYWGQGTLVTVSSASTKGPSVFPLAPSSKS TSGGTAALGCLVKDYFPEPVTVSWNSGALTSGVHTFPAV LQSSGLYSLSSVVTVPSSSLGTQTYICNVNHKPSNTKVD KKVEPKSCDKTHTCPPCPAPELLGGPSVFLFPPKPKDTL MISRTPEVTCVVVDVSHEDPEVKFNWYVDGVEVHNAKTK PREEQYNSTYRVVSVLTVLHQDWLNGKEYKCKVSNKALP APIEKTISKAKGQPREPQVYTLPPSREEMTKNQVSLTCL VKGFYPSDIAVEWESNGQPENNYKTTPPVLDSDGSFFLY SKLTVDKSRWQQGNVFSCSVMHEALHNHYTQKSLSLSPG K |
| | GOLIMUMAB VL | SEQ ID NO.: 88 | EIVLTQSPATLSLSPGERATLSCRASQSVYSYLAWYQQK PGQAPRLLIYDASNRATGIPARFSGSGSGTDFTLTISSL EPEDFAVYYCQQRSNWPPFTFGPGTKVDIK |
| | CL | SEQ ID NO.: 17 | RTVAAPSVFIFPPSDEQLKSGTASVVCLLNNFYPREAKV QWKVDNALQSGNSQESVTEQDSKDSTYSLSSTLTLSKAD YEKHKVYACEVTHQGLSSPVTKSFNRGEC |
| | Linker | | None |
| | LY VH | SEQ ID NO.: 22 | QVQLVQSGAEVKKPGSSVKVSCKASGYSFTDYHIHWVRQ APGQGLEWMGVINPMYGTTDYNQRFKGRVTITADESTST AYMELSSLRSEDTAVYYCARYDYFTGTGVYWGQGTLVTV SS |
| | CH1 | SEQ ID NO.: 19 | ASTKGPSVFPLAPSSKSTSGGTAALGCLVKDYFPEPVTV SWNSGALTSGVHTFPAVLQSSGLYSLSSVVTVPSSSLGT QTYICNVNHKPSNTKVDKKVEPKSC |

TABLE 14-continued

Amino acid sequences of anti-TNF/IL-17 FIT-Ig molecules

| Protein | Protein region | SEQ ID NO: | Sequence 12345678901234567890 |
|---|---|---|---|
| | Fc | SEQ ID NO.: 20 | DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| Anti-TNF/IL-17 FIT9-Ig POLYPEPTIDE #2 | | SEQ ID NO.: 89 | QVQLVESGGGVVQPGRSLRLSCAASGFIFSSYAMHWVRQAPGNGLEWVAFMSYDGSNKKYADSVKGRFTISRDNSKNTLYLQMNSLRAEDTAVYYCARDRGIAAGGNYYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | GOLIMUMAB VH | SEQ ID NO.: 90 | QVQLVESGGGVVQPGRSLRLSCAASGFIFSSYAMHWVRQAPGNGLEWVAFMSYDGSNKKYADSVKGRFTISRDNSKNTLYLQMNSLRAEDTAVYYCARDRGIAAGGNYYYYGMDVWGQGTTVTVSS |
| | CH1 | SEQ ID NO.: 19 | ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| Anti-IL-TNF/IL-17 FIT9-Ig POLYPEPTIDE #3 | | SEQ ID NO.: 91 | DIVMTQTPLSLSVTPGQPASISCRSSRSLVHSRGNTYLHWYLQKPGQSPQLLIYKVSNRFIGVPDRFSGSGSGTDFTLKISRVEAEDVGVYYCSQSTHLPFTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | LY VL | SEQ ID NO.: 16 | DIVMTQTPLSLSVTPGQPASISCRSSRSLVHSRGNTYLHWYLQKPGQSPQLLIYKVSNRFIGVPDRFSGSGSGTDFTLKISRVEAEDVGVYYCSQSTHLPFTFGQGTKLEIK |
| | CL | SEQ ID NO.: 17 | RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

Example 3.2 Expression, Purification, and Analysis of Anti-TNF/IL-17 FIT-Ig Proteins All DNA constructs of each FIT-Ig were subcloned into pBOS based vectors, and sequenced to ensure accuracy. Construct #1, #2, and #3 of FIT9-Ig were transiently co-expressed using Polyethyleneimine (PEI) in 293E cells as described previously and FIT9-Ig proteins were purified by protein A chromatography. The expression level was 10-23 mg/L. The purified protein was subjected to functional analysis using cell-based assays for IL-17 (production of GROα by Hs27 cells) and TNF (production of IL-8 by L929 cells). The neutralization potency of FIT9-Ig against human TNF was 11.6 pM (compared to 15.9 pM by Golimumab in the same experiment), as against human IL-17 was 122 pM (compared to 51.5 pM by LY in the same experiment). Overall FIT9-Ig maintained the biological activities of the parental mAbs.

Example 4: Construction, Expression, and Purification of Anti-CTLA-4/PD-1 Fabs-In-Tandem Immunoglobulin (FIT-Ig)

Another FIT-Ig that can bind to human CTLA-4 and human PD-1 (FIT10-Ig) was generated using anti-CTLA-4 mAb Ipilimumab, and anti-PD-1 mAb Nivolumab, in the 3-polypeptide construct, as shown in FIG. 1. To generate FIT10-Ig construct #1, the VL-CL of Ipilimumab was fused directly to the N-terminus of Nivolumab heavy chain (as shown in Table 15). The construct #2 is VH-CH1 of Ipilimumab and the 3d construct is VL-CL of Nivolumab. The 3 constructs for FIT-Ig were co-transfected in 293 cells, resulting in the expression and secretion of FIT10-Ig proteins.

Example 4.1 Molecular Cloning of Anti-CTLA-4/PD-1 FIT-Ig

The molecular cloning method is similar as that for anti-hIL-17/hIL-20 FIT-Ig. The final sequences of anti-CTLA-4/PD-1 FIT-Ig are described in Table 16.

TABLE 15

Anti-CTLA-4/PD-1 FIT-Ig molecule and constructs.

| FIT-Ig molecule | Construct #1 | Linker | Construct #2 | Construct #3 |
|---|---|---|---|---|
| FIT10-Ig | $VL_{CTLA-4}$-CL-$VH_{PD-1}$-CH1-Fc | No linker | $VH_{CTLA-4}$-CH1 | $VL_{PD-1}$-CL |

TABLE 16

Amino acid sequences of anti-CTLA-4/PD-1 FIT-Ig molecules

| Protein | Protein region | SEQ ID NO: | Sequence 12345678901234567890 |
|---|---|---|---|
| Anti-CTLA-4/PD-1 FIT10-Ig POLYPEPTIDE #1 | | SEQ ID NO.: 92 | EIVLTQSPGTLSLSPGERATLSCRASQSVGSSYLAWYQQKPGQ<br>APRLLIYGAFSRATGIPDRFSGSGSGTDFTLTISRLEPEDFAV<br>YYCQQYGSSPWTFGQGTKVEIKRTVAAPSVFIFPPSDEQLKSG<br>TASVVCLLNNFYPREAKVQWKVDNALQSGNSQESVTEQDSKDS<br>TYSLSSTLTLSKADYEKHKVYACEVTHQGLSSPVTKSFNRGEC<br>QVQLVESGGGVVQPGRSLRLDCKASGITFSNSGMHWVRQAPGK<br>GLEWVAVIWYDGSKRYYADSVKGRFTISRDNSKNTLFLQMNSL<br>RAEDTAVYYCATNDDYWGQGTLVTVSSASTKGPSVFPLAPSSK<br>STSGGTAALGCLVKDYFPEPVTVSWNSGALTSGVHTFPAVLQS<br>SGLYSLSSVVTVPSSSLGTQTYICNVNHKPSNTKVDKKVEPKS<br>CDKTHTCPPCPAPELLGGPSVFLFPPKPKDTLMISRTPEVTCV<br>VVDVSHEDPEVKFNWYVDGVEVHNAKTKPREEQYNSTYRVVSV<br>LTVLHQDWLNGKEYKCKVSNKALPAPIEKTISKAKGQPREPQV<br>YTLPPSREEMTKNQVSLTCLVKGFYPSDIAVEWESNGQPENNY<br>KTTPPVLDSDGSFFLYSKLTVDKSRWQQGNVFSCSVMHEALHN<br>HYTQKSLSLSPGK |
| | IPILIMUMAB VL | SEQ ID NO.: 93 | EIVLTQSPGTLSLSPGERATLSCRASQSVGSSYLAWYQQKPGQ<br>APRLLIYGAFSRATGIPDRFSGSGSGTDFTLTISRLEPEDFAV<br>YYCQQYGSSPWTFGQGTKVEIK |
| | CL | SEQ ID NO.: 17 | RTVAAPSVFIFPPSDEQLKSGTASVVCLLNNFYPREAKVQWKV<br>DNALQSGNSQESVTEQDSKDSTYSLSSTLTLSKADYEKHKVYA<br>CEVTHQGLSSPVTKSFNRGEC |
| | Linker | | None |
| | NIVOLUMAB VH | SEQ ID NO.: 94 | QVQLVESGGGVVQPGRSLRLDCKASGITFSNSGMHWVRQAPGK<br>GLEWVAVIWYDGSKRYYADSVKGRFTISRDNSKNTLFLQMNSL<br>RAEDTAVYYCATNDDYWGQGTLVTVSS |
| | CH1 | SEQ ID NO.: 19 | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKKVEPKSC |
| | Fc | SEQ ID NO.: 20 | DKTHTCPPCPAPELLGGPSVFLFPPKPKDTLMISRTPEVTCVV<br>VDVSHEDPEVKFNWYVDGVEVHNAKTKPREEQYNSTYRVVSVL<br>TVLHQDWLNGKEYKCKVSNKALPAPIEKTISKAKGQPREPQVY<br>TLPPSREEMTKNQVSLTCLVKGFYPSDIAVEWESNGQPENNYK<br>TTPPVLDSDGSFFLYSKLTVDKSRWQQGNVFSCSVMHEALHNH<br>YTQKSLSLSPGK |
| Anti-CTLA-4/PD-1 FIT10-Ig POLYPEPTIDE #2 | | SEQ ID NO.: 95 | QVQLVESGGGVVQPGRSLRLSCAASGFTFSSYTMHWVRQAPGK<br>GLEWVTFISYDGNNKYYADSVKGRFTISRDNSKNTLYLQMNSL<br>RAEDTAIYYCARTGWLGPFDYWGQGTLVTVSSASTKGPSVFPL<br>APSSKSTSGGTAALGCLVKDYFPEPVTVSWNSGALTSGVHTFP<br>AVLQSSGLYSLSSVVTVPSSSLGTQTYICNVNHKPSNTKVDKK<br>VEPKSC |
| | IPILIMUMAB VH | SEQ ID NO.: 96 | QVQLVESGGGVVQPGRSLRLSCAASGFTFSSYTMHWVRQAPGK<br>GLEWVTFISYDGNNKYYADSVKGRFTISRDNSKNTLYLQMNSL<br>RAEDTAIYYCARTGWLGPFDYWGQGTLVTVSS |
| | CH1 | SEQ ID NO.: 19 | ASTKGPSVFPLAPSSKSTSGGTAALGCLVKDYFPEPVTVSWNS<br>GALTSGVHTFPAVLQSSGLYSLSSVVTVPSSSLGTQTYICNVN<br>HKPSNTKVDKKVEPKSC |
| Anti-CTLA-4/PD-1 FIT10-Ig POLYPEPTIDE #3 | | SEQ ID NO.: 97 | EIVLTQSPATLSLSPGERATLSCRASQSVSSYLAWYQQKPGQA<br>PRLLIYDASNRATGIPARFSGSGSGTDFTLTISSLEPEDFAVY<br>YCQQSSNWPRTFGQGTKVEIKRTVAAPSVFIFPPSDEQLKSGT<br>ASVVCLLNNFYPREAKVQWKVDNALQSGNSQESVTEQDSKDST<br>YSLSSTLTLSKADYEKHKVYACEVTHQGLSSPVTKSFNRGEC |
| | NivolumabVL | SEQ ID NO.: 98 | EIVLTQSPATLSLSPGERATLSCRASQSVSSYLAWYQQKPGQA<br>PRLLIYDASNRATGIPARFSGSGSGTDFTLTISSLEPEDFAVY<br>YCQQSSNWPRTFGQGTKVEIK |
| | CL | SEQ ID NO.: 17 | RTVAAPSVFIFPPSDEQLKSGTASVVCLLNNFYPREAKVQWKV<br>DNALQSGNSQESVTEQDSKDSTYSLSSTLTLSKADYEKHKVYA<br>CEVTHQGLSSPVTKSFNRGEC |

Figure 5A:
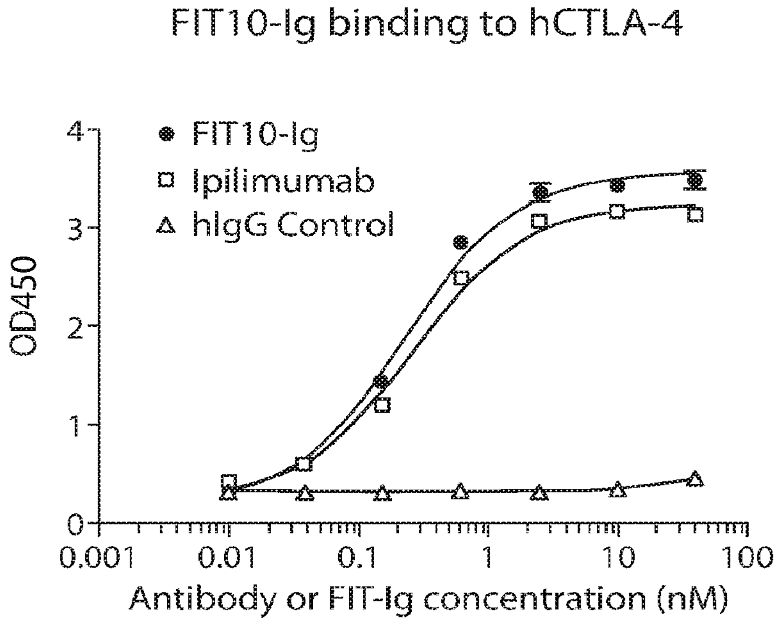
FIG. 5A shows the binding to CTLA-4 by FIT10-Ig or the parental antibodies Ipilimumab and Nivolumab, as assessed by ELISA.
Figure 5B:
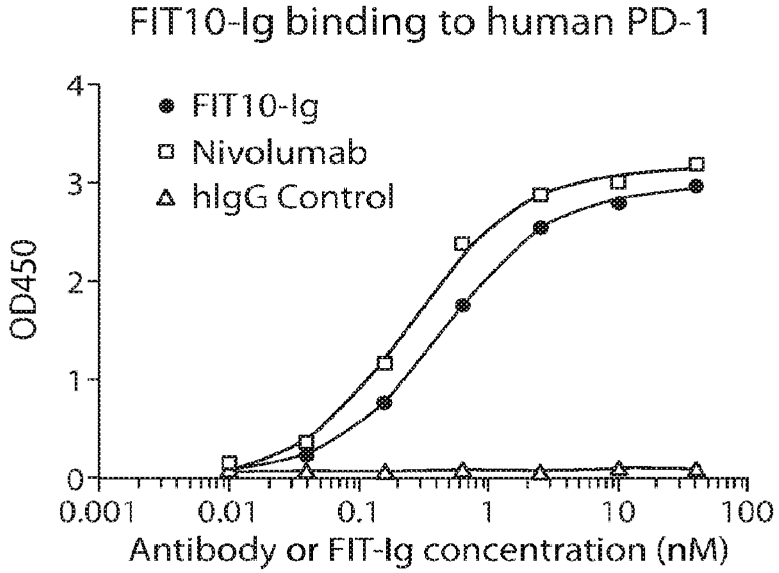
FIG. 5B shows the binding to PD-1 by FIT10-Ig or the parental antibodies Ipilimumab and Nivolumab, as assessed by ELISA.

Example 4.2 Expression, Purification, and Functional Analysis of Anti-CTLA-4/PD-1 FIT-Ig Proteins All DNA constructs of each FIT-Ig were subcloned into pBOS based vectors, and sequenced to ensure accuracy. Construct #1, #2, and #3 of FIT10-Ig were transiently co-expressed using Polyethyleneimine (PEI) in 293E cells as described previously and FIT9-Ig proteins were purified by protein A chromatography to 9800 monomeric full protein. The expression levels were up to 43 mg/L. The purified protein was subjected to binding analysis using ELISA against recombinant CTLA-4Ig and PD-1. Briefly, for binding to CTLA-4, human CTLA-4Ig (R&D Systems) was immobilized on 96-well plates, followed by routine wash and blocking procedures. Then FIT-10-Ig or Ipilimumab at various concentrations were added to the plate, followed by incubation and multiple wash steps, and detected with anti-human Fab-HRP. For binding to PD-1, human PD-1 (with a his tag) (R&D Systems) was immobilized on 96-well plates, followed by routine wash and blocking procedures. Then FIT-10-Ig or Nivolumab at various concentrations were added to the plate, followed by incubation and multiple wash steps, and detected with anti-human Fc-HRP (FIG. 5). It appears that FIT10-Ig was able to bind both CTLA-4 (A) and PD-1 (B) with similar activities as the parental mAbs Ipilimumab and Nivolumab, respectively.

Figure 6:
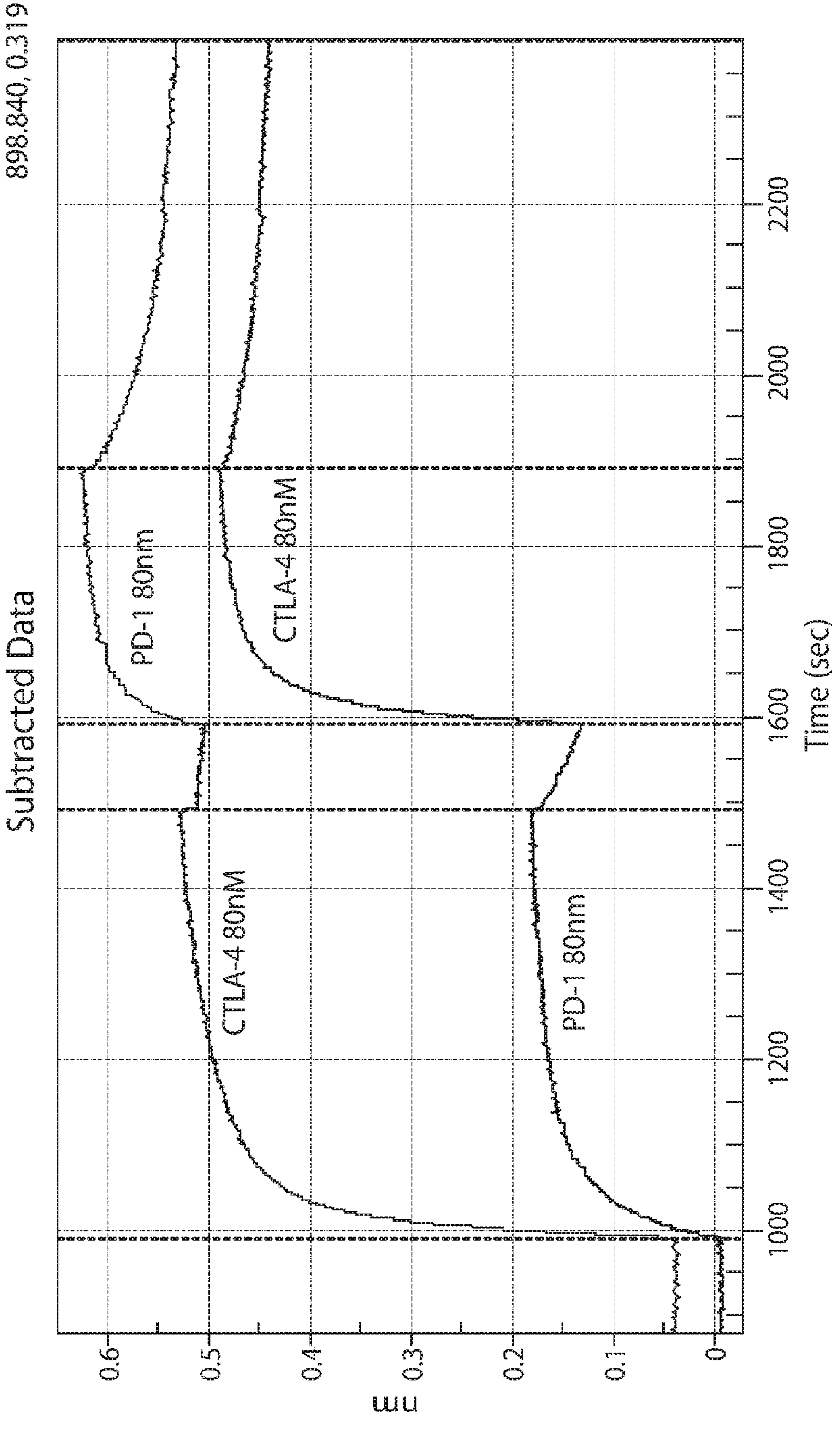
FIG. 6 shows a multiple binding study of FIT10-Ig against both CTLA-4 and PD-1. Binding to CTLA-4 followed by PD-1; and binding by PD-1 followed by CTLA-4 are both shown as indicated in FIG. 6.
Figure 7A:
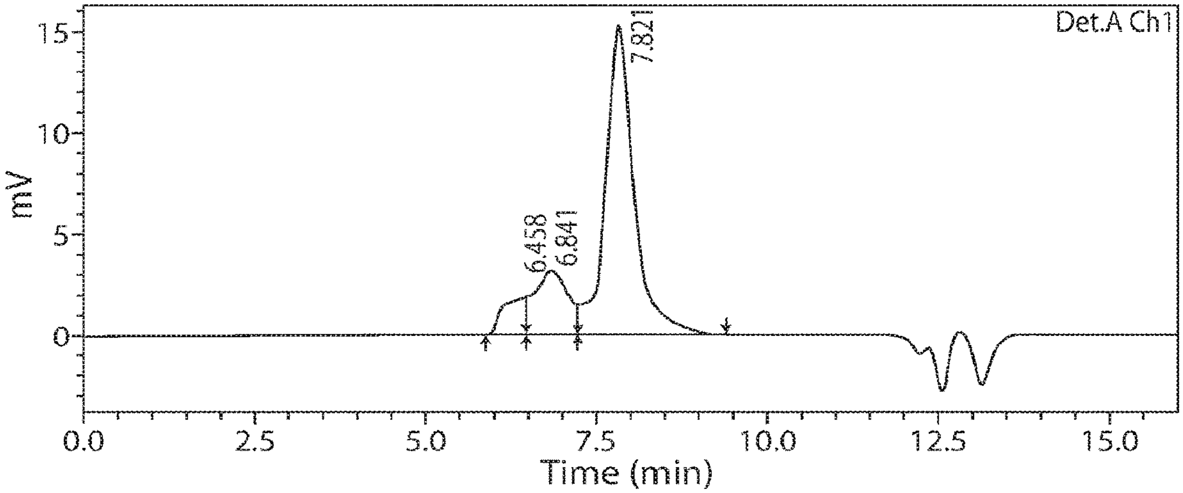
FIG. 7*a*-7*i* show the SEC profiles for FIT12a-Ig (EGFR/PD-L1.
Figure 7B:
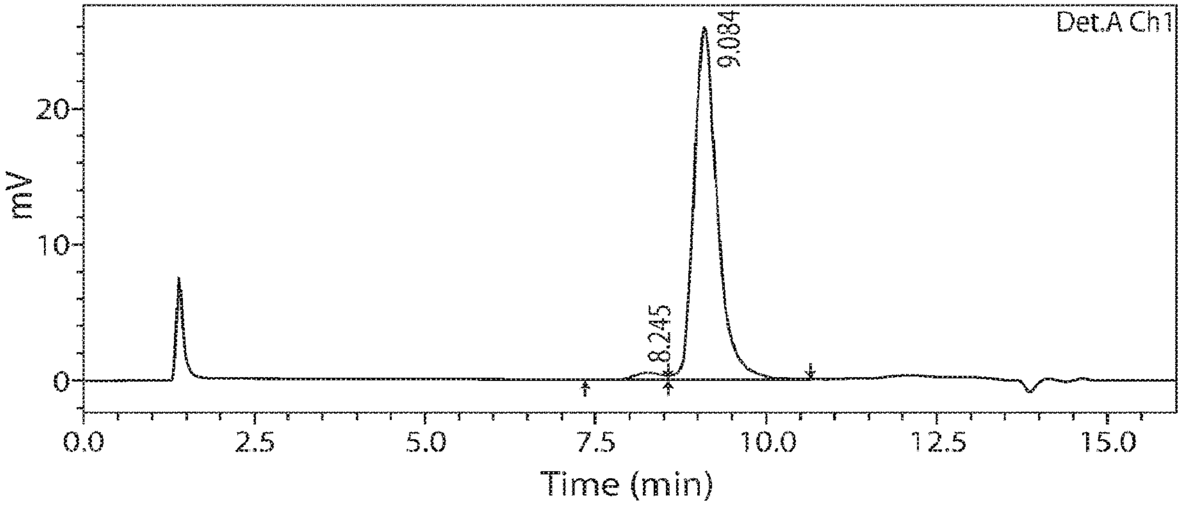
Figure 7C:
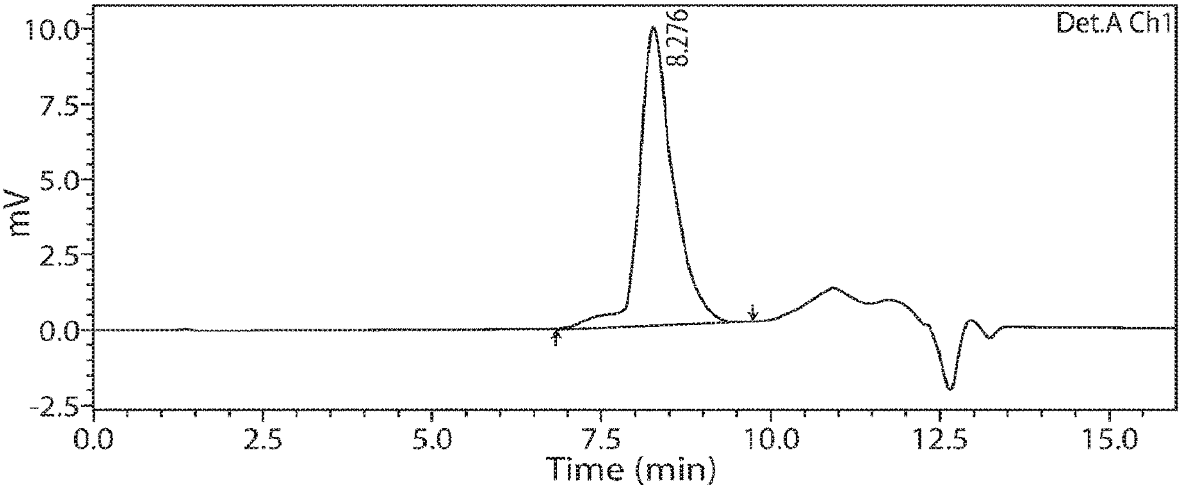
Figure 7D:
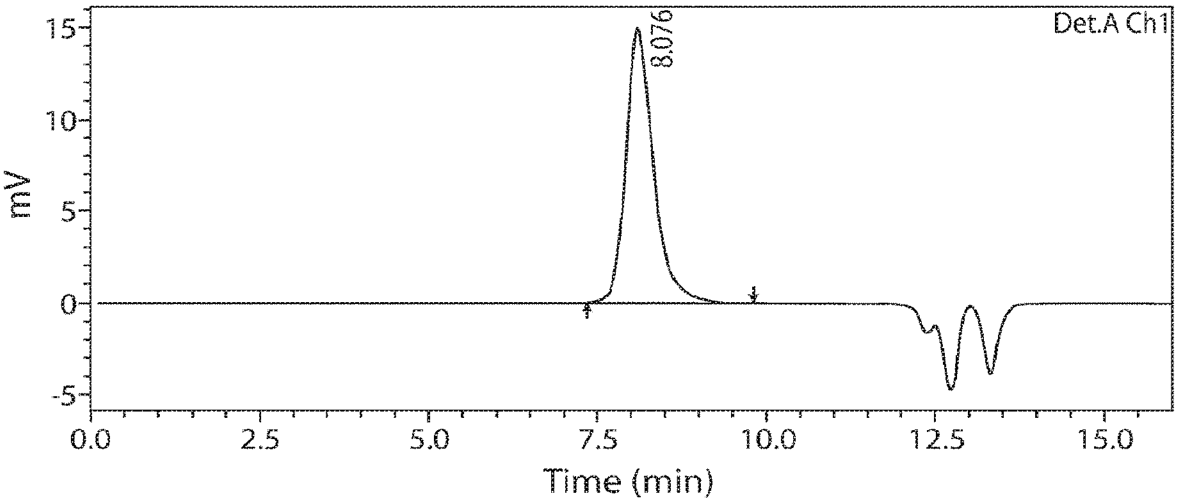
Figure 7E:
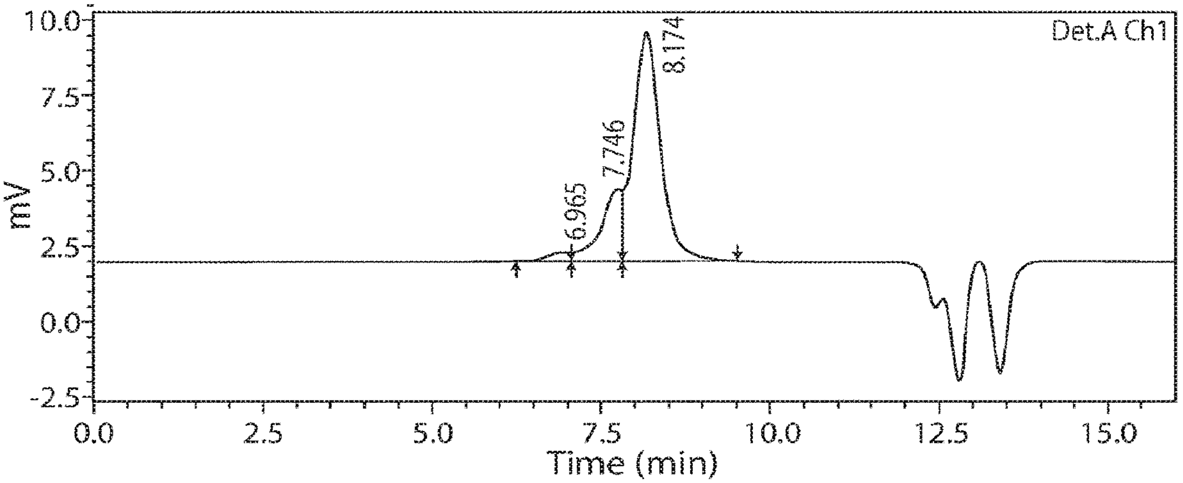
Figure 7F:
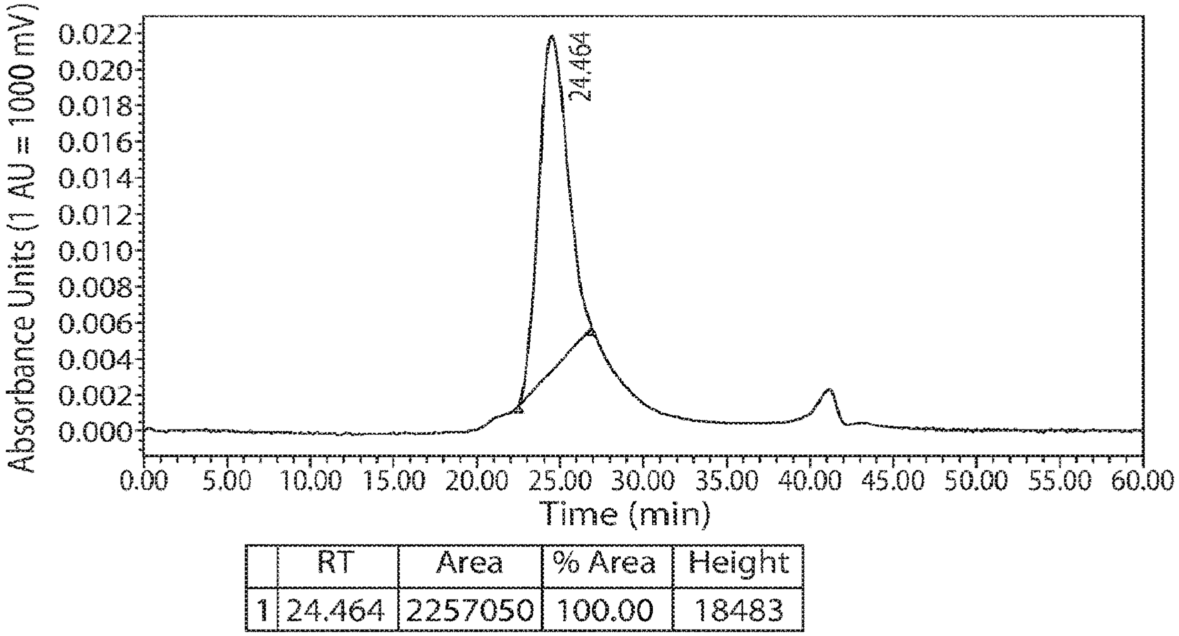
Figure 7G:
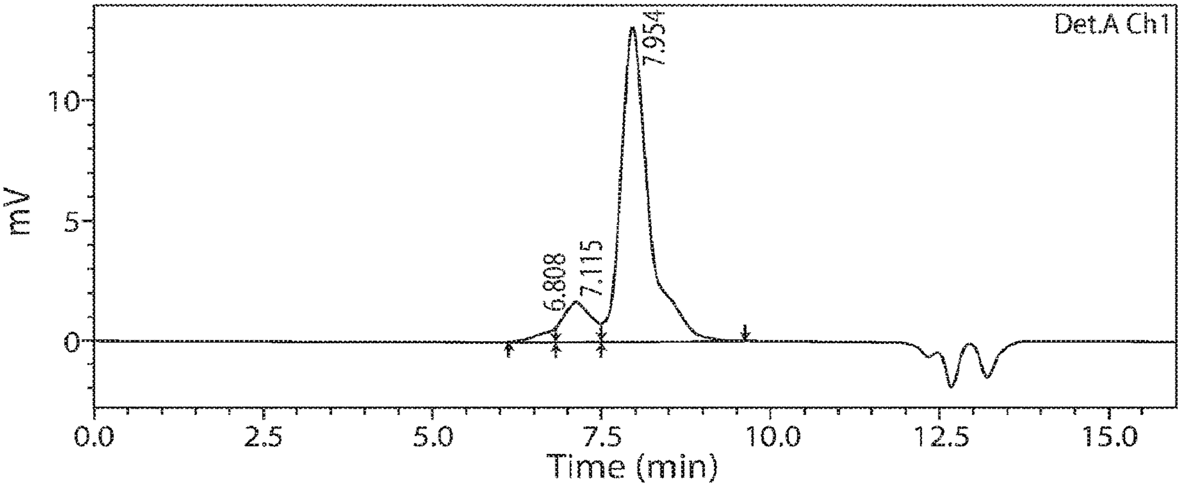
Figure 7H:
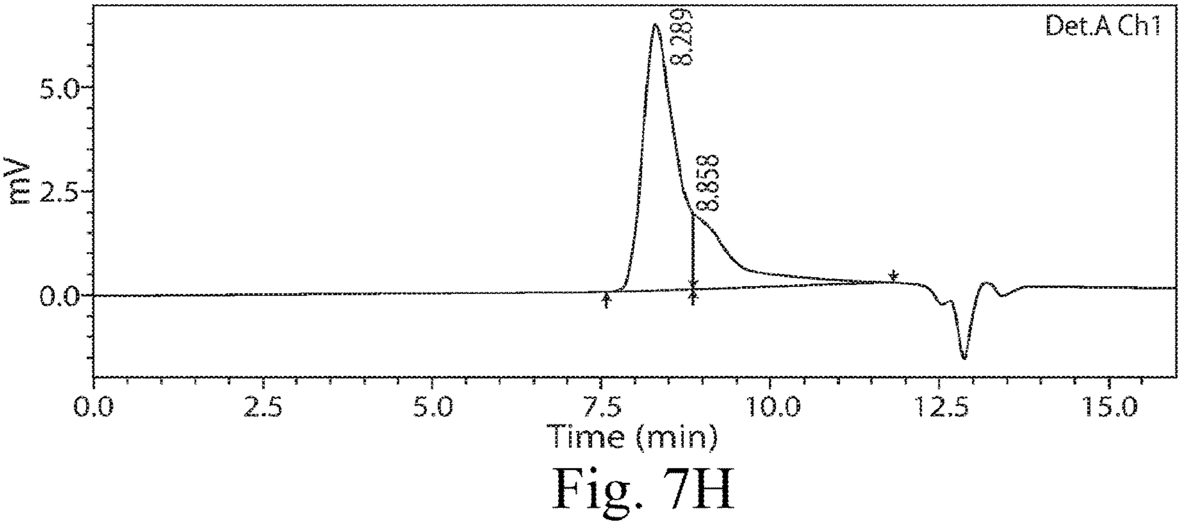
Figure 7I:
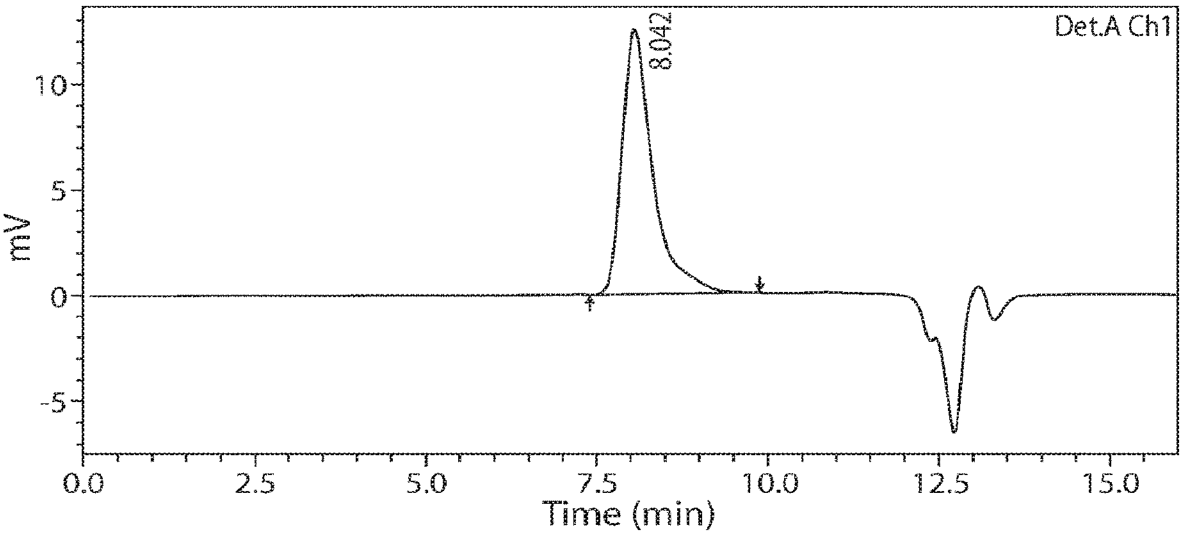

In addition, multiple-antigen binding study was done using OctetRed to determine if FIT10-Ig was able to bind recombinant CTLA-4 and PD-1 simultaneously. Briefly, FIT10-Ig was immobilize on AR2G sensor at concentration of 10 μg/ml, followed by binding of CTLA-4Ig and then PD-1 (or PD-1 first, then CTLA-4Ig) in assay buffer (PBS pH 7.4, 0.1% BSA, 0.02% Tween), with concentration at 80 nM. At the end of the experiment, the surface was regenerated with 10 mM glycine at pH1.5 five times (FIG. 6). This experiment shows that FIT10-Ig was able to bind PD-1 when it had already bound to CTLA-4, and vice versa, indicating that FIT10-Ig was able to bind both CTLA-4Ig and PD-1 simultaneously.

Example 5: Construction, Expression, and Purification of Additional Fabs-In-Tandem Immunoglobulin (FIT-Ig)

FIT-Ig having specificity for EGFR and PD-L1; cMet and EGFR; Factor IXa and Factor X; Her3 and IGF-1R; DLL-4 and VEGF; CD20 and CD3; Her3 and EGFR; PD-1 and PD-L1; and Her3 and PD-1 were constructed as in the foregoing Examples. These exemplary FIT-Ig and their corresponding sequences are provided below in Table 17. Table 18 provides the expression level in 293E cells and the SEC profile for each of the FIT-Ig.

TABLE 17

Amino acid sequences of additional exemplary FIT-Ig

| Name Target (mAb) | Protein region | SEQ ID NO | Sequence |
|---|---|---|---|
| FIT12a-Ig EGFR (panitumumab)/ PD-L1 (1B12) | Pani VL-hCk-1B12VH-hCg1 | 99 | MDMRVPAQLLGLLLLWFPGSRCDIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVQSGAEVKKPGSSVKVSCKTSGDTFSSYAISWVRQAPGQGLEWMGGIIPIFGRAHYAQKFQGRVTITADESTSTAYMELSSLRSEDTAVYFCARKFHFVSGSPFGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Pani VH-CH1h | 100 | MEFGLSWLFLVAILKGVQCQVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | 1B12 VL-hCk | 101 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| FIT13a-Ig cMet (h1332)/EGFR (panitumumab) | h1332VL-hCk-PaniVH-hCg1 | 102 | MDMRVPAQLLGLLLLWFPGSRCDIQMTQSPSSVSASVGDRVTITCRASQGINTWLAWYQQKPGKAPKLLIYAASSLKSGVPSRFSGSGSGTDFTLTISSLQPEDFATYYCQQANSFPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | h1332 VH-CH1h | 103 | MEFGLSWLFLVAILKGVQCQVQLVQSGAEVKKPGASVKVSCKASGYTFTSYGFSWVRQAPGQGLEWMGWISASNGNTYYAQKLQGRVTMTTDTSTSTAYMELRSLRSDDTAVYYCARVYADYADYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |

TABLE 17-continued

Amino acid sequences of additional exemplary FIT-Ig

| Name Target (mAb) | Protein region | SEQ ID NO | Sequence |
|---|---|---|---|
| | Pani VL-hCk | 104 | MDMRVPAQLLGLLLLWFPGSRCDIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| FIT14-Ig Factor IXa/ FactorX | FIX VL-hCk-FX-VH-hCg4 | 105 | MDMRVPAQLLGLLLLWFPGSRCDIQMTQSPSSLSASVGDRVTITCKASRNIERQLAWYQQKPGQAPELLIYQASRKESGVPDRFSGSRYGTDFTLTISSLQPEDIATYYCQQYSDPPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVQSGSELKKPGASVKVSCKASGYTFTDNNMDWVRQAPGQGLEWMGDINTRSGGSIYNEEFQDRVIMTVDKSTDTAYMELSSLRSEDTATYHCARRKSYGYYLDEWGEGTLVTVSSASTKGPSVFPLAPCSRSTSESTAALGCLVKDYFPEPVTVSWNSGALTSGVHTFPAVLQSSGLYSLSSVVTVPSSSLGTQTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQYNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSKLTVDKSRWQEGNVFSCSVMHEALHNHYTQESLSLSP |
| | F-IX VH-CH1h | 106 | MEFGLSWLFLVAILKGVQCQVQLVESGGGLVQPGGSLRLSCAASGFTFSYYDIQWVRQAPGKGLEWVSSISPSGQSTYYRREVKGRFTISRDNSKNTLYLQMNSLRAEDTAVYYCARRTGREYGGGWYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | F-X VL-hCk | 107 | MDMRVPAQLLGLLLLWFPGSRCDIQMTQSPSSLSASVGDRVTITCKASRNIERQLAWYQQKPGQAPELLIYQASRKESGVPDRFSGSRYGTDFTLTISSLQPEDIATYYCQQYSDPPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| FIT16a-Ig Her3 (paritumumab)/ IGF-1R (figitumumab) | Paritu VL-hCk-figituVH-hCg1 | 108 | MDMRVPAQLLGLLLLWFPGSRCDIEMTQSPDSLAVSLGERATINCRSSQSVLYSSSNRNYLAWYQQNPGQPPKLLIYWASTRESGVPDRFSGSGSGTDFTLTISSLQAEDVAVYYCQQYYSTPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECEVQLLESGGGLVQPGGSLRLSCTASGFTFSSYAMNWVRQAPGKGLEWVSAISGSGGTTFYADSVKGRFTISRDNSRTTLYLQMNSLRAEDTAVYYCAKDLGWSDSYYYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Patritumab-CH1h | 109 | MEFGLSWLFLVAILKGVQCQVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Figitu VL-hCk | 110 | MDMRVPAQLLGLLLLWFPGSRCDIQMTQFPSSLSASVGDRVTITCRASQGIRNDLGWYQQKPGKAPKRLIYAASRLHRGVPSRFSGSGSGTEFTLTISSLQPEDFATYYCLQHNSYPCSFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| FIT17a-Ig DLL-4 (demcizumab)/ VEGF (bevicizumab) | Demci VL-hCk-Bevci VH-hCg1 | 111 | MDMRVPAQLLGLLLLWFPGSRCDIVMTQSPDSLAVSLGERATISCRASESVDNYGISFMKWFQQKPGQPPKLLIYAASNQGSGVPDRFSGSGSGTDFTLTISSLQAEDVAVYYCQQSKEVPWTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECEVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYG |

TABLE 17-continued

Amino acid sequences of additional exemplary FIT-Ig

| Name Target (mAb) | Protein region | SEQ ID NO | Sequence |
|---|---|---|---|
| | | | SSHWYFDVWGQGTLVTVSSASTKGPSVFPLAPSSKSTSGGTAA<br>LGCLVKDYFPEPVTVSWNSGALTSGVHTFPAVLQSSGLYSLSS<br>VVTVPSSSLGTQTYICNVNHKPSNTKVDKKVEPKSCDKTHTCP<br>PCPAPELLGGPSVFLFPPKPKDTLMISRTPEVTCVVVDVSHED<br>PEVKFNWYVDGVEVHNAKTKPREEQYNSTYRVVSVLTVLHQDW<br>LNGKEYKCKVSNKALPAPIEKTISKAKGQPREPQVYTLPPSRE<br>EMTKNQVSLTCLVKGFYPSDIAVEWESNGQPENNYKTTPPVLD<br>SDGSFFLYSKLTVDKSRWQQGNVFSCSVMHEALHNHYTQKSLS<br>LSPGK |
| | Demci-CH1h | 112 | MEFGLSWLFLVAILKGVQCQVQLVQSGAEVKKPGASVKISCKA<br>SGYSFTAYYIHWVKQAPGQGLEWIGYISSYNGATNYNQKFKGR<br>VTFTTDTSTSTAYMELRSLRSDDTAVYYCARDYDYDVGMDYWG<br>QGTLVTVSSASTKGPSVFPLAPSSKSTSGGTAALGCLVKDYFP<br>EPVTVSWNSGALTSGVHTFPAVLQSSGLYSLSSVVTVPSSSLG<br>TQTYICNVNHKPSNTKVDKKVEPKSC |
| | Bevci VL-hCk | 113 | MDMRVPAQLLGLLLLWFPGSRCDIQMTQSPSSLSASVGDRVTI<br>TCSASQDISNYLNWYQQKPGKAPKVLIYFTSSLHSGVPSRFSG<br>SGSGTDFTLTISSLQPEDFATYYCQQYSTVPWTFGQGTKVEIK<br>RTVAAPSVFIFPPSDEQLKSGTASVVCLLNNFYPREAKVQWKV<br>DNALQSGNSQESVTEQDSKDSTYSLSSTLTLSKADYEKHKVYA<br>CEVTHQGLSSPVTKSFNRGEC |
| FIT18a-Ig CD20 (ofatumumab)/ CD3 | OfatuVL-hCk-CD3mAb VH-hCg1mut | 114 | MDMRVPAQLLGLLLLWFPGSRCEIVLTQSPATLSLSPGERATL<br>SCRASQSVSSYLAWYQQKPGQAPRLLIYDASNRATGIPARFSG<br>SGSGTDFTLTISSLEPEDFAVYYCQQRSNWPITFGQGTRLEIK<br>RTVAAPSVFIFPPSDEQLKSGTASVVCLLNNFYPREAKVQWKV<br>DNALQSGNSQESVTEQDSKDSTYSLSSTLTLSKADYEKHKVYA<br>CEVTHQGLSSPVTKSFNRGECEVQLLESGGGLVQPGGSLKLSC<br>AASGFTFNTYAMNWVRQAPGKGLEWVARIRSKYNNYATYYADS<br>VKDRFTISRDDSKNTAYLQMNNLKTEDTAVYYCVRHGNFGNSY<br>VSWFAYWGQGTLVTVSSASTKGPSVFPLAPSSKSTSGGTAALG<br>CLVKDYFPEPVTVSWNSGALTSGVHTFPAVLQSSGLYSLSSVV<br>TVPSSSLGTQTYICNVNHKPSNTKVDKKVEPKSCDKTHTCPPC<br>PAPEAAGGPSVFLFPPKPKDTLMISRTPEVTCVVVDVSHEDPE<br>VKFNWYVDGVEVHNAKTKPREEQYNSTYRVVSVLTVLHQDWLN<br>GKEYKCKVSNKALPAPIEKTISKAKGQPREPQVYTLPPSREEM<br>TKNQVSLTCLVKGFYPSDIAVEWESNGQPENNYKTTPPVLDSD<br>GSFFLYSKLTVDKSRWQQGNVFSCSVMHEALHNHYTQKSLSLS<br>PGK |
| | Ofatu VH-CH1 | 115 | MEFGLSWLFLVAILKGVQCEVQLVESGGGLVQPGRSLRLSCAA<br>SGFTFNDYAMHWVRQAPGKGLEWVSTISWNSGSIGYADSVKGR<br>FTISRDNAKKSLYLQMNSLRAEDTALYYCAKDIQYGNYYYGMD<br>VWGQGTTVTVSSASTKGPSVFPLAPSSKSTSGGTAALGCLVKD<br>YFPEPVTVSWNSGALTSGVHTFPAVLQSSGLYSLSSVVTVPSS<br>SLGTQTYICNVNHKPSNTKVDKKVEPKSC |
| | CD3mAb VL-hCL | 116 | MTWTPLLFLTLLLHCTGSLSELVVTQEPSLTVSPGGTVTLTCR<br>SSTGAVTTSNYANWVQQKPGQAPRGLIGGTNKRAPGTPARFSG<br>SLLGGKAALTLSGVQPEDEAEYYCALWYSNLWVFGGGTKLTVL<br>GQPKAAPSVTLFPPSSEELQANKATLVCLISDFYPGAVTVAWK<br>ADSSPVKAGVETTTPSKQSNNKYAASSYLSLTPEQWKSHRSYS<br>CQVTHEGSTVEKTVAPTECS |
| FIT19a-Ig Her3 (patritumab)/ EGFR (panitumumab) | patritu VL-hCk-PaniVH-hCg1 | 117 | MDMRVPAQLLGLLLLWFPGSRCDIEMTQSPDSLAVSLGERATI<br>NCRSSQSVLYSSSNRNYLAWYQQNPGQPPKLLIYWASTRESGV<br>PDRFSGSGSGTDFTLTISSLQAEDVAVYYCQQYYSTPRTFGQG<br>TKVEIKRTVAAPSVFIFPPSDEQLKSGTASVVCLLNNFYPREA<br>KVQWKVDNALQSGNSQESVTEQDSKDSTYSLSSTLTLSKADYE<br>KHKVYACEVTHQGLSSPVTKSFNRGECQVQLQESGPGLVKPSE<br>TLSLTCTVSGGSVSSGDYYWTWIRQSPGKGLEWIGHIYYSGNT<br>NYNPSLKSRLTISIDTSKTQFSLKLSSVTAADTAIYYCVRDRV<br>TGAFDIWGQGTMVTVSSASTKGPSVFPLAPSSKSTSGGTAALG<br>CLVKDYFPEPVTVSWNSGALTSGVHTFPAVLQSSGLYSLSSVV<br>TVPSSSLGTQTYICNVNHKPSNTKVDKKVEPKSCDKTHTCPPC<br>PAPELLGGPSVFLFPPKPKDTLMISRTPEVTCVVVDVSHEDPE<br>VKFNWYVDGVEVHNAKTKPREEQYNSTYRVVSVLTVLHQDWLN<br>GKEYKCKVSNKALPAPIEKTISKAKGQPREPQVYTLPPSREEM<br>TKNQVSLTCLVKGFYPSDIAVEWESNGQPENNYKTTPPVLDSD<br>GSFFLYSKLTVDKSRWQQGNVFSCSVMHEALHNHYTQKSLSLS<br>PGK |
| | Patritumab-CH1 | 118 | MEFGLSWLFLVAILKGVQCQVQLQQWGAGLLKPSETLSLTCAV<br>YGGSFSGYYWSWIRQPPGKGLEWIGEINHSGSTNYNPSLKSRV<br>TISVETSKNQFSLKLSSVTAADTAVYYCARDKWTWYFDLWGRG<br>TLVTVSSASTKGPSVFPLAPSSKSTSGGTAALGCLVKDYFPEP<br>VTVSWNSGALTSGVHTFPAVLQSSGLYSLSSVVTVPSSSLGTQ |

TABLE 17-continued

| Amino acid sequences of additional exemplary FIT-Ig | | | |
|---|---|---|---|
| Name Target (mAb) | Protein region | SEQ ID NO | Sequence |
| | | | TYICNVNHKPSNTKVDKKVEPKSC |
| | Pani VL-hCk | 119 | MDMRVPAQLLGLLLLWFPGSRCDIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| FIT20a-Ig PD-1 (nivolumab)/ PD-L1 (1B12) | Nivolu VL-hCk-1B12 VH-hCg1Mut | 120 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVQSGAEVKKPGSSVKVSCKTSGDTFSSYAISWVRQAPGQGLEWMGGIIPIFGRAHYAQKFQGRVTITADESTSTAYMELSSLRSEDTAVYFCARKFHFVSGSPFGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Nivo VH-CH1 | 121 | MEFGLSWLFLVAILKGVQCQVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | 1B12 VL-hCk | 122 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| FIT22a-Ig Her3 (patritumab)/ PD-1 (nivolumab) | patritu VL-hCk-Nivolu VH-hCg1mut | 123 | MDMRVPAQLLGLLLLWFPGSRCDIEMTQSPDSLAVSLGERATINCRSSQSVLYSSSNRNYLAWYQQNPGQPPKLLIYWASTRESGVPDRFSGSGSGTDFTLTISSLQAEDVAVYYCQQYYSTPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Patritumab-CH1 | 124 | MEFGLSWLFLVAILKGVQCQVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | NivoVL-hCK | 125 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 18

| Expression level in 293E cells and SEC profile for FIT-Igs | | |
|---|---|---|
| Name<br>Target (mAb) | Expression Level<br>in 293E cells<br>(mg/L) | SEC Profile<br>(% monomeric fraction) |
| FIT12a-Ig<br>EGFR (panitumumab)/<br>PD-L1 (IB12) | 0.26 | 74.72 |
| FIT13a-Ig<br>cMet (h1332)/<br>EGFR (panitumumab) | 0.705 | 97.70 |
| FIT14-Ig<br>Factor IXa/<br>Factor X | 0.135 | 100.00 |
| FIT16a-Ig<br>Her3 (paritumumab)/<br>IGF-1R (figitumumab) | 0.15 | 100.00 |
| FIT17a-Ig<br>DLL-4 (demcizumab)/<br>VEGF (bevicizumab) | 0.11 | 78.384 |
| FIT18a-Ig<br>CD20 (ofatumumab)/CD3 | 0.39 | 100.00 |
| FIT19a-Ig<br>Her3 (patritumab)/<br>EGFR (panitumumab) | 0.37 | 86.762 |
| FIT20a-Ig<br>PD-1 (nivolumab)/<br>PD-L1 (1B12) | 0.51 | 73.721 |
| FIT22a-Ig<br>Her3 (patritumab)/<br>PD-1 (nivolumab) | 0.098 | 100.00 |

The SEC profiles for each of the FIT-Ig of Tables 17 and 18 are also provided in FIG. 7*a*-7*i*.

Figure 8:
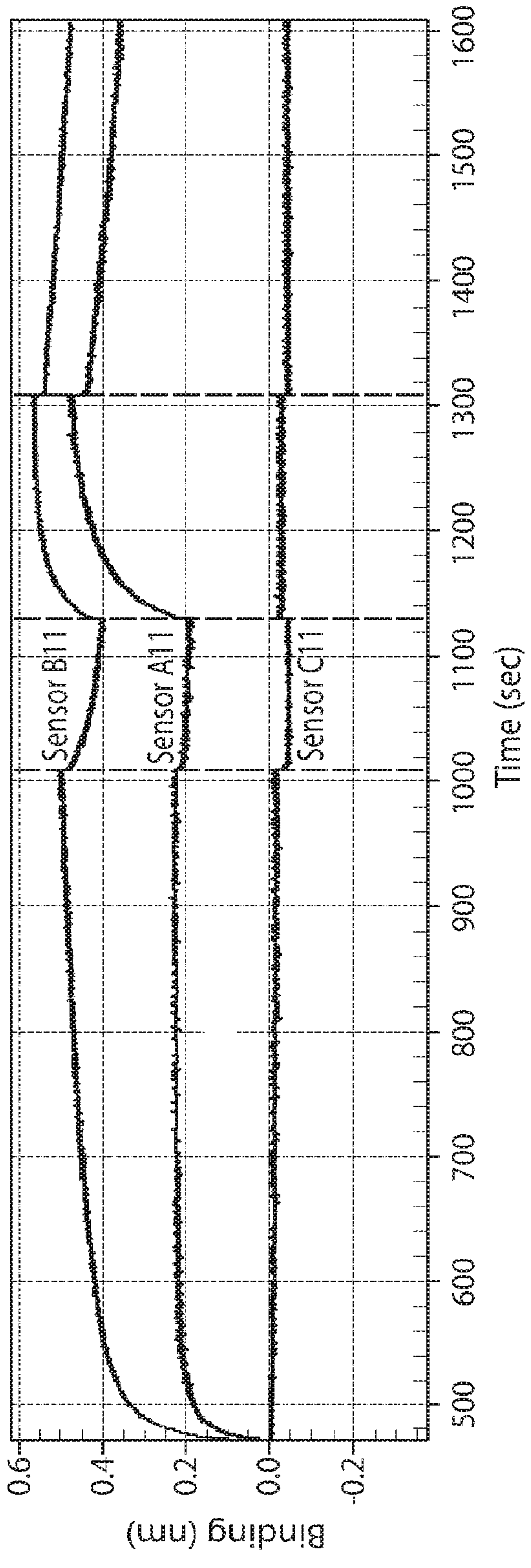
FIG. 8 shows a multiple binding study of FIT13a-Ig against both cMet and EGFR.

Functional binding data for FIT13a-Ig are provided below in Table 19. In addition, a multiple-antigen binding study was performed to determine if FIT13a-Ig was able to bind cMet and EGFR. The results of the study are shown in FIG. 8, and show that FIT13a-Ig was able to bind both cMet and EGFR simultaneously.

TABLE 19

| Functional binding data for FIT13a-Ig | | | | |
|---|---|---|---|---|
| Ig | Target | Kon | Koff | KD |
| mAb-h1332 | c-met | 2.61E+05 | 6.87E−04 | 2.63E−09 |
| FIT-Ig13a | | 2.94E+05 | 7.26E−04 | 2.47E−09 |
| Panitumumab | hEGFR | 3.61E+05 | 5.59E−04 | 1.55E−09 |
| FIT-Ig13a | | 2.69E+05 | 4.07E−04 | 1.52E−09 |

Functional binding data for the Factor IXa binding activity of FIT14-Ig are provided below in Table 20.

TABLE 20

| Functional binding data for FIT14-Ig | | | | |
|---|---|---|---|---|
| Ig | Target | Kon | Koff | KD |
| Factor IXa mAb | Factor IXa | 2.74E+04 | 3.55E−04 | 1.30E−08 |
| FIT-Ig 014 | | 3.35E+04 | 3.32E−04 | 9.90E−09 |
| Factor X mAb | Factor X | | | |
| FIT-Ig 14 | | | | |

The results of the study show that additional FIT-Ig can be constructed, expressed, and purified and will exhibit functional binding to the target proteins.

Example 6: Construction, Expression, and Purification of New Anti-CTLA-4/PD-1 Fabs-in-Tandem Immunoglobulin (FIT-Ig)

New FIT-Ig having specificity for CTLA4 and PD1 were constructed as in the foregoing Examples. These exemplary FIT-Ig and their corresponding sequences are provided below in Table 21. Table 21 provides the expression level in 293E cells and the SEC profile for each of the FIT-Ig.

TABLE 21

| Amino acid sequences of additional exemplary FIT-Ig for CTLA4 and PD1 | | | |
|---|---|---|---|
| Name<br>Target (mAb)<br>mAb1 (upper domain)/mAb2 (lower domain) | Protein region | SEQ ID NO | Sequences |
| NBS3-Ig<br>CTLA4 (ipilimumab)/<br>PD-1 (nivolumab) | Long chain (IpiliVL-hCk-NivoluVH-hCg1mut) | 126 | MDMRVPAQLLGLLLLWFPGSRC**EIVLTQSPGTLSLSPGER**<br>**ATLSCRASQSVGSSYLAWYQQKPGQAPRLLIYGAFSRAT**G<br>**IPDRFSGSGSGTDFTLTISRLEPEDFAVYYCQQYGSSPWT**<br>**FGQGTKVEIK**RTVAAPSVFIFPPSDEQLKSGTASVVCLLN<br>NFYPREAKVQWKVDNALQSGNSQESVTEQDSKDSTYSLSS<br>TLTLSKADYEKHKVYACEVTHQGLSSPVTKSFNRGEC**QVQ**<br>**LVESGGGVVQPGRSLRLDCKASGITFSNSGMHWVRQAPGK**<br>**GLEWVAVIWYDGSKRYYADSVKGRFTISRDNSKNTLFLQM**<br>**NSLRAEDTAVYYCATNDDYWGQGTLVTVSS**ASTKGPSVFP<br>LAPSSKSTSGGTAALGCLVKDYFPEPVTVSWNSGALTSGV<br>HTFPAVLQSSGLYSLSSVVTVPSSSLGTQTYICNVNHKPS<br>NTKVDKKVEPKSCDKTHTCPPCPAPEAAGGPSVFLFPPKP<br>KDTLMISRTPEVTCVVVDVSHEDPEVKFNWYVDGVEVHNA<br>KTKPREEQYNSTYRVVSVLTVLHQDWLNGKEYKCKVSNKA<br>LPAPIEKTISKAKGQPREPQVYTLPPSREEMTKNQVSLTC<br>LVKGFYPSDIAVEWESNGQPENNYKTTPPVLDSDGSFFLY<br>SKLTVDKSRWQQGNVFSCSVMHEALHNHYTQKSLSLSPGK |
| | Ipili VL | 127 | EIVLTQSPGTLSLSPGERATLSCRASQSVGSSYLAWYQQK<br>PGQAPRLLIYGAFSRATGIPDRFSGSGSGTDFTLTISRLE<br>PEDFAVYYCQQYGSSPWTFGQGTKVEIK |

TABLE 21-continued

Amino acid sequences of additional exemplary FIT-Ig for CTLA4 and PD1

| Name Target (mAb) mAb1 (upper domain)/mAb2 (lower domain) | Protein region | SEQ ID NO | Sequences |
|---|---|---|---|
| | Ipili VL - CDR1 | 128 | RASQSVGSSYLA |
| | Ipili VL - CDR2 | 129 | GAFSRAT |
| | Ipili VL - CDR3 | 130 | QQYGSSPWT |
| | NivoluVH | 131 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS |
| | Nivolu VH - CDR1 | 132 | NSGMH |
| | Nivolu VH - CDR2 | 133 | VIWYDGSKRYYADSVKG |
| | Nivolu VH - CDR3 | 134 | NDDY |
| | Short Chai #1 (Ipili VH-CH1) | 135 | MEFGLSWLFLVAILKGVQC**QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Ipili VH | 136 | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSS |
| | Ipili VH - CDR1 | 137 | SYTMH |
| | Ipili VH - CDR2 | 138 | FISYDGNNKYYADSVKG |
| | Ipili VH - CDR3 | 139 | TGWLGPFDY |
| | Short Chain #2 (Nivolu VL-hCK) | 140 | MDMRVPAQLLGLLLLWFPGSRC**EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Nivolu VL | 141 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVE1K |
| | Nivolu VL - CDR1 | 142 | RASQSVSSYLA |
| | Nivolu VL - CDR2 | 143 | DASNRAT |
| | Nivolu VL - CDR3 | 144 | QQSSNWPRT |
| NBS3R - Ig PD-1(nivolumab)/CTLA4 (ipilimumab) | Long Chain (Nivolu VL-hCk-Ipili VH-hCg1mut) | 145 | MDMRVPAQLLGLLLLWFPGSRC**EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC**QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Nivolu VL | 146 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVE1K |
| | Nivolu VL - CDR1 | 147 | RASQSVSSYLA |
| | Nivolu VL - CDR2 | 148 | DASNRAT |
| | Nivolu VL - CDR3 | 149 | QQSSNWPRT |
| | Ipili VH | 150 | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSS |
| | Ipili VH - CDR1 | 151 | SYTMH |
| | Ipili VH - CDR2 | 152 | FISYDGNNKYYADSVKG |
| | Ipili VH - CDR3 | 153 | TGWLGPFDY |
| | Short Chain #1 (Nivolu VH-CH1) | 154 | MEFGLSWLFLVAILKGVQC**QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |

TABLE 21-continued

Amino acid sequences of additional exemplary FIT-Ig for CTLA4 and PD1

| Name Target (mAb) mAb1 (upper domain)/mAb2 (lower domain) | Protein region | SEQ ID NO | Sequences |
|---|---|---|---|
| | Nivolu VH | 155 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS |
| | Nivolu VH - CDR1 | 156 | GMH |
| | Nivolu VH - CDR2 | 157 | VIWYDGSKRYYADSVKG |
| | Nivolu VH - CDR3 | 158 | NDDY |
| | Short Chain #2 (Ipili VL-hCK) | 159 | MDMRVPAQLLGLLLLWFPGSRCEIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Ipili VL | 160 | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK |
| | Ipili VL - CDR1 | 161 | RASQSVGSSYLA |
| | Ipili VL - CDR2 | 162 | GAFSRAT |
| | Ipili VL - CDR3 | 163 | YGSSPWT |
| NBS3-C-Ig CTLA4 (ipilimumab)/ PD-1(nivolumab) | LongChain (IpiliVL-hCk-NivoluVH-hCg4): | 164 | MDMRVPAQLLGLLLLWFPGSRCEIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVESGGGVVQPGRSLRLDCKASGIITSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| | IpiliVL | 165 | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK |
| | IpiliVL - CDR1 | 166 | RASQSVGSSYLA |
| | IpiliVL - CDR2 | 167 | GAFSRAT |
| | IpiliVL - CDR3 | 168 | QQYGSS |
| | NivoluVH | 169 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS |
| | NivoluVH - CDR1 | 170 | NSGMH |
| | NivoluVH - CDR2 | 171 | VIWYDGSKRYYADSVKG |
| | NivoluVH - CDR3 | 172 | NDDY |
| | Short Chain #1 (Ipili VH-CH1) | 173 | MEFGLSWLFLVAILKGVQCQVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Ipili VH | 174 | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSS |
| | Ipili VH - CDR1 | 175 | SYTMH |
| | Ipili VH - CDR2 | 176 | FISYDGNNKYYADSVKG |
| | Ipili VH - CDR3 | 177 | TGWLGPFDY |
| | Short Chain #2 (Nivolu VL-hCK) | 178 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 21-continued

Amino acid sequences of additional exemplary FIT-Ig for CTLA4 and PD1

| Name Target (mAb) mAb1 (upper domain)/mAb2 (lower domain) | Protein region | SEQ ID NO | Sequences |
|---|---|---|---|
| | Nivolu VL | 179 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK |
| | Nivolu VL - CDR1 | 180 | RASQSVSSYLA |
| | Nivolu VL - CDR2 | 181 | DASNRAT |
| | Nivolu VL - CDR3 | 182 | QQSSNWPRT |
| NBS3R-C-Ig PD-1(nivolumab)/CTLA4 (ipilimumab) | Long Chain (Nivolu VL-hCk-Ipili VH-hCg1mut) | 183 | MDMRVPAQLLGLLLLWFPGSRC**EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC**QVQLVESGGGVVQPGRSLRLSCAASGFITSSYTMHWVRQAPGKGLEWVTFISYDGNNKYYADSVKGRFTISRDNSKNTLYLQMNSLRAEDTAIYYCARTGWLGPFDYWGQGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Nivolu VL | 184 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVE1K |
| | Nivolu VL - CDR1 | 185 | RASQSVSSYLA |
| | Nivolu VL - CDR2 | 186 | DASNRAT |
| | Nivolu VL - CDR3 | 187 | QQSSNWPRT |
| | Ipili VH | 188 | QVQLVESGGGVVQPGRSLRLSCAASGFTFSSYTMHWVRQAPGKGLEWVTFISYDGNNKYYADSVKGRFTISRDNSKNTLYLQMNSLRAEDTAIYYCARTGWLGPFDYWGQGTLVTVSS |
| | Ipili VH - CDR1 | 189 | SYTMH |
| | Ipili VH - CDR2 | 190 | FISYDGNNKYYADSVKG |
| | Ipili VH - CDR3 | 191 | TGWLGPFDY |
| | Short Chain #1 (Nivolu VH-IgG4-CH1) | 192 | MEFGLSWLFLVAILKGVQC**QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS**ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVES |
| | Nivolu VH | 193 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS |
| | Nivolu VH - CDR1 | 194 | NSGMH |
| | Nivolu VH - CDR2 | 195 | VIWYDGSKRYYADSVKG |
| | Nivolu VH - CDR3 | 196 | NDDY |
| | Short Chain #2 (Ipili VL-hCK) | 197 | MDMRVPAQLLGLLLLWFPGSRC**EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Ipili VL | 198 | EIVLTQSPGTLSLSPGERATLSCRASQSVGSSYLAWYQQKPGQAPRLLIYGAFSRATGIPDRFSGSGSGTDFTLTISRLEPEDFAVYYCQQYGSSPWTFGQGTKVEIK |
| | Ipili VL - CDR1 | 199 | RASQSVGSSYLA |
| | Ipili VL - CDR2 | 200 | GAFSRAT |
| | Ipili VL - CDR3 | 201 | QQYGSSPWT |

The long chain and short chain comprise a leader sequence, which can be either MDMRVPAQLLGLLLLWFPGSRC (SEQ ID NO: 487), or MEFGLSWLFLVAILKGVQC (SEQ ID NO: 488).

TABLE 22

| SEC Profile/Expression level in 293E cells: | | |
|---|---|---|
| FIT-Ig | Monomer % in SEC | Expression level(mg/L) |
| NBS3 | >95% | 24.6 |
| NBS3R | 100% | 6.3 |
| NBS3-C | 98.28 | 9.6 |
| NBS3R-C | 100% | 4.0 |

Expression level was evaluated in small scale production without any optimization, except NBS3. All SEC samples are under one step Protein A purification. FIT-Ig in both IgG1 and IgG4 format can be produced as homogeneous protein from 293 cells.

Functional Studies

Functional binding data for these antibodies is provided below in Table 23. The data suggests that the affinity was not affected by changing IgG constant sequences, but can be improved by place certain Fab in upper domain.

TABLE 23

| Functional binding data | | | | |
|---|---|---|---|---|
| Captured Antibody | Antigen | ka (1/Ms) | kd (1/s) | KD (M) |
| NBS3R-C | PD1-his | 3.412E+5 | 0.001407 | 4.123E−9 |
| NBS3R | | 3.315E+5 | 0.001402 | 4.228E−9 |
| NBS3-C | | 1.746E+5 | 0.002457 | 1.408E−8 |
| NBS3 | | 1.868E+5 | 0.002605 | 1.395E−8 |
| NBS3R-C | CTLA-4, his | 7.79E+04 | 0.001573 | 2.02E−08 |
| NBS3R | | 9.85E+04 | 0.001166 | 1.18E−08 |
| NBS3-C | | 1.93E+05 | 0.001123 | 5.82E−09 |
| NBS3 | | 2.05E+05 | 0.001096 | 5.34E−09 |

Figure 9A:
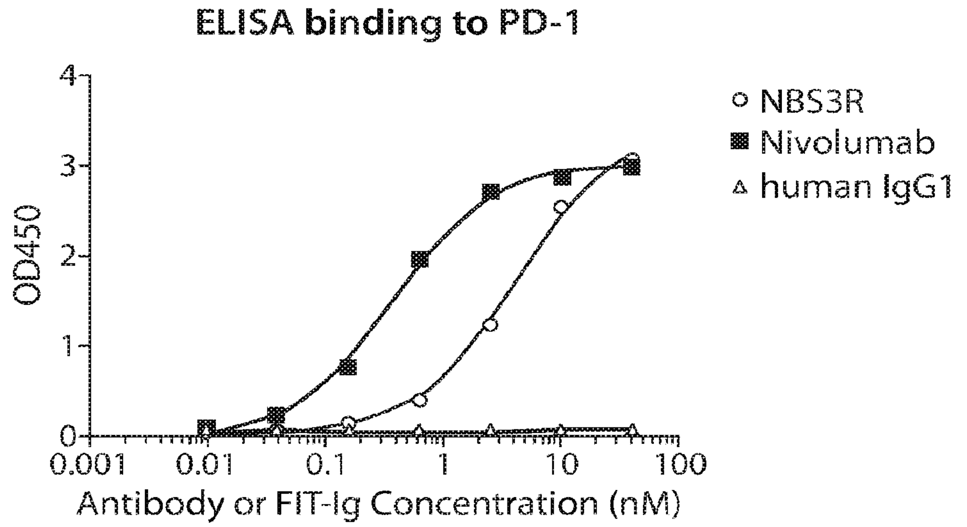
FIG. 9A and FIG. 9B show the binding of NBSR or the parental antibody Nivolumab to PD-1 (FIG. 9A) or CTLA-4 (FIG. 9B), as assessed by ELISA. Human IgG1 was included as a control.
Figure 9B:
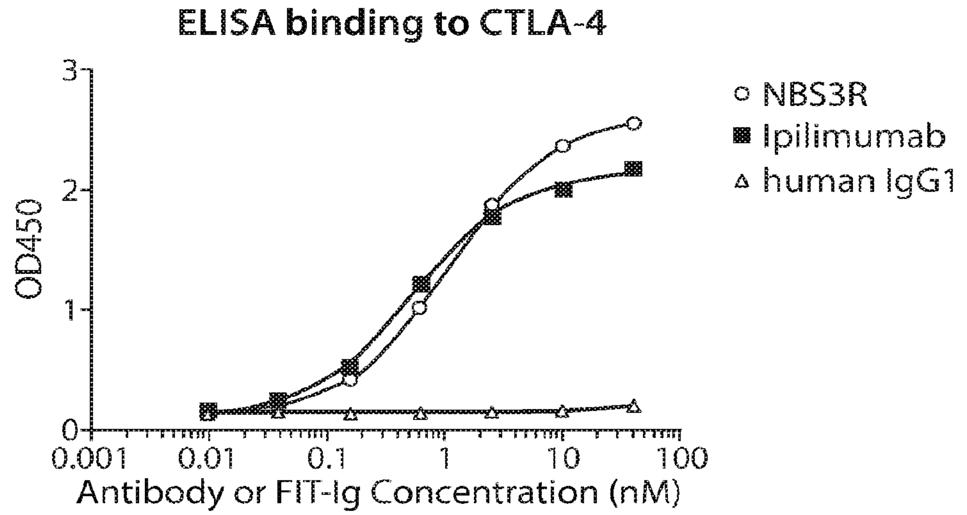

ELISA binding study: ELISA binding of NBS3R was tested. Briefly, for binding to CTLA-4, human CTLA-4Ig (R&D Systems) was immobilized on 96-well plates, followed by routine wash and blocking procedures. Then FIT-Ig or related monoclonal antibodies at various concentrations were added to the plate, followed by incubation and multiple wash steps, and detected with anti-human Fab-HRP. For binding to PD-1, human PD-1 (with a his tag) (R&D Systems) was immobilized on 96-well plates, followed by routine wash and blocking procedures. Then NBS3R or Nivolumab at various concentrations was added to the plate, followed by incubation and multiple wash steps, and detected with anti-human Fc-HRP. It appears that NBS3R was able to bind both CTLA-4 (A) and PD-1 (B), respectively. The result is shown in FIG. 9A and Figure. 9B.

Figure 10:
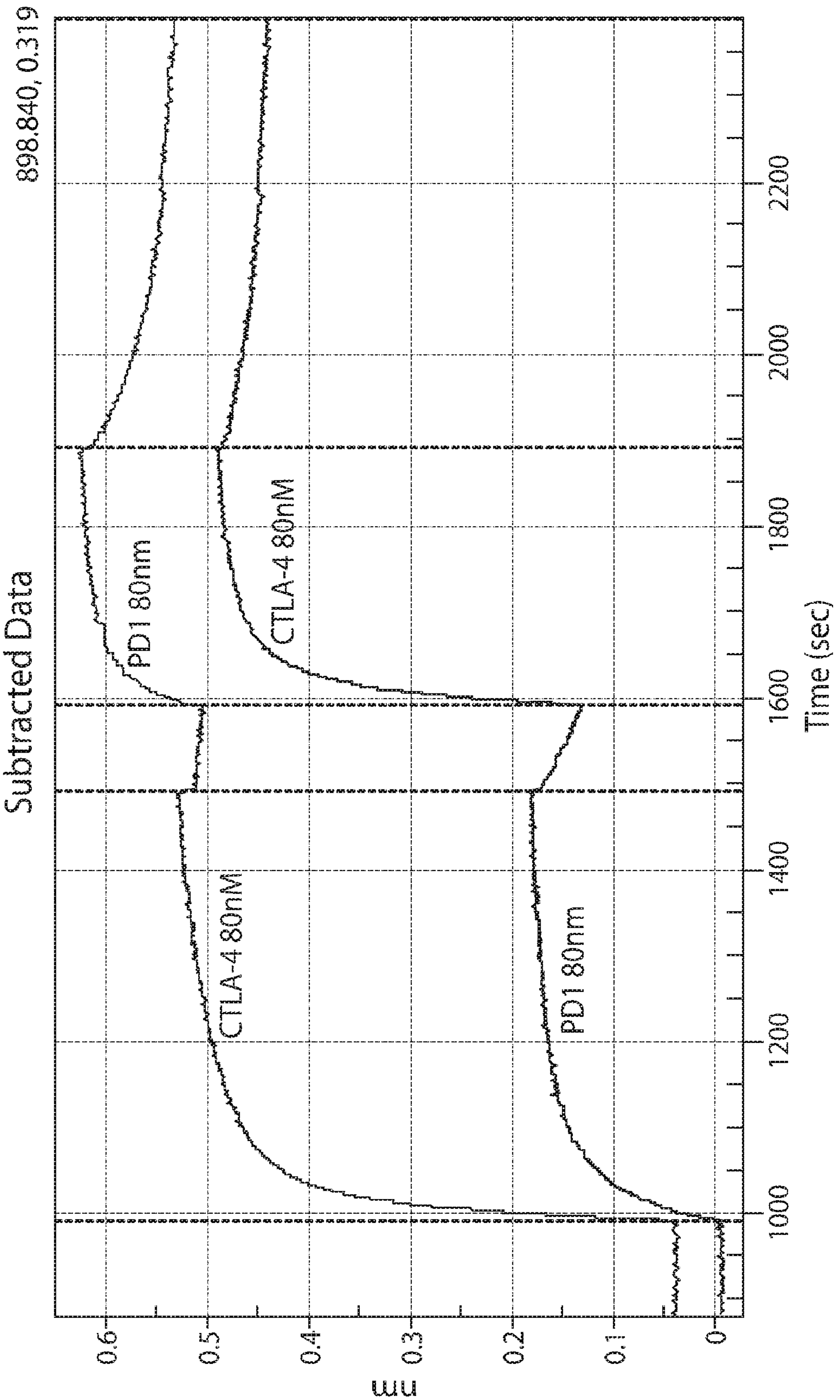
FIG. 10 shows a multiple binding study of NBS3 against both CTLA-4 and PD-1. Binding to CTLA-4 followed by PD-1; and binding by PD-1 followed by CTLA-4 are both shown as indicated.

Multiple binding study: A multiple binding study of NBS3 was also carried out. The result is shown in Figure. 10.

Thermo stability study: Thermo stability test was also performed on these antibodies, the result of which is shown in Table 24. The melting temperature was measured by DSC.

TABLE 24

| Thermo stability test | | | | |
|---|---|---|---|---|
| | Tm (° C.) | | | |
| Antibody Code | $T_{m1}$ (° C.) | $T_{m2}$ (° C.) | $T_{m3}$ (° C.) | $T_{m4}$ (° C.) |
| NBS3R-c | 57.38 | 70.24 | 74.42 | 82.38 |
| NBS3R | 69.78 | 75.54 | 82.75 | |
| NBS3-c | 68.4 | 75.03 | | |
| NBS3 | 69.38 | 75.01 | 82.52 | |

Storage stability study: The storage stability of NBS3 was assessed by SEC-HPLC method, and result is shown in Table 25. Samples were treated by freeze/thaw cycle for one time, two times or three times, no aggregation or degradation was observed by SEC-HPLC profile. Samples was treated at 4° C., 25° C. or 40° C. for 1 day, 3 days or 7 days, no aggregation or degradation was observed by SEC-HPLC profile.

TABLE 25

| Storage stability of NBS3 | | | |
|---|---|---|---|
| Sample Name | Rel. Area % 1 | Rel. Area % 2 | Rel. Area % 3 |
| NBS3_D0 | 0.77 | 99.23 | n.a. |
| NBS3_F/T1 | 1.23 | 98.77 | n.a. |
| NBS3_F/T2 | 1.32 | 98.68 | n.a. |
| NBS3_F/T3 | 1.39 | 98.61 | n.a. |
| NBS3_4C-D1 | 1.45 | 98.55 | n.a. |
| NBS3_25C-D1 | 1.45 | 98.55 | n.a. |
| NBS3_40C-D1 | 1.44 | 98.56 | n.a. |
| NBS3_4C-D3 | 1.49 | 98.51 | n.a. |
| NBS3_25C-D3 | 1.50 | 98.50 | n.a. |
| NBS3_40C-D3 | 1.62 | 97.85 | 0.53 |
| NBS3_4C-D7 | 1.61 | 98.39 | n.a. |
| NBS3_25C-D7 | 1.67 | 98.33 | n.a. |
| NBS3_40C-D7 | 1.76 | 97.70 | 0.55 |

Figures 11A, 11B:
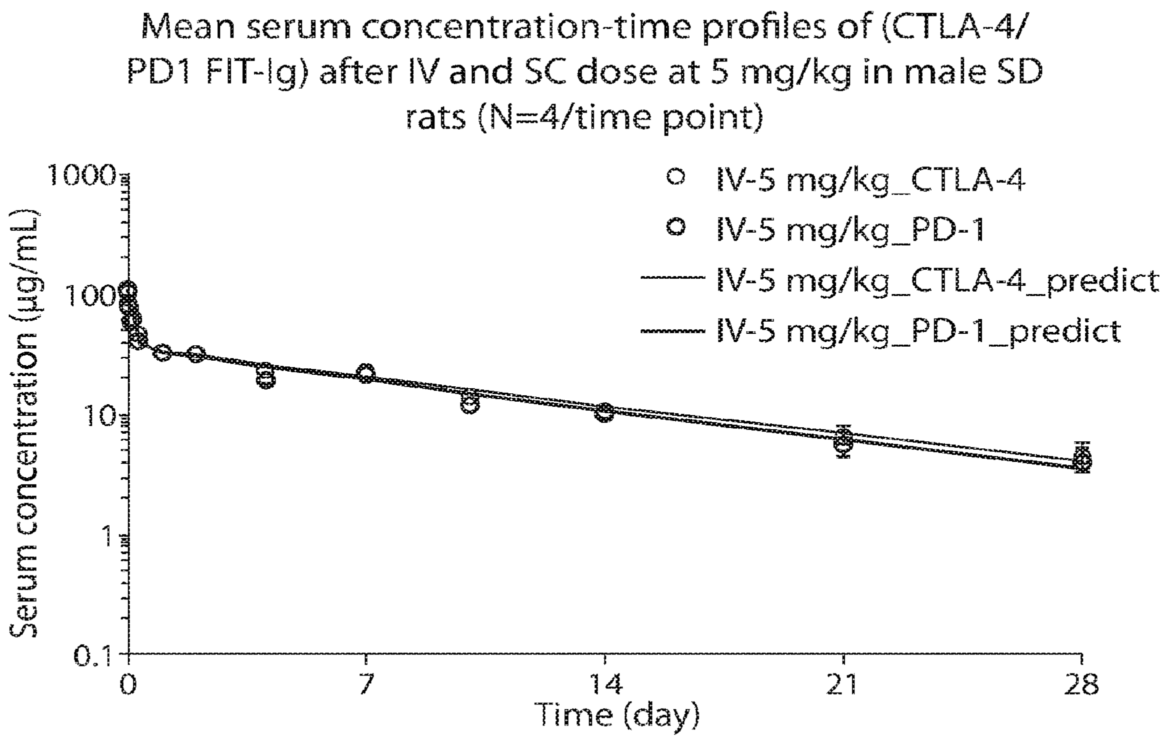
FIG. 11A shows mean serum concentration-time profiles of 5 mg/kg NBS3 administered intravenously (IV) or subcutaneously (SC).
FIG. 11B provides the detail PK parameters of this study.

NBS3 was further tested in rat PK study, and the result is shown in FIG. 11A and FIG. 11B. The purpose of this study was to evaluate the pharmacokinetic of NBS3 following single intravenous (IV) or subcutaneous (SC) administrations in SD rats. The IV dose was administered via foot dorsal vein injection and SC dose was administered via subcutaneous injection. At the designated time-points, the animals were restrained manually, and approximately 240 μL blood/time point was collected via tail vein puncture or cardiac puncture into tubes. The blood samples were placed at room temperature for 0.5 hr. Then blood samples were centrifuged (10000 g, 5 min under 4° C.) to obtain the serum samples. The serum samples were immediately stored at −80° C. until analysis. Samples were analyzed together with dosing solution via ELISA. The measured dosing concentration was used for the PK parameter calculation.

Figure 12:
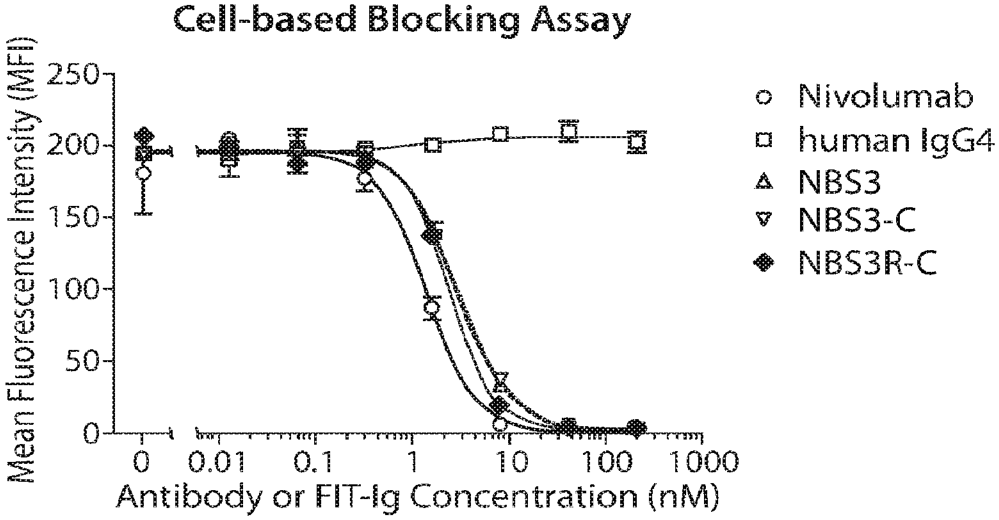
FIG. 12 shows cell-based receptor blocking assay of NBS3, NBS3-C, NBS3R-C compared to the parental antibody Nivolumab. Human IgG4 was included as a control.

NBS3, NBS3-C, and NBS3R-C were tested in cell-based receptor blocking assay. Briefly, PD1-Fc was immobilized on 96-well plates, followed by routine wash and blocking procedures. Then diluted FIT-Ig and biotinylated PD-L1-Fc was added to each well, followed by incubation and multiple wash steps, and detected with Streptavidin-HRP. The result is shown in FIG. 12.

NBS3, NBS3-C, and NBS3R-C were further tested in MLR (Mixed Lymphocyte Reaction) assays and PBMC SEB-stimulation assay for their functional activity.

Figure 13A:
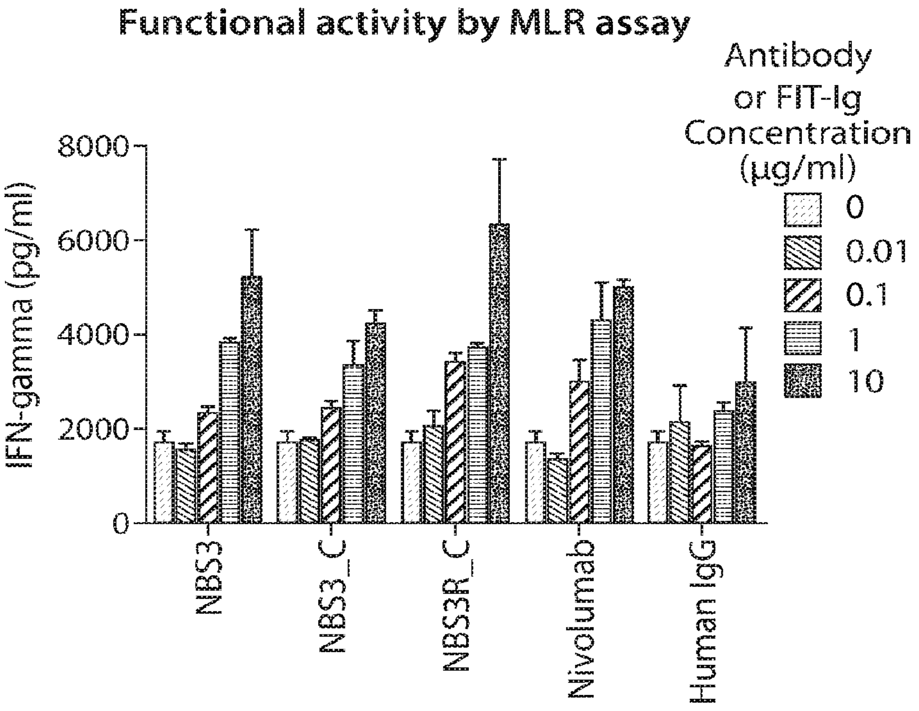
FIG. 13A shows functional activity of NBS3, NBS3-C, and NBS3R-C in MLR assays, when compared to the parental antibody Nivolumab at a concentration of 0, 0.01, 0.1, 1, or 10 μg/ml. The induction of IFN-7 was measured for each antibody. Human IgG was included as a control.
Figure 13B:
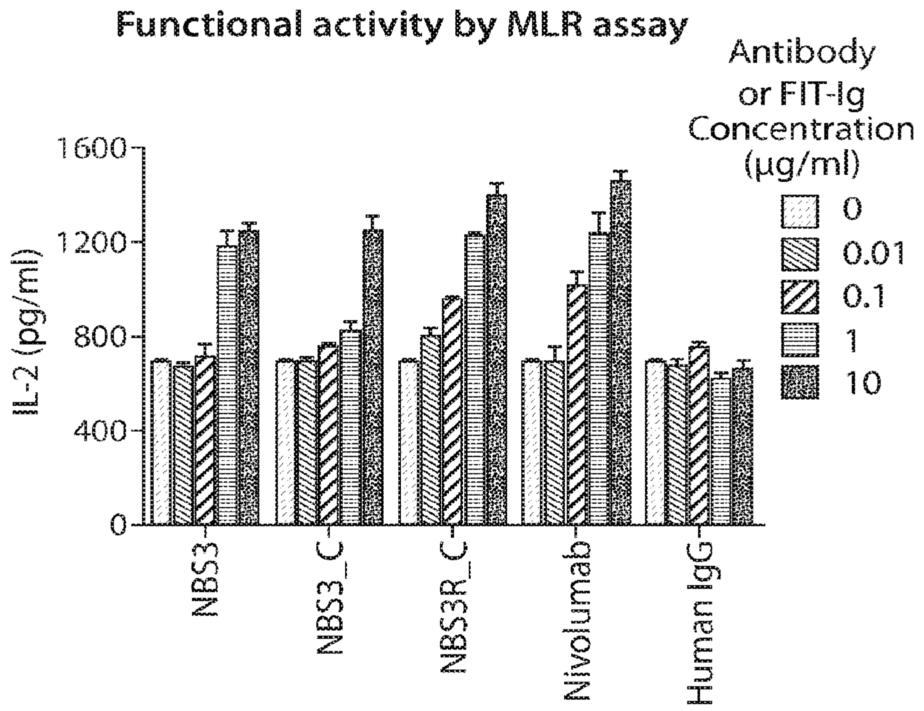
FIG. 13B shows the induction of IL-2 by these antibodies.

In the MLR assays, mixed lymphocyte reaction was performed using monocyte-derived dendritic cells from one donor and allogeneic CD4 T cells from another donor. The whole blood samples were collected from healthy donors, and PBMC were isolated from whole blood using Ficoll-Pague gradient centrifugation. On day 1, PBMC from one donor was isolated and diluted with serum-free RPMI 1640 at $1\times10^6$/ml. The diluted PBMC was seeded into 6-well tissue culture plate at 3 ml/well and incubated for 3 h. Supernatant was removed and unattached cells were washed off. The attached monocyte were polarized into dendritic cells with 250 U/ml IL-4 and 500 U/ml GM-CSF in RPMI1640 with 10% FBS. The medium was replaced with fresh IL-4 and GM-CSF at day 4. At day 7, immature DC was collected and treated with 1 μg/ml LPS in RPMI 1640 with 10% FBS for additional 24 h for maturation. At Day 8, CD4 T cells were isolated from another donor PBMC by negative selection and adjusted to final concentration at $2\times10^6$ cells/ml. Mature DC were treated with mitomycin C at 37° C. for 1.5 hr. Then DC were washed with PBS and adjusted to final concentration at $1\times10^6$ cells/ml. CD4 T cells (Responder cells) were added into 96 well plate at 100 μl/well and pre-treated with test antibody at diluted concentration for 30 minutes. Then mature DC (Stimulator cells) were added into the well at 100 μl/well. The final volume of each well is 200 μl. The MLR were incubated at 37 degree for 72 hr for IL-2 test and 120 hr for IFN-gamma test respectively using ELISA. The result is shown in FIG. 13A and FIG. 13B.

Figure 14:
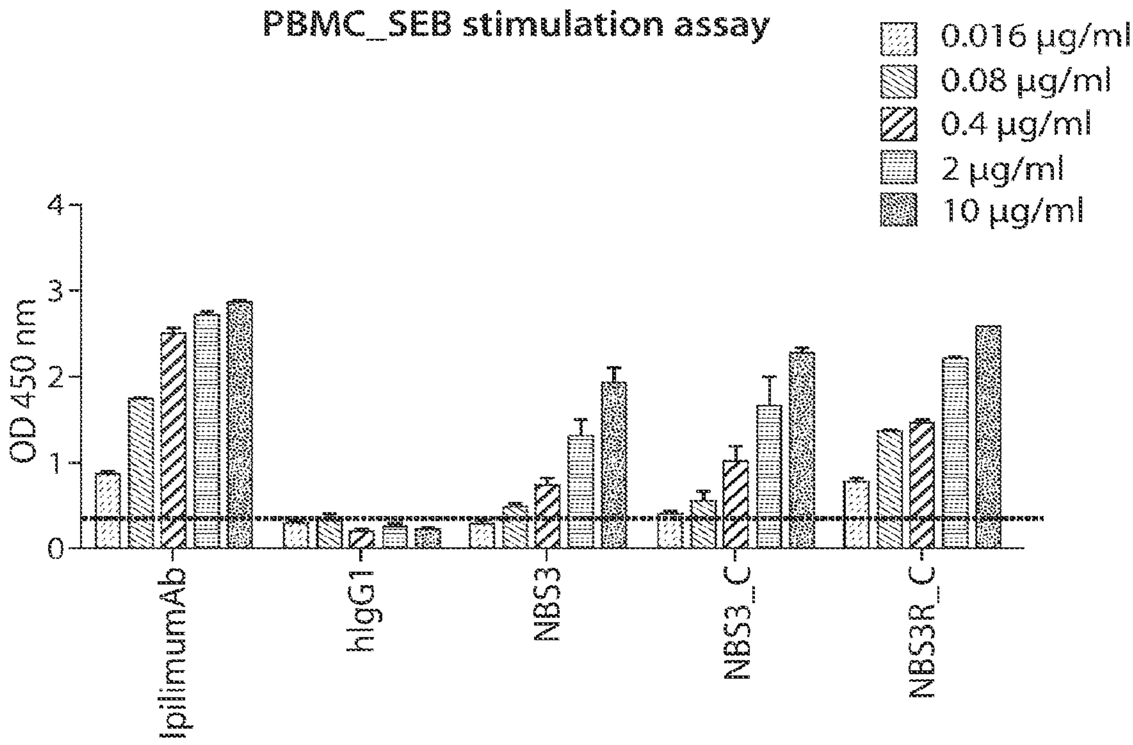
FIG. 14 shows functional activity of NBS3, NBS3-C, and NBS3R-C in PBMC SEB-stimulation assays when compared to the parental antibody ipilimumab, at a concentration of 0.016. 0.08, 0.4, 2, or 10 μg/ml. The IL-2 cytokine production in the supernatant was detected by ELISA.

In the PBMC SEB-stimulation assays, PBMC were isolated from healthy donor blood by Ficoll-Pague gradient centrifugation. The isolated PBMC were seeded into 96-well tissue culture plate at $1\times10^5$ cells/well. Then the PBMC were pre-treated with diluted test antibodies for 30 min. *Staphylococcus* enterotoxin B (SEB) was added into cell culture medium with final concentration at 100 ng/ml. The final assay volume was 200 μl/well. The cells were cultured for 96 hr and the culture supernatant was collected. IL-2 cytokine production in the supernatant was detected by ELISA. The result is shown in FIG. 14.

Example 7: Construction, Expression, and Purification of Additional Anti-EGFR/PD-L1 Fabs-In-Tandem Immunoglobulin (FIT-Ig)

New FIT-Igs having specificity for EGFR and PD-L1 were constructed as in the foregoing Examples. These exemplary FIT-Igs and their corresponding sequences are provided below in Table 26. Table 27 provides the expression level in 293E cells and the SEC profile for each of the FIT-Ig.

TABLE 26

Amino acid sequences of additional exemplary FIT-Ig for EGFR and PD-L1

| Name Target (mAb) mAb1 (upper domain)/mAb2 (lower domain) | Protein region | SEQ ID NO | Sequences |
|---|---|---|---|
| FIT012b - Ig EGFR (panitumumab)/ PD-L1 (1B12) | Long Chain (Pani VL-hCk-1B12VH-hCg1) | 202 | MDMRVPAQLLGLLLLWFPGSRC**DIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC**QVQLVQSGAEVKKPGSSVKVSCKTSGDTFSSYAISWVRQAPGQGLEWMGGIIPIFGRAHYAQKFQGRVTITADESTSTAYMELSSLRSEDTAVYFCARKFHFVSGSPFGMDVWGQGTTVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Pani VL | 203 | DIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIK |
| | Pani VL - CDR1 | 204 | QASQDISNYL |
| | Pani VL - CDR2 | 205 | DASNLET |
| | Pani VL - CDR3 | 206 | QHFDHLPLA |
| | 1B12VH | 207 | QVQLVQSGAEVKKPGSSVKVSCKTSGDTFSSYAISWVRQAPGQGLEWMGGIIPIFGRAHYAQKFQGRVTITADESTSTAYMELSSLRSEDTAVYFCARKFHFVSGSPFGMDVWGQGTTVTVSS |
| | 1B12VH - CDR1 | 208 | SYAIS |
| | 1B12VH - CDR2 | 209 | GIIPIFGRAHYAQKFQG |
| | 1B12VH - CDR3 | 210 | KFHFVSGSPFGMDV |
| | Short Chain #1 (Pani VH-CH1h) | 211 | MEFGLSWLFLVAILKGVQC**QVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |

TABLE 26-continued

Amino acid sequences of additional exemplary FIT-Ig for EGFR and PD-L1

| Name Target (mAb) mAb1 (upper domain)/mAb2 (lower domain) | Protein region | SEQ ID NO | Sequences |
|---|---|---|---|
| | Pani VH | 212 | QVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSS |
| | Pani VH - CDR1 | 213 | SGDYYWT |
| | Pani VH - CDR2 | 214 | HIYYSGNTNYNPSLKS |
| | Pani VH - CDR3 | 215 | DRVTGAFDI |
| | Short Chain #2 (1B12 VL-hCk) | 216 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 1B12 VL | 217 | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK |
| | 1B12 VL - CDR1 | 218 | RASQSVSSYLA |
| | 1B12 VL - CDR2 | 219 | DASNRAT |
| | 1B12 VL - CDR3 | 220 | QQRSNWPT |
| | Long Chain (Pani VL-hCk-10A5VH-hCg1) | 221 | MDMRVPAQLLGLLLLWFPGSRCDIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVQSGAEVKKPGASVKVSCKASGYTFTSYDVHWVRQAPGQRLEWMGWLHADTGITKFSQKFQGRVTITRDTSASTAYMELSSLRSEDTAVYYCARERIQLWFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Pani VL | 222 | DIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIK |
| | Pani VL - CDR1 | 223 | QASQDISNYLN |
| | Pani VL - CDR2 | 224 | DASNLET |
| | Pani VL - CDR3 | 225 | QHFDHLPLA |
| | 10A5VH | 226 | QVQLVQSGAEVKKPGASVKVSCKASGYTFTSYDVHWVRQAPGQRLEWMGWLHADTGITKFSQKFQGRVTITRDTSASTAYMELSSLRSEDTAVYYCARERIQLWFDYWGQGTLVTVSS |
| | 10A5VH - CDR1 | 227 | SYDVH |
| | 10A5VH - CDR2 | 228 | WLHADTGITKFSQKFQG |
| | 10A5VH - CDR3 | 229 | ERIQLWFDY |
| | Short Chain #1 (Pani VH-CH1h) | 230 | MEFGLSWLFLVAILKGVQCQVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Pani VH | 231 | QVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSS |
| | Pani VH - CDR1 | 232 | SGDYYWT |
| | Pani VH - CDR2 | 233 | HIYYSGNTNYNPSLKS |
| | Pani VH - CDR3 | 234 | DRVTGAFDI |
| | Short Chain #2 (10A5 VL-hCk) | 235 | MDMRVPAQLLGLLLLWFPGSRCDIQMTQSPSSLSASVGDRVTITCRASQGISSWLAWYQQKPEKAPKSLIYAASSLQSGVPSRFSGSGSGTDFTLTISSLQPEDFATYYCQQYNSYPYTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 26-continued

| Amino acid sequences of additional exemplary FIT-Ig for EGFR and PD-L1 | | | |
|---|---|---|---|
| Name Target (mAb) mAb1 (upper domain)/mAb2 (lower domain) | Protein region | SEQ ID NO | Sequences |
| | 10A5 VL | 236 | DIQMTQSPSSLSASVGDRVTITCRASQGISSWLAWYQQKPEKAPKSLIYAASSLQSGVPSRFSGSGSGTDFTLTISSLQPEDFATYYCQQYNSYPYTFGQGTKLEIK |
| | 10A5 VL - CDR1 | 237 | RASQGISSWLA |
| | 10A5 VL - CDR2 | 238 | AASSLQS |
| | 10A5 VL - CDR3 | 239 | QQYNSYPYT |

TABLE 27

| SEC Profile/Expression level in 293E cells: | | |
|---|---|---|
| FIT-Ig | Monomer % in SEC | Expression level(mg/L) |
| FIT012b - Ig | 74.72% | 5.3 |
| FIT012d - Ig | >87% | 1.05 |

The SEC profile and expression data suggest that FIT012d exhibited better purity than FIT012b by changing PD-L1 antibody sequences.

Functional binding data for these two antibodies is provided below in Table 28 and Table 29. The data suggests that the affinity was not affected by changing IgG constant sequences, but can be improved by place certain Fab in upper domain.

TABLE 28

| Functional binding data of FIT012b | | | | | |
|---|---|---|---|---|---|
| Ig | Target | Kon | Koff | KD | IC50 |
| Panitumumab | 1(EGFR) | 2.42E+05 | 4.48E−04 | 1.85E−09 | |
| FIT012b | | 3.08E+05 | 7.83E−04 | 2.54E−09 | |
| 1B12 | 2(PD-L1) | 2.35E+05 | 2.14E−03 | 9.08E−09 | |
| FIT012b | | 6.97E+05 | 2.71E−03 | 3.89E−09 | |

TABLE 29

| Functional binding data of FIT012d | | | | | |
|---|---|---|---|---|---|
| Ig | Target | Kon | Koff | KD | IC50 |
| Panitumumab | 1(EGFR) | 1.05E+05 | 4.91E−05 | 4.66E−10 | |
| FIT012d | | 1.03E+05 | 4.92E−05 | 4.76E−10 | |
| 10A5 | 2(PD-L1) | 8.91E+05 | 6.54E−04 | 7.35E−10 | |
| FIT012d | | 1.03E+06 | 6.00E−04 | 5.80E−10 | |

Figure 15:
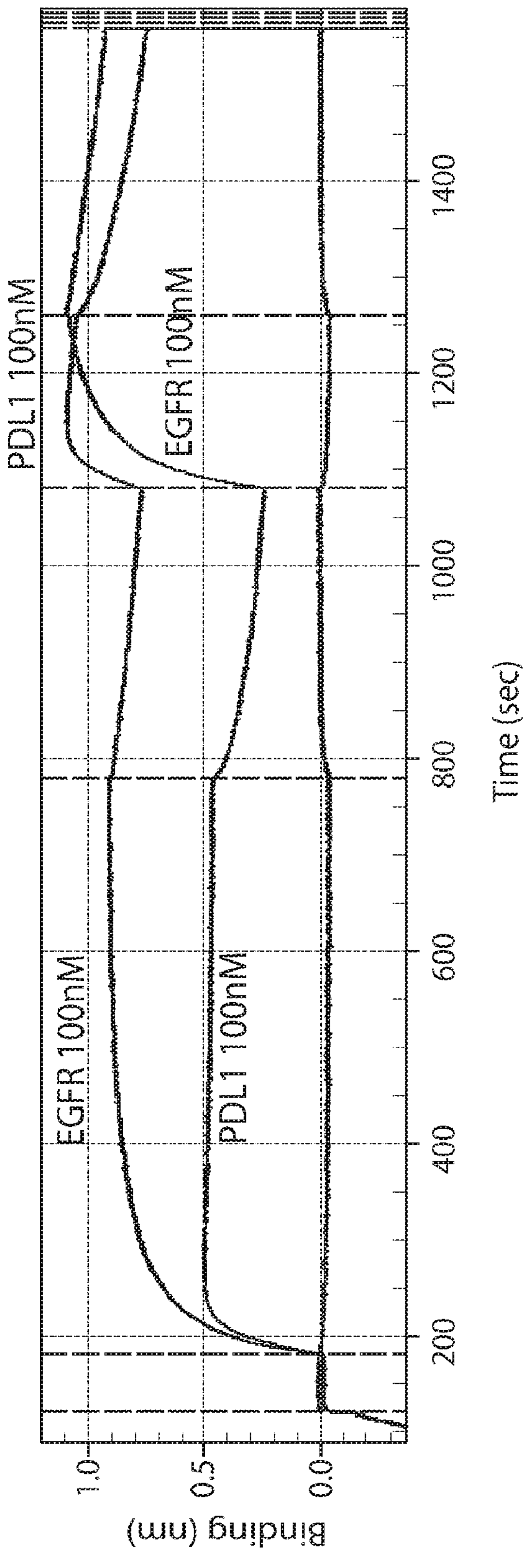
FIG. 15 shows a multiple binding study of FIT012b against both EGFR and PD-L1. Binding to human EGFR followed by human PD-L1; and binding by human PD-L1 followed by human EGFR are both shown as indicated.
Figure 16A:
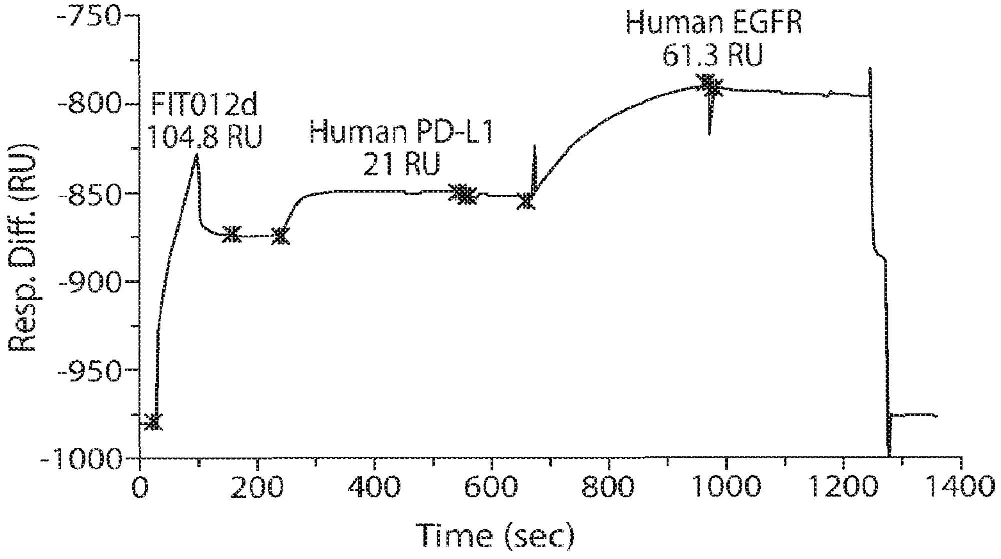
FIG. 16A and FIG. 16B show a multiple binding study of FIT012d against both human EGFR and human PD-L1. Binding to human EGFR followed by human PD-L1 (FIG. 16A); and binding by human PD-L1 followed by human EGFR (FIG. 16B) are both shown as indicated.
Figure 16B:
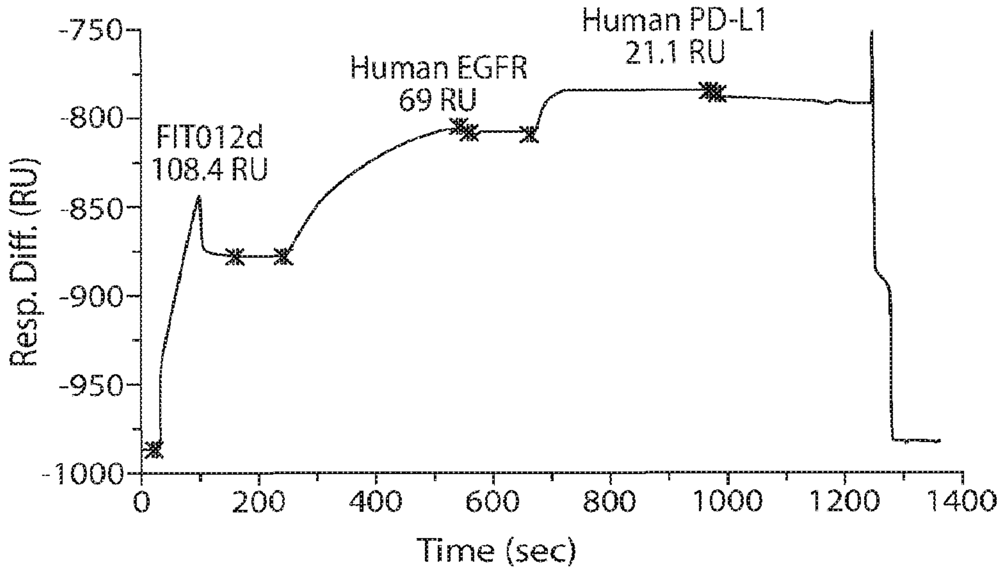

A multiple binding study of FIT012b and FIT012d was also carried out. The result is shown in FIG. 15 (FIT012b) and FIG. 16A to FIG. 16B (FIT012d).

Example 8: Construction, Expression, and Purification of Anti-cMet/EGFR Fabs-In-Tandem Immunoglobulin (FIT-Ig)

New FIT-Ig having specificity for cMet and EGFR was constructed as in the foregoing Examples. This exemplary FIT-Ig and its corresponding sequences are provided below in Table 30. Table 31 provides the expression level in 293E cells and the SEC profile for each of the FIT-Ig.

TABLE 30

| Amino acid sequences of additional exemplary FIT-Ig for cMet and EGFR | | | |
|---|---|---|---|
| Name Target (mAb) mAb1 (upper domain)/mAb2 (lower domain) | Protein region | SEQ ID NO | Sequences |
| FIT013a cMet (h1332 (13.3.2L-A91T,H-42K,S97T)) | Long Chain (h1332 VL-hCk-Pani VH-hCg1) | 240 | MDMRVPAQLLGLLLLWFPGSRC**DIQMTQSPSSVSASVGDRVTITCRASQGINTWLAWYQQKPGKAPKLLIYAASSLKSGVPSRFSGSGSGTDFTLTISSLQPEDFATYYCQQANSFPLT**F**GGGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC**QVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCK |

TABLE 30-continued

Amino acid sequences of additional exemplary FIT-Ig for cMet and EGFR

| Name Target (mAb) mAb1 (upper domain)/mAb2 (lower domain) | Protein region | SEQ ID NO | Sequences |
|---|---|---|---|
| | | | VSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | h1332 VL | 241 | DIQMTQSPSSVSASVGDRVTITCRASQGINTWLAWYQQKPGKAPKLLIYAASSLKSGVPSRFSGSGSGTDFTLTISSLQPEDFATYYCQQANSFPLTFGGGTKVEIK |
| | h1332 VL - CDR1 | 242 | RASQGINTWLA |
| | h1332 VL - CDR2 | 243 | AASSLKS |
| | h1332 VL - CDR3 | 244 | QQANSFPLT |
| | Pani VH | 245 | QVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSS |
| | Pani VH - CDR1 | 246 | SGDYYWT |
| | Pani VH - CDR2 | 247 | HIYYSGNTNYNPSLKS |
| | Pani VH - CDR3 | 248 | DRVTGAFDI |
| | Short Chain #1 (h1332 VH-CH1) | 249 | MEFGLSWLFLVAILKGVQC**QVQLVQSGAEVKKPGASVKVSCKASGYTFTSYGFSWVRQAPGQGLEWMGWISASNGNTYYAQKLQGRVTMTTDTSTSTAYMELRSLRSDDTAVYYCARVYADYADYWGQGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | h1332 VH | 250 | QVQLVQSGAEVKKPGASVKVSCKASGYTFTSYGFSWVRQAPGQGLEWMGWISASNGNTYYAQKLQGRVTMTTDTSTSTAYMELRSLRSDDTAVYYCARVYADYADYWGQGTLVTVSS |
| | h1332 VH - CDR1 | 251 | SYGFS |
| | h1332 VH - CDR2 | 252 | WISASNGNTYYAQKLQG |
| | h1332 VH - CDR3 | 253 | VYADYADY |
| | Short Chain #2 (Pani VL-hCk) | 254 | MDMRVPAQLLGLLLLWFPGSRC**DIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Pani VL | 255 | DIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIK |
| | Pani VL - CDR1 | 256 | QASQDISNYLN |
| | Pani VL - CDR2 | 257 | DASNLET |
| | Pani VL - CDR3 | 258 | QHFDHLPLA |

TABLE 31

SEC Profile/Expression level in 293E cells:

| FIT-Ig | Monomer % in SEC | Expression level(mg/L) |
|---|---|---|
| FIT013a | 98.48% | 22 |

Stability Data

The storage stability of FIT013a was assessed by SEC-HPLC method, and result is shown in Table 32. Samples were treated by freeze/thaw cycle for one time, two times or three times, no aggregation or degradation was observed by SEC-HPLC profile. Samples was treated at 4° C., 25° C. or 40° C. for 1 day, 3 days or 7 days, no aggregation or degradation was observed by SEC-HPLC profile.

TABLE 32

Storage stability of FIT013a

| Sample Name | Rel. Area % agg | Rel. Area % mono | Rel. Area % clip |
|---|---|---|---|
| FIT013a_D0 | 2.95 | 97.05 | n.a. |
| FIT013a_F/T1 | 3.26 | 96.74 | n.a. |
| FIT013a_F/T2 | 3.38 | 96.62 | n.a. |
| FIT013a_F/T3 | 3.47 | 96.53 | n.a. |
| FIT013a_4C-D1 | 3.56 | 96.44 | n.a. |
| FIT013a_25C-D1 | 3.66 | 96.34 | n.a. |
| FIT013a_40C-D1 | 3.72 | 96.22 | 0.06 |
| FIT013a_4C-D3 | 3.63 | 96.37 | n.a. |
| FIT013a_25C-D3 | 3.65 | 96.35 | n.a. |
| FIT013a_40C-D3 | 3.76 | 96.16 | 0.08 |
| FIT013a_4C-D7 | 3.64 | 96.36 | n.a. |
| FIT013a_25C-D7 | 3.72 | 96.28 | n.a. |
| FIT013a_40C-D7 | 3.95 | 95.92 | 0.12 |

Functional Study: Protein based binding data for FIT013a is provided below in Table 33 and Table 34.

TABLE 33

| Functional binding data of FIT013a (human cMet/human EGFR) | | | | | |
|---|---|---|---|---|---|
| Ig | Target | Kon | Koff | KD | IC50 |
| H1332 | 1 (human | 4.14E+05 | 5.27E−04 | 1.27E−09 | |
| FIT013a | cMet) | 4.75E+05 | 5.02E−04 | 1.06E−09 | |
| Panitumumab | 2 (human | 8.43E+04 | 5.10E−05 | 6.05E−10 | |
| FIT013a | EGFR) | 1.09E+05 | 5.84E−05 | 5.34E−10 | |

TABLE 34

| Functional binding data of FIT013a (Cyno cMEt/Cyno EGFR) | | | | | |
|---|---|---|---|---|---|
| Ig | Target | Kon | Koff | KD | IC50 |
| H1332 | 1 (Cyno | 2.21E+05 | 1.00E−03 | 4.53E−09 | |
| FIT013a | cMet) | 2.86E+05 | 9.74E−04 | 3.40E−09 | |
| Panitumumab | 2 (Cyno | 5.87E+05 | 2.12E−04 | 3.62E−10 | |
| FIT013a | EGFR) | 2.66E+05 | 1.54E−04 | 5.77E−10 | |

Figure 17:
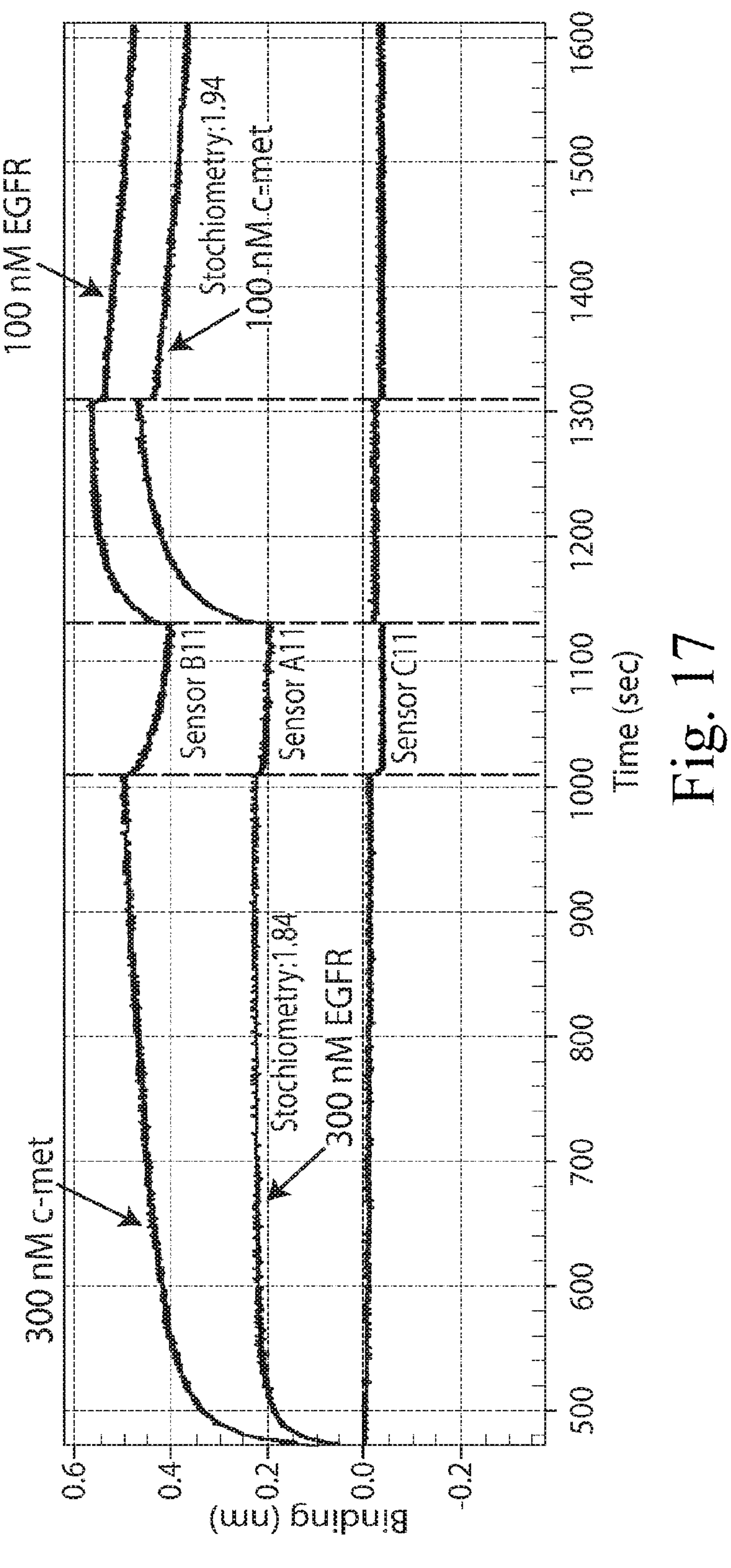
FIG. 17 shows a multiple binding study of FIT013a against both cMet and EGFR. Binding to cMet followed by EGFR; and binding by EGFR followed by cMet are both shown as indicated.

A multiple binding study of FIT013a was also carried out. The result is shown in FIG. 17.

Further, the binding activity of FIT013a in cancer cell lines was determined by flow cytometry using BD FACSVerse. Cells grown in culture were detached from flask with trypsin-free medium and collected. The collected cells were washed in PBS buffer containing 2% FBS. Cells were then aliquot and incubated with 1:5 serially diluted FIT013a on ice for 1 hr. The starting working concentration of FTI013a was 20 μg/ml. Cells were washed, resuspended and incubated with 1:100 diluted Alexa Fluor® 488 labeled mouse anti-human IgG1 (Invitrogen, Cat. No. A-10631) on ice protected from light for 1 hr. Cells were washed and signal was detected with a BD FACSVerse flow cytometer according to manufacture's protocols.

These experiments demonstrate that FIT013a can bind to many cancer cell lines, like NCI-H1993, HCC827, MKN-45, SGC-7901, EBC-1, A549, KP4, NCI-H292, NCI-H1975, etc. Geometric mean fluorescence intensity (MFI) and EC50 for each cell lines are listed in the Table 35.

TABLE 35

| Cell based binding data for FIT013a | | |
|---|---|---|
| Cell lines | MFI | EC50 (nM) |
| NCI-H1993 | 447 | 37.14 |
| HCC827 | 2000 | 41.33 |
| MKN-45 | 2050 | 8.89 |
| SGC-7901 | 590 | 2.53 |
| EBC-1 | 6000 | 1.5 |
| A549 | 1000 | 0.62 |
| KP4 | 345 | 0.31 |
| NCI-H292 | 920 | 0.58 |
| HCI-H1975 | 507 | — |

In addition, FACS assays were conducted to measure FIT013a's dual binding to membrane c-Met and EGFR to show its multiple binding activity.

Several cell lines were used n this assay. MKN-45 (human gastric adenocarcinoma cells) expressed high level of c-Met and low level of EGFR. SGC-7901 (human gastric cancer) expressed high level of EGFR and low level of c-Met. NCI-H1975 (human non-small cell lung cancer) expressed equal level of c-Met and EGFR.

Cells grown in culture were detached from flask with trypsin-free medium and collected. The collected cells were washed in PBS buffer containing 2% FBS. Cells were aliquot and incubated with serially diluted FIT013a or FIT013a-Fab on ice for 1 hr. Cells were then washed and incubated with 1 μg/ml biotinylated human c-MET or biotinylated EGFR on ice for 1 hr. Cells were resuspended and incubated with 4 μg/ml Alexa Fluor® 488 labeled Streptavidin (Invitrogen, Cat. No S32354) on ice protected from light for 1 hr. Cells were washed and signal was detected with a BD FACSVerse flow cytometer according to manufacture's protocols.

Figure 18A:
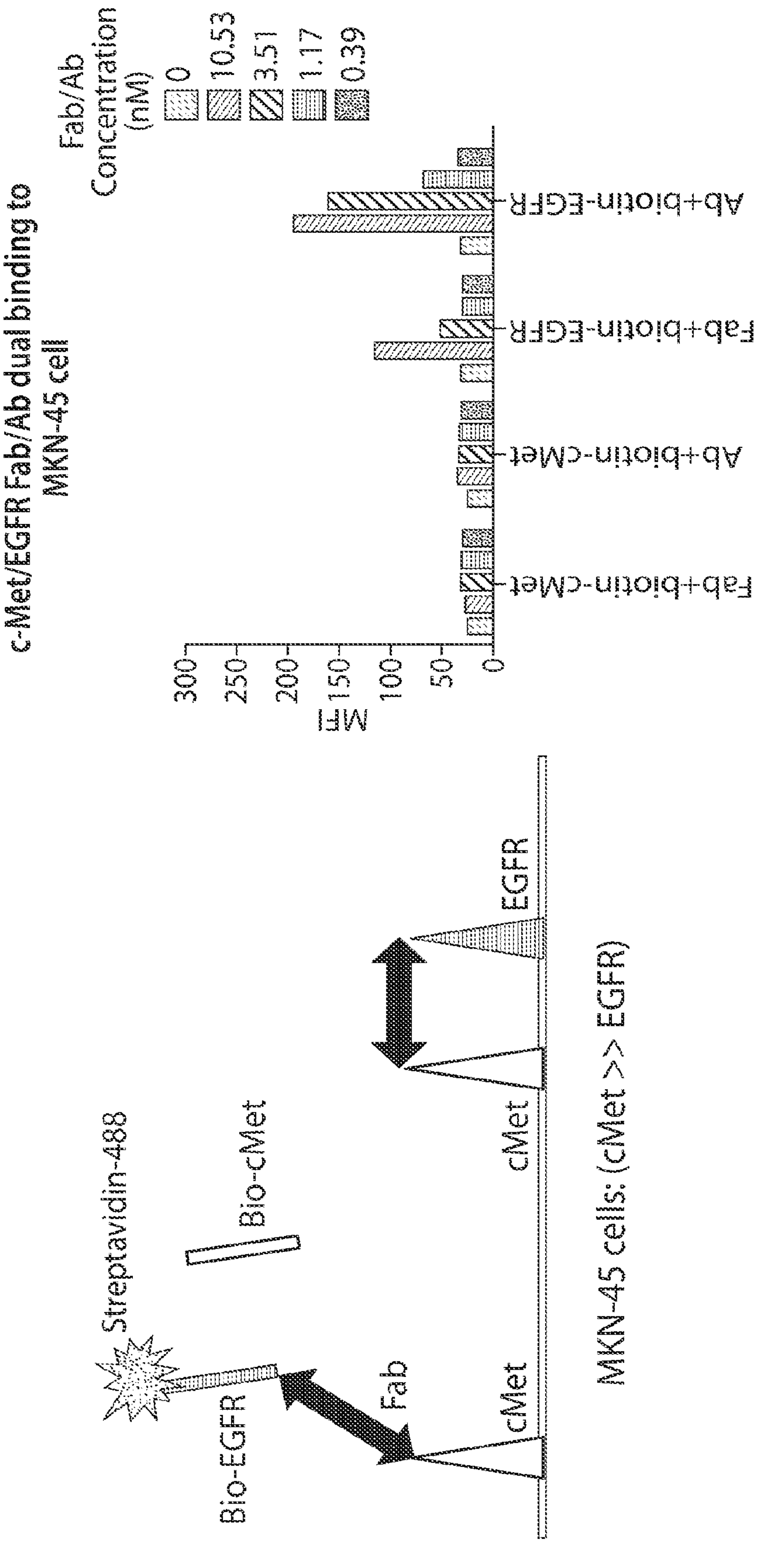
FIG. 18A to FIG. 18C show FACS assays in which FIT013a's binding activity to membrane c-Met and EGFR was tested.
Figure 18B:
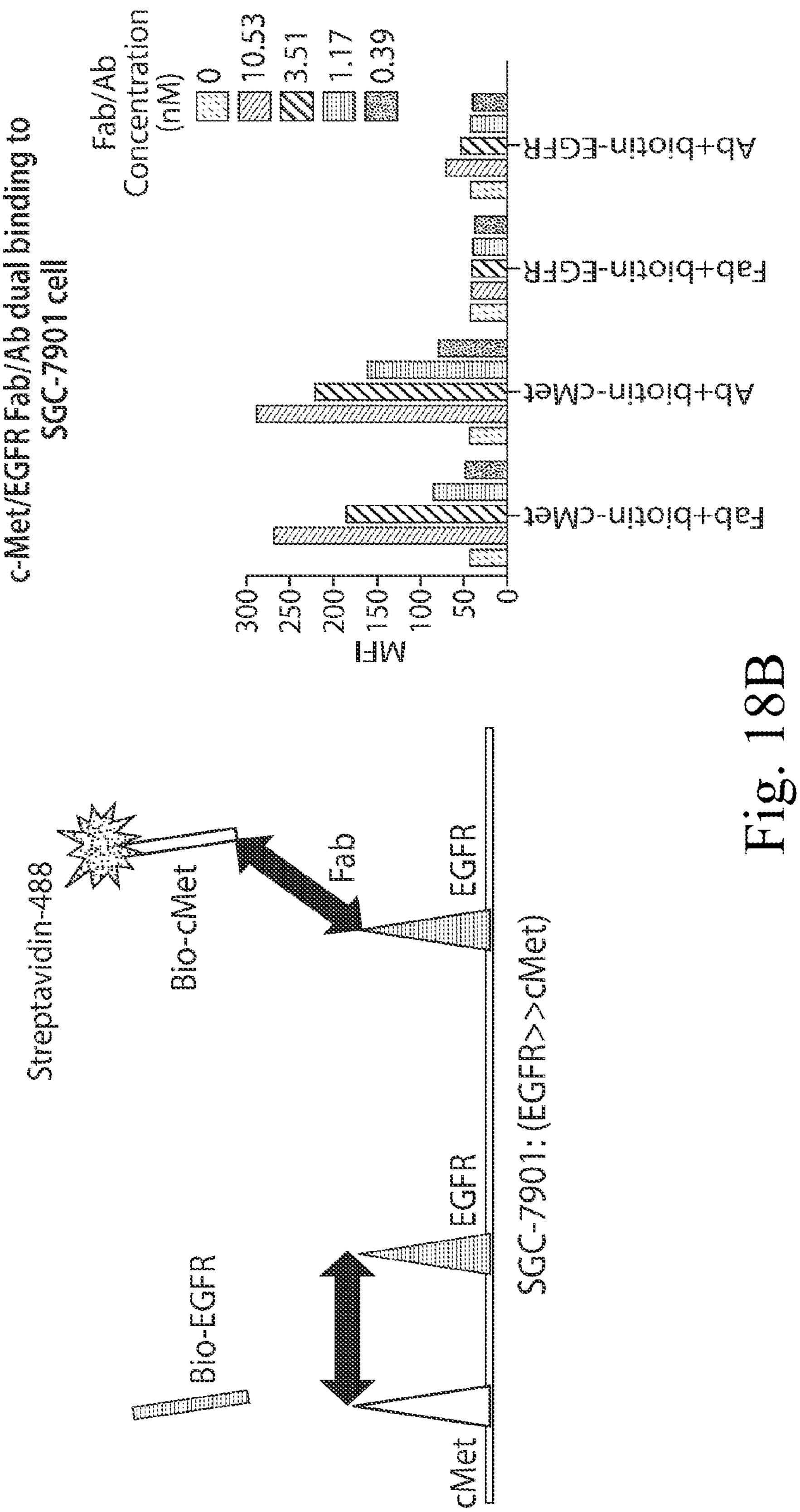
Figure 18C:
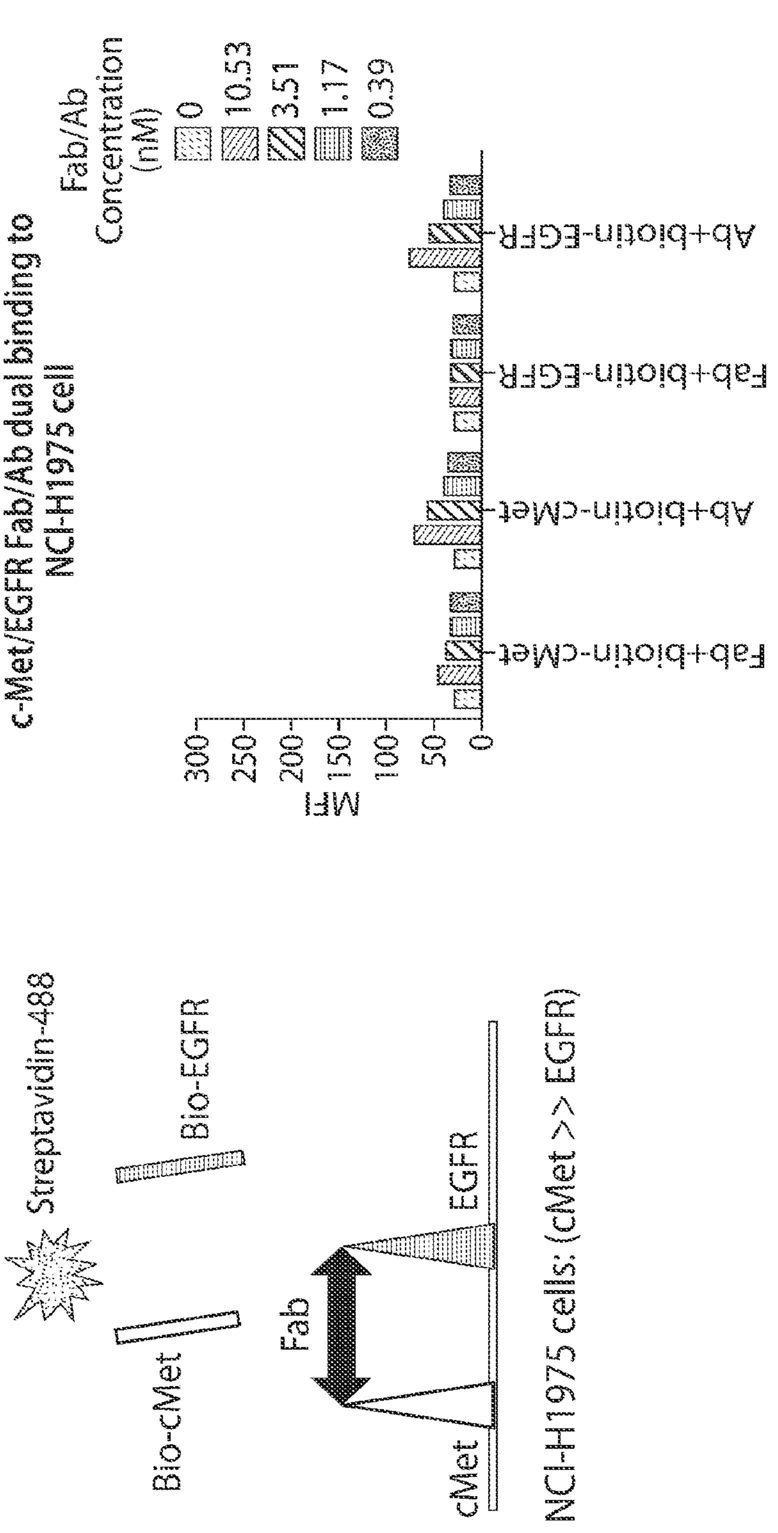

When cell membrane expression level c-Met is much higher than EGFR (e.g., on MKN-45 cell), c-Met binding cite of FIT013a and FIT013a-Fab can be occupied by membrane c-Met, the free EGFR binding cite of FIT013a and FIT013a-Fab can be detected by biotinylated EGFR. When cell membrane expression level EGFR is much higher than c-Met (e.g., on SGC-7901), EGFR binding cite of FIT013a and FIT013a-Fab can be occupied by membrane EGFR, the free c-Met binding cite of FIT013a and FIT013a-Fab can be detected by biotinylated c-Met. When cell membrane expression level c-Met is equal to EGFR (e.g., on NCI-H1975 cell), c-Met and EGFR binding cites of FIT013a and FIT013a-Fab are occupied simultaneously, no free EGFR or c-Met binding cite of FIT013a and FIT013a-Fab can be detected. As demonstrated in FIG. 18A to FIG. 18C, FIT013a and FIT013a-Fab can simultaneously bind to two receptors c-Met and EGFR on the cell surface.

Figure 19:
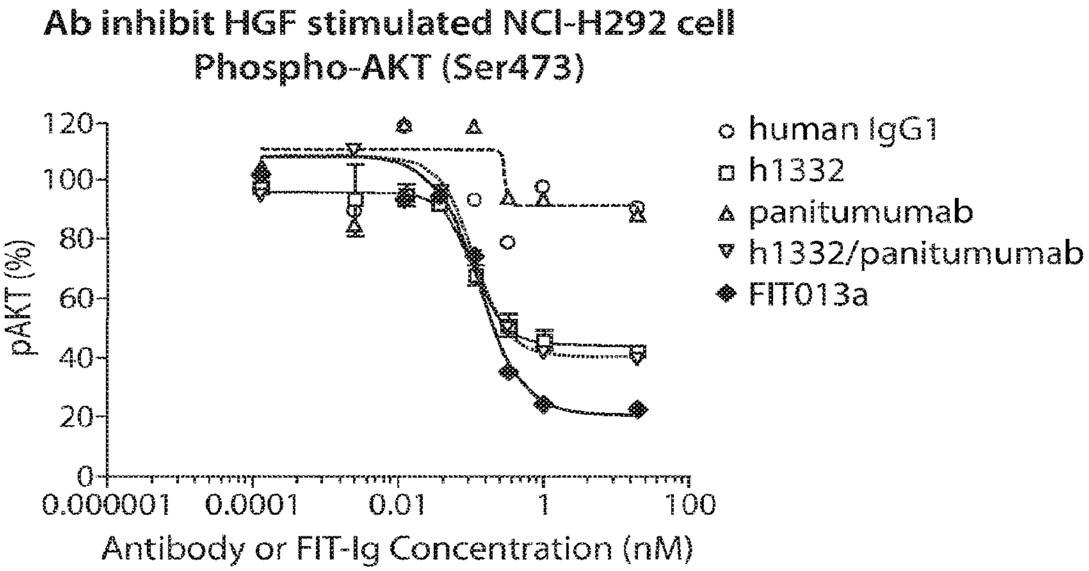
FIG. 19 shows FIT013a's ability of inhibiting HGF induced AKT phosphorylation in NCI-H292 cells. FIT013a, h1332, panitumumab, a combination of h1332/panitumumab, and human IgG1 were added to cells and incubated for 30 mins and then 40 ng/ml HGF was added to the assay plate for 5 mins. The cells were lysed and AKT phosphorylation was detected by ERK phospho-T202/Y204 kit.

Signaling assay: Next, FIT013a was used to inhibit HGF induced AKT phosphorylation in cells. NCI-H292 cells were plated at $2\times10^5$ per well in 96-well plate and serum starved overnight. Serially diluted FIT013a or other related Abs were added to plate and incubate for 30 mins and then 40 ng/ml HGF was added to the assay plate for 5 mins. The cells were lysed and AKT phosphorylation was detected by ERK phospho-T202/Y204 kit (Cisbio, Cat: 64AKSPEG). The experiment demonstrates that FIT013a shows superior activity than mAbs combo in neutralizing HGF induced AKT phosphorylation in NCI-H292 cell. FIT013a inhibited 80% of AKT phosphorylation while EGFR and c-Met antibody combo inhibit 60% of AKT phosphorylation, see FIG. 19.

Figure 20:
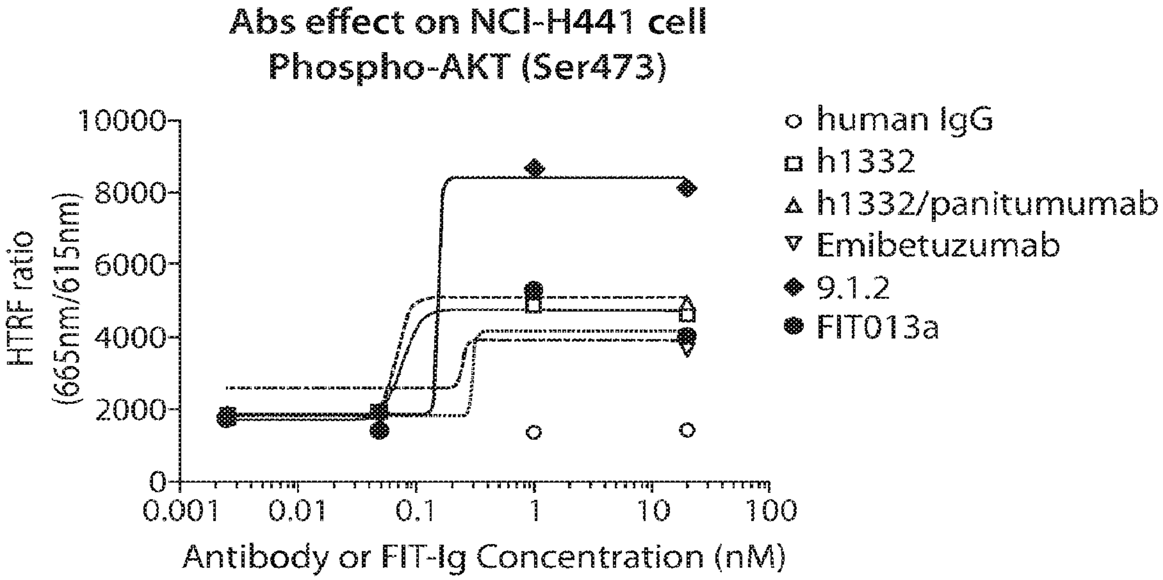
FIG. 20 shows FIT013a's agonist effect in the absence of HGF as measured by AKT phosphorylation. Serially diluted FIT013a or other Abs (h1332, a combination of h1332/panitumumab, emibetuzumab, 9.1.2, and human IgG1) were added to cells and incubate for 30 mins. The cells were lysed and AKT phosphorylation was detected by ERK phospho-T202/Y204 kit.
Figure 21A:
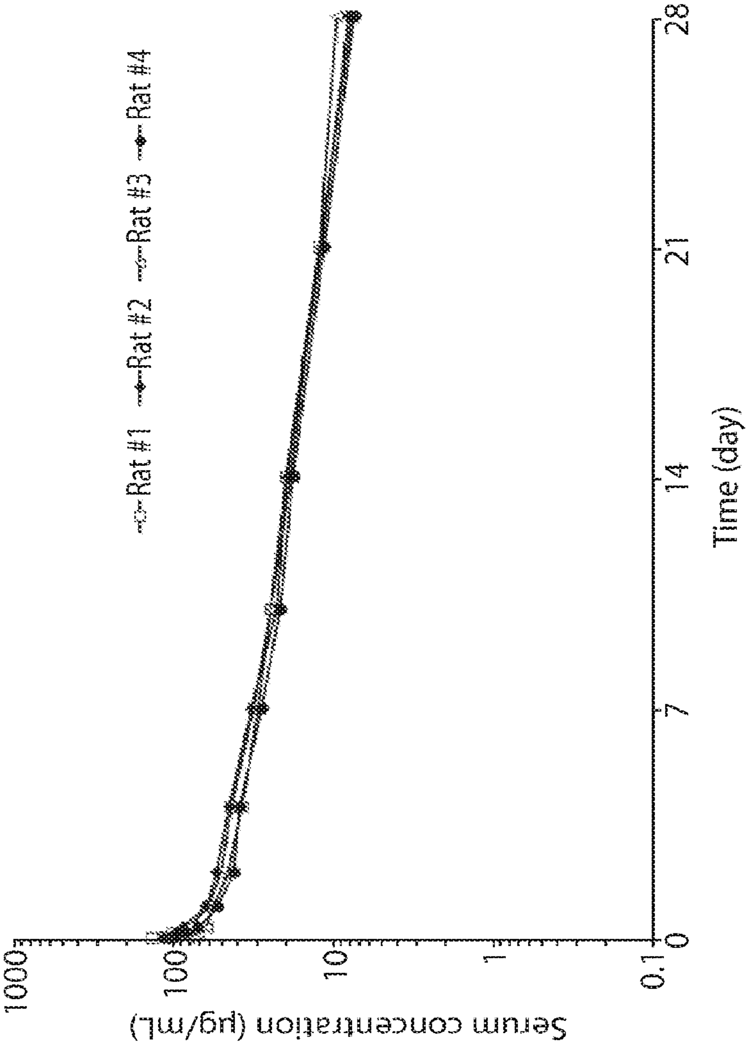
FIG. 21A shows individual serum concentration-time profiles of FIT013a (c-met/EGFR) after an IV dose of 5 mg/kg in male SD rats (N=4/time point, c-met plate).
Figure 21B:
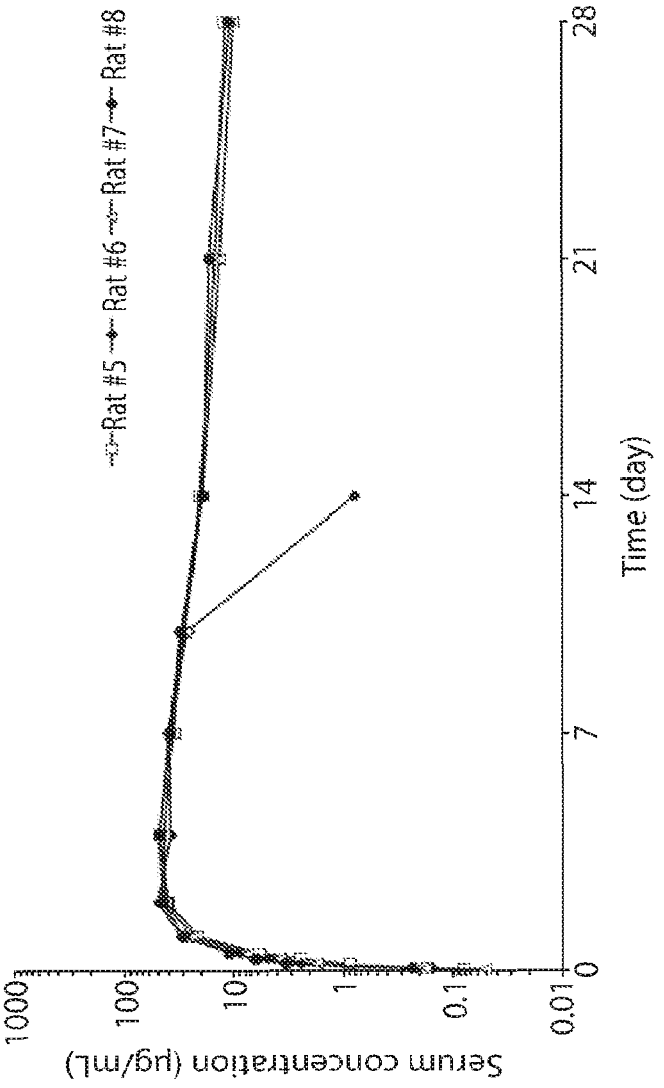
FIG. 21B shows individual serum concentration-time profiles of FIT013a (c-met/EGFR) after a SC dose of 5 mg/kg in male SD rats (N=4/time point, c-met plate).
Figure 21C:
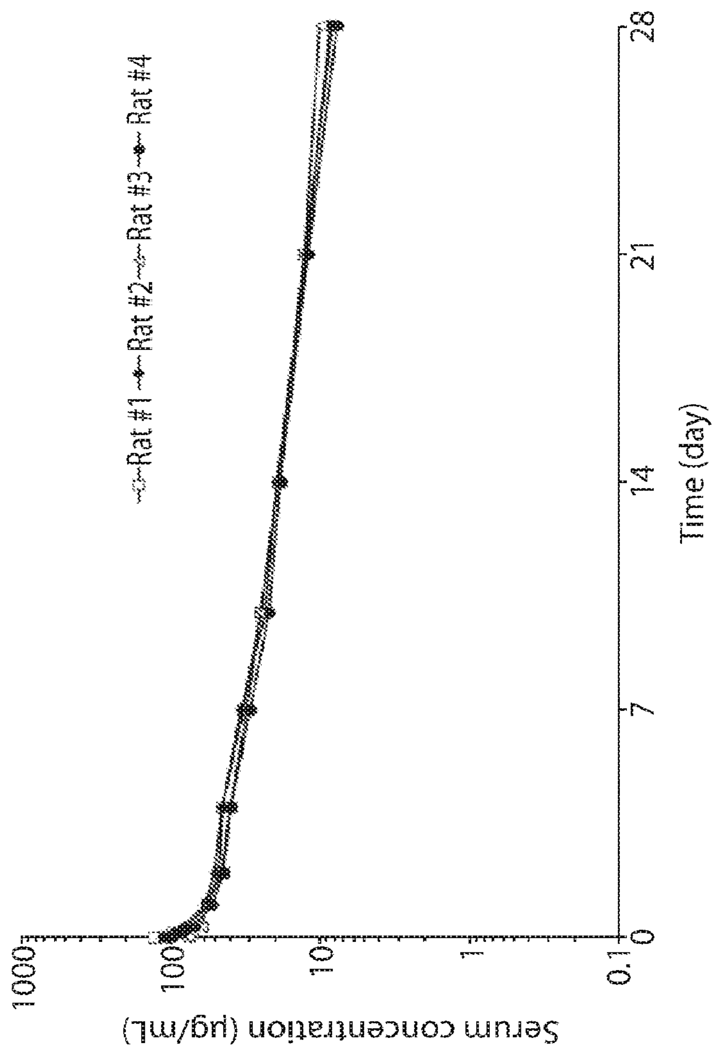
FIG. 21C shows individual serum concentration-time profiles of FIT013a (c-Met/EGFR) after an IV dose of 5 mg/kg in male SD rats (N=4/time point, EGFR plate).
Figure 21D:
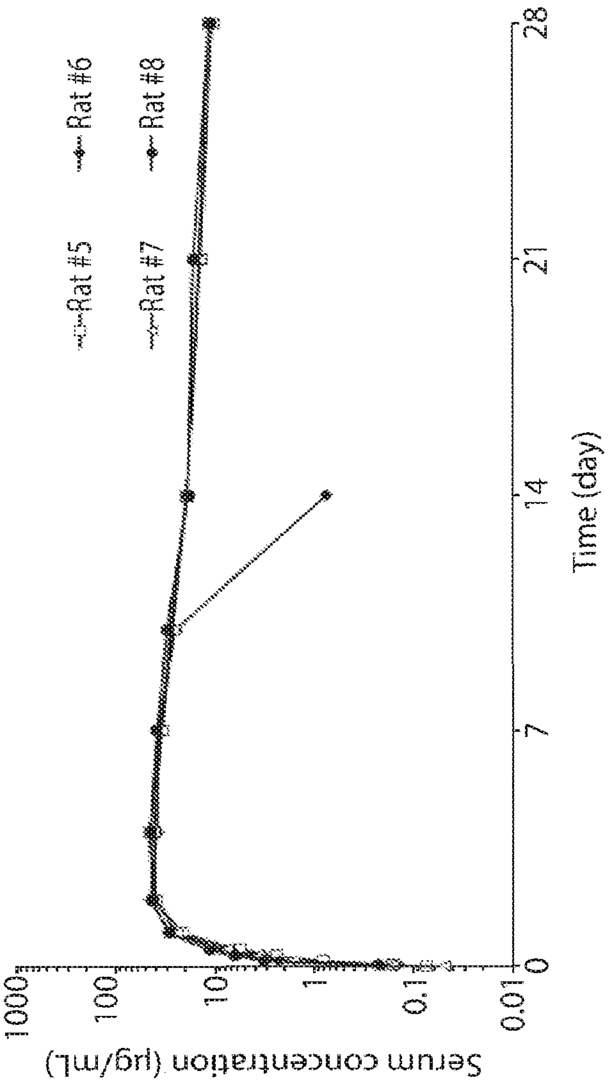
FIG. 21D shows individual serum concentration-time profiles of FIT013a (c-met/EGFR) after a SC dose of 5 mg/kg in male SD rats (N=4/time point, EGFR plate).

Agonist assay: Agonist effect of c-Met, EGFR antibody in FIT013a was tested by AKT phosphorylation. NCI-H441 cells were plated at $2\times10^5$ per well in 96-well plate and serum starved overnight. Serially diluted FIT013a or other related Abs were added to plate and incubate for 30 mins. The cells were lysed and AKT phosphorylation was detected by ERK phospho-T202/Y204 kit (Cisbio, Cat: 64AKSPEG). As shown in FIG. 20, the experiment demonstrates that FIT013a showed weak agonist effect in absence of HGF.

Receptor depletion study: FIT013a was tested to see if it can deplete both c-Met and EGFR on cell membrane. The c-Met antibody, EGFR antibody and FIT013a were incubated with H441 cell for more than 16 hrs at 37° C. and then EGFR and c-Met remaining on the cell surface was detected by FACS. The result indicates that FIT013a can deplete near 70% of cell membrane c-Met and EGFR, higher than the c-Met antibody or the EGFR antibody, see Table 36.

TABLE 36

| Receptor depletion by FIT013a | | |
|---|---|---|
| H441 cell | EGFR Depletion (%) | c-Met Depletion (%) |
| h1332 | 0.0 | 54.0 |
| Panitumumab | 56.6 | 0.0 |
| FIT013a | 65.9 | 64.5 |

Rat PK study: The purpose of this study was to evaluate the pharmacokinetic of FIT013a (c-met/EGFR) following single intravenous (IV) or subcutaneous (SC) administrations in SD rats. For IV and SC dosing, the test article FIT013a (c-met/EGFR) was dissolved (in 10 mM sodium citrate, 50 mM NaCl, pH 6.0) at 2.3 mg/mL (lot: 160408001). A total of 8 male SD rats, approximately 195-208 g of body weight, purchased from SLAC Laboratory Animal Co. LTD. with Qualification No.: SCXK (SH) 2008001659659, were used in this study. The dosing and sampling is designed as Table 37.

TABLE 37

| Treatment Group | Treatment | No. of animals | Route of admin. | Dose Level (mg/kg) | Solution Conc. (mg/mL) | Dose Volume (mL/kg) | Time points |
|---|---|---|---|---|---|---|---|
| Dosing and Sampling Design | | | | | | | |
| 1 | FIT013a (c-met/EGFR) | 4 | IV | 5 | 2 | 2.5 | Sampling at 0, 10 min, 1, 4, 8, 24 hr, 2, 4, 7, 10, 14, 21, 28 d, serial bleeding via tail vein for serum only. ~240 uL blood per time point. |
| 2 | FIT013a (c-met/EGFR) | 4 | SC | 5 | 2 | 2.5 | Sampling at 0, 30 min, 1, 4, 8, 12, 24 hr, 2, 4, 7, 10, 14, 21, 28 d, serial bleeding via tail vein for serum only. ~240 uL blood per time point. |

The IV dose was administered via foot dorsal vein injection and SC dose was administered via subcutaneous injection. At the designated time-points, the animals were restrained manually, and approximately 240 μL blood/time point was collected via tail vein puncture or cardiac puncture into tubes. The blood samples were placed at room temperature for 0.5 hr. Then blood samples were centrifuged (10000 g, 5 min under 4° C.) to obtain the serum samples. The serum samples were immediately stored at −80° C. until analysis. The samples were detected by ELISA using c-Met and EGFR protein respectively. The concentration-time data of FIT013a (c-met/EGFR) in rat serum for IV and SC studies are listed in Table 38 to Table 41, and are illustrated in FIG. 21A to FIG. 21D.

TABLE 38

Serum concentration-time data and pharmacokinetic parameters of FIT013a (c-met/EGFR) after an IV dose at 5 mg/kg in male SD rats (c-met plate)

| Dose | Dose | Sampling time | Concentration (μg/mL) | | | | Mean | | |
|---|---|---|---|---|---|---|---|---|---|
| (mg/kg) | route | (Day) | Rat #1 | Rat #2 | Rat #3 | Rat #4 | (μg/mL) | SD | CV (%) |
| 5 | IV | 0 | BQL | BQL | BQL | BQL | BQL | NA | NA |
| c-met plate | | 0.00694 | 138 | 118 | 82.0 | 108 | 112 | 23.3 | 20.9 |
| | | 0.0417 | 114 | 105 | 74.3 | 99.3 | 98.2 | 17.0 | 17.4 |
| | | 0.167 | 103 | 97.8 | 71.7 | 83.8 | 89.0 | 14.0 | 15.8 |
| | | 0.333 | 79.1 | 87.9 | 62.8 | 70.9 | 75.2 | 10.8 | 14.4 |
| | | 1 | 60.8 | 62.8 | 56.3 | 53.6 | 58.4 | 4.17 | 7.14 |
| | | 2 | 51.0 | 54.2 | 45.4 | 42.6 | 48.3 | 5.27 | 10.9 |
| | | 4 | 44.0 | 45.5 | 37.7 | 39.0 | 41.5 | 3.81 | 9.17 |
| | | 7 | 31.9 | 33.1 | 29.6 | 28.6 | 30.8 | 2.06 | 6.68 |
| | | 10 | 24.7 | 22.7 | 24.4 | 21.8 | 23.4 | 1.40 | 5.97 |
| | | 14 | 20.0 | 19.7 | 18.5 | 18.0 | 19.1 | 0.946 | 4.96 |
| | | 21 | 12.3 | 11.9 | 12.1 | 11.5 | 12.0 | 0.319 | 2.67 |
| | | 28 | 7.68 | 8.12 | 9.53 | 7.43 | 8.19 | 0.938 | 11.5 |

TABLE 38-continued

Serum concentration-time data and pharmacokinetic parameters of FIT013a (c-met/EGFR) after an IV dose at 5 mg/kg in male SD rats (c-met plate)

| PK parameters | Unit | Rat #1 | Rat #2 | Rat #3 | Rat #4 | Mean | SD | CV (%) |
|---|---|---|---|---|---|---|---|---|
| CL | mL/day/kg | 6.24 | 6.14 | 6.21 | 6.86 | 6.36 | 0.335 | 5.27 |
| Vss | mL/kg | 82.5 | 82.7 | 105 | 97.6 | 91.8 | 11.0 | 12.0 |
| V1 | mL/kg | 38.2 | 44.4 | 65.3 | 47.6 | 48.9 | 11.6 | 23.8 |
| Alpha $t_{1/2}$ | day | 0.235 | 0.491 | 0.879 | 0.309 | 0.478 | 0.288 | 60.2 |
| Beta $t_{1/2}$ | day | 9.46 | 9.80 | 12.3 | 10.21 | 10.4 | 1.26 | 12.1 |
| AUC | Day × μg/mL | 802 | 815 | 805 | 729 | 788 | 39.5 | 5.02 |
| MRT | day | 13.2 | 13.5 | 16.8 | 14.2 | 14.4 | 1.65 | 11.4 |

TABLE 39

Serum concentration-time data and pharmacokinetic parameters of FIT013a (c-met/EGFR) after a SC dose of 5 mg/kg in male SD rats (c-met plate)

| Dose (mg/kg) | Dose route | Sampling time (Day) | Concentration (μg/mL) Rat #5 | Rat #6 | Rat #7 | Rat #8 | Mean (μg/mL) | SD | CV (%) |
|---|---|---|---|---|---|---|---|---|---|
| 5 | SC | 0 | BQL | BQL | BQL | BQL | BQL | NA | NA |
| c-Met plate | | 0.00694 | 0.0780 | BQL | 0.0500 | BQL | 0.0640 | NA | NA |
| | | 0.0417 | 0.167 | 0.150 | 0.172 | 0.228 | 0.179 | 0.0338 | 18.9 |
| | | 0.167 | 0.865 | 2.38 | 1.70 | 3.28 | 2.06 | 1.03 | 49.9 |
| | | 0.333 | 2.44 | 4.89 | 3.66 | 6.17 | 4.29 | 1.60 | 37.4 |
| | | 0.5 | 5.69 | 8.74 | 7.37 | 10.8 | 8.16 | 2.18 | 26.7 |
| | | 1 | 21.3 | 29.5 | 23.6 | 28.3 | 25.7 | 3.85 | 15.0 |
| | | 2 | 39.4 | 47.9 | 40.9 | 43.7 | 43.0 | 3.73 | 8.69 |
| | | 4 | 47.4 | 36.8 | 42.3 | 47.2 | 43.4 | 5.01 | 11.5 |
| | | 7 | 36.8 | 38.5 | 34.4 | 37.7 | 36.9 | 1.76 | 4.78 |
| | | 10 | 28.8 | 25.7 | 27.0 | 29.9 | 27.9 | 1.85 | 6.64 |
| | | 14 | 19.8 | *0.753 | 18.5 | 18.6 | 19.0 | 0.748 | 3.94 |
| | | 21 | 14.2 | BQL | 12.8 | 16.2 | 14.4 | 1.67 | 11.6 |
| | | 28 | 11.6 | BQL | 9.52 | 10.5 | 10.5 | 1.03 | 9.74 |
| **PK parameters** | **Unit** | | **Rat #5** | **Rat #6** | **Rat #7** | **Rat #8** | **Mean** | **SD** | **CV (%)** |
| $T_{max}$ | day | | 4.00 | 2.00 | 4.00 | 4.00 | 3.50 | 1.00 | 28.6 |
| $C_{max}$ | μg/ml | | 47.4 | 47.9 | 42.3 | 47.2 | 46.2 | 2.63 | 5.70 |
| Terminal $t_{1/2}$ | day | | 11.6 | 11.6 | 11.4 | 12.0 | 11.7 | 0.262 | 2.24 |
| $AUC_{last}$ | Day × μg/ml | | 656 | 344 | 611 | 680 | 573 | 155 | 27.1 |
| $AUC_{INF}$ | Day × μg/ml | | 850 | 775 | 767 | 863 | 814 | 49.8 | 6.12 |
| CL/F | mL/day/kg | | 5.88 | 6.45 | 6.52 | 5.79 | 6.16 | 0.376 | 6.11 |
| F | % | | 108 | 98.4 | 97.4 | 110 | 103 | 6.32 | 6.12 |

*The serum concentration of these time point were excluded from mean value and PK parameters calculation due to the posibility of anti-drug antibody.

TABLE 40

Serum concentration-time data and pharmacokinetic parameters of FIT013a (c-met/EGFR) after an IV dose at 5 mg/kg in male SD rats (EGFR plate)

| Dose (mg/kg) | Dose route | Sampling time (Day) | Concentration (μg/mL) Rat #1 | Rat #2 | Rat #3 | Rat #4 | Mean (μg/mL) | SD | CV (%) |
|---|---|---|---|---|---|---|---|---|---|
| 5 | IV | 0 | BQL | BQL | BQL | BQL | BQL | NA | NA |
| EGFR plate | | 0.00694 | 130 | 115 | 80.0 | 105 | 107 | 21.0 | 19.6 |
| | | 0.0417 | 111 | 103 | 75.8 | 97.3 | 96.9 | 15.2 | 15.7 |
| | | 0.167 | 98.0 | 95.5 | 72.3 | 83.4 | 87.3 | 11.9 | 13.6 |
| | | 0.333 | 76.2 | 83.6 | 62.1 | 70.8 | 73.2 | 9.06 | 12.4 |
| | | 1 | 57.0 | 59.3 | 56.6 | 53.1 | 56.5 | 2.59 | 4.58 |
| | | 2 | 47.6 | 50.9 | 45.6 | 44.6 | 47.2 | 2.79 | 5.92 |
| | | 4 | 45.6 | 45.3 | 39.9 | 39.8 | 42.6 | 3.27 | 7.67 |
| | | 7 | 32.7 | 33.8 | 31.1 | 29.5 | 31.8 | 1.88 | 5.90 |
| | | 10 | 25.1 | 23.6 | 25.2 | 22.3 | 24.0 | 1.37 | 5.69 |
| | | 14 | 19.2 | 19.7 | 19.1 | 18.4 | 19.1 | 0.524 | 2.75 |
| | | 21 | 12.8 | 12.2 | 12.8 | 12.1 | 12.5 | 0.365 | 2.92 |

TABLE 40-continued

Serum concentration-time data and pharmacokinetic parameters of FIT013a (c-met/EGFR) after an IV dose at 5 mg/kg in male SD rats (EGFR plate)

| | | | | | | | | |
|---|---|---|---|---|---|---|---|---|
| | | 28 | 8.38 | 8.62 | 10.0 | 7.71 | 8.68 | 0.973 | 11.2 |

| PK parameters | Unit | Rat #1 | Rat #2 | Rat #3 | Rat #4 | Mean | SD | CV (%) |
|---|---|---|---|---|---|---|---|---|
| CL | mL/day/kg | 6.14 | 6.09 | 5.98 | 6.66 | 6.22 | 0.302 | 4.86 |
| Vss | mL/kg | 86.3 | 85.2 | 102 | 96.0 | 92.3 | 7.94 | 8.61 |
| V1 | mL/kg | 39.7 | 44.8 | 65.3 | 48.7 | 49.6 | 11.1 | 22.3 |
| Alpha $t_{1/2}$ | day | 0.222 | 0.368 | 0.795 | 0.306 | 0.423 | 0.255 | 60.3 |
| Beta $t_{1/2}$ | day | 10.0 | 10.0 | 12.3 | 10.3 | 10.7 | 1.09 | 10.2 |
| AUC | Day × μg/mL | 815 | 821 | 836 | 751 | 806 | 37.6 | 4.67 |
| MRT | day | 14.1 | 14.0 | 17.0 | 14.4 | 14.9 | 1.44 | 9.70 |

TABLE 41

Serum concentration-time data and pharmacokinetic parameters of FIT013a (c-met/EGFR) after a SC dose at 5 mg/kg in male SD rats (EGFRplate)

| Dose (mg/kg) | Dose route | Sampling time (Day) | Concentration (μg/mL) Rat #5 | Rat #6 | Rat #7 | Rat #8 | Mean (μg/mL) | SD | CV(%) |
|---|---|---|---|---|---|---|---|---|---|
| 5 | SC | 0 | BQL | BQL | BQL | BQL | BQL | NA | NA |
| EGFR plate | | 0.00694 | 0.0760 | BQL | 0.0490 | BQL | 0.0625 | NA | NA |
| | | 0.0417 | 0.164 | 0.144 | 0.167 | 0.231 | 0.177 | 0.0377 | 21.4 |
| | | 0.167 | 0.836 | 2.32 | 1.66 | 3.30 | 2.03 | 1.04 | 51.4 |
| | | 0.333 | 2.45 | 4.45 | 3.74 | 6.37 | 4.25 | 1.64 | 38.5 |
| | | 0.5 | 5.85 | 8.61 | 7.69 | 11.6 | 8.45 | 2.42 | 28.6 |
| | | 1 | 21.6 | 27.7 | 24.5 | 29.8 | 25.9 | 3.61 | 14.0 |
| | | 2 | 41.5 | 45.3 | 40.0 | 43.8 | 42.6 | 2.39 | 5.60 |
| | | 4 | 46.2 | 38.9 | 41.9 | 46.2 | 43.3 | 3.56 | 8.22 |
| | | 7 | 35.9 | 37.3 | 34.7 | 39.6 | 36.9 | 2.13 | 5.77 |
| | | 10 | 28.5 | 25.0 | 26.8 | 30.6 | 27.7 | 2.40 | 8.65 |
| | | 14 | 19.3 | *0.768 | 19.4 | 19.0 | 19.2 | 0.183 | 0.950 |
| | | 21 | 14.7 | BQL | 13.9 | 16.5 | 15.0 | 1.33 | 8.84 |
| | | 28 | 11.7 | BQL | 10.5 | 11.4 | 11.2 | 0.601 | 5.37 |

| PK parameters | Unit | Rat #5 | Rat #6 | Rat #7 | Rat #8 | Mean | SD | CV (%) |
|---|---|---|---|---|---|---|---|---|
| $T_{max}$ | day | 4.00 | 2.00 | 4.00 | 4.00 | 3.50 | 1.00 | 28.6 |
| $C_{max}$ | μg/ml | 46.2 | 45.3 | 41.9 | 46.2 | 44.9 | 2.03 | 4.51 |
| Terminal $t_{1/2}$ | day | 13.1 | 9.38 | 12.4 | 12.3 | 11.8 | 1.66 | 14.0 |
| $AUC_{last}$ | Day × μg/ml | 653 | 339 | 625 | 694 | 578 | 162 | 28.0 |
| $AUC_{INF}$ | Day × μg/ml | 875 | 677 | 813 | 896 | 815 | 98.8 | 12.1 |
| CL/F | mL/day/kg | 5.72 | 7.39 | 6.15 | 5.58 | 6.21 | 0.823 | 13.3 |
| F | % | 109 | 84.0 | 101 | 111 | 101 | 12.3 | 12.1 |

*The serum concentration of these time point were excluded from mean value and PK parameters calculation due to the posibility of anti-drug antibody.

NCI-H1975-HGF Xenograft Model Tumor Distribution Study

In this study, serum and tumor concentration of FIT013a was measured 24 hrs after single IP dose in NCI-H1975-HGF tumor bearing nude BALB/c Mice.

NCI-H1975-HGF cells were subcutaneously inoculated to nude BALB/c mice. When the average tumor volume reached to 200-250 $mm^3$, the mice were randomly allocated to four groups, FIT013a, H1332, Panitumumab and vehicle group. FIT013a group was single IP dose, 16 mg/kg; H1332 or Panitumumab was single IP dose, 10 mg/kg. Vehicle group was dosed with formulation buffer 10 mM sodium citrate, 50 mM NaCl, pH 6.0. 24 hrs after dosing, tumor and serum were collect. Tumors were homogenized and the supernatant was collected for the following ELISA study. FIT013a, Panitumumab, and H1332 were quantified by using generic hIgG ELISA method for both serum and tumor.

Figure 22:
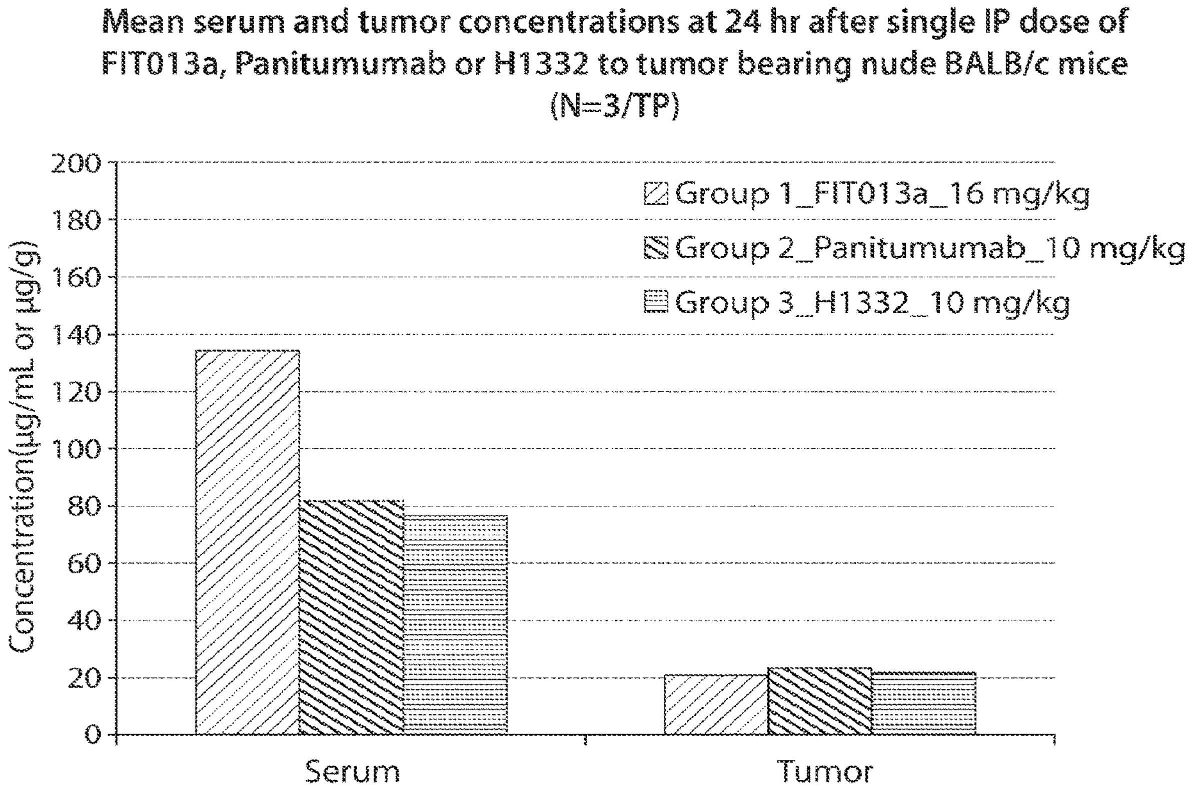
FIG. 22 shows distributions of FIT013a, panitumumab, and H1332 in the serum and tumor in nude BALB/c mice (N=3 animal/group) inoculated with NCI-H1975-HGF tumor cells.

The experiment demonstrates that FIT013a showed comparable distribution activity in serum and tumor with monoclonal antibodies, see FIG. 22.

NCI-H1975-HGF Xenograft Model Efficacy Study

In this study, the efficacy of FIT013a was measured in NCI-H1975-HGF xenograft model.

NCI-H1975-HGF cells were subcutaneously inoculated to nude BALB/c mice. When the average tumor volume reached to 100-130 $mm^3$, and the largest tumor volume was less than 140 $mm^3$. The mice were randomly allocated to four groups, FIT013a, H1332, Panitumumab and vehicle group. The antibodies were dosed two times/week i.p. for three weeks. The dosing for FIT013a was 16 mg/kg, for H1332 or Panitumumab was 10 mg/kg. Vehicle group was dosed with formulation buffer, 10 mM sodium citrate, 50 mM NaCl, pH 6.0. The tumor volume and mouse body weight was measured twice/week. Percentage tumor growth inhibition (% TGI) was defined as the difference between the control-treated group mean tumor volume (MTV) and the test antibody-treated group MTV.

Figure 23:
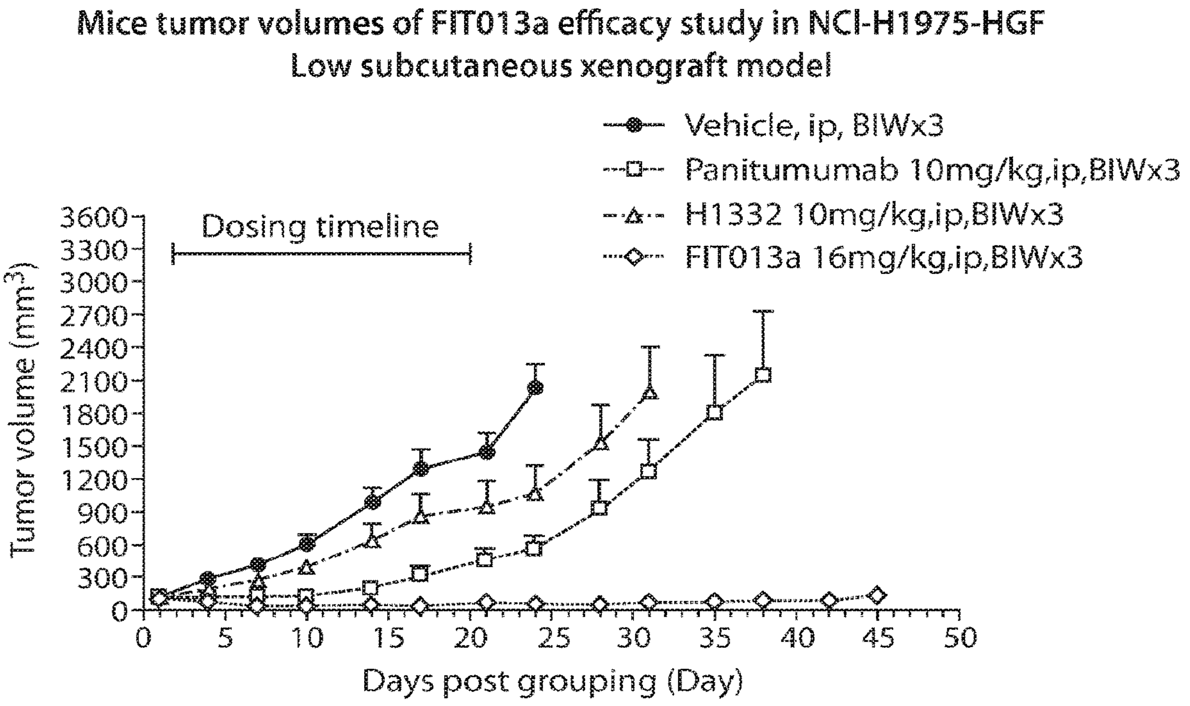
FIG. 23 shows the efficacy of FIT013a, panitumumab, H1332, vehicle in inhibiting tumor size in nude BALB/c mice (N=8 animal/group) inoculated with NCI-H1975-HGF tumor cells. The antibodies were dosed two times/week i.p. for three weeks. The dosing for FIT013a was 16 mg/kg, for H1332 or Panitumumab was 10 mg/kg.

The experiment demonstrates that FIT013a showed FIT013a showed better efficacy than EGFR or c-Met monoclonal Ab, see FIG. 23.

Example 9: Study of Anti-Factor IXa/Factor X Fabs-In-Tandem Immunoglobulin (FIT-Ig)

FIT-Ig having specificity for Factor IXa and Factor X was constructed as in the foregoing Examples. This exemplary FIT-Ig and its corresponding sequences are provided below in Table 42. Table 43 provides the expression level in 293E cells and the SEC profile for each of the FIT-Ig.

TABLE 42

Amino acid sequences of additional exemplary FIT-Ig for cMEt and EGFR

| Name Target (mAb) mAb1 (upper domain)/mAb2 (lower domain) | Protein region | SEQ ID NO | Sequences |
|---|---|---|---|
| FIT014a Factor IX (Factor IX Ab)/Factor X (Factor X Ab) | Long Chain (FIX VL-hCk-FX-VH-hCg4) | 259 | MDMRVPAQLLGLLLLWFPGSRCDIQMTQSPSSLSASVGDRVTITCKASRNIERQLAWYQQKPGQAPELLIYQASRKESGVPDRFSGSRYGTDFTLTISSLQPEDIATYYCQQYSDPPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVQSGSELKKPGASVKVSCKASGYTFTDNNMDWVRQAPGQGLEWMGDINTRSGGSIYNEEFQDRVIMTVDKSTDTAYMELSSLRSEDTATYHCARRKSYGYYLDEWGEGTLVTVSSASTKGPSVFPLAPCSRSTSESTAALGCLVKDYFPEPVTVSWNSGALTSGVHTFPAVLQSSGLYSLSSVVTVPSSSLGTQTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQYNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSKLTVDKSRWQEGNVFSCSVMHEALHNHYTQESLSLSP |
| | FIX VL | 260 | DIQMTQSPSSLSASVGDRVTITCKASRNIERQLAWYQQKPGQAPELLIYQASRKESGVPDRFSGSRYGTDFTLTISSLQPEDIATYYCQQYSDPPLTFGGGTKVEIK |
| | FIX VL - CDR1 | 261 | KASRNIERQLA |
| | FIX VL - CDR2 | 262 | QASRKES |
| | FIX VL - CDR3 | 263 | QQYSDPPLT |
| | FX-VH | 264 | QVQLVQSGSELKKPGASVKVSCKASGYTFTDNNMDWVRQAPGQGLEWMGDINTRSGGSIYNEEFQDRVIMTVDKSTDTAYMELSSLRSEDTATYHCARRKSYGYYLDEWGEGTLVTVSS |
| | FX-VH - CDR1 | 265 | DNNMD |
| | FX-VH - CDR2 | 266 | DINTRSGGSIYNEEFQD |
| | FX-VH - CDR3 | 267 | RKSYGYYLDE |
| | Short Chain #1 (F-IX VH-CH1h) | 268 | MEFGLSWLFLVAILKGVQCQVQLVESGGGLVQPGGSLRLSCAASGFTFSYYDIQWVRQAPGKGLEWVSSISPSGQSTYYRREVKGRFTISRDNSKNTLYLQMNSLRAEDTAVYYCARRTGREYGGGWYFDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | F-IX VH | 269 | QVQLVESGGGLVQPGGSLRLSCAASGFTFSYYDIQWVRQAPGKGLEWVSSISPSGQSTYYRREVKGRFTISRDNSKNTLYLQMNSLRAEDTAVYYCARRTGREYGGGWYFDYWGQGTLVTVSS |
| | F-IX VH - CDR1 | 270 | SYYDIQ |
| | F-IX VH - CDR2 | 271 | SISPSGQSTYYRREVKG |
| | F-IX VH - CDR3 | 272 | RTGREYGGGWYFDY |
| | Short Chain #2 (F-X VL-hCk) | 273 | MDMRVPAQLLGLLLLWFPGSRCDIQMTQSPSSLSASVGDRVTITCKASRNIERQLAWYQQKPGQAPELLIYQASRKESGVPDRFSGSRYGTDFTLTISSLQPEDIATYYCQQYSDPPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 42-continued

| Amino acid sequences of additional exemplary FIT-Ig for cMEt and EGFR | | | |
|---|---|---|---|
| Name Target (mAb) mAb1 (upper domain)/mAb2 (lower domain) | Protein region | SEQ ID NO | Sequences |
| | F-X VL | 274 | DIQMTQSPSSLSASVGDRVTITCKASRNIERQLAWYQQKPGQAPELLIYQASRKESGVPDRFSGSRYGTDFTLTISSLQPEDIATYYCQQYSDPPLTFGGGTKVEIK |
| | F-X VL - CDR1 | 275 | KASRNIERQLA |
| | F-X VL - CDR2 | 276 | QASRKES |
| | F-X VL - CDR3 | 277 | QQYSDPPLT |

TABLE 43

| SEC Profile/Expression level in 293E cells: | | |
|---|---|---|
| FIT-Ig | Monomer % in SEC | Expression level (mg/L) |
| FIT014a | 98.8% | 10.5 |

Functional Study

Affinity measurement by surface plasmon resonance: The kinetics of FIT-Ig binding to hFactor IX and hFactor X (Enzyme Research Laboratory) was determined by surface plasmon resonance with a Biacore X100 instrument (Biacore AB, Uppsala, Sweden) using HBS-EP (10 mM HEPES, pH 7.4, 150 mM NaCl, 3 mM EDTA, and 0.005% surfactant P20) at 25° C. Briefly, goat anti-human IgG Fc fragment specific polyclonal antibody (Pierce Biotechnology Inc, Rockford, Ill.) was directly immobilized across a CM5 research grade biosensor chip using a standard amine coupling kit according to manufacturer's instructions. Purified FIT-Ig samples were diluted in HEPES-buffered saline for capture across goat anti-human IgG Fc specific reaction surfaces and injected over reaction matrices at a flow rate of 5 μl/min. The association and dissociation rate constants, kon (M-1s-1) and koff (s-1) were determined under a continuous flow rate of 30 μL/min. Rate constants were derived by making kinetic binding measurements at 500 nM antigen concentrations. The equilibrium dissociation constant (M) of the reaction between FIT-Ig and the target proteins was then calculated from the kinetic rate constants by the following formula: KD=koff/kon. Aliquots of antigen samples were also simultaneously injected over a blank reference and reaction CM surface to record and subtract any nonspecific binding background to eliminate the majority of the refractive index change and injection noise. Surfaces were regenerated with two subsequent 25 ml injections of 10 mM Glycine (pH 1.5) at a flow rate of 10 μL/min. The anti-Fc antibody immobilized surfaces were completely regenerated and retained their full capture capacity over twelve cycles. Protein based binding data for FIT014a is provided below in Table 44.

TABLE 44

| Functional binding data of FIT014 | | | | |
|---|---|---|---|---|
| Ig | Target | Kon | Koff | KD |
| Factor IX mAb | Factor IX | 2.74E+04 | 3.55E−04 | 1.30E−08 |
| FIT-Ig 014a | | 3.35E+04 | 3.32E−04 | 9.91E−09 |

TABLE 44-continued

| Functional binding data of FIT014 | | | | |
|---|---|---|---|---|
| Ig | Target | Kon | Koff | KD |
| Factor X mAb | Factor X | 3.15E+04 | 1.42E−03 | 4.51E−08 |
| FIT-Ig 014a | | 7.75E+04 | 7.76E−04 | 1.00E−08 |

Figure 24:
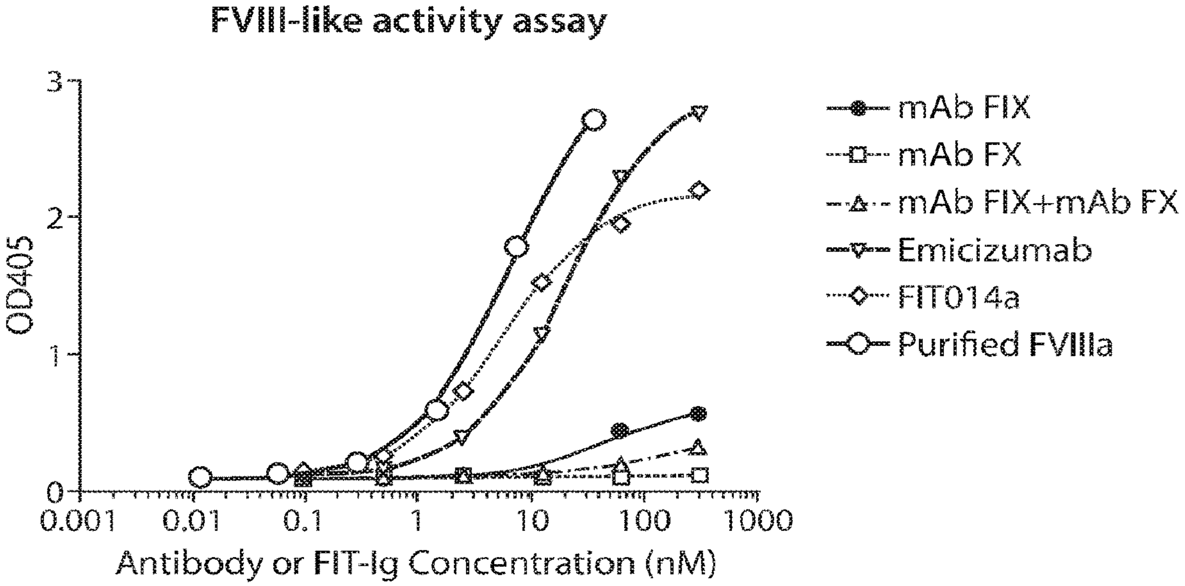
FIG. 24 shows enzyme assay for Factor VIIIa-like activity using BIOPHEN FVIII.C kit (Hyphen-Biomed). Samples containing mAb FIX, mAb FX, a combination of mAb FIX and mAb FX, Emicizumab, FIT014a, and purified FVIIIa were analyzed.

Factor VIIIa-like activity assay: FVIIIa-like activity of the FIT-Ig was evaluated by an enzyme assay according to manufacturer's instructions of BIOPHEN FVIII:C kit (Hyphen-Biomed, 221402-RUO). The result indicates that FIT014a has comparable FVIIIa like activity with Emicizumab and purified FVIIIa, while monoclonal antibody of Factor IX and Factor X, as well as a combination of them, has no activity, see FIG. 24.

Figure 25:
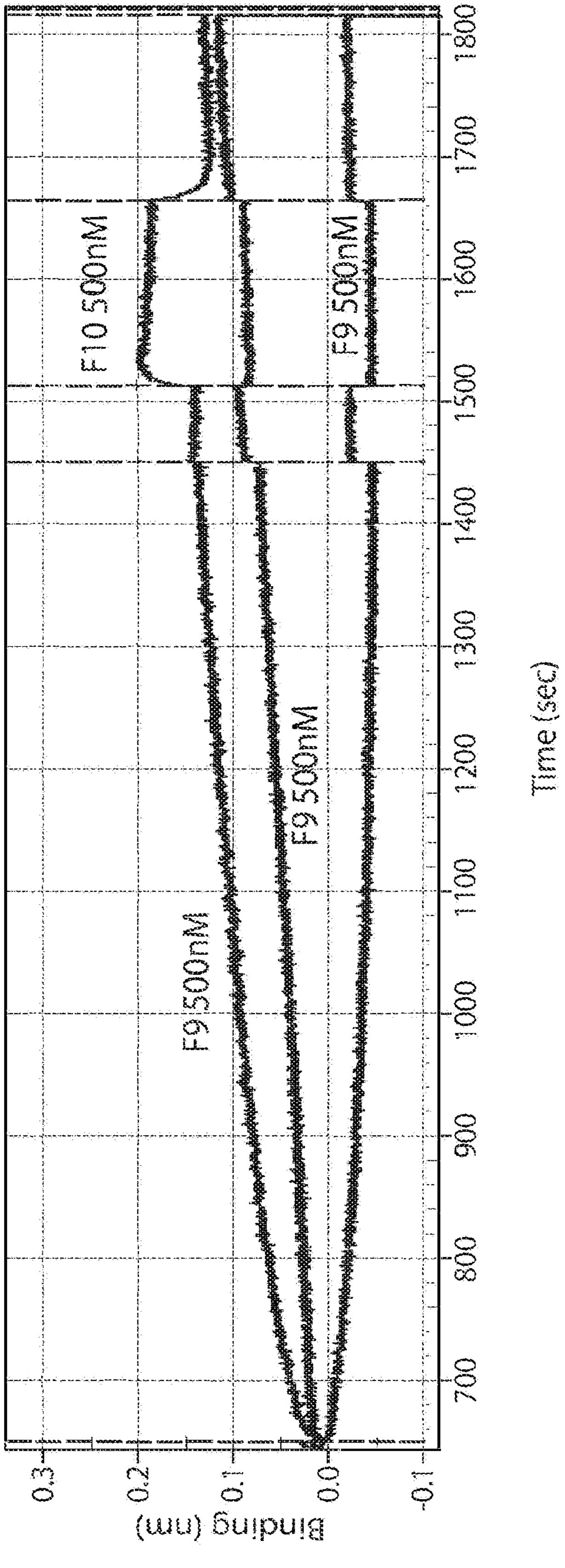
FIG. 25 shows a multiple binding study of FIT014a against both FIX and FX. Binding to FIX followed by FX; and binding by FX followed by FIX are both shown as indicated.

Multiple-antigen binding study: this study was done using OctetRed to determine if FIT014a is able to bind hFactor IX and hFactor X simultaneously. Briefly, FIT014a was immobilize on AR2G sensor at concentration of 10 μg/ml, followed by binding of hFactor IX and then hFactor X (Enzyme Research Laboratory) in assay buffer (PBS pH 7.4, 0.1% BSA, 0.02% Tween), with concentration at 500 nM. At the end of the experiment, the surface was regenerated with 10 mM glycine at pH1.5 five times. This experiment shows that FIT014a is able to bind hFactor X when it had already bound to hFactor IX, indicating that FIT014a is able to bind both hFactor IX and hFactor X simultaneously, see FIG. 25.

Stability study: FIT014a protein samples in citrate buffer (pH=6.0) were individually incubated at constant 4° C., 25° C. and 40° C. for 1 day, 3 days or 7 days. Similarly, FIT014a protein samples were freeze-thawed once, twice or three times. The fractions of intact full monomeric protein of all samples was detected by SEC-HPLC, with 10 μg of each protein sample injected into Ultimate 3000 HPLC equipping Superdex200 5/150 GL at flow rate 0.3 mL/min for 15 min, and data was recorded and analyzed using Chromeleon software supplied by the manufacturer. Table 45 shows that FIT014a remained full intact monomeric molecule under these thermo-challenged conditions.

TABLE 45

| Storage stability of FIT014 | | | |
|---|---|---|---|
| Sample Name | Rel. Area % 1 | Rel. Area % 2 | Rel. Area % 3 |
| FIT014_D0 | 6.28 | 93.32 | 0.40 |
| FIT014_F/T1 | 6.86 | 92.25 | 0.89 |
| FIT014-F/T2 | 6.72 | 92.36 | 0.93 |
| FIT014_F/T3 | 6.80 | 92.03 | 1.16 |

TABLE 45-continued

| Storage stability of FIT014 | | | |
|---|---|---|---|
| Sample Name | Rel. Area % 1 | Rel. Area % 2 | Rel. Area % 3 |
| FIT014_4C-D1 | 6.19 | 93.51 | 0.30 |
| FIT014_25C-D1 | 6.81 | 92.24 | 0.95 |
| FIT014_40C-D1 | 6.60 | 92.36 | 1.04 |
| FIT014_4C-D3 | 6.63 | 92.42 | 0.95 |
| FIT014_25C-D3 | 6.92 | 92.02 | 1.07 |
| FIT014_40C-D3 | 6.60 | 92.15 | 1.25 |
| FIT014_4C-D7 | 6.68 | 92.45 | 0.87 |
| FIT014_25C-D7 | 6.58 | 92.39 | 1.03 |
| FIT014_40C-D7 | 6.94 | 91.74 | 1.32 |

Figure 26:
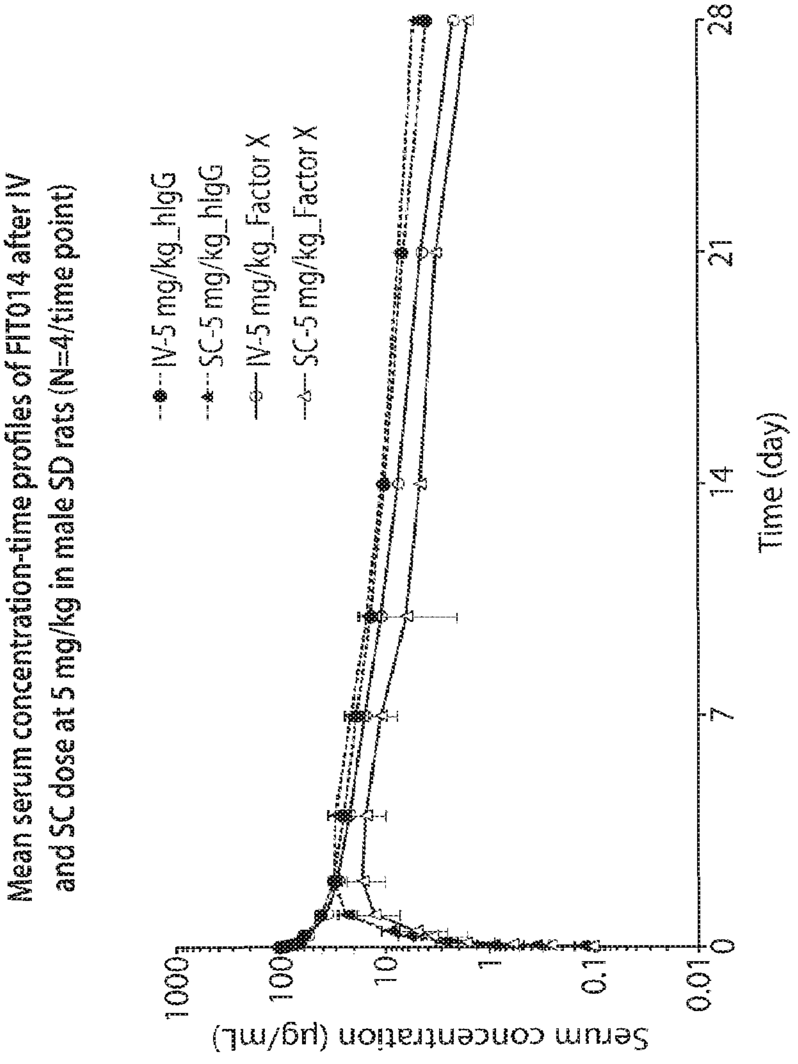
FIG. 26 shows mean serum concentration-time profiles of 5 mg/kg FIT014a administered intravenously (IV) or subcutaneously (SC) on either hIgG plate or Factor X plate. Antibody concentrations in rat serum samples were detected by ELISA with LLOQ of 62.5 ng/mL. On hIgG plate, the coating protein is anti-hIgG Fc, and the detection antibody is anti-hIgG Fab. On Factor X plate, the coating protein is Factor X, while the detection antibody is anti-human-IgG Fc.

Rat PK study: FIT014a was subjected to PK study in rat, and the result is shown in FIG. 26 and Table 46. Antibody concentrations in rat serum samples were detected by ELISA with LLOQ of 62.5 ng/mL. On hIgG plate, the coating protein is anti-hIgG Fc, and the detection antibody is anti-hIgG Fab. On Factor X plate, the coating protein is hFactor X, while the detection antibody is anti-human-IgG Fc.

TABLE 46

| Rat PK data for FIT014a | | | | |
|---|---|---|---|---|
| | hIgG plate | | Factor X plate | |
| PK parameters | IV, 5 mg/kg | SC, 5 mg/kg | IV, 5 mg/kg | SC, 5 mg/kg |
| CL, mL/day/kg | 11.2 | NA | 14.5 | NA |
| Alpha $t_{1/2}$, Day | 0.329 | NA | 0.233 | NA |
| Beta $t_{1/2}$, day | 8.79 | 6.90 | 7.03 | 5.76 |
| V1, mL/kg | 54.0 | NA | 52.6 | NA |
| $T_{max}$, day | 0.00347 | 3.00 | 0.00347 | 2.50 |
| $C_{max}$, μg/mL | 104 | 30.7 | 105 | 16.3 |
| F (%) | NA | 73.8 | NA | 48.3 |

Example 10: Study of Anti-HER3/IGF-1R Fabs-In-Tandem Immunoglobulin (FIT-Ig)

FIT-Ig having specificity for HER3 and IGF-1R was constructed as in the foregoing Examples. This exemplary FIT-Ig and its corresponding sequences are provided below in Table 47. Table 48 provides the expression level in 293E cells and the SEC profile for the FIT-Ig.

TABLE 47

| Amino acid sequences of additional exemplary FIT-Ig for HER3 and IGF-1R | | | |
|---|---|---|---|
| Name Target (mAb) mAb1 (upper domain)/mAb2 (lower domain) | Protein region | SEQ ID NO | Sequences |
| FIT016a HER3 (Patritumab)/IGF 1R (Figitumumab) | Long Chain (paritu VL-hCk-FigituVH-hCg1) | 278 | MDMRVPAQLLGLLLLWFPGSRC**DIEMTQSPDSLAVSLGERATINCRSSQSVLYSSSNRNYLAWYQQNPGQPPKLLIYWASTRESGVPDRFSGSGSGTDFTLTISSLQAEDVAVYYCQQYYSTPRTFGQGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC**EVQLLESGGGLVQPGGSLRLSCTASGFTFSSYAMNWVRQAPGKGLEWVSAISGSGGTTFYADSVKGRFTISRDNSRTTLYLQMNSLRAEDTAVYYCAKDLGWSDSYYYYYGMDVWGQGTTVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | paritu VL | 279 | DIEMTQSPDSLAVSLGERATINCRSSQSVLYSSSNRNYLAWYQQNPGQPPKLLIYWASTRESGVPDRFSGSGSGTDFTLTISSLQAEDVAVYYCQQYYSTPRTFGQGTKVEIK |
| | paritu VL - CDR1 | 280 | RSSQSVLYSSSNRNYLA |
| | paritu VL - CDR2 | 281 | WASTRES |
| | paritu VL - CDR3 | 282 | QQYYSTPRT |
| | FigituVH | 283 | EVQLLESGGGLVQPGGSLRLSCTASGFTFSSYAMNWVRQAPGKGLEWVSAISGSGGTTFYADSVKGRFTISRDNSRTTLYLQMNSLRAEDTAVYYCAKDLGWSDSYYYYYGMDVWGQGTTVTVSS |

TABLE 47-continued

| Amino acid sequences of additional exemplary FIT-Ig for HER3 and IGF-1R | | | |
|---|---|---|---|
| Name Target (mAb) mAb1 (upper domain)/mAb2 (lower domain) | Protein region | SEQ ID NO | Sequences |
| | FigituVH - CDR1 | 284 | SYAMN |
| | FigituVH - CDR2 | 285 | AISGSGGTTFYADSVKG |
| | FigituVH - CDR3 | 286 | DLGWSDSYYYYYGMDV |
| | Short Chain #1 (PatritumabVH - CH1) | 287 | MEFGLSWLFLVAILKGVQC**QVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | PatritumabVH | 288 | QVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSS |
| | PatritumabVH - CDR1 | 289 | GYYWS |
| | PatritumabVH - CDR2 | 290 | EINHSGSTNYNPSLKS |
| | PatritumabVH - CDR3 | 291 | DKWTWYFDL |
| | Short Chain #2 (Figitu VL-hCk) | 292 | MDMRVPAQLLGLLLLWFPGSRC**DIQMTQFPSSLSASVGDRVTITCRASQGIRNDLGWYQQKPGKAPKRLIYAASRLHRGVPSRFSGSGSGTEFTLTISSLQPEDFATYYCLQHNSYPCSFGQGTKLEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Figitu VL | 293 | DIQMTQFPSSLSASVGDRVTITCRASQGIRNDLGWYQQKPGKAPKRLIYAASRLHRGVPSRFSGSGSGTEFTLTISSLQPEDFATYYCLQHNSYPCSFGQGTKLEIK |
| | Figitu VL - CDR1 | 294 | RASQGIRNDLG |
| | Figitu VL - CDR2 | 295 | AASRLHR |
| | Figitu VL - CDR3 | 296 | LQHNSYPCS |

TABLE 48

| SEC Profile/Expression level in 293E cells: | | |
|---|---|---|
| FIT-Ig | Monomer % in SEC | Expression level(mg/L) |
| FIT016a | 99.54% | 16 |

Functional Studies

Functional binding study: Functional binding data for FIT016a is provided below in Table 49.

TABLE 49

| Functional binding data | | | | | |
|---|---|---|---|---|---|
| Ig | Target | Kon | Koff | KD | IC50 |
| Patritumab | 1 (HER3) | 3.17E+05 | 2.85E−04 | 9.00E−10 | |
| FIT016a | | 3.19E+05 | 3.19E−04 | 1.00E−09 | |

TABLE 49-continued

| Functional binding data | | | | | |
|---|---|---|---|---|---|
| Ig | Target | Kon | Koff | KD | IC50 |
| Figitumumab | 2 (IGF1R) | 1.30E+05 | 9.48E−05 | 7.29E−10 | |
| FIT016a | | 3.38E+04 | 9.19E−05 | 2.72E−09 | |

Figure 27:
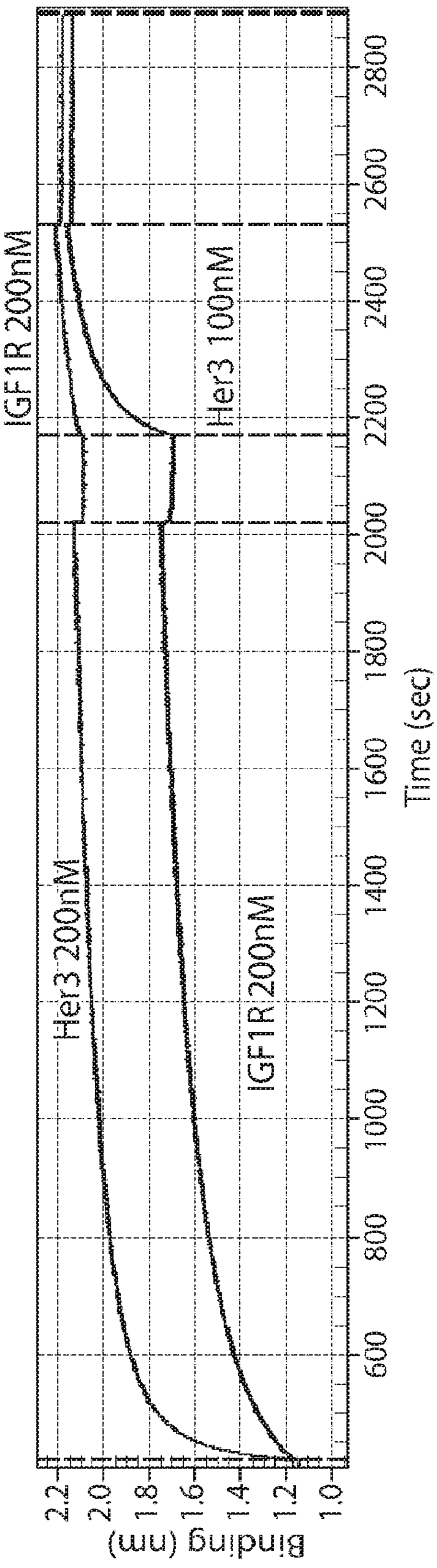
FIG. 27 shows a multiple binding study of FIT016a against both Her3 and IGF1R Binding to Her3 followed by IGF1R; and binding by IGF1R followed by Her3 are both shown as indicated.

Multiple-antigen binding study: this study was done using OctetRed to determine if FIT016a is able to bind Her3 and IGF1R simultaneously. This experiment shows that FIT016a is able to bind Her3 when it had already bound to IGF1R, indicating that FIT016a is able to bind both Her3 and IGF-1R simultaneously, see FIG. 27.

Example 11: Study of Anti-DLL4/VEGF Fabs-In-Tandem Immunoglobulin (FIT-Ig)

FIT-Ig having specificity for DLL4 and IGF1R was constructed as in the foregoing Examples. This exemplary FIT-Ig and its corresponding sequences are provided below in Table 50. Table 51 provides the expression level in 293E cells and the SEC profile for the FIT-Ig.

TABLE 50

Amino acid sequences of additional exemplary FIT-Ig for HER3 and IGF-IR

| Name Target (mAb) mAb1 (upper domain)/mAb2 (lower domain) | Protein region | SEQ ID NO | Sequences |
|---|---|---|---|
| FIT017a DLL4(demcizumab)/ VEGF(bevcizumab) | Long Chain (Demci VL-hCk-Bevci VH-hCg1) | 297 | MDMRVPAQLLGLLLLWFPGSRC**DIVMTQSPDSLAVSLGERATISCRASESVDNYGISFMKWFQQKPGQPPKLLIYAASNQGSGVPDRFSGSGSGTDFTLTISSLQAEDVAVYYCQQSKEVPWTFGGGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC**EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Demci VL | 298 | DIVMTQSPDSLAVSLGERATISCRASESVDNYGISFMKWFQQKPGQPPKLLIYAASNQGSGVPDRFSGSGSGTDFTLTISSLQAEDVAVYYCQQSKEVPWTFGGGTKVEIK |
| | Demci VL - CDR1 | 299 | RASESVDNYGISFMK |
| | Demci VL - CDR2 | 300 | AASNQGS |
| | Demci VL - CDR3 | 301 | QQSKEVPWT |
| | Bevci VH | 302 | EVQLVESGGGLVQPGGSLRLSCAASGYTFTNYGMNWVRQAPGKGLEWVGWINTYTGEPTYAADFKRRFTFSLDTSKSTAYLQMNSLRAEDTAVYYCAKYPHYYGSSHWYFDVWGQGTLVTVSS |
| | Bevci VH - CDR1 | 303 | NYGMN |
| | Bevci VH - CDR2 | 304 | WINTYTGEPTYAADFKR |
| | Bevci VH - CDR3 | 305 | YPHYYGSSHWYFDV |
| | Short Chain #1 (Demci VH-CH1h) | 306 | MEFGLSWLFLVAILKGVQC**QVQLVQSGAEVKKPGASVKISCKASGYSFTAYYIHWVKQAPGQGLEWIGYISSYNGATNYNQKFKGRVTFTTDTSTSTAYMELRSLRSDDTAVYYCARDYDYDVGMDYWGQGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Demci VH | 307 | QVQLVQSGAEVKKPGASVKISCKASGYSFTAYYIHWVKQAPGQGLEWIGYISSYNGATNYNQKFKGRVTFTTDTSTSTAYMELRSLRSDDTAVYYCARDYDYDVGMDYWGQGTLVTVSS |
| | Demci VH - CDR1 | 308 | AYYIH |
| | Demci VH - CDR2 | 309 | YISSYNGATNYNQKFKG |
| | Demci VH - CDR3 | 310 | DYDYDVGMDY |
| | Short Chain #2 (Bevci VL-hCk)) | 311 | MDMRVPAQLLGLLLLWFPGSRC**DIQMTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Bevci VL | 312 | DIQMTQSPSSLSASVGDRVTITCSASQDISNYLNWYQQKPGKAPKVLIYFTSSLHSGVPSRFSGSGSGTDFTLTISSLQPEDFATYYCQQYSTVPWTFGQGTKVEIK |
| | Bevci VL - CDR1 | 313 | SASQDISNYLN |
| | Bevci VL - CDR2 | 314 | FTSSLHS |
| | Bevci VL - CDR3 | 315 | QQYSTVPWT |

TABLE 51

| SEC Profile/Expression level in 293E cells: | | |
|---|---|---|
| FIT-Ig | Monomer % in SEC | Expression level (mg/L) |
| FIT017a | >82% | 2.2 |

Functional Studies

Functional binding study: Functional binding data for FIT017a is provided below in Table 52.

TABLE 52

| Functional binding data | | | | | |
|---|---|---|---|---|---|
| Ig | Target | Kon | Koff | KD | IC50 |
| demcizumab | 1 (DLL4) | 1.74E+05 | 1.28E−04 | 7.36E−09 | |
| FIT017a | | 1.88E+05 | 1.28E−04 | 6.81E−09 | |

TABLE 52-continued

| Functional binding data | | | | | |
|---|---|---|---|---|---|
| Ig | Target | Kon | Koff | KD | IC50 |
| bevcizumab | 2 (VEGF) | 3.46E+05 | 2.43E−06 | 7.04E−12 | |
| FIT017a | | 3.50E+05 | 1.28E−05 | 3.65E−11 | |

Figure 28:
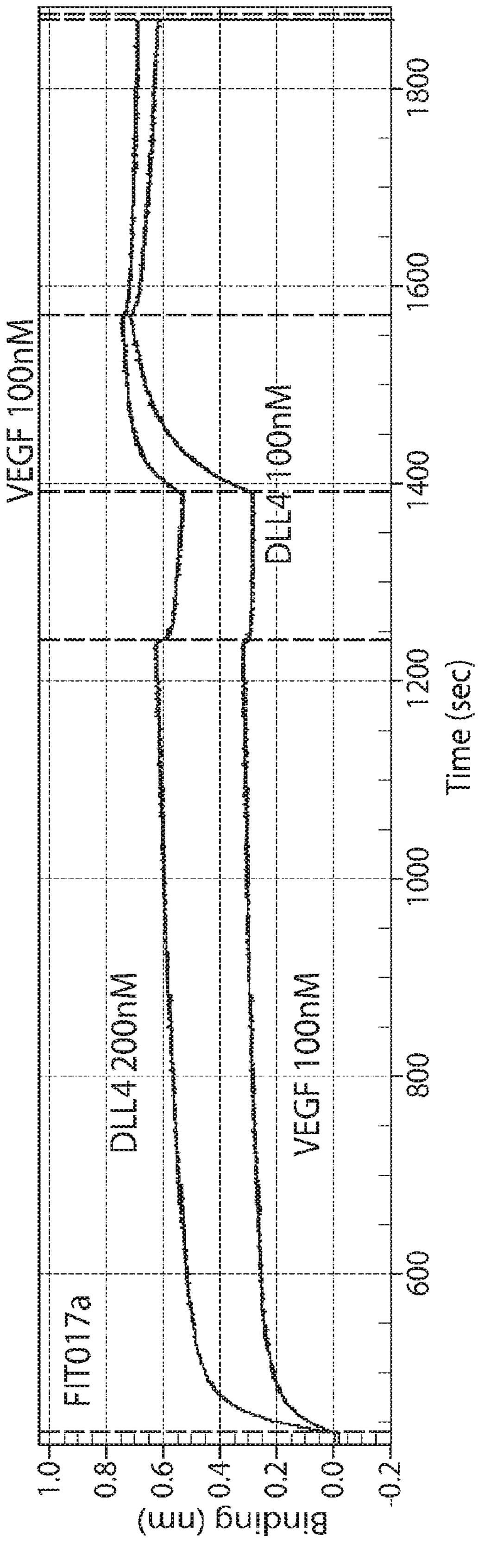
FIG. 28 shows a multiple binding study of FIT017a against both DLL4 and VEGF Binding to DLL4 followed by VEGF; and binding by VEGF followed by DLL4 are both shown as indicated.

Multiple-antigen binding study: this study was done using OctetRed to determine if FIT017a is able to bind DLL4 and VEGF simultaneously. This experiment shows that FIT017a is able to bind DLL4 when it had already bound to VEGF, indicating that FIT017a is able to bind both DLL4 and VEGF simultaneously, see FIG. 28.

Example 12: Study of Anti-CD20/CD3 Fabs-In-Tandem Immunoglobulin (FIT-Ig)

FIT-Ig having specificity for CD20 and CD3 was constructed as in the foregoing Examples. This exemplary FIT-Ig and its corresponding sequences are provided below in Table 53. Table 54 provides the expression level in 293E cells and the SEC profile for the FIT-Ig.

TABLE 53

| Amino acid sequences of additional exemplary FIT-Ig for CD20 and CD3 | | | |
|---|---|---|---|
| Name Target (mAb) mAb1 (upper domain)/mAb2 (lower domain) | Protein region | SEQ ID NO | Sequences |
| FIT018a CD20(Ofatumumab)/ CD3 mAb (described in US2009/0252683, incorporated by reference) | Long Chain (OfatuVL-hCk-CD3mAb VH-hCg1mut) | 316 | MDMRVFAQLLGLLLLWFPGSRC**EIVLTQSPATLSLSPGERATLSCRASQSVSSYLAWYQQKPGQAPRLLIYDASNRATGIPARFSGSGSGTDFTLTISSLEPEDFAVYYCQQRSNWPITFGQGTRLEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC**EVQLLESGGGLVQPGGSLKLSCAASGFTFNTYAMNWVRQAPGKGLEWVARIRSKYNNYATYYADSVKDRFTISRDDSKNTAYLQMNNLKTEDTAVYYCVRHGNFGNSYVSWFAYWGQGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Ofatu VL | 317 | EIVLTQSPATLSLSPGERATLSCRASQSVSSYLAWYQQKPGQAPRLLIYDASNRATGIPARFSGSGSGTDFTLTISSLEPEDFAVYYCQQRSNWPITFGQGTRLEIK |
| | OfatuVL - CDR1 | 318 | RASQSVSSYLA |
| | OfatuVL - CDR2 | 319 | DASNRAT |
| | OfatuVL - CDR3 | 320 | QQRSNWPIT |
| | CD3mAb VH | 321 | EVQLLESGGGLVQPGGSLKLSCAASGFTFNTYAMNWVRQAPGKGLEWVARIRSKYNNYATYYADSVKDRFTISRDDSKNTAYLQMNNLKTEDTAVYYCVRHGNFGNSYVSWFAYWGQGTLVTVSS |
| | CD3mAb VH - CDR1 | 322 | TYAMN |
| | CD3mAb VH - CDR2 | 323 | RIRSKYNNYATYYADSVKD |
| | CD3mAb VH - CDR3 | 324 | HGNFGNSYVSWFAY |
| | Short Chain #1 (Ofatu VH-CH1) | 325 | MEFGLSWLFLVAILKGVQC**EVQLVESGGGLVQPGRSLRLSCAASGETFNDYAMHWVRQAPGKGLEWVSTISWNSGSIGYADSVKGRFTISRDNAKKSLYLQMNSLRAEDTALYYCAKDIQYGNYYYGMDVWGQGTTVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |

TABLE 53-continued

| Amino acid sequences of additional exemplary FIT-Ig for CD20 and CD3 | | | |
|---|---|---|---|
| Name Target (mAb) mAb1 (upper domain)/mAb2 (lower domain) | Protein region | SEQ ID NO | Sequences |
| | Ofatu VH | 326 | EVQLVESGGGLVQPGRSLRLSCAASGFTFNDYAMHWVRQAPGKGLEWVSTISWNSGSIGYADSVKGRFTISRDNAKKSLYLQMNSLRAEDTALYYCAKDIQYGNYYYGMDVWGQGTTVTVSS |
| | Ofatu VH - CDR1 | 327 | DYAMH |
| | Ofatu VH - CDR2 | 328 | TISWNSGSIGYADSVKG |
| | Ofatu VH - CDR3 | 329 | DIQYGNYYYGMDV |
| | Short Chain #2 (CD3mAb VL-hCL) | 330 | MTWTPLLFLTLLLHCTGSLS**ELVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL**GQPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS |
| | CD3mAb VL | 331 | ELVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVL |
| | CD3mAb VL - CDR1 | 332 | RSSTGAVTTSNYAN |
| | CD3mAb VL - CDR2 | 333 | GTNKRAP |
| | CD3mAb VL - CDR3 | 334 | ALWYSNLWV |

TABLE 54

| SEC Profile/Expression level in 293E cells: | | |
|---|---|---|
| FIT-Ig | Monomer % in SEC | Expression level (mg/L) |
| FIT017a | 97.03% | 7.8 |

Functional Studies

Functional binding study: Functional binding data for FIT018a is provided below in Table 55.

TABLE 55

| Functional binding data | | | | | |
|---|---|---|---|---|---|
| Ig | Target | Kon | Koff | KD | IC50 |
| Ofatumumab FIT018a | 1 (CD20) | | | | |
| CD3 mAb | 2 (CD3e) | 6.69E+05 | 8.86E−05 | 1.32E−10 | |
| FIT018a | | 7.79E+05 | 1.22E−04 | 1.57E−10 | |

Figure 29A:
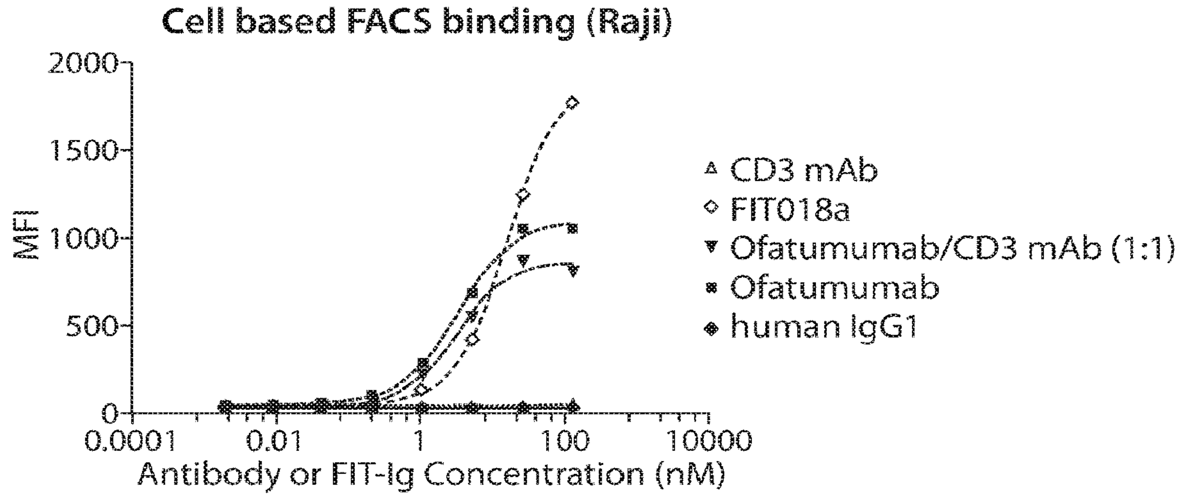
FIG. 29A and FIG. 29B show cell based FACS binding assays of FIT018a compared to its related parental antibodies (CD3 mAb, Ofatumumab, and a combination of CD3 mAb and Ofatumumab), and human IgG1 for their ability of binding to CD20 and CD3 on human B cells and human T cells. In the assay of FIG. 29A, human B cell line Raji was used. In the assay of FIG. 29B, human T cell line Jurkat was used.
Figure 29B:
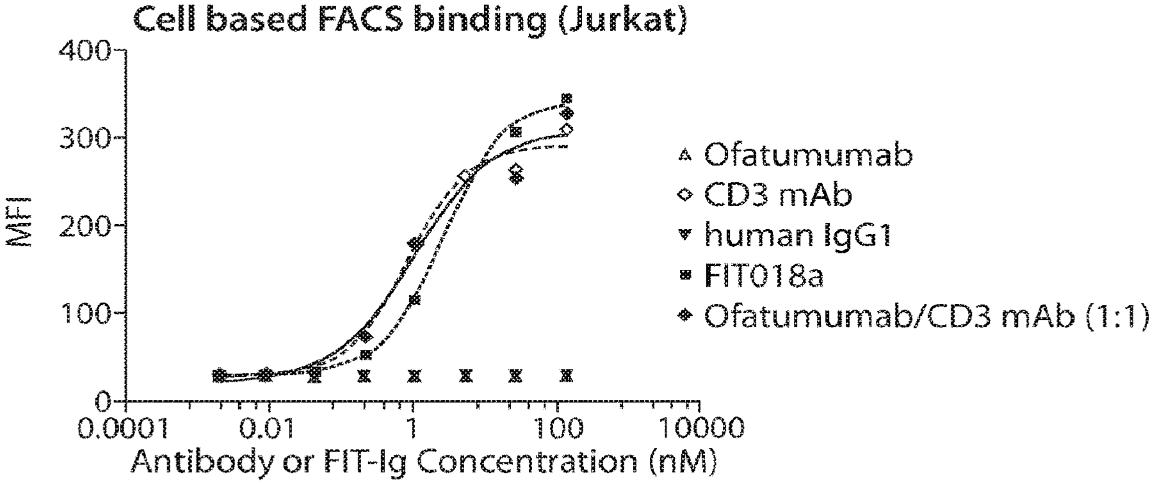
Figure 30A:
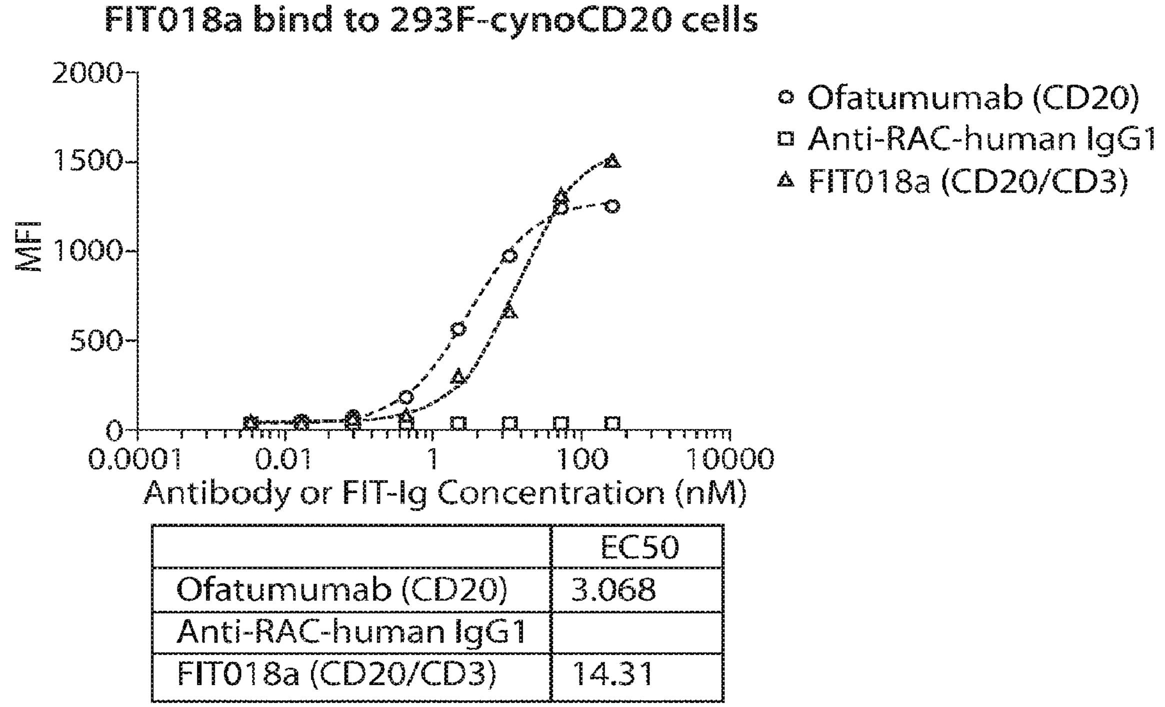
FIG. 30A shows cell based FACS binding assays of FIT018a compared to ofatumumab (CD20) and anti-RAC-human IgG1 for their ability of binding to cynomolgus CD20 cells.
Figure 30B:
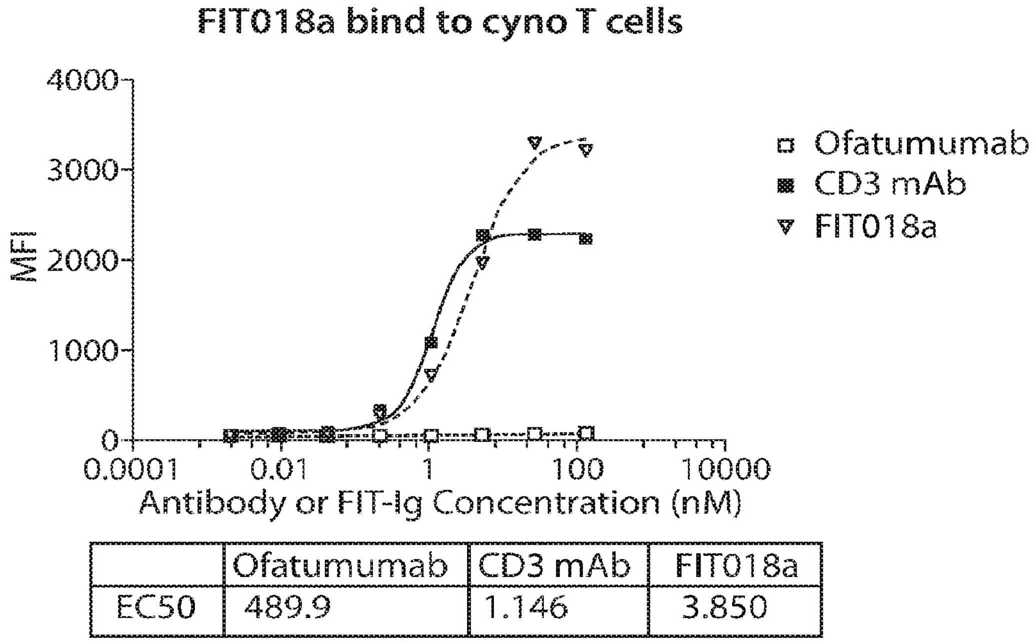
FIG. 30B shows cell based FACS binding assays of FIT018a compared to ofatumumab (CD20), CD3 mAb for their ability of binding to cynomolgus T cells.

Cell based binding study: The binding activity of FIT018a to human or cynomolgus B cell and T cell were determined by flow cytometry using BD FACSVerse. Raji cell was used for detecting human B cell binding. Jurakt cell was used for detecting human T cell binding. Primary cynomolgus T cell was used for detecting cynomolgus T cell binding. HEK 293 cell transit transfected with cynoCD20 was used for detecting cynomolgus B cell binding. Cells were washed in PBS buffer containing 2% FBS. Cells were then aliquot and incubated with 1:5 serially diluted FIT018a on ice for 1 hr. The starting working concentration of FIT018a was 20 μg/ml. Cells were washed, resuspended and incubated with 1:100 diluted Alexa Fluor® 488 labeled mouse anti-human IgG1 (Invitrogen, Cat. No. A-10631) on ice protected from light for 1 hr. Cells were washed and signal was detected with a BD FACSVerse flow cytometer according to manufacture's protocols. These experiments demonstrate that FIT018a can bind to human B cell and T cell (Raji is human B cell line and Jurkat is human T cell line), see FIG. 29A and FIG. 29B. FIT018a can also bind to cynomolgus CD20 and CD3, see FIG. 30A and FIG. 30B.

Figure 31A:
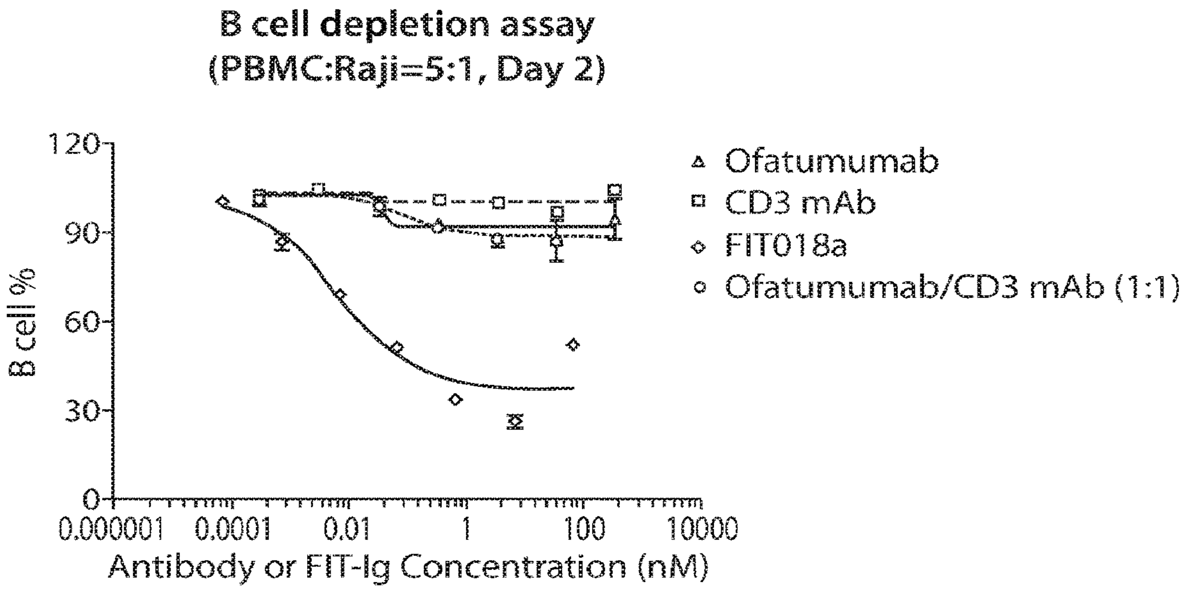
FIG. 31A and FIG. 31B show the ability of FIT018a, Ofatumumab, CD3 mAb, and a combination ofatumumab and CD3 mAb (1:1) in inducing apoptosis of human B cell (Raji) at day 2 (FIG. 31A) and day 3 (FIG. 31B), as measured in B-cell depletion assays.
Figure 31B:
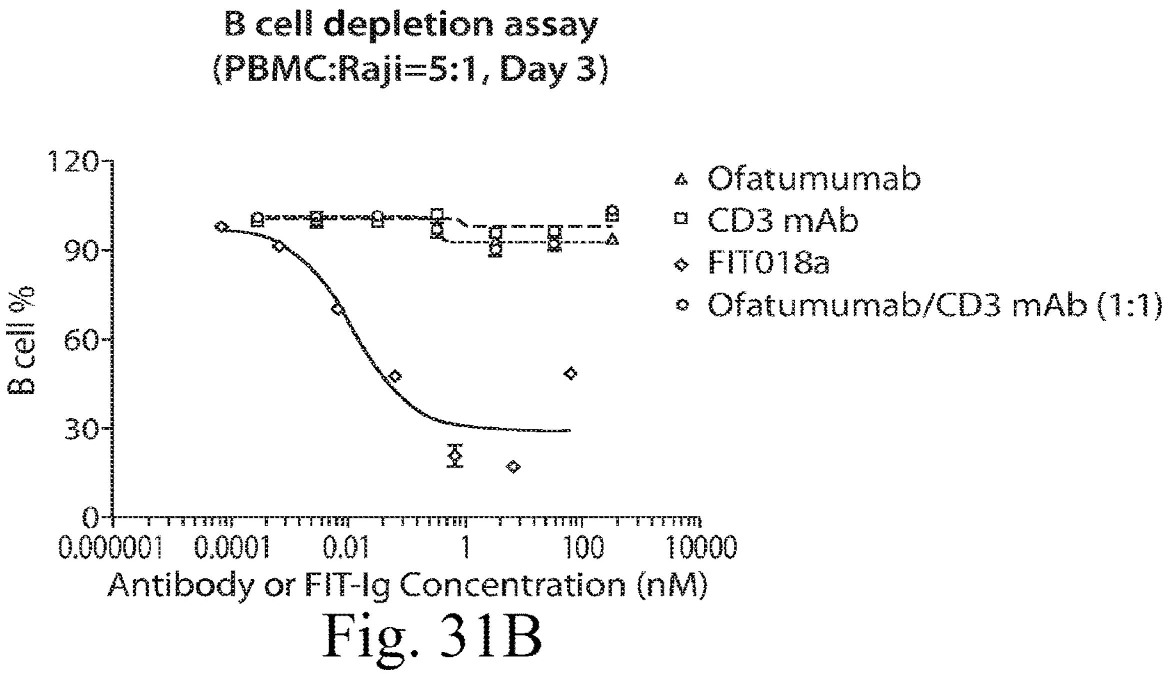

B-cell depletion assay: The in vitro activity of FIT018a was measured by B3-cell depletion assay. Human PBMCs were isolated by Ficoll Paque Plus (GE HEALTHCARE, cat: GE17144002) according to manufacture's instruction. Target cell Raji was harvested and seeded to assay plate at $5\times10^4$ per well. Antibodies were serially diluted and added to assay plate. $2.5\times10^5$ per well PBMCs were added to assay plate and incubate for 2 days or 3 days. After incubation, B cell was detected by anti-CD19 antibody using FACS machine. The experiments demonstrate that FIT018a can induce B cell apoptosis, see FIG. 31A and FIG. 31B.

Example 13: Study of Anti-HER3/EGFR Fabs-In-Tandem Immunoglobulin (FIT-Ig)

FIT-Ig having specificity for HER3 and EGFR was constructed as in the foregoing Examples. This exemplary FIT-Ig and corresponding sequences are provided below in Table 56. Table 57 provides the expression level in 293E cells and the SEC profile for the FIT-Ig.

TABLE 56

Amino acid sequences of additional exemplary FIT-Ig for HER3 and EGFR

| Name Target (mAb) mAb1 (upper domain)/mAb2 (lower domain) | Protein region | SEQ ID NO | Sequences |
|---|---|---|---|
| FIT019a - Ig HER3(patritumab/ EGFR(Panitumumab) | Long Chain (patritu VL-hCk-PaniVH-hCg1) | 335 | MDMRVPAQLLGLLLLWFPGSRCDIEMTQSPDSLAVSLGERATINCRSSQSVLYSSSNRNYLAWYQQNPGQPPKLLIYWASTRESGVPDRFSGSGSGTDFTLTISSLQAEDVAVYYCQQYYSTPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | patritu VL | 336 | DIEMTQSPDSLAVSLGERATINCRSSQSVLYSSSNRNYLAWYQQNPGQPPKLLIYWASTRESGVPDRFSGSGSGTDFTLTISSLQAEDVAVYYCQQYYSTPRTFGQGTKVEIK |
| | patritu VL - CDR1 | 337 | RSSQSVLYSSSNRNYLA |
| | patritu VL - CDR2 | 338 | WASTRES |
| | patritu VL - CDR3 | 339 | QYYSTPRT |
| | PaniVH | 340 | QVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSS |
| | Pani VH - CDR1 | 341 | SGDYYWT |
| | Pani VH - CDR2 | 342 | HIYYSGNTNYNPSLKS |
| | Pani VH - CDR3 | 343 | DRVTGAFDI |
| | Short Chain #1 (Patritumab VH-CH1) | 344 | MEFGLSWLFLVAILKGVQCQVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Patritumab VH | 345 | QVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSS |
| | Patritumab VH - CDR1 | 346 | GYYWS |
| | Patritumab VH - CDR2 | 347 | EINHSGSTNYNPSLKS |
| | Patritumab VH - CDR3 | 348 | DKWTWYFDL |
| | Short Chain #2 (Pani VL-hCk) | 349 | MDMRVPAQLLGLLLLWFPGSRCDIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Pani VL | 350 | DIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIK |
| | Pani VL - CDR1 | 351 | QASQDISNYLN |
| | Pani VL - CDR2 | 352 | DASNLET |
| | Pani VL - CDR3 | 353 | QHFDHLPLA |

TABLE 56-continued

Amino acid sequences of additional exemplary FIT-Ig for HER3 and EGFR

| Name Target (mAb) mAb1 (upper domain)/mAb2 (lower domain) | Protein region | SEQ ID NO | Sequences |
|---|---|---|---|
| FIT019b - Ig EGFR (Panitumumab)/ HER3 (patritumab) | Long Chain (Panitu VL-hCk-Patritu-hCg1) | 354 | MDMRVPAQLLGLLLLWFPGSRC**DIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC**QVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Panitu VL | 355 | DIQMTQSPSSLSASVGDRVTITCQASQDISNYLNWYQQKPGKAPKLLIYDASNLETGVPSRFSGSGSGTDFTFTISSLQPEDIATYFCQHFDHLPLAFGGGTKVEIK |
| | Panitu VL - CDR1 | 356 | QASQDISNYLN |
| | Panitu VL - CDR2 | 357 | DASNLET |
| | Panitu VL - CDR3 | 358 | QHFDHLPLA |
| | PatrituVH | 359 | QVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSS |
| | Patritu VH - CDR1 | 360 | GYYWS |
| | Patritu VH - CDR2 | 361 | EINHSGSTNYNPSLKS |
| | Patritu VH - CDR3 | 362 | DKWTWYFDL |
| | Short Chain #1 (Panitu VH-CH1) | 363 | MEFGLSWLFLVAILKGVQC**QVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Panitu VH | 364 | QVQLQESGPGLVKPSETLSLTCTVSGGSVSSGDYYWTWIRQSPGKGLEWIGHIYYSGNTNYNPSLKSRLTISIDTSKTQFSLKLSSVTAADTAIYYCVRDRVTGAFDIWGQGTMVTVSS |
| | Panitu VH - CDR1 | 365 | DYYWT |
| | Panitu VH - CDR2 | 366 | HIYYSGNTNYNPSLKS |
| | Panitu VH - CDR3 | 367 | DRVTGAFDI |
| | Short Chain #2 (Patritu VL-hCk) | 368 | MDMRVPAQLLGLLLLWFPGSRC**DIEMTQSPDSLAVSLGERATINCRSSQSVLYSSSNRNYLAWYQQNPGQPPKLLIYWASTRESGVPDRFSGSGSGTDFTLTISSLQAEDVAVYYCQQYYSTPRTFGQGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Patritu VL | 369 | DIEMTQSPDSLAVSLGERATINCRSSQSVLYSSSNRNYLAWYQQNPGQPPKLLIYWASTRESGVPDRFSGSGSGTDFTLTISSLQAEDVAVYYCQQYYSTPRTFGQGTKVEIK |
| | Patritu VL - CDR1 | 370 | RSSQSVLYSSSNRNYLA |
| | Patritu VL - CDR2 | 371 | WASTRES |
| | Patritu VL - CDR3 | 372 | QQYYSTPRT |

TABLE 57

| SEC Profile/Expression level in 293E cells: | | |
|---|---|---|
| FIT-Ig | Monomer % in SEC | Expression level (mg/L) |
| FIT019a | >86% | 15.6 |
| FIT019b | 96.7% | 10.2 |

Functional Studies

Functional binding study: Functional binding data for FIT019a and FIT019b is provided below in Table 58 and Table 59, respectively.

TABLE 58

| Functional binding data of FIT019a | | | | | |
|---|---|---|---|---|---|
| Ig | Target | Kon | Koff | KD | IC50 |
| Patritumab | 1(Her3) | 1.59E+05 | 4.80E−06 | 3.02E−11 | |
| FIT019a | | 1.57E+05 | 5.05E−06 | 3.21E−11 | |
| Panitumumab | 2(EGFR) | 4.45E+05 | 4.92E−04 | 1.10E−09 | |
| FIT019a | | 2.86E+05 | 3.91E−04 | 1.37E−09 | |

TABLE 59

| Functional binding data of FIT019b | | | | | |
|---|---|---|---|---|---|
| Ig | Target | Kon | Koff | KD | IC50 |
| Panitumumab | 1(EGFR) | 8.43E+04 | 5.10E−05 | 6.05E−10 | |
| FIT019b | | 2.84E+05 | 9.60E−05 | 3.38E−10 | |
| Patritumab | 2(Her3) | 3.17E+05 | 2.85E−04 | 9.00E−10 | |
| FIT019b | | 1.20E+05 | 2.37E−04 | 1.98E−09 | |

Figure 32:
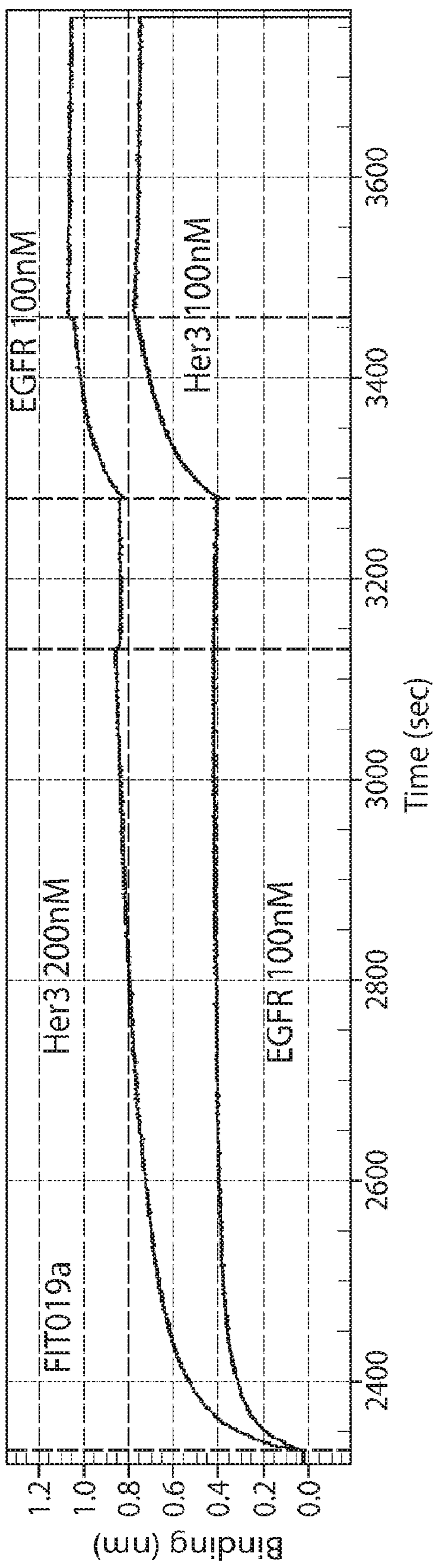
FIG. 32 shows a multiple binding study of FIT019a against both Her3 and EGFR. Binding to Her3 followed by EGFR, and binding by EGFR followed by Her3 are both shown as indicated.
Figure 33A:
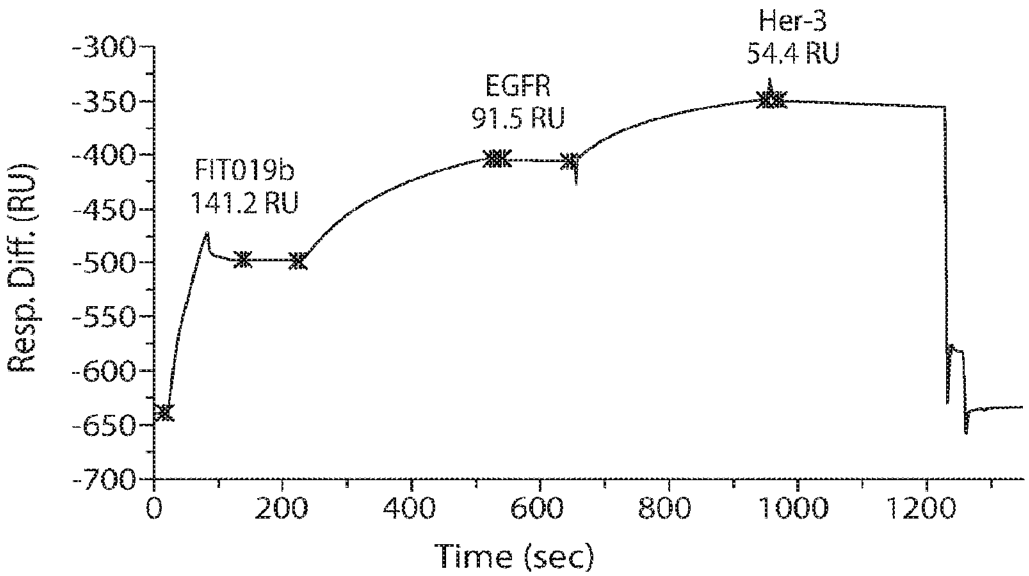
FIG. 33A and FIG. 33B show a multiple binding study of FIT019b against both Her3 and hEGFR. Binding to EGFR followed by Her3 (FIG. 33A); and binding by Her3 followed by EGFR (FIG. 33B) are both shown as indicated.
Figure 33B:
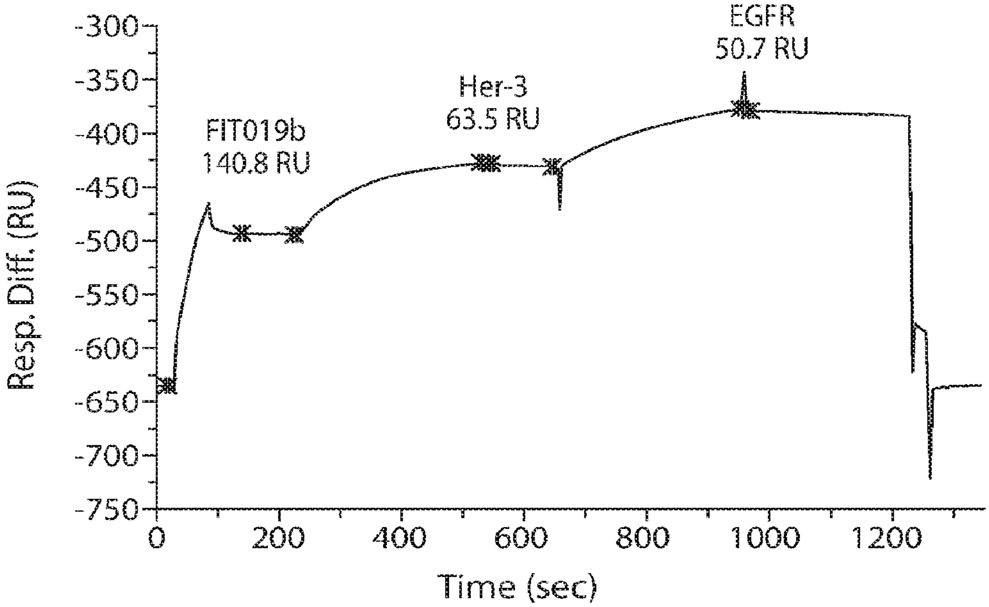

Multiple binding study: A multiple binding study of FIT019a and FIT019b was carried out. The result is shown in FIG. 32 (FIT019a) and FIG. 33A to FIG. 33B (FIT019b), respectively. The result indicates that both FIT019a and FIT019b can bind to HER3 and EGFR simultaneously.

Example 14: Study of Anti-PD-L1/PD-1 Fabs-In-Tandem Immunoglobulin (FIT-Ig)

FIT-Ig having specificity for PD-L1 and PD-1 was constructed as in the foregoing Examples. This exemplary FIT-Ig and its corresponding sequences are provided below in Table 60. Table 61 provides the expression level in 293E cells and the SEC profile for the FIT-Ig.

TABLE 60

| Amino acid sequences of additional exemplary FIT-Ig for PD-L1 and PD-1 | | | |
|---|---|---|---|
| Name Target (mAb) mAb1 (upper domain)/mAb2 (lower domain) | Protein region | SEQ ID NO | Sequences |
| FIT020b PD-L1 (1B12)/PD-1 (nivolumab) | Long Chain (1B12 VL-hCk-Nivolu VH-hCg1Mut) | 373 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | I1B12 VL | 374 | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK |
| | 1B12 VL - CDR1 | 375 | RASQSVSSYLA |
| | 1B12 VL - CDR2 | 376 | DASNRAT |
| | 1B12 VL - CDR3 | 377 | QQRSNWPT |
| | NivoluVH | 378 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS |
| | NivoluVH - CDR1 | 379 | NSGMH |
| | NivoluVH - CDR2 | 380 | VIWYDGSKRYYADSVKG |
| | NivoluVH - CDR3 | 381 | NDDY |
| | Short Chain #1 (1B12 VH-CH1) | 382 | MEFGLSWLFLVAILKGVQCQVQLVQSGAEVEKPGSSVKVSCKTSGDIFSSYAISWVRQAPGQGLEWMGGIIPIFGRAHYAQKFQGRVTITADESTSTAYMELSSLRSEDTAVYFCARKFHFVSGSPFGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | 1B12 VH | 383 | QVQLVQSGAEVKKPGSSVKVSCKTSGDTFSSYAISWVRQAPGQGLEWMGGIIPIFGRAHYAQKFQGRVTITADESTSTAYMELSSLRSEDTAVYFCARKFHFVSGSPFGMDVWGQGTTVTVSS |

TABLE 60-continued

Amino acid sequences of additional exemplary FIT-Ig for PD-L1 and PD-1

| Name Target (mAb) mAb1 (upper domain)/mAb2 (lower domain) | Protein region | SEQ ID NO | Sequences |
|---|---|---|---|
| | 1B12 VH - CDR1 | 384 | SYAIS |
| | 1B12 VH - CDR2 | 385 | GIIPIFGRAHYAQKFQG |
| | 1B12 VH - CDR3 | 386 | KFHFVSGSPFGMDV |
| | Short Chain #2 (Nivolu VL-hCK) | 387 | MDMRVPAQLLGLLLLWFPGSRC**EIVLTQSPATLSLSPGE RATLSCRASQSVSSYLAWYQQKPGQAPRLLIYDASNRAT GIPARFSGSGSGTDFTLTISSLEPEDFAVYYCQQSSNWP RTFGQGTKVEIK**RTVAAPSVFIFPPSDEQLKSGTASVVC LLNNFYPREAKVQWKVDNALQSGNSQESVTEQDSKDSTY SLSSTLTLSKADYEKHKVYACEVTHQGLSSPVTKSFNRG EC |
| | Nivolu VL | 388 | EIVLTQSPATLSLSPGERATLSCRASQSVSSYLAWYQQK PGQAPRLLIYDASNRATGIPARFSGSGSGTDFTLTISSL EPEDFAVYYCQQSSNWPRTFGQGTKVEIK |
| | Nivolu VL - CDR1 | 389 | RASQSVSSYLA |
| | Nivolu VL - CDR2 | 390 | DASNRAT |
| | Nivolu VL - CDR3 | 391 | QQSSNWPRT |

TABLE 61

SEC Profile/Expression level in 293E cells:

| FIT-Ig | Monomer % in SEC | Expression level (mg/L) |
|---|---|---|
| FIT020b | 100% | 6.2 |

Affinity measurement by surface plasmon resonance: The kinetics of FIT-Ig binding to rhPD-L1 and rhPD-1 was determined by surface plasmon resonance with a Biacore X100 instrument (Biacore AB, Uppsala, Sweden) using HBS-EP (10 mM HEPES, pH 7.4, 150 mM NaCl, 3 mM EDTA, and 0.005% surfactant P20) at 25° C. Briefly, for rhPD-L1 and rhPD-1 was directly immobilized at 40 RU across a CM5 research grade biosensor chip using a standard amine coupling kit according to manufacturer's instructions. Rate constants were derived by making kinetic binding measurements at seven different antigen concentrations ranging from 1 to 40 nM. The equilibrium dissociation constant (M) of the reaction between FIT-Ig and the target proteins was then calculated from the kinetic rate constants by the following formula: KD=koff/kon. Aliquots of FIT-Ig/Ab samples were also simultaneously injected over a blank reference and reaction CM surface to record and subtract any nonspecific binding background to eliminate the majority of the refractive index change and injection noise. Surfaces were regenerated with two subsequent 25 ml injections of 10 mM Glycine (pH 1.5) at a flow rate of 10 μL/min. Functional binding data for FIT020b is provided below in Table 62.

TABLE 62

Functional binding data

| Ig | Target | Kon | Koff | KD | IC50 |
|---|---|---|---|---|---|
| 1B12 | 1(PD-L1) | 6.77E+05 | 2.72E−04 | 4.02E−10 | |
| FIT020b | | 2.92E+05 | 1.85E−04 | 6.34E−10 | |
| Nivolumab | 2(PD1) | 5.00E+05 | 1.76E−04 | 3.52E−10 | |
| FIT020b | | 8.89E+04 | 3.02E−04 | 3.39E−09 | |

Figure 34A:
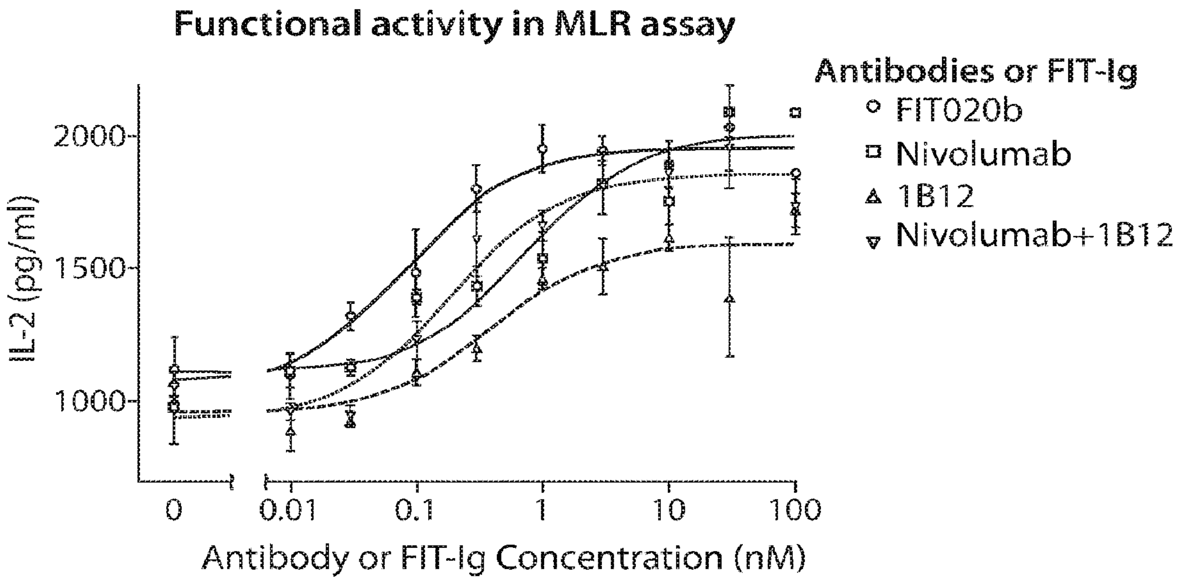
FIG. 34A shows functional activity of FIT020b in MLR assays, when compared to the parental antibody Nivolumab, 1B12 and a combination of Nivolumab and 1B12 (1:1) at a concentration of 0, 0.01, 0.1, 1, 10, or 100 nM, as measured by the level of induced IL-2.
Figure 34B:
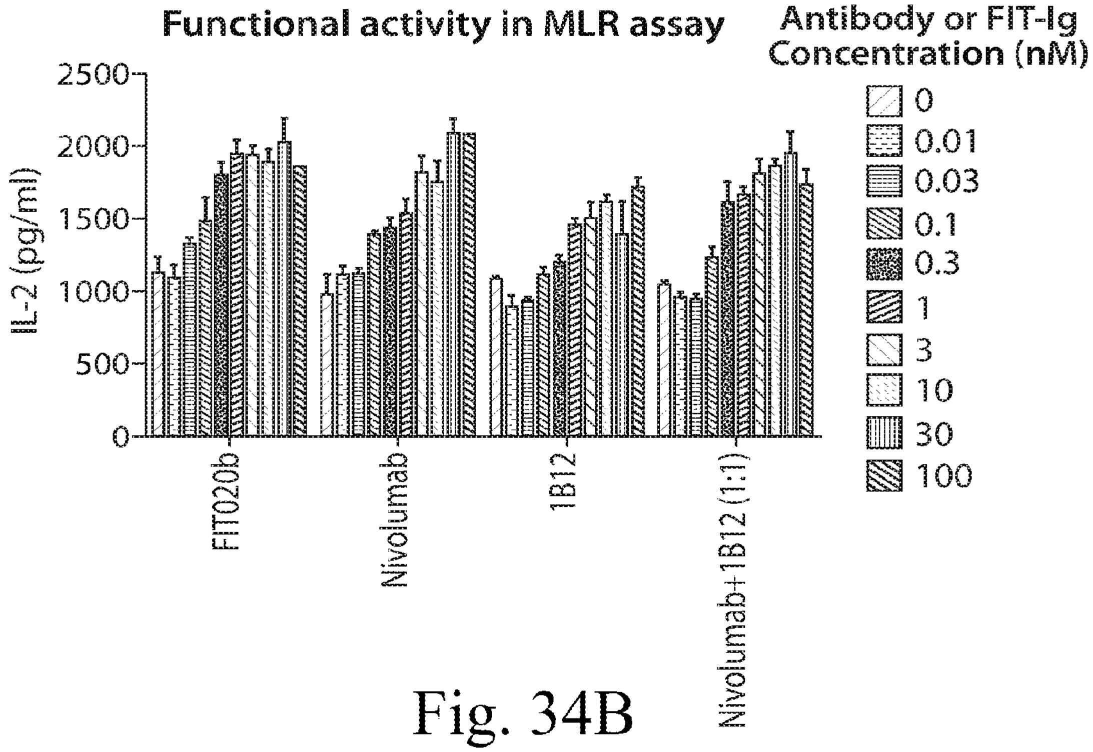
FIG. 34B shows the induction of IL-2 at a concentration of 0, 0.01, 0.03, 0.1, 0.3, 1, 3, 10, 30, and 100 nM by these antibodies.

Functional activity test by MLR assay: Mixed lymphocyte reaction was performed using monocyte-derived dendritic cells from one donor and allogeneic CD4 T cells from another donor. The whole blood samples were collected from healthy donors, and PBMC were isolated from whole blood using Ficoll-Pague gradient centrifugation. On day 1, PBMC from one donor was isolated and diluted with serum-free RPMI 1640 at $1\times10^6$/ml. The diluted PBMC was seeded into 6-well tissue culture plate at 3 ml/well and incubated for 3 h. Supernatant was removed and unattached cells were washed off. The attached monocyte were polarized into dendritic cells with 250 U/ml IL-4 and 500 U/ml GM-CSF in RPMI1640 with 10% FBS. The medium was replaced with fresh IL-4 and GM-CSF at day 4. At day 7, immature DC was collected and treated with 1 μg/ml LPS in RPMI 1640 with 10% FBS for additional 24 h for maturation. At Day 8, CD4 T cells were isolated from another donor PBMC by negative selection and adjusted to final concentration at $2\times10^6$ cells/ml. Mature DC were treated with mitomycin C at 37° C. for 1.5 hr. Then DC were washed with PBS and adjusted to final concentration at $1\times10^6$ cells/ml. CD4 T cells (Responder cells) were added into 96 well plate at 100 μl/well and pre-treated with test antibody at diluted concentration for 30 minutes. Then mature DC (Stimulator cells) were added into the well at 100 μl/well. The final volume of each well is 200 μl. The MLR were incubated at 37 degree for 72 hr for IL-2 test. The result is shown in FIG. 34A and FIG. 34B.

Figure 35:
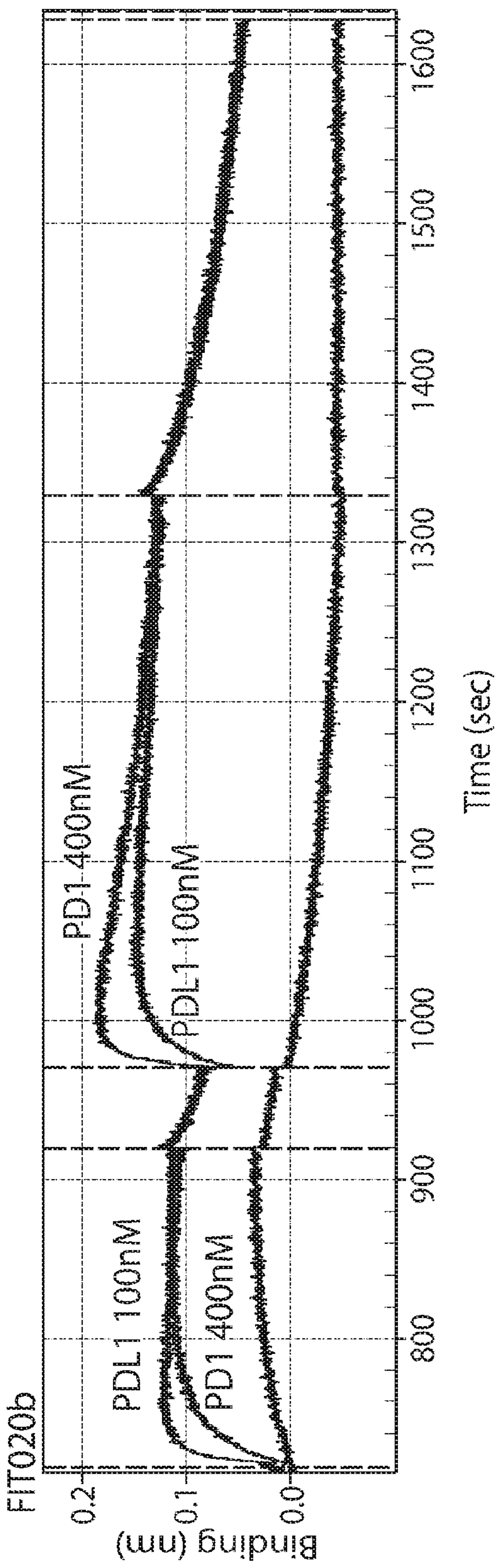
FIG. 35 shows a multiple binding study of FIT020b against both PD-L1 and PD-1. Binding to PD-L1 followed by PD-1; and binding by PD-1 followed by PD-L1 are both shown as indicated.

Multiple binding study: A multiple binding study of FIT020b was carried out. The result is shown in FIG. 35. The result indicates that FIT020b can bind to PD-L1 and PD-1 simultaneously.

Example 15: Study of Anti-CD20/CD-22 Fabs-In-Tandem Immunoglobulin (FIT-Ig)

FIT-Ig having specificity for CD20 and CD22 was constructed as in the foregoing Examples. This exemplary FIT-Ig and its corresponding sequences are provided below in Table 63. Table 64 provides the expression level in 293E cells and the SEC profile for the FIT-Ig.

TABLE 63

Amino acid sequences of additional exemplary FIT-Ig for CD20 and CD22

| Name Target (mAb) mAb1 (upper domain)/mAb2 (lower domain) | Protein region | SEQ ID NO | Sequences |
|---|---|---|---|
| FIT021b CD20 (Ofatumumab)/ CD22 (Epratuzumab) | Long Chain (Ofatu VL-hCk-Epratu VH-hCg1) | 392 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQRSNWPITFGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVQSGAEVKKPGSSVKVSCKASGYTFTSYWLHWVRQAPGQGLEWIGYINPRNDYTEYNQNFKDKATITADESTNTAYMELSSLRSEDTAFYFCARRDITTFYWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | OfatuVL | 393 | EIVLTQSPATLSLSPGERATLSCRASQSVSSYLAWYQQKPGQAPRLLIYDASNRATGIPARFSGSGSGTDFTLTISSLEPEDFAVYYCQQRSNWPITFGQGTRLEIK |
| | Ofatu VL - CDR1 | 394 | RASQSVSSYLA |
| | Ofatu VL - CDR2 | 395 | DASNRAT |
| | Ofatu VL - CDR3 | 396 | QQRSNWPIT |
| | Epratu VH | 397 | QVQLVQSGAEVKKPGSSVKVSCKASGYTFTSYWLHWVRQAPGQGLEWIGYINPRNDYTEYNQNFKDKATITADESTNTAYMELSSLRSEDTAFYFCARRDITTFYWGQGTTVTVSS |
| | Epratu VH - CDR1 | 398 | SYWLH |
| | Epratu VH - CDR2 | 399 | YINPRNDYTEYNQNFKD |
| | Epratu VH - CDR3 | 400 | RDITTFY |
| | Short Chain #1 (Ofatu VH-CH1) | 401 | MEFGLSWLFLVAILKGVQCEVQLVESGGGLVQPGRSLRLSCAASGFTFNDYAMHWVRQAPGKGLEWVSTISWNSGSIGYADSVKGRFTISRDNAKKSLYLQMNSLRAEDTALYYCAKDIQYGNYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Ofatu VH | 402 | EVQLVESGGGLVQPGRSLRLSCAASGFTFNDYAMHWVRQAPGKGLEWVSTISWNSGSIGYADSVKGRFTISRDNAKKSLYLQMNSLRAEDTALYYCAKDIQYGNYYYGMDVWGQGTTVTVSS |
| | Ofatu VH - CDR1 | 403 | DYAMH |
| | Ofatu VH - CDR2 | 404 | TISWNSGSIGYADSVKG |
| | Ofatu VH - CDR3 | 405 | DIQYGNYYYGMDV |
| | Short Chain #2 (Epratu VL-hCk) | 406 | MDMRVPAQLLGLLLLWFPGSRCDIQLTQSPSSLSASVGDRVTMSCKSSQSVLYSANHKNYLAWYQQKPGKAPKLLIYWASTRESGVPSRFSGSGSGTDFTFTISSLQPEDIATYYCHQYLSSWTFGGGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Epratu VL | 407 | DIQLTQSPSSLSASVGDRVTMSCKSSQSVLYSANHKNYLAWYQQKPGKAPKLLIYWASTRESGVPSRFSGSGSGTDFTFTISSLQPEDIATYYCHQYLSSWTFGGGTKLEIK |
| | Epratu VL - CDR1 | 408 | KSSQSVLYSANHKNYLA |
| | Epratu VL - CDR2 | 409 | WASTRES |
| | Epratu VL - CDR3 | 410 | HQYLSSWT |

TABLE 64

| SEC Profile/Expression level in 293E cells: | | |
|---|---|---|
| FIT-Ig | Monomer % in SEC | Expression level (mg/L) |
| FIT021b | 100% | 4.9 |

Functional Studies

Figure 36A:
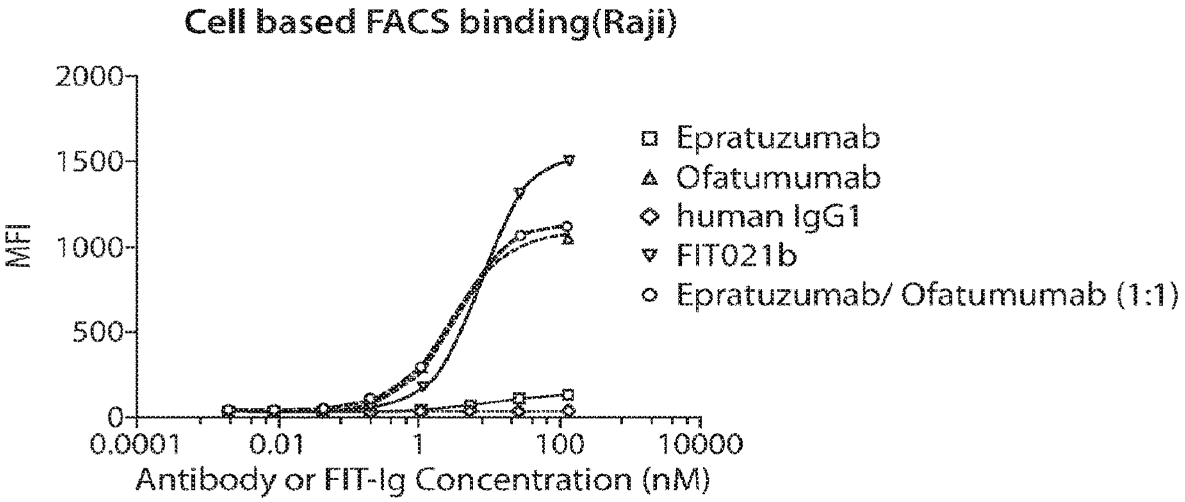
FIG. 36A and FIG. 36B show cell based FACS binding assays of FIT021b compared to its related parental antibodies (Ofatumumab, Epratuzumab, and a combination ofatumumab and Epratuzumab (1:1)), and human IgG1 for its ability of binding to human B cells. In the assay of FIG. 36A, human B cell line Raji was used. In the assay of FIG. 36B, human B cell line Daudi was used.
Figure 36B:
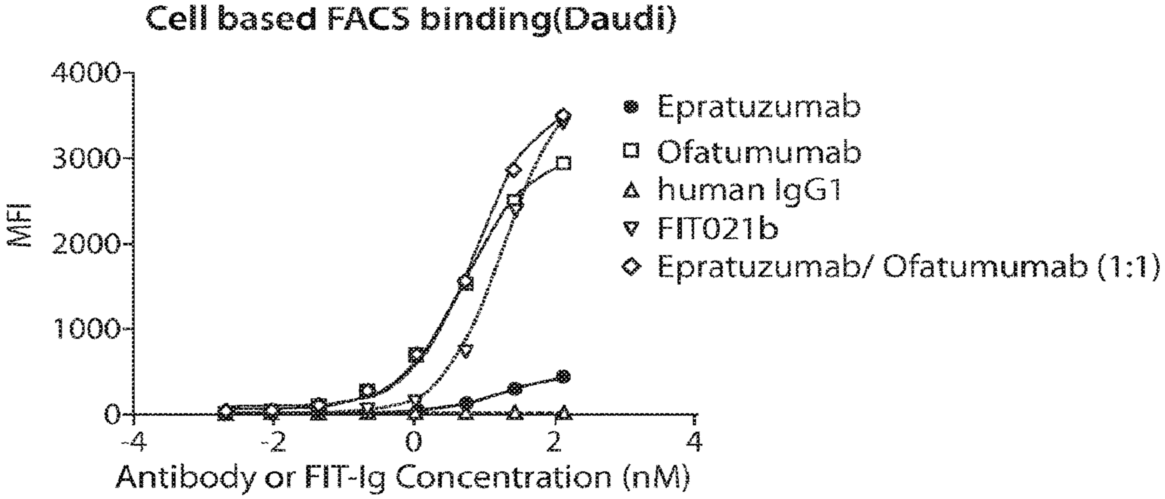

Cell based binding study: The binding activity of FIT021b to B lymphoma cell lines Raji or Daudi were determined by flow cytometry using BD FACSVerse. Cells were washed in PBS buffer containing 2% FBS. Cells were then aliquot and incubated with 1:5 serially diluted FIT021b on ice for 1 hr. The starting working concentration of FIT021b was 20 μg/ml. Cells were washed, resuspended and incubated with 1:100 diluted Alexa Fluor® 488 labeled mouse anti-human IgG1 (Invitrogen, Cat. No. A-10631) on ice protected from light for 1 hr. Cells were washed and signal was detected with a BD FACSVerse flow cytometer according to manufacture's protocols. These experiments demonstrate that FIT021b can bind to B lymphoma cell lines Raji or Daudi, see FIG. 36A and FIG. 36B.

Example 16: Study of Anti-HER3/PD-1 Fabs-In-Tandem Immunoglobulin (FIT-h2)

FIT-Ig having specificity for HER3 and PD1 was constructed as in the foregoing Examples. This exemplary FIT-Ig and its corresponding sequences are provided below in Table 65. Table 66 provides the expression level in 293E cells and the SEC profile for the FIT-Ig.

TABLE 65

Amino acid sequences of additional exemplary FIT-Ig for HER3 and PD-1

| Name Target (mAb) mAb1 (upper domain)/mAb2 (lower domain) | Protein region | SEQ ID NO | Sequences |
|---|---|---|---|
| FIT022a HER3 (patritumab)/ PD-1 (nivolumab) | Long Chain (patritu VL-hCk-Nivolu VH-hCg1mut) | 411 | MDMRVPAQLLGLLLLWFPGSRC**DIEMTQSPDSLAVSLGERATINCRSSQSVLYSSSNRNYLAWYQQNPGQPPKLLIYWASTRESGVPDRFSGSGSGTDFTLTISSLQAEDVAVYYCQQYYSTPRTFGQGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC**QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | patrituVL | 412 | DIEMTQSPDSLAVSLGERATINCRSSQSVLYSSSNRNYLAWYQQNPGQPPKLLIYWASTRESGVPDRFSGSGSGTDFTLTISSLQAEDVAVYYCQQYYSTPRTFGQGTKVEIK |
| | patritu VL - CDR1 | 413 | RSSQSVLYSSSNRNYLA |
| | patritu VL - CDR2 | 414 | WASTRES |
| | patritu VL - CDR3 | 415 | QQYYSTPRT |
| | Nivolu VH | 416 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS |
| | Nivolu VH - CDR1 | 417 | NSGMH |
| | Nivolu VH - CDR2 | 418 | VIWYDGSKRYYADSVKG |
| | Nivolu VH - CDR3 | 419 | NDDY |
| | Short Chain #1 (Patritumab-CH1) | 420 | MEFGLSWLFLVAILKGVQC**QVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Patritumab VH | 421 | QVQLQQWGAGLLKPSETLSLTCAVYGGSFSGYYWSWIRQPPGKGLEWIGEINHSGSTNYNPSLKSRVTISVETSKNQFSLKLSSVTAADTAVYYCARDKWTWYFDLWGRGTLVTVSS |
| | Patritumab VH - CDR1 | 422 | GYYWS |
| | Patritumab VH - CDR2 | 423 | EINHSGSTNYNPSLKS |
| | Patritumab VH - CDR3 | 424 | DKWTWYFDL |
| | Short Chain#2 (NivoVL-hCK) | 425 | MDMRVPAQLLGLLLLWFPGSRC**EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK**RTVAAPSVFIFPPSDEQLKSGTASVVCLLNNFYPREAKVQWKVDNALQSGNSQESVTEQDSKDSTY |

TABLE 65-continued

Amino acid sequences of additional exemplary FIT-Ig for HER3 and PD-1

| Name Target (mAb) mAb1 (upper domain)/mAb2 (lower domain) | Protein region | SEQ ID NO | Sequences |
|---|---|---|---|
| | | | SLSSTLTLSKADYEKHKVYACEVTHQGLSSPVTKSFNRGEC |
| | Nivo VL | 426 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK |
| | Nivo VL - CDR1 | 427 | RASQSVSSYLA |
| | Nivo VL - CDR2 | 428 | DASNRAT |
| | Nivo VL - CDR3 | 429 | QQSSNWPRT |

TABLE 66

SEC Profile/Expression level in 293E cells:

| FIT-Ig | Monomer % in SEC | Expression level (mg/L) |
|---|---|---|
| FIT022a | 100% | 1.6 |

Functional Studies

Affinity measurement by surface plasmon resonance: The kinetics of FIT022a-Ig binding to Her-3-his and hPD-1-Fc was determined by surface plasmon resonance. The result is shown in Table 67.

TABLE 67

Functional binding data for FIT022a

| Ig | Target | Kon | Koff | KD | IC50 |
|---|---|---|---|---|---|
| Patritumab | Her3-his | 2.43E+05 | 3.12E−04 | 1.28E−09 | |
| FIT022a | | 2.68E+05 | 3.23E−04 | 1.21E−09 | |
| Nivolumab | hPD1-Fc | 5.00E+05 | 1.76E−04 | 3.52E−10 | |
| FIT022a | | 1.29E+05 | 3.01E−04 | 2.34E−09 | |

Figure 37:
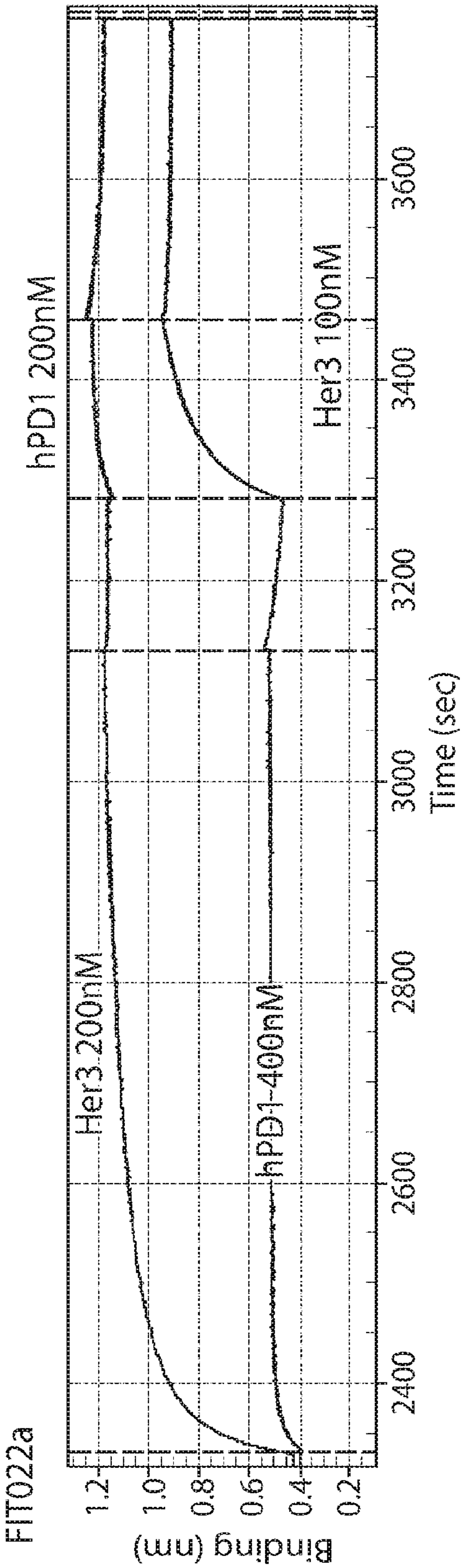
FIG. 37 shows a multiple binding study of FIT022a against both Her3 and human PD-1. Binding to Her3 followed by human PD-1; and binding by human PD-1 followed by Her3 are both shown as indicated

Multiple binding study: A multiple binding study of FIT022a was carried out. The result is shown in FIG. 37. The result indicates that FIT022a can bind to PD-L1 and PD-1 simultaneously.

Figure 38A:
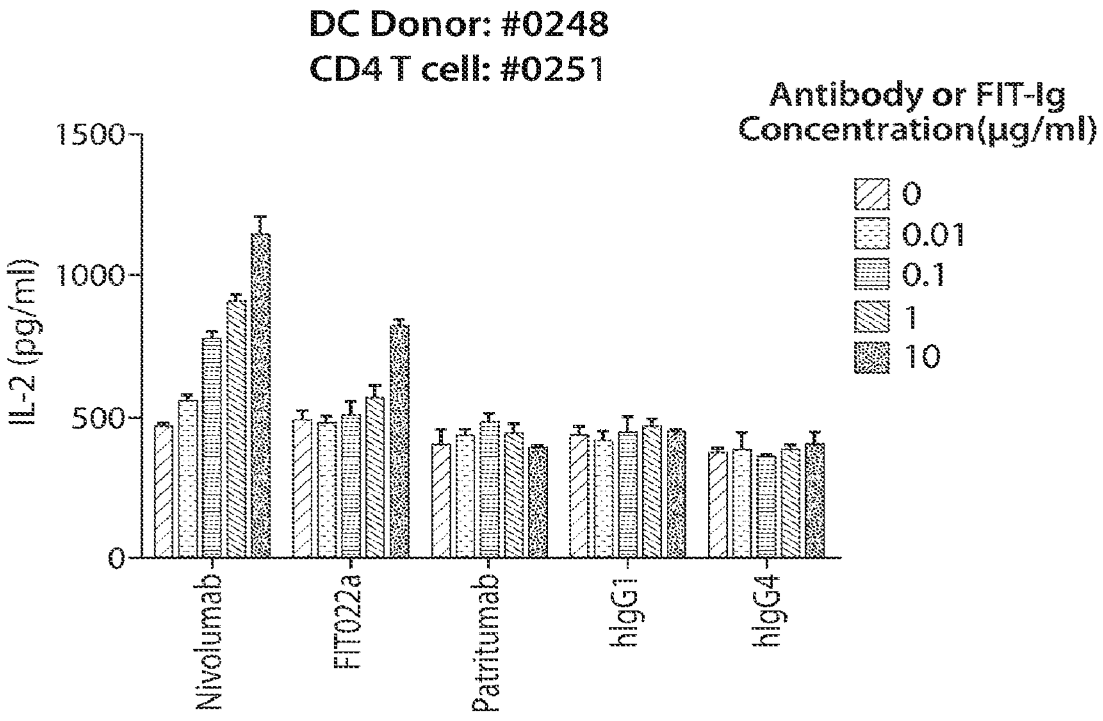
FIG. 38A shows functional activity of FIT022a in MLR assays, when compared to the parental antibody Nivolumab and Patritumab at a concentration of 0, 0.01, 0.1, 1, or 10 μg/ml. The induction of LI-2 was measured for each antibody. Human IgG1 and human IgG4 were included as controls.
Figure 38B:
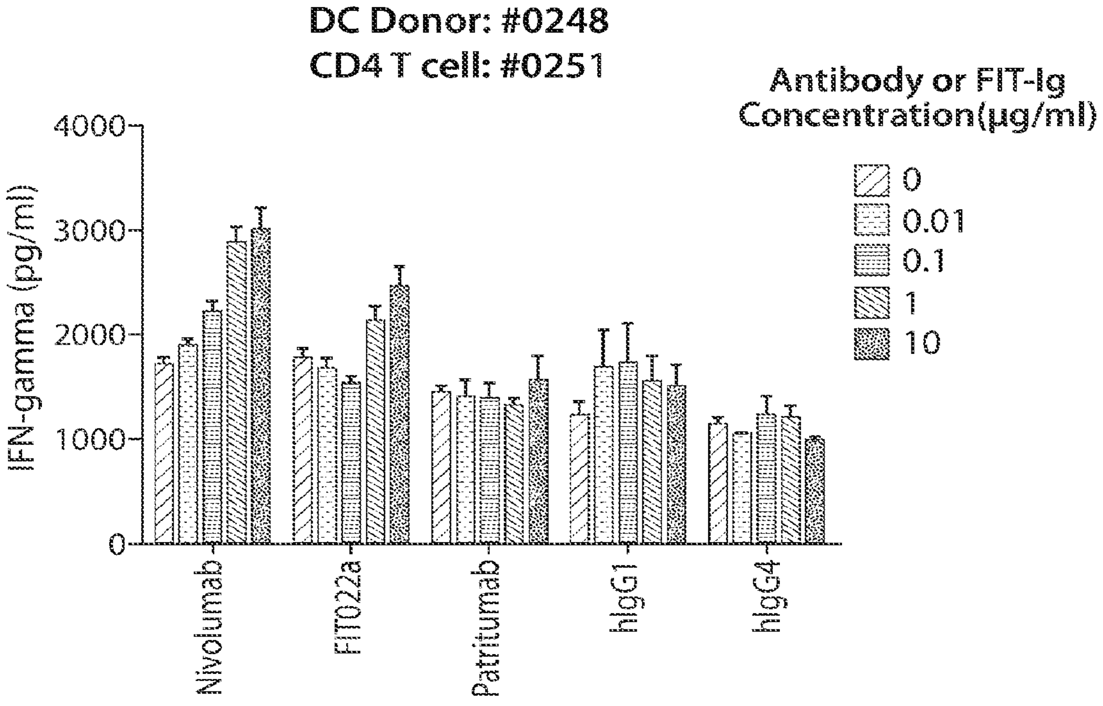
FIG. 38B shows the induction of IFN-γ by these antibodies.

MLR functional assay: Mixed lymphocyte reaction was performed using monocyte-derived dendritic cells from one donor and allogeneic CD4 T cells from another donor. The whole blood samples were collected from healthy donors, and PBMC were isolated from whole blood using Ficoll-Pague gradient centrifugation. On day 1, PBMC from one donor was isolated and diluted with serum-free RPMI 1640 at $1\times10^6$/ml. The diluted PBMC was seeded into 6-well tissue culture plate at 3 ml/well and incubated for 3 h. Supernatant was removed and unattached cells were washed off. The attached monocyte were polarized into dendritic cells with 250 U/ml IL-4 and 500 U/ml GM-CSF in RPMI1640 with 10% FBS. The medium was replaced with fresh IL-4 and GM-CSF at day 4. At day 7, immature DC was collected and treated with 1 μg/ml LPS in RPMI 1640 with 10% FBS for additional 24 h for maturation. At Day 8, CD4 T cells were isolated from another donor PBMC by negative selection and adjusted to final concentration at 2x10e6 cells/ml. Mature DC were treated with mitomycin C at 37° C. for 1.5 hr. Then DC were washed with PBS and adjusted to final concentration at $1\times10^6$ cells/ml. CD4 T cells (Responder cells) were added into 96 well plate at 100 μl/well and pre-treated with test antibody at diluted concentration for 30 minutes. Then mature DC (Stimulator cells) were added into the well at 100 μl/well. The final volume of each well is 200 μl. The MLR were incubated at 37 degree for 72 hr for IL-2 test and 120 hr for IFN-gamma test respectively using ELISA. The result is shown in FIG. 38A and FIG. 38B.

Example 17: Study of Anti-cMet/PD-L1 Fabs-In-Tandem Immunoglobulin (FIT-Ig)

FIT-Ig having specificity for cMet and PD-L1 was constructed as in the foregoing Examples. This exemplary FIT-Ig and its corresponding sequences are provided below in Table 68. Table 69 provides the expression level in 293E cells and the SEC profile for the FIT-Ig.

TABLE 68

Amino acid sequences of additional exemplary FIT-Ig for cMet and PD-L1

| Name Target (mAb) mAb1 (upper domain)/mAb2 (lower domain) | Protein region | SEQ ID NO | Sequences |
|---|---|---|---|
| FIT023a cMet (h1332)/ PD-L1 (1B12) | Long Chain(h1332 VL-hCk-1B12 VH-hCg1) | 430 | MDMRVPAQLLGLLLLWFPGSRC**DIQMTQSPSSVSASVGDRVTITCRASQGINTWLAWYQQKPGKAPKLLIYAASSLKSGVPSRFSGSGSGTDFTLTISSLQPEDFATYYCQQANSFPLTFGGGTKVEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC**QVQLVQSGAEVKKPGSSVKVSCKTSGDTFSSYAISWVRQAPGQGLEWMGGIIPIFGRAHYAQKFQGRVTITADEST** |

TABLE 68-continued

Amino acid sequences of additional exemplary FIT-Ig for cMet and PD-L1

| Name Target (mAb) mAb1 (upper domain)/mAb2 (lower domain) | Protein region | SEQ ID NO | Sequences |
|---|---|---|---|
| | | | STAYMELSSLRSEDTAVYFCARKFHFVSGSPFGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | h1332 VL | 431 | DIQMTQSPSSVSASVGDRVTITCRASQGINTWLAWYQQKPGKAPKLLIYAASSLKSGVPSRFSGSGSGTDFTLTISSLQPEDFATYYCQQANSFPLTFGGGTKVEIK |
| | h1332 VL - CDR1 | 432 | RASQGINTWLA |
| | h1332 VL - CDR2 | 433 | AASSLKS |
| | h1332 VL - CDR3 | 434 | QQANSFPLT |
| | 1B12 VH | 435 | QVQLVQSGAEVKKPGSSVKVSCKTSGDTFSSYAISWVRQAPGQGLEWMGGIIPIFGRAHYAQKFQGRVTITADESTSTAYMELSSLRSEDTAVYFCARKFHFVSGSPFGMDVWGQGTTVTVSS |
| | 1B12 VH-CDR1 | 436 | SYAIS |
| | 1B12 VH-CDR2 | 437 | GIIPIFGRAHY |
| | 1B12 VH-CDR3 | 438 | KFHFVSGSPFGMDV |
| | Short Chain #1 (h1332 VH-CH1) | 439 | MEFGLSWLFLVAILKGVQCQVQLVQSGAEVKKPGASVKVSCKASGYTFTSYGFSWVRQAPGQGLEWMGWISASNGNTYYAQKLQGRVTMTTDTSTSTAYMELRSLRSDDTAVYYCARVYADYADYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | h1332 VH | 440 | QVQLVQSGAEVKKPGASVKVSCKASGYTFTSYGFSWVRQAPGQGLEWMGWISASNGNTYYAQKLQGRVTMTTDTSTSTAYMELRSLRSDDTAVYYCARVYADYADYWGQGTLVTVSS |
| | h1332 VH - CDR1 | 441 | SYGFS |
| | h1332 VH - CDR2 | 442 | WISASNGNTYYAQKLQG |
| | h1332 VH - CDR3 | 443 | VYADYADY |
| | Short Chain #2 (1B12 VL-hCK) | 444 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 1B12 VL | 445 | EIVLTQSPATLSLSPGERATLSCRASQSVSSYLAWYQQKPGQAPRLLIYDASNRATGIPARFSGSGSGTDFTLTISSLEPEDFAVYYCQQRSNWPTFGQGTKVEIK |
| | 1B12 VL-CDR1 | 446 | RASQSVSSYLA |
| | 1B12 VL-CDR2 | 447 | DASNRAT |
| | 1B12 VL-CDR3 | 448 | QQRSNWPT |

TABLE 69

SEC Profile/Expression level in 293E cells:

| FIT-Ig | Monomer % in SEC | Expression level (mg/L) |
|---|---|---|
| FIT023a | 97.49% | 5.94 |

Functional Studies

Affinity measurement by surface plasmon resonance: The kinetics of FIT023a-Ig binding to cMet and PD-L1 was determined by surface plasmon resonance. The result is shown in Table 70.

TABLE 70

Functional binding data for FIT023a

| Ig | Target | Kon | Koff | KD |
|---|---|---|---|---|
| H1332 | 1(cMet) | 2.47E+05 | 5.39E−04 | 2.19E−09 |
| FIT023a | | 3.42E+05 | 5.10E−04 | 1.49E−09 |
| 1B12 | 2(PD-L1) | 3.21E+06 | 2.28E−03 | 7.08E−10 |
| FIT023a | | 2.84E+06 | 2.08E−03 | 7.31E−10 |

Figure 39A:
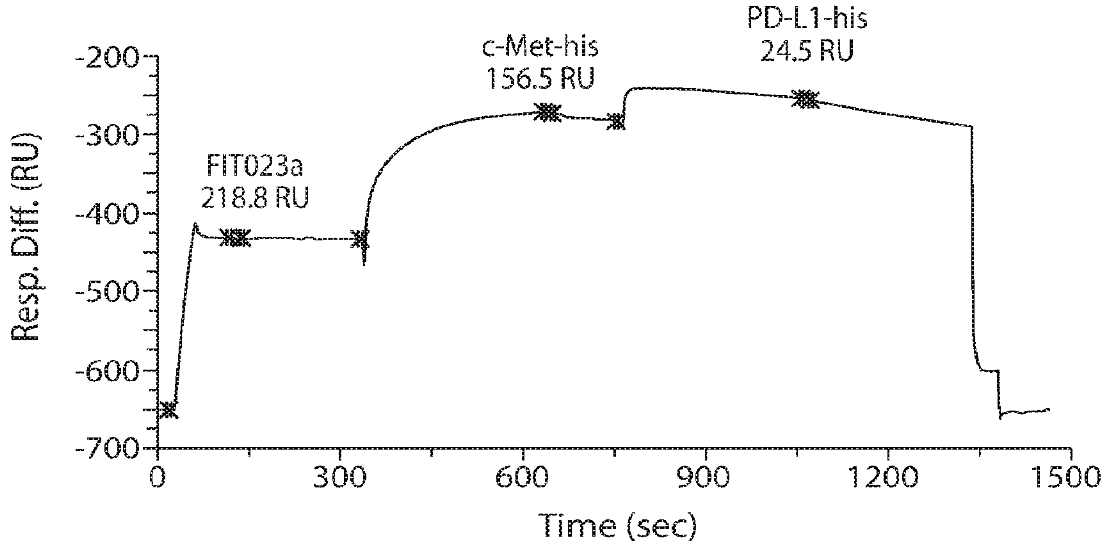
FIG. 39A and FIG. 39B show a multiple binding study of FIT023a against both cMet-his and PD-L1-his. Binding to cMet-his followed by PD-L1-his (FIG. 39A); and binding by PD-L1-his followed by cMet-his (FIG. 39B) are both shown as indicated.
Figure 39B:
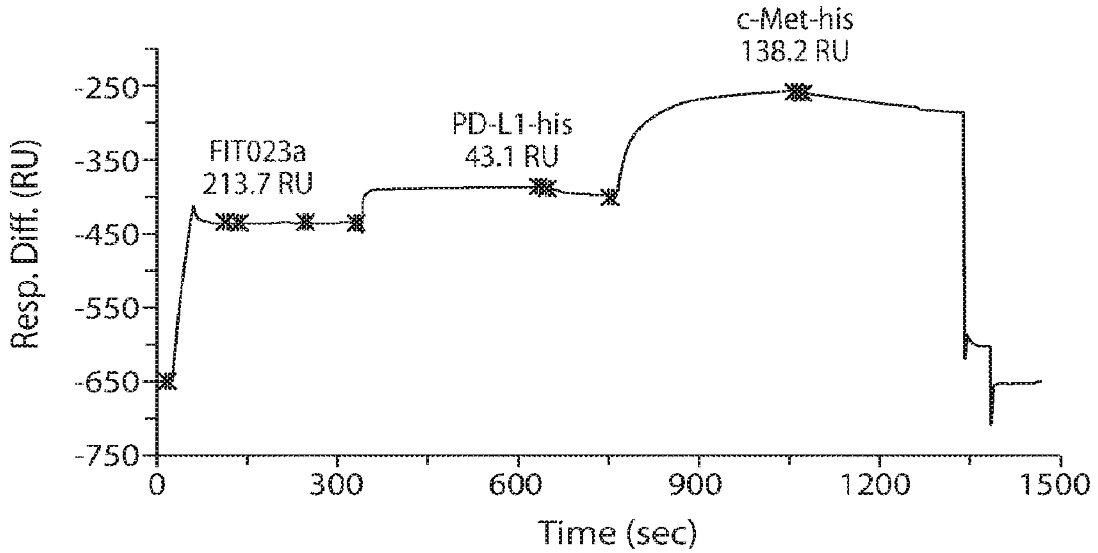
Figure 40A:
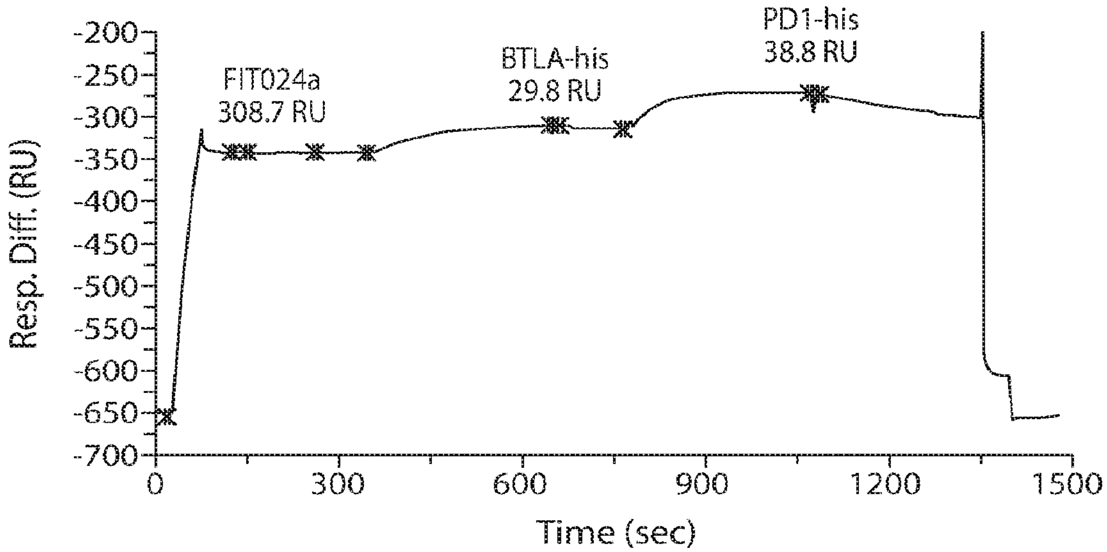
FIG. 40A and FIG. 40B show a multiple binding study of FIT024a against both BTLA-his and PD1-his. Binding to BTLA-his followed by PD1-his (FIG. 40A); and binding by PD1-his followed by BTLA-his (FIG. 40B) are both shown as indicated.
Figure 40B:
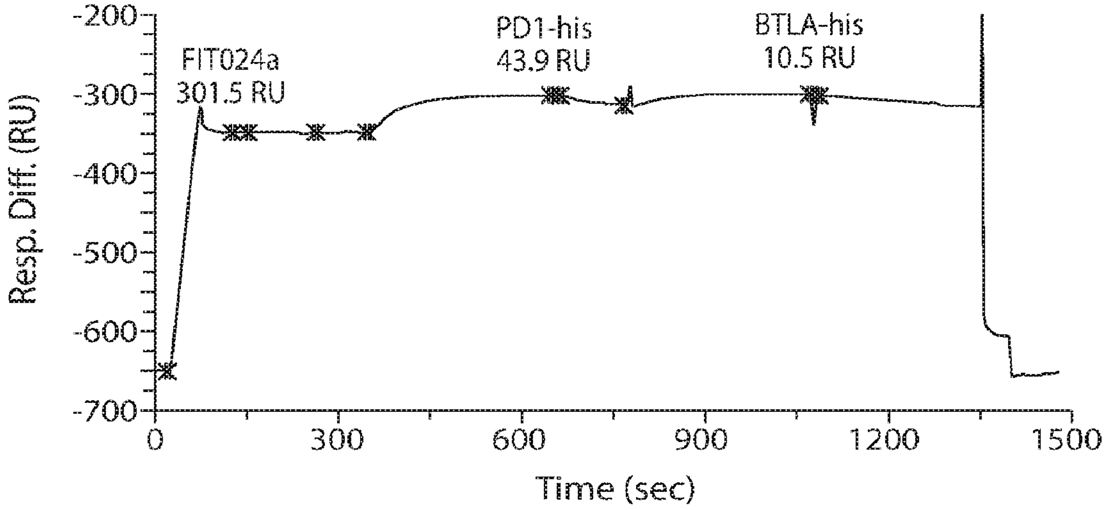
Figure 41A:
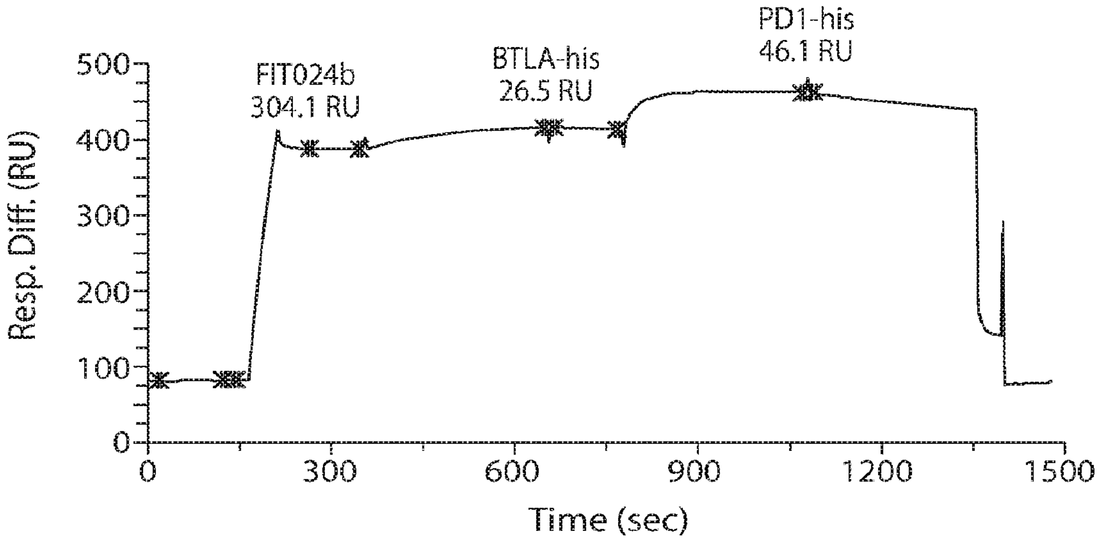
FIG. 41A and FIG. 41B show a multiple binding study of FIT024b against both BTLA-his and PD1-his. Binding to BT:A-his followed by PD1-his (FIG. 41A); and binding by PD1-his followed by BTLA-his (FIG. 41B) are both shown as indicated.
Figure 41B:
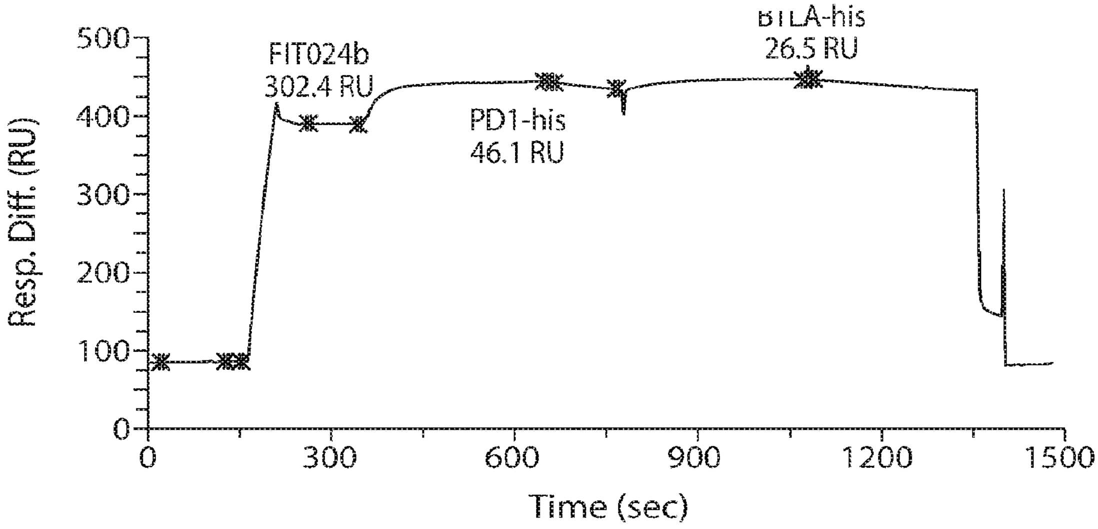

Multiple binding study: A multiple binding study of FIT023a was carried out. The result is shown in FIG. 39A and FIG. 39B. The result indicates that FIT023a can bind to cMet and PD-L1 simultaneously.

Example 18: Study of Anti-BTLA/PD-1 Fabs-In-Tandem Immunoglobulin (FIT-Ig)

FIT-Ig having specificity for BTLA and PD-L1 were constructed as in the foregoing Examples. This exemplary FIT-Ig and their corresponding sequences are provided below in Table 71. Table 72 provides the expression level in 293E cells and the SEC profile for the FIT-Ig. Both FIT024a and FIT024b have good purity after one-step Protein A purification.

TABLE 71

Amino acid sequences of additional exemplary FIT-Ig for BTLA and PD-1

| Name Target (mAb) mAb1 (upper domain)/mAb2 (lower domain) | Protein region | SEQ ID NO | Sequences |
|---|---|---|---|
| FIT024a-Ig BTLA (6A5)/ PD-1 (Nivolumab) | Long Chain (6A5 VL-hCk-Nivolu VH-hCg1mut) | 449 | MDMRVPAQLLGLLLLWFPGSRCEIVLTQSPGTLSLSPGERATLSCRASQSVSSTYLAWYQQKPGQAPRLLIYGASSRATGIPDRFSGSGSGTDFTLTISRLEPEDFAVYYCQQYGSSPPITFGQGTRLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | 6A5 VL | 450 | EIVLTQSPGTLSLSPGERATLSCRASQSVSSTYLAWYQQKPGQAPRLLIYGASSRATGIPDRFSGSGSGTDFTLTISRLEPEDFAVYYCQQYGSSPPITFGQGTRLEIK |
| | 6A5 VL - CDR1 | 451 | RASQSVSSTYLA |
| | 6A5 VL - CDR2 | 452 | GASSRAT |
| | 6A5 VL - CDR3 | 453 | QQYGSSPPIT |
| | Nivolu VH | 454 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS |
| | Nivolu VH - CDR1 | 455 | NSGMH |
| | Nivolu VH - CDR2 | 456 | VIWYDGSKRYYADSVKG |
| | Nivolu VH - CDR3 | 457 | NDDY |
| | Short Chain #1 (6A5 VH-CH1) | 458 | MEFGLSWLFLVAILKGVQCQITLKESGPTLVKPTQTLTLTCTFSGFSLSTSGVGVGWIRQPPGKALEWLALIYWDDDKRYSPSLKSRLTITKDTSKNQVVLTMANMDPVDTATYYCAHIRITEVRGVIISYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | 6A5 VH | 459 | QITLKESGPTLVKPTQTLTLTCTFSGFSLSTSGVGVGWIRQPPGKALEWLALIYWDDDKRYSPSLKSRLTITKDTSKNQVVLTMANMDPVDTATYYCAHIRITEVRGVIISYYGMDVWGQGTTVTVSS |
| | 6A5 VH - CDR1 | 460 | TSGVGVG |
| | 6A5 VH - CDR2 | 461 | LIYWDDDKRYSPSLKS |
| | 6A5 VH - CDR3 | 462 | IRITEVRGVIISYYGMDV |
| | Short Chain #2 (Nivolu VL-hCK) | 463 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | Nivolu VL | 464 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK |
| | Nivolu VL-CDR1 | 465 | RASQSVSSYLA |
| | Nivolu VL-CDR2 | 466 | DASNRAT |
| | Nivolu VL-CDR3 | 467 | QQSSNWPRT |
| FIT024b-Ig PD-1 (Nivolumab)/ BTLA (6A5) | Long Chain (Nivolu VL-hCk-6A5 VH-hCg1mut) | 468 | MDMRVPAQLLGLLLLWFPGSRCEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECQITLKESGPTLVKPTQTLTLTCTFSGESLSTSGVGVG |

TABLE 71-continued

Amino acid sequences of additional exemplary FIT-Ig for BTLA and PD-1

| Name Target (mAb) mAb1 (upper domain)/mAb2 (lower domain) | Protein region | SEQ ID NO | Sequences |
|---|---|---|---|
| | | | **WIRQPPGKALEWLALIYWDDDKRYSPSLKSRLTITKDTSKNQVVLTMANMDPVDTATYYCAHIRITEVRGVIISYYGMDVWGQGTTVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| | Nivolu VL | 469 | EIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTKVEIK |
| | Nivolu VL - CDR1 | 470 | RASQSVSSYLA |
| | Nivolu VL - CDR2 | 471 | DASNRAT |
| | Nivolu VL - CDR3 | 472 | QQSSNWPRT |
| | 6A5 VH | 473 | QITLKESGPTLVKPTQTLTLTCTFSGFSLSTSGVGVGWIRQPPGKALEWLALIYWDDDKRYSPSLKSRLTITKDTSKNQVVLTMANMDPVDTATYYCAHIRITEVRGVIISYYGMDVWGQGTTVTVSS |
| | 6A5 VH - CDR1 | 474 | TSGVGVG |
| | 6A5 VH - CDR2 | 475 | LIYWDDDKRYSPSLKS |
| | 6A5 VH - CDR3 | 476 | IRITEVRGVIISYYGMDV |
| | Short Chain #1 (Nivolu VH-CH1) | 477 | MEFGLSWLFLVAILKGVQC**QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS**ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSC |
| | Nivolu VH | 478 | QVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCATNDDYWGQGTLVTVSS |
| | Nivolu VH - CDR1 | 479 | NSGMH |
| | Nivolu VH - CDR2 | 480 | VIWYDGSKRYYADSVKG |
| | Nivolu VH - CDR3 | 481 | NDDY |
| | Short Chain #2 (6A5 VL-hCK) | 482 | MDMRVPAQLLGLLLLWFPGSRC**EIVLTQSPGTLSLSPGERATLSCRASQSVSSTYLAWYQQKPGQAPRLLIYGASSRATGIPDRFSGSGSGTDFTLTISRLEPEDFAVYYCQQYGSSPPITFGQGTRLEIK**RTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| | 6A5 VL | 483 | EIVLTQSPGTLSLSPGERATLSCRASQSVSSTYLAWYQQKPGQAPRLLIYGASSRATGIPDRFSGSGSGTDFTLTISRLEPEDFAVYYCQQYGSSPPITFGQGTRLEIK |
| | 6A5 VL - CDR1 | 484 | RASQSVSSTYLA |
| | 6A5 VL - CDR2 | 485 | GASSRAT |
| | 6A5 VL - CDR3 | 486 | QQYGSSPPIT |

TABLE 72

SEC Profile/Expression level in 293E cells:

| FIT-Ig | Monomer % in SEC | Expression level (mg/L) |
|---|---|---|
| FIT024a | 99.68% | 9.3 |
| FIT024b | 98.61% | 13.0 |

Functional Studies

Affinity measurement by surface plasmon resonance: The kinetics of FIT024a-Ig and FIT024b-Ig binding to BTLA4 and PD-1 was determined by surface plasmon resonance. The result is shown in Table 73.

TABLE 73

Functional binding data for FIT024a and FIT024b

| Ig | Target | Kon | Koff | KD |
|---|---|---|---|---|
| 6A5 | BTLA-his | 6.68E+04 | 7.34E−04 | 1.10E−08 |
| FIT024a | | 6.16E+04 | 8.05E−04 | 1.31E−08 |
| FIT024b | | 4.45E+04 | 8.14E−04 | 1.83E−08 |
| Nivolumab | hPD1-his | 3.76E+05 | 1.39E−03 | 3.70E−09 |
| FIT024a | | 1.76E+05 | 2.58E−03 | 1.46E−08 |
| FIT024b | | 3.53E+05 | 1.48E−03 | 4.20E−09 |

Multiple binding study: A multiple binding study of FIT024a and FIT024b was carried out. The result is shown in FIG. 40A to FIG. 40B and FIG. 41A to FIG. 41B. The result indicates that both FIT024a and FIT024b can bind to BTLA4 and PD-1 simultaneously.

Figure 42A:
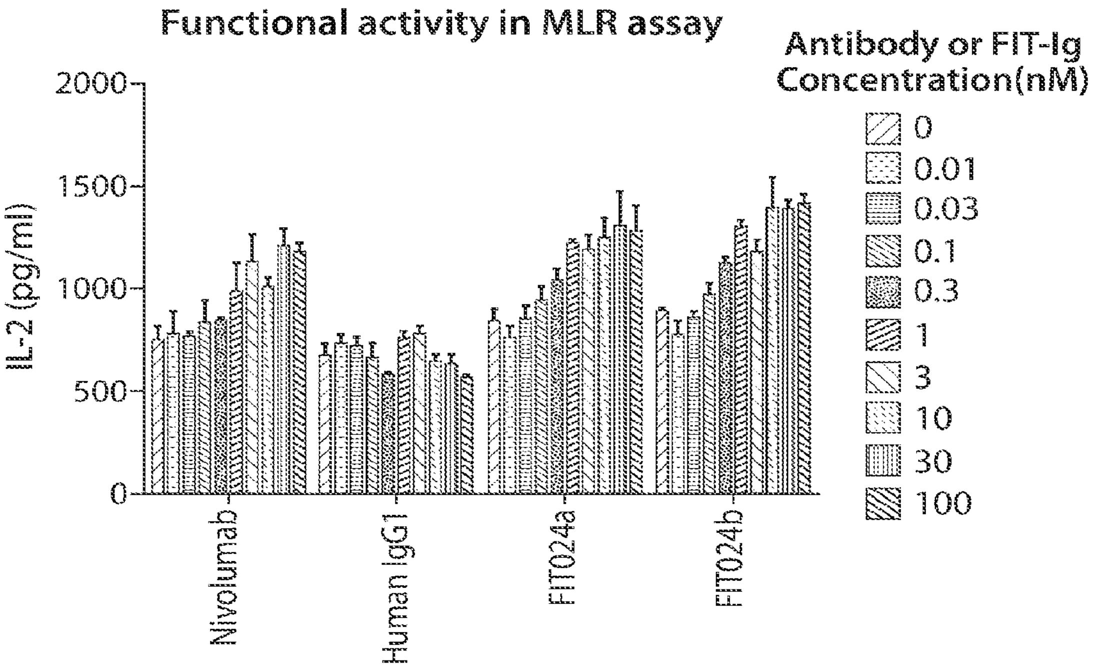
FIG. 42A shows functional activity of FIT024a and FIT024b in MLR assays, when compared to the parental antibody Nivolumab at a concentration of 0, 0.01, 0.03, 0.1, 0.3, 1, 3, 10, 30, or 100 nM, as measured by the level of induced IL-2. Human IgG1 was included as a control.
Figure 42B:
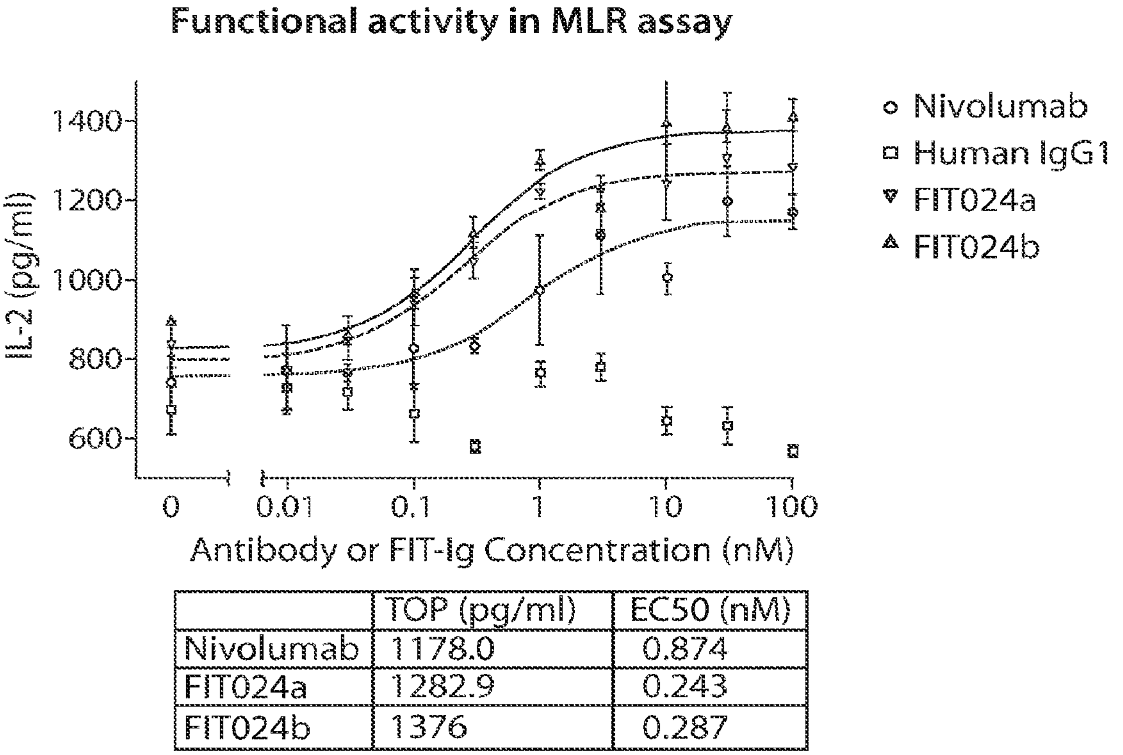
FIG. 42B shows the induction of IL-2 at a concentration of 0, 0.01, 0.1, 1, 10, or 100 by these antibodies.

MLR functional assay: Mixed lymphocyte reaction was performed using monocyte-derived dendritic cells from one donor and allogeneic CD4 T cells from another donor. The whole blood samples were collected from healthy donors, and PBMC were isolated from whole blood using Ficoll-Pague gradient centrifugation. On day 1, PBMC from one donor was isolated and diluted with serum-free RPMI 1640 at $1\times10^6$/ml. The diluted PBMC was seeded into 6-well tissue culture plate at 3 ml/well and incubated for 3 h. Supernatant was removed and unattached cells were washed off. The attached monocyte were polarized into dendritic cells with 250 U/ml IL-4 and 500 U/ml GM-CSF in RPMI1640 with 10% FBS. The medium was replaced with fresh IL-4 and GM-CSF at day 4. At day 7, immature DC was collected and treated with 1 μg/ml LPS in RPMI 1640 with 10% FBS for additional 24 h for maturation. At Day 8, CD4 T cells were isolated from another donor PBMC by negative selection and adjusted to final concentration at 2×10e6 cells/ml. Mature DC were treated with mitomycin C at 37° C. for 1.5 hr. Then DC were washed with PBS and adjusted to final concentration at $1\times10^6$ cells/ml. CD4 T cells (Responder cells) were added into 96 well plate at 100 μl/well and pre-treated with test antibody at diluted concentration for 30 minutes. Then mature DC (Stimulator cells) were added into the well at 100 μl/well. The final volume of each well is 200 μl. The MLR were incubated at 37 degree for 72 hr for IL-2 test. The result is shown in FIG. 42A and FIG. 42B. Both FIT024a and FIT024b have higher activity to enhance T cell activation in MLR study compared to Nivolumab.

All publications, patent applications, and issued patents cited in this specification are herein incorporated by reference as if each individual publication, patent application, or issued patent were specifically and individually indicated to be incorporated by reference in its entirety.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

What is claimed is:

1. An isolated nucleic acid sequence comprising a coding sequence for a first polypeptide chain of a bispecific binding protein, wherein the bispecific binding protein binds antigen A and antigen B and comprises three polypeptide chains, wherein a first polypeptide chain comprises, from amino terminus to carboxy terminus, either (1) $VL_A$-CL-$VH_B$-CH1-Fc or (2) $VH_B$-CH1-$VL_A$-CL-Fc, wherein $VL_A$ is an antibody light chain variable domain of a first parental antibody that binds antigen A, CL is an antibody light chain constant domain, $VH_B$ is an antibody heavy chain variable domain from a second parental antibody that binds antigen B, and CH1 is a first constant domain of an antibody heavy chain;

a second polypeptide chain comprises, from amino terminus to carboxy terminus, $VH_A$-CH1, wherein $VH_A$ is a heavy chain variable domain of the first parental antibody that binds antigen A and CH1 is a first constant domain of an antibody heavy chain; and a third polypeptide chain comprises, from amino terminus to carboxy terminus, $VL_B$-CL, wherein $VL_B$ is a light chain variable domain of the second parental antibody that binds antigen B and CL is an antibody light chain constant domain;

wherein the bispecific binding protein binds antigens A and B, wherein A is cMet and B is EGFR, and wherein domain $VL_A$ comprises $VL_A$ CDR1 having amino acid sequence SEQ ID NO: 242, $VL_A$ CDR2 having amino acid sequence SEQ ID NO:243, and $VL_A$ CDR3 having amino acid sequence SEQ ID NO:244; variable domain $VH_A$ comprises $VH_A$ CDR1 having amino acid sequence SEQ ID NO:251, $VH_A$ CDR2 having amino acid sequence SEQ ID NO:252, and $VH_A$ CDR3 having amino acid sequence SEQ ID NO:253; variable domain $VL_B$ comprises $VL_B$ CDR1 having amino acid sequence SEQ ID NO:256, $VL_B$ CDR2 having amino acid sequence SEQ ID NO:257, and $VL_B$ CDR3 having amino acid sequence SEQ ID NO:258; and variable domain $VH_B$ comprises $VH_B$ CDR1 having amino acid sequence SEQ ID NO: 246, $VH_B$ CDR2 having amino acid sequence SEQ ID NO:247, and $VH_B$ CDR3 having amino acid sequence SEQ ID NO:248.

2. The isolated nucleic acid according to claim 1, further comprising a coding sequence for the second polypeptide chain of the bispecific binding protein and/or a coding sequence for the third polypeptide chain of the bispecific binding protein.

3. The isolated nucleic acid according to claim 1, wherein the bispecific binding protein binds antigens A and B, wherein A is cMet and B is EGFR, and wherein said bispecific binding protein comprises $VL_A$ having amino acid sequence SEQ ID NO: 241, $VH_A$ having amino acid sequence SEQ ID NO:250, $VL_B$ having amino acid sequence SEQ ID NO:255, and $VH_B$ having amino acid sequence SEQ ID NO:245.

4. The isolated nucleic acid according to claim 3, wherein the bispecific binding protein binds antigen A and B, wherein A is cMet and B is EGFR, and wherein said bispecific binding protein comprises first polypeptide chain having amino acid sequence residues 23-685 of SEQ ID NO:240, second polypeptide chain having amino acid sequence residues 20-239 of SEQ ID NO:249, and third polypeptide chain having amino acid sequence residues 23-236 of SEQ ID NO:254.

5. A recombinant expression vector comprising the isolated nucleic acid sequence of claim 1.

6. The expression vector according to claim 5, wherein the expression vector is pcDNA; pTT; pTT3; pEFBOS; pBV; pJV; pcDNA3.1 TOPO; pEF6 TOPO or pBJ.

7. A host cell comprising the isolated nucleic acid sequence(s) of claim 1.

8. The host cell according to claim 7, wherein the host cell is a prokaryotic cell.

9. The host cell according to claim 8, wherein the host cell is *Escherichia coli*.

10. The host cell according to claim 7, wherein the host cell is a eukaryotic cell.

11. The host cell according to claim 10, wherein the eukaryotic cell is a protist cell, animal cell, plant cell, fungal cell, insect cell or mammalian cell.

12. The host cell according to claim 11, wherein the mammalian cell is a 293 cell, COS cell, NS0 cell, or CHO cell, the fungal cell is *Saccharomyces cerevisiae*; or the insect cell is Sf9.

13. A method of producing a bispecific binding protein comprising culturing the host cell of claim 7 in a culture medium under conditions sufficient to produce the bispecific binding protein, wherein the binding protein binds antigen A and antigen B and comprises three polypeptide chains, wherein a first polypeptide chain comprises, from amino terminus to carboxyl terminus, either (i) $VL_A$-CL-$VH_B$-CH1-Fc, or (ii) $VH_B$-CH1-$VL_A$-CL-Fc, wherein $VL_A$ is an antibody light chain variable domain of a first parental antibody that binds antigen A, CL is an antibody light chain constant domain, $VH_B$ is an antibody heavy chain variable domain from a second parental antibody that binds antigen B, and CH1 is a first constant domain of an antibody heavy chain;

a second polypeptide chain comprises, from amino terminus to carboxy terminus, $VH_A$-CH1, wherein $VH_A$ is a heavy chain variable domain of the first parental antibody that binds antigen A and CH1 is a first constant domain of an antibody heavy chain; and a third polypeptide chain comprises, from amino terminus to carboxy terminus, $VL_B$-CL, wherein $VL_B$ is a light chain variable domain of the second parental antibody that binds antigen B and CL is an antibody light chain constant domain;

wherein the bispecific binding protein binds antigens A and B, wherein A is cMet and B is EGFR, and wherein variable domain $VL_A$ comprises $VL_A$ CDR1 having amino acid sequence SEQ ID NO:242, $VL_A$ CDR2 having amino acid sequence SEQ ID NO:243, and $VL_A$ CDR3 having amino acid sequence SEQ ID NO:244; variable domain $VH_A$ comprises $VH_A$ CDR1 having amino acid sequence SEQ ID NO:251, $VH_A$ CDR2 having amino acid sequence SEQ ID NO:252, and $VH_A$ CDR3 having amino acid sequence SEQ ID NO:253; variable domain $VL_B$ comprises $VL_B$ CDR1 having amino acid sequence SEQ ID NO:256, $VL_B$ CDR2 having amino acid sequence SEQ ID NO:257, and $VL_B$ CDR3 having amino acid sequence SEQ ID NO:258; and variable domain $VH_B$ comprises $VH_B$ CDR1 having amino acid sequence SEQ ID NO:246, $VH_B$ CDR2 having amino acid sequence SEQ ID NO: 247, and $VH_B$ CDR3 having amino acid sequence SEQ ID NO:248.

14. A method of treating diseases or disorders in a subject in need thereof, wherein the method comprises administering to the subject an effective amount of a bispecific binding protein, wherein the binding protein binds antigen A and antigen B and comprises three polypeptide chains, wherein a first polypeptide chain comprises, from amino terminus to carboxyl terminus, either (i) $VL_A$-CL-$VH_B$-CH1-Fc, or (ii) $VH_B$-CH1-$VL_A$-CL-Fc, wherein $VL_A$ is an antibody light chain variable domain of a first parental antibody that binds antigen A, CL is an antibody light chain constant domain, $VH_B$ is an antibody heavy chain variable domain from a second parental antibody that binds antigen B, and CH1 is a first constant domain of an antibody heavy chain;

a second polypeptide chain comprises, from amino terminus to carboxy terminus, $VH_A$-CH1, wherein $VH_A$ is a heavy chain variable domain of the first parental antibody that binds antigen A and CH1 is a first constant domain of an antibody heavy chain; and a third polypeptide chain comprises, from amino terminus to carboxy terminus, $VL_B$-CL, wherein $VL_B$ is a light chain variable domain of the second parental antibody that binds antigen B and CL is an antibody light chain constant domain;

wherein the bispecific binding protein binds antigens A and B, wherein A is cMet and B is EGFR, and wherein variable domain $VL_A$ comprises $VL_A$ CDR1 having amino acid sequence SEQ ID NO:242, $VL_A$ CDR2 having amino acid sequence SEQ ID NO:243, and $VL_A$ CDR3 having amino acid sequence SEQ ID NO:244; variable domain $VH_A$ comprises $VH_A$ CDR1 having amino acid sequence SEQ ID NO:251, $VH_A$ CDR2 having amino acid sequence SEQ ID NO:252, and $VH_A$ CDR3 having amino acid sequence SEQ ID NO:253; variable domain $VL_B$ comprises $VL_B$ CDR1 having amino acid sequence SEQ ID NO:256, $VL_B$ CDR2 having amino acid sequence SEQ ID NO:257, and $VL_B$ CDR3 having amino acid sequence SEQ ID NO:258; and variable domain $VH_B$ comprises $VH_B$ CDR1 having amino acid sequence SEQ ID NO:246, $VH_B$ CDR2 having amino acid sequence SEQ ID NO: 247, and $VH_B$ CDR3 having amino acid sequence SEQ ID NO: 248, wherein the diseases or disorders are asthma, rheumatoid arthritis, systemic lupus erythematosus, multiple sclerosis, Alzheimer's disease, Parkinson's disease, infectious diseases and disorders, such as psoriasis, psoriatic arthritis, dermatitis, systemic sclerosis, inflammatory bowel disease (IBD), Crohn's disease, ulcerative colitis, respiratory distress syndrome, meningitis, encephalitis, uveitis, glomerulonephritis, eczema, asthma, atherosclerosis, leukocyte adhesion deficiency, Raynaud's syndrome, Sjögren's syndrome, juvenile onset diabetes, Reiter's disease, Behçet's disease, immune complex nephritis, IgA nephropathy, IgM polyneuropathies, immune-mediated thrombocytopenias, such as acute idiopathic thrombocytopenic purpura and chronic idiopathic thrombocytopenia purpura, hemolytic anemia, myasthenia gravis, lupus nephritis, atopic dermatitis, pemphigus, Graves' disease, severe acute respiratory distress syndrome, choreoretinitis, Hashimoto's thyroiditis, Wegener's granulomatosis, Omenn's syndrome, chronic renal failure, acute infectious mononucleosis, HIV, herpes virus associated diseases, type 1 diabetes, graft versus host disease (GVHD); immune disorders associated with graft transplantation rejection; T cell lymphoma, T cell acute lymphoblastic leukemia, testicular angiocentric T cell lymphoma, benign lymphocytic angiitis, primary myxedema, pernicious anemia, autoimmune atrophic gastritis, Addison's disease, insulin dependent diabetes mellitis, good pasture's syndrome, sympathetic ophthalmia, idiopathic thrombocytopenia, primary biliary cirrhosis, chronic action hepatitis, ulceratis colitis, Sjogren's syndrome, rheumatoid arthritis, polymyositis, scleroderma, mixed connective tissue disease, pemphigus vulgaris, pemphigoid, ankylosing spondylitis, aplastic anemia, autoimmune hepatitis, coeliac disease, dermatomyositis, Goodpasture's syndrome, Guillain-Barre syndrome, idiopathic leucopenia, idiopathic thrombocytopenia purpura, male infertility, phacogenic uveitis, primary myxoedema, Reiter's syndrome, stiff man syndrome, thyrotoxicosis, ulceritive colitis, breast cancer, ovarian cancer, lung cancer, colorectal cancer, anal cancer, prostate cancer, kidney cancer, bladder cancer, head and neck cancer, pancreatic cancer, skin cancer, oral cancer, esophageal cancer, vaginal cancer, cervical cancer, cancer of the spleen, testicular cancer, cancer of the thymus, squamous cell carcinoma, small cell lung cancer, non-small cell lung cancer, blastoma, sarcom, adenocarcinoma of the lung, squamous cell carcinoma of the lung, peritoneal carcinoma, dermal cancer, dermal or intraocular melanoma, rectal cancer, perianal cancer, esophageal cancer, small intestine cancer, endocrine gland cancer, parathyroid cancer, adrenal gland cancer, soft tissue sarcoma, urethral cancer, male/female genital tract cancer, nerve cancer, chronic or acute leukemia, lymphocyte lymphoma, hepatoma, stomach cancer, glioblastoma, ovarian cancer, liver cancer, hepatic tumor, colon cancer, large intestine cancer, endometrial cancer, uterine cancer, salivary gland cancer, renal cancer, vulvar cancer, thyroid cancer, gestational diabetes, chronic thromboembolic diseases or disorders associated with fibrin formation including vascular disorders such as deep venous thrombosis, arterial thrombosis, stroke, tumor metastasis, thrombolysis, arteriosclerosis and restenosis following angioplasty, septic shock, septicemia, hypotension, adult respiratory distress syndrome (ARDS), disseminated intravascular coagulopathy (DIC), sarcoidosis, arterial arteriosclerosis, peptic ulcers, burns, pancreatitis, polycystic ovarian disease (POD), endometriosis, uterine fibroid, benign prostate hypertrophy, T-cell acute lymphoblastic leukemia (T-ALL), cerebral autosomal dominant arteriopathy with subcortical infarcts and leukoencephalopathy (CADASIL), tetralogy of Fallot (TOF), Alagille syndrome (AS), macular degeneration and age-related macular degeneration diseases, inflammatory fibrosis (e.g., scleroderma, lung fibrosis, and cirrhosis), osteoarthritis, osteoporosis, asthma (including allergic asthma), allergies, chronic obstructive pulmonary disease (COPD), juvenile early-onset Type I diabetes, transplant rejection, or SLE.

* * * * *

SEQUENCE LISTING

```
Sequence total quantity: 519
SEQ ID NO: 1           moltype = DNA  length = 31
FEATURE                Location/Qualifiers
misc_feature           1..31
                       note = Oligonucleotide primer
source                 1..31
                       mol_type = other DNA
                       organism = synthetic construct
SEQUENCE: 1
caggtgcagc tggtgcagag cggcgccgaa g                           31

SEQ ID NO: 2           moltype = DNA  length = 51
FEATURE                Location/Qualifiers
misc_feature           1..51
                       note = Oligonucleotide primer
source                 1..51
                       mol_type = other DNA
                       organism = synthetic construct
SEQUENCE: 2
gctggacctg agagcctgaa ccgccaccac cacactctcc cctgttgaag c     51

SEQ ID NO: 3           moltype = DNA  length = 52
FEATURE                Location/Qualifiers
misc_feature           1..52
                       note = Oligonucleotide primer
source                 1..52
                       mol_type = other DNA
                       organism = synthetic construct
SEQUENCE: 3
ggtggtggcg gttcaggctc tcaggtccag cttgtgcaat ctggcgccga gg    52

SEQ ID NO: 4           moltype = DNA  length = 36
FEATURE                Location/Qualifiers
misc_feature           1..36
                       note = Oligonucleotide primer
source                 1..36
                       mol_type = other DNA
                       organism = synthetic construct
SEQUENCE: 4
gtctgcggcc gctcatttac ccggagacag ggagag                      36
```

```
SEQ ID NO: 5            moltype = DNA  length = 31
FEATURE                 Location/Qualifiers
misc_feature            1..31
                        note = Oligonucleotide primer
source                  1..31
                        mol_type = other DNA
                        organism = synthetic construct
SEQUENCE: 5
taagcgtacg gtggctgcac catctgtctt c                                  31

SEQ ID NO: 6            moltype = DNA  length = 59
FEATURE                 Location/Qualifiers
misc_feature            1..59
                        note = Oligonucleotide primer
source                  1..59
                        mol_type = other DNA
                        organism = synthetic construct
SEQUENCE: 6
cggcgccaga ttgcacaagc tggacctggc ctgaaccaca ctctcccctg ttgaagctc   59

SEQ ID NO: 7            moltype = DNA  length = 51
FEATURE                 Location/Qualifiers
misc_feature            1..51
                        note = Oligonucleotide primer
source                  1..51
                        mol_type = other DNA
                        organism = synthetic construct
SEQUENCE: 7
gctggacctg agagcctgaa ccgccaccac cacactctcc cctgttgaag c           51

SEQ ID NO: 8            moltype = DNA  length = 52
FEATURE                 Location/Qualifiers
misc_feature            1..52
                        note = Oligonucleotide primer
source                  1..52
                        mol_type = other DNA
                        organism = synthetic construct
SEQUENCE: 8
ggtggtggcg gttcaggctc tcaggtccag cttgtgcaat ctggcgccga gg          52

SEQ ID NO: 9            moltype = DNA  length = 59
FEATURE                 Location/Qualifiers
misc_feature            1..59
                        note = Oligonucleotide primer
source                  1..59
                        mol_type = other DNA
                        organism = synthetic construct
SEQUENCE: 9
tacctcggcg ccagattgca caagctggac ctgacactct cccctgttga agctctttg   59

SEQ ID NO: 10           moltype = DNA  length = 56
FEATURE                 Location/Qualifiers
misc_feature            1..56
                        note = Oligonucleotide primer
source                  1..56
                        mol_type = other DNA
                        organism = synthetic construct
SEQUENCE: 10
catgacacct taacagaggc cccaggtcgt tttacctcgg cgccagattg cacaag      56

SEQ ID NO: 11           moltype = DNA  length = 37
FEATURE                 Location/Qualifiers
misc_feature            1..37
                        note = Oligonucleotide primer
source                  1..37
                        mol_type = other DNA
                        organism = synthetic construct
SEQUENCE: 11
caataagctt tacatgacac cttaacagag gccccag                           37

SEQ ID NO: 12           moltype = DNA  length = 40
FEATURE                 Location/Qualifiers
misc_feature            1..40
                        note = Oligonucleotide primer
source                  1..40
                        mol_type = other DNA
                        organism = synthetic construct
SEQUENCE: 12
tcgagcggcc gctcaacaag atttgggctc aactttcttg                        40
```

```
SEQ ID NO: 13          moltype = DNA  length = 51
FEATURE                Location/Qualifiers
misc_feature           1..51
                       note = Oligonucleotide primer
source                 1..51
                       mol_type = other DNA
                       organism = synthetic construct
SEQUENCE: 13
gctgctgctg tggttccccg gctcgcgatg cgctatacag ttgacacagt c           51

SEQ ID NO: 14          moltype = DNA  length = 53
FEATURE                Location/Qualifiers
misc_feature           1..53
                       note = Oligonucleotide primer
source                 1..53
                       mol_type = other DNA
                       organism = synthetic construct
SEQUENCE: 14
gaagatgaag acagatggtg cagccaccgt acgcttgatc tctacctttg ttc         53

SEQ ID NO: 15          moltype = AA  length = 676
FEATURE                Location/Qualifiers
REGION                 1..676
                       note = Anti-IL-17/IL-20 FIT1-Ig polypeptide
source                 1..676
                       mol_type = protein
                       organism = synthetic construct
SEQUENCE: 15
DIVMTQTPLS LSVTPGQPAS ISCRSSRSLV HSRGNTYLHW YLQKPGQSPQ LLIYKVSNRF  60
IGVPDRFSGS GSGTDFTLKI SRVEAEDVGV YYCSQSTHLP FTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGECQ VQLVQSGAEV KRPGASVKVS  240
CKASGYTFTN DIIHWVRQAP GQRLEWMGWI NAGYGNTQYS QNFQDRVSIT RDTSASTAYM  300
ELISLRSEDT AVYYCAREPL WFGESSPHDY YGMDVWGQGT TVTVSSASTK GPSVFPLAPS  360
SKSTSGGTAA LGCLVKDYFP EPVTVSWNSG ALTSGVHTFP AVLQSSGLYS LSSVVTVPSS  420
SLGTQTYICN VNHKPSNTKV DKKVEPKSCD KTHTCPPCPA PELLGGPSVF LFPPKPKDTL  480
MISRTPEVTC VVVDVSHEDP EVKFNWYVDG VEVHNAKTKP REEQYNSTYR VVSVLTVLHQ  540
DWLNGKEYKC KVSNKALPAP IEKTISKAKG QPREPQVYTL PPSREEMTKN QVSLTCLVKG  600
FYPSDIAVEW ESNGQPENNY KTTPPVLDSD GSFFLYSKLT VDKSRWQQGN VFSCSVMHEA  660
LHNHYTQKSL SLSPGK                                                  676

SEQ ID NO: 16          moltype = AA  length = 112
FEATURE                Location/Qualifiers
source                 1..112
                       mol_type = protein
                       organism = Homo sapiens
SEQUENCE: 16
DIVMTQTPLS LSVTPGQPAS ISCRSSRSLV HSRGNTYLHW YLQKPGQSPQ LLIYKVSNRF  60
IGVPDRFSGS GSGTDFTLKI SRVEAEDVGV YYCSQSTHLP FTFGQGTKLE IK          112

SEQ ID NO: 17          moltype = AA  length = 107
FEATURE                Location/Qualifiers
source                 1..107
                       mol_type = protein
                       organism = Homo sapiens
SEQUENCE: 17
RTVAAPSVFI FPPSDEQLKS GTASVVCLLN NFYPREAKVQ WKVDNALQSG NSQESVTEQD  60
SKDSTYSLSS TLTLSKADYE KHKVYACEVT HQGLSSPVTK SFNRGEC                107

SEQ ID NO: 18          moltype = AA  length = 127
FEATURE                Location/Qualifiers
source                 1..127
                       mol_type = protein
                       organism = Mus sp.
SEQUENCE: 18
QVQLVQSGAE VKRPGASVKV SCKASGYTFT NDIIHWVRQA PGQRLEWMGW INAGYGNTQY  60
SQNFQDRVSI TRDTSASTAY MELISLRSED TAVYYCAREP LWFGESSPHD YYGMDVWGQG  120
TTVTVSS                                                            127

SEQ ID NO: 19          moltype = AA  length = 103
FEATURE                Location/Qualifiers
source                 1..103
                       mol_type = protein
                       organism = Homo sapiens
SEQUENCE: 19
ASTKGPSVFP LAPSSKSTSG GTAALGCLVK DYFPEPVTVS WNSGALTSGV HTFPAVLQSS  60
GLYSLSSVVT VPSSSLGTQT YICNVNHKPS NTKVDKKVEP KSC                    103
```

```
SEQ ID NO: 20          moltype = AA  length = 227
FEATURE                Location/Qualifiers
source                 1..227
                       mol_type = protein
                       organism = Homo sapiens
SEQUENCE: 20
DKTHTCPPCP APELLGGPSV FLFPPKPKDT LMISRTPEVT CVVVDVSHED PEVKFNWYVD  60
GVEVHNAKTK PREEQYNSTY RVVSVLTVLH QDWLNGKEYK CKVSNKALPA PIEKTISKAK  120
GQPREPQVYT LPPSREEMTK NQVSLTCLVK GFYPSDIAVE WESNGQPENN YKTTPPVLDS  180
DGSFFLYSKL TVDKSRWQQG NVFSCSVMHE ALHNHYTQKS LSLSPGK                227

SEQ ID NO: 21          moltype = AA  length = 222
FEATURE                Location/Qualifiers
REGION                 1..222
                       note = Anti-IL-17/IL-20 FIT1-Ig polypeptide
source                 1..222
                       mol_type = protein
                       organism = synthetic construct
SEQUENCE: 21
QVQLVQSGAE VKKPGSSVKV SCKASGYSFT DYHIHWVRQA PGQGLEWMGV INPMYGTTDY  60
NQRFKGRVTI TADESTSTAY MELSSLRSED TAVYYCARYD YFTGTGVYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SC                     222

SEQ ID NO: 22          moltype = AA  length = 119
FEATURE                Location/Qualifiers
source                 1..119
                       mol_type = protein
                       organism = Homo sapiens
SEQUENCE: 22
QVQLVQSGAE VKKPGSSVKV SCKASGYSFT DYHIHWVRQA PGQGLEWMGV INPMYGTTDY  60
NQRFKGRVTI TADESTSTAY MELSSLRSED TAVYYCARYD YFTGTGVYWG QGTLVTVSS   119

SEQ ID NO: 23          moltype = AA  length = 214
FEATURE                Location/Qualifiers
REGION                 1..214
                       note = Anti-IL-17/IL-20 FIT1-Ig polypeptide
source                 1..214
                       mol_type = protein
                       organism = synthetic construct
SEQUENCE: 23
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPLTFGG GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 24          moltype = AA  length = 107
FEATURE                Location/Qualifiers
source                 1..107
                       mol_type = protein
                       organism = Mus sp.
SEQUENCE: 24
AIQLTQSPSS LSASVGDRVT ITCRASQGIS SALAWYQQKP GKAPKLLIYD ASSLESGVPS  60
RFSGSGSGTD FTLTISSLQP EDFATYYCQQ FNSYPLTFGG GTKVEIK                107

SEQ ID NO: 25          moltype = AA  length = 679
FEATURE                Location/Qualifiers
REGION                 1..679
                       note = Anti-IL-17/IL-20 FIT2-Ig polypeptide
source                 1..679
                       mol_type = protein
                       organism = synthetic construct
SEQUENCE: 25
DIVMTQTPLS LSVTPGQPAS ISCRSSRSLV HSRGNTYLHW YLQKPGQSPQ LLIYKVSNRF  60
IGVPDRFSGS GSGTDFTLKI SRVEAEDVGV YYCSQSTHLP FTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGECG SGQVQLVQSG AEVKRPGASV  240
KVSCKASGYT FTNDIIHWVR QAPGQRLEWM GWINAGYGNT QYSQNFQDRV SITRDTSAST  300
AYMELISLRS EDTAVYYCAR EPLWFGESSP HDYYGMDVWG QGTTVTVSSA STKGPSVFPL  360
APSSKSTSGG TAALGCLVKD YFPEPVTVSW NSGALTSGVH TFPAVLQSSG LYSLSSVVTV  420
PSSSLGTQTY ICNVNHKPSN TKVDKKVEPK SCDKTHTCPP CPAPELLGGP SVFLFPPKPK  480
DTLMISRTPE VTCVVVDVSH EDPEVKFNWY VDGVEVHNAK TKPREEQYNS TYRVVSVLTV  540
LHQDWLNGKE YKCKVSNKAL PAPIEKTISK AKGQPREPQV YTLPPSREEM TKNQVSLTCL  600
VKGFYPSDIA VEWESNGQPE NNYKTTPPVL DSDGSFFLYS KLTVDKSRWQ QGNVFSCSVM  660
HEALHNHYTQ KSLSLSPGK                                               679

SEQ ID NO: 26          moltype =   length =
SEQUENCE: 26
000
```

```
SEQ ID NO: 27          moltype = AA  length = 683
FEATURE                Location/Qualifiers
REGION                 1..683
                       note = Anti-IL-17/IL-20 FIT3-Ig polypeptide
source                 1..683
                       mol_type = protein
                       organism = synthetic construct
SEQUENCE: 27
DIVMTQTPLS LSVTPGQPAS ISCRSSRSLV HSRGNTYLHW YLQKPGQSPQ LLIYKVSNRF  60
IGVPDRFSGS GSGTDFTLKI SRVEAEDVGV YYCSQSTHLP FTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGECG GGGSGSQVQL VQSGAEVKRP  240
GASVKVSCKA SGYTFTNDII HWVRQAPGQR LEWMGWINAG YGNTQYSQNF QDRVSITRDT  300
SASTAYMELI SLRSEDTAVY YCAREPLWFG ESSPHDYYGM DVWGQGTTVT VSSASTKGPS  360
VFPLAPSSKS TSGGTAALGC LVKDYFPEPV TVSWNSGALT SGVHTFPAVL QSSGLYSLSS  420
VVTVPSSSLG TQTYICNVNH KPSNTKVDKK VEPKSCDKTH TCPPCPAPEL LGGPSVFLFP  480
PKPKDTLMIS RTPEVTCVVV DVSHEDPEVK FNWYVDGVEV HNAKTKPREE QYNSTYRVVS  540
VLTVLHQDWL NGKEYKCKVS NKALPAPIEK TISKAKGQPR EPQVYTLPPS REEMTKNQVS  600
LTCLVKGFYP SDIAVEWESN GQPENNYKTT PPVLDSDGSF FLYSKLTVDK SRWQQGNVFS  660
CSVMHEALHN HYTQKSLSLS PGK                                         683

SEQ ID NO: 28          moltype = AA  length = 7
FEATURE                Location/Qualifiers
REGION                 1..7
                       note = peptide linker sequence
source                 1..7
                       mol_type = protein
                       organism = synthetic construct
SEQUENCE: 28
GGGGSGS                                                           7

SEQ ID NO: 29          moltype = AA  length = 436
FEATURE                Location/Qualifiers
REGION                 1..436
                       note = Anti-IL-17/IL-20 FIT4-Ig polypeptide
source                 1..436
                       mol_type = protein
                       organism = synthetic construct
SEQUENCE: 29
QVQLVQSGAE VKKPGSSVKV SCKASGYSFT DYHIHWVRQA PGQGLEWMGV INPMYGTTDY  60
NQRFKGRVTI TADESTSTAY MELSSLRSED TAVYYCARYD YFTGTGVYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCAIQLTQSP SSLSASVGDR  240
VTITCRASQG ISSALAWYQQ KPGKAPKLLI YDASSLESGV PSRFSGSGSG TDFTLTISSL  300
QPEDFATYYC QQFNSYPLTF GGGTKVEIKR TVAAPSVFIF PPSDEQLKSG TASVVCLLNN  360
FYPREAKVQW KVDNALQSGN SQESVTEQDS KDSTYSLSST LTLSKADYEK HKVYACEVTH  420
QGLSSPVTKS FNRGEC                                                 436

SEQ ID NO: 30          moltype = AA  length = 439
FEATURE                Location/Qualifiers
REGION                 1..439
                       note = Anti-IL-17/IL-20 FIT5-Ig polypeptide
source                 1..439
                       mol_type = protein
                       organism = synthetic construct
SEQUENCE: 30
QVQLVQSGAE VKKPGSSVKV SCKASGYSFT DYHIHWVRQA PGQGLEWMGV INPMYGTTDY  60
NQRFKGRVTI TADESTSTAY MELSSLRSED TAVYYCARYD YFTGTGVYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCGSGAIQLT QSPSSLSASV  240
GDRVTITCRA SQGISSALAW YQQKPGKAPK LLIYDASSLE SGVPSRFSGS GSGTDFTLTI  300
SSLQPEDFAT YYCQQFNSYP LTFGGGTKVE IKRTVAAPSV FIFPPSDEQL KSGTASVVCL  360
LNNFYPREAK VQWKVDNALQ SGNSQESVTE QDSKDSTYSL SSTLTLSKAD YEKHKVYACE  420
VTHQGLSSPV TKSFNRGEC                                              439

SEQ ID NO: 31          moltype = AA  length = 443
FEATURE                Location/Qualifiers
REGION                 1..443
                       note = Anti-IL-17/IL-20 FIT6-Ig polypeptide
source                 1..443
                       mol_type = protein
                       organism = synthetic construct
SEQUENCE: 31
QVQLVQSGAE VKKPGSSVKV SCKASGYSFT DYHIHWVRQA PGQGLEWMGV INPMYGTTDY  60
NQRFKGRVTI TADESTSTAY MELSSLRSED TAVYYCARYD YFTGTGVYWG QGTLVTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SCGGGGSGSA IQLTQSPSSL  240
SASVGDRVTI TCRASQGISS ALAWYQQKPG KAPKLLIYDA SSLESGVPSR FSGSGSGTDF  300
```

```
TLTISSLQPE DFATYYCQQF NSYPLTFGGG TKVEIKRTVA APSVFIFPPS DEQLKSGTAS  360
VVCLLNNFYP REAKVQWKVD NALQSGNSQE SVTEQDSKDS TYSLSSTLTL SKADYEKHKV  420
YACEVTHQGL SSPVTKSFNR GEC                                          443

SEQ ID NO: 32          moltype = DNA  length = 36
FEATURE                Location/Qualifiers
misc_feature           1..36
                       note = Oligonucleotide primer
source                 1..36
                       mol_type = other DNA
                       organism = synthetic construct
SEQUENCE: 32
gtctgcggcc gctcatttac ccggagacag ggagag                            36

SEQ ID NO: 33          moltype = DNA  length = 40
FEATURE                Location/Qualifiers
misc_feature           1..40
                       note = Oligonucleotide primer
source                 1..40
                       mol_type = other DNA
                       organism = synthetic construct
SEQUENCE: 33
tcgagcggcc gctcaacaag atttgggctc aactttcttg                        40

SEQ ID NO: 34          moltype = DNA  length = 22
FEATURE                Location/Qualifiers
misc_feature           1..22
                       note = Oligonucleotide primer
source                 1..22
                       mol_type = other DNA
                       organism = synthetic construct
SEQUENCE: 34
caggtccagc tgcagcagtc tg                                           22

SEQ ID NO: 35          moltype = DNA  length = 59
FEATURE                Location/Qualifiers
misc_feature           1..59
                       note = Oligonucleotide primer
source                 1..59
                       mol_type = other DNA
                       organism = synthetic construct
SEQUENCE: 35
gcctgcgaag tcacccatca gggcctgagc tcgcccgtca caaagagctt caacagggg   59

SEQ ID NO: 36          moltype = DNA  length = 50
FEATURE                Location/Qualifiers
misc_feature           1..50
                       note = Oligonucleotide primer
source                 1..50
                       mol_type = other DNA
                       organism = synthetic construct
SEQUENCE: 36
tacgagaaac acaaagtcta cgcctgcgaa gtcacccatc agggcctgag             50

SEQ ID NO: 37          moltype = DNA  length = 50
FEATURE                Location/Qualifiers
misc_feature           1..50
                       note = Oligonucleotide primer
source                 1..50
                       mol_type = other DNA
                       organism = synthetic construct
SEQUENCE: 37
tgacgctgag caaagcagac tacgagaaac acaaagtcta cgcctgcgaa             50

SEQ ID NO: 38          moltype = DNA  length = 59
FEATURE                Location/Qualifiers
misc_feature           1..59
                       note = Oligonucleotide primer
source                 1..59
                       mol_type = other DNA
                       organism = synthetic construct
SEQUENCE: 38
ctcgcccgtc acaaagagct tcaacagggg agagtgtgaa gtgcagctgg tggagtctg   59

SEQ ID NO: 39          moltype = DNA  length = 51
FEATURE                Location/Qualifiers
misc_feature           1..51
                       note = Oligonucleotide primer
source                 1..51
```

```
                         mol_type = other DNA
                         organism = synthetic construct
SEQUENCE: 39
gctgctgctg tggttccccg gctcgcgatg cgaaattgtg ttgacacagt c          51

SEQ ID NO: 40            moltype = DNA  length = 52
FEATURE                  Location/Qualifiers
misc_feature             1..52
                         note = Oligonucleotide primer
source                   1..52
                         mol_type = other DNA
                         organism = synthetic construct
SEQUENCE: 40
aagatgaaga cagatggtgc agccaccgta cgtttaatct ccagtcgtgt cc         52

SEQ ID NO: 41            moltype = AA  length = 665
FEATURE                  Location/Qualifiers
REGION                   1..665
                         note = OKT3/Ofatumumab FIT7-Ig polypeptide
source                   1..665
                         mol_type = protein
                         organism = synthetic construct
SEQUENCE: 41
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GECEVQLVES GGGLVQPGRS LRLSCAASGF  240
TFNDYAMHWV RQAPGKGLEW VSTISWNSGS IGYADSVKGR FTISRDNAKK SLYLQMNSLR  300
AEDTALYYCA KDIQYGNYYY GMDVWGQGTT VTVSSASTKG PSVFPLAPSS KSTSGGTAAL  360
GCLVKDYFPE PVTVSWNSGA LTSGVHTFPA VLQSSGLYSL SSVVTVPSSS LGTQTYICNV  420
NHKPSNTKVD KKVEPKSCDK THTCPPCPAP ELLGGPSVFL FPPKPKDTLM ISRTPEVTCV  480
VVDVSHEDPE VKFNWYVDGV EVHNAKTKPR EEQYNSTYRV VSVLTVLHQD WLNGKEYKCK  540
VSNKALPAPI EKTISKAKGQ PREPQVYTLP PSREEMTKNQ VSLTCLVKGF YPSDIAVEWE  600
SNGQPENNYK TTPPVLDSDG SFFLYSKLTV DKSRWQQGNV FSCSVMHEAL HNHYTQKSLS  660
LSPGK                                                             665

SEQ ID NO: 42            moltype = AA  length = 106
FEATURE                  Location/Qualifiers
source                   1..106
                         mol_type = protein
                         organism = Mus sp.
SEQUENCE: 42
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEIN                106

SEQ ID NO: 43            moltype = AA  length = 122
FEATURE                  Location/Qualifiers
source                   1..122
                         mol_type = protein
                         organism = Homo sapiens
SEQUENCE: 43
EVQLVESGGG LVQPGRSLRL SCAASGFTFN DYAMHWVRQA PGKGLEWVST ISWNSGSIGY  60
ADSVKGRFTI SRDNAKKSLY LQMNSLRAED TALYYCAKDI QYGNYYYGMD VWGQGTTVTV  120
SS                                                                122

SEQ ID NO: 44            moltype = AA  length = 222
FEATURE                  Location/Qualifiers
REGION                   1..222
                         note = OKT3/Ofatumumab FIT7-Ig polypeptide
source                   1..222
                         mol_type = protein
                         organism = synthetic construct
SEQUENCE: 44
QVQLQQSGAE LARPGASVKM SCKASGYTFT RYTMHWVKQR PGQGLEWIGY INPSRGYTNY  60
NQKFKDKATL TTDKSSSTAY MQLSSLTSED SAVYYCARYY DDHYCLDYWG QGTTLTVSSA  120
STKGPSVFPL APSSKSTSGG TAALGCLVKD YFPEPVTVSW NSGALTSGVH TFPAVLQSSG  180
LYSLSSVVTV PSSSLGTQTY ICNVNHKPSN TKVDKKVEPK SC                    222

SEQ ID NO: 45            moltype = AA  length = 119
FEATURE                  Location/Qualifiers
source                   1..119
                         mol_type = protein
                         organism = Mus sp.
SEQUENCE: 45
QVQLQQSGAE LARPGASVKM SCKASGYTFT RYTMHWVKQR PGQGLEWIGY INPSRGYTNY  60
NQKFKDKATL TTDKSSSTAY MQLSSLTSED SAVYYCARYY DDHYCLDYWG QGTTLTVSS   119

SEQ ID NO: 46            moltype = AA  length = 214
FEATURE                  Location/Qualifiers
```

```
REGION                1..214
                      note = OKT3/Ofatumumab FIT7-Ig polypeptide
source                1..214
                      mol_type = protein
                      organism = synthetic construct
SEQUENCE: 46
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPITFGQ GTRLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 47         moltype = AA  length = 107
FEATURE               Location/Qualifiers
source                1..107
                      mol_type = protein
                      organism = Homo sapiens
SEQUENCE: 47
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPITFGQ GTRLEIK                107

SEQ ID NO: 48         moltype = AA  length = 672
FEATURE               Location/Qualifiers
REGION                1..672
                      note = OKT3/Ofatumumab FIT8-Ig polypeptide
source                1..672
                      mol_type = protein
                      organism = synthetic construct
SEQUENCE: 48
QIVLTQSPAI MSASPGEKVT MTCSASSSVS YMNWYQQKSG TSPKRWIYDT SKLASGVPAH  60
FRGSGSGTSY SLTISGMEAE DAATYYCQQW SSNPFTFGSG TKLEINRTVA APSVFIFPPS  120
DEQLKSGTAS VVCLLNNFYP REAKVQWKVD NALQSGNSQE SVTEQDSKDS TYSLSSTLTL  180
SKADYEKHKV YACEVTHQGL SSPVTKSFNR GECGGGGSGS EVQLVESGGG LVQPGRSLRL  240
SCAASGFTFN DYAMHWVRQA PGKGLEWVST ISWNSGSIGY ADSVKGRFTI SRDNAKKSLY  300
LQMNSLRAED TALYYCAKDI QYGNYYYGMD VWGQGTTVTV SSASTKGPSV FPLAPSSKST  360
SGGTAALGCL VKDYFPEPVT VSWNSGALTS GVHTFPAVLQ SSGLYSLSSV VTVPSSSLGT  420
QTYICNVNHK PSNTKVDKKV EPKSCDKTHT CPPCPAPELL GGPSVFLFPP KPKDTLMISR  480
TPEVTCVVVD VSHEDPEVKF NWYVDGVEVH NAKTKPREEQ YNSTYRVVSV LTVLHQDWLN  540
GKEYKCKVSN KALPAPIEKT ISKAKGQPRE PQVYTLPPSR EEMTKNQVSL TCLVKGFYPS  600
DIAVEWESNG QPENNYKTTP PVLDSDGSFF LYSKLTVDKS RWQQGNVFSC SVMHEALHNH  660
YTQKSLSLSP GK                                                      672

SEQ ID NO: 49         moltype =   length =
SEQUENCE: 49
000

SEQ ID NO: 50         moltype =   length =
SEQUENCE: 50
000

SEQ ID NO: 51         moltype =   length =
SEQUENCE: 51
000

SEQ ID NO: 52         moltype = AA  length = 4
FEATURE               Location/Qualifiers
REGION                1..4
                      note = peptide linker sequence
source                1..4
                      mol_type = protein
                      organism = synthetic construct
SEQUENCE: 52
GGGS                                                               4

SEQ ID NO: 53         moltype = AA  length = 4
FEATURE               Location/Qualifiers
REGION                1..4
                      note = peptide linker sequence
source                1..4
                      mol_type = protein
                      organism = synthetic construct
SEQUENCE: 53
SGGG                                                               4

SEQ ID NO: 54         moltype = AA  length = 5
FEATURE               Location/Qualifiers
REGION                1..5
                      note = peptide linker sequence
source                1..5
                      mol_type = protein
```

```
                        organism = synthetic construct
SEQUENCE: 54
GGGGS                                                          5

SEQ ID NO: 55           moltype = AA  length = 8
FEATURE                 Location/Qualifiers
REGION                  1..8
                        note = peptide linker sequence
source                  1..8
                        mol_type = protein
                        organism = synthetic construct
SEQUENCE: 55
GGGGSGGS                                                       8

SEQ ID NO: 56           moltype = AA  length = 10
FEATURE                 Location/Qualifiers
REGION                  1..10
                        note = peptide linker sequence
source                  1..10
                        mol_type = protein
                        organism = synthetic construct
SEQUENCE: 56
GGGGSGGGGS                                                     10

SEQ ID NO: 57           moltype = AA  length = 15
FEATURE                 Location/Qualifiers
REGION                  1..15
                        note = peptide linker sequence
source                  1..15
                        mol_type = protein
                        organism = synthetic construct
SEQUENCE: 57
GGGGSGGGGS GGGGS                                               15

SEQ ID NO: 58           moltype = AA  length = 16
FEATURE                 Location/Qualifiers
REGION                  1..16
                        note = peptide linker sequence
source                  1..16
                        mol_type = protein
                        organism = synthetic construct
SEQUENCE: 58
AKTTPKLEEG EFSEAR                                              16

SEQ ID NO: 59           moltype = AA  length = 17
FEATURE                 Location/Qualifiers
REGION                  1..17
                        note = peptide linker sequence
source                  1..17
                        mol_type = protein
                        organism = synthetic construct
SEQUENCE: 59
AKTTPKLEEG EFSEARV                                             17

SEQ ID NO: 60           moltype = AA  length = 9
FEATURE                 Location/Qualifiers
REGION                  1..9
                        note = peptide linker sequence
source                  1..9
                        mol_type = protein
                        organism = synthetic construct
SEQUENCE: 60
AKTTPKLGG                                                      9

SEQ ID NO: 61           moltype = AA  length = 10
FEATURE                 Location/Qualifiers
REGION                  1..10
                        note = peptide linker sequence
source                  1..10
                        mol_type = protein
                        organism = synthetic construct
SEQUENCE: 61
SAKTTPKLGG                                                     10

SEQ ID NO: 62           moltype = AA  length = 16
FEATURE                 Location/Qualifiers
REGION                  1..16
                        note = peptide linker sequence
source                  1..16
```

```
                         mol_type = protein
                         organism = synthetic construct
SEQUENCE: 62
KTTPKLEEGE FSEARV                                                         16

SEQ ID NO: 63            moltype = AA  length = 6
FEATURE                  Location/Qualifiers
REGION                   1..6
                         note = peptide linker sequence
source                   1..6
                         mol_type = protein
                         organism = synthetic construct
SEQUENCE: 63
SAKTTP                                                                    6

SEQ ID NO: 64            moltype = AA  length = 10
FEATURE                  Location/Qualifiers
REGION                   1..10
                         note = peptide linker sequence
source                   1..10
                         mol_type = protein
                         organism = synthetic construct
SEQUENCE: 64
SAKTTPKLGG                                                                10

SEQ ID NO: 65            moltype = AA  length = 6
FEATURE                  Location/Qualifiers
REGION                   1..6
                         note = peptide linker sequence
source                   1..6
                         mol_type = protein
                         organism = synthetic construct
SEQUENCE: 65
RADAAP                                                                    6

SEQ ID NO: 66            moltype = AA  length = 9
FEATURE                  Location/Qualifiers
REGION                   1..9
                         note = peptide linker sequence
source                   1..9
                         mol_type = protein
                         organism = synthetic construct
SEQUENCE: 66
RADAAPTVS                                                                 9

SEQ ID NO: 67            moltype = AA  length = 12
FEATURE                  Location/Qualifiers
REGION                   1..12
                         note = peptide linker sequence
source                   1..12
                         mol_type = protein
                         organism = synthetic construct
SEQUENCE: 67
RADAAAAGGP GS                                                             12

SEQ ID NO: 68            moltype = AA  length = 27
FEATURE                  Location/Qualifiers
REGION                   1..27
                         note = peptide linker sequence
source                   1..27
                         mol_type = protein
                         organism = synthetic construct
SEQUENCE: 68
RADAAAAGGG GSGGGGSGGG GSGGGGS                                             27

SEQ ID NO: 69            moltype = AA  length = 6
FEATURE                  Location/Qualifiers
REGION                   1..6
                         note = peptide linker sequence
source                   1..6
                         mol_type = protein
                         organism = synthetic construct
SEQUENCE: 69
SAKTTP                                                                    6

SEQ ID NO: 70            moltype = AA  length = 10
FEATURE                  Location/Qualifiers
REGION                   1..10
                         note = peptide linker sequence
```

```
source                 1..10
                       mol_type = protein
                       organism = synthetic construct
SEQUENCE: 70
SAKTTPKLGG                                                    10

SEQ ID NO: 71          moltype = AA  length = 18
FEATURE                Location/Qualifiers
REGION                 1..18
                       note = peptide linker sequence
source                 1..18
                       mol_type = protein
                       organism = synthetic construct
SEQUENCE: 71
SAKTTPKLEE GEFSEARV                                           18

SEQ ID NO: 72          moltype = AA  length = 5
FEATURE                Location/Qualifiers
REGION                 1..5
                       note = peptide linker sequence
source                 1..5
                       mol_type = protein
                       organism = synthetic construct
SEQUENCE: 72
ADAAP                                                         5

SEQ ID NO: 73          moltype = AA  length = 12
FEATURE                Location/Qualifiers
REGION                 1..12
                       note = peptide linker sequence
source                 1..12
                       mol_type = protein
                       organism = synthetic construct
SEQUENCE: 73
ADAAPTVSIF PP                                                 12

SEQ ID NO: 74          moltype = AA  length = 5
FEATURE                Location/Qualifiers
REGION                 1..5
                       note = peptide linker sequence
source                 1..5
                       mol_type = protein
                       organism = synthetic construct
SEQUENCE: 74
TVAAP                                                         5

SEQ ID NO: 75          moltype = AA  length = 12
FEATURE                Location/Qualifiers
REGION                 1..12
                       note = peptide linker sequence
source                 1..12
                       mol_type = protein
                       organism = synthetic construct
SEQUENCE: 75
TVAAPSVFIF PP                                                 12

SEQ ID NO: 76          moltype = AA  length = 6
FEATURE                Location/Qualifiers
REGION                 1..6
                       note = peptide linker sequence
source                 1..6
                       mol_type = protein
                       organism = synthetic construct
SEQUENCE: 76
QPKAAP                                                        6

SEQ ID NO: 77          moltype = AA  length = 13
FEATURE                Location/Qualifiers
REGION                 1..13
                       note = peptide linker sequence
source                 1..13
                       mol_type = protein
                       organism = synthetic construct
SEQUENCE: 77
QPKAAPSVTL FPP                                                13

SEQ ID NO: 78          moltype = AA  length = 6
FEATURE                Location/Qualifiers
REGION                 1..6
```

```
                        note = peptide linker sequence
source                  1..6
                        mol_type = protein
                        organism = synthetic construct
SEQUENCE: 78
AKTTPP                                                              6

SEQ ID NO: 79           moltype = AA  length = 13
FEATURE                 Location/Qualifiers
REGION                  1..13
                        note = peptide linker sequence
source                  1..13
                        mol_type = protein
                        organism = synthetic construct
SEQUENCE: 79
AKTTPPSVTP LAP                                                      13

SEQ ID NO: 80           moltype = AA  length = 6
FEATURE                 Location/Qualifiers
REGION                  1..6
                        note = peptide linker sequence
source                  1..6
                        mol_type = protein
                        organism = synthetic construct
SEQUENCE: 80
AKTTAP                                                              6

SEQ ID NO: 81           moltype = AA  length = 13
FEATURE                 Location/Qualifiers
REGION                  1..13
                        note = peptide linker sequence
source                  1..13
                        mol_type = protein
                        organism = synthetic construct
SEQUENCE: 81
AKTTAPSVYP LAP                                                      13

SEQ ID NO: 82           moltype = AA  length = 6
FEATURE                 Location/Qualifiers
REGION                  1..6
                        note = peptide linker sequence
source                  1..6
                        mol_type = protein
                        organism = synthetic construct
SEQUENCE: 82
ASTKGP                                                              6

SEQ ID NO: 83           moltype = AA  length = 13
FEATURE                 Location/Qualifiers
REGION                  1..13
                        note = peptide linker sequence
source                  1..13
                        mol_type = protein
                        organism = synthetic construct
SEQUENCE: 83
ASTKGPSVFP LAP                                                      13

SEQ ID NO: 84           moltype = AA  length = 15
FEATURE                 Location/Qualifiers
REGION                  1..15
                        note = peptide linker sequence
source                  1..15
                        mol_type = protein
                        organism = synthetic construct
SEQUENCE: 84
GENKVEYAPA LMALS                                                    15

SEQ ID NO: 85           moltype = AA  length = 15
FEATURE                 Location/Qualifiers
REGION                  1..15
                        note = peptide linker sequence
source                  1..15
                        mol_type = protein
                        organism = synthetic construct
SEQUENCE: 85
GPAKELTPLK EAKVS                                                    15

SEQ ID NO: 86           moltype = AA  length = 15
FEATURE                 Location/Qualifiers
```

```
REGION              1..15
                    note = peptide linker sequence
source              1..15
                    mol_type = protein
                    organism = synthetic construct
SEQUENCE: 86
GHEAAAVMQV QYPAS                                              15

SEQ ID NO: 87       moltype = AA  length = 664
FEATURE             Location/Qualifiers
REGION              1..664
                    note = TNF/IL-17 FIT9-Ig polypeptide
source              1..664
                    mol_type = protein
                    organism = synthetic construct
SEQUENCE: 87
EIVLTQSPAT LSLSPGERAT LSCRASQSVY SYLAWYQQKP GQAPRLLIYD ASNRATGIPA  60
RFSGSGSGTD FTLTISSLEP EDFAVYYCQQ RSNWPPFTFG PGTKVDIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGECQVQLV QSGAEVKKPG SSVKVSCKAS  240
GYSFTDYHIH WVRQAPGQGL EWMGVINPMY GTTDYNQRFK GRVTITADES TSTAYMELSS  300
LRSEDTAVYY CARYDYFTGT GVYWGQGTLV TVSSASTKGP SVFPLAPSSK STSGGTAALG  360
CLVKDYFPEP VTVSWNSGAL TSGVHTFPAV LQSSGLYSLS SVVTVPSSSL GTQTYICNVN  420
HKPSNTKVDK KVEPKSCDKT HTCPPCPAPE LLGGPSVFLF PPKPKDTLMI SRTPEVTCVV  480
VDVSHEDPEV KFNWYVDGVE VHNAKTKPRE EQYNSTYRVV SVLTVLHQDW LNGKEYKCKV  540
SNKALPAPIE KTISKAKGQP REPQVYTLPP SREEMTKNQV SLTCLVKGFY PSDIAVEWES  600
NGQPENNYKT TPPVLDSDGS FFLYSKLTVD KSRWQQGNVF SCSVMHEALH NHYTQKSLSL  660
SPGK                                                          664

SEQ ID NO: 88       moltype = AA  length = 108
FEATURE             Location/Qualifiers
source              1..108
                    mol_type = protein
                    organism = Homo sapiens
SEQUENCE: 88
EIVLTQSPAT LSLSPGERAT LSCRASQSVY SYLAWYQQKP GQAPRLLIYD ASNRATGIPA  60
RFSGSGSGTD FTLTISSLEP EDFAVYYCQQ RSNWPPFTFG PGTKVDIK              108

SEQ ID NO: 89       moltype = AA  length = 229
FEATURE             Location/Qualifiers
REGION              1..229
                    note = TNF/IL-17 FIT9-Ig polypeptide
source              1..229
                    mol_type = protein
                    organism = synthetic construct
SEQUENCE: 89
QVQLVESGGG VVQPGRSLRL SCAASGFIFS SYAMHWVRQA PGNGLEWVAF MSYDGSNKKY  60
ADSVKGRFTI SRDNSKNTLY LQMNSLRAED TAVYYCARDR GIAAGGNYYY YGMDVWGQGT  120
TVTVSSASTK GPSVFPLAPS SKSTSGGTAA LGCLVKDYFP EPVTVSWNSG ALTSGVHTFP  180
AVLQSSGLYS LSSVVTVPSS SLGTQTYICN VNHKPSNTKV DKKVEPKSC             229

SEQ ID NO: 90       moltype = AA  length = 126
FEATURE             Location/Qualifiers
source              1..126
                    mol_type = protein
                    organism = Homo sapiens
SEQUENCE: 90
QVQLVESGGG VVQPGRSLRL SCAASGFIFS SYAMHWVRQA PGNGLEWVAF MSYDGSNKKY  60
ADSVKGRFTI SRDNSKNTLY LQMNSLRAED TAVYYCARDR GIAAGGNYYY YGMDVWGQGT  120
TVTVSS                                                        126

SEQ ID NO: 91       moltype = AA  length = 219
FEATURE             Location/Qualifiers
REGION              1..219
                    note = TNF/IL-17 FIT9-Ig polypeptide
source              1..219
                    mol_type = protein
                    organism = synthetic construct
SEQUENCE: 91
DIVMTQTPLS LSVTPGQPAS ISCRSSRSLV HSRGNTYLHW YLQKPGQSPQ LLIYKVSNRF  60
IGVPDRFSGS GSGTDFTLKI SRVEAEDVGV YYCSQSTHLP FTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                    219

SEQ ID NO: 92       moltype = AA  length = 658
FEATURE             Location/Qualifiers
REGION              1..658
                    note = CTLA-4/PD-1 FIT10-Ig polypeptide
source              1..658
```

```
                         mol_type = protein
                         organism = synthetic construct
SEQUENCE: 92
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIKRT VAAPSVFIFP  120
PSDEQLKSGT ASVVCLLNNF YPREAKVQWK VDNALQSGNS QESVTEQDSK DSTYSLSSTL  180
TLSKADYEKH KVYACEVTHQ GLSSPVTKSF NRGECQVQLV ESGGGVVQPG RSLRLDCKAS  240
GITFSNSGMH WVRQAPGKGL EWVAVIWYDG SKRYYADSVK GRFTISRDNS KNTLFLQMNS  300
LRAEDTAVYY CATNDDYWGQ GTLVTVSSAS TKGPSVFPLA PSSKSTSGGT AALGCLVKDY  360
FPEPVTVSWN SGALTSGVHT FPAVLQSSGL YSLSSVVTVP SSSLGTQTYI CNVNHKPSNT  420
KVDKKVEPKS CDKTHTCPPC PAPELLGGPS VFLFPPKPKD TLMISRTPEV TCVVVDVSHE  480
DPEVKFNWYV DGVEVHNAKT KPREEQYNST YRVVSVLTVL HQDWLNGKEY KCKVSNKALP  540
APIEKTISKA KGQPREPQVY TLPPSREEMT KNQVSLTCLV KGFYPSDIAV EWESNGQPEN  600
NYKTTPPVLD SDGSFFLYSK LTVDKSRWQQ GNVFSCSVMH EALHNHYTQK SLSLSPGK    658

SEQ ID NO: 93            moltype = AA  length = 108
FEATURE                  Location/Qualifiers
source                   1..108
                         mol_type = protein
                         organism = Homo sapiens
SEQUENCE: 93
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIK               108

SEQ ID NO: 94            moltype = AA  length = 113
FEATURE                  Location/Qualifiers
source                   1..113
                         mol_type = protein
                         organism = Homo sapiens
SEQUENCE: 94
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 95            moltype = AA  length = 221
FEATURE                  Location/Qualifiers
REGION                   1..221
                         note = CTLA-4/PD-1 FIT10-Ig polypeptide
source                   1..221
                         mol_type = protein
                         organism = synthetic construct
SEQUENCE: 95
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSSAS  120
TKGPSVFPLA PSSKSTSGGT AALGCLVKDY FPEPVTVSWN SGALTSGVHT FPAVLQSSGL  180
YSLSSVVTVP SSSLGTQTYI CNVNHKPSNT KVDKKVEPKS C                      221

SEQ ID NO: 96            moltype = AA  length = 118
FEATURE                  Location/Qualifiers
source                   1..118
                         mol_type = protein
                         organism = Homo sapiens
SEQUENCE: 96
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSS    118

SEQ ID NO: 97            moltype = AA  length = 214
FEATURE                  Location/Qualifiers
REGION                   1..214
                         note = CTLA-4/PD-1 FIT10-Ig polypeptide
source                   1..214
                         mol_type = protein
                         organism = synthetic construct
SEQUENCE: 97
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                              214

SEQ ID NO: 98            moltype = AA  length = 107
FEATURE                  Location/Qualifiers
source                   1..107
                         mol_type = protein
                         organism = Homo sapiens
SEQUENCE: 98
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK                107

SEQ ID NO: 99            moltype = AA  length = 689
FEATURE                  Location/Qualifiers
```

```
REGION                  1..689
                        note = EGFR/PD-L1 FIT12a (Pani VL-hCk-1B12VH-hCg1)
source                  1..689
                        mol_type = protein
                        organism = synthetic construct
SEQUENCE: 99
MDMRVPAQLL GLLLLWFPGS RCDIQMTQSP SSLSASVGDR VTITCQASQD ISNYLNWYQQ  60
KPGKAPKLLI YDASNLETGV PSRFSGSGSG TDFTFTISSL QPEDIATYFC QHFDHLPLAF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
VQSGAEVKKP GSSVKVSCKT SGDTFSSYAI SWVRQAPGQG LEWMGGIIPI FGRAHYAQKF  300
QGRVTITADE STSTAYMELS SLRSEDTAVY FCARKFHFVS GSPFGMDVWG QGTTVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPELLGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL PAPIEKTISK AKGQPREPQV YTLPPSREEM  600
TKNQVSLTCL VKGFYPSDIA VEWESNGQPE NNYKTTPPVL DSDGSFFLYS KLTVDKSRWQ  660
QGNVFSCSVM HEALHNHYTQ KSLSLSPGK                                  689

SEQ ID NO: 100          moltype = AA  length = 241
FEATURE                 Location/Qualifiers
source                  1..241
                        mol_type = protein
                        organism = Homo sapiens
SEQUENCE: 100
MEFGLSWLFL VAILKGVQCQ VQLQESGPGL VKPSETLSLT CTVSGGSVSS GDYYWTWIRQ  60
SPGKGLEWIG HIYYSGNTNY NPSLKSRLTI SIDTSKTQFS LKLSSVTAAD TAIYYCVRDR  120
VTGAFDIWGQ GTMVTVSSAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKKVEPKS  240
C                                                                241

SEQ ID NO: 101          moltype = AA  length = 235
FEATURE                 Location/Qualifiers
source                  1..235
                        mol_type = protein
                        organism = Homo sapiens
SEQUENCE: 101
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQRSNWPTFG  120
QGTKVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 102          moltype = AA  length = 685
FEATURE                 Location/Qualifiers
REGION                  1..685
                        note = cMET/EGFR FIT13a polypeptide 1 (h1332
                         VL-hCk-PaniVH-hCg1)
source                  1..685
                        mol_type = protein
                        organism = synthetic construct
SEQUENCE: 102
MDMRVPAQLL GLLLLWFPGS RCDIQMTQSP SSVSASVGDR VTITCRASQG INTWLAWYQQ  60
KPGKAPKLLI YAASSLKSGV PSRFSGSGSG TDFTLTISSL QPEDFATYYC QQANSFPLTF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
QESGPGLVKP SETLSLTCTV SGGSVSSGDY YWTWIRQSPG KGLEWIGHIY YSGNTNYNPS  300
LKSRLTISID TSKTQFSLKL SSVTAADTAI YYCVRDRVTG AFDIWGQGTM VTVSSASTKG  360
PSVFPLAPSS KSTSGGTAAL GCLVKDYFPE PVTVSWNSGA LTSGVHTFPA VLQSSGLYSL  420
SSVVTVPSSS LGTQTYICNV NHKPSNTKVD KKVEPKSCDK THTCPPCPAP ELLGGPSVFL  480
FPPKPKDTLM ISRTPEVTCV VVDVSHEDPE VKFNWYVDGV EVHNAKTKPR EEQYNSTYRV  540
VSVLTVLHQD WLNGKEYKCK VSNKALPAPI EKTISKAKGQ PREPQVYTLP PSREEMTKNQ  600
VSLTCLVKGF YPSDIAVEWE SNGQPENNYK TTPPVLDSDG SFFLYSKLTV DKSRWQQGNV  660
FSCSVMHEAL HNHYTQKSLS LSPGK                                      685

SEQ ID NO: 103          moltype = AA  length = 239
FEATURE                 Location/Qualifiers
source                  1..239
                        mol_type = protein
                        organism = Homo sapiens
SEQUENCE: 103
MEFGLSWLFL VAILKGVQCQ VQLVQSGAEV KKPGASVKVS CKASGYTFTS YGFSWVRQAP  60
GQGLEWMGWI SASNGNTYYA QKLQGRVTMT TDTSTSTAYM ELRSLRSDDT AVYYCARVYA  120
DYADYWGQGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSC   239

SEQ ID NO: 104          moltype = AA  length = 236
FEATURE                 Location/Qualifiers
source                  1..236
                        mol_type = protein
```

```
                          organism = Homo sapiens
SEQUENCE: 104
MDMRVPAQLL GLLLLWFPGS RCDIQMTQSP SSLSASVGDR VTITCQASQD ISNYLNWYQQ  60
KPGKAPKLLI YDASNLETGV PSRFSGSGSG TDFTFTISSL QPEDIATYFC QHFDHLPLAF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 105            moltype = AA  length = 680
FEATURE                   Location/Qualifiers
REGION                    1..680
                          note = Factor IX/Factor X FIT14 polypeptide 1 (FIX
                           VL-hCk-FX-VH-hCg4)
source                    1..680
                          mol_type = protein
                          organism = synthetic construct
SEQUENCE: 105
MDMRVPAQLL GLLLLWFPGS RCDIQMTQSP SSLSASVGDR VTITCKASRN IERQLAWYQQ  60
KPGQAPELLI YQASRKESGV PDRFSGSRYG TDFTLTISSL QPEDIATYYC QQYSDPPLTF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
VQSGSELKKP GASVKVSCKA SGYTFTDNNM DWVRQAPGQG LEWMGDINTR SGGSIYNEEF  300
QDRVIMTVDK STDTAYMELS SLRSEDTATY HCARRKSYGY YLDEWGEGTL VTVSSASTKG  360
PSVFPLAPCS RSTSESTAAL GCLVKDYFPE PVTVSWNSGA LTSGVHTFPA VLQSSGLYSL  420
SSVVTVPSSS LGTQTYTCNV DHKPSNTKVD KRVESKYGPP CPPCPAPEFL GGPSVFLFPP  480
KPKDTLMISR TPEVTCVVVD VSQEDPEVQF NWYVDGVEVH NAKTKPREEQ YNSTYRVVSV  540
LTVLHQDWLN GKEYKCKVSN KGLPSSIEKT ISKAKGQPRE PQVYTLPPSQ EEMTKNQVSL  600
TCLVKGFYPS DIAVEWESNG QPENNYKTTP PVLDSDGSFF LYSKLTVDKS RWQEGNVFSC  660
SVMHEALHNH YTQESLSLSP                                              680

SEQ ID NO: 106            moltype = AA  length = 245
FEATURE                   Location/Qualifiers
source                    1..245
                          mol_type = protein
                          organism = Homo sapiens
SEQUENCE: 106
MEFGLSWLFL VAILKGVQCQ VQLVESGGGL VQPGGSLRLS CAASGFTFSY YDIQWVRQAP  60
GKGLEWVSSI SPSGQSTYYR REVKGRFTIS RDNSKNTLYL QMNSLRAEDT AVYYCARRTG  120
REYGGGWYFD YWGQGTLVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSC                                                              245

SEQ ID NO: 107            moltype = AA  length = 236
FEATURE                   Location/Qualifiers
source                    1..236
                          mol_type = protein
                          organism = Homo sapiens
SEQUENCE: 107
MDMRVPAQLL GLLLLWFPGS RCDIQMTQSP SSLSASVGDR VTITCKASRN IERQLAWYQQ  60
KPGQAPELLI YQASRKESGV PDRFSGSRYG TDFTLTISSL QPEDIATYYC QQYSDPPLTF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 108            moltype = AA  length = 697
FEATURE                   Location/Qualifiers
REGION                    1..697
                          note = Her3/IGF1R FIT16a polypeptide 1(paritu
                           VL-hCk-FigituVH-hCg1)
source                    1..697
                          mol_type = protein
                          organism = synthetic construct
SEQUENCE: 108
MDMRVPAQLL GLLLLWFPGS RCDIEMTQSP DSLAVSLGER ATINCRSSQS VLYSSSNRNY  60
LAWYQQNPGQ PPKLLIYWAS TRESGVPDRF SGSGSGTDFT LTISSLQAED VAVYYCQQYY  120
STPRTFGQGT KVEIKRTVAA PSVFIFPPSD EQLKSGTASV VCLLNNFYPR EAKVQWKVDN  180
ALQSGNSQES VTEQDSKDST YSLSSTLTLS KADYEKHKVY ACEVTHQGLS SPVTKSFNRG  240
ECEVQLLESG GGLVQPGGSL RLSCTASGFT FSSYAMNWVR QAPGKGLEWV SAISGSGGTT  300
FYADSVKGRF TISRDNSRTT LYLQMNSLRA EDTAVYYCAK DLGWSDSYYY YYGMDVWGQG  360
TTVTVSSAST KGPSVFPLAP SSKSTSGGTA ALGCLVKDYF PEPVTVSWNS GALTSGVHTF  420
PAVLQSSGLY SLSSVVTVPS SSLGTQTYIC NVNHKPSNTK VDKKVEPKSC DKTHTCPPCP  480
APELLGGPSV FLFPPKPKDT LMISRTPEVT CVVVDVSHED PEVKFNWYVD GVEVHNAKTK  540
PREEQYNSTY RVVSVLTVLH QDWLNGKEYK CKVSNKALPA PIEKTISKAK GQPREPQVYT  600
LPPSREEMTK NQVSLTCLVK GFYPSDIAVE WESNGQPENN YKTTPPVLDS DGSFFLYSKL  660
TVDKSRWQQG NVFSCSVMHE ALHNHYTQKS LSLSPGK                           697

SEQ ID NO: 109            moltype = AA  length = 239
FEATURE                   Location/Qualifiers
source                    1..239
                          mol_type = protein
                          organism = Homo sapiens
```

```
SEQUENCE: 109
MEFGLSWLFL VAILKGVQCQ VQLQQWGAGL LKPSETLSLT CAVYGGSFSG YYWSWIRQPP  60
GKGLEWIGEI NHSGSTNYNP SLKSRVTISV ETSKNQFSLK LSSVTAADTA VYYCARDKWT  120
WYFDLWGRGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSC   239

SEQ ID NO: 110         moltype = AA  length = 236
FEATURE                Location/Qualifiers
source                 1..236
                       mol_type = protein
                       organism = Homo sapiens
SEQUENCE: 110
MDMRVPAQLL GLLLLWFPGS RCDIQMTQFP SSLSASVGDR VTITCRASQG IRNDLGWYQQ  60
KPGKAPKRLI YAASRLHRGV PSRFSGSGSG TEFTLTISSL QPEDFATYYC LQHNSYPCSF  120
GQGTKLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 111         moltype = AA  length = 693
FEATURE                Location/Qualifiers
REGION                 1..693
                       note = DLL4/VEGF FIT17a polypeptide 1 (Demci VL-hCk-Bevci
                        VH-hCg1)
source                 1..693
                       mol_type = protein
                       organism = synthetic construct
SEQUENCE: 111
MDMRVPAQLL GLLLLWFPGS RCDIVMTQSP DSLAVSLGER ATISCRASES VDNYGISFMK  60
WFQQKPGQPP KLLIYAASNQ GSGVPDRFSG SGSGTDFTLT ISSLQAEDVA VYYCQQSKEV  120
PWTFGGGTKV EIKRTVAAPS VFIFPPSDEQ LKSGTASVVC LLNNFYPREA KVQWKVDNAL  180
QSGNSQESVT EQDSKDSTYS LSSTLTLSKA DYEKHKVYAC EVTHQGLSSP VTKSFNRGEC  240
EVQLVESGGG LVQPGGSLRL SCAASGYTFT NYGMNWVRQA PGKGLEWVGW INTYTGEPTY  300
AADFKRRFTF SLDTSKSTAY LQMNSLRAED TAVYYCAKYP HYYGSSHWYF DVWGQGTLVT  360
VSSASTKGPS VFPLAPSSKS TSGGTAALGC LVKDYFPEPV TVSWNSGALT SGVHTFPAVL  420
QSSGLYSLSS VVTVPSSSLG TQTYICNVNH KPSNTKVDKK VEPKSCDKTH TCPPCPAPEL  480
LGGPSVFLFP PKPKDTLMIS RTPEVTCVVV DVSHEDPEVK FNWYVDGVEV HNAKTKPREE  540
QYNSTYRVVS VLTVLHQDWL NGKEYKCKVS NKALPAPIEK TISKAKGQPR EPQVYTLPPS  600
REEMTKNQVS LTCLVKGFYP SDIAVEWESN GQPENNYKTT PPVLDSDGSF FLYSKLTVDK  660
SRWQQGNVFS CSVMHEALHN HYTQKSLSLS PGK                              693

SEQ ID NO: 112         moltype = AA  length = 241
FEATURE                Location/Qualifiers
source                 1..241
                       mol_type = protein
                       organism = Homo sapiens
SEQUENCE: 112
MEFGLSWLFL VAILKGVQCQ VQLVQSGAEV KKPGASVKIS CKASGYSFTA YYIHWVKQAP  60
GQGLEWIGYI SSYNGATNYN QKFKGRVTFT TDTSTSTAYM ELRSLRSDDT AVYYCARDYD  120
YDVGMDYWGQ GTLVTVSSAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKKVEPKS  240
C                                                                 241

SEQ ID NO: 113         moltype = AA  length = 236
FEATURE                Location/Qualifiers
source                 1..236
                       mol_type = protein
                       organism = Homo sapiens
SEQUENCE: 113
MDMRVPAQLL GLLLLWFPGS RCDIQMTQSP SSLSASVGDR VTITCSASQD ISNYLNWYQQ  60
KPGKAPKVLI YFTSSLHSGV PSRFSGSGSG TDFTLTISSL QPEDFATYYC QQYSTVPWTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 114         moltype = AA  length = 691
FEATURE                Location/Qualifiers
REGION                 1..691
                       note = CD20/CD3 FIT18a polypeptide 1 (OfatuVL-hCk-CD3mAb
                        VH-hCg1mut)
source                 1..691
                       mol_type = protein
                       organism = synthetic construct
SEQUENCE: 114
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQRSNWPITF  120
GQGTRLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECEVQL  240
LESGGGLVQP GGSLKLSCAA SGFTFNTYAM NWVRQAPGKG LEWVARIRSK YNNYATYYAD  300
SVKDRFTISR DDSKNTAYLQ MNNLKTEDTA VYYCVRHGNF GNSYVSWFAY WGQGTLVTVS  360
SASTKGPSVF PLAPSSKSTS GGTAALGCLV KDYFPEPVTV SWNSGALTSG VHTFPAVLQS  420
SGLYSLSSVV TVPSSSLGTQ TYICNVNHKP SNTKVDKKVE PKSCDKTHTC PPCPAPEAAG  480
```

```
GPSVFLFPPK PKDTLMISRT PEVTCVVVDV SHEDPEVKFN WYVDGVEVHN AKTKPREEQY  540
NSTYRVVSVL TVLHQDWLNG KEYKCKVSNK ALPAPIEKTI SKAKGQPREP QVYTLPPSRE  600
EMTKNQVSLT CLVKGFYPSD IAVEWESNGQ PENNYKTTPP VLDSDGSFFL YSKLTVDKSR  660
WQQGNVFSCS VMHEALHNHY TQKSLSLSPG K                                 691

SEQ ID NO: 115          moltype = AA  length = 244
FEATURE                 Location/Qualifiers
source                  1..244
                        mol_type = protein
                        organism = Homo sapiens
SEQUENCE: 115
MEFGLSWLFL VAILKGVQCE VQLVESGGGL VQPGRSLRLS CAASGFTFND YAMHWVRQAP  60
GKGLEWVSTI SWNSGSIGYA DSVKGRFTIS RDNAKKSLYL QMNSLRAEDT ALYYCAKDIQ  120
YGNYYYGMDV WGQGTTVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKKVE  240
PKSC                                                              244

SEQ ID NO: 116          moltype = AA  length = 235
FEATURE                 Location/Qualifiers
source                  1..235
                        mol_type = protein
                        organism = Homo sapiens
SEQUENCE: 116
MTWTPLLFLT LLLHCTGSLS ELVVTQEPSL TVSPGGTVTL TCRSSTGAVT TSNYANWVQQ  60
KPGQAPRGLI GGTNKRAPGT PARFSGSLLG GKAALTLSGV QPEDEAEYYC ALWYSNLWVF  120
GGGTKLTVLG QPKAAPSVTL FPPSSEELQA NKATLVCLIS DFYPGAVTVA WKADSSPVKA  180
GVETTTPSKQ SNNKYAASSY LSLTPEQWKS HRSYSCQVTH EGSTVEKTVA PTECS       235

SEQ ID NO: 117          moltype = AA  length = 691
FEATURE                 Location/Qualifiers
REGION                  1..691
                        note = Her3/EGFR FIT19a polypeptide 1 (patritu
                         VL-hCk-PaniVH-hCg1)
source                  1..691
                        mol_type = protein
                        organism = synthetic construct
SEQUENCE: 117
MDMRVPAQLL GLLLLWFPGS RCDIEMTQSP DSLAVSLGER ATINCRSSQS VLYSSSNRNY  60
LAWYQQNPGQ PPKLLIYWAS TRESGVPDRF SGSGSGTDFT LTISSLQAED VAVYYCQQYY  120
STPRTFGQGT KVEIKRTVAA PSVFIFPPSD EQLKSGTASV VCLLNNFYPR EAKVQWKVDN  180
ALQSGNSQES VTEQDSKDST YSLSSTLTLS KADYEKHKVY ACEVTHQGLS SPVTKSFNRG  240
ECQVQLQESG PGLVKPSETL SLTCTVSGGS VSSGDYYWTW IRQSPGKGLE WIGHIYYSGN  300
TNYNPSLKSR LTISIDTSKT QFSLKLSSVT AADTAIYYCV RDRVTGAFDI WGQGTMVTVS  360
SASTKGPSVF PLAPSSKSTS GGTAALGCLV KDYFPEPVTV SWNSGALTSG VHTFPAVLQS  420
SGLYSLSSVV TVPSSSLGTQ TYICNVNHKP SNTKVDKKVE PKSCDKTHTC PPCPAPELLG  480
GPSVFLFPPK PKDTLMISRT PEVTCVVVDV SHEDPEVKFN WYVDGVEVHN AKTKPREEQY  540
NSTYRVVSVL TVLHQDWLNG KEYKCKVSNK ALPAPIEKTI SKAKGQPREP QVYTLPPSRE  600
EMTKNQVSLT CLVKGFYPSD IAVEWESNGQ PENNYKTTPP VLDSDGSFFL YSKLTVDKSR  660
WQQGNVFSCS VMHEALHNHY TQKSLSLSPG K                                 691

SEQ ID NO: 118          moltype = AA  length = 239
FEATURE                 Location/Qualifiers
source                  1..239
                        mol_type = protein
                        organism = Homo sapiens
SEQUENCE: 118
MEFGLSWLFL VAILKGVQCQ VQLQQWGAGL LKPSETLSLT CAVYGGSFSG YYWSWIRQPP  60
GKGLEWIGEI NHSGSTNYNP SLKSRVTISV ETSKNQFSLK LSSVTAADTA VYYCARDKWT  120
WYFDLWGRGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSC   239

SEQ ID NO: 119          moltype = AA  length = 236
FEATURE                 Location/Qualifiers
source                  1..236
                        mol_type = protein
                        organism = Homo sapiens
SEQUENCE: 119
MDMRVPAQLL GLLLLWFPGS RCDIQMTQSP SSLSASVGDR VTITCQASQD ISNYLNWYQQ  60
KPGKAPKLLI YDASNLETGV PSRFSGSGSG TDFTFTISSL QPEDIATYFC QHFDHLPLAF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 120          moltype = AA  length = 689
FEATURE                 Location/Qualifiers
REGION                  1..689
                        note = PD-1/PD-L1 FIT20a polypeptide 1 (Nivolu VL-hCk-1B12
                         VH-hCg1Mut)
source                  1..689
                        mol_type = protein
```

```
                         organism = synthetic construct
SEQUENCE: 120
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQSSNWPRTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
VQSGAEVKKP GSSVKVSCKT SGDTFSSYAI SWVRQAPGQG LEWMGGIIPI FGRAHYAQKF  300
QGRVTITADE STSTAYMELS SLRSEDTAVY FCARKFHFVS GSPFGMDVWG QGTTVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPELLGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL PAPIEKTISK AKGQPREPQV YTLPPSREEM  600
TKNQVSLTCL VKGFYPSDIA VEWESNGQPE NNYKTTPPVL DSDGSFFLYS KLTVDKSRWQ  660
QGNVFSCSVM HEALHNHYTQ KSLSLSPGK                                   689

SEQ ID NO: 121           moltype = AA  length = 235
FEATURE                  Location/Qualifiers
source                   1..235
                         mol_type = protein
                         organism = Homo sapiens
SEQUENCE: 121
MEFGLSWLFL VAILKGVQCQ VQLVESGGGV VQPGRSLRLD CKASGITFSN SGMHWVRQAP  60
GKGLEWVAVI WYDGSKRYYA DSVKGRFTIS RDNSKNTLFL QMNSLRAEDT AVYYCATNDD  120
YWGQGTLVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKKV EPKSC       235

SEQ ID NO: 122           moltype = AA  length = 235
FEATURE                  Location/Qualifiers
source                   1..235
                         mol_type = protein
                         organism = Homo sapiens
SEQUENCE: 122
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQRSNWPTFG  120
QGTKVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 123           moltype = AA  length = 685
FEATURE                  Location/Qualifiers
REGION                   1..685
                         note = Her3/PD-1 FIT22a polypeptide 1 (patritu
                          VL-hCk-Nivolu VH-hCg1mut)
source                   1..685
                         mol_type = protein
                         organism = synthetic construct
SEQUENCE: 123
MDMRVPAQLL GLLLLWFPGS RCDIEMTQSP DSLAVSLGER ATINCRSSQS VLYSSSNRNY  60
LAWYQQNPGQ PPKLLIYWAS TRESGVPDRF SGSGSGTDFT LTISSLQAED VAVYYCQQYY  120
STPRTFGQGT KVEIKRTVAA PSVFIFPPSD EQLKSGTASV VCLLNNFYPR EAKVQWKVDN  180
ALQSGNSQES VTEQDSKDST YSLSSTLTLS KADYEKHKVY ACEVTHQGLS SPVTKSFNRG  240
ECQVQLVESG GGVVQPGRSL RLDCKASGIT FSNSGMHWVR QAPGKGLEWV AVIWYDGSKR  300
YYADSVKGRF TISRDNSKNT LFLQMNSLRA EDTAVYYCAT NDDYWGQGTL VTVSSASTKG  360
PSVFPLAPSS KSTSGGTAAL GCLVKDYFPE PVTVSWNSGA LTSGVHTFPA VLQSSGLYSL  420
SSVVTVPSSS LGTQTYICNV NHKPSNTKVD KKVEPKSCDK THTCPPCPAP ELLGGPSVFL  480
FPPKPKDTLM ISRTPEVTCV VVDVSHEDPE VKFNWYVDGV EVHNAKTKPR EEQYNSTYRV  540
VSVLTVLHQD WLNGKEYKCK VSNKALPAPI EKTISKAKGQ PREPQVYTLP PSREEMTKNQ  600
VSLTCLVKGF YPSDIAVEWE SNGQPENNYK TTPPVLDSDG SFFLYSKLTV DKSRWQQGNV  660
FSCSVMHEAL HNHYTQKSLS LSPGK                                       685

SEQ ID NO: 124           moltype = AA  length = 239
FEATURE                  Location/Qualifiers
source                   1..239
                         mol_type = protein
                         organism = Homo sapiens
SEQUENCE: 124
MEFGLSWLFL VAILKGVQCQ VQLQQWGAGL LKPSETLSLT CAVYGGSFSG YYWSWIRQPP  60
GKGLEWIGEI NHSGSTNYNP SLKSRVTISV ETSKNQFSLK LSSVTAADTA VYYCARDKWT  120
WYFDLWGRGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSC   239

SEQ ID NO: 125           moltype = AA  length = 236
FEATURE                  Location/Qualifiers
source                   1..236
                         mol_type = protein
                         organism = Homo sapiens
SEQUENCE: 125
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQSSNWPRTF  120
GQGTKVEIKR TVAAPSVFIF PPSDEQLKSG TASVVCLLNN FYPREAKVQW KVDNALQSGN  180
```

```
SQESVTEQDS KDSTYSLSST LTLSKADYEK HKVYACEVTH QGLSSPVTKS FNRGEC      236

SEQ ID NO: 126          moltype = AA  length = 680
FEATURE                 Location/Qualifiers
REGION                  1..680
                        note = Long chain (IpiliVL-hCk-NivoluVH-hCg1mut)
source                  1..680
                        mol_type = protein
                        organism = synthetic construct
SEQUENCE: 126
MDMRVPAQLL GLLLLWFPGS RCEIVLTQSP GTLSLSPGER ATLSCRASQS VGSSYLAWYQ  60
QKPGQAPRLL IYGAFSRATG IPDRFSGSGS GTDFTLTISR LEPEDFAVYY CQQYGSSPWT  120
FGQGTKVEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGECQVQ  240
LVESGGGVVQ PGRSLRLDCK ASGITFSNSG MHWVRQAPGK GLEWVAVIWY DGSKRYYADS  300
VKGRFTISRD NSKNTLFLQM NSLRAEDTAV YYCATNDDYW GQGTLVTVSS ASTKGPSVFP  360
LAPSSKSTSG GTAALGCLVK DYFPEPVTVS WNSGALTSGV HTFPAVLQSS GLYSLSSVVT  420
VPSSSLGTQT YICNVNHKPS NTKVDKKVEP KSCDKTHTCP PCPAPEAAGG PSVFLFPPKP  480
KDTLMISRTP EVTCVVVDVS HEDPEVKFNW YVDGVEVHNA KTKPREEQYN STYRVVSVLT  540
VLHQDWLNGK EYKCKVSNKA LPAPIEKTIS KAKGQPREPQ VYTLPPSREE MTKNQVSLTC  600
LVKGFYPSDI AVEWESNGQP ENNYKTTPPV LDSDGSFFLY SKLTVDKSRW QQGNVFSCSV  660
MHEALHNHYT QKSLSLSPGK                                              680

SEQ ID NO: 127          moltype = AA  length = 108
FEATURE                 Location/Qualifiers
REGION                  1..108
                        note = Ipili VL
source                  1..108
                        mol_type = protein
                        organism = synthetic construct
SEQUENCE: 127
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIK              108

SEQ ID NO: 128          moltype = AA  length = 12
FEATURE                 Location/Qualifiers
REGION                  1..12
                        note = Ipili VL - CDR1
source                  1..12
                        mol_type = protein
                        organism = synthetic construct
SEQUENCE: 128
RASQSVGSSY LA                                                      12

SEQ ID NO: 129          moltype = AA  length = 7
FEATURE                 Location/Qualifiers
REGION                  1..7
                        note = Ipili VL - CDR2
source                  1..7
                        mol_type = protein
                        organism = synthetic construct
SEQUENCE: 129
GAFSRAT                                                            7

SEQ ID NO: 130          moltype = AA  length = 9
FEATURE                 Location/Qualifiers
REGION                  1..9
                        note = Ipili VL - CDR3
source                  1..9
                        mol_type = protein
                        organism = synthetic construct
SEQUENCE: 130
QQYGSSPWT                                                          9

SEQ ID NO: 131          moltype = AA  length = 113
FEATURE                 Location/Qualifiers
REGION                  1..113
                        note = NivoluVH
source                  1..113
                        mol_type = protein
                        organism = synthetic construct
SEQUENCE: 131
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 132          moltype = AA  length = 5
FEATURE                 Location/Qualifiers
REGION                  1..5
                        note = Nivolu VH - CDR1
```

```
source                  1..5
                        mol_type = protein
                        organism = synthetic construct
SEQUENCE: 132
NSGMH                                                                5

SEQ ID NO: 133          moltype = AA  length = 17
FEATURE                 Location/Qualifiers
REGION                  1..17
                        note = Nivolu VH - CDR2
source                  1..17
                        mol_type = protein
                        organism = synthetic construct
SEQUENCE: 133
VIWYDGSKRY YADSVKG                                                   17

SEQ ID NO: 134          moltype = AA  length = 4
FEATURE                 Location/Qualifiers
REGION                  1..4
                        note = Nivolu VH - CDR3
source                  1..4
                        mol_type = protein
                        organism = synthetic construct
SEQUENCE: 134
NDDY                                                                 4

SEQ ID NO: 135          moltype = AA  length = 240
FEATURE                 Location/Qualifiers
REGION                  1..240
                        note = Short Chain 1 (Ipili VH-CH1)
source                  1..240
                        mol_type = protein
                        organism = synthetic construct
SEQUENCE: 135
MEFGLSWLFL VAILKGVQCQ VQLVESGGGV VQPGRSLRLS CAASGFTFSS YTMHWVRQAP  60
GKGLEWVTFI SYDGNNKYYA DSVKGRFTIS RDNSKNTLYL QMNSLRAEDT AIYYCARTGW  120
LGPFDYWGQG TLVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240

SEQ ID NO: 136          moltype = AA  length = 118
FEATURE                 Location/Qualifiers
REGION                  1..118
                        note = Ipili VH
source                  1..118
                        mol_type = protein
                        organism = synthetic construct
SEQUENCE: 136
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSS    118

SEQ ID NO: 137          moltype = AA  length = 5
FEATURE                 Location/Qualifiers
REGION                  1..5
                        note = Ipili VH - CDR1
source                  1..5
                        mol_type = protein
                        organism = synthetic construct
SEQUENCE: 137
SYTMH                                                                5

SEQ ID NO: 138          moltype = AA  length = 17
FEATURE                 Location/Qualifiers
REGION                  1..17
                        note = Ipili VH - CDR2
source                  1..17
                        mol_type = protein
                        organism = synthetic construct
SEQUENCE: 138
FISYDGNNKY YADSVKG                                                   17

SEQ ID NO: 139          moltype = AA  length = 9
FEATURE                 Location/Qualifiers
REGION                  1..9
                        note = Ipili VH - CDR3
source                  1..9
                        mol_type = protein
                        organism = synthetic construct
SEQUENCE: 139
TGWLGPFDY                                                            9
```

```
SEQ ID NO: 140          moltype = AA  length = 236
FEATURE                 Location/Qualifiers
REGION                  1..236
                        note = Short Chain 2 (Nivolu VL-hCK)
source                  1..236
                        mol_type = protein
                        organism = synthetic construct
SEQUENCE: 140
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQSSNWPRTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 141          moltype = AA  length = 107
FEATURE                 Location/Qualifiers
REGION                  1..107
                        note = Nivolu VL
source                  1..107
                        mol_type = protein
                        organism = synthetic construct
SEQUENCE: 141
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK               107

SEQ ID NO: 142          moltype = AA  length = 11
FEATURE                 Location/Qualifiers
REGION                  1..11
                        note = Nivolu VL - CDR1
source                  1..11
                        mol_type = protein
                        organism = synthetic construct
SEQUENCE: 142
RASQSVSSYL A                                                     11

SEQ ID NO: 143          moltype = AA  length = 7
FEATURE                 Location/Qualifiers
REGION                  1..7
                        note = Nivolu VL - CDR2
source                  1..7
                        mol_type = protein
                        organism = synthetic construct
SEQUENCE: 143
DASNRAT                                                          7

SEQ ID NO: 144          moltype = AA  length = 9
FEATURE                 Location/Qualifiers
REGION                  1..9
                        note = Nivolu VL - CDR3
source                  1..9
                        mol_type = protein
                        organism = synthetic construct
SEQUENCE: 144
QQSSNWPRT                                                        9

SEQ ID NO: 145          moltype = AA  length = 684
FEATURE                 Location/Qualifiers
REGION                  1..684
                        note = Long Chain (Nivolu VL-hCk-Ipili VH-hCg1mut)
source                  1..684
                        mol_type = protein
                        organism = synthetic construct
SEQUENCE: 145
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQSSNWPRTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
VESGGGVVQP GRSLRLSCAA SGFTFSSYTM HWVRQAPGKG LEWVTFISYD GNNKYYADSV  300
KGRFTISRDN SKNTLYLQMN SLRAEDTAIY YCARTGWLGP FDYWGQGTLV TVSSASTKGP  360
SVFPLAPSSK STSGGTAALG CLVKDYFPEP VTVSWNSGAL TSGVHTFPAV LQSSGLYSLS  420
SVVTVPSSSL GTQTYICNVN HKPSNTKVDK KVEPKSCDKT HTCPPCPAPE AAGGPSVFLF  480
PPKPKDTLMI SRTPEVTCVV VDVSHEDPEV KFNWYVDGVE VHNAKTKPRE EQYNSTYRVV  540
SVLTVLHQDW LNGKEYKCKV SNKALPAPIE KTISKAKGQP REPQVYTLPP SREEMTKNQV  600
SLTCLVKGFY PSDIAVEWES NGQPENNYKT TPPVLDSDGS FFLYSKLTVD KSRWQQGNVF  660
SCSVMHEALH NHYTQKSLSL SPGK                                       684

SEQ ID NO: 146          moltype = AA  length = 107
FEATURE                 Location/Qualifiers
REGION                  1..107
```

```
                         note = Nivolu VL
source                   1..107
                         mol_type = protein
                         organism = synthetic construct
SEQUENCE: 146
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK                107

SEQ ID NO: 147           moltype = AA  length = 11
FEATURE                  Location/Qualifiers
REGION                   1..11
                         note = Nivolu VL - CDR1
source                   1..11
                         mol_type = protein
                         organism = synthetic construct
SEQUENCE: 147
RASQSVSSYL A                                                       11

SEQ ID NO: 148           moltype = AA  length = 7
FEATURE                  Location/Qualifiers
REGION                   1..7
                         note = Nivolu VL - CDR2
source                   1..7
                         mol_type = protein
                         organism = synthetic construct
SEQUENCE: 148
DASNRAT                                                            7

SEQ ID NO: 149           moltype = AA  length = 9
FEATURE                  Location/Qualifiers
REGION                   1..9
                         note = Nivolu VL - CDR3
source                   1..9
                         mol_type = protein
                         organism = synthetic construct
SEQUENCE: 149
QQSSNWPRT                                                          9

SEQ ID NO: 150           moltype = AA  length = 118
FEATURE                  Location/Qualifiers
REGION                   1..118
                         note = Ipili VH
source                   1..118
                         mol_type = protein
                         organism = synthetic construct
SEQUENCE: 150
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSS    118

SEQ ID NO: 151           moltype = AA  length = 5
FEATURE                  Location/Qualifiers
REGION                   1..5
                         note = Ipili VH - CDR1
source                   1..5
                         mol_type = protein
                         organism = synthetic construct
SEQUENCE: 151
SYTMH                                                              5

SEQ ID NO: 152           moltype = AA  length = 17
FEATURE                  Location/Qualifiers
REGION                   1..17
                         note = Ipili VH - CDR2
source                   1..17
                         mol_type = protein
                         organism = synthetic construct
SEQUENCE: 152
FISYDGNNKY YADSVKG                                                 17

SEQ ID NO: 153           moltype = AA  length = 9
FEATURE                  Location/Qualifiers
REGION                   1..9
                         note = Ipili VH - CDR3
source                   1..9
                         mol_type = protein
                         organism = synthetic construct
SEQUENCE: 153
TGWLGPFDY                                                          9
```

```
SEQ ID NO: 154          moltype = AA  length = 235
FEATURE                 Location/Qualifiers
REGION                  1..235
                        note = Short Chain 1 (Nivolu VH-CH1)
source                  1..235
                        mol_type = protein
                        organism = synthetic construct
SEQUENCE: 154
MEFGLSWLFL VAILKGVQCQ VQLVESGGGV VQPGRSLRLD CKASGITFSN SGMHWVRQAP  60
GKGLEWVAVI WYDGSKRYYA DSVKGRFTIS RDNSKNTLFL QMNSLRAEDT AVYYCATNDD  120
YWGQGTLVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKKV EPKSC       235

SEQ ID NO: 155          moltype = AA  length = 113
FEATURE                 Location/Qualifiers
REGION                  1..113
                        note = Nivolu VH
source                  1..113
                        mol_type = protein
                        organism = synthetic construct
SEQUENCE: 155
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 156          moltype =   length =
SEQUENCE: 156
000

SEQ ID NO: 157          moltype = AA  length = 17
FEATURE                 Location/Qualifiers
REGION                  1..17
                        note = Nivolu VH - CDR2
source                  1..17
                        mol_type = protein
                        organism = synthetic construct
SEQUENCE: 157
VIWYDGSKRY YADSVKG                                                 17

SEQ ID NO: 158          moltype = AA  length = 4
FEATURE                 Location/Qualifiers
REGION                  1..4
                        note = Nivolu VH - CDR3
source                  1..4
                        mol_type = protein
                        organism = synthetic construct
SEQUENCE: 158
NDDY                                                               4

SEQ ID NO: 159          moltype = AA  length = 237
FEATURE                 Location/Qualifiers
REGION                  1..237
                        note = Short Chain 2 (Ipili VL-hCK)
source                  1..237
                        mol_type = protein
                        organism = synthetic construct
SEQUENCE: 159
MDMRVPAQLL GLLLLWFPGS RCEIVLTQSP GTLSLSPGER ATLSCRASQS VGSSYLAWYQ  60
QKPGQAPRLL IYGAFSRATG IPDRFSGSGS GTDFTLTISR LEPEDFAVYY CQQYGSSPWT  120
FGQGTKVEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 160          moltype = AA  length = 108
FEATURE                 Location/Qualifiers
REGION                  1..108
                        note = Ipili VL
source                  1..108
                        mol_type = protein
                        organism = synthetic construct
SEQUENCE: 160
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIK               108

SEQ ID NO: 161          moltype = AA  length = 12
FEATURE                 Location/Qualifiers
REGION                  1..12
                        note = Ipili VL - CDR1
source                  1..12
                        mol_type = protein
                        organism = synthetic construct
```

```
SEQUENCE: 161
RASQSVGSSY LA                                                   12

SEQ ID NO: 162          moltype = AA  length = 7
FEATURE                 Location/Qualifiers
REGION                  1..7
                        note = Ipili VL - CDR2
source                  1..7
                        mol_type = protein
                        organism = synthetic construct
SEQUENCE: 162
GAFSRAT                                                         7

SEQ ID NO: 163          moltype = AA  length = 7
FEATURE                 Location/Qualifiers
REGION                  1..7
                        note = Ipili VL - CDR3
source                  1..7
                        mol_type = protein
                        organism = synthetic construct
SEQUENCE: 163
YGSSPWT                                                         7

SEQ ID NO: 164          moltype = AA  length = 677
FEATURE                 Location/Qualifiers
REGION                  1..677
                        note = Long Chain (IpiliVL-hCk-NivoluVH-hCg4)
source                  1..677
                        mol_type = protein
                        organism = synthetic construct
SEQUENCE: 164
MDMRVPAQLL GLLLLWFPGS RCEIVLTQSP GTLSLSPGER ATLSCRASQS VGSSYLAWYQ  60
QKPGQAPRLL IYGAFSRATG IPDRFSGSGS GTDFTLTISR LEPEDFAVYY CQQYGSSPWT  120
FGQGTKVEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGECQVQ  240
LVESGGGVVQ PGRSLRLDCK ASGITFSNSG MHWVRQAPGK GLEWVAVIWY DGSKRYYADS  300
VKGRFTISRD NSKNTLFLQM NSLRAEDTAV YYCATNDDYW GQGTLVTVSS ASTKGPSVFP  360
LAPCSRSTSE STAALGCLVK DYFPEPVTVS WNSGALTSGV HTFPAVLQSS GLYSLSSVVT  420
VPSSSLGTKT YTCNVDHKPS NTKVDKRVES KYGPPCPPCP APEFLGGPSV FLFPPKPKDT  480
LMISRTPEVT CVVVDVSQED PEVQFNWYVD GVEVHNAKTK PREEQFNSTY RVVSVLTVLH  540
QDWLNGKEYK CKVSNKGLPS SIEKTISKAK GQPREPQVYT LPPSQEEMTK NQVSLTCLVK  600
GFYPSDIAVE WESNGQPENN YKTTPPVLDS DGSFFLYSRL TVDKSRWQEG NVFSCSVMHE  660
ALHNHYTQKS LSLSLGK                                              677

SEQ ID NO: 165          moltype = AA  length = 108
FEATURE                 Location/Qualifiers
REGION                  1..108
                        note = IpiliVL
source                  1..108
                        mol_type = protein
                        organism = synthetic construct
SEQUENCE: 165
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIK             108

SEQ ID NO: 166          moltype = AA  length = 12
FEATURE                 Location/Qualifiers
REGION                  1..12
                        note = IpiliVL - CDR1
source                  1..12
                        mol_type = protein
                        organism = synthetic construct
SEQUENCE: 166
RASQSVGSSY LA                                                   12

SEQ ID NO: 167          moltype = AA  length = 7
FEATURE                 Location/Qualifiers
REGION                  1..7
                        note = IpiliVL - CDR2
source                  1..7
                        mol_type = protein
                        organism = synthetic construct
SEQUENCE: 167
GAFSRAT                                                         7

SEQ ID NO: 168          moltype = AA  length = 6
FEATURE                 Location/Qualifiers
REGION                  1..6
                        note = IpiliVL - CDR3
```

```
source                  1..6
                        mol_type = protein
                        organism = synthetic construct
SEQUENCE: 168
QQYGSS                                                                   6

SEQ ID NO: 169          moltype = AA  length = 113
FEATURE                 Location/Qualifiers
REGION                  1..113
                        note = NivoluVH
source                  1..113
                        mol_type = protein
                        organism = synthetic construct
SEQUENCE: 169
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 170          moltype = AA  length = 5
FEATURE                 Location/Qualifiers
REGION                  1..5
                        note = NivoluVH - CDR1
source                  1..5
                        mol_type = protein
                        organism = synthetic construct
SEQUENCE: 170
NSGMH                                                                    5

SEQ ID NO: 171          moltype = AA  length = 17
FEATURE                 Location/Qualifiers
REGION                  1..17
                        note = NivoluVH - CDR2
source                  1..17
                        mol_type = protein
                        organism = synthetic construct
SEQUENCE: 171
VIWYDGSKRY YADSVKG                                                       17

SEQ ID NO: 172          moltype = AA  length = 4
FEATURE                 Location/Qualifiers
REGION                  1..4
                        note = NivoluVH - CDR3
source                  1..4
                        mol_type = protein
                        organism = synthetic construct
SEQUENCE: 172
NDDY                                                                     4

SEQ ID NO: 173          moltype = AA  length = 240
FEATURE                 Location/Qualifiers
REGION                  1..240
                        note = Short Chain 1 (Ipili VH-CH1)
source                  1..240
                        mol_type = protein
                        organism = synthetic construct
SEQUENCE: 173
MEFGLSWLFL VAILKGVQCQ VQLVESGGGV VQPGRSLRLS CAASGFTFSS YTMHWVRQAP  60
GKGLEWVTFI SYDGNNKYYA DSVKGRFTIS RDNSKNTLYL QMNSLRAEDT AIYYCARTGW  120
LGPFDYWGQG TLVTVSSAST KGPSVFPLAP SSKSTSGGTA ALGCLVKDYF PEPVTVSWNS  180
GALTSGVHTF PAVLQSSGLY SLSSVVTVPS SSLGTQTYIC NVNHKPSNTK VDKKVEPKSC  240

SEQ ID NO: 174          moltype = AA  length = 118
FEATURE                 Location/Qualifiers
REGION                  1..118
                        note = Ipili VH
source                  1..118
                        mol_type = protein
                        organism = synthetic construct
SEQUENCE: 174
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSS    118

SEQ ID NO: 175          moltype = AA  length = 5
FEATURE                 Location/Qualifiers
REGION                  1..5
                        note = Ipili VH - CDR1
source                  1..5
                        mol_type = protein
                        organism = synthetic construct
SEQUENCE: 175
```

```
SYTMH                                                          5

SEQ ID NO: 176          moltype = AA  length = 17
FEATURE                 Location/Qualifiers
REGION                  1..17
                        note = Ipili VH - CDR2
source                  1..17
                        mol_type = protein
                        organism = synthetic construct
SEQUENCE: 176
FISYDGNNKY YADSVKG                                             17

SEQ ID NO: 177          moltype = AA  length = 9
FEATURE                 Location/Qualifiers
REGION                  1..9
                        note = Ipili VH - CDR3
source                  1..9
                        mol_type = protein
                        organism = synthetic construct
SEQUENCE: 177
TGWLGPFDY                                                      9

SEQ ID NO: 178          moltype = AA  length = 236
FEATURE                 Location/Qualifiers
REGION                  1..236
                        note = Short Chain 2 (Nivolu VL-hCK)
source                  1..236
                        mol_type = protein
                        organism = synthetic construct
SEQUENCE: 178
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQSSNWPRTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 179          moltype = AA  length = 107
FEATURE                 Location/Qualifiers
REGION                  1..107
                        note = Nivolu VL
source                  1..107
                        mol_type = protein
                        organism = synthetic construct
SEQUENCE: 179
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK               107

SEQ ID NO: 180          moltype = AA  length = 11
FEATURE                 Location/Qualifiers
REGION                  1..11
                        note = Nivolu VL - CDR1
source                  1..11
                        mol_type = protein
                        organism = synthetic construct
SEQUENCE: 180
RASQSVSSYL A                                                   11

SEQ ID NO: 181          moltype = AA  length = 7
FEATURE                 Location/Qualifiers
REGION                  1..7
                        note = Nivolu VL - CDR2
source                  1..7
                        mol_type = protein
                        organism = synthetic construct
SEQUENCE: 181
DASNRAT                                                        7

SEQ ID NO: 182          moltype = AA  length = 9
FEATURE                 Location/Qualifiers
REGION                  1..9
                        note = Nivolu VL - CDR3
source                  1..9
                        mol_type = protein
                        organism = synthetic construct
SEQUENCE: 182
QQSSNWPRT                                                      9

SEQ ID NO: 183          moltype = AA  length = 684
FEATURE                 Location/Qualifiers
REGION                  1..684
```

```
                        note = Long Chain (Nivolu VL-hCk-Ipili VH-hCg1mut)
source                  1..684
                        mol_type = protein
                        organism = synthetic construct
SEQUENCE: 183
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQSSNWPRTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
VESGGGVVQP GRSLRLSCAA SGFTFSSYTM HWVRQAPGKG LEWVTFISYD GNNKYYADSV  300
KGRFTISRDN SKNTLYLQMN SLRAEDTAIY YCARTGWLGP FDYWGQGTLV TVSSASTKGP  360
SVFPLAPSSK STSGGTAALG CLVKDYFPEP VTVSWNSGAL TSGVHTFPAV LQSSGLYSLS  420
SVVTVPSSSL GTQTYICNVN HKPSNTKVDK KVEPKSCDKT HTCPPCPAPE AAGGPSVFLF  480
PPKPKDTLMI SRTPEVTCVV VDVSHEDPEV KFNWYVDGVE VHNAKTKPRE EQYNSTYRVV  540
SVLTVLHQDW LNGKEYKCKV SNKALPAPIE KTISKAKGQP REPQVYTLPP SREEMTKNQV  600
SLTCLVKGFY PSDIAVEWES NGQPENNYKT TPPVLDSDGS FFLYSKLTVD KSRWQQGNVF  660
SCSVMHEALH NHYTQKSLSL SPGK                                        684

SEQ ID NO: 184          moltype = AA  length = 107
FEATURE                 Location/Qualifiers
REGION                  1..107
                        note = Nivolu VL
source                  1..107
                        mol_type = protein
                        organism = synthetic construct
SEQUENCE: 184
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK               107

SEQ ID NO: 185          moltype = AA  length = 11
FEATURE                 Location/Qualifiers
REGION                  1..11
                        note = Nivolu VL - CDR1
source                  1..11
                        mol_type = protein
                        organism = synthetic construct
SEQUENCE: 185
RASQSVSSYL A                                                      11

SEQ ID NO: 186          moltype = AA  length = 7
FEATURE                 Location/Qualifiers
REGION                  1..7
                        note = Nivolu VL - CDR2
source                  1..7
                        mol_type = protein
                        organism = synthetic construct
SEQUENCE: 186
DASNRAT                                                           7

SEQ ID NO: 187          moltype = AA  length = 9
FEATURE                 Location/Qualifiers
REGION                  1..9
                        note = Nivolu VL - CDR3
source                  1..9
                        mol_type = protein
                        organism = synthetic construct
SEQUENCE: 187
QQSSNWPRT                                                         9

SEQ ID NO: 188          moltype = AA  length = 118
FEATURE                 Location/Qualifiers
REGION                  1..118
                        note = Ipili VH
source                  1..118
                        mol_type = protein
                        organism = synthetic construct
SEQUENCE: 188
QVQLVESGGG VVQPGRSLRL SCAASGFTFS SYTMHWVRQA PGKGLEWVTF ISYDGNNKYY  60
ADSVKGRFTI SRDNSKNTLY LQMNSLRAED TAIYYCARTG WLGPFDYWGQ GTLVTVSS   118

SEQ ID NO: 189          moltype = AA  length = 5
FEATURE                 Location/Qualifiers
REGION                  1..5
                        note = Ipili VH - CDR1
source                  1..5
                        mol_type = protein
                        organism = synthetic construct
SEQUENCE: 189
SYTMH                                                             5
```

```
SEQ ID NO: 190          moltype = AA  length = 17
FEATURE                 Location/Qualifiers
REGION                  1..17
                        note = Ipili VH - CDR2
source                  1..17
                        mol_type = protein
                        organism = synthetic construct
SEQUENCE: 190
FISYDGNNKY YADSVKG                                                17

SEQ ID NO: 191          moltype = AA  length = 9
FEATURE                 Location/Qualifiers
REGION                  1..9
                        note = Ipili VH - CDR3
source                  1..9
                        mol_type = protein
                        organism = synthetic construct
SEQUENCE: 191
TGWLGPFDY                                                         9

SEQ ID NO: 192          moltype = AA  length = 232
FEATURE                 Location/Qualifiers
REGION                  1..232
                        note = Short Chain 1 (Nivolu VH-IgG4-CH1)
source                  1..232
                        mol_type = protein
                        organism = synthetic construct
SEQUENCE: 192
MEFGLSWLFL VAILKGVQCQ VQLVESGGGV VQPGRSLRLD CKASGITFSN SGMHWVRQAP  60
GKGLEWVAVI WYDGSKRYYA DSVKGRFTIS RDNSKNTLFL QMNSLRAEDT AVYYCATNDD  120
YWGQGTLVTV SSASTKGPSV FPLAPCSRST SESTAALGCL VKDYFPEPVT VSWNSGALTS  180
GVHTFPAVLQ SSGLYSLSSV VTVPSSSLGT KTYTCNVDHK PSNTKVDKRV ES          232

SEQ ID NO: 193          moltype = AA  length = 113
FEATURE                 Location/Qualifiers
REGION                  1..113
                        note = Nivolu VH
source                  1..113
                        mol_type = protein
                        organism = synthetic construct
SEQUENCE: 193
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 194          moltype = AA  length = 5
FEATURE                 Location/Qualifiers
REGION                  1..5
                        note = Nivolu VH - CDR1
source                  1..5
                        mol_type = protein
                        organism = synthetic construct
SEQUENCE: 194
NSGMH                                                             5

SEQ ID NO: 195          moltype = AA  length = 17
FEATURE                 Location/Qualifiers
REGION                  1..17
                        note = Nivolu VH - CDR2
source                  1..17
                        mol_type = protein
                        organism = synthetic construct
SEQUENCE: 195
VIWYDGSKRY YADSVKG                                                17

SEQ ID NO: 196          moltype = AA  length = 4
FEATURE                 Location/Qualifiers
REGION                  1..4
                        note = Nivolu VH - CDR3
source                  1..4
                        mol_type = protein
                        organism = synthetic construct
SEQUENCE: 196
NDDY                                                              4

SEQ ID NO: 197          moltype = AA  length = 237
FEATURE                 Location/Qualifiers
REGION                  1..237
                        note = Short Chain 2 (Ipili VL-hCK)
```

```
source                  1..237
                        mol_type = protein
                        organism = synthetic construct
SEQUENCE: 197
MDMRVPAQLL GLLLLWFPGS RCEIVLTQSP GTLSLSPGER ATLSCRASQS VGSSYLAWYQ  60
QKPGQAPRLL IYGAFSRATG IPDRFSGSGS GTDFTLTISR LEPEDFAVYY CQQYGSSPWT  120
FGQGTKVEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 198          moltype = AA  length = 108
FEATURE                 Location/Qualifiers
REGION                  1..108
                        note = Ipili VL
source                  1..108
                        mol_type = protein
                        organism = synthetic construct
SEQUENCE: 198
EIVLTQSPGT LSLSPGERAT LSCRASQSVG SSYLAWYQQK PGQAPRLLIY GAFSRATGIP  60
DRFSGSGSGT DFTLTISRLE PEDFAVYYCQ QYGSSPWTFG QGTKVEIK               108

SEQ ID NO: 199          moltype = AA  length = 12
FEATURE                 Location/Qualifiers
REGION                  1..12
                        note = Ipili VL - CDR1
source                  1..12
                        mol_type = protein
                        organism = synthetic construct
SEQUENCE: 199
RASQSVGSSY LA                                                      12

SEQ ID NO: 200          moltype = AA  length = 7
FEATURE                 Location/Qualifiers
REGION                  1..7
                        note = Ipili VL - CDR2
source                  1..7
                        mol_type = protein
                        organism = synthetic construct
SEQUENCE: 200
GAFSRAT                                                            7

SEQ ID NO: 201          moltype = AA  length = 9
FEATURE                 Location/Qualifiers
REGION                  1..9
                        note = Ipili VL - CDR3
source                  1..9
                        mol_type = protein
                        organism = synthetic construct
SEQUENCE: 201
QQYGSSPWT                                                          9

SEQ ID NO: 202          moltype = AA  length = 689
FEATURE                 Location/Qualifiers
REGION                  1..689
                        note = Long Chain (Pani VL-hCk-1B12VH-hCg1)
source                  1..689
                        mol_type = protein
                        organism = synthetic construct
SEQUENCE: 202
MDMRVPAQLL GLLLLWFPGS RCDIQMTQSP SSLSASVGDR VTITCQASQD ISNYLNWYQQ  60
KPGKAPKLLI YDASNLETGV PSRFSGSGSG TDFTFTISSL QPEDIATYFC QHFDHLPLAF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
VQSGAEVKKP GSSVKVSCKT SGDTFSSYAI SWVRQAPGQG LEWMGGIIPI FGRAHYAQKF  300
QGRVTITADE STSTAYMELS SLRSEDTAVY FCARKFHFVS GSPFGMDVWG QGTTVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPELLGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL PAPIEKTISK AKGQPREPQV YTLPPSREEM  600
TKNQVSLTCL VKGFYPSDIA VEWESNGQPE NNYKTTPPVL DSDGSFFLYS KLTVDKSRWQ  660
QGNVFSCSVM HEALHNHYTQ KSLSLSPGK                                    689

SEQ ID NO: 203          moltype = AA  length = 107
FEATURE                 Location/Qualifiers
REGION                  1..107
                        note = Pani VL
source                  1..107
                        mol_type = protein
                        organism = synthetic construct
SEQUENCE: 203
```

```
DIQMTQSPSS LSASVGDRVT ITCQASQDIS NYLNWYQQKP GKAPKLLIYD ASNLETGVPS  60
RFSGSGSGTD FTFTISSLQP EDIATYFCQH FDHLPLAFGG GTKVEIK               107

SEQ ID NO: 204          moltype = AA  length = 11
FEATURE                 Location/Qualifiers
REGION                  1..11
                        note = Pani VL - CDR1
source                  1..11
                        mol_type = protein
                        organism = synthetic construct
SEQUENCE: 204
QASQDISNYL N                                                       11

SEQ ID NO: 205          moltype = AA  length = 7
FEATURE                 Location/Qualifiers
REGION                  1..7
                        note = Pani VL - CDR2
source                  1..7
                        mol_type = protein
                        organism = synthetic construct
SEQUENCE: 205
DASNLET                                                            7

SEQ ID NO: 206          moltype = AA  length = 9
FEATURE                 Location/Qualifiers
REGION                  1..9
                        note = Pani VL - CDR3
source                  1..9
                        mol_type = protein
                        organism = synthetic construct
SEQUENCE: 206
QHFDHLPLA                                                          9

SEQ ID NO: 207          moltype = AA  length = 123
FEATURE                 Location/Qualifiers
REGION                  1..123
                        note = 1B12VH
source                  1..123
                        mol_type = protein
                        organism = synthetic construct
SEQUENCE: 207
QVQLVQSGAE VKKPGSSVKV SCKTSGDTFS SYAISWVRQA PGQGLEWMGG IIPIFGRAHY  60
AQKFQGRVTI TADESTSTAY MELSSLRSED TAVYFCARKF HFVSGSPFGM DVWGQGTTVT  120
VSS                                                                123

SEQ ID NO: 208          moltype = AA  length = 5
FEATURE                 Location/Qualifiers
REGION                  1..5
                        note = 1B12VH - CDR1
source                  1..5
                        mol_type = protein
                        organism = synthetic construct
SEQUENCE: 208
SYAIS                                                              5

SEQ ID NO: 209          moltype = AA  length = 17
FEATURE                 Location/Qualifiers
REGION                  1..17
                        note = 1B12VH - CDR2
source                  1..17
                        mol_type = protein
                        organism = synthetic construct
SEQUENCE: 209
GIIPIFGRAH YAQKFQG                                                 17

SEQ ID NO: 210          moltype = AA  length = 14
FEATURE                 Location/Qualifiers
REGION                  1..14
                        note = 1B12VH - CDR3
source                  1..14
                        mol_type = protein
                        organism = synthetic construct
SEQUENCE: 210
KFHFVSGSPF GMDV                                                    14

SEQ ID NO: 211          moltype = AA  length = 241
FEATURE                 Location/Qualifiers
REGION                  1..241
                        note = Short Chain 1 (Pani VH-CH1h)
```

```
source                  1..241
                        mol_type = protein
                        organism = synthetic construct
SEQUENCE: 211
MEFGLSWLFL VAILKGVQCQ VQLQESGPGL VKPSETLSLT CTVSGGSVSS GDYYWTWIRQ  60
SPGKGLEWIG HIYYSGNTNY NPSLKSRLTI SIDTSKTQFS LKLSSVTAAD TAIYYCVRDR  120
VTGAFDIWGQ GTMVTVSSAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKKVEPKS  240
C                                                                 241

SEQ ID NO: 212          moltype = AA  length = 119
FEATURE                 Location/Qualifiers
REGION                  1..119
                        note = Pani VH
source                  1..119
                        mol_type = protein
                        organism = synthetic construct
SEQUENCE: 212
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSS   119

SEQ ID NO: 213          moltype = AA  length = 7
FEATURE                 Location/Qualifiers
REGION                  1..7
                        note = Pani VH - CDR1
source                  1..7
                        mol_type = protein
                        organism = synthetic construct
SEQUENCE: 213
SGDYYWT                                                           7

SEQ ID NO: 214          moltype = AA  length = 16
FEATURE                 Location/Qualifiers
REGION                  1..16
                        note = Pani VH - CDR2
source                  1..16
                        mol_type = protein
                        organism = synthetic construct
SEQUENCE: 214
HIYYSGNTNY NPSLKS                                                 16

SEQ ID NO: 215          moltype = AA  length = 9
FEATURE                 Location/Qualifiers
REGION                  1..9
                        note = Pani VH - CDR3
source                  1..9
                        mol_type = protein
                        organism = synthetic construct
SEQUENCE: 215
DRVTGAFDI                                                         9

SEQ ID NO: 216          moltype = AA  length = 235
FEATURE                 Location/Qualifiers
REGION                  1..235
                        note = Short Chain 2 (1B12 VL-hCk)
source                  1..235
                        mol_type = protein
                        organism = synthetic construct
SEQUENCE: 216
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQRSNWPTFG  120
QGTKVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 217          moltype = AA  length = 106
FEATURE                 Location/Qualifiers
REGION                  1..106
                        note = 1B12 VL
source                  1..106
                        mol_type = protein
                        organism = synthetic construct
SEQUENCE: 217
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                106

SEQ ID NO: 218          moltype = AA  length = 11
FEATURE                 Location/Qualifiers
REGION                  1..11
                        note = 1B12 VL - CDR1
```

```
source                  1..11
                        mol_type = protein
                        organism = synthetic construct
SEQUENCE: 218
RASQSVSSYL A                                                        11

SEQ ID NO: 219          moltype = AA  length = 7
FEATURE                 Location/Qualifiers
REGION                  1..7
                        note = 1B12 VL - CDR2
source                  1..7
                        mol_type = protein
                        organism = synthetic construct
SEQUENCE: 219
DASNRAT                                                             7

SEQ ID NO: 220          moltype = AA  length = 8
FEATURE                 Location/Qualifiers
REGION                  1..8
                        note = 1B12 VL - CDR3
source                  1..8
                        mol_type = protein
                        organism = synthetic construct
SEQUENCE: 220
QQRSNWPT                                                            8

SEQ ID NO: 221          moltype = AA  length = 684
FEATURE                 Location/Qualifiers
REGION                  1..684
                        note = Long Chain (Pani VL-hCk-10A5VH-hCg1)
source                  1..684
                        mol_type = protein
                        organism = synthetic construct
SEQUENCE: 221
MDMRVPAQLL GLLLLWFPGS RCDIQMTQSP SSLSASVGDR VTITCQASQD ISNYLNWYQQ  60
KPGKAPKLLI YDASNLETGV PSRFSGSGSG TDFTFTISSL QPEDIATYFC QHFDHLPLAF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
VQSGAEVKKP GASVKVSCKA SGYTFTSYDV HWVRQAPGQR LEWMGWLHAD TGITKFSQKF  300
QGRVTITRDT SASTAYMELS SLRSEDTAVY YCARERIQLW FDYWGQGTLV TVSSASTKGP  360
SVFPLAPSSK STSGGTAALG CLVKDYFPEP VTVSWNSGAL TSGVHTFPAV LQSSGLYSLS  420
SVVTVPSSSL GTQTYICNVN HKPSNTKVDK KVEPKSCDKT HTCPPCPAPE LLGGPSVFLF  480
PPKPKDTLMI SRTPEVTCVV VDVSHEDPEV KFNWYVDGVE VHNAKTKPRE EQYNSTYRVV  540
SVLTVLHQDW LNGKEYKCKV SNKALPAPIE KTISKAKGQP REPQVYTLPP SREEMTKNQV  600
SLTCLVKGFY PSDIAVEWES NGQPENNYKT TPPVLDSDGS FFLYSKLTVD KSRWQQGNVF  660
SCSVMHEALH NHYTQKSLSL SPGK                                          684

SEQ ID NO: 222          moltype = AA  length = 107
FEATURE                 Location/Qualifiers
REGION                  1..107
                        note = Pani VL
source                  1..107
                        mol_type = protein
                        organism = synthetic construct
SEQUENCE: 222
DIQMTQSPSS LSASVGDRVT ITCQASQDIS NYLNWYQQKP GKAPKLLIYD ASNLETGVPS  60
RFSGSGSGTD FTFTISSLQP EDIATYFCQH FDHLPLAFGG GTKVEIK                 107

SEQ ID NO: 223          moltype = AA  length = 11
FEATURE                 Location/Qualifiers
REGION                  1..11
                        note = Pani VL - CDR1
source                  1..11
                        mol_type = protein
                        organism = synthetic construct
SEQUENCE: 223
QASQDISNYL N                                                        11

SEQ ID NO: 224          moltype = AA  length = 7
FEATURE                 Location/Qualifiers
REGION                  1..7
                        note = Pani VL - CDR2
source                  1..7
                        mol_type = protein
                        organism = synthetic construct
SEQUENCE: 224
DASNLET                                                             7

SEQ ID NO: 225          moltype = AA  length = 9
```

```
FEATURE                Location/Qualifiers
REGION                 1..9
                       note = Pani VL - CDR3
source                 1..9
                       mol_type = protein
                       organism = synthetic construct
SEQUENCE: 225
QHFDHLPLA                                                              9

SEQ ID NO: 226         moltype = AA  length = 118
FEATURE                Location/Qualifiers
REGION                 1..118
                       note = 10A5VH
source                 1..118
                       mol_type = protein
                       organism = synthetic construct
SEQUENCE: 226
QVQLVQSGAE VKKPGASVKV SCKASGYTFT SYDVHWVRQA PGQRLEWMGW LHADTGITKF  60
SQKFQGRVTI TRDTSASTAY MELSSLRSED TAVYYCARER IQLWFDYWGQ GTLVTVSS    118

SEQ ID NO: 227         moltype = AA  length = 5
FEATURE                Location/Qualifiers
REGION                 1..5
                       note = 10A5VH - CDR1
source                 1..5
                       mol_type = protein
                       organism = synthetic construct
SEQUENCE: 227
SYDVH                                                                  5

SEQ ID NO: 228         moltype = AA  length = 17
FEATURE                Location/Qualifiers
REGION                 1..17
                       note = 10A5VH - CDR2
source                 1..17
                       mol_type = protein
                       organism = synthetic construct
SEQUENCE: 228
WLHADTGITK FSQKFQG                                                     17

SEQ ID NO: 229         moltype = AA  length = 9
FEATURE                Location/Qualifiers
REGION                 1..9
                       note = 10A5VH - CDR3
source                 1..9
                       mol_type = protein
                       organism = synthetic construct
SEQUENCE: 229
ERIQLWFDY                                                              9

SEQ ID NO: 230         moltype = AA  length = 241
FEATURE                Location/Qualifiers
REGION                 1..241
                       note = Short Chain 1 (Pani VH-CH1h)
source                 1..241
                       mol_type = protein
                       organism = synthetic construct
SEQUENCE: 230
MEFGLSWLFL VAILKGVQCQ VQLQESGPGL VKPSETLSLT CTVSGGSVSS GDYYWTWIRQ  60
SPGKGLEWIG HIYYSGNTNY NPSLKSRLTI SIDTSKTQFS LKLSSVTAAD TAIYYCVRDR  120
VTGAFDIWGQ GTMVTVSSAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKKVEPKS  240
C                                                                      241

SEQ ID NO: 231         moltype = AA  length = 119
FEATURE                Location/Qualifiers
REGION                 1..119
                       note = Pani VH
source                 1..119
                       mol_type = protein
                       organism = synthetic construct
SEQUENCE: 231
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSS   119

SEQ ID NO: 232         moltype = AA  length = 7
FEATURE                Location/Qualifiers
REGION                 1..7
                       note = Pani VH - CDR1
```

```
source                  1..7
                        mol_type = protein
                        organism = synthetic construct
SEQUENCE: 232
SGDYYWT                                                        7

SEQ ID NO: 233          moltype = AA  length = 16
FEATURE                 Location/Qualifiers
REGION                  1..16
                        note = Pani VH - CDR2
source                  1..16
                        mol_type = protein
                        organism = synthetic construct
SEQUENCE: 233
HIYYSGNTNY NPSLKS                                              16

SEQ ID NO: 234          moltype = AA  length = 9
FEATURE                 Location/Qualifiers
REGION                  1..9
                        note = Pani VH - CDR3
source                  1..9
                        mol_type = protein
                        organism = synthetic construct
SEQUENCE: 234
DRVTGAFDI                                                      9

SEQ ID NO: 235          moltype = AA  length = 236
FEATURE                 Location/Qualifiers
REGION                  1..236
                        note = Short Chain 2 (10A5 VL-hCk)
source                  1..236
                        mol_type = protein
                        organism = synthetic construct
SEQUENCE: 235
MDMRVPAQLL GLLLLWFPGS RCDIQMTQSP SSLSASVGDR VTITCRASQG ISSWLAWYQQ  60
KPEKAPKSLI YAASSLQSGV PSRFSGSGSG TDFTLTISSL QPEDFATYYC QQYNSYPYTF  120
GQGTKLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 236          moltype = AA  length = 107
FEATURE                 Location/Qualifiers
REGION                  1..107
                        note = 10A5 VL
source                  1..107
                        mol_type = protein
                        organism = synthetic construct
SEQUENCE: 236
DIQMTQSPSS LSASVGDRVT ITCRASQGIS SWLAWYQQKP EKAPKSLIYA ASSLQSGVPS  60
RFSGSGSGTD FTLTISSLQP EDFATYYCQQ YNSYPYTFGQ GTKLEIK                107

SEQ ID NO: 237          moltype = AA  length = 11
FEATURE                 Location/Qualifiers
REGION                  1..11
                        note = 10A5 VL - CDR1
source                  1..11
                        mol_type = protein
                        organism = synthetic construct
SEQUENCE: 237
RASQGISSWL A                                                   11

SEQ ID NO: 238          moltype = AA  length = 7
FEATURE                 Location/Qualifiers
REGION                  1..7
                        note = 10A5 VL - CDR2
source                  1..7
                        mol_type = protein
                        organism = synthetic construct
SEQUENCE: 238
AASSLQS                                                        7

SEQ ID NO: 239          moltype = AA  length = 9
FEATURE                 Location/Qualifiers
REGION                  1..9
                        note = 10A5 VL - CDR3
source                  1..9
                        mol_type = protein
                        organism = synthetic construct
SEQUENCE: 239
QQYNSYPYT                                                      9
```

```
SEQ ID NO: 240          moltype = AA  length = 685
FEATURE                 Location/Qualifiers
REGION                  1..685
                        note = Long Chain (h1332 VL-hCk-Pani VH-hCg1)
source                  1..685
                        mol_type = protein
                        organism = synthetic construct
SEQUENCE: 240
MDMRVPAQLL GLLLLWFPGS RCDIQMTQSP SSVSASVGDR VTITCRASQG INTWLAWYQQ  60
KPGKAPKLLI YAASSLKSGV PSRFSGSGSG TDFTLTISSL QPEDFATYYC QQANSFPLTF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
QESGPGLVKP SETLSLTCTV SGGSVSSGDY YWTWIRQSPG KGLEWIGHIY YSGNTNYNPS  300
LKSRLTISID TSKTQFSLKL SSVTAADTAI YYCVRDRVTG AFDIWGQGTM VTVSSASTKG  360
PSVFPLAPSS KSTSGGTAAL GCLVKDYFPE PVTVSWNSGA LTSGVHTFPA VLQSSGLYSL  420
SSVVTVPSSS LGTQTYICNV NHKPSNTKVD KKVEPKSCDK THTCPPCPAP ELLGGPSVFL  480
FPPKPKDTLM ISRTPEVTCV VVDVSHEDPE VKFNWYVDGV EVHNAKTKPR EEQYNSTYRV  540
VSVLTVLHQD WLNGKEYKCK VSNKALPAPI EKTISKAKGQ PREPQVYTLP PSREEMTKNQ  600
VSLTCLVKGF YPSDIAVEWE SNGQPENNYK TTPPVLDSDG SFFLYSKLTV DKSRWQQGNV  660
FSCSVMHEAL HNHYTQKSLS LSPGK                                       685

SEQ ID NO: 241          moltype = AA  length = 107
FEATURE                 Location/Qualifiers
REGION                  1..107
                        note = h1332 VL
source                  1..107
                        mol_type = protein
                        organism = synthetic construct
SEQUENCE: 241
DIQMTQSPSS VSASVGDRVT ITCRASQGIN TWLAWYQQKP GKAPKLLIYA ASSLKSGVPS  60
RFSGSGSGTD FTLTISSLQP EDFATYYCQQ ANSFPLTFGG GTKVEIK               107

SEQ ID NO: 242          moltype = AA  length = 11
FEATURE                 Location/Qualifiers
REGION                  1..11
                        note = h1332 VL - CDR1
source                  1..11
                        mol_type = protein
                        organism = synthetic construct
SEQUENCE: 242
RASQGINTWL A                                                      11

SEQ ID NO: 243          moltype = AA  length = 7
FEATURE                 Location/Qualifiers
REGION                  1..7
                        note = h1332 VL - CDR2
source                  1..7
                        mol_type = protein
                        organism = synthetic construct
SEQUENCE: 243
AASSLKS                                                           7

SEQ ID NO: 244          moltype = AA  length = 9
FEATURE                 Location/Qualifiers
REGION                  1..9
                        note = h1332 VL - CDR3
source                  1..9
                        mol_type = protein
                        organism = synthetic construct
SEQUENCE: 244
QQANSFPLT                                                         9

SEQ ID NO: 245          moltype = AA  length = 119
FEATURE                 Location/Qualifiers
REGION                  1..119
                        note = Pani VH
source                  1..119
                        mol_type = protein
                        organism = synthetic construct
SEQUENCE: 245
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSS   119

SEQ ID NO: 246          moltype = AA  length = 7
FEATURE                 Location/Qualifiers
REGION                  1..7
                        note = Pani VH - CDR1
source                  1..7
```

```
                        mol_type = protein
                        organism = synthetic construct
SEQUENCE: 246
SGDYYWT                                                          7

SEQ ID NO: 247          moltype = AA  length = 16
FEATURE                 Location/Qualifiers
REGION                  1..16
                        note = Pani VH - CDR2
source                  1..16
                        mol_type = protein
                        organism = synthetic construct
SEQUENCE: 247
HIYYSGNTNY NPSLKS                                                16

SEQ ID NO: 248          moltype = AA  length = 9
FEATURE                 Location/Qualifiers
REGION                  1..9
                        note = Pani VH - CDR3
source                  1..9
                        mol_type = protein
                        organism = synthetic construct
SEQUENCE: 248
DRVTGAFDI                                                        9

SEQ ID NO: 249          moltype = AA  length = 239
FEATURE                 Location/Qualifiers
REGION                  1..239
                        note = Short Chain 1 (h1332 VH-CH1)
source                  1..239
                        mol_type = protein
                        organism = synthetic construct
SEQUENCE: 249
MEFGLSWLFL VAILKGVQCQ VQLVQSGAEV KKPGASVKVS CKASGYTFTS YGFSWVRQAP  60
GQGLEWMGWI SASNGNTYYA QKLQGRVTMT TDTSTSTAYM ELRSLRSDDT AVYYCARVYA  120
DYADYWGQGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSC   239

SEQ ID NO: 250          moltype = AA  length = 117
FEATURE                 Location/Qualifiers
REGION                  1..117
                        note = h1332 VH
source                  1..117
                        mol_type = protein
                        organism = synthetic construct
SEQUENCE: 250
QVQLVQSGAE VKKPGASVKV SCKASGYTFT SYGFSWVRQA PGQGLEWMGW ISASNGNTYY  60
AQKLQGRVTM TTDTSTSTAY MELRSLRSDD TAVYYCARVY ADYADYWGQG TLVTVSS     117

SEQ ID NO: 251          moltype = AA  length = 5
FEATURE                 Location/Qualifiers
REGION                  1..5
                        note = h1332 VH - CDR1
source                  1..5
                        mol_type = protein
                        organism = synthetic construct
SEQUENCE: 251
SYGFS                                                            5

SEQ ID NO: 252          moltype = AA  length = 17
FEATURE                 Location/Qualifiers
REGION                  1..17
                        note = h1332 VH - CDR2
source                  1..17
                        mol_type = protein
                        organism = synthetic construct
SEQUENCE: 252
WISASNGNTY YAQKLQG                                               17

SEQ ID NO: 253          moltype = AA  length = 8
FEATURE                 Location/Qualifiers
REGION                  1..8
                        note = h1332 VH - CDR3
source                  1..8
                        mol_type = protein
                        organism = synthetic construct
SEQUENCE: 253
VYADYADY                                                         8
```

```
SEQ ID NO: 254         moltype = AA  length = 236
FEATURE                Location/Qualifiers
REGION                 1..236
                       note = Short Chain 2 (Pani VL-hCk)
source                 1..236
                       mol_type = protein
                       organism = synthetic construct
SEQUENCE: 254
MDMRVPAQLL GLLLLWFPGS RCDIQMTQSP SSLSASVGDR VTITCQASQD ISNYLNWYQQ  60
KPGKAPKLLI YDASNLETGV PSRFSGSGSG TDFTFTISSL QPEDIATYFC QHFDHLPLAF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 255         moltype = AA  length = 107
FEATURE                Location/Qualifiers
REGION                 1..107
                       note = Pani VL
source                 1..107
                       mol_type = protein
                       organism = synthetic construct
SEQUENCE: 255
DIQMTQSPSS LSASVGDRVT ITCQASQDIS NYLNWYQQKP GKAPKLLIYD ASNLETGVPS  60
RFSGSGSGTD FTFTISSLQP EDIATYFCQH FDHLPLAFGG GTKVEIK                107

SEQ ID NO: 256         moltype = AA  length = 11
FEATURE                Location/Qualifiers
REGION                 1..11
                       note = Pani VL - CDR1
source                 1..11
                       mol_type = protein
                       organism = synthetic construct
SEQUENCE: 256
QASQDISNYL N                                                       11

SEQ ID NO: 257         moltype = AA  length = 7
FEATURE                Location/Qualifiers
REGION                 1..7
                       note = Pani VL - CDR2
source                 1..7
                       mol_type = protein
                       organism = synthetic construct
SEQUENCE: 257
DASNLET                                                            7

SEQ ID NO: 258         moltype = AA  length = 9
FEATURE                Location/Qualifiers
REGION                 1..9
                       note = Pani VL - CDR3
source                 1..9
                       mol_type = protein
                       organism = synthetic construct
SEQUENCE: 258
QHFDHLPLA                                                          9

SEQ ID NO: 259         moltype = AA  length = 680
FEATURE                Location/Qualifiers
REGION                 1..680
                       note = Long Chain (FIX VL-hCk-FX-VH-hCg4)
source                 1..680
                       mol_type = protein
                       organism = synthetic construct
SEQUENCE: 259
MDMRVPAQLL GLLLLWFPGS RCDIQMTQSP SSLSASVGDR VTITCKASRN IERQLAWYQQ  60
KPGQAPELLI YQASRKESGV PDRFSGSRYG TDFTLTISSL QPEDIATYYC QQYSDPPLTF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
VQSGSELKKP GASVKVSCKA SGYTFTDNNM DWVRQAPGQG LEWMGDINTR SGGSIYNEEF  300
QDRVIMTVDK STDTAYMELS SLRSEDTATY HCARRKSYGY YLDEWGEGTL VTVSSASTKG  360
PSVFPLAPCS RSTSESTAAL GCLVKDYFPE PVTVSWNSGA LTSGVHTFPA VLQSSGLYSL  420
SSVVTVPSSS LGTQTYTCNV DHKPSNTKVD KRVESKYGPP CPPCPAPEFL GGPSVFLFPP  480
KPKDTLMISR TPEVTCVVVD VSQEDPEVQF NWYVDGVEVH NAKTKPREEQ YNSTYRVVSV  540
LTVLHQDWLN GKEYKCKVSN KGLPSSIEKT ISKAKGQPRE PQVYTLPPSQ EEMTKNQVSL  600
TCLVKGFYPS DIAVEWESNG QPENNYKTTP PVLDSDGSFF LYSKLTVDKS RWQEGNVFSC  660
SVMHEALHNH YTQESLSLSP                                              680

SEQ ID NO: 260         moltype = AA  length = 107
FEATURE                Location/Qualifiers
REGION                 1..107
                       note = FIX VL
```

```
source                  1..107
                        mol_type = protein
                        organism = synthetic construct
SEQUENCE: 260
DIQMTQSPSS LSASVGDRVT ITCKASRNIE RQLAWYQQKP GQAPELLIYQ ASRKESGVPD  60
RFSGSRYGTD FTLTISSLQP EDIATYYCQQ YSDPPLTFGG GTKVEIK                107

SEQ ID NO: 261          moltype = AA  length = 11
FEATURE                 Location/Qualifiers
REGION                  1..11
                        note = FIX VL - CDR1
source                  1..11
                        mol_type = protein
                        organism = synthetic construct
SEQUENCE: 261
KASRNIERQL A                                                       11

SEQ ID NO: 262          moltype = AA  length = 7
FEATURE                 Location/Qualifiers
REGION                  1..7
                        note = FIX VL - CDR2
source                  1..7
                        mol_type = protein
                        organism = synthetic construct
SEQUENCE: 262
QASRKES                                                            7

SEQ ID NO: 263          moltype = AA  length = 9
FEATURE                 Location/Qualifiers
REGION                  1..9
                        note = FIX VL - CDR3
source                  1..9
                        mol_type = protein
                        organism = synthetic construct
SEQUENCE: 263
QQYSDPPLT                                                          9

SEQ ID NO: 264          moltype = AA  length = 119
FEATURE                 Location/Qualifiers
REGION                  1..119
                        note = FX-VH
source                  1..119
                        mol_type = protein
                        organism = synthetic construct
SEQUENCE: 264
QVQLVQSGSE LKKPGASVKV SCKASGYTFT DNNMDWVRQA PGQGLEWMGD INTRSGGSIY  60
NEEFQDRVIM TVDKSTDTAY MELSSLRSED TATYHCARRK SYGYYLDEWG EGTLVTVSS   119

SEQ ID NO: 265          moltype = AA  length = 5
FEATURE                 Location/Qualifiers
REGION                  1..5
                        note = FX-VH - CDR1
source                  1..5
                        mol_type = protein
                        organism = synthetic construct
SEQUENCE: 265
DNNMD                                                              5

SEQ ID NO: 266          moltype = AA  length = 17
FEATURE                 Location/Qualifiers
REGION                  1..17
                        note = FX-VH - CDR2
source                  1..17
                        mol_type = protein
                        organism = synthetic construct
SEQUENCE: 266
DINTRSGGSI YNEEFQD                                                 17

SEQ ID NO: 267          moltype = AA  length = 10
FEATURE                 Location/Qualifiers
REGION                  1..10
                        note = FX-VH - CDR3
source                  1..10
                        mol_type = protein
                        organism = synthetic construct
SEQUENCE: 267
RKSYGYYLDE                                                         10

SEQ ID NO: 268          moltype = AA  length = 245
```

```
FEATURE               Location/Qualifiers
REGION                1..245
                      note = Short Chain 1 (F-IX VH-CH1h)
source                1..245
                      mol_type = protein
                      organism = synthetic construct
SEQUENCE: 268
MEFGLSWLFL VAILKGVQCQ VQLVESGGGL VQPGGSLRLS CAASGFTFSY YDIQWVRQAP  60
GKGLEWVSSI SPSGQSTYYR REVKGRFTIS RDNSKNTLYL QMNSLRAEDT AVYYCARRTG  120
REYGGGWYFD YWGQGTLVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSC                                                              245

SEQ ID NO: 269        moltype = AA  length = 123
FEATURE               Location/Qualifiers
REGION                1..123
                      note = F-IX VH
source                1..123
                      mol_type = protein
                      organism = synthetic construct
SEQUENCE: 269
QVQLVESGGG LVQPGGSLRL SCAASGFTFS YYDIQWVRQA PGKGLEWVSS ISPSGQSTYY  60
RREVKGRFTI SRDNSKNTLY LQMNSLRAED TAVYYCARRT GREYGGGWYF DYWGQGTLVT  120
VSS                                                                123

SEQ ID NO: 270        moltype = AA  length = 6
FEATURE               Location/Qualifiers
REGION                1..6
                      note = F-IX VH - CDR1
source                1..6
                      mol_type = protein
                      organism = synthetic construct
SEQUENCE: 270
SYYDIQ                                                             6

SEQ ID NO: 271        moltype = AA  length = 17
FEATURE               Location/Qualifiers
REGION                1..17
                      note = F-IX VH - CDR2
source                1..17
                      mol_type = protein
                      organism = synthetic construct
SEQUENCE: 271
SISPSGQSTY YRREVKG                                                 17

SEQ ID NO: 272        moltype = AA  length = 14
FEATURE               Location/Qualifiers
REGION                1..14
                      note = F-IX VH - CDR3
source                1..14
                      mol_type = protein
                      organism = synthetic construct
SEQUENCE: 272
RTGREYGGGW YFDY                                                    14

SEQ ID NO: 273        moltype = AA  length = 236
FEATURE               Location/Qualifiers
REGION                1..236
                      note = Short Chain 2 (F-X VL-hCk)
source                1..236
                      mol_type = protein
                      organism = synthetic construct
SEQUENCE: 273
MDMRVPAQLL GLLLLWFPGS RCDIQMTQSP SSLSASVGDR VTITCKASRN IERQLAWYQQ  60
KPGQAPELLI YQASRKESGV PDRFSGSRYG TDFTLTISSL QPEDIATYYC QQYSDPPLTF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 274        moltype = AA  length = 107
FEATURE               Location/Qualifiers
REGION                1..107
                      note = F-X VL
source                1..107
                      mol_type = protein
                      organism = synthetic construct
SEQUENCE: 274
DIQMTQSPSS LSASVGDRVT ITCKASRNIE RQLAWYQQKP GQAPELLIYQ ASRKESGVPD  60
RFSGSRYGTD FTLTISSLQP EDIATYYCQQ YSDPPLTFGG GTKVEIK                107
```

```
SEQ ID NO: 275          moltype = AA  length = 11
FEATURE                 Location/Qualifiers
REGION                  1..11
                        note = F-X VL - CDR1
source                  1..11
                        mol_type = protein
                        organism = synthetic construct
SEQUENCE: 275
KASRNIERQL A                                                          11

SEQ ID NO: 276          moltype = AA  length = 7
FEATURE                 Location/Qualifiers
REGION                  1..7
                        note = F-X VL - CDR2
source                  1..7
                        mol_type = protein
                        organism = synthetic construct
SEQUENCE: 276
QASRKES                                                               7

SEQ ID NO: 277          moltype = AA  length = 9
FEATURE                 Location/Qualifiers
REGION                  1..9
                        note = F-X VL - CDR3
source                  1..9
                        mol_type = protein
                        organism = synthetic construct
SEQUENCE: 277
QQYSDPPLT                                                             9

SEQ ID NO: 278          moltype = AA  length = 697
FEATURE                 Location/Qualifiers
REGION                  1..697
                        note = Long Chain (paritu VL-hCk-FigituVH-hCg1)
source                  1..697
                        mol_type = protein
                        organism = synthetic construct
SEQUENCE: 278
MDMRVPAQLL GLLLLWFPGS RCDIEMTQSP DSLAVSLGER ATINCRSSQS VLYSSSNRNY  60
LAWYQQNPGQ PPKLLIYWAS TRESGVPDRF SGSGSGTDFT LTISSLQAED VAVYYCQQYY  120
STPRTFGQGT KVEIKRTVAA PSVFIFPPSD EQLKSGTASV VCLLNNFYPR EAKVQWKVDN  180
ALQSGNSQES VTEQDSKDST YSLSSTLTLS KADYEKHKVY ACEVTHQGLS SPVTKSFNRG  240
ECEVQLLESG GGLVQPGGSL RLSCTASGFT FSSYAMNWVR QAPGKGLEWV SAISGSGGTT  300
FYADSVKGRF TISRDNSRTT LYLQMNSLRA EDTAVYYCAK DLGWSDSYYY YYGMDVWGQG  360
TTVTVSSAST KGPSVFPLAP SSKSTSGGTA ALGCLVKDYF PEPVTVSWNS GALTSGVHTF  420
PAVLQSSGLY SLSSVVTVPS SSLGTQTYIC NVNHKPSNTK VDKKVEPKSC DKTHTCPPCP  480
APELLGGPSV FLFPPKPKDT LMISRTPEVT CVVVDVSHED PEVKFNWYVD GVEVHNAKTK  540
PREEQYNSTY RVVSVLTVLH QDWLNGKEYK CKVSNKALPA PIEKTISKAK GQPREPQVYT  600
LPPSREEMTK NQVSLTCLVK GFYPSDIAVE WESNGQPENN YKTTPPVLDS DGSFFLYSKL  660
TVDKSRWQQG NVFSCSVMHE ALHNHYTQKS LSLSPGK                            697

SEQ ID NO: 279          moltype = AA  length = 113
FEATURE                 Location/Qualifiers
REGION                  1..113
                        note = paritu VL
source                  1..113
                        mol_type = protein
                        organism = synthetic construct
SEQUENCE: 279
DIEMTQSPDS LAVSLGERAT INCRSSQSVL YSSSNRNYLA WYQQNPGQPP KLLIYWASTR  60
ESGVPDRFSG SGSGTDFTLT ISSLQAEDVA VYYCQQYYST PRTFGQGTKV EIK          113

SEQ ID NO: 280          moltype = AA  length = 17
FEATURE                 Location/Qualifiers
REGION                  1..17
                        note = paritu VL - CDR1
source                  1..17
                        mol_type = protein
                        organism = synthetic construct
SEQUENCE: 280
RSSQSVLYSS SNRNYLA                                                    17

SEQ ID NO: 281          moltype = AA  length = 7
FEATURE                 Location/Qualifiers
REGION                  1..7
                        note = paritu VL - CDR2
source                  1..7
                        mol_type = protein
                        organism = synthetic construct
```

```
SEQUENCE: 281
WASTRES                                                          7

SEQ ID NO: 282         moltype = AA  length = 9
FEATURE                Location/Qualifiers
REGION                 1..9
                       note = paritu VL - CDR3
source                 1..9
                       mol_type = protein
                       organism = synthetic construct
SEQUENCE: 282
QQYYSTPRT                                                        9

SEQ ID NO: 283         moltype = AA  length = 125
FEATURE                Location/Qualifiers
REGION                 1..125
                       note = FigituVH
source                 1..125
                       mol_type = protein
                       organism = synthetic construct
SEQUENCE: 283
EVQLLESGGG LVQPGGSLRL SCTASGFTFS SYAMNWVRQA PGKGLEWVSA ISGSGGTTFY  60
ADSVKGRFTI SRDNSRTTLY LQMNSLRAED TAVYYCAKDL GWSDSYYYYY GMDVWGQGTT  120
VTVSS                                                            125

SEQ ID NO: 284         moltype = AA  length = 5
FEATURE                Location/Qualifiers
REGION                 1..5
                       note = FigituVH - CDR1
source                 1..5
                       mol_type = protein
                       organism = synthetic construct
SEQUENCE: 284
SYAMN                                                            5

SEQ ID NO: 285         moltype = AA  length = 17
FEATURE                Location/Qualifiers
REGION                 1..17
                       note = FigituVH - CDR2
source                 1..17
                       mol_type = protein
                       organism = synthetic construct
SEQUENCE: 285
AISGSGGTTF YADSVKG                                               17

SEQ ID NO: 286         moltype = AA  length = 16
FEATURE                Location/Qualifiers
REGION                 1..16
                       note = FigituVH - CDR3
source                 1..16
                       mol_type = protein
                       organism = synthetic construct
SEQUENCE: 286
DLGWSDSYYY YYGMDV                                                16

SEQ ID NO: 287         moltype = AA  length = 239
FEATURE                Location/Qualifiers
REGION                 1..239
                       note = Short Chain 1 (PatritumabVH -CH1)
source                 1..239
                       mol_type = protein
                       organism = synthetic construct
SEQUENCE: 287
MEFGLSWLFL VAILKGVQCQ VQLQQWGAGL LKPSETLSLT CAVYGGSFSG YYWSWIRQPP  60
GKGLEWIGEI NHSGSTNYNP SLKSRVTISV ETSKNQFSLK LSSVTAADTA VYYCARDKWT  120
WYFDLWGRGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSC   239

SEQ ID NO: 288         moltype = AA  length = 117
FEATURE                Location/Qualifiers
REGION                 1..117
                       note = PatritumabVH
source                 1..117
                       mol_type = protein
                       organism = synthetic construct
SEQUENCE: 288
QVQLQQWGAG LLKPSETLSL TCAVYGGSFS GYYWSWIRQP PGKGLEWIGE INHSGSTNYN  60
PSLKSRVTIS VETSKNQFSL KLSSVTAADT AVYYCARDKW TWYFDLWGRG TLVTVSS     117
```

```
SEQ ID NO: 289          moltype = AA  length = 5
FEATURE                 Location/Qualifiers
REGION                  1..5
                        note = PatritumabVH - CDR1
source                  1..5
                        mol_type = protein
                        organism = synthetic construct
SEQUENCE: 289
GYYWS                                                                   5

SEQ ID NO: 290          moltype = AA  length = 16
FEATURE                 Location/Qualifiers
REGION                  1..16
                        note = PatritumabVH - CDR2
source                  1..16
                        mol_type = protein
                        organism = synthetic construct
SEQUENCE: 290
EINHSGSTNY NPSLKS                                                       16

SEQ ID NO: 291          moltype = AA  length = 9
FEATURE                 Location/Qualifiers
REGION                  1..9
                        note = PatritumabVH - CDR3
source                  1..9
                        mol_type = protein
                        organism = synthetic construct
SEQUENCE: 291
DKWTWYFDL                                                               9

SEQ ID NO: 292          moltype = AA  length = 236
FEATURE                 Location/Qualifiers
REGION                  1..236
                        note = Short Chain 2 (Figitu VL-hCk)
source                  1..236
                        mol_type = protein
                        organism = synthetic construct
SEQUENCE: 292
MDMRVPAQLL GLLLLWFPGS RCDIQMTQFP SSLSASVGDR VTITCRASQG IRNDLGWYQQ  60
KPGKAPKRLI YAASRLHRGV PSRFSGSGSG TEFTLTISSL QPEDFATYYC LQHNSYPCSF  120
GQGTKLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 293          moltype = AA  length = 107
FEATURE                 Location/Qualifiers
REGION                  1..107
                        note = Figitu VL
source                  1..107
                        mol_type = protein
                        organism = synthetic construct
SEQUENCE: 293
DIQMTQFPSS LSASVGDRVT ITCRASQGIR NDLGWYQQKP GKAPKRLIYA ASRLHRGVPS  60
RFSGSGSGTE FTLTISSLQP EDFATYYCLQ HNSYPCSFGQ GTKLEIK                107

SEQ ID NO: 294          moltype = AA  length = 11
FEATURE                 Location/Qualifiers
REGION                  1..11
                        note = Figitu VL - CDR1
source                  1..11
                        mol_type = protein
                        organism = synthetic construct
SEQUENCE: 294
RASQGIRNDL G                                                            11

SEQ ID NO: 295          moltype = AA  length = 7
FEATURE                 Location/Qualifiers
REGION                  1..7
                        note = Figitu VL - CDR2
source                  1..7
                        mol_type = protein
                        organism = synthetic construct
SEQUENCE: 295
AASRLHR                                                                 7

SEQ ID NO: 296          moltype = AA  length = 9
FEATURE                 Location/Qualifiers
REGION                  1..9
                        note = Figitu VL - CDR3
source                  1..9
```

```
                        mol_type = protein
                        organism = synthetic construct
SEQUENCE: 296
LQHNSYPCS                                                      9

SEQ ID NO: 297          moltype = AA  length = 693
FEATURE                 Location/Qualifiers
REGION                  1..693
                        note = Long Chain (Demci VL-hCk-Bevci VH-hCg1)
source                  1..693
                        mol_type = protein
                        organism = synthetic construct
SEQUENCE: 297
MDMRVPAQLL GLLLLWFPGS RCDIVMTQSP DSLAVSLGER ATISCRASES VDNYGISFMK  60
WFQQKPGQPP KLLIYAASNQ GSGVPDRFSG SGSGTDFTLT ISSLQAEDVA VYYCQQSKEV  120
PWTFGGGTKV EIKRTVAAPS VFIFPPSDEQ LKSGTASVVC LLNNFYPREA KVQWKVDNAL  180
QSGNSQESVT EQDSKDSTYS LSSTLTLSKA DYEKHKVYAC EVTHQGLSSP VTKSFNRGEC  240
EVQLVESGGG LVQPGGSLRL SCAASGYTFT NYGMNWVRQA PGKGLEWVGW INTYTGEPTY  300
AADFKRRFTF SLDTSKSTAY LQMNSLRAED TAVYYCAKYP HYYGSSHWYF DVWGQGTLVT  360
VSSASTKGPS VFPLAPSSKS TSGGTAALGC LVKDYFPEPV TVSWNSGALT SGVHTFPAVL  420
QSSGLYSLSS VVTVPSSSLG TQTYICNVNH KPSNTKVDKK VEPKSCDKTH TCPPCPAPEL  480
LGGPSVFLFP PKPKDTLMIS RTPEVTCVVV DVSHEDPEVK FNWYVDGVEV HNAKTKPREE  540
QYNSTYRVVS VLTVLHQDWL NGKEYKCKVS NKALPAPIEK TISKAKGQPR EPQVYTLPPS  600
REEMTKNQVS LTCLVKGFYP SDIAVEWESN GQPENNYKTT PPVLDSDGSF FLYSKLTVDK  660
SRWQQGNVFS CSVMHEALHN HYTQKSLSLS PGK                           693

SEQ ID NO: 298          moltype = AA  length = 111
FEATURE                 Location/Qualifiers
REGION                  1..111
                        note = Demci VL
source                  1..111
                        mol_type = protein
                        organism = synthetic construct
SEQUENCE: 298
DIVMTQSPDS LAVSLGERAT ISCRASESVD NYGISFMKWF QQKPGQPPKL LIYAASNQGS  60
GVPDRFSGSG SGTDFTLTIS SLQAEDVAVY YCQQSKEVPW TFGGGTKVEI K           111

SEQ ID NO: 299          moltype = AA  length = 15
FEATURE                 Location/Qualifiers
REGION                  1..15
                        note = Demci VL - CDR1
source                  1..15
                        mol_type = protein
                        organism = synthetic construct
SEQUENCE: 299
RASESVDNYG ISFMK                                               15

SEQ ID NO: 300          moltype = AA  length = 7
FEATURE                 Location/Qualifiers
REGION                  1..7
                        note = Demci VL - CDR2
source                  1..7
                        mol_type = protein
                        organism = synthetic construct
SEQUENCE: 300
AASNQGS                                                        7

SEQ ID NO: 301          moltype = AA  length = 9
FEATURE                 Location/Qualifiers
REGION                  1..9
                        note = Demci VL - CDR3
source                  1..9
                        mol_type = protein
                        organism = synthetic construct
SEQUENCE: 301
QQSKEVPWT                                                      9

SEQ ID NO: 302          moltype = AA  length = 123
FEATURE                 Location/Qualifiers
REGION                  1..123
                        note = Bevci VH
source                  1..123
                        mol_type = protein
                        organism = synthetic construct
SEQUENCE: 302
EVQLVESGGG LVQPGGSLRL SCAASGYTFT NYGMNWVRQA PGKGLEWVGW INTYTGEPTY  60
AADFKRRFTF SLDTSKSTAY LQMNSLRAED TAVYYCAKYP HYYGSSHWYF DVWGQGTLVT  120
VSS                                                            123
```

```
SEQ ID NO: 303          moltype = AA  length = 5
FEATURE                 Location/Qualifiers
REGION                  1..5
                        note = Bevci VH - CDR1
source                  1..5
                        mol_type = protein
                        organism = synthetic construct
SEQUENCE: 303
NYGMN                                                              5

SEQ ID NO: 304          moltype = AA  length = 17
FEATURE                 Location/Qualifiers
REGION                  1..17
                        note = Bevci VH - CDR2
source                  1..17
                        mol_type = protein
                        organism = synthetic construct
SEQUENCE: 304
WINTYTGEPT YAADFKR                                                 17

SEQ ID NO: 305          moltype = AA  length = 14
FEATURE                 Location/Qualifiers
REGION                  1..14
                        note = Bevci VH - CDR3
source                  1..14
                        mol_type = protein
                        organism = synthetic construct
SEQUENCE: 305
YPHYYGSSHW YFDV                                                    14

SEQ ID NO: 306          moltype = AA  length = 241
FEATURE                 Location/Qualifiers
REGION                  1..241
                        note = Short Chain 1(Demci VH -CH1h)
source                  1..241
                        mol_type = protein
                        organism = synthetic construct
SEQUENCE: 306
MEFGLSWLFL VAILKGVQCQ VQLVQSGAEV KKPGASVKIS CKASGYSFTA YYIHWVKQAP  60
GQGLEWIGYI SSYNGATNYN QKFKGRVTFT TDTSTSTAYM ELRSLRSDDT AVYYCARDYD  120
YDVGMDYWGQ GTLVTVSSAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKKVEPKS  240
C                                                                  241

SEQ ID NO: 307          moltype = AA  length = 119
FEATURE                 Location/Qualifiers
REGION                  1..119
                        note = Demci VH
source                  1..119
                        mol_type = protein
                        organism = synthetic construct
SEQUENCE: 307
QVQLVQSGAE VKKPGASVKI SCKASGYSFT AYYIHWVKQA PGQGLEWIGY ISSYNGATNY  60
NQKFKGRVTF TTDTSTSTAY MELRSLRSDD TAVYYCARDY DYDVGMDYWG QGTLVTVSS   119

SEQ ID NO: 308          moltype = AA  length = 5
FEATURE                 Location/Qualifiers
REGION                  1..5
                        note = Demci VH - CDR1
source                  1..5
                        mol_type = protein
                        organism = synthetic construct
SEQUENCE: 308
AYYIH                                                              5

SEQ ID NO: 309          moltype = AA  length = 17
FEATURE                 Location/Qualifiers
REGION                  1..17
                        note = Demci VH - CDR2
source                  1..17
                        mol_type = protein
                        organism = synthetic construct
SEQUENCE: 309
YISSYNGATN YNQKFKG                                                 17

SEQ ID NO: 310          moltype = AA  length = 10
FEATURE                 Location/Qualifiers
REGION                  1..10
                        note = Demci VH - CDR3
```

```
source                  1..10
                        mol_type = protein
                        organism = synthetic construct
SEQUENCE: 310
DYDYDVGMDY                                                      10

SEQ ID NO: 311          moltype = AA  length = 236
FEATURE                 Location/Qualifiers
REGION                  1..236
                        note = Short Chain 2 (Bevci VL-hCk)
source                  1..236
                        mol_type = protein
                        organism = synthetic construct
SEQUENCE: 311
MDMRVPAQLL GLLLLWFPGS RCDIQMTQSP SSLSASVGDR VTITCSASQD ISNYLNWYQQ  60
KPGKAPKVLI YFTSSLHSGV PSRFSGSGSG TDFTLTISSL QPEDFATYYC QQYSTVPWTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 312          moltype = AA  length = 107
FEATURE                 Location/Qualifiers
REGION                  1..107
                        note = Bevci VL
source                  1..107
                        mol_type = protein
                        organism = synthetic construct
SEQUENCE: 312
DIQMTQSPSS LSASVGDRVT ITCSASQDIS NYLNWYQQKP GKAPKVLIYF TSSLHSGVPS  60
RFSGSGSGTD FTLTISSLQP EDFATYYCQQ YSTVPWTFGQ GTKVEIK               107

SEQ ID NO: 313          moltype = AA  length = 11
FEATURE                 Location/Qualifiers
REGION                  1..11
                        note = Bevci VL - CDR1
source                  1..11
                        mol_type = protein
                        organism = synthetic construct
SEQUENCE: 313
SASQDISNYL N                                                    11

SEQ ID NO: 314          moltype = AA  length = 7
FEATURE                 Location/Qualifiers
REGION                  1..7
                        note = Bevci VL - CDR2
source                  1..7
                        mol_type = protein
                        organism = synthetic construct
SEQUENCE: 314
FTSSLHS                                                         7

SEQ ID NO: 315          moltype = AA  length = 9
FEATURE                 Location/Qualifiers
REGION                  1..9
                        note = Bevci VL - CDR3
source                  1..9
                        mol_type = protein
                        organism = synthetic construct
SEQUENCE: 315
QQYSTVPWT                                                       9

SEQ ID NO: 316          moltype = AA  length = 691
FEATURE                 Location/Qualifiers
REGION                  1..691
                        note = Long Chain (OfatuVL-hCk-CD3mAb VH-hCg1mut)
source                  1..691
                        mol_type = protein
                        organism = synthetic construct
SEQUENCE: 316
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQRSNWPITF  120
GQGTRLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECEVQL  240
LESGGGLVQP GGSLKLSCAA SGFTFNTYAM NWVRQAPGKG LEWVARIRSK YNNYATYYAD  300
SVKDRFTISR DDSKNTAYLQ MNNLKTEDTA VYYCVRHGNF GNSYVSWFAY WGQGTLVTVS  360
SASTKGPSVF PLAPSSKSTS GGTAALGCLV KDYFPEPVTV SWNSGALTSG VHTFPAVLQS  420
SGLYSLSSVV TVPSSSLGTQ TYICNVNHKP SNTKVDKKVE PKSCDKTHTC PPCPAPEAAG  480
GPSVFLFPPK PKDTLMISRT PEVTCVVVDV SHEDPEVKFN WYVDGVEVHN AKTKPREEQY  540
NSTYRVVSVL TVLHQDWLNG KEYKCKVSNK ALPAPIEKTI SKAKGQPREP QVYTLPPSRE  600
EMTKNQVSLT CLVKGFYPSD IAVEWESNGQ PENNYKTTPP VLDSDGSFFL YSKLTVDKSR  660
```

```
WQQGNVFSCS VMHEALHNHY TQKSLSLSPG K                               691

SEQ ID NO: 317          moltype = AA  length = 107
FEATURE                 Location/Qualifiers
REGION                  1..107
                        note = OfatuVL
source                  1..107
                        mol_type = protein
                        organism = synthetic construct
SEQUENCE: 317
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPITFGQ GTRLEIK              107

SEQ ID NO: 318          moltype = AA  length = 11
FEATURE                 Location/Qualifiers
REGION                  1..11
                        note = OfatuVL - CDR1
source                  1..11
                        mol_type = protein
                        organism = synthetic construct
SEQUENCE: 318
RASQSVSSYL A                                                     11

SEQ ID NO: 319          moltype = AA  length = 7
FEATURE                 Location/Qualifiers
REGION                  1..7
                        note = OfatuVL CDR2
source                  1..7
                        mol_type = protein
                        organism = synthetic construct
SEQUENCE: 319
DASNRAT                                                          7

SEQ ID NO: 320          moltype = AA  length = 9
FEATURE                 Location/Qualifiers
REGION                  1..9
                        note = OfatuVL - CDR3
source                  1..9
                        mol_type = protein
                        organism = synthetic construct
SEQUENCE: 320
QQRSNWPIT                                                        9

SEQ ID NO: 321          moltype = AA  length = 125
FEATURE                 Location/Qualifiers
REGION                  1..125
                        note = CD3mAb VH
source                  1..125
                        mol_type = protein
                        organism = synthetic construct
SEQUENCE: 321
EVQLLESGGG LVQPGGSLKL SCAASGFTFN TYAMNWVRQA PGKGLEWVAR IRSKYNNYAT  60
YYADSVKDRF TISRDDSKNT AYLQMNNLKT EDTAVYYCVR HGNFGNSYVS WFAYWGQGTL  120
VTVSS                                                            125

SEQ ID NO: 322          moltype = AA  length = 5
FEATURE                 Location/Qualifiers
REGION                  1..5
                        note = CD3mAb VH CDR1
source                  1..5
                        mol_type = protein
                        organism = synthetic construct
SEQUENCE: 322
TYAMN                                                            5

SEQ ID NO: 323          moltype = AA  length = 19
FEATURE                 Location/Qualifiers
REGION                  1..19
                        note = CD3mAb VH CDR2
source                  1..19
                        mol_type = protein
                        organism = synthetic construct
SEQUENCE: 323
RIRSKYNNYA TYYADSVKD                                             19

SEQ ID NO: 324          moltype = AA  length = 14
FEATURE                 Location/Qualifiers
REGION                  1..14
                        note = CD3mAb VH CDR3
```

```
source                  1..14
                        mol_type = protein
                        organism = synthetic construct
SEQUENCE: 324
HGNFGNSYVS WFAY                                                   14

SEQ ID NO: 325          moltype = AA  length = 244
FEATURE                 Location/Qualifiers
REGION                  1..244
                        note = Short Chain 1 (Ofatu VH-CH1)
source                  1..244
                        mol_type = protein
                        organism = synthetic construct
SEQUENCE: 325
MEFGLSWLFL VAILKGVQCE VQLVESGGGL VQPGRSLRLS CAASGFTFND YAMHWVRQAP  60
GKGLEWVSTI SWNSGSIGYA DSVKGRFTIS RDNAKKSLYL QMNSLRAEDT ALYYCAKDIQ  120
YGNYYYGMDV WGQGTTVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKKVE  240
PKSC                                                              244

SEQ ID NO: 326          moltype = AA  length = 122
FEATURE                 Location/Qualifiers
REGION                  1..122
                        note = Ofatu VH
source                  1..122
                        mol_type = protein
                        organism = synthetic construct
SEQUENCE: 326
EVQLVESGGG LVQPGRSLRL SCAASGFTFN DYAMHWVRQA PGKGLEWVST ISWNSGSIGY  60
ADSVKGRFTI SRDNAKKSLY LQMNSLRAED TALYYCAKDI QYGNYYYGMD VWGQGTTVTV  120
SS                                                                122

SEQ ID NO: 327          moltype = AA  length = 5
FEATURE                 Location/Qualifiers
REGION                  1..5
                        note = Ofatu VH - CDR1
source                  1..5
                        mol_type = protein
                        organism = synthetic construct
SEQUENCE: 327
DYAMH                                                             5

SEQ ID NO: 328          moltype = AA  length = 17
FEATURE                 Location/Qualifiers
REGION                  1..17
                        note = Ofatu VH - CDR2
source                  1..17
                        mol_type = protein
                        organism = synthetic construct
SEQUENCE: 328
TISWNSGSIG YADSVKG                                                17

SEQ ID NO: 329          moltype = AA  length = 13
FEATURE                 Location/Qualifiers
REGION                  1..13
                        note = Ofatu VH - CDR3
source                  1..13
                        mol_type = protein
                        organism = synthetic construct
SEQUENCE: 329
DIQYGNYYYG MDV                                                    13

SEQ ID NO: 330          moltype = AA  length = 235
FEATURE                 Location/Qualifiers
REGION                  1..235
                        note = Short Chain 2 (CD3mAb VL-hCL)
source                  1..235
                        mol_type = protein
                        organism = synthetic construct
SEQUENCE: 330
MTWTPLLFLT LLLHCTGSLS ELVVTQEPSL TVSPGGTVTL TCRSSTGAVT TSNYANWVQQ  60
KPGQAPRGLI GGTNKRAPGT PARFSGSLLG GKAALTLSGV QPEDEAEYYC ALWYSNLWVF  120
GGGTKLTVLG QPKAAPSVTL FPPSSEELQA NKATLVCLIS DFYPGAVTVA WKADSSPVKA  180
GVETTTPSKQ SNNKYAASSY LSLTPEQWKS HRSYSCQVTH EGSTVEKTVA PTECS       235

SEQ ID NO: 331          moltype = AA  length = 109
FEATURE                 Location/Qualifiers
REGION                  1..109
                        note = CD3mAb VL
```

```
source                1..109
                      mol_type = protein
                      organism = synthetic construct
SEQUENCE: 331
ELVVTQEPSL TVSPGGTVTL TCRSSTGAVT TSNYANWVQQ KPGQAPRGLI GGTNKRAPGT  60
PARFSGSLLG GKAALTLSGV QPEDEAEYYC ALWYSNLWVF GGGTKLTVL             109

SEQ ID NO: 332        moltype = AA  length = 14
FEATURE               Location/Qualifiers
REGION                1..14
                      note = CD3mAb VL - CDR1
source                1..14
                      mol_type = protein
                      organism = synthetic construct
SEQUENCE: 332
RSSTGAVTTS NYAN                                                    14

SEQ ID NO: 333        moltype = AA  length = 7
FEATURE               Location/Qualifiers
REGION                1..7
                      note = CD3mAb VL - CDR2
source                1..7
                      mol_type = protein
                      organism = synthetic construct
SEQUENCE: 333
GTNKRAP                                                            7

SEQ ID NO: 334        moltype = AA  length = 9
FEATURE               Location/Qualifiers
REGION                1..9
                      note = CD3mAb VL - CDR3
source                1..9
                      mol_type = protein
                      organism = synthetic construct
SEQUENCE: 334
ALWYSNLWV                                                          9

SEQ ID NO: 335        moltype = AA  length = 691
FEATURE               Location/Qualifiers
REGION                1..691
                      note = Long Chain (patritu VL-hCk-PaniVH-hCg1)
source                1..691
                      mol_type = protein
                      organism = synthetic construct
SEQUENCE: 335
MDMRVPAQLL GLLLLWFPGS RCDIEMTQSP DSLAVSLGER ATINCRSSQS VLYSSSNRNY  60
LAWYQQNPGQ PPKLLIYWAS TRESGVPDRF SGSGSGTDFT LTISSLQAED VAVYYCQQYY  120
STPRTFGQGT KVEIKRTVAA PSVFIFPPSD EQLKSGTASV VCLLNNFYPR EAKVQWKVDN  180
ALQSGNSQES VTEQDSKDST YSLSSTLTLS KADYEKHKVY ACEVTHQGLS SPVTKSFNRG  240
ECQVQLQESG PGLVKPSETL SLTCTVSGGS VSSGDYYWTW IRQSPGKGLE WIGHIYYSGN  300
TNYNPSLKSR LTISIDTSKT QFSLKLSSVT AADTAIYYCV RDRVTGAFDI WGQGTMVTVS  360
SASTKGPSVF PLAPSSKSTS GGTAALGCLV KDYFPEPVTV SWNSGALTSG VHTFPAVLQS  420
SGLYSLSSVV TVPSSSLGTQ TYICNVNHKP SNTKVDKKVE PKSCDKTHTC PPCPAPELLG  480
GPSVFLFPPK PKDTLMISRT PEVTCVVVDV SHEDPEVKFN WYVDGVEVHN AKTKPREEQY  540
NSTYRVVSVL TVLHQDWLNG KEYKCKVSNK ALPAPIEKTI SKAKGQPREP QVYTLPPSRE  600
EMTKNQVSLT CLVKGFYPSD IAVEWESNGQ PENNYKTTPP VLDSDGSFFL YSKLTVDKSR  660
WQQGNVFSCS VMHEALHNHY TQKSLSLSPG K                                 691

SEQ ID NO: 336        moltype = AA  length = 113
FEATURE               Location/Qualifiers
REGION                1..113
                      note = patritu VL
source                1..113
                      mol_type = protein
                      organism = synthetic construct
SEQUENCE: 336
DIEMTQSPDS LAVSLGERAT INCRSSQSVL YSSSNRNYLA WYQQNPGQPP KLLIYWASTR  60
ESGVPDRFSG SGSGTDFTLT ISSLQAEDVA VYYCQQYYST PRTFGQGTKV EIK         113

SEQ ID NO: 337        moltype = AA  length = 17
FEATURE               Location/Qualifiers
REGION                1..17
                      note = patritu VL - CDR1
source                1..17
                      mol_type = protein
                      organism = synthetic construct
SEQUENCE: 337
RSSQSVLYSS SNRNYLA                                                 17
```

```
SEQ ID NO: 338          moltype = AA  length = 7
FEATURE                 Location/Qualifiers
REGION                  1..7
                        note = patritu VL CDR2
source                  1..7
                        mol_type = protein
                        organism = synthetic construct
SEQUENCE: 338
WASTRES                                                   7

SEQ ID NO: 339          moltype = AA  length = 8
FEATURE                 Location/Qualifiers
REGION                  1..8
                        note = patritu VL - CDR3
source                  1..8
                        mol_type = protein
                        organism = synthetic construct
SEQUENCE: 339
QYYSTPRT                                                  8

SEQ ID NO: 340          moltype = AA  length = 119
FEATURE                 Location/Qualifiers
REGION                  1..119
                        note = PaniVH
source                  1..119
                        mol_type = protein
                        organism = synthetic construct
SEQUENCE: 340
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSS   119

SEQ ID NO: 341          moltype = AA  length = 7
FEATURE                 Location/Qualifiers
REGION                  1..7
                        note = Pani VH - CDR1
source                  1..7
                        mol_type = protein
                        organism = synthetic construct
SEQUENCE: 341
SGDYYWT                                                   7

SEQ ID NO: 342          moltype = AA  length = 16
FEATURE                 Location/Qualifiers
REGION                  1..16
                        note = Pani VH - CDR2
source                  1..16
                        mol_type = protein
                        organism = synthetic construct
SEQUENCE: 342
HIYYSGNTNY NPSLKS                                         16

SEQ ID NO: 343          moltype = AA  length = 9
FEATURE                 Location/Qualifiers
REGION                  1..9
                        note = Pani VH - CDR3
source                  1..9
                        mol_type = protein
                        organism = synthetic construct
SEQUENCE: 343
DRVTGAFDI                                                 9

SEQ ID NO: 344          moltype = AA  length = 239
FEATURE                 Location/Qualifiers
REGION                  1..239
                        note = Short Chain 1 (Patritumab VH -CH1)
source                  1..239
                        mol_type = protein
                        organism = synthetic construct
SEQUENCE: 344
MEFGLSWLFL VAILKGVQCQ VQLQQWGAGL LKPSETLSLT CAVYGGSFSG YYWSWIRQPP  60
GKGLEWIGEI NHSGSTNYNP SLKSRVTISV ETSKNQFSLK LSSVTAADTA VYYCARDKWT  120
WYFDLWGRGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSC   239

SEQ ID NO: 345          moltype = AA  length = 117
FEATURE                 Location/Qualifiers
REGION                  1..117
                        note = Patritumab VH
source                  1..117
```

```
                         mol_type = protein
                         organism = synthetic construct
SEQUENCE: 345
QVQLQQWGAG LLKPSETLSL TCAVYGGSFS GYYWSWIRQP PGKGLEWIGE INHSGSTNYN  60
PSLKSRVTIS VETSKNQFSL KLSSVTAADT AVYYCARDKW TWYFDLWGRG TLVTVSS     117

SEQ ID NO: 346           moltype = AA  length = 5
FEATURE                  Location/Qualifiers
REGION                   1..5
                         note = PatritumabVH - CDR1
source                   1..5
                         mol_type = protein
                         organism = synthetic construct
SEQUENCE: 346
GYYWS                                                              5

SEQ ID NO: 347           moltype = AA  length = 16
FEATURE                  Location/Qualifiers
REGION                   1..16
                         note = Patritumab VH - CDR2
source                   1..16
                         mol_type = protein
                         organism = synthetic construct
SEQUENCE: 347
EINHSGSTNY NPSLKS                                                  16

SEQ ID NO: 348           moltype = AA  length = 9
FEATURE                  Location/Qualifiers
REGION                   1..9
                         note = PatritumabVH - CDR3
source                   1..9
                         mol_type = protein
                         organism = synthetic construct
SEQUENCE: 348
DKWTWYFDL                                                          9

SEQ ID NO: 349           moltype = AA  length = 237
FEATURE                  Location/Qualifiers
REGION                   1..237
                         note = Short Chain 2 (Pani VL-hCk)
source                   1..237
                         mol_type = protein
                         organism = synthetic construct
SEQUENCE: 349
MDMRVPAQLL GLLLLWFPGS RCDIQMTQSP SSLSASVGDR VTITCQASQD ISNYLNWYQQ  60
KPGKAPKLLI YDASNLETGV PSPRFSGSGS GTDFTFTISS LQPEDIATYF CQHFDHLPLA  120
FGGGTKVEIK RTVAAPSVFI FPPSDEQLKS GTASVVCLLN NFYPREAKVQ WKVDNALQSG  180
NSQESVTEQD SKDSTYSLSS TLTLSKADYE KHKVYACEVT HQGLSSPVTK SFNRGEC     237

SEQ ID NO: 350           moltype = AA  length = 107
FEATURE                  Location/Qualifiers
REGION                   1..107
                         note = Pani VL
source                   1..107
                         mol_type = protein
                         organism = synthetic construct
SEQUENCE: 350
DIQMTQSPSS LSASVGDRVT ITCQASQDIS NYLNWYQQKP GKAPKLLIYD ASNLETGVPS  60
RFSGSGSGTD FTFTISSLQP EDIATYFCQH FDHLPLAFGG GTKVEIK                107

SEQ ID NO: 351           moltype = AA  length = 11
FEATURE                  Location/Qualifiers
REGION                   1..11
                         note = Pani VL - CDR1
source                   1..11
                         mol_type = protein
                         organism = synthetic construct
SEQUENCE: 351
QASQDISNYL N                                                       11

SEQ ID NO: 352           moltype = AA  length = 7
FEATURE                  Location/Qualifiers
REGION                   1..7
                         note = Pani VL - CDR2
source                   1..7
                         mol_type = protein
                         organism = synthetic construct
SEQUENCE: 352
DASNLET                                                            7
```

```
SEQ ID NO: 353          moltype = AA  length = 9
FEATURE                 Location/Qualifiers
REGION                  1..9
                        note = Pani VL - CDR3
source                  1..9
                        mol_type = protein
                        organism = synthetic construct
SEQUENCE: 353
QHFDHLPLA                                                          9

SEQ ID NO: 354          moltype = AA  length = 683
FEATURE                 Location/Qualifiers
REGION                  1..683
                        note = Long Chain (Panitu VL-hCk-Patritu-hCg1)
source                  1..683
                        mol_type = protein
                        organism = synthetic construct
SEQUENCE: 354
MDMRVPAQLL GLLLLWFPGS RCDIQMTQSP SSLSASVGDR VTITCQASQD ISNYLNWYQQ  60
KPGKAPKLLI YDASNLETGV PSRFSGSGSG TDFTFTISSL QPEDIATYFC QHFDHLPLAF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
QQWGAGLLKP SETLSLTCAV YGGSFSGYYW SWIRQPPGKG LEWIGEINHS GSTNYNPSLK  300
SRVTISVETS KNQFSLKLSS VTAADTAVYY CARDKWTWYF DLWGRGTLVT VSSASTKGPS  360
VFPLAPSSKS TSGGTAALGC LVKDYFPEPV TVSWNSGALT SGVHTFPAVL QSSGLYSLSS  420
VVTVPSSSLG TQTYICNVNH KPSNTKVDKK VEPKSCDKTH TCPPCPAPEL LGGPSVFLFP  480
PKPKDTLMIS RTPEVTCVVV DVSHEDPEVK FNWYVDGVEV HNAKTKPREE QYNSTYRVVS  540
VLTVLHQDWL NGKEYKCKVS NKALPAPIEK TISKAKGQPR EPQVYTLPPS REEMTKNQVS  600
LTCLVKGFYP SDIAVEWESN GQPENNYKTT PPVLDSDGSF FLYSKLTVDK SRWQQGNVFS  660
CSVMHEALHN HYTQKSLSLS PGK                                          683

SEQ ID NO: 355          moltype = AA  length = 107
FEATURE                 Location/Qualifiers
REGION                  1..107
                        note = Panitu VL
source                  1..107
                        mol_type = protein
                        organism = synthetic construct
SEQUENCE: 355
DIQMTQSPSS LSASVGDRVT ITCQASQDIS NYLNWYQQKP GKAPKLLIYD ASNLETGVPS  60
RFSGSGSGTD FTFTISSLQP EDIATYFCQH FDHLPLAFGG GTKVEIK                107

SEQ ID NO: 356          moltype = AA  length = 11
FEATURE                 Location/Qualifiers
REGION                  1..11
                        note = Panitu VL - CDR1
source                  1..11
                        mol_type = protein
                        organism = synthetic construct
SEQUENCE: 356
QASQDISNYL N                                                       11

SEQ ID NO: 357          moltype = AA  length = 7
FEATURE                 Location/Qualifiers
REGION                  1..7
                        note = Panitu VL CDR2
source                  1..7
                        mol_type = protein
                        organism = synthetic construct
SEQUENCE: 357
DASNLET                                                            7

SEQ ID NO: 358          moltype = AA  length = 9
FEATURE                 Location/Qualifiers
REGION                  1..9
                        note = Panitu VL - CDR3
source                  1..9
                        mol_type = protein
                        organism = synthetic construct
SEQUENCE: 358
QHFDHLPLA                                                          9

SEQ ID NO: 359          moltype = AA  length = 117
FEATURE                 Location/Qualifiers
REGION                  1..117
                        note = PatrituVH
source                  1..117
                        mol_type = protein
```

```
                        organism = synthetic construct
SEQUENCE: 359
QVQLQQWGAG LLKPSETLSL TCAVYGGSFS GYYWSWIRQP PGKGLEWIGE INHSGSTNYN  60
PSLKSRVTIS VETSKNQFSL KLSSVTAADT AVYYCARDKW TWYFDLWGRG TLVTVSS     117

SEQ ID NO: 360          moltype = AA  length = 5
FEATURE                 Location/Qualifiers
REGION                  1..5
                        note = Patritu VH - CDR1
source                  1..5
                        mol_type = protein
                        organism = synthetic construct
SEQUENCE: 360
GYYWS                                                              5

SEQ ID NO: 361          moltype = AA  length = 16
FEATURE                 Location/Qualifiers
REGION                  1..16
                        note = Patritu VH - CDR2
source                  1..16
                        mol_type = protein
                        organism = synthetic construct
SEQUENCE: 361
EINHSGSTNY NPSLKS                                                  16

SEQ ID NO: 362          moltype = AA  length = 9
FEATURE                 Location/Qualifiers
REGION                  1..9
                        note = Patritu VH - CDR3
source                  1..9
                        mol_type = protein
                        organism = synthetic construct
SEQUENCE: 362
DKWTWYFDL                                                          9

SEQ ID NO: 363          moltype = AA  length = 241
FEATURE                 Location/Qualifiers
REGION                  1..241
                        note = Short Chain 1 (Panitu VH -CH1)
source                  1..241
                        mol_type = protein
                        organism = synthetic construct
SEQUENCE: 363
MEFGLSWLFL VAILKGVQCQ VQLQESGPGL VKPSETLSLT CTVSGGSVSS GDYYWTWIRQ  60
SPGKGLEWIG HIYYSGNTNY NPSLKSRLTI SIDTSKTQFS LKLSSVTAAD TAIYYCVRDR  120
VTGAFDIWGQ GTMVTVSSAS TKGPSVFPLA PSSKSTSGGT AALGCLVKDY FPEPVTVSWN  180
SGALTSGVHT FPAVLQSSGL YSLSSVVTVP SSSLGTQTYI CNVNHKPSNT KVDKKVEPKS  240
C                                                                  241

SEQ ID NO: 364          moltype = AA  length = 119
FEATURE                 Location/Qualifiers
REGION                  1..119
                        note = Panitu VH
source                  1..119
                        mol_type = protein
                        organism = synthetic construct
SEQUENCE: 364
QVQLQESGPG LVKPSETLSL TCTVSGGSVS SGDYYWTWIR QSPGKGLEWI GHIYYSGNTN  60
YNPSLKSRLT ISIDTSKTQF SLKLSSVTAA DTAIYYCVRD RVTGAFDIWG QGTMVTVSS   119

SEQ ID NO: 365          moltype = AA  length = 5
FEATURE                 Location/Qualifiers
REGION                  1..5
                        note = PanituVH - CDR1
source                  1..5
                        mol_type = protein
                        organism = synthetic construct
SEQUENCE: 365
DYYWT                                                              5

SEQ ID NO: 366          moltype = AA  length = 16
FEATURE                 Location/Qualifiers
REGION                  1..16
                        note = Panitu VH - CDR2
source                  1..16
                        mol_type = protein
                        organism = synthetic construct
SEQUENCE: 366
HIYYSGNTNY NPSLKS                                                  16
```

```
SEQ ID NO: 367         moltype = AA  length = 9
FEATURE                Location/Qualifiers
REGION                 1..9
                       note = PanituVH - CDR3
source                 1..9
                       mol_type = protein
                       organism = synthetic construct
SEQUENCE: 367
DRVTGAFDI                                                          9

SEQ ID NO: 368         moltype = AA  length = 242
FEATURE                Location/Qualifiers
REGION                 1..242
                       note = Short Chain 2 (Patritu VL-hCk)
source                 1..242
                       mol_type = protein
                       organism = synthetic construct
SEQUENCE: 368
MDMRVPAQLL GLLLLWFPGS RCDIEMTQSP DSLAVSLGER ATINCRSSQS VLYSSSNRNY  60
LAWYQQNPGQ PPKLLIYWAS TRESGVPDRF SGSGSGTDFT LTISSLQAED VAVYYCQQYY  120
STPRTFGQGT KVEIKRTVAA PSVFIFPPSD EQLKSGTASV VCLLNNFYPR EAKVQWKVDN  180
ALQSGNSQES VTEQDSKDST YSLSSTLTLS KADYEKHKVY ACEVTHQGLS SPVTKSFNRG  240
EC                                                                 242

SEQ ID NO: 369         moltype = AA  length = 113
FEATURE                Location/Qualifiers
REGION                 1..113
                       note = PatrituVL
source                 1..113
                       mol_type = protein
                       organism = synthetic construct
SEQUENCE: 369
DIEMTQSPDS LAVSLGERAT INCRSSQSVL YSSSNRNYLA WYQQNPGQPP KLLIYWASTR  60
ESGVPDRFSG SGSGTDFTLT ISSLQAEDVA VYYCQQYYST PRTFGQGTKV EIK         113

SEQ ID NO: 370         moltype = AA  length = 17
FEATURE                Location/Qualifiers
REGION                 1..17
                       note = PatrituVL - CDR1
source                 1..17
                       mol_type = protein
                       organism = synthetic construct
SEQUENCE: 370
RSSQSVLYSS SNRNYLA                                                 17

SEQ ID NO: 371         moltype = AA  length = 7
FEATURE                Location/Qualifiers
REGION                 1..7
                       note = PatrituVL - CDR2
source                 1..7
                       mol_type = protein
                       organism = synthetic construct
SEQUENCE: 371
WASTRES                                                            7

SEQ ID NO: 372         moltype = AA  length = 9
FEATURE                Location/Qualifiers
REGION                 1..9
                       note = PatrituVL - CDR3
source                 1..9
                       mol_type = protein
                       organism = synthetic construct
SEQUENCE: 372
QQYYSTPRT                                                          9

SEQ ID NO: 373         moltype = AA  length = 678
FEATURE                Location/Qualifiers
REGION                 1..678
                       note = Long Chain (1B12 VL-hCk-Nivolu VH-hCg1Mut)
source                 1..678
                       mol_type = protein
                       organism = synthetic construct
SEQUENCE: 373
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQRSNWPTFG  120
QGTKVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGECQVQLV  240
ESGGGVVQPG RSLRLDCKAS GITFSNSGMH WVRQAPGKGL EWVAVIWYDG SKRYYADSVK  300
```

```
GRFTISRDNS KNTLFLQMNS LRAEDTAVYY CATNDDYWGQ GTLVTVSSAS TKGPSVFPLA  360
PSSKSTSGGT AALGCLVKDY FPEPVTVSWN SGALTSGVHT FPAVLQSSGL YSLSSVVTVP  420
SSSLGTQTYI CNVNHKPSNT KVDKKVEPKS CDKTHTCPPC PAPELLGGPS VFLFPPKPKD  480
TLMISRTPEV TCVVVDVSHE DPEVKFNWYV DGVEVHNAKT KPREEQYNST YRVVSVLTVL  540
HQDWLNGKEY KCKVSNKALP APIEKTISKA KGQPREPQVY TLPPSREEMT KNQVSLTCLV  600
KGFYPSDIAV EWESNGQPEN NYKTTPPVLD SDGSFFLYSK LTVDKSRWQQ GNVFSCSVMH  660
EALHNHYTQK SLSLSPGK                                                678

SEQ ID NO: 374         moltype = AA  length = 106
FEATURE                Location/Qualifiers
REGION                 1..106
                       note = I1B12 VL
source                 1..106
                       mol_type = protein
                       organism = synthetic construct
SEQUENCE: 374
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                 106

SEQ ID NO: 375         moltype = AA  length = 11
FEATURE                Location/Qualifiers
REGION                 1..11
                       note = 1B12 VL - CDR1
source                 1..11
                       mol_type = protein
                       organism = synthetic construct
SEQUENCE: 375
RASQSVSSYL A                                                       11

SEQ ID NO: 376         moltype = AA  length = 7
FEATURE                Location/Qualifiers
REGION                 1..7
                       note = 1B12 VL - CDR2
source                 1..7
                       mol_type = protein
                       organism = synthetic construct
SEQUENCE: 376
DASNRAT                                                            7

SEQ ID NO: 377         moltype = AA  length = 8
FEATURE                Location/Qualifiers
REGION                 1..8
                       note = 1B12 VL - CDR3
source                 1..8
                       mol_type = protein
                       organism = synthetic construct
SEQUENCE: 377
QQRSNWPT                                                           8

SEQ ID NO: 378         moltype = AA  length = 113
FEATURE                Location/Qualifiers
REGION                 1..113
                       note = NivoluVH
source                 1..113
                       mol_type = protein
                       organism = synthetic construct
SEQUENCE: 378
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 379         moltype = AA  length = 5
FEATURE                Location/Qualifiers
REGION                 1..5
                       note = NivoluVH - CDR1
source                 1..5
                       mol_type = protein
                       organism = synthetic construct
SEQUENCE: 379
NSGMH                                                              5

SEQ ID NO: 380         moltype = AA  length = 17
FEATURE                Location/Qualifiers
REGION                 1..17
                       note = NivoluVH - CDR2
source                 1..17
                       mol_type = protein
                       organism = synthetic construct
SEQUENCE: 380
VIWYDGSKRY YADSVKG                                                 17
```

```
SEQ ID NO: 381          moltype = AA  length = 4
FEATURE                 Location/Qualifiers
REGION                  1..4
                        note = NivoluVH - CDR3
source                  1..4
                        mol_type = protein
                        organism = synthetic construct
SEQUENCE: 381
NDDY                                                              4

SEQ ID NO: 382          moltype = AA  length = 245
FEATURE                 Location/Qualifiers
REGION                  1..245
                        note = Short Chain 1 (1B12 VH-CH1)
source                  1..245
                        mol_type = protein
                        organism = synthetic construct
SEQUENCE: 382
MEFGLSWLFL VAILKGVQCQ VQLVQSGAEV KKPGSSVKVS CKTSGDTFSS YAISWVRQAP  60
GQGLEWMGGI IPIFGRAHYA QKFQGRVTIT ADESTSTAYM ELSSLRSEDT AVYFCARKFH  120
FVSGSPFGMD VWGQGTTVTV SSASTKGPSV FPLAPSSKST SGGTAALGCL VKDYFPEPVT  180
VSWNSGALTS GVHTFPAVLQ SSGLYSLSSV VTVPSSSLGT QTYICNVNHK PSNTKVDKKV  240
EPKSC                                                             245

SEQ ID NO: 383          moltype = AA  length = 123
FEATURE                 Location/Qualifiers
REGION                  1..123
                        note = 1B12 VH
source                  1..123
                        mol_type = protein
                        organism = synthetic construct
SEQUENCE: 383
QVQLVQSGAE VKKPGSSVKV SCKTSGDTFS SYAISWVRQA PGQGLEWMGG IIPIFGRAHY  60
AQKFQGRVTI TADESTSTAY MELSSLRSED TAVYFCARKF HFVSGSPFGM DVWGQGTTVT  120
VSS                                                               123

SEQ ID NO: 384          moltype = AA  length = 5
FEATURE                 Location/Qualifiers
REGION                  1..5
                        note = 1B12 VH - CDR1
source                  1..5
                        mol_type = protein
                        organism = synthetic construct
SEQUENCE: 384
SYAIS                                                             5

SEQ ID NO: 385          moltype = AA  length = 17
FEATURE                 Location/Qualifiers
REGION                  1..17
                        note = 1B12 VH - CDR2
source                  1..17
                        mol_type = protein
                        organism = synthetic construct
SEQUENCE: 385
GIIPIFGRAH YAQKFQG                                                17

SEQ ID NO: 386          moltype = AA  length = 14
FEATURE                 Location/Qualifiers
REGION                  1..14
                        note = 1B12 VH - CDR3
source                  1..14
                        mol_type = protein
                        organism = synthetic construct
SEQUENCE: 386
KFHFVSGSPF GMDV                                                   14

SEQ ID NO: 387          moltype = AA  length = 236
FEATURE                 Location/Qualifiers
REGION                  1..236
                        note = Short Chain 2 (Nivolu VL-hCK)
source                  1..236
                        mol_type = protein
                        organism = synthetic construct
SEQUENCE: 387
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQSSNWPRTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236
```

```
SEQ ID NO: 388         moltype = AA  length = 107
FEATURE                Location/Qualifiers
REGION                 1..107
                       note = Nivolu VL
source                 1..107
                       mol_type = protein
                       organism = synthetic construct
SEQUENCE: 388
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK                107

SEQ ID NO: 389         moltype = AA  length = 11
FEATURE                Location/Qualifiers
REGION                 1..11
                       note = Nivolu VL - CDR1
source                 1..11
                       mol_type = protein
                       organism = synthetic construct
SEQUENCE: 389
RASQSVSSYL A                                                       11

SEQ ID NO: 390         moltype = AA  length = 7
FEATURE                Location/Qualifiers
REGION                 1..7
                       note = Nivolu VL - CDR2
source                 1..7
                       mol_type = protein
                       organism = synthetic construct
SEQUENCE: 390
DASNRAT                                                            7

SEQ ID NO: 391         moltype = AA  length = 9
FEATURE                Location/Qualifiers
REGION                 1..9
                       note = Nivolu VL - CDR3
source                 1..9
                       mol_type = protein
                       organism = synthetic construct
SEQUENCE: 391
QQSSNWPRT                                                          9

SEQ ID NO: 392         moltype = AA  length = 682
FEATURE                Location/Qualifiers
REGION                 1..682
                       note = Long Chain (Ofatu VL-hCk-Epratu VH-hCg1)
source                 1..682
                       mol_type = protein
                       organism = synthetic construct
SEQUENCE: 392
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQRSNWPITF  120
GQGTRLEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
VQSGAEVKKP GSSVKVSCKA SGYTFTSYWL HWVRQAPGQG LEWIGYINPR NDYTEYNQNF  300
KDKATITADE STNTAYMELS SLRSEDTAFY FCARRDITTF YWGQGTTVTV SSASTKGPSV  360
FPLAPSSKST SGGTAALGCL VKDYFPEPVT VSWNSGALTS GVHTFPAVLQ SSGLYSLSSV  420
VTVPSSSLGT QTYICNVNHK PSNTKVDKKV EPKSCDKTHT CPPCPAPELL GGPSVFLFPP  480
KPKDTLMISR TPEVTCVVVD VSHEDPEVKF NWYVDGVEVH NAKTKPREEQ YNSTYRVVSV  540
LTVLHQDWLN GKEYKCKVSN KALPAPIEKT ISKAKGQPRE PQVYTLPPSR EEMTKNQVSL  600
TCLVKGFYPS DIAVEWESNG QPENNYKTTP PVLDSDGSFF LYSKLTVDKS RWQQGNVFSC  660
SVMHEALHNH YTQKSLSLSP GK                                           682

SEQ ID NO: 393         moltype = AA  length = 107
FEATURE                Location/Qualifiers
REGION                 1..107
                       note = OfatuVL
source                 1..107
                       mol_type = protein
                       organism = synthetic construct
SEQUENCE: 393
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPITFGQ GTRLEIK                107

SEQ ID NO: 394         moltype = AA  length = 11
FEATURE                Location/Qualifiers
REGION                 1..11
                       note = Ofatu VL - CDR1
source                 1..11
```

```
                         mol_type = protein
                         organism = synthetic construct
SEQUENCE: 394
RASQSVSSYL A                                                  11

SEQ ID NO: 395           moltype = AA  length = 7
FEATURE                  Location/Qualifiers
REGION                   1..7
                         note = Ofatu VL - CDR2
source                   1..7
                         mol_type = protein
                         organism = synthetic construct
SEQUENCE: 395
DASNRAT                                                       7

SEQ ID NO: 396           moltype = AA  length = 9
FEATURE                  Location/Qualifiers
REGION                   1..9
                         note = Ofatu VL - CDR3
source                   1..9
                         mol_type = protein
                         organism = synthetic construct
SEQUENCE: 396
QQRSNWPIT                                                     9

SEQ ID NO: 397           moltype = AA  length = 116
FEATURE                  Location/Qualifiers
REGION                   1..116
                         note = Epratu VH
source                   1..116
                         mol_type = protein
                         organism = synthetic construct
SEQUENCE: 397
QVQLVQSGAE VKKPGSSVKV SCKASGYTFT SYWLHWVRQA PGQGLEWIGY INPRNDYTEY  60
NQNFKDKATI TADESTNTAY MELSSLRSED TAFYFCARRD ITTFYWGQGT TVTVSS      116

SEQ ID NO: 398           moltype = AA  length = 5
FEATURE                  Location/Qualifiers
REGION                   1..5
                         note = Epratu VH - CDR1
source                   1..5
                         mol_type = protein
                         organism = synthetic construct
SEQUENCE: 398
SYWLH                                                         5

SEQ ID NO: 399           moltype = AA  length = 17
FEATURE                  Location/Qualifiers
REGION                   1..17
                         note = Epratu VH - CDR2
source                   1..17
                         mol_type = protein
                         organism = synthetic construct
SEQUENCE: 399
YINPRNDYTE YNQNFKD                                            17

SEQ ID NO: 400           moltype = AA  length = 7
FEATURE                  Location/Qualifiers
REGION                   1..7
                         note = Epratu VH - CDR3
source                   1..7
                         mol_type = protein
                         organism = synthetic construct
SEQUENCE: 400
RDITTFY                                                       7

SEQ ID NO: 401           moltype = AA  length = 244
FEATURE                  Location/Qualifiers
REGION                   1..244
                         note = Short Chain 1 (Ofatu VH-CH1)
source                   1..244
                         mol_type = protein
                         organism = synthetic construct
SEQUENCE: 401
MEFGLSWLFL VAILKGVQCE VQLVESGGGL VQPGRSLRLS CAASGFTFND YAMHWVRQAP  60
GKGLEWVSTI SWNSGSIGYA DSVKGRFTIS RDNAKKSLYL QMNSLRAEDT ALYYCAKDIQ  120
YGNYYYGMDV WGQGTTVTVS SASTKGPSVF PLAPSSKSTS GGTAALGCLV KDYFPEPVTV  180
SWNSGALTSG VHTFPAVLQS SGLYSLSSVV TVPSSSLGTQ TYICNVNHKP SNTKVDKKVE  240
PKSC                                                          244
```

```
SEQ ID NO: 402          moltype = AA  length = 122
FEATURE                 Location/Qualifiers
REGION                  1..122
                        note = Ofatu VH
source                  1..122
                        mol_type = protein
                        organism = synthetic construct
SEQUENCE: 402
EVQLVESGGG LVQPGRSLRL SCAASGFTFN DYAMHWVRQA PGKGLEWVST ISWNSGSIGY  60
ADSVKGRFTI SRDNAKKSLY LQMNSLRAED TALYYCAKDI QYGNYYYGMD VWGQGTTVTV  120
SS                                                                122

SEQ ID NO: 403          moltype = AA  length = 5
FEATURE                 Location/Qualifiers
REGION                  1..5
                        note = Ofatu VH - CDR1
source                  1..5
                        mol_type = protein
                        organism = synthetic construct
SEQUENCE: 403
DYAMH                                                             5

SEQ ID NO: 404          moltype = AA  length = 17
FEATURE                 Location/Qualifiers
REGION                  1..17
                        note = Ofatu VH - CDR2
source                  1..17
                        mol_type = protein
                        organism = synthetic construct
SEQUENCE: 404
TISWNSGSIG YADSVKG                                                17

SEQ ID NO: 405          moltype = AA  length = 13
FEATURE                 Location/Qualifiers
REGION                  1..13
                        note = Ofatu VH - CDR3
source                  1..13
                        mol_type = protein
                        organism = synthetic construct
SEQUENCE: 405
DIQYGNYYYG MDV                                                    13

SEQ ID NO: 406          moltype = AA  length = 241
FEATURE                 Location/Qualifiers
REGION                  1..241
                        note = Short Chain 2 (Epratu VL-hCk)
source                  1..241
                        mol_type = protein
                        organism = synthetic construct
SEQUENCE: 406
MDMRVPAQLL GLLLLWFPGS RCDIQLTQSP SSLSASVGDR VTMSCKSSQS VLYSANHKNY  60
LAWYQQKPGK APKLLIYWAS TRESGVPSRF SGSGSGTDFT FTISSLQPED IATYYCHQYL  120
SSWTFGGGTK LEIKRTVAAP SVFIFPPSDE QLKSGTASVV CLLNNFYPRE AKVQWKVDNA  180
LQSGNSQESV TEQDSKDSTY SLSSTLTLSK ADYEKHKVYA CEVTHQGLSS PVTKSFNRGE  240
C                                                                 241

SEQ ID NO: 407          moltype = AA  length = 112
FEATURE                 Location/Qualifiers
REGION                  1..112
                        note = Epratu VL
source                  1..112
                        mol_type = protein
                        organism = synthetic construct
SEQUENCE: 407
DIQLTQSPSS LSASVGDRVT MSCKSSQSVL YSANHKNYLA WYQQKPGKAP KLLIYWASTR  60
ESGVPSRFSG SGSGTDFTFT ISSLQPEDIA TYYCHQYLSS WTFGGGTKLE IK         112

SEQ ID NO: 408          moltype = AA  length = 17
FEATURE                 Location/Qualifiers
REGION                  1..17
                        note = Epratu VL - CDR1
source                  1..17
                        mol_type = protein
                        organism = synthetic construct
SEQUENCE: 408
KSSQSVLYSA NHKNYLA                                                17

SEQ ID NO: 409          moltype = AA  length = 7
```

```
FEATURE                Location/Qualifiers
REGION                 1..7
                       note = Epratu VL - CDR2
source                 1..7
                       mol_type = protein
                       organism = synthetic construct
SEQUENCE: 409
WASTRES                                                      7

SEQ ID NO: 410         moltype = AA  length = 8
FEATURE                Location/Qualifiers
REGION                 1..8
                       note = Epratu VL - CDR3
source                 1..8
                       mol_type = protein
                       organism = synthetic construct
SEQUENCE: 410
HQYLSSWT                                                     8

SEQ ID NO: 411         moltype = AA  length = 685
FEATURE                Location/Qualifiers
REGION                 1..685
                       note = Long Chain (patritu VL-hCk-Nivolu VH-hCg1mut)
source                 1..685
                       mol_type = protein
                       organism = synthetic construct
SEQUENCE: 411
MDMRVPAQLL GLLLLWFPGS RCDIEMTQSP DSLAVSLGER ATINCRSSQS VLYSSSNRNY  60
LAWYQQNPGQ PPKLLIYWAS TRESGVPDRF SGSGSGTDFT LTISSLQAED VAVYYCQQYY  120
STPRTFGQGT KVEIKRTVAA PSVFIFPPSD EQLKSGTASV VCLLNNFYPR EAKVQWKVDN  180
ALQSGNSQES VTEQDSKDST YSLSSTLTLS KADYEKHKVY ACEVTHQGLS SPVTKSFNRG  240
ECQVQLVESG GGVVQPGRSL RLDCKASGIT FSNSGMHWVR QAPGKGLEWV AVIWYDGSKR  300
YYADSVKGRF TISRDNSKNT LFLQMNSLRA EDTAVYYCAT NDDYWGQGTL VTVSSASTKG  360
PSVFPLAPSS KSTSGGTAAL GCLVKDYFPE PVTVSWNSGA LTSGVHTFPA VLQSSGLYSL  420
SSVVTVPSSS LGTQTYICNV NHKPSNTKVD KKVEPKSCDK THTCPPCPAP ELLGGPSVFL  480
FPPKPKDTLM ISRTPEVTCV VVDVSHEDPE VKFNWYVDGV EVHNAKTKPR EEQYNSTYRV  540
VSVLTVLHQD WLNGKEYKCK VSNKALPAPI EKTISKAKGQ PREPQVYTLP PSREEMTKNQ  600
VSLTCLVKGF YPSDIAVEWE SNGQPENNYK TTPPVLDSDG SFFLYSKLTV DKSRWQQGNV  660
FSCSVMHEAL HNHYTQKSLS LSPGK                                  685

SEQ ID NO: 412         moltype = AA  length = 113
FEATURE                Location/Qualifiers
REGION                 1..113
                       note = patrituVL
source                 1..113
                       mol_type = protein
                       organism = synthetic construct
SEQUENCE: 412
DIEMTQSPDS LAVSLGERAT INCRSSQSVL YSSSNRNYLA WYQQNPGQPP KLLIYWASTR  60
ESGVPDRFSG SGSGTDFTLT ISSLQAEDVA VYYCQQYYST PRTFGQGTKV EIK        113

SEQ ID NO: 413         moltype = AA  length = 17
FEATURE                Location/Qualifiers
REGION                 1..17
                       note = patritu VL - CDR1
source                 1..17
                       mol_type = protein
                       organism = synthetic construct
SEQUENCE: 413
RSSQSVLYSS SNRNYLA                                           17

SEQ ID NO: 414         moltype = AA  length = 7
FEATURE                Location/Qualifiers
REGION                 1..7
                       note = patritu VL - CDR2
source                 1..7
                       mol_type = protein
                       organism = synthetic construct
SEQUENCE: 414
WASTRES                                                      7

SEQ ID NO: 415         moltype = AA  length = 9
FEATURE                Location/Qualifiers
REGION                 1..9
                       note = patritu VL - CDR3
source                 1..9
                       mol_type = protein
                       organism = synthetic construct
SEQUENCE: 415
```

```
QQYYSTPRT                                                      9

SEQ ID NO: 416          moltype = AA  length = 113
FEATURE                 Location/Qualifiers
REGION                  1..113
                        note = Nivolu VH
source                  1..113
                        mol_type = protein
                        organism = synthetic construct
SEQUENCE: 416
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 417          moltype = AA  length = 5
FEATURE                 Location/Qualifiers
REGION                  1..5
                        note = Nivolu VH - CDR1
source                  1..5
                        mol_type = protein
                        organism = synthetic construct
SEQUENCE: 417
NSGMH                                                          5

SEQ ID NO: 418          moltype = AA  length = 17
FEATURE                 Location/Qualifiers
REGION                  1..17
                        note = Nivolu VH - CDR2
source                  1..17
                        mol_type = protein
                        organism = synthetic construct
SEQUENCE: 418
VIWYDGSKRY YADSVKG                                             17

SEQ ID NO: 419          moltype = AA  length = 4
FEATURE                 Location/Qualifiers
REGION                  1..4
                        note = Nivolu VH - CDR3
source                  1..4
                        mol_type = protein
                        organism = synthetic construct
SEQUENCE: 419
NDDY                                                           4

SEQ ID NO: 420          moltype = AA  length = 239
FEATURE                 Location/Qualifiers
REGION                  1..239
                        note = Short Chain 1 (Patritumab -CH1)
source                  1..239
                        mol_type = protein
                        organism = synthetic construct
SEQUENCE: 420
MEFGLSWLFL VAILKGVQCQ VQLQQWGAGL LKPSETLSLT CAVYGGSFSG YYWSWIRQPP  60
GKGLEWIGEI NHSGSTNYNP SLKSRVTISV ETSKNQFSLK LSSVTAADTA VYYCARDKWT  120
WYFDLWGRGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSC   239

SEQ ID NO: 421          moltype = AA  length = 117
FEATURE                 Location/Qualifiers
REGION                  1..117
                        note = Patritumab VH
source                  1..117
                        mol_type = protein
                        organism = synthetic construct
SEQUENCE: 421
QVQLQQWGAG LLKPSETLSL TCAVYGGSFS GYYWSWIRQP PGKGLEWIGE INHSGSTNYN  60
PSLKSRVTIS VETSKNQFSL KLSSVTAADT AVYYCARDKW TWYFDLWGRG TLVTVSS     117

SEQ ID NO: 422          moltype = AA  length = 5
FEATURE                 Location/Qualifiers
REGION                  1..5
                        note = Patritumab VH - CDR1
source                  1..5
                        mol_type = protein
                        organism = synthetic construct
SEQUENCE: 422
GYYWS                                                          5

SEQ ID NO: 423          moltype = AA  length = 16
FEATURE                 Location/Qualifiers
```

```
REGION                  1..16
                        note = Patritumab VH - CDR2
source                  1..16
                        mol_type = protein
                        organism = synthetic construct
SEQUENCE: 423
EINHSGSTNY NPSLKS                                                   16

SEQ ID NO: 424          moltype = AA  length = 9
FEATURE                 Location/Qualifiers
REGION                  1..9
                        note = Patritumab VH - CDR3
source                  1..9
                        mol_type = protein
                        organism = synthetic construct
SEQUENCE: 424
DKWTWYFDL                                                           9

SEQ ID NO: 425          moltype = AA  length = 236
FEATURE                 Location/Qualifiers
REGION                  1..236
                        note = Short Chain 2 (NivoVL-hCK)
source                  1..236
                        mol_type = protein
                        organism = synthetic construct
SEQUENCE: 425
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQSSNWPRTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 426          moltype = AA  length = 107
FEATURE                 Location/Qualifiers
REGION                  1..107
                        note = Nivo VL
source                  1..107
                        mol_type = protein
                        organism = synthetic construct
SEQUENCE: 426
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK                107

SEQ ID NO: 427          moltype = AA  length = 11
FEATURE                 Location/Qualifiers
REGION                  1..11
                        note = Nivo VL - CDR1
source                  1..11
                        mol_type = protein
                        organism = synthetic construct
SEQUENCE: 427
RASQSVSSYL A                                                        11

SEQ ID NO: 428          moltype = AA  length = 7
FEATURE                 Location/Qualifiers
REGION                  1..7
                        note = Nivo VL - CDR2
source                  1..7
                        mol_type = protein
                        organism = synthetic construct
SEQUENCE: 428
DASNRAT                                                             7

SEQ ID NO: 429          moltype = AA  length = 9
FEATURE                 Location/Qualifiers
REGION                  1..9
                        note = Nivo VL - CDR3
source                  1..9
                        mol_type = protein
                        organism = synthetic construct
SEQUENCE: 429
QQSSNWPRT                                                           9

SEQ ID NO: 430          moltype = AA  length = 689
FEATURE                 Location/Qualifiers
REGION                  1..689
                        note = Long Chain (h1332 VL-hCk-1B12 VH-hCg1)
source                  1..689
                        mol_type = protein
                        organism = synthetic construct
```

```
SEQUENCE: 430
MDMRVPAQLL GLLLLWFPGS RCDIQMTQSP SSVSASVGDR VTITCRASQG INTWLAWYQQ  60
KPGKAPKLLI YAASSLKSGV PSRFSGSGSG TDFTLTISSL QPEDFATYYC QQANSFPLTF  120
GGGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQVQL  240
VQSGAEVKKP GSSVKVSCKT SGDTFSSYAI SWVRQAPGQG LEWMGGIIPI FGRAHYAQKF  300
QGRVTITADE STSTAYMELS SLRSEDTAVY FCARKFHFVS GSPFGMDVWG QGTTVTVSSA  360
STKGPSVFPL APSSKSTSGG TAALGCLVKD YFPEPVTVSW NSGALTSGVH TFPAVLQSSG  420
LYSLSSVVTV PSSSLGTQTY ICNVNHKPSN TKVDKKVEPK SCDKTHTCPP CPAPELLGGP  480
SVFLFPPKPK DTLMISRTPE VTCVVVDVSH EDPEVKFNWY VDGVEVHNAK TKPREEQYNS  540
TYRVVSVLTV LHQDWLNGKE YKCKVSNKAL PAPIEKTISK AKGQPREPQV YTLPPSREEM  600
TKNQVSLTCL VKGFYPSDIA VEWESNGQPE NNYKTTPPVL DSDGSFFLYS KLTVDKSRWQ  660
QGNVFSCSVM HEALHNHYTQ KSLSLSPGK                                  689

SEQ ID NO: 431         moltype = AA  length = 107
FEATURE                Location/Qualifiers
REGION                 1..107
                       note = h1332 VL
source                 1..107
                       mol_type = protein
                       organism = synthetic construct
SEQUENCE: 431
DIQMTQSPSS VSASVGDRVT ITCRASQGIN TWLAWYQQKP GKAPKLLIYA ASSLKSGVPS  60
RFSGSGSGTD FTLTISSLQP EDFATYYCQQ ANSFPLTFGG GTKVEIK              107

SEQ ID NO: 432         moltype = AA  length = 11
FEATURE                Location/Qualifiers
REGION                 1..11
                       note = h1332 VL - CDR1
source                 1..11
                       mol_type = protein
                       organism = synthetic construct
SEQUENCE: 432
RASQGINTWL A                                                     11

SEQ ID NO: 433         moltype = AA  length = 7
FEATURE                Location/Qualifiers
REGION                 1..7
                       note = h1332 VL - CDR2
source                 1..7
                       mol_type = protein
                       organism = synthetic construct
SEQUENCE: 433
AASSLKS                                                          7

SEQ ID NO: 434         moltype = AA  length = 9
FEATURE                Location/Qualifiers
REGION                 1..9
                       note = h1332 VL - CDR3
source                 1..9
                       mol_type = protein
                       organism = synthetic construct
SEQUENCE: 434
QQANSFPLT                                                        9

SEQ ID NO: 435         moltype = AA  length = 123
FEATURE                Location/Qualifiers
REGION                 1..123
                       note = 1B12 VH
source                 1..123
                       mol_type = protein
                       organism = synthetic construct
SEQUENCE: 435
QVQLVQSGAE VKKPGSSVKV SCKTSGDTFS SYAISWVRQA PGQGLEWMGG IIPIFGRAHY  60
AQKFQGRVTI TADESTSTAY MELSSLRSED TAVYFCARKF HFVSGSPFGM DVWGQGTTVT  120
VSS                                                              123

SEQ ID NO: 436         moltype = AA  length = 5
FEATURE                Location/Qualifiers
REGION                 1..5
                       note = 1B12 VH - CDR1
source                 1..5
                       mol_type = protein
                       organism = synthetic construct
SEQUENCE: 436
SYAIS                                                            5

SEQ ID NO: 437         moltype = AA  length = 11
FEATURE                Location/Qualifiers
```

```
REGION                  1..11
                        note = 1B12 VH - CDR2
source                  1..11
                        mol_type = protein
                        organism = synthetic construct
SEQUENCE: 437
GIIPIFGRAH Y                                                      11

SEQ ID NO: 438          moltype = AA  length = 14
FEATURE                 Location/Qualifiers
REGION                  1..14
                        note = 1B12 VH - CDR3
source                  1..14
                        mol_type = protein
                        organism = synthetic construct
SEQUENCE: 438
KFHFVSGSPF GMDV                                                   14

SEQ ID NO: 439          moltype = AA  length = 239
FEATURE                 Location/Qualifiers
REGION                  1..239
                        note = Short Chain 1 (h1332 VH-CH1)
source                  1..239
                        mol_type = protein
                        organism = synthetic construct
SEQUENCE: 439
MEFGLSWLFL VAILKGVQCQ VQLVQSGAEV KKPGASVKVS CKASGYTFTS YGFSWVRQAP  60
GQGLEWMGWI SASNGNTYYA QKLQGRVTMT TDTSTSTAYM ELRSLRSDDT AVYYCARVYA  120
DYADYWGQGT LVTVSSASTK GPSVFPLAPS SKSTSGGTAA LGCLVKDYFP EPVTVSWNSG  180
ALTSGVHTFP AVLQSSGLYS LSSVVTVPSS SLGTQTYICN VNHKPSNTKV DKKVEPKSC   239

SEQ ID NO: 440          moltype = AA  length = 117
FEATURE                 Location/Qualifiers
REGION                  1..117
                        note = h1332 VH
source                  1..117
                        mol_type = protein
                        organism = synthetic construct
SEQUENCE: 440
QVQLVQSGAE VKKPGASVKV SCKASGYTFT SYGFSWVRQA PGQGLEWMGW ISASNGNTYY  60
AQKLQGRVTM TTDTSTSTAY MELRSLRSDD TAVYYCARVY ADYADYWGQG TLVTVSS     117

SEQ ID NO: 441          moltype = AA  length = 5
FEATURE                 Location/Qualifiers
REGION                  1..5
                        note = h1332 VH - CDR1
source                  1..5
                        mol_type = protein
                        organism = synthetic construct
SEQUENCE: 441
SYGFS                                                             5

SEQ ID NO: 442          moltype = AA  length = 17
FEATURE                 Location/Qualifiers
REGION                  1..17
                        note = h1332 VH - CDR2
source                  1..17
                        mol_type = protein
                        organism = synthetic construct
SEQUENCE: 442
WISASNGNTY YAQKLQG                                                17

SEQ ID NO: 443          moltype = AA  length = 8
FEATURE                 Location/Qualifiers
REGION                  1..8
                        note = h1332 VH - CDR3
source                  1..8
                        mol_type = protein
                        organism = synthetic construct
SEQUENCE: 443
VYADYADY                                                          8

SEQ ID NO: 444          moltype = AA  length = 235
FEATURE                 Location/Qualifiers
REGION                  1..235
                        note = Short Chain 2 (1B12 VL-hCK)
source                  1..235
                        mol_type = protein
                        organism = synthetic construct
```

```
SEQUENCE: 444
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQRSNWPTFG  120
QGTKVEIKRT VAAPSVFIFP PSDEQLKSGT ASVVCLLNNF YPREAKVQWK VDNALQSGNS  180
QESVTEQDSK DSTYSLSSTL TLSKADYEKH KVYACEVTHQ GLSSPVTKSF NRGEC       235

SEQ ID NO: 445         moltype = AA  length = 106
FEATURE                Location/Qualifiers
REGION                 1..106
                       note = 1B12 VL
source                 1..106
                       mol_type = protein
                       organism = synthetic construct
SEQUENCE: 445
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPTFGQG TKVEIK                 106

SEQ ID NO: 446         moltype = AA  length = 11
FEATURE                Location/Qualifiers
REGION                 1..11
                       note = 1B12 VL - CDR1
source                 1..11
                       mol_type = protein
                       organism = synthetic construct
SEQUENCE: 446
RASQSVSSYL A                                                       11

SEQ ID NO: 447         moltype = AA  length = 7
FEATURE                Location/Qualifiers
REGION                 1..7
                       note = 1B12 VL - CDR2
source                 1..7
                       mol_type = protein
                       organism = synthetic construct
SEQUENCE: 447
DASNRAT                                                            7

SEQ ID NO: 448         moltype = AA  length = 8
FEATURE                Location/Qualifiers
REGION                 1..8
                       note = 1B12 VL - CDR3
source                 1..8
                       mol_type = protein
                       organism = synthetic construct
SEQUENCE: 448
QQRSNWPT                                                           8

SEQ ID NO: 449         moltype = AA  length = 681
FEATURE                Location/Qualifiers
REGION                 1..681
                       note = Long Chain (6A5 VL-hCk-Nivolu VH-hCg1mut)
source                 1..681
                       mol_type = protein
                       organism = synthetic construct
SEQUENCE: 449
MDMRVPAQLL GLLLLWFPGS RCEIVLTQSP GTLSLSPGER ATLSCRASQS VSSTYLAWYQ  60
QKPGQAPRLL IYGASSRATG IPDRFSGSGS GTDFTLTISR LEPEDFAVYY CQQYGSSPPI  120
TFGQGTRLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGECQV  240
QLVESGGGVV QPGRSLRLDC KASGITFSNS GMHWVRQAPG KGLEWVAVIW YDGSKRYYAD  300
SVKGRFTISR DNSKNTLFLQ MNSLRAEDTA VYYCATNDDY WGQGTLVTVS SASTKGPSVF  360
PLAPSSKSTS GGTAALGCLV KDYFPEPVTV SWNSGALTSG VHTFPAVLQS SGLYSLSSVV  420
TVPSSSLGTQ TYICNVNHKP SNTKVDKKVE PKSCDKTHTC PPCPAPEAAG GPSVFLFPPK  480
PKDTLMISRT PEVTCVVVDV SHEDPEVKFN WYVDGVEVHN AKTKPREEQY NSTYRVVSVL  540
TVLHQDWLNG KEYKCKVSNK ALPAPIEKTI SKAKGQPREP QVYTLPPSRE EMTKNQVSLT  600
CLVKGFYPSD IAVEWESNGQ PENNYKTTPP VLDSDGSFFL YSKLTVDKSR WQQGNVFSCS  660
VMHEALHNHY TQKSLSLSPG K                                            681

SEQ ID NO: 450         moltype = AA  length = 109
FEATURE                Location/Qualifiers
REGION                 1..109
                       note = 6A5 VL
source                 1..109
                       mol_type = protein
                       organism = synthetic construct
SEQUENCE: 450
EIVLTQSPGT LSLSPGERAT LSCRASQSVS STYLAWYQQK PGQAPRLLIY GASSRATGIP  60
DRFSGSGSGT DFTLTISRLE PEDFAVYYCQ QYGSSPPITF GQGTRLEIK              109
```

```
SEQ ID NO: 451          moltype = AA  length = 12
FEATURE                 Location/Qualifiers
REGION                  1..12
                        note = 6A5 VL - CDR1
source                  1..12
                        mol_type = protein
                        organism = synthetic construct
SEQUENCE: 451
RASQSVSSTY LA                                                     12

SEQ ID NO: 452          moltype = AA  length = 7
FEATURE                 Location/Qualifiers
REGION                  1..7
                        note = 6A5 VL - CDR2
source                  1..7
                        mol_type = protein
                        organism = synthetic construct
SEQUENCE: 452
GASSRAT                                                           7

SEQ ID NO: 453          moltype = AA  length = 10
FEATURE                 Location/Qualifiers
REGION                  1..10
                        note = 6A5 VL - CDR3
source                  1..10
                        mol_type = protein
                        organism = synthetic construct
SEQUENCE: 453
QQYGSSPPIT                                                        10

SEQ ID NO: 454          moltype = AA  length = 113
FEATURE                 Location/Qualifiers
REGION                  1..113
                        note = Nivolu VH
source                  1..113
                        mol_type = protein
                        organism = synthetic construct
SEQUENCE: 454
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 455          moltype = AA  length = 5
FEATURE                 Location/Qualifiers
REGION                  1..5
                        note = NivoluVH - CDR1
source                  1..5
                        mol_type = protein
                        organism = synthetic construct
SEQUENCE: 455
NSGMH                                                             5

SEQ ID NO: 456          moltype = AA  length = 17
FEATURE                 Location/Qualifiers
REGION                  1..17
                        note = NivoluVH - CDR2
source                  1..17
                        mol_type = protein
                        organism = synthetic construct
SEQUENCE: 456
VIWYDGSKRY YADSVKG                                                17

SEQ ID NO: 457          moltype = AA  length = 4
FEATURE                 Location/Qualifiers
REGION                  1..4
                        note = NivoluVH - CDR3
source                  1..4
                        mol_type = protein
                        organism = synthetic construct
SEQUENCE: 457
NDDY                                                              4

SEQ ID NO: 458          moltype = AA  length = 250
FEATURE                 Location/Qualifiers
REGION                  1..250
                        note = Short Chain 1 (6A5 VH-CH1)
source                  1..250
                        mol_type = protein
                        organism = synthetic construct
SEQUENCE: 458
```

```
MEFGLSWLFL VAILKGVQCQ ITLKESGPTL VKPTQTLTLT CTFSGFSLST SGVGVGWIRQ  60
PPGKALEWLA LIYWDDDKRY SPSLKSRLTI TKDTSKNQVV LTMANMDPVD TATYYCAHIR  120
ITEVRGVIIS YYGMDVWGQG TTVTVSSAST KGPSVFPLAP SSKSTSGGTA ALGCLVKDYF  180
PEPVTVSWNS GALTSGVHTF PAVLQSSGLY SLSSVVTVPS SSLGTQTYIC NVNHKPSNTK  240
VDKKVEPKSC                                                        250

SEQ ID NO: 459          moltype = AA  length = 128
FEATURE                 Location/Qualifiers
REGION                  1..128
                        note = 6A5 VH
source                  1..128
                        mol_type = protein
                        organism = synthetic construct
SEQUENCE: 459
QITLKESGPT LVKPTQTLTL TCTFSGFSLS TSGVGVGWIR QPPGKALEWL ALIYWDDDKR  60
YSPSLKSRLT ITKDTSKNQV VLTMANMDPV DTATYYCAHI RITEVRGVII SYYGMDVWGQ  120
GTTVTVSS                                                          128

SEQ ID NO: 460          moltype = AA  length = 7
FEATURE                 Location/Qualifiers
REGION                  1..7
                        note = 6A5 VH - CDR1
source                  1..7
                        mol_type = protein
                        organism = synthetic construct
SEQUENCE: 460
TSGVGVG                                                           7

SEQ ID NO: 461          moltype = AA  length = 16
FEATURE                 Location/Qualifiers
REGION                  1..16
                        note = 6A5 VH - CDR2
source                  1..16
                        mol_type = protein
                        organism = synthetic construct
SEQUENCE: 461
LIYWDDDKRY SPSLKS                                                 16

SEQ ID NO: 462          moltype = AA  length = 18
FEATURE                 Location/Qualifiers
REGION                  1..18
                        note = 6A5 VH - CDR3
source                  1..18
                        mol_type = protein
                        organism = synthetic construct
SEQUENCE: 462
IRITEVRGVI ISYYGMDV                                               18

SEQ ID NO: 463          moltype = AA  length = 236
FEATURE                 Location/Qualifiers
REGION                  1..236
                        note = Short Chain 2 (Nivolu VL-hCK)
source                  1..236
                        mol_type = protein
                        organism = synthetic construct
SEQUENCE: 463
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQSSNWPRTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGEC      236

SEQ ID NO: 464          moltype = AA  length = 107
FEATURE                 Location/Qualifiers
REGION                  1..107
                        note = Nivolu VL
source                  1..107
                        mol_type = protein
                        organism = synthetic construct
SEQUENCE: 464
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK               107

SEQ ID NO: 465          moltype = AA  length = 11
FEATURE                 Location/Qualifiers
REGION                  1..11
                        note = Nivolu VL - CDR1
source                  1..11
                        mol_type = protein
                        organism = synthetic construct
```

```
SEQUENCE: 465
RASQSVSSYL A                                                     11

SEQ ID NO: 466          moltype = AA  length = 7
FEATURE                 Location/Qualifiers
REGION                  1..7
                        note = Nivolu VL - CDR2
source                  1..7
                        mol_type = protein
                        organism = synthetic construct
SEQUENCE: 466
DASNRAT                                                          7

SEQ ID NO: 467          moltype = AA  length = 9
FEATURE                 Location/Qualifiers
REGION                  1..9
                        note = Nivolu VL - CDR3
source                  1..9
                        mol_type = protein
                        organism = synthetic construct
SEQUENCE: 467
QQSSNWPRT                                                        9

SEQ ID NO: 468          moltype = AA  length = 694
FEATURE                 Location/Qualifiers
REGION                  1..694
                        note = Long Chain (Nivolu VL-hCk-6A5 VH-hCg1mut)
source                  1..694
                        mol_type = protein
                        organism = synthetic construct
SEQUENCE: 468
MDMRVPAQLL GLLLLWFPGS RCEIVLTQSP ATLSLSPGER ATLSCRASQS VSSYLAWYQQ  60
KPGQAPRLLI YDASNRATGI PARFSGSGSG TDFTLTISSL EPEDFAVYYC QQSSNWPRTF  120
GQGTKVEIKR TVAAPSVFIF PPSDEQLKSG TASVVCLLNN FYPREAKVQW KVDNALQSGN  180
SQESVTEQDS KDSTYSLSST LTLSKADYEK HKVYACEVTH QGLSSPVTKS FNRGECQITL  240
KESGPTLVKP TQTLTLTCTF SGFSLSTSGV GVGWIRQPPG KALEWLALIY WDDDKRYSPS  300
LKSRLTITKD TSKNQVVLTM ANMDPVDTAT YYCAHIRITE VRGVIISYYG MDVWGQGTTV  360
TVSSASTKGP SVFPLAPSSK STSGGTAALG CLVKDYFPEP VTVSWNSGAL TSGVHTFPAV  420
LQSSGLYSLS SVVTVPSSSL GTQTYICNVN HKPSNTKVDK KVEPKSCDKT HTCPPCPAPE  480
AAGGPSVFLF PPKPKDTLMI SRTPEVTCVV VDVSHEDPEV KFNWYVDGVE VHNAKTKPRE  540
EQYNSTYRVV SVLTVLHQDW LNGKEYKCKV SNKALPAPIE KTISKAKGQP REPQVYTLPP  600
SREEMTKNQV SLTCLVKGFY PSDIAVEWES NGQPENNYKT TPPVLDSDGS FFLYSKLTVD  660
KSRWQQGNVF SCSVMHEALH NHYTQKSLSL SPGK                            694

SEQ ID NO: 469          moltype = AA  length = 107
FEATURE                 Location/Qualifiers
REGION                  1..107
                        note = Nivolu VL
source                  1..107
                        mol_type = protein
                        organism = synthetic construct
SEQUENCE: 469
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ SSNWPRTFGQ GTKVEIK              107

SEQ ID NO: 470          moltype = AA  length = 11
FEATURE                 Location/Qualifiers
REGION                  1..11
                        note = Nivolu VL - CDR1
source                  1..11
                        mol_type = protein
                        organism = synthetic construct
SEQUENCE: 470
RASQSVSSYL A                                                     11

SEQ ID NO: 471          moltype = AA  length = 7
FEATURE                 Location/Qualifiers
REGION                  1..7
                        note = Nivolu VL - CDR2
source                  1..7
                        mol_type = protein
                        organism = synthetic construct
SEQUENCE: 471
DASNRAT                                                          7

SEQ ID NO: 472          moltype = AA  length = 9
FEATURE                 Location/Qualifiers
REGION                  1..9
                        note = Nivolu VL - CDR3
```

```
source                  1..9
                        mol_type = protein
                        organism = synthetic construct
SEQUENCE: 472
QQSSNWPRT                                                        9

SEQ ID NO: 473          moltype = AA  length = 128
FEATURE                 Location/Qualifiers
REGION                  1..128
                        note = 6A5 VH
source                  1..128
                        mol_type = protein
                        organism = synthetic construct
SEQUENCE: 473
QITLKESGPT LVKPTQTLTL TCTFSGFSLS TSGVGVGWIR QPPGKALEWL ALIYWDDDKR  60
YSPSLKSRLT ITKDTSKNQV VLTMANMDPV DTATYYCAHI RITEVRGVII SYYGMDVWGQ  120
GTTVTVSS                                                         128

SEQ ID NO: 474          moltype = AA  length = 7
FEATURE                 Location/Qualifiers
REGION                  1..7
                        note = 6A5 VH - CDR1
source                  1..7
                        mol_type = protein
                        organism = synthetic construct
SEQUENCE: 474
TSGVGVG                                                          7

SEQ ID NO: 475          moltype = AA  length = 16
FEATURE                 Location/Qualifiers
REGION                  1..16
                        note = 6A5 VH - CDR2
source                  1..16
                        mol_type = protein
                        organism = synthetic construct
SEQUENCE: 475
LIYWDDDKRY SPSLKS                                                16

SEQ ID NO: 476          moltype = AA  length = 18
FEATURE                 Location/Qualifiers
REGION                  1..18
                        note = 6A5 VH - CDR3
source                  1..18
                        mol_type = protein
                        organism = synthetic construct
SEQUENCE: 476
IRITEVRGVI ISYYGMDV                                              18

SEQ ID NO: 477          moltype = AA  length = 235
FEATURE                 Location/Qualifiers
REGION                  1..235
                        note = Short Chain 1 (Nivolu VH-CH1)
source                  1..235
                        mol_type = protein
                        organism = synthetic construct
SEQUENCE: 477
MEFGLSWLFL VAILKGVQCQ VQLVESGGGV VQPGRSLRLD CKASGITFSN SGMHWVRQAP  60
GKGLEWVAVI WYDGSKRYYA DSVKGRFTIS RDNSKNTLFL QMNSLRAEDT AVYYCATNDD  120
YWGQGTLVTV SSASTKGPSV FPLAPSSKST SGGTAALGCL VKDYFPEPVT VSWNSGALTS  180
GVHTFPAVLQ SSGLYSLSSV VTVPSSSLGT QTYICNVNHK PSNTKVDKKV EPKSC       235

SEQ ID NO: 478          moltype = AA  length = 113
FEATURE                 Location/Qualifiers
REGION                  1..113
                        note = Nivolu VH
source                  1..113
                        mol_type = protein
                        organism = synthetic construct
SEQUENCE: 478
QVQLVESGGG VVQPGRSLRL DCKASGITFS NSGMHWVRQA PGKGLEWVAV IWYDGSKRYY  60
ADSVKGRFTI SRDNSKNTLF LQMNSLRAED TAVYYCATND DYWGQGTLVT VSS         113

SEQ ID NO: 479          moltype = AA  length = 5
FEATURE                 Location/Qualifiers
REGION                  1..5
                        note = Nivolu VH - CDR1
source                  1..5
                        mol_type = protein
                        organism = synthetic construct
```

```
SEQUENCE: 479
NSGMH                                                      5

SEQ ID NO: 480          moltype = AA  length = 17
FEATURE                 Location/Qualifiers
REGION                  1..17
                        note = Nivolu VH - CDR2
source                  1..17
                        mol_type = protein
                        organism = synthetic construct
SEQUENCE: 480
VIWYDGSKRY YADSVKG                                         17

SEQ ID NO: 481          moltype = AA  length = 4
FEATURE                 Location/Qualifiers
REGION                  1..4
                        note = Nivolu VH - CDR3
source                  1..4
                        mol_type = protein
                        organism = synthetic construct
SEQUENCE: 481
NDDY                                                       4

SEQ ID NO: 482          moltype = AA  length = 238
FEATURE                 Location/Qualifiers
REGION                  1..238
                        note = Short Chain 2 (6A5 VL-hCK)
source                  1..238
                        mol_type = protein
                        organism = synthetic construct
SEQUENCE: 482
MDMRVPAQLL GLLLLWFPGS RCEIVLTQSP GTLSLSPGER ATLSCRASQS VSSTYLAWYQ  60
QKPGQAPRLL IYGASSRATG IPDRFSGSGS GTDFTLTISR LEPEDFAVYY CQQYGSSPPI  120
TFGQGTRLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238

SEQ ID NO: 483          moltype = AA  length = 109
FEATURE                 Location/Qualifiers
REGION                  1..109
                        note = 6A5 VL
source                  1..109
                        mol_type = protein
                        organism = synthetic construct
SEQUENCE: 483
EIVLTQSPGT LSLSPGERAT LSCRASQSVS STYLAWYQQK PGQAPRLLIY GASSRATGIP  60
DRFSGSGSGT DFTLTISRLE PEDFAVYYCQ QYGSSPPITF GQGTRLEIK              109

SEQ ID NO: 484          moltype = AA  length = 12
FEATURE                 Location/Qualifiers
REGION                  1..12
                        note = 6A5 VL - CDR1
source                  1..12
                        mol_type = protein
                        organism = synthetic construct
SEQUENCE: 484
RASQSVSSTY LA                                              12

SEQ ID NO: 485          moltype = AA  length = 7
FEATURE                 Location/Qualifiers
REGION                  1..7
                        note = 6A5 VL - CDR2
source                  1..7
                        mol_type = protein
                        organism = synthetic construct
SEQUENCE: 485
GASSRAT                                                    7

SEQ ID NO: 486          moltype = AA  length = 10
FEATURE                 Location/Qualifiers
REGION                  1..10
                        note = 6A5 VL - CDR3
source                  1..10
                        mol_type = protein
                        organism = synthetic construct
SEQUENCE: 486
QQYGSSPPIT                                                 10

SEQ ID NO: 487          moltype = AA  length = 22
FEATURE                 Location/Qualifiers
```

```
REGION                1..22
                      note = leader sequence
source                1..22
                      mol_type = protein
                      organism = synthetic construct
SEQUENCE: 487
MDMRVPAQLL GLLLLWFPGS RC                                          22

SEQ ID NO: 488        moltype = AA  length = 19
FEATURE               Location/Qualifiers
REGION                1..19
                      note = leader sequence
source                1..19
                      mol_type = protein
                      organism = synthetic construct
SEQUENCE: 488
MEFGLSWLFL VAILKGVQC                                              19

SEQ ID NO: 489        moltype = AA  length = 4
FEATURE               Location/Qualifiers
REGION                1..4
                      note = linker sequence
source                1..4
                      mol_type = protein
                      organism = synthetic construct
SEQUENCE: 489
GGGS                                                              4

SEQ ID NO: 490        moltype = AA  length = 4
FEATURE               Location/Qualifiers
REGION                1..4
                      note = Linker sequence
source                1..4
                      mol_type = protein
                      organism = synthetic construct
SEQUENCE: 490
SGGG                                                              4

SEQ ID NO: 491        moltype = AA  length = 5
FEATURE               Location/Qualifiers
REGION                1..5
                      note = Linker sequence
source                1..5
                      mol_type = protein
                      organism = synthetic construct
SEQUENCE: 491
GGGGS                                                             5

SEQ ID NO: 492        moltype = AA  length = 7
FEATURE               Location/Qualifiers
REGION                1..7
                      note = Linker sequence
source                1..7
                      mol_type = protein
                      organism = synthetic construct
SEQUENCE: 492
GGGGSGS                                                           7

SEQ ID NO: 493        moltype = AA  length = 8
FEATURE               Location/Qualifiers
REGION                1..8
                      note = Linker sequence
source                1..8
                      mol_type = protein
                      organism = synthetic construct
SEQUENCE: 493
GGGGSGGS                                                          8

SEQ ID NO: 494        moltype = AA  length = 10
FEATURE               Location/Qualifiers
REGION                1..10
                      note = Linker sequence
source                1..10
                      mol_type = protein
                      organism = synthetic construct
SEQUENCE: 494
GGGGSGGGGS                                                        10

SEQ ID NO: 495        moltype = AA  length = 15
```

```
FEATURE              Location/Qualifiers
REGION               1..15
                     note = Linker sequence
source               1..15
                     mol_type = protein
                     organism = synthetic construct
SEQUENCE: 495
GGGGSGGGGS GGGGS                                                  15

SEQ ID NO: 496       moltype = AA  length = 16
FEATURE              Location/Qualifiers
REGION               1..16
                     note = Linker sequence
source               1..16
                     mol_type = protein
                     organism = synthetic construct
SEQUENCE: 496
AKTTPKLEEG EFSEAR                                                 16

SEQ ID NO: 497       moltype = AA  length = 17
FEATURE              Location/Qualifiers
REGION               1..17
                     note = Linker sequence
source               1..17
                     mol_type = protein
                     organism = synthetic construct
SEQUENCE: 497
AKTTPKLEEG EFSEARV                                                17

SEQ ID NO: 498       moltype = AA  length = 9
FEATURE              Location/Qualifiers
REGION               1..9
                     note = Linker sequence
source               1..9
                     mol_type = protein
                     organism = synthetic construct
SEQUENCE: 498
AKTTPKLGG                                                         9

SEQ ID NO: 499       moltype = AA  length = 10
FEATURE              Location/Qualifiers
REGION               1..10
                     note = Linker sequence
source               1..10
                     mol_type = protein
                     organism = synthetic construct
SEQUENCE: 499
SAKTTPKLGG                                                        10

SEQ ID NO: 500       moltype = AA  length = 6
FEATURE              Location/Qualifiers
REGION               1..6
                     note = Linker sequence
source               1..6
                     mol_type = protein
                     organism = synthetic construct
SEQUENCE: 500
SAKTTP                                                            6

SEQ ID NO: 501       moltype = AA  length = 6
FEATURE              Location/Qualifiers
REGION               1..6
                     note = Linker sequence
source               1..6
                     mol_type = protein
                     organism = synthetic construct
SEQUENCE: 501
RADAAP                                                            6

SEQ ID NO: 502       moltype = AA  length = 9
FEATURE              Location/Qualifiers
REGION               1..9
                     note = Linker sequence
source               1..9
                     mol_type = protein
                     organism = synthetic construct
SEQUENCE: 502
RADAAPTVS                                                         9
```

```
SEQ ID NO: 503          moltype = AA  length = 12
FEATURE                 Location/Qualifiers
REGION                  1..12
                        note = Linker sequence
source                  1..12
                        mol_type = protein
                        organism = synthetic construct
SEQUENCE: 503
RADAAAAGGP GS                                                        12

SEQ ID NO: 504          moltype = AA  length = 27
FEATURE                 Location/Qualifiers
REGION                  1..27
                        note = Linker sequence
source                  1..27
                        mol_type = protein
                        organism = synthetic construct
SEQUENCE: 504
RADAAAAGGG GSGGGGSGGG GSGGGGS                                        27

SEQ ID NO: 505          moltype = AA  length = 18
FEATURE                 Location/Qualifiers
REGION                  1..18
                        note = Linker sequence
source                  1..18
                        mol_type = protein
                        organism = synthetic construct
SEQUENCE: 505
SAKTTPKLEE GEFSEARV                                                  18

SEQ ID NO: 506          moltype = AA  length = 5
FEATURE                 Location/Qualifiers
REGION                  1..5
                        note = Linker sequence
source                  1..5
                        mol_type = protein
                        organism = synthetic construct
SEQUENCE: 506
ADAAP                                                                5

SEQ ID NO: 507          moltype = AA  length = 12
FEATURE                 Location/Qualifiers
REGION                  1..12
                        note = Linker sequence
source                  1..12
                        mol_type = protein
                        organism = synthetic construct
SEQUENCE: 507
ADAAPTVSIF PP                                                        12

SEQ ID NO: 508          moltype = AA  length = 5
FEATURE                 Location/Qualifiers
REGION                  1..5
                        note = Linker sequence
source                  1..5
                        mol_type = protein
                        organism = synthetic construct
SEQUENCE: 508
TVAAP                                                                5

SEQ ID NO: 509          moltype = AA  length = 12
FEATURE                 Location/Qualifiers
REGION                  1..12
                        note = Linker sequence
source                  1..12
                        mol_type = protein
                        organism = synthetic construct
SEQUENCE: 509
TVAAPSVFIF PP                                                        12

SEQ ID NO: 510          moltype = AA  length = 6
FEATURE                 Location/Qualifiers
REGION                  1..6
                        note = Linker sequence
source                  1..6
                        mol_type = protein
                        organism = synthetic construct
SEQUENCE: 510
QPKAAP                                                               6
```

```
SEQ ID NO: 511          moltype = AA  length = 13
FEATURE                 Location/Qualifiers
REGION                  1..13
                        note = Linker sequence
source                  1..13
                        mol_type = protein
                        organism = synthetic construct
SEQUENCE: 511
QPKAAPSVTL FPP                                                  13

SEQ ID NO: 512          moltype = AA  length = 6
FEATURE                 Location/Qualifiers
REGION                  1..6
                        note = Linker sequence
source                  1..6
                        mol_type = protein
                        organism = synthetic construct
SEQUENCE: 512
AKTTPP                                                          6

SEQ ID NO: 513          moltype = AA  length = 13
FEATURE                 Location/Qualifiers
REGION                  1..13
                        note = Linker sequence
source                  1..13
                        mol_type = protein
                        organism = synthetic construct
SEQUENCE: 513
AKTTPPSVTP LAP                                                  13

SEQ ID NO: 514          moltype = AA  length = 13
FEATURE                 Location/Qualifiers
REGION                  1..13
                        note = Linker sequence
source                  1..13
                        mol_type = protein
                        organism = synthetic construct
SEQUENCE: 514
AKTTAPSVYP LAP                                                  13

SEQ ID NO: 515          moltype = AA  length = 6
FEATURE                 Location/Qualifiers
REGION                  1..6
                        note = Linker sequence
source                  1..6
                        mol_type = protein
                        organism = synthetic construct
SEQUENCE: 515
ASTKGP                                                          6

SEQ ID NO: 516          moltype = AA  length = 13
FEATURE                 Location/Qualifiers
REGION                  1..13
                        note = Linker sequence
source                  1..13
                        mol_type = protein
                        organism = synthetic construct
SEQUENCE: 516
ASTKGPSVFP LAP                                                  13

SEQ ID NO: 517          moltype = AA  length = 15
FEATURE                 Location/Qualifiers
REGION                  1..15
                        note = Linker sequence
source                  1..15
                        mol_type = protein
                        organism = synthetic construct
SEQUENCE: 517
GENKVEYAPA LMALS                                                15

SEQ ID NO: 518          moltype = AA  length = 15
FEATURE                 Location/Qualifiers
REGION                  1..15
                        note = Linker sequence
source                  1..15
                        mol_type = protein
                        organism = synthetic construct
SEQUENCE: 518
```

```
GPAKELTPLK EAKVS                                                      15

SEQ ID NO: 519          moltype = AA  length = 15
FEATURE                 Location/Qualifiers
REGION                  1..15
                        note = Linker sequence
source                  1..15
                        mol_type = protein
                        organism = synthetic construct
SEQUENCE: 519
GHEAAAVMQV QYPAS                                                      15
```